(12) United States Patent
Wang et al.

(10) Patent No.: US 10,500,194 B2
(45) Date of Patent: Dec. 10, 2019

(54) COVALENT SMALL MOLECULE DCN1 INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Shaomeng Wang, Superior Township, MI (US); Haibin Zhou, Ann Arbor, MI (US); Jianfeng Lu, Ann Arbor, MI (US); Liu Liu, Ann Arbor, MI (US); Jeanne Stuckey, Fenton, MI (US); Liangyou Rui, Ann Arbor, MI (US); Yi Sun, Superior Township, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/949,799

(22) Filed: Apr. 10, 2018

(65) Prior Publication Data
US 2018/0289677 A1    Oct. 11, 2018

Related U.S. Application Data

(60) Provisional application No. 62/483,640, filed on Apr. 10, 2017.

(51) Int. Cl.
| | | |
|---|---|---|
| C07D 277/64 | (2006.01) | |
| C07D 405/12 | (2006.01) | |
| A61K 31/428 | (2006.01) | |
| A61K 31/4523 | (2006.01) | |
| A61K 31/496 | (2006.01) | |
| A61K 31/5377 | (2006.01) | |
| A61P 1/16 | (2006.01) | |
| A61K 31/454 | (2006.01) | |
| A61K 31/497 | (2006.01) | |

(52) U.S. Cl.
CPC ............. *A61K 31/428* (2013.01); *A61P 1/16* (2018.01); *C07D 277/64* (2013.01); *C07D 405/12* (2013.01); *A61K 31/454* (2013.01); *A61K 31/497* (2013.01); *A61K 31/5377* (2013.01)

(58) Field of Classification Search
CPC .. A61K 31/428; A61K 31/454; A61K 31/497; A61K 31/5377; A61K 31/4523; A61K 31/496; C07D 277/64; C07D 405/12
See application file for complete search history.

(56) References Cited

FOREIGN PATENT DOCUMENTS

WO    WO-2017/049295 A1    3/2017

OTHER PUBLICATIONS

Zhou et al. Structure-based design of highly potent small-molecule inhibitors of DCN1-UBC12 protein-protein interaction, Oral presentation, Apr. 6, 2017, 253rd ACS National Meeting, Medicinal Chemistry Division, Abstract MEDI 377.*
Andérica-Romero et al., Cullin 3 as a novel target in diverse pathologies, Redox Biol., 1:366-72 (2013).
Bedford et al., Ubiquitin-like protein conjugation and the ubiquitin-proteasome system as drug targets, Nat. Rev. Drug Discov., 10(1):29-46 (2011).
Bomprezzi, Dimethyl fumarate in the treatment of relapsing-remitting multiple sclerosis: an overview, Ther. Adv. Neurol. Disord., 8(1):20-30 (2015).
Brownell et al., Substrate-assisted inhibition of ubiquitin-like protein-activating enzymes: the NEDD8 E1 inhibitor MLN4924 forms a NEDD8-AMP mimetic in situ, Mol. Cell, 37(1):102-11 (2010).
Buendia et al., Nrf2-ARE pathway: An emerging target against oxidative stress and neuroinflammation in neurodegenerative diseases, Pharmacol. Ther., 157:84-104 (2016).
Bulatov et al., Targeting Cullin-RING E3 ubiquitin ligases for drug discovery: structure, assembly and small-molecule modulation, Biochem. J., 467(3):365-86 (2015).
Bulinski et al., Overexpression of MAP4 inhibits organelle motility and trafficking in vivo, J. Cell Sci., 110(Pt. 24):3055-64 (1997).
Canning et al., New strategies to inhibit KEAP1 and the Cul3-based E3 ubiquitin ligases, Biochem. Soc. Trans., 42(1):103-7 (2014).
Ciechanover et al., The ubiquitin-proteasome pathway: the complexity and myriad functions of proteins death, Proc. Natl. Acad. Sci. USA, 95(6):2727-30 (1998).
Cullinan et al., The Keap1-BTB protein is an adaptor that bridges Nrf2 to a Cul3-based E3 ligase: oxidative stress sensing by a Cul3-Keap1 ligase, Mol. Cell Biol., 24(19):8477-86 (2004).
De Zeeuw et al., Bardoxolone methyl in type 2 diabetes and stage 4 chronic kidney disease, N. Engl. J. Med., 369(26):2492-503 (2013).
Deshaies et al., Control of cullin-ring ubiquitin ligase activity by nedd8, Subcell Biochem., 54:41-56 (2010).
Duda et al., Structural insights into NEDD8 activation of cullin-RING ligases: conformational control of conjugation, Cell, 134(6):995-1006 (2008).
Genschik et al., The emerging family of CULLIN3-RING ubiquitin ligases (CRL3s): cellular functions and disease implications, EMBO J., 32(17):2307-20 (2013).
Gong et al., Identification of the activating and conjugating enzymes of the NEDD8 conjugation pathway, J. Biol. Chem., 274(17):12036-42 (1999).
Gorrini et al., Modulation of oxidative stress as an anticancer strategy, Nat. Rev. Drug Discov., 12(12):931-47 (2013).
Hayes et al., The Nrf2 regulatory network provides an interface between redox and intermediary metabolism, Trends Biochem. Sci., 39(4):199-218 (2014).

(Continued)

*Primary Examiner* — Irina Neagu
(74) *Attorney, Agent, or Firm* — Marshall, Gerstein & Borun LLP

(57) ABSTRACT

Small molecule covalent inhibitors of DCN1 and compositions containing the same are disclosed. Methods of using the DCN1 covalent inhibitors in the treatment of diseases and conditions wherein inhibition of DCN1 provides a benefit, like oxidative stress-related diseases and conditions, neurodegenerative diseases and conditions, metabolic disorders, and muscular nerve degeneration, also are disclosed.

22 Claims, 9 Drawing Sheets

(56) References Cited

OTHER PUBLICATIONS

Hershko, The ubiquitin system for protein degradation and some of its roles in the control of the cell division cycle, Cell Death Differ., 12(9):1191-7 (2005).
Huang et al., A unique E1-E2 interaction required for optimal conjugation of the ubiquitin-like protein NEDD8, Nat. Struct. Mol. Biol., 11(10):927-35 (2004).
Kane et al., Bortezomib for the treatment of mantle cell lymphoma, Clin. Cancer Res., 13(18 Pt. 1):5291-4 (2007).
Kane et al., Velcade: U.S. FDA approval for the treatment of multiple myeloma progressing on prior therapy, Oncologist, 8(6):508-13 (2003).
Keuss et al., Characterization of the mammalian family of DCN-type NEDD8 E3 ligases, J. Cell Sci., 129(7):1441-54 (2016).
Kim et al., SCCRO (DCUN1D1) is an essential component of the E3 complex for neddylation, J. Biol. Chem., 283(48):33211-20 (2008).
Kobayashi et al., Oxidative stress sensor Keap1 functions as an adaptor for Cul3-based E3 ligase to regulate proteasomal degradation of Nrf2, Mol. Cell Biol., 24(16):7130-9 (2004).
Kurz et al., Dcn1 functions as a scaffold-type E3 ligase for cullin neddylation, Mol. Cell., 29(1):23-35 (2008).
Liby et al., Synthetic oleanane triterpenoids: multifunctional drugs with a broad range of applications for prevention and treatment of chronic disease, Pharmacol. Rev., 64(4):972-1003 (2012).
Ma, Role of nrf2 in oxidative stress and toxicity, Annu. Rev. Pharmacol. Toxicol., 53:401-26 (2013).
Martinez Molina et al., Monitoring drug target engagement in cells and tissues using the cellular thermal shift assay, Science, 341(6141):84-7 (2013).
McCormack, Carfilzomib: in relapsed, or relapsed and refractory, multiple myeloma, Drugs, 72(15):2023-32 (2012).
Monda et al., Structural conservation of distinctive N-terminal acetylation-dependent interactions across a family of mammalian NEDD8 ligation enzymes, Structure, 21(1):42-53 (2013).
Muhlradt et al., Epothilone B stabilizes microtubuli of macrophages like taxol without showing taxol-like endotoxin activity, Cancer Res., 57(16):3344-6 (1997).
Nalepa et al., Drug discovery in the ubiquitin-proteasome system, Nat. Rev. Drug Discov., 5(7):596-613 (2006).
Nicolaou et al., Synthesis of epothilones A and B in solid and solution phase, Nature, 387(6630):268-72 (1997).
Nishitani et al., Two E3 ubiquitin ligases, SCF-Skp2 and DDB1-Cul4, target human Cdt1 for proteolysis, EMBO J., 25(5):1126-36 (2006).
Panda et al., Differential effects of vinblastine on polymerization and dynamics at opposite microtubule ends, J. Biol. Chem., 271(47):29807-12 (1996).
Panda et al., Stabilization of microtubule dynamics by estramustine by binding to a novel site in tubulin: a possible mechanistic basis for its antitumor action, Proc. Natl. Acad. Sci. USA, 94(20):10560-4 (1997).
Petroski et al., Function and regulation of cullin-RING ubiquitin ligases, Nat. Rev. Mol. Cell Biol., 6(1):9-20 (2005).
Scott et al., A dual E3 mechanism for Rub1 ligation to Cdc53, Mol. Cell, 39(5):784-96 (2010).
Scott et al., N-terminal acetylation acts as an avidity enhancer within an interconnected multiprotein complex, Science, 334(6056):674-8 (2011).
Scott et al., Structure of a RING E3 trapped in action reveals ligation mechanism for the ubiquitin-like protein NEDD8, Cell, 157(7):1671-84 (2014).
Soucy et al., An inhibitor of NEDD8-activating enzyme as a new approach to treat cancer, Nature, 458(7239):732-6 (2009).
Soucy et al., Targeting NEDD8-activated cullin-RING ligases for the treatment of cancer, Clin. Cancer Res., 15912):3912-6 (2009).
Soucy et al., The NEDD8 Conjugation Pathway and Its Relevance in Cancer Biology and Therapy, Genes Cancer, 1(7):708-16 (2010).
Sporn et al., NRF2 and cancer: the good, the bad and the importance of context, Nat. Rev. Cancer, 12(8):564-71 (2012).
Suzuki et al., Toward clinical application of the Keap1-Nrf2 pathway, Trends Pharmacol. Sci., 34(6):340-6 (2013).
Vasquez et al., Nanomolar concentrations of nocodazole alter microtubule dynamic instability in vivo and in vitro, Mol. Biol. Cell, 8(6):973-85 (1997).
Venugopal et al., Nrf2 and Nrf1 in association with Jun proteins regulate antioxidant response element-mediated expression and coordinated induction of genes encoding detoxifying enzymes, Oncogene, 17(24):3145-56 (1998).
Watson et al., NEDD8 pathways in cancer, Sine Quibus Non, Cancer Cell, 19(2):168-76 (2011).
Yang et al., Analysis of Flexibility and Hotspots in Bcl-xL and Mcl-1 Proteins for the Design of Selective Small-Molecule Inhibitors, ACS Med. Chem. Lett., 3(4):308-12 (2012).
Yang et al., Computational analysis of protein hotspots, ACS Med. Chem. Lett., 1(3):125-9 (2010).
Yang et al., Hydrophobic Binding Hot Spots of Bcl-xL Protein-Protein Interfaces by Cosolvent Molecular Dynamics Simulation, ACS Med. Chem. Lett., 2(4):280-4 (2011).
Yoon et al., Acetaminophen-Induced Hepatotoxicity: a Comprehensive Update, J. Clin. Transl. Hepatol., 4(2):131-42 (2016).
Zhao et al., Cullin-RING Ligases as attractive anti-cancer targets, Curr. Pharm. Des., 19(18):3215-25 (2013).
Zhao et al., Targeting Neddylation pathways to inactivate cullin-RING ligases for anticancer therapy, Antioxid. Redox. Signal., 21(17):2383-400 (2014).
International Application No. PCT/US2018/026789, International Search Report and Written Opinion, dated Jun. 14, 2018.
Zhou et al., A potent small-molecule inhibitor of the DCN1-UBC12 interaction that selectively blocks cullin 3 neddylation, Nat. Commun., 8(1):1150 (2017).

* cited by examiner

COVALENT SMALL MOLECULE DCN1 INHIBITORS AND THERAPEUTIC METHODS USING THE SAME

CROSS-REFERENCE TO RELATED APPLICATIONS

This application claims the benefit of U.S. provisional Patent Application No. 62/483,640 filed Apr. 10, 2017, incorporated herein by reference in its entirety.

FIELD OF THE INVENTION

The present invention relates to small molecule DCN1 inhibitors which bind covalently to the protein, and to therapeutic methods of treating conditions and diseases wherein inhibition of DCN1 provides a benefit.

BACKGROUND OF THE INVENTION

The regulated destruction of intracellular proteins is controlled by the ubiquitin-proteasome system (UPS) via tagging the ubiquitin on the proteins, and is essential to cellular protein homeostasis (1,2). The UPS has been extensively pursued as a drug target (3,4), with two proteasome inhibitors, Bortezomib and Carfilzomib, having been approved for the treatment of multiple myeloma (5-7).

The Cullin-Ring ligases (CRL), a central component of the UPS, regulate the turnover of approximately 20% of cellular proteins, and the dysregulation of CRLs plays a critical role in various human diseases, including cancer, cardiovascular diseases, neurodegenerative disorders, and viral infections (8-11). The activation of CRLs is controlled by NEDD8 (neural precursor cell expressed developmentally downregulated protein 8), a ubiquitin-like protein (9,10,12). Analogous to the process of ubiquitination, neddylation is a process by which the ubiquitin-like protein NEDD8 is conjugated to its target proteins.

The neddylation cascade begins with the activation of NEDD8 by an E1 enzyme, the NEDD8 activating enzyme (NAE), followed by transfer of the activated NEDD8 to one of two NEDD8-specific E2 enzymes, UBC12 and UBE2F. In the final step of this cascade, an E3 enzyme catalyzes the transfer of NEDD8 from E2 to target substrates (13). The enzymes of the NEDD8 pathway have been pursued as potential therapeutic targets (14-17) and MLN4924, an inhibitor of the E1 enzyme NAE, was shown to suppress tumor cell growth both in vitro and in vivo (18). Mechanistically, MLN4924 inhibits NAE enzymatic activity through formation of a covalent NEDD8-MLN4924 adduct, which in turn inactivates CRLs, leading to accumulation of CRL substrates (18,19). MLN4924 is currently being tested in clinical trials for the treatment of human cancers (20).

Schulman et al. have defined both the structural and biochemical mechanisms underlying the E1-E2-E3 cascade reaction in the NEDD8 pathway (13, 21-23). Schulman et al. further demonstrated that DCN1, a scaffold-like E3 ligase, facilitates the transfer of NEDD8 from UBC12 to cullins through its interaction with UBC12 and enhances the enzymatic activity of cullins (13,22,23). The co-crystal structure of the DCN1-UBC12 complex 22,23 reveals that UBC12 interacts with DCN1 through two distinct sites and the N-terminally acetylated UBC12 peptide binds to a well-defined pocket in DCN1.

To date, no small-molecule inhibitors of the DCN1-UBC12 interaction have been advanced into clinical development. Accordingly, a need still exists in the art for small molecule inhibitors of the UBC12-DCN1 protein-protein interaction, having physical and pharmacological properties that permit use of such inhibitors in a range of therapeutic applications in which modulation of the activity of cullins may have a therapeutic benefit.

Inhibitors of protein-protein interactions are generally considered to be difficult drugs to develop, because even when there is a well defined binding pocket on one of the proteins to target, that is rarely the totality of the mutual binding surface between the two entities. When inhibiting receptors or enzymes, there is often a small molecule ligand or cofactor which can be competed against, or a catalytic machinery which can be interfered with irrespective of substrate binding, and this allows relatively low affinity inhibitors to be potential drugs. However, with protein-protein interaction inhibitors (PPI inhibitors) it is frequently infeasible to block the whole of the interaction site between the two proteins, and if one is only blocking a part of the interaction site, very high affinity ligands are required in order to compete with the partner protein which will interact with a much larger protein surface than the inhibitor. Even with very good binding pockets, it is difficult to push binding affinities into the frequently required low picomolar range.

One answer to achieve highly potent inhibition of the protein-protein interaction is to use an inhibitor which forms a covalent bond to its target protein, as bond formation makes the effective binding between inhibitor and target protein much stronger. In recent years, this approach has been systematized, especially in the kinase inhibitor field, where a combination of intrinsically high affinity ligands, combined with a very precisely placed weak electrophile, usually close to a highly nucleophilic cysteine residue, has been shown to produce inhibitors which bind very strongly indeed to the target protein, but which are of intrinsically low enough chemical reactivity to have usable pharmacokinetics and acceptable off target toxicity profiles. For examples Afatinib, Ibrutinib and Osimertinib are all successful anticancer drugs which covalently attach to a cysteine on the edge of the ATP-binding domain in a small subset of kinases.

DCN1 has a cysteine ($Cys^{115}$) on the edge of its deep UBC12 binding pocket, and in a suitable place whereby DCN1 inhibitors of the chemotype described in a previous patent application [U.S. Provisional Application No. 62/477, 498], and illustrated herewithin, should be able to present a suitable electrophile in a manner to allow formation of a covalent bond between the cysteine sulfur atom and the abovementioned electrophile. Compounds of the present invention can bind to DCN1 as covalent inhibitors of the interaction between DCN1 and UBC12, and this leads to a major, highly consequential boost in their potency for these molecules as compared to their non-covalent inhibitor counterparts.

SUMMARY OF THE INVENTION

The present invention is directed to small-molecule inhibitors designed to bind to the UBC12 binding site in DCN1 (hereafter called DCN1 inhibitors), and to form a covalent bond between their electrophilic moiety and $Cys^{115}$ of DCN1, to compositions comprising the inhibitors, and to methods of using the inhibitors in a therapeutic treatment of conditions and diseases wherein inhibition of the UBC12 binding site in DCN1 provides a benefit. In particularly, the present compounds are potent inhibitors of the DCN1-UBC12 protein-protein interaction. The inhibitors block neddylation of cullin 3. The inhibitors also block neddylation of other cullins, although at higher concentrations than those used for inhibition of the neddylation of cullin 3.

More particularly, the present invention is directed to compounds having a structural formula (I),

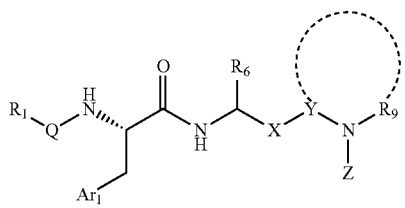

wherein;

Q is C=O, C=S or $SO_2$;

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

X is selected from a bond, $CR_7R_8$, $CR_7R_8NR_{12}$, $CR_7R_8NR_{12}CO$, $CR_7R_8NR_{12}CONR_{12}$, $CR_7R_8NR_{12}SO_2$, $CR_7R_8O$, $CR_7R_8S(O)x$ $CONR_{12}$;

Y is selected from $C_{1-6}$ alkylidyl, $C_{3-6}$ cycloalkylidyl, $C_{4-7}$ heterocloalkylidyl, arylene, heteroarylene, aryl(m)ethylene, heteroaryl(m)ethylene, fused $C_{5-8}$ bicycloalkylidyl or $C_{5-9}$ spirocycloalkylidyl;

Or Y and $R_9$ are taken together with the nitrogen atom to which they are attached to form a heterocyclic or heteroaryl ring of four to seven members, optionally including any chemically stable combination of one to three groups selected from O, C=O, N, $NR_5$ and S;

Z is

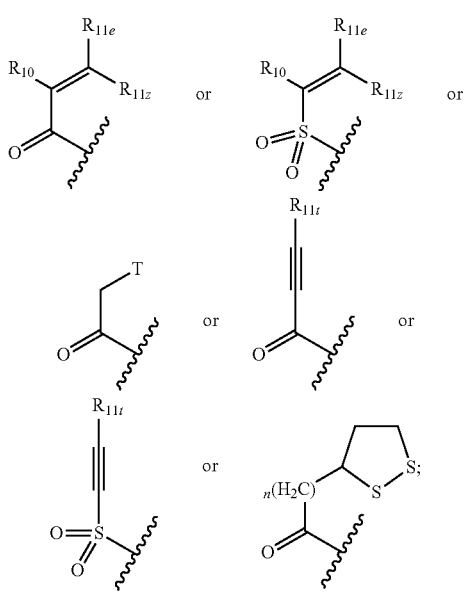

$R_1$ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl. $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_7$ and $R_8$ may be independently H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, or taken together with the C atom to which they are attached, form a carbonyl group, a thionyl group, an oxime, a hydrazone, $C_{3-6}$ cycloalkyl, substituted $C_{3-6}$ cycloalkyl, $C_{4-6}$ cycloalkenyl substituted $C_{4-6}$ cycloalkenyl or $C_{4-7}$ heterocycloalkyl:

$R_9$ is selected from the group consisting of H, $C_{1-6}$ alkyl, substituted $C_{1-6}$ alkyl, $C_{3-6}$ alkenyl, substituted $C_{3-6}$ alkenyl, $C_{3-6}$ alkynyl, substituted $C_{3-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl or $C_{4-7}$ heterocycloalkyl:

$R_{10}$ is H, F, Cl, $CF_3$, $CHF_2$, $(CH_2)_nNR_3R_4$, $CH_2SO_2R_{12}$, $CH_2OCOR_{12}$, CN or $R_{12}$;

$R_{11e}$ is H, $R_{12}$, $(CH_2)_nR_2$, $CF_2(CH_2)xR_2$, $COR_5$, $CO_2R_5$ or $CONR_3R_4$;

$R_{11z}$ is H, F, Cl, $CF_3$, $CHF_2$, $CF_2R_{12}$ or $R_{12}$;

Or $R_{11e}$ and $R_{11z}$ may be taken together with the $sp^2$ carbon atom to which both are bonded to form an alicyclic ring of 4 to 7 members where one of the ring atoms may be $NR_{12}$, O, or $S(O)_x$, optionally substituted with halogen, oxo, OH, $OR_5$, $NR_3R_4$;

Or $R_{11e}$ and $R_{11z}$ taken together may be $R_{11e}R_{11z}C=$, forming an allenyl group;

Or $R_{10}$ and $R_{11e}$ may be taken together with the $sp^2$ C atoms to which they are attached to form a partially saturated carbocyclic or heterocyclic ring of 5-7 atoms, with up to two of the ring atoms being O, $S(O)_x$, $NR_{12}$, and said ring may be substituted with hydroxy, oxo, $C_{1-6}$ alkoxy, R$_{11t}$ is C$_{1-6}$ alkyl, C$_{3-6}$ cycloalkyl, aryl, heteroaryl, C$_{4-7}$ heterocycloalkyl, CH$_2$NR$_3$R$_4$;

R$_{12}$ is H or C$_{1-6}$ alkyl, either straight chain or branched;

T is halogen, SS—C$_{1-6}$ lower alkyl, pentafluorophenoxy, tetrafluorophenoxy:

n is 1, 2 or 3;

x is 0, 1, or 2;

or a pharmaceutically acceptable salt, hydrate, or solvate thereof.

In one embodiment, the present invention provides a method of treating a condition or disease by administering a therapeutically effective amount of a compound of structural formula (I) to an individual in need thereof. The disease or condition of interest is treatable by inhibition of DCN1, for example, an oxidative stress-related disease or a neurodegenerative disease.

Another embodiment of the present invention is to provide a composition comprising (a) a DCN1 inhibitor of structural formula (I) and (b) an excipient and/or pharmaceutically acceptable carrier useful in treating diseases or conditions wherein inhibition of DCN1 provides a benefit.

Another embodiment of the present invention is to utilize a composition comprising a compound of structural formula (I) and an optional second therapeutically active agent in a method of treating an individual for a disease or condition wherein inhibition of DCN provides a benefit.

In a further embodiment, the invention provides for use of a composition comprising a DCN1 inhibitor of structural formula (I) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a DCN inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

Another embodiment is a method of blocking an interaction between DCN1 and its binding partners, including, but not limited to, UBC12 and UBC2E, in cells comprising contacting the cells with a compound of structural formula (I).

In other embodiments, blocking the interaction between DCN1 and its binding partners in cells by contacting the cells with a compound of structural formula (I) leads to one or more of (a) selective inhibition of cullin 3 activity; (b) accumulation of protein substrates of cullin 3; (c) upregulation of NRF2, a known cullin 3 substrate; (d) modulation of a set of genes regulated by NRF2; (e) a therapeutic benefit in human diseases or conditions by modulation of the activity of cullin 3; and (f) a therapeutic benefit in human diseases or conditions by modulation of the activity of NRF2.

DETAILED DESCRIPTION OF THE INVENTION

Figure 1:
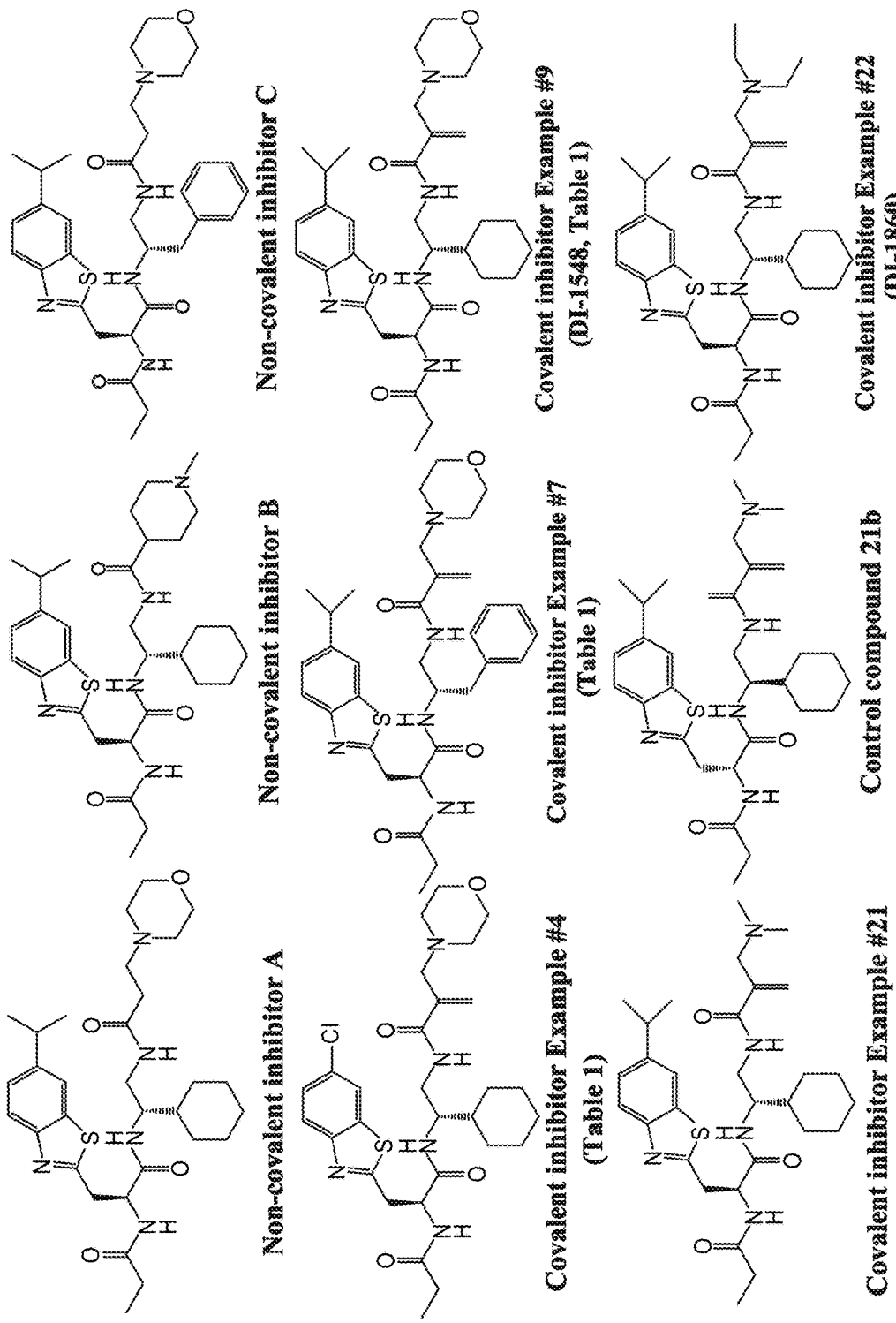
FIG. 1 depicts chemical structures of examples of representative non-covalent and covalent DCN1 inhibitors.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "DCN1" as used herein means a protein that functions as a Scaffold-Type E3 Ligase for cullin neddylation.

The term "a disease or condition wherein inhibition of DCN1 provides a benefit" pertains to a condition in which DCN1, and/or an action of DCN1, is important or necessary, e.g., for the onset, progress, expression of that disease or condition, or a disease or a condition which is known to be treated by a DCN1 inhibition. An example of such a condition includes, but is not limited to, an oxidative stress-related disease, a neurodegenerative disease, cancer, a cardiovascular disease, or tissue regeneration. One of ordinary skill in the art is readily able to determine whether a compound treats a disease or condition mediated by DCN1 for any particular cell type, for example, by assays which conveniently can be used to assess the activity of particular compounds.

The term "second therapeutic agent" refers to a therapeutic agent different from a DCN1 inhibitor of structural formula (I) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, compounds of structural formula (I) are potent inhibitors of DCN1 and can be used in treating diseases and conditions wherein inhibition of DCN1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of structural formula (I) to an individual in need of such treatment.

Within the meaning of the invention, "treatment" includes the treatment of acute or chronic signs, symptoms, and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other oxidative stress-related disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce DCN1 interactions in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a DCN1 inhibitor of structural formula (I) can be administered at the same time or sequentially in any order at different points in time as a second therapeutic agent. A present DCN1 inhibitor and the second therapeutic agent can be administered separately, in any appropriate form and by any suitable route. When a present DCN1 inhibitor and the second therapeutic agent are not administered concurrently, it is understood that they can be administered in any order to a subject in need thereof. For example, a present DCN1 inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a DCN1 inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein are intended to merely serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

To date, most small-molecule modulators targeting UPS components contain a chemically reactive group and act as covalent inhibitors. These include FDA-approved Bortezomib (5,6), Carfilzomib (7), and dimethyl fumarate (38), and MLN4924 (18), RTA402 and RTA408 (39-41), which currently are in clinical development. Thus the use of covalent inhibitors in this general mechanistic approach to disease modulation is well precedented, although the above-mentioned covalent inhibitors either target the S26 proteasome or KEAP1, whereas compounds of the current invention inhibit one very specific step in the ubiquitination pathway, which would be expected to give a very different biological phenotype to the known irreversible inhibitors of the UPS.

The present invention targets the DCN1-UBC12 protein-protein interaction as a strategy for modulation of protein turnover. DCN1 is a component of neddylation E3 ligase and plays a role in modulation of the activity of cullins. The co-crystal structure of DCN1 complexed with UBC12 revealed that the UBC12 peptide-binding pocket in DCN1 could accommodate a small-molecule inhibitor for blocking the DCN1-UBC12 protein-protein interaction. Said co-crystal structures also showed that the portion of the inhibitor which is directed towards the solvent binds to DCN1 in a manner which would allow a weak electrophile on that part of the inhibitor to be placed in close proximity, and a suitable orientation, to form a covalent bond with the sulfur atom of Cys119. The present invention therefore is directed to a new class of potent covalent inhibitors of the DCN1-UBC12 protein-protein interaction, which form a covalent bond to Cys119 of DCN1.

Recent evidence suggests that the dysfunction of cullin 3 is associated with various human diseases, including metabolic disorders, neurodegeneration, and cancer (42-44). Modulation of cullin 3 therefore can have a therapeutic potential for the treatment of human diseases. Compared to the global inhibition of neddylation of all cullins by MLN4924, a compound of structural formula (I) is a selective inhibitor of the neddylation of cellular CUL3. A compound of structural formula (I) increases the level of NRF2 protein, a well known substrate of cullin 3, leading to upregulation of two detoxification enzymes NQO1 and HO1. In comparison, MLN4924, a NAE inhibitor, globally increases the abundance of all cullin-targeted proteins examined. Therefore, compounds of structural formula (I) serves as excellent chemical probes for a study of cullin 3 and its role in different biological processes and human diseases.

As the master regulator of antioxidant responses, NRF2 regulates about 200 genes involved in cytoprotection, lipid metabolism, and gene transcription. Activation of NRF2 can have a therapeutic benefit against various oxidative stress-related diseases, including cancer, neurodegenerative disease, cardiovascular disease, acute lung injury, chronic obstructive pulmonary diseases, autoimmune disease, and inflammation (36, 45, 46, 47). One NRF2 inducer, dimethyl fumarate, has recently been approved by the FDA as first-line therapy for relapsing-remitting multiple sclerosis (MS) (38). Another series of NRF2 inducers under clinical development are synthetic derivatives of oleanoic acid (39,40). A common mechanism of these compounds is that they are covalent modulators targeting Keap1. In comparison, a compound of structural formula (I) activates NRF2 by blocking the DCN1-UBC12 protein-protein interaction and selectively inhibiting the activity of cullin 3, thus engaging a different mechanism of action. The DCN1 inhibitors of the present invention therefore are useful in the treatment of a variety of diseases and conditions in subjects in need of such treatment.

The present invention is directed to compounds having a structural formula (I).

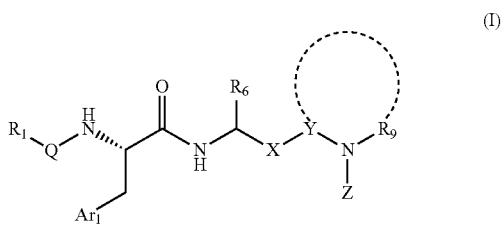

wherein;

Q is C=O, C=S or $SO_2$;

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

T is halogen, SS—$C_{1-6}$ lower alkyl, pentafluorophenoxy, tetrafluorophenoxy:

X is selected from a bond, $CR_7R_8$, $CR_7R_8NR_{12}$, $CR_7R_8NR_{12}CO$, $CR_7R_8NR_{12}CONR_{12}$, $CR_7R_8NR_{12}SO_2$, $CR_7R_8O$, $CR_7R_8S(O)_x$ $CONR_{12}$;

Y is selected from $C_{1-6}$ alkylidyl, $C_{3-6}$ cycloalkylidyl, $C_{4-7}$ heterocloalkylidyl, arylene, heteroarylene, aryl(m)ethylene, heteroaryl(m)ethylene, fused $C_{5-8}$ bicycloalkylidyl or $C_{5-9}$ spirocycloalkylidyl;

Or Y and $R_9$ are taken together with the nitrogen atom to which they are attached to form a heterocyclic or heteroaryl ring of four to seven members, optionally including any chemically stable combination of one to three groups selected from O, C=O, N, $NR_5$ and S;

Z is

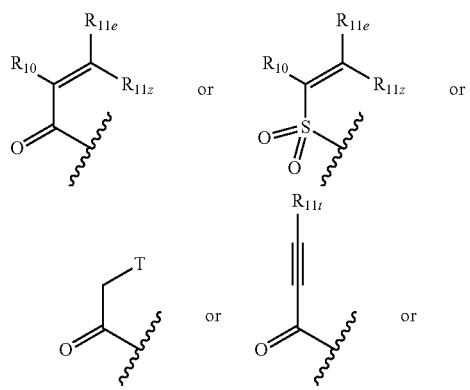

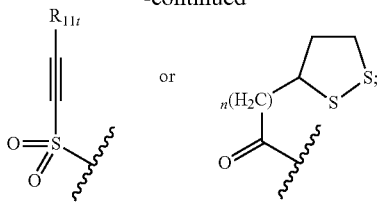

$R_1$ is selected from the group consisting of H, $C_{1-6}$ alkyl, $C_{3-6}$ cycloalkyl, $C_{3-6}$ cycloalkylmethylene, NHMe, N(Me)$_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_7$ and $R_8$ may be independently H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, or taken together with the C atom to which they are attached, form a carbonyl group, a thionyl group, an oxime, a hydrazone, $C_{3-6}$ cycloalkyl, substituted $C_{3-6}$ cycloalkyl, $C_{4-6}$ cycloalkenyl substituted $C_{4-6}$ cycloalkenyl or $C_{4-7}$ heterocycloalkyl:

$R_9$ is selected from the group consisting of H, $C_{1-6}$ alkyl, substituted $C_{1-6}$ alkyl, $C_{3-6}$ alkenyl, substituted $C_{3-6}$ alkenyl, $C_{3-6}$ alkynyl, substituted $C_{3-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl or $C_{4-7}$ heterocycloalkyl:

$R_{10}$ is H, F, Cl, $CF_3$, $CHF_2$, $(CH_2)_nNR_3R_4$, $CH_2SO_2R_{12}$, $CH_2OCOR_{12}$, CN or $R_{12}$;

$R_{11e}$ is H, $R_{12}$, $(CH_2)_nR_2$, $CF_2(CH_2)_xR_2$, $COR_5$, $CO_2R_5$ or $CONR_3R_4$;

$R_{11z}$ is H, F, Cl, $CF_3$, $CHF_2$, $CF_2R_{12}$ or $R_{12}$;

Or $R_{11e}$ and $R_{11z}$ may be taken together with the sp$^2$ carbon atom to which both are bonded to form an alicyclic ring of 4 to 7 members where one of the ring atoms may be $NR_{12}$, O, or $S(O)_x$, optionally substituted with halogen, oxo, OH, $OR_5$, $NR_3R_4$;

Or $R_{11e}$ and $R_{11z}$ taken together may be $R_{11e}R_{11z}$C=, forming an allenyl group;

Or $R_{10}$ and $R_{11e}$ may be taken together with the sp$^2$ C atoms to which they are attached to form a partially saturated carbocyclic or heterocyclic ring of 5-7 atoms, with up to two of the ring atoms being O, $S(O)_x$, $NR_{12}$, and said ring may be substituted with hydroxy, oxo, $C_{1-6}$ alkoxy, $R_{11t}$ is $C_{1-6}$ alkyl, $C_{3-6}$ cycloalkyl, aryl, heteroaryl, $C_{4-7}$ heterocycloalkyl, $CH_2NR_3R_4$;

$R_{12}$ is H or $C_{1-6}$ alkyl, either straight chain or branched;

n is 1, 2 or 3;

x is 0, 1, or 2;

or a pharmaceutically acceptable salt, hydrate, or solvate thereof.

An embodiment of the invention involves a compound of formula (I)

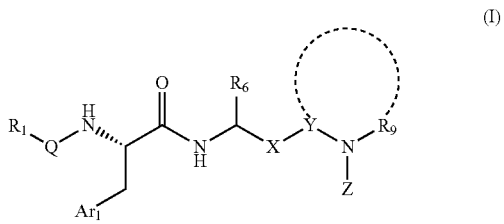

(I)

wherein;

Q is C=O;

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

X is selected from a bond, $CR_7R_8$, $CR_7R_8NR_{12}$, $CR_7R_8NR_{12}CO$, $CR_7R_8NR_{12}CONR_{12}$, $CR_7R_8NR_{12}SO_2$, $CR_7R_8O$, $CR_7R_8S(O)x$ $CONR_{12}$;

Y is selected from $C_{1-6}$ alkylidyl, $C_{3-6}$ cycloalkylidyl, $C_{4-7}$ heterocloalkylidyl, arylene, heteroarylene, aryl(m)ethylene, heteroaryl(m)ethylene;

Or Y and $R_9$ are taken together with the nitrogen atom to which they are attached to form a heterocyclic or heteroaryl ring of four to seven members, optionally including any chemically stable combination of one to three groups selected from O, C=O, N, $NR_5$ and S;

Z is

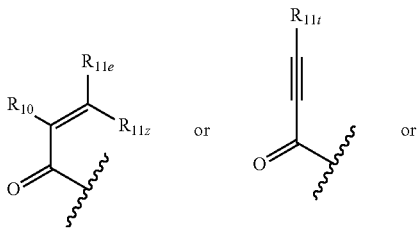

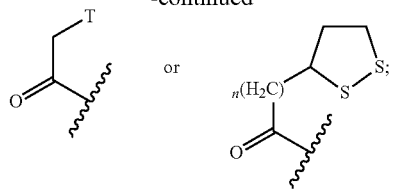

R$_1$ is selected from the group consisting of H, C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, C$_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-7}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;

R$_5$ is selected from the group consisting of hydrogen, CF$_3$, CHF$_2$, C$_{1-6}$ alkyl, allyl, propargyl, C$_{3-6}$ cycloalkyl, C$_{1-6}$ alkyl-C$_{4-6}$ cycloalkenyl, C$_{4-7}$ heterocycloalkyl, aryl, heteroaryl, C$_{1-6}$ alkyl-C$_{3-6}$ cycloalkyl, C$_{1-6}$ alkyl-C$_{4-7}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-7}$ heterocycloalkyl, aryl, and heteroaryl;

R$_6$ is selected from the group consisting of C$_{1-6}$ alkyl, C$_{3-6}$ cycloalkyl, C$_{2-6}$ alkenyl, C$_{4-6}$ cycloalkenyl, C$_{4-7}$ heterocycloalkyl, C$_{2-6}$ alkynyl, C$_{1-6}$ alkyl-C$_{3-6}$ cycloalkyl. C$_{1-6}$ alkyl-C$_{4-6}$ cycloalkenyl, C$_{1-6}$ alkyl-C$_{4-7}$ heterocycloalkyl, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;

R$_7$ and R$_8$ may be independently H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, or taken together with the C atom to which they are attached, form a carbonyl group, a thionyl group, an oxime, a hydrazone, C$_{3-6}$ cycloalkyl, substituted C$_{3-6}$ cycloalkyl, C$_{4-6}$ cycloalkenyl substituted C$_{4-6}$ cycloalkenyl or C$_{4-7}$ heterocycloalkyl:

R$_9$ is selected from the group consisting of H, C$_{1-6}$ alkyl, substituted C$_{1-6}$ alkyl, C$_{3-6}$ alkenyl, substituted C$_{3-6}$ alkenyl, C$_{3-6}$ alkynyl, substituted C$_{3-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl or C$_{4-7}$ heterocycloalkyl:

R$_{10}$ is H, F, CF$_3$, CHF$_2$, (CH$_2$)$_n$NR$_3$R$_4$, CN or R$_{12}$;

R$_{11e}$ is H, R$_{12}$, (CH$_2$)$_n$R$_2$, CF$_2$(CH$_2$)$_x$R$_2$, COR$_5$, CO$_2$R$_5$ or CONR$_3$R$_4$;

R$_{11z}$ is H, F, Cl, CF$_3$, CHF$_2$;

Or R$_{11e}$ and R$_{11z}$ may be taken together with the sp$^2$ carbon atom to which both are bonded to form an alicyclic ring of 4 to 7 members where one of the ring atoms may be NR$_{12}$, O, or S(O)$_x$, optionally substituted with halogen, oxo, OH, OR$_5$, NR$_3$R$_4$;

Or R$_{10}$ and R$_{11e}$ may be taken together with the sp$^2$ C atoms to which they are attached to form a partially saturated carbocyclic or heterocyclic ring of 5-7 atoms, with up to two of the ring atoms being O, S(O)$_x$, NR$_{12}$, and said ring may be substituted with hydroxy, oxo, C$_{1-6}$ alkoxy, R$_{11t}$ is C$_{1-6}$ alkyl, C$_{3-6}$ cycloalkyl, C$_{4-7}$ heterocycloalkyl, CH$_2$NR$_3$R$_4$;

R$_{12}$ is H or C$_{1-6}$ alkyl, either straight chain or branched;

T is halogen;

n is 1, 2 or 3;

x is 0, 1, or 2;

or a pharmaceutically acceptable salt, hydrate, or solvate thereof.

In another embodiment of the invention the compound is a compound of formula (1)

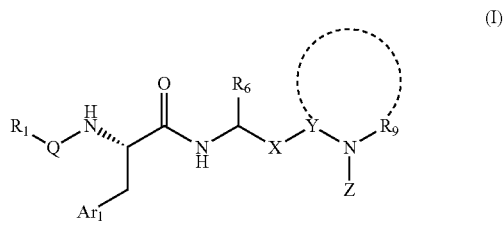

(I)

wherein;

Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substituents;

T is halogen:

X—Y is selected from the group consisting of:

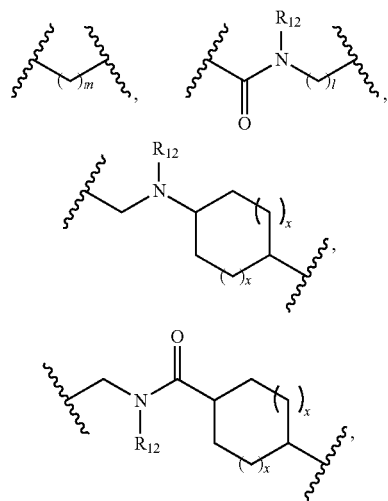

-continued

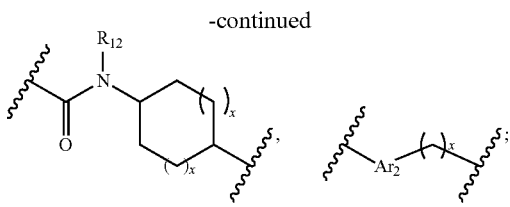

such that Ar$_2$ is monocyclic arylene or heteroarylene;
Z is

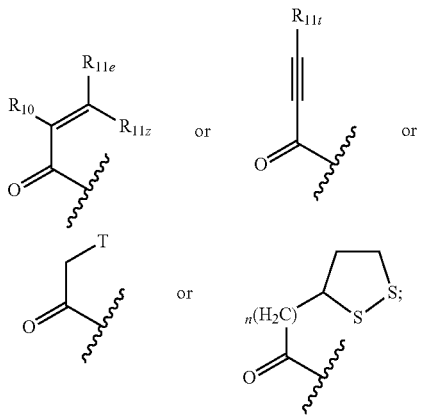

R$_1$ is selected from the group consisting of H, C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, C$_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-7}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;

R$_5$ is selected from the group consisting of hydrogen, CF$_3$, CHF$_2$, C$_{1-6}$ alkyl, allyl, propargyl, C$_{3-6}$ cycloalkyl, C$_{1-6}$ alkyl-C$_{4-6}$ cycloalkenyl, C$_{4-7}$ heterocycloalkyl, aryl, heteroaryl, C$_{1-6}$ alkyl-C$_{3-6}$ cycloalkyl, C$_{1-6}$ alkyl-C$_{4-7}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-7}$ heterocycloalkyl, aryl, and heteroaryl;

R$_6$ is selected from the group consisting of C$_{1-6}$ alkyl, C$_{3-6}$ cycloalkyl, C$_{2-6}$ alkenyl, C$_{4-6}$ cycloalkyl, C$_{4-7}$ heterocycloalkyl, C$_{2-6}$ alkynyl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-7}$ heterocycloalkyl, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;

R$_9$ is selected from the group consisting of H, C$_{1-6}$ alkyl, substituted C$_{1-6}$ alkyl, C$_{3-6}$ alkenyl, substituted C$_{3-6}$ alkenyl, C$_{3-6}$ alkynyl, substituted C$_{3-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl or C$_{4-7}$ heterocycloalkyl;

R$_{10}$ is H, (CH$_2$)$_n$NR$_3$R$_4$, CN or R$_{12}$;
R$_{11e}$ is H, R$_{12}$, or (CH$_2$)$_n$NR$_3$R$_4$;
R$_{11z}$ is H, F, Cl, CF$_3$, CHF$_2$;
Or R$_{10}$ and R$_{11e}$ may be taken together with the sp$^2$ C atoms to which they are attached to form a partially saturated carbocyclic or heterocyclic ring of 5-7 atoms, with up to two of the ring atoms being O, S(O)$_x$, NR$_{12}$, and said ring may be substituted with hydroxy, oxo, C$_{1-6}$ alkoxy, R$_{11t}$ is C$_{1-6}$ alkyl, C$_{3-6}$ cycloalkyl, C$_{4-7}$ heterocycloalkyl, CH$_2$NR$_3$R$_4$;

R$_{12}$ is H or C$_{1-6}$ alkyl, either straight chain or branched;
l is 2-4;
m is 2-6;
n is 1, 2 or 3;
x is independently 0, 1, or 2;
or a pharmaceutically acceptable salt, hydrate, or solvate thereof.

In another embodiment of the invention the compound is a compound of formula (1)

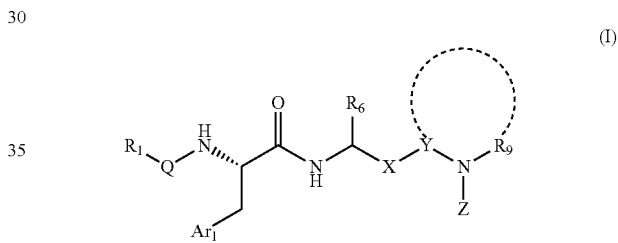

(I)

wherein;
Q is C=O;
Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substituents;

X, Y and R$_9$ are taken together with the nitrogen atom to which they are attached to form a ring which selected from the group consisting of:
Z is

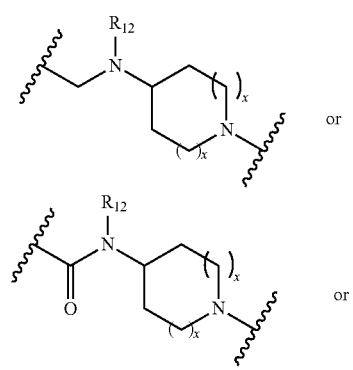

$R_1$

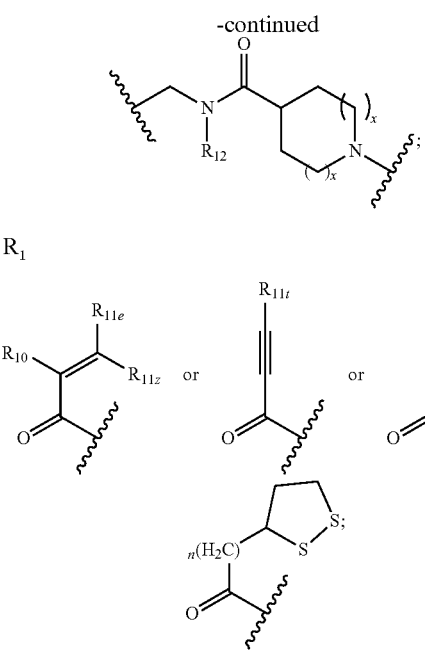

is selected from the group consisting of H, $C_{1-6}$ alkyl, $C_{3-6}$ cycloalkyl, $C_{3-6}$ cycloalkylmethylene, NHMe, N(Me)$_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_{10}$ is H, $(CH_2)_n NR_3R_4$, CN or $R_{12}$;
$R_{11e}$ is H, $R_{12}$, or $(CH_2)_n NR_3R_4$;
$R_{11z}$ is H, F, Cl, $CF_3$, $CHF_2$;

Or $R_{10}$ and $R_{11e}$ may be taken together with the sp$^2$ C atoms to which they are attached to form a partially saturated carbocyclic or heterocyclic ring of 5-7 atoms, with up to two of the ring atoms being O, S(O)$_x$, NR$_{12}$, and said ring may be substituted with hydroxy, oxo, $C_{1-6}$ alkoxy, $R_{11t}$ is $C_{1-6}$ alkyl, $C_{3-6}$ cycloalkyl, $C_{4-7}$ heterocycloalkyl, $CH_2NR_3R_4$;

$R_{12}$ is H or $C_{1-6}$ alkyl, either straight chain or branched;
T is halogen:
m is 2-6;
n is 1, 2 or 3;
x is independently 0, 1, or 2;
or a pharmaceutically acceptable salt, hydrate, or solvate thereof.

In certain preferred embodiment of the invention the compound is a compound of formula (1)

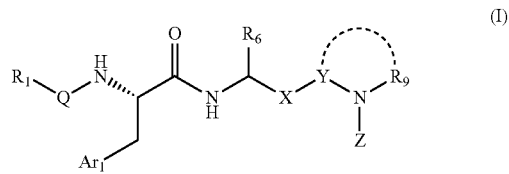

(I)

wherein;
Q is C=O;
Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R2 substitutents;

X—Y is selected from the group consisting of:

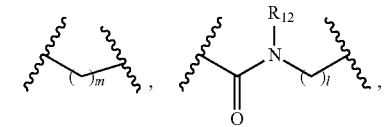

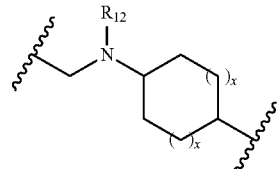

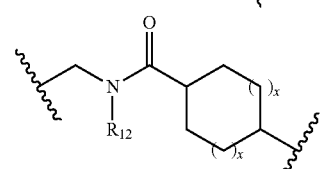

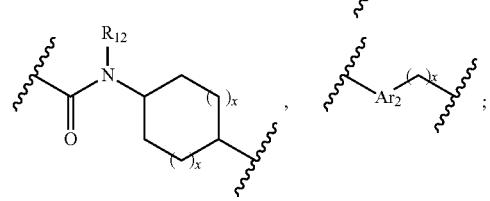

such that Ar$_2$ is monocyclic arylene or heteroarylene;
Z is

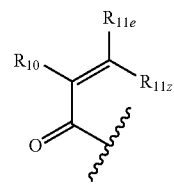

$R_1$ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl. $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_9$ is H;
$R_{10}$ is H, CN or $CH_2NR_3R_4$;
$R_{11e}$ and $R_{11z}$ are H or one may be $R_{12}$;
$R_{12}$ is H or $C_{1-6}$ alkyl, either straight chain or branched;
l is 2-4;
m is 2-6;
n is 1, 2 or 3;
x is independently 0, 1, or 2;
or a pharmaceutically acceptable salt, hydrate, or solvate thereof.

In certain preferred embodiments of the invention the compound is a compound of formula (1)

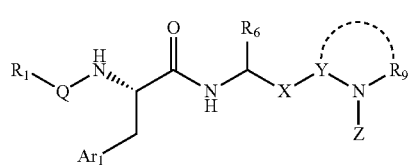

wherein;
Q is C=O;
$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

X, Y and $R_9$ are taken together with the nitrogen atom to which they are attached to form a ring which selected from the group consisting of:

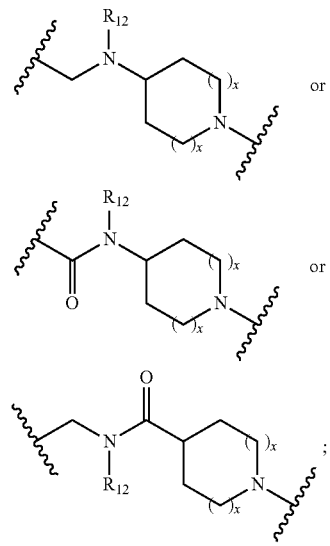

Z is

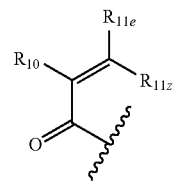

$R_1$ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl. $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_{10}$ is H, CN or CH2NR3R4;

$R_{11e}$ and $R_{11z}$ are H or one may be $R_{12}$;

$R_{12}$ is H or $C_{1-6}$ alkyl, either straight chain or branched;

m is 2-6;

n is 1, 2 or 3;

x is independently 0, 1, or 2;

or a pharmaceutically acceptable salt, hydrate, or solvate thereof.

In certain more preferred embodiments the compound is of Formula (II)

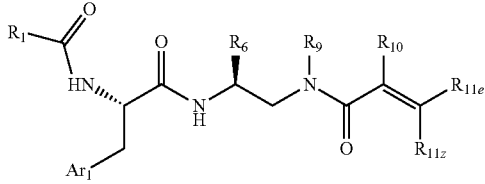

(II)

wherein:

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

$R_1$ is selected from the group consisting of H, $C_{1-6}$ alkyl, $C_{3-6}$ cycloalkyl, $C_{3-6}$ cycloalkylmethylene, NHMe, N(Me)$_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl. $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_9$ is selected from the group consisting of H, $C_{1-6}$ alkyl, substituted $C_{1-6}$ alkyl, $C_{3-6}$ alkenyl, substituted $C_{3-6}$ alkenyl, $C_{3-6}$ alkynyl, substituted $C_{3-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl or $C_{4-7}$ heterocycloalkyl:

$R_{10}$ is H, F, Cl, $CF_3$, $CHF_2$, $(CH_2)_nNR_3R_4$, $CH_2SO_2R_{12}$, $CH_2OCOR_{12}$, CN or $R_{12}$;

$R_{11e}$ is H, $R_{12}$, $(CH_2)_nR_2$, $CF_2(CH_2)_xR_2$, $COR_5$, $CO_2R_5$ or $CONR_3R_4$;

$R_{11z}$ is H, F, Cl, $CF_3$, $CHF_2$, $CF_2R_{12}$ or $R_{12}$;

Or $R_{11e}$ and $R_{11z}$ may be taken together with the sp$^2$ carbon atom to which both are bonded to form an alicyclic ring of 4 to 7 members where one of the ring atoms may be $NR_{12}$, O, or $S(O)_x$, optionally substituted with halogen, oxo, OH, $OR_5$, $NR_3R_4$;

Or $R_{11e}$ and $R_{11z}$ taken together may be $R_{11e}R_{11z}C=$, forming an allenyl group;

Or $R_{10}$ and $R_{11e}$ may be taken together with the sp$^2$ C atoms to which they are attached to form a partially saturated carbocyclic or heterocyclic ring of 5-7 atoms, with up to two of the ring atoms being O, $S(O)_x$, $NR_{12}$, and said ring may be substituted with hydroxy, oxo, $C_{1-6}$ alkoxy, $R_{11t}$ is $C_{1-6}$ alkyl, $C_{3-6}$ cycloalkyl, aryl, heteroaryl, $C_{4-7}$ heterocycloalkyl, $CH_2NR_3R_4$;

$R_{12}$ is H or $C_{1-6}$ alkyl, either straight chain or branched;

n is 1, 2 or 3;

x is 0, 1, or 2;

or a pharmaceutically acceptable salt, hydrate, or solvate thereof.

In some highly preferred embodiments the compound is of Formula (III)

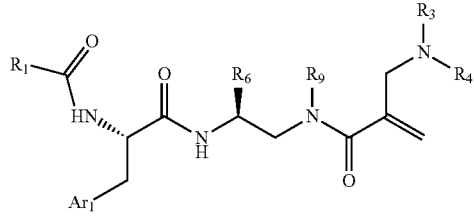

(III)

wherein:

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

$R_1$ is selected from the group consisting of H, $C_{1-6}$ alkyl, $C_{3-6}$ cycloalkyl, $C_{3-6}$ cycloalkylmethylene, NHMe, N(Me)$_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, C$_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-7}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;

R$_5$ is selected from the group consisting of hydrogen, CF$_3$, CHF$_2$, C$_{1-6}$ alkyl, allyl, propargyl, C$_{3-6}$ cycloalkyl, C$_{1-6}$ alkyl-C$_{4-6}$ cycloalkenyl, C$_{4-7}$ heterocycloalkyl, aryl, heteroaryl, C$_{1-6}$ alkyl-C$_{3-6}$ cycloalkyl, C$_{1-6}$ alkyl-C$_{4-7}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-7}$ heterocycloalkyl, aryl, and heteroaryl;

R$_6$ is selected from the group consisting of C$_{1-6}$ alkyl, C$_{3-6}$ cycloalkyl, C$_{2-6}$ alkenyl, C$_{4-6}$ cycloalkenyl, C$_{4-7}$ heterocycloalkyl, C$_{2-6}$ alkynyl, C$_{1-6}$ alkyl-C$_{3-6}$ cycloalkyl. C$_{1-6}$ alkyl-C$_{4-6}$ cycloalkenyl, C$_{1-6}$ alkyl-C$_{4-7}$ heterocycloalkyl, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;

R$_9$ is selected from the group consisting of H, C$_{1-6}$ alkyl, substituted C$_{1-6}$ alkyl, C$_{3-6}$ alkenyl, substituted C$_{3-6}$ alkenyl, C$_{3-6}$ alkynyl, substituted C$_{3-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl or C$_{4-7}$ heterocycloalkyl:

n is 1, 2 or 3;

x is 0, 1, or 2;

or a pharmaceutically acceptable salt, hydrate, or solvate thereof.

In some more highly preferred embodiments the compound is of Formula (III)

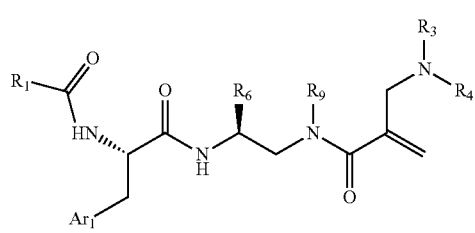

(III)

wherein:

Ar$_1$ is benzothiazol-2-yl, benzoxazol-2-yl, naphth-2-yl, 4-methyl-5-phenylthiazole, 4-methyl-5-phenyloxazole and imidazo[1,2-a]pyrid-2-yl, whereby each 6-membered aromatic ring in may be substituted with up to two R$_2$ substituents selected from C$_{1-6}$ lower alkyl, CF$_3$, and halogen;

R$_1$ is methyl, ethyl, methylamino, cyclopropyl, isopropyl or n-propyl;

R$_3$ and R$_4$, independently, are selected from the group consisting of C$_{1-6}$ alkyl, allyl, C$_{3-6}$ cycloalkyl, C$_{4-7}$ heterocyclyl, or are taken together with the nitrogen atom to which they are attached to form a ring of four to seven members, optionally including any chemically stable combination of one to three O, C=O, NR$_5$ and S;

R$_5$ is C$_{1-4}$ alkyl, C$_{1-4}$ acyl, C$_{2-4}$ hydroxyalkyl, C$_{1-2}$ alkoxy-C$_{2-4}$ alkyl, oxetan-3-yl, oxolan-3-yl, oxan-4-yl, N-methylazetidin-3-yl, N-methylpyrrolidin-3-yl or N-methylpiperidin-4-yl;

R$_6$ is benzyl, isopropyl, [R]- or [S]-2-butyl, 3-pentyl, cyclopentyl, cyclohexyl, cyclohexylmethyl, cyclpentylmethyl, 4-tetrahydrofuranyl or isopropyl;

R$_9$ is H, C$_{1-4}$ alkyl, C$_{2-4}$ hydroxyalkyl, C$_{1-2}$ alkoxy-C$_{2-4}$ alkyl, oxetan-3-yl, oxolan-3-yl, oxan-4-yl, N-methylazetidin-3-yl, N-methylpyrrolidin-3-yl or N-methylpiperidin-4-yl;

In some preferred embodiments, Ar$_1$ can be, but is not limited to,

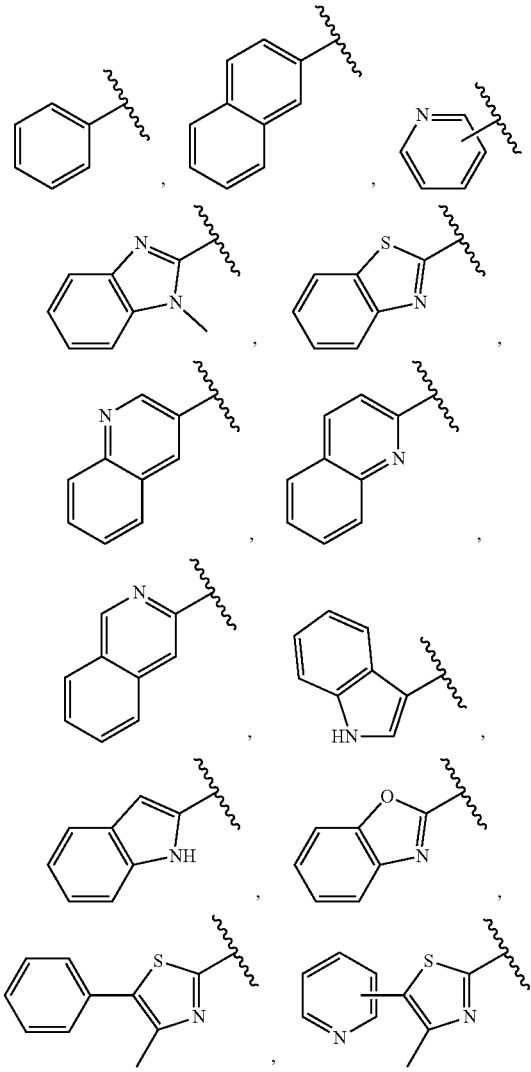

-continued

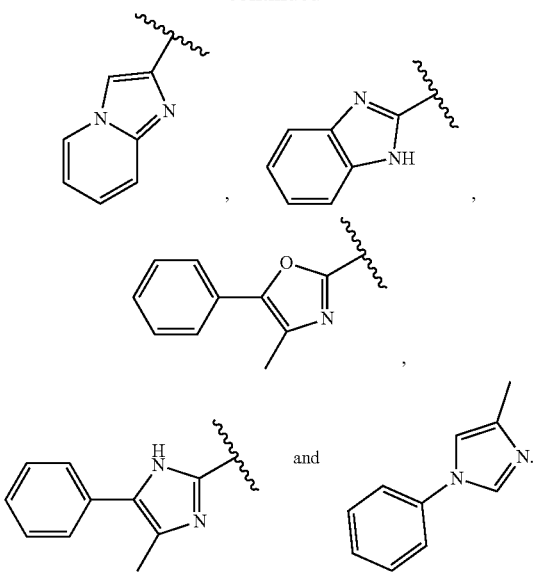

The above examples illustrate embodiments having a single $R_2$ substituent, it is understood that Ar1 groups can be free of an $R_2$ substituent or contain one to four $R_2$ substituents.

In some embodiments, $R_1$ can be, but is not limited to,

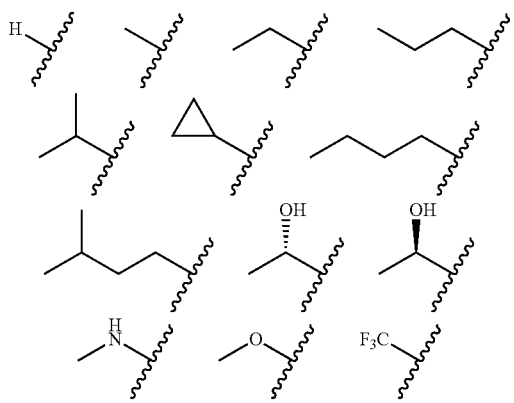

In some embodiments, $R_6$ can be, but is not limited to

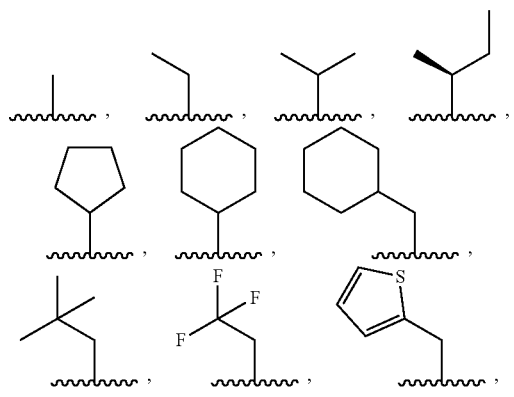

-continued

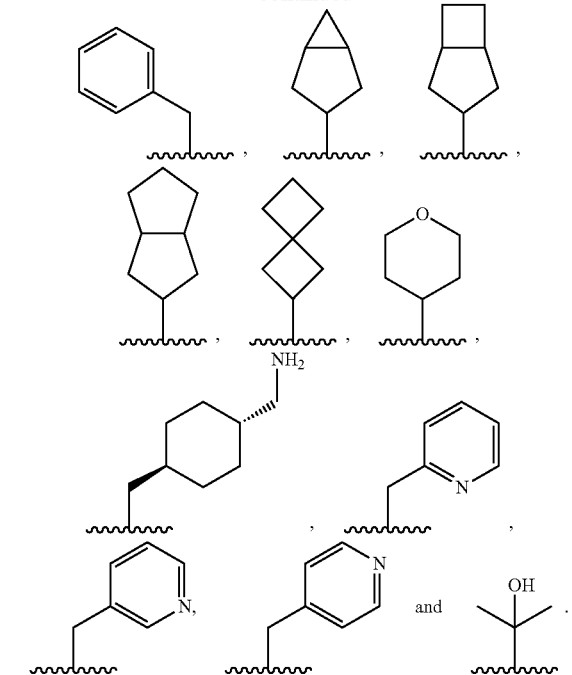

In some embodiments $R_9$ can be H

In some embodiments X can be a bond or $CH_2$ or CO or $CONR_{12}$.

In some embodiments Y can be methylidyl, arylene, heteroarylene, arylmethylene, heteroarylmethylene, In some embodiments $R_9$ can be H

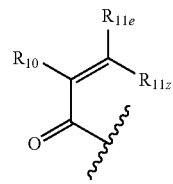

In some embodiments Z can be

In certain preferred embodiments in a compound of Formula (1):

$Ar_1$ is selected from 2-benzothienyl, 2-naphthyl, 2-benzoxazolyl, 2-imidazo[1,2-a]pyridinyl or 4-methyl-5-(3-halophenyl)thiazol-2-yl, wherein there are one or $R_2$ substituents on the B-ring of the bicycle, selected from the group chloro, bromo. methyl, $CF_3$, methyl ethyl isopropyl and cyclopropyl.

$R_1$ is selected from H, methyl, ethyl, propyl, isopropyl, cyclopropyl, methylamino and methoxy.

$R_6$ is selected from [S]-butyl, cyclopentyl, cyclohexyl, 4-tetrahydropyranyl, benzyl, cyclohexylmethyl, 2-, 3-, and 4-pyridylmethylene, and trans-4-aminomethylcyclohexylmethylenyl.

X is a bond, $CH_2$, $CH_2NH$ or $CH_2O$.

Y is $CH_2$, arylene, hetroarylene

Or $R_9$ and Y taken together are, azetidin-3-yl, pyrrolidin-3-yl, pipidin-3-yl, pipidin-4-yl.

Z is

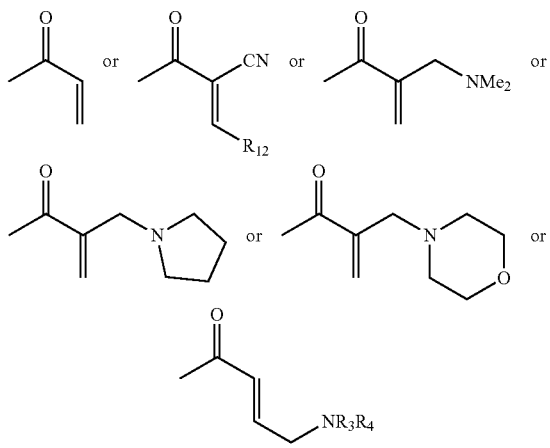

In more preferred embodiments wherein compounds are of Formula (I):

$Ar_1$ is benzothiazol-2-yl, imidazo[1,5-a]pyridine-2-yl, or 5-phenylthiazol-2-yl or 2-naphthyl.

$R_1$ is methyl, ethyl, isopropyl, cyclopropyl or methylamino.

Wherein there are one or $R_2$ substituents on the B-ring of the bicycle, selected from the group chloro, bromo. methyl, $CF_3$, methyl ethyl isopropyl and cyclopropyl.

$R_6$ is cyclopentyl, cyclohexyl, 4-tetrahydropyranyl, [S]-2-butyl, benzyl, 3-tetrahydrofuranyl, cyclohexylmethyl.

X is a bond;
Y is $CH_2$;
Z is

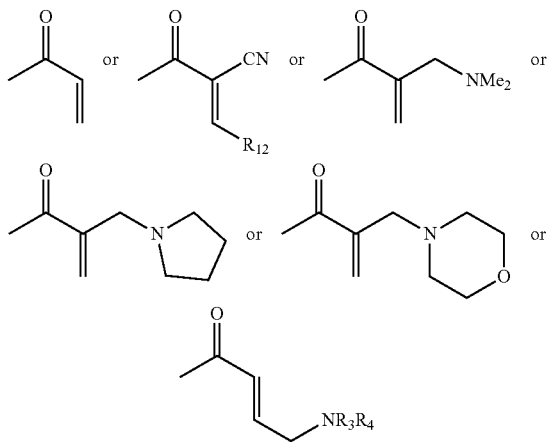

The compounds of formula (I) inhibit DCN1 and are useful in the treatment of a variety of diseases and conditions. In particular, the compounds of structural formula (I) are used in methods of treating a disease or condition wherein inhibition of DCN1 provides a benefit, for example, oxidative stress-related disease, including cancers, neurodegenerative diseases, cardiovascular diseases, acute lung injury, autoimmune diseases, chronic obstructive pulmonary disease, inflammation, and multiple sclerosis. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof, e.g., a chemotherapeutic agent and/or radiation known as useful in treating a particular cancer.

As used herein, the term "halo" is defined as encompassing fluoro, chloro, bromo, and iodo.

The term "hydroxy" is defined as —OH.

The term "alkoxy" is defined as —OR, wherein R is alkyl.

The term "amino" is defined as —$NH_2$, and the term "alkylamino" and "dialkylamino" are defined as —$NR_2$, wherein at least one R is alkyl and the second R is alkyl or hydrogen.

The term "nitro" is defined as —$NO_2$.

The term "cyano" is defined as —CN.

The term "trifluoromethyl" is defined as —$CF_3$.

The term "trifluoromethoxy" is defined as —$OCF_3$.

The term "azido" is defined as —$N_3$.

The term "carboxyl" is defined as —$CO_2R$, where R is H or alkyl.

The term "carbamoyl" is defined as —$CON(R)_2$, wherein R, independently, is H or alkyl.

The term "alkylthio" is defined as —SR, wherein R is alkyl.

The term "alkylsulfinyl" is defined as —S(O)R, wherein R is alkyl.

The term "alkylsulfonyl" is defined as —$S(O_2)R$, wherein R is alkyl.

The term "alkylsulfonamido" is defined as —$S(O_2)NHR$, wherein R is alkyl.

The term "alkylsulfamoyl" is defined as —$NHS(O_2)R$, wherein R is alkyl.

The term "allyl" is defined as $CH_2$=$CHCH_2$—.

The term "proparyl" is defined as CH=$CCH_2$—.

As used herein, groups such as

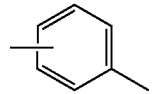

is an abbreviation for

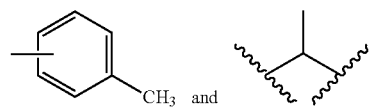

is an abbreviation for

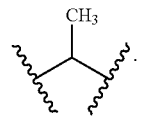 [SMILES: *C(*)C]

Lower alkyl is $C_{1-6}$alkyl, either straight chain or branched. Examples include methyl, ethyl, n-propyl i-propyl, n-butyl, [R]- or [S]-isobutyl, t-butyl, n-pentyl, [R]- or [S]-2-pentyl, 3 pentyl, [R]- or [S]-3-methylbut-2-yl, 1,1-dimethylpropyl, 2,2-dimethylpropyl, n-hexyl, [R]- or [S]-2-hexyl, [R]- or [S]-3-hexyl, [R]- or [S]-2-methylpent-1-yl,

[R]- or [S]-2-methylpent-3-yl, [R]- or [S]-4-methylpent-2-yl, 2-methylpent-2-yl, [RR]-, [RS]-, [SR]- or [SS]-3-methylpent-2-yl, [R]- or [S]-3-methylpent-1-yl, 4-methylpent-1-yl, 3-methylpent-2-yl, 3-methylpent-3-yl, 2,2-dimethylbut-1-yl, 3,3-dimethylbut-1-yl, [R]- or [S]-3,3-dimethylbut-2-yl, or [R]- or [S]-2,3-dimethylbut-1-yl, 2,3-dimethylbut-2-yl.

Lower alkenyl is $C_{2-6}$alkenyl, either straight chain or branched. Examples include ethenyl, prop-1-en-1-yl, prop-1-en-2-yl, prop-2-en-1-yl, E- and Z-but-1-en-1-yl, E- or Z-but-2-en-1-yl, but-3-en-1-yl, [R]- or [S]-but-3-en-2-yl, E- or Z-but-2-en-2-yl, 2-methylprop-1-en-1-yl, 2-methylprop-2-en-1-yl, E- or Z-pent-1-en-1-yl, E- or Z-pent-2-en-1-yl, E- or Z-pent-2-en-2-yl, E- or Z-pent-2-en-3-yl, E- or Z-pent-3-en-1-yl, [R]- or [S]-E- or [R]- or [S]—Z-pent-3-en-2-yl, pent-4-en-1-yl, [R]- or [S]-pent-1-en-3-yl, [R]- or [S]-pent-4-en-2-yl, E- or Z-2-methylbut-1-en-1-yl, [R]- or [S}-2-methylbut-3-en-1-yl, 2-methylbut-3-en-2-yl, 3-methylbut-1-en-2-yl, [R]- or [S}-3-methylbut-1-en-1-yl, [R]- or [S}-2-methylbut-2-en-1-yl, 3-methylbut-2-en-1-yl, 3-methylbut-2-en-2-yl, [R]- or [S}-3-methylbut-3-en-2-yl, 3-methylbut-3-en-1-yl, 2-ethylprop-2-en-1-yl, E- or Z-hex-1-en-1-yl, hex-1-en-2-yl, [R]- or [S]-hex-1-en-3-yl, [R]- or [S]-hex-5-en-3-yl, [R]- or [S]-hex-5-en-2-yl, hex-5-en-1-yl, E- or Z-hex-2-en-1-yl, E- or Z-hex-2-en-2-yl, E- or Z-hex-2-en-3-yl, [R]- or [S]-E- or [R]- or [S]—Z-hex-4-en-3-yl, [R]- or [S]-E- or [R]- or [S]—Z-hex-4-en-2-yl, E- or Z-hex-4-en-1-yl, E- or Z-hex-3-en-1-yl, [R]- or [S]-E- or [R]- or [S]—Z-hex-3-en-2-yl, E- or Z-hex-3-en-3-yl, E- or Z-2-methylpent-1-en-1-yl, 2-propylprop-2-en-1-yl, [R]- or [S}-2-methylpent-1-en-3-yl, [R]- or [S}-4-methylpent-4-en-2-yl, 4-methylpent-4-en-1-yl, E- or Z-2-methylpent-2-en-1-yl, 2-methylpent-2-en-3-yl, [R]- or [S]-4-methylpent-3-en-2-yl, 4-methylpent-3-en-1-yl, [R]- or [S]-E- or [R]- or [S]—Z-2-methylpent-2-en-1-yl, E- or Z-2-methylpent-3-en-2-yl, E- or Z-2-methylpent-3-en-3-yl, E- or Z-4-methylpent-2-en-2-yl, E- or Z-4-methylpent-2-en-1-yl, [R]- or [S]-2-methylpent-4-en-1-yl, [R]- or [S]-4-methylpent-1-en-3-yl, E- or Z-4-methylpent-1-en-1-yl, 2-methylpent-4-en-2-yl, 4-methylpent-1-en-2-yl, E- or Z-3,3-dimethylbut-1-en-1-yl, 3,3-dimethylbut-1-en-2-yl, 2,2-dimethylbut-3-en-1-yl, E- or Z-2,3-dimethylbut-1-en-1-yl, 2,3-dimethylbut-3-en-2-yl, [R]- or [S]-2,3-dimethylbut-3-en-1-yl, 2-(1methylethyl)prop-2-en-1-yl, or 2,3-dimethylbyt-2-en-1-yl.

Lower alkynyl is $C_{2-6}$alkynyl, either straight chain or branched. Examples include ethylnyl, prop-1-yn-1-yl, prop-2-yn-1-yl, but-1-yn-1-yl, but-2-yn-1-yl, but-3-yn-1-yl, [R]- or [S]-but-3-yn-2-yl, 3-methylbut-1-yn-1-yl, 2-methylbut-3-yn-3-yl, [R]- or [S]-2-methylbut-3-yn-1-yl, hex-1-yn-1-yl, [R]- or [S]-hex-1-yn-3-yl, [R]- or [S]-hex-5-yn-3-yl, [R]- or [S]-hex-5-yn-2-yl, hex-5-yn-1-yl, hex-2-yn-1-yl, [R]- or [S]-hex-4-yn-3-yl, [R]- or [S]-hex-4-yn-2-yl, hex-4-yn-1-yl, hex-3-yn-1-yl, [R]- or [S]-hex-3-yn-2-yl, 4-methylpent-1-yn-1-yl, [R]- or [S]-4-methylpent-1-yn-3-yl, 2-methylpent-4-yn-2-yl, [R]- or [S]-2-methylpent-4-yn-1-yl, [R]- or [S]-3-methylpent-1-yn-1-yl, [R]- or [S]-3-methylpent-1-yn-3-yl, [RR]-, [RS]-, [SR]- or [SS]-3-methylpent-4-yn-2-yl, [R]- or [S]-3-methylpent-4-yn-1-yl, [R]- or [S]-2-ethylbut-3-yn-1-yl, 3,3-dimethylbut-1-yn-1-yl, or 3,3-dimethylbut-3-yn-1-yl.

Lower cycloalkyl is $C_{3-8}$ cycloalkyl. Examples include cyclopropyl, cyclobutyl, cyclopentyl, cyclohexyl, cycloheptyl, and cyclooctyl.

Lower cycloalkenyl is $C_{4-8}$ cycloalkenyl. Examples include cyclobut-1-en-1-yl, [R]- or [S]-cyclobut-2-en-1-yl, cyclopent-1-en-1-yl, [R]- or [S]-cyclopent-2-en-1-yl, cyclopent-3-en-1-yl, cyclohex-1-en-1-yl, [R]- or [S]-cyclohex-2-en-1-yl, [R]- or [S]-cyclohex-3-en-1-yl, cyclohept-1-en-1-yl, [R]- or [S]-cyclohept-2-en-1-yl, [R]- or [S]-cyclohept-3-en-1-yl, cyclohept-4-en-1-yl, cyclooct-1-en-1-yl, [R]- or [S]-cyclooct-2-en-1-yl, [R]- or [S]-cyclooct-3-en-1-yl, and [R]- or [S]-cyclooct-4-en-1-yl, Heterocyclo defines rings of four to eight atoms which contain between one and three heteroatoms, chosen from O, $NR_5$ and $S(O)_x$, with the proviso that the species obey the valence laws, and be chemically stable. Rings may be linked at any position allowed by the valence laws, including N, N+ and SIV or SVI heteroatoms. Representative examples include azetidine, oxetane, thietane, oxolane, pyrrolidine, thiolane, piperidine, oxane, thiane, azepane, oxapane, azocane, oxacane, thiacane, pyrazolidine, imidazolidine, 1,3-dioxolane, 1,2-dithiolane, 1,3-dithiolane, 1,2-diazinane, 1,3-diazinane, piperazine, 1,3-dioxane, 1,4-dioxane, 1,2-dithiane, 1,3-dithiane, 1,4-dithiane, 1,2-diazepane, 1,3-diazepane, 1,4-diazepane, 1,3-dioxepane, 1,4-dioxepane, 1,2-dithiepane, 1,3-dithiepane, 1,4-dithiepane, 1,2-diazocane, 1,3-diazocane, 1,4-diazocane, 1,5-diazocane, 1,3-dioxocane, 1,4-dioxocane, 1,5-dioxocane, 1,2-dithiocane, 1,3-dithiocane, 1,4-dithiocane, 1,5-dithiocane, 1,2-oxazolidine, 1,3-oxazolidine, 1,3-thiazolidine, 1,3-oxathialane, 1,2-oxazane, 1,3-oxazane, morpholine, 1,3-thiazane, thiomorpholine, 1,3-oxathiane, 1,4-oxathiane, 1,2-oxazepane, 1,3-oxazepane, 1,4-oxazepane, 1,3-oxathiepane, 1,4-oxathiepane, 1,3-thiazepane, 1,4-thiazepane, 1,2-oxazocane, 1,3-oxazocane, 1,4-oxazocane, 1,5-oxazocane, 1,3-oxathiocane, 1,4-oxathiocane, 1,5-oxathiocane, 1,3-thiazocane, 1,4-thiazocane, 1,5-thiazocane, 1,2,5-triazepane, 1,4,5-oxadiazepane, 1,2,5-oxadiazepane, 1,4,5-dioxazepane, 1,4,5-thiadiazepane, 1,2,5-triazocane, 1,4,5-oxadiazocane, 1,2,5-oxadiazocane, 1,2,6-oxadiazocane, 1,4,8-dioxazocane, 1,5,8-dioxazocane, 1,3,6-dioxazocane, 1,3,6-oxathiazocane, 1,4,5-oxathiazocane, 1,5,6-oxathiazocane, 1,4,5-oxadiazocane, 1,3,6-dioxathiocane, 1,3,7-dioxathiocane, 1,3,6-oxadithiocane, 1,4,7-oxadithiocane, 1,3,6-oxadithiocane, 1,3,6-trithiocane, 1,2-thiazolane-1,1,dioxide, 1,2,5-thiadiazolane-1,1,dioxide, 1,2-thiazinane-1,1,dioxide, 1,2,6-thiadiazinane-1,1,dioxide, 1,4-dithiane-1,1-dioxide, 1,4-dithiane-1,1,4,4-tetroxide, 1,4-oxathiane-1,1-dioxide, 1,4-thiazinane-1,1-dioxide, 1,4-oxathiepane-1,1-dioxide, 1,2-thiazepane-1,1-dioxide, 1,4-thiazepane 1,1-dioxide, 1,4-dithiepane-1,1-dioxide, 1,4-dithiepane-1,1,4,4-tetroxide, 1,2,5-thiadiazepane-1,1-dioxide, 1,2,7-thiadiazepane-1,1-dioxide, 1,4,7-oxathiazepane-1,1-dioxide, 1,4,7-dithiazepane-1,1-dioxide, 1,4,7-dithiazepane-1,1,4,4-tetroxide, 1,4-dithiocane-1,1-dioxide, 1,5-dithiocane-1,1-dioxide, 1,4-dithiocane-1,1,4,4-tetroxide, 1,5-dithiocane-1,1,5,5-tetroxide, 1,4,8-oxathiazocane-1,1-dioxide, 1,5,8-oxathiazocane-1,1-dioxide, 1,4,5-oxathiazocane-1,1-dioxide, 1,5,6-oxathiazocane-1,1-dioxide, 1,4,8-thiadiazocane-1,1-dioxide, 1,5,8-thiadiazocane-1,1-dioxide, 1,4,5-thiadiazocane-1,1-dioxide, 1,2,8-thiadiazocane-1,1-dioxide, 1,3,6-oxadithiocane-1,1-dioxide, 1,3,6-oxadithiocane-1,1,3,3-tetroxide, 1,3,6-dithiazocane-1,1-dioxide, 1,3,6-dithiazocane-1,1,3,3-tetroxide, 1,3,8-dithiazocane-1,1-dioxide, 1,3,8-dithiazocane-1,1,3,3-tetroxide, 1,4,8-dithiazocane-1,1-dioxide, 1,4,8-dithiazocane-1,1,4,4-tetroxide, 1,5,2-dithiazocane-1,1-dioxide, 1,5,2-dithiazocane-1,1,5,5-tetroxide, 1,3,6-trithiocane-6,6-dioxide, 1,3,6-trithiocane-1,1-dioxide, 1,3,6-trithiocane-1,1,3,3-tetroxide, 1,3,6-trithiocane-1,1,6,6-tetroxide, and 1,3,6-trithiocane-1,1,3,3,6,6-hexoxide.

Bicycloalkyl is bicyclic structures of 5-12 carbon atoms, the two rings of which may be have fused, bridged, or spiro junctions. All chemically feasible diastereoisomers and enantiomers are included in the definition, as illustrated for bicyclo[2.1.0]pentyl below, where the point of attachment is marked by 1.

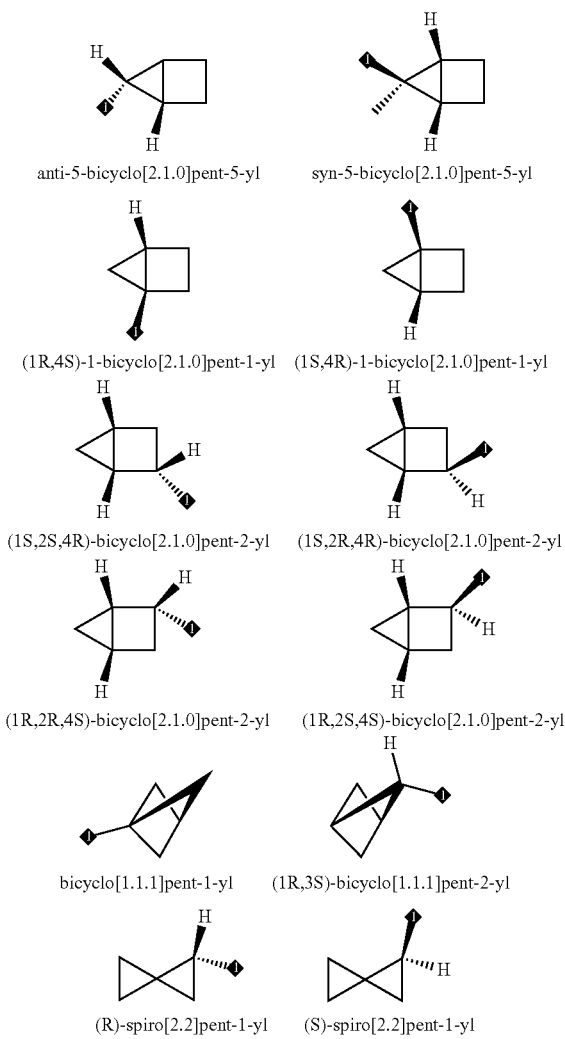

Heterobicyclo includes the structures defined for bicycloalkyl, where between one and four carbon atoms have been replaced with heteroatoms, chosen from O, $NR_5$ and $S(O)_x$, with the proviso that the species obey the valence laws, and be chemically stable, and with the further proviso that no heteroatoms are placed in three membered rings, or more than one heteroatom is placed in a four membered ring, unless explicitly stated. Rings may be linked at any position allowed by the valence laws, including N, N+ and SIV or SVI heteroatoms.

Aryl is phenyl, indenyl, indenyl, naphthyl, azulenyl, fluorenyl, anthracenyl, phenanthrenyl, all of which may be optionally substituted with up to four substituents independently chosen from, halogen, lower alkyl, lower alkenyl, lower alkynyl, OH, lower alkoxy, lower acyloxy, amino, lower acylamino, lower alkylamino, lower dialkylamino, lower S(O)xalkyl, trifluoromethyl, carbaldehyde, carboxy, lower carboxyalkyl, carboxamido, lower carboxamidoalkyl, and lower carboxamidodialkyl, Heteroaryl is pyrrole, pyrazole, imidazole, 1,2,3-triazole, 1,2,4-triazole, tetrazole, furan, oxazole, isoxazole, thiophene, thiazole, isothiazole, 1,2,4-oxadiazole, 1,2,5-oxadiazole, 1,2,3-thiadiazole, 1,2,4-thiadiazole, 1,2,5-thiadiazole, pyridine, pyridazine, pyrimidine, pyrazine, 1,2,3-triazine, 1,2,4-triazine, 1,3,5-triazine, or 1,2,4,5-tetrazine.

Polycycloheteroaryl is a fused bicyclic or tricyclic aromatic ring system of 8 to 12 atoms, at least one of which but not more than five (for bicycles), or seven (for tricycles) must O, N, NR, or S. Such polycyclic rings may include pyrrolo[2,3-b]pyrrole, pyrrolo[3,2-b]pyrrole, pyrrolo[2,3-c]pyrrole, pyrrolo[3,4-c]pyrrole, pyrrolo[2,3-b]furan, pyrrolo[3,2-b]furan, pyrrolo[3,4-b]furan, pyrrolo[2,3-c]furan, pyrrolo[3,4-c]furan, pyrrolo[2,3-b]thiophene, pyrrolo[3,4-b]thiophene, pyrrolo[3,2-b]thiophene, pyrrolo[2,3-c]thiophene, pyrrolo[3,4-c] thiophene, furano[2,3-b]furan, furano[3,2-b]furan, furano[2,3-c]furan, furano[3,4-c]furan, furano[2,3-b]thiophene, furano[3,4-b]thiophene, furano[3,2-b]thiophene, furano[2,3-c] thiophene, furano[3,4-c] thiophene, thieno[2,3-b]thiophene, thieno[3,2-b]thiophene, thieno[2,3-c]thiophene, thieno[3,4-c]thiophene, pyrrolo[2,3-c]pyrazole, pyrrolo[3,2-c]pyrazole, pyrrolo[3,4-c]pyrazole, furano[2,3-c]pyrazole, furano[3,2-c]pyrazole, furano[3,4-c]pyrazole, thieno[2,3-c]pyrazole, thieno[3,2-c]pyrazole, thieno[3,4-c]pyrazole, pyrrolo[2,3-d]imidazole, pyrrolo[3,4-d]imidazole, furano[2,3-d]imidazole, furano[3,4-d]imidazole, thieno[2,3-d]imidazole, thieno[3,4-d]imidazole, pyrrolo[2,3-d]-1,2,3-triazole, pyrrolo[3,4-d]-1,2,3-triazole, furano[2,3-d]-1,2,3-triazole, furano[3,4-d]-1,2,3-triazole, thieno[2,3-d]-1,2,3-triazole, thieno[3,4-d]-1,2,3-triazole, pyrrolo[3,2-d]isoxazole, pyrrolo[2,3-c]isoxazole, pyrrolo[3,4-d]isoxazole, pyrrolo[3,4-c]isoxazole, pyrrolo[2,3-d]isoxazole, pyrrolo[3,2-c]isoxazole, furano[3,2-d]isoxazole, furano[2,3-c]isoxazole, furano[3,4-d]isoxazole, furano[3,4-c]isoxazole, furano[2,3-d]isoxazole, furano[3,2-c]isoxazole, thieno[3,2-d]isoxazole, thieno[2,3-c]isoxazole, thieno[3,4-d]isoxazole, thieno[3,4-c]isoxazole, thieno[2,3-d]isoxazole, thieno[3,2-c]isoxazole, pyrrolo[3,2-d]oxazole, pyrrolo[2,3-d]oxazole, pyrrolo[3,4-d]oxazole, furano[3,2-d]oxazole, furano[2,3-d]oxazole, furano[3,4-d]oxazole, thieno[3,2-d]oxazole, thieno[2,3-d]oxazole, thieno[3,4-d]oxazole, pyrrolo[3,2-d]isothiazole, pyrrolo[2,3-c]isothiazole, pyrrolo[3,4-d]isothiazole, pyrrolo[3,4-c]isothiazole, pyrrolo[2,3-d]isothiazole, pyrrolo[3,2-c]isothiazole, furano[3,2-d]isothiazole, furano[2,3-c]isothiazole, furano[3,4-d]isothiazole, furano[3,4-c]isothiazole, furano[2,3-d]isothiazole, furano[3,2-c]isothiazole, thieno[3,2-d]isothiazole, thieno[2,3-c]isothiazole, thieno[3,4-d]isothiazole, thieno[3,4-c]isothiazole, thieno[2,3-d]isothiazole, thieno[3,2-c]isothiazole, pyrrolo[3,2-d]thiazole, pyrrolo[2,3-d]thiazole, pyrrolo[3,4-d]thiazole, furano[3,2-d]thiazole, furano[2,3-d]thiazole, furano[3,4-d]thiazole, thieno[3,2-d]thiazole, thieno[2,3-d]thiazole, thieno[3,4-d]thiazole, pyrrolo[3,2-d]-1,2,3-thiadiazole, pyrrolo[2,3-d]-1,2,3-thiadiazole, pyrrolo[3,4-d]-1,2,3-thiadiazole, furano[3,2-d]-1,2,3-thiadiazole, furano[2,3-d]-1,2,3-thiadiazole, furano[3,4-d]-1,2,3-thiadiazole, thieno[3,2-d]-1,2,3-thiadiazole, thieno[2,3-d]-1,2,3-thiadiazole, thieno[3,4-d]-1,2,3-thiadiazole, pyrrolo[2,3-c]-1,2,5-oxadiazole, pyrrolo[3,4-c]-1,2,5-oxadiazole, furano[2,3-c]-1,2,5-oxadiazole, furano[3,4-c]-1,2,5-oxadiazole, thieno[2,3-c]-1,2,5-oxadiazole, thieno[3,4-c]-1,2,5-oxadiazole, pyrrolo[2,3-c]-1,2,5-thiadiazole, pyrrolo[3,4-c]-1,2,5-thiadiazole, furano[2,3-c]-1,2,5-thiadiazole, furano[3,4-c]-1,2,5-thiadiazole, thieno[2,3-c]-1,2,5-thiadiazole, thieno[3,4-c]-1,2,5-thiadiazole, pyrazolo[3,4-c]pyrazole, pyrazolo[4,3-c]pyrazole, imidazo[4,5-c]pyrazole, pyrazolo[4,3-d]triazole, imidazo[4,5-d]triazole, pyrazolo[3,4-c]isoxazole, pyrazolo[4,3-d]isoxazole, pyrazolo[4,3-c]isoxazole, pyrazolo[3,4-d]isoxazole, pyrazolo[4,3-d]oxazole, pyrazolo[3,4-d]oxazole, imidazo[4, 5-c]isoxazole, imidazo[5,4-d]isoxazole, isoxazolo[3,4-d]triazole, oxazolo[4,5-d]triazole, pyrazolo[3,4-c]isothiazole, pyrazolo[4,3-d]isothiazole, pyrazolo[4,3-c]isothiazole, pyrazolo[3,4-d]isothiazole, pyrazolo[4,3-d]thiazole, pyrazolo[3,4-d]thiazole, imidazo[4,5-c]isothiazole, imidazo[5,4-d]isothiazole, isothiazolo[3,4-d]triazole, thiazolo[4,5-d]triazole, isoxazolo[3,4-c]isoxazole, isoxazolo[4,5-d]isoxazole, isoxazolo[5,4-c]isoxazole, isoxazolo[4,3-c]isoxazole, isoxazolo[4,5-c]isoxazole, isoxazolo[5,4-d]isoxazole, isoxazolo[3,4-d]oxazole, isoxazolo[4,3-d]oxazole, isoxazolo[4,5-d]oxazole, isoxazolo[5,4-d]oxazole, oxazolo[4,5-d]oxazole, oxazolo[5,4-d]oxazole, isoxazolo[3,4-c]isothiazole, isoxazolo[4,5-d]isothiazole, isoxazolo[5,4-c]isothiazole, isoxazolo[3,4-d]isothiazole, isoxazolo[4,3-c]isothiazole, isoxazolo[4,5-c]isothiazole, isoxazolo[3,4-d]isothiazole, isoxazolo[5,4-d]isothiazole, isoxazolo[3,4-d]thiazole, oxazolo[5,4-d]isothiazole, isoxazolo[4,3-d]thiazole, oxazolo[4,5-d]isothiazole, isoxazolo[4,5-d]thiazole, oxazolo[5,4-c]isothiazole, isoxazolo[5,4-d]thiazole, oxazolo[4,5-c]isothiazole, oxazolo[4,5-d]thiazole, oxazolo[5,4-d]thiazole, isothiazolo[3,4-c]isothiazole, isothiazolo[4,5-d]isothiazole, isothiazolo[5,4-c]isothiazole, isothiazolo[4,3-c]isothiazole, isothiazolo[4,5-c]isothiazole, isothiazolo[5,4-d]isothiazole, isothiazolo[3,4-d]thiazole, isothiazolo[4,3-d]thiazole, isothiazolo[4,5-d]thiazole, isothiazolo[5,4-d]thiazole, thiazolo[4,5-d]thiazole, thiazolo[5,4-d]thiazole, pyrazolo[5,4-d]-1,2,3-thiadiazole, pyrazolo[3,4-d]-1,2,3-thiadiazole, imidazo[4,5-d]-1,2,3-thiadiazole, isoxazolo[4,3-d]-1,2,3-thiadiazole, isothiazolo[4,3-d]-1,2,3-thiadiazole, isoxazolo[4,5-d]-1,2,3-thiadiazole, isothiazolo[4,5-d]-1,2,3-thiadiazole, isoxazolo[3,4-d]-1,2,3-thiadiazole, isothiazolo[3,4-d]-1,2,3-thiadiazole, isoxazolo[5,4-d]-1,2,3-thiadiazole, isothiazolo[5,4-d]-1,2,3-thiadiazole, oxazolo[4,5-d]-1,2,3-thiadiazole, thiazolo[4,5-d]-1,2,3-thiadiazole, oxazolo[5,4-d]-1,2,3-thiadiazole, thiazolo[5,4-d]-1,2,3-thiadiazole, pyrazolo[4,3-d]-1,2,5-thiadiazole, pyrazolo[4,3-d]-1,2,5-oxadiazole, isoxazolo[4,3-d]-1,2,5-thiadiazole, isothiazolo[4,3-d]-1,2,5-thiadiazole, isoxazolo[4,3-d]-1,2,5-oxadiazole, isothiazolo[4,3-d]-1,2,5-oxadiazole, isoxazolo[4,5-d]-1,2,5-thiadiazole, isothiazolo[4,5-d]-1,2,5-thiadiazole, isoxazolo[4,5-d]-1,2,5-oxadiazole, isothiazolo[4,5-d]-1,2,5-oxadiazole, imidazo[4,5-d]-1,2,5-thiadiazole, imidazo[4,5-d]-1,2,5-oxadiazole, oxazolo[4,5-d]-1,2,5-thiadiazole, thiazolo[4,5-d]-1,2,5-thiadiazole, oxazolo[4,5-d]-1,2,5-oxadiazole, thiazolo[4,5-d]-1,2,5-oxadiazole, pyrrolo[1,2-b] thiazole, imidazo[1,2-b]pyrazole, imidazo[1,2-a]imidazole, imidazo[2,1-b]thiazole, imidazo[2,1-c]-1,2,4-triazole, thiazolo[2,3-c]-1,2,4-triazole, imidazo[1,2-b]-1,2,4-triazole, thiazolo[3,2-b]-1,2,4-triazole, oxazolo[3,2-b]-1,2,4-triazole, thiazolo[3,2-b]-1,2,4-triazole, triazolo[1,5-b]1,3,4-oxadiazole, triazolo[1,5-b]1,3,4-thiadiazole, indole, isoindole, benzofuran, isobenzofuran, benzothiophene, isobenzothiophene, indolizine, indazole, benzimidazole, benzoxazole, benzoisooxazole, benzothiazole, benzoisothiazole, pyrazolo[1,5-a]pyridine, imidazo[1,5-a]pyridine, imidazo[1,2-a]pyridine, benzotriazole, benzo-1,2,5-oxadiazole benzo-1,2,3-thiadiazole, benzo-1,2,5-thiadiazole, pyrrolo[2,3-b]pyridine, pyrrolo[2,3-c]pyridine, pyrrolo[3,2-c]pyridine, pyrrolo[3,2-b]pyridine, furano[2,3-b]pyridine, furano [2,3-c]pyridine, furano[3,2-c]pyridine, furano [3,2-b]pyridine, thieno[2,3-b]pyridine, thieno [2,3-c]pyridine, thieno [3,2-c]pyridine, thieno [3,2-b]pyridine, pyrazolo[3,4-b]pyridine, pyrazolo [3,4-c]pyridine, pyrazolo [4,3-c]pyridine, pyrazolo [4,3-b]pyridine, isoxazolo[3,4-b]pyridine, isoxazolo[5,4-c]pyridine, isoxazolo[4,3-c]pyridine, isoxazolo[5,4-b]pyridine, isothiazolo[5,4-b]pyridine, isothiazolo[5,4-c]pyridine, isothiazolo[4,5-c]pyridine, isothiazolo[4,5-b]pyridine, imidazo[4,5-b]pyridine, imidazo[4,5-c]pyridine, oxazolo[5,4-b]pyridine, oxazolo[5,4-c]pyridine, oxazolo[4,5-c]pyridine, oxazolo[4,5-b]pyridine, thiazolo[5,4-b]pyridine, thiazolo[5,4-c]pyridine, thiazolo[4,5-c]pyridine, thiazolo[4,5-b]pyridine, 1,2,3-thiadiazolo[5,4-b]pyridine, 1,2,3-thiadiazolo[5,4-c]pyridine, 1,2,3-thiadiazolo[4,5-c]pyridine, 1,2,3-thiadiazolo[4,5-b]pyridine, 1,2,5-thiadiazolo[4,5-c]pyridine, 1,2,5-thiadiazolo[4,5-b]pyridine, 1,2,5-oxadiazolo[4,5-c]pyridine, 1,2,5-oxadiazolo[4,5-b]pyridine, pyrazolo[2,3-b]pyridazine, imidazo[3,4-b]pyridazine, imidazo[3,2-b]pyridazine, pyrazolo[2,3-c]pyrimidine, imidazo[3,4-c]pyrimidine, imidazo[1,2-c]pyrimidine, pyrazolo[5,1-c]pyrazine, imidazo[5,1-c]pyrazine, imidazo[1,2-c]pyrazine, pyrazolo[2,3-a]pyrimidine, imidazo[3,4-a]pyrimidine, imidazo[3,2-a]pyrimidine, pyrrolo[2,3-c]pyridazine, furano[2,3-c]pyridazine, thieno[2,3-c]pyridazine, pyrrolo[3,2-c]pyridazine, furano[3,2-c]pyridazine, thieno[3,2-c]pyridazine, pyrrolo[2,3-d]pyridazine, furano[2,3-d]pyridazine, thieno[2,3-d]pyridazine, pyrrolo[2,3-d]pyrimidine, furano[2,3-d]pyrimidine, thieno[2,3-d]pyrimidine, pyrrolo[3,2-d]pyrimidine, furano[3,2-d]pyrimidine, thieno[3,2-d]pyrimidine, pyrrolo[2,3-b]pyrazine, furano[2,3-b]pyrazine, thieno[2,3-b]pyrazine, 1,2,3-triazolo[1,5-b]pyridazine, 1,2,4-triazolo[4,3-b]pyridazine, 1,2,4-triazolo[1,5-b]pyridazine, 1,2,3-triazolo[1,5-c]pyrimidine, 1,2,4-triazolo[4,3-c]pyrimidine, 1,2,4-triazolo[1,5-c]pyrimidine, 1,2,3-triazolo[1,5-a]pyrazine, 1,2,4-triazolo[4,3-a]pyrazine, 1,2,4-triazolo[1,5-a]pyrazine, 1,2,3-triazolo[1,5-a]pyrimidine, 1,2,4-triazolo[4,3-a]pyrimidine, 1,2,4-triazolo[1,5-a]pyrimidine, pyrazolo[3,4-c]pyridazine, isothiazolo[5,4-c]pyridazine, isoxazolo[5,4-c]pyridazine, imidazo[4,5-c]pyridazine, thiazolo[5,4-c]pyridazine, oxazolo[5,4-c]pyridazine, pyrazolo[3,4-d]pyrimidine, isothiazolo[5,4-d]pyrimidine, isoxazolo[5,4-d]pyrimidine, imidazo[4,5-d]pyrimidine, thiazolo[5,4-d]pyrimidine, oxazolo[5,4-d]pyrimidine, pyrazolo[4,3-d]pyrimidine, isothiazolo[4,5-d]pyrimidine, isoxazolo[4,5-d]pyrimidine, thiazolo[4,5-d]pyrimidine, oxazolo[4,5-d]pyrimidine, pyrazolo[3,4-b]pyrazine, isothiazolo[4,5-b]pyrazine, isoxazolo[4,5-b]pyrazine, imidazo[4,5-b]pyrazine, thiazolo[4,5-b]pyrazine, oxazolo[4,5-b]pyrazine, 1,2,3-triazolo[1,5-b]-1,2,4-triazine, 1,2,3-triazolo[5,1-f]-1,2,4-triazine, 1,2,3-triazolo[1,5-d]-1,2,4-triazine, 1,2,3-triazolo[5,1-c]-1,2,4-triazine, 1,2,4-triazolo[5,1-f]-1,2,4-triazine, 1,2,4-triazolo[3,4-f]-1,2,4-triazine, 1,2,4-triazolo[4,3-d]-1,2,4-triazine, 1,2,4-triazolo[1,5-d]-1,2,4-triazine, 1,2,3-triazolo[1,5-a]-1,3,5-triazine, 1,2,4-triazolo[1,5-a]-1,3,5-triazine, 1,2,4-triazolo[4,3-a]-1,3,5-triazine, 1,2,4-triazolo[3,4-c]-1,2,4-triazine, 1,2,4-triazolo[5,1-c]-1,2,4-triazine, 1,2,3-triazolo[4,5-c]pyridazine, 1,2,3-triazolo[4,5-d]pyrimidine, 1,2,3-triazolo[4,5-b]pyrazine, 1,2,3-triazolo[4,5-d]pyridazine, 1,2,3-thiadiazolo[4,5-d]pyridazine, 1,2,3-thiadiazolo[4,5-d]pyrimidine, 1,2,3-thiadiazolo[5,4-d]pyrimidine, 1,2,5-thiadiazolo[3,4-d]pyrimidine, 1,2,5-oxadiazolo[3,4-d]pyrimidine, 1,2,5-oxadiazolo[3,4-d]pyridazine, 1,2,5-thiadiazolo[3,4-d]pyridazine, 1,2,5-oxadiazolo[3,4-d]pyrazine, 1,2,5-thiadiazolo[3,4-d]pyrazine, pyrazolo[3,4-d]-1,2,3-triazine, pyrazolo[4,3-e]-1,2,4-triazine, pyrazolo[3,4-e]-1,2,4-triazine, pyrazolo[4,3-d]-1,2,3-triazine, imidazo[4,5-d]-1,2,3-triazine, imidazo[4,5-e]-1,2,4-triazine, oxazolo[4,5-e]-1,2,4-triazine, oxazolo[5,4-e]-1,2,4-triazine, oxazolo[5,4-d]-1,2,3-triazine, thiazolo[5,4-d]-1,2,3-triazine, thiazolo[5,4-e]-1,2,4-triazine, thiazolo[4,5-e]-1,2,4-triazine, isothiazolo[4.5-d]-1,2,3-triazine, isoxazolo[4.5-d]-1,2,3-triazine, isoxazolo[5,4-d]-1,2,3-triazine, isoxazolo[4.5-e]-1,2,4-triazine, isoxazolo[4.3,d]-1,2,3-triazine, isothiazolo[4.3,d]-1,2,3-triazine, quinoline, isoquinoline, cinnoline, quinazoline, phthalazine, quinoxaline, 1,5- naphthyridine, 1,6-naphthyridine, 1,7-naphthyridine, 1,8-naphthyridine, 2,5-naphthyridine, 2,6-naphthyridine, 2,7-naphthyridine, pyrido[2,3-c]pyridazine, pyrido[3,4-c]pyridazine, pyrido[4,3-c]pyridazine, pyrido[3,2-c]pyridazine, pyrido[2,3-d]pyrimidine, pyrido[3,4-d]pyrimidine, pyrido[4,3-d]pyrimidine, pyrido[3,2-d]pyrimidine, pyrido[2,3-d]pyridazine, pyrido[3,4-d]pyridazine, pyrido[2,3-b]pyrazine, pyrido[3,4-b]pyrazine, pyridazo[3,4-c]pyridazine, pyridazo[4,5-c]pyridazine, pyridazo[4,5-c]pyridazine, pyrimido[5,4-c]pyridazine, pyrimido[4,5-c]pyridazine, pyrazino[2,3-c]pyridazine, pyrimido[4,5-d]pyridazine, pyrazino[2,3-d]pyridazine, pyrimido[4,5-d]-1,2,3-triazine, pyrimido[5,4-d]-1,2,3-triazine, pyrimido[4,5-e]-1,2,4-triazine, pyrimido[5,4-e]-1,2,4-triazine, and pyrazino[2,3-e]-1,2,4-triazine. Tricycles can be made by a 1,2-fusion of phenyl, or any of the earlier mentioned heteroaryl rings, to two adjacent, non-bridging atoms of any of the abovementioned bicycles, with the provisos that the valence rules be obeyed, the resultant tricycle be an aromatic entity, and that the fused tricycle contains no more than seven total heteroatoms.

All alkyl, alkenyl, alkynyl, cycloalkyl, cycloalkenyl, heterocyclyl, aryl, heteroaryl, and alkoxy groups can be optionally substituted with 1-3 groups independently selected from halo, hydroxy, alkoxy, oxo, lower acyloxy, amino, alkylamino, dialkylamino, alkylthio, alkylsulfonyl, heterocyclyl, aryl, heteroaryl, with the provisos that no carbon-linked substituent may iterate more than twice in total, and that the substituents produce chemically stable molecules.

All stereoisomers of compounds are claimed, except where a specific stereochemistry is delineated at a chiral center.

All analogues where hydrogen is replaced with deuterium are also claimed.

Additionally, salts of the compounds of structural formula (I) also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Various compounds of the present invention can exist as salts. Pharmaceutically acceptable salts of compounds of structural formula (I) often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid or base having a suitable counterion. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I), as well as pharmaceutically acceptable salts, thereof.

Specific compounds of the present invention, and representative binding affinity to DCN1 protein, include, but are not limited to, compounds having a structure set forth below in Table 1.

| Example | Structure | Binding affinity to DCN1 (IC$_{50}$, nM) |
|---|---|---|
| 1 | 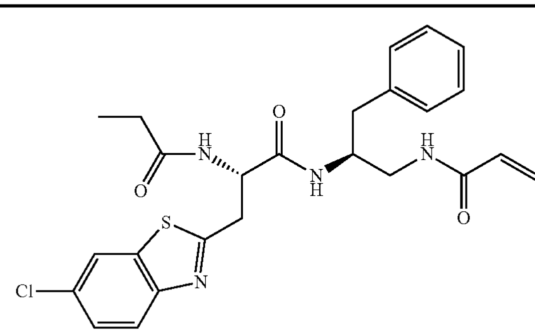 | 205 |

-continued
| Example | Structure | Binding affinity to DCN1 (IC$_{50}$, nM) |
|---|---|---|
| 2 | 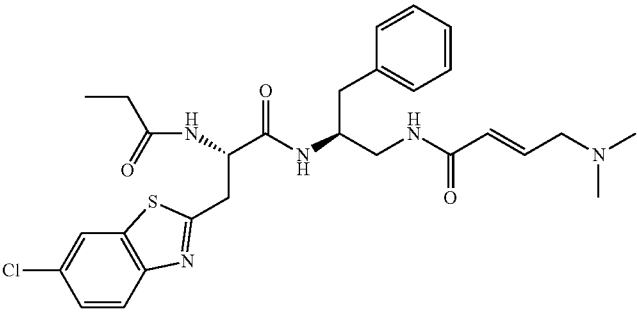 [SMILES: CCC(=O)N[C@@H](Cc1nc2ccc(Cl)cc2s1)C(=O)N[C@H](CNC(=O)/C=C/CN(C)C)Cc1ccccc1] | 153 |
| 3 | 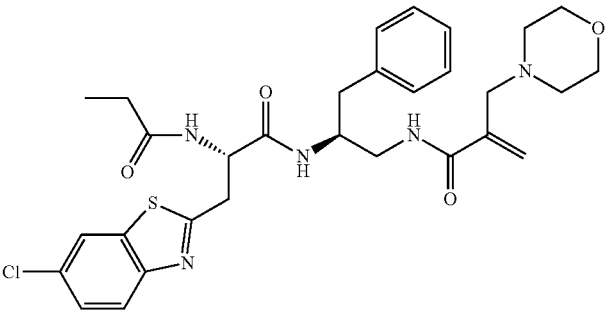 [SMILES: C=C(CN1CCOCC1)C(=O)NC[C@H](Cc1ccccc1)NC(=O)[C@H](Cc1nc2ccc(Cl)cc2s1)NC(=O)CC] | 156 |
| 4 | 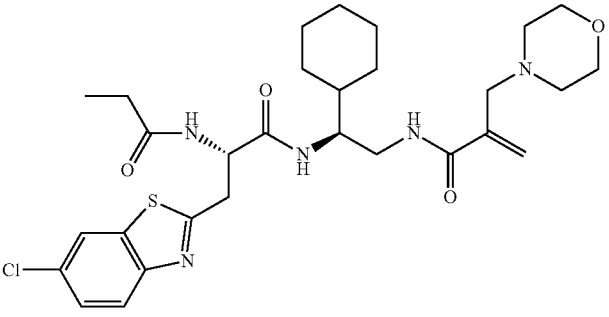 [SMILES: C=C(CN1CCOCC1)C(=O)NC[C@@H](NC(=O)[C@H](Cc1nc2ccc(Cl)cc2s1)NC(=O)CC)C1CCCCC1] | 41.6 |
| 5 | 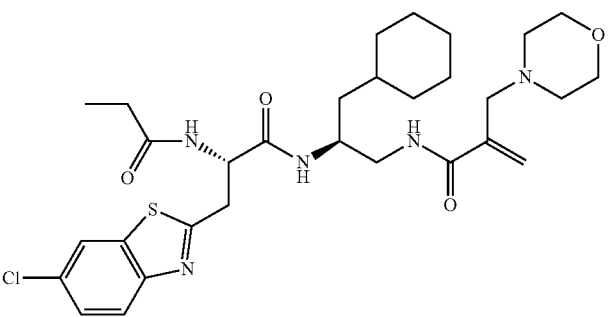 [SMILES: C=C(CN1CCOCC1)C(=O)NC[C@H](CC1CCCCC1)NC(=O)[C@H](Cc1nc2ccc(Cl)cc2s1)NC(=O)CC] | 80.7 |

-continued

| Example | Structure | Binding affinity to DCN1 (IC$_{50}$, nM) |
|---|---|---|
| 6 | 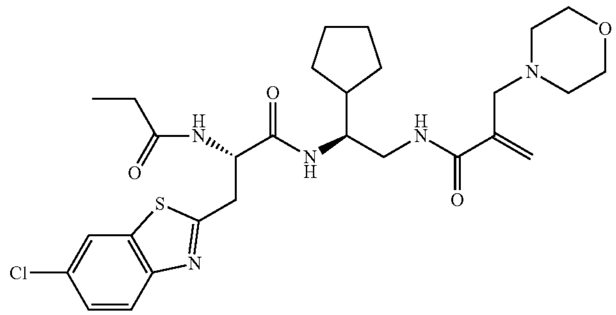 [SMILES: C=C(CN1CCOCC1)C(=O)NC[C@@H](NC(=O)[C@H](Cc1nc2ccc(Cl)cc2s1)NC(=O)CC)C1CCCC1] | 135 |
| 7 | 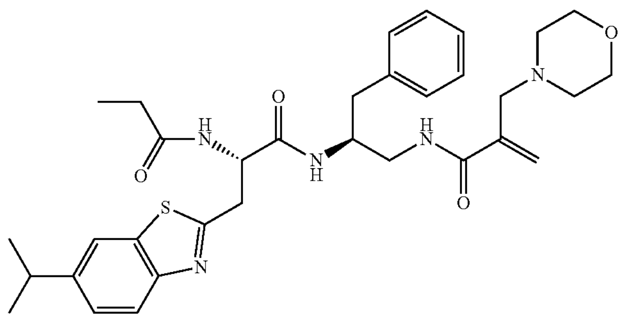 [SMILES: C=C(CN1CCOCC1)C(=O)NC[C@H](Cc1ccccc1)NC(=O)[C@H](Cc1nc2ccc(C(C)C)cc2s1)NC(=O)CC] | 37.4 |
| 8 | 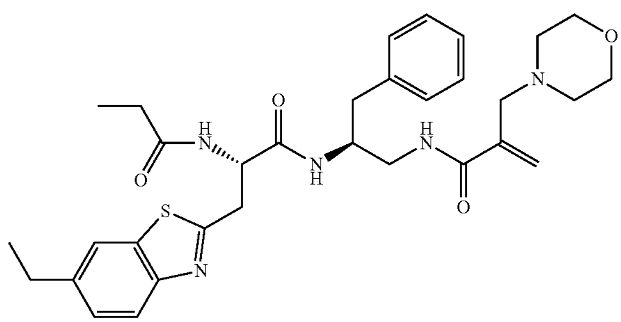 [SMILES: C=C(CN1CCOCC1)C(=O)NC[C@H](Cc1ccccc1)NC(=O)[C@H](Cc1nc2ccc(CC)cc2s1)NC(=O)CC] | 99.8 |
| 9 | 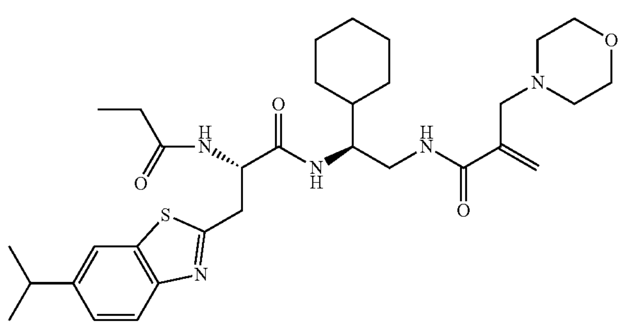 [SMILES: C=C(CN1CCOCC1)C(=O)NC[C@@H](NC(=O)[C@H](Cc1nc2ccc(C(C)C)cc2s1)NC(=O)CC)C1CCCCC1] | 66.5 |

-continued

| Example | Structure | Binding affinity to DCN1 (IC$_{50}$, nM) |
|---|---|---|
| 10 | 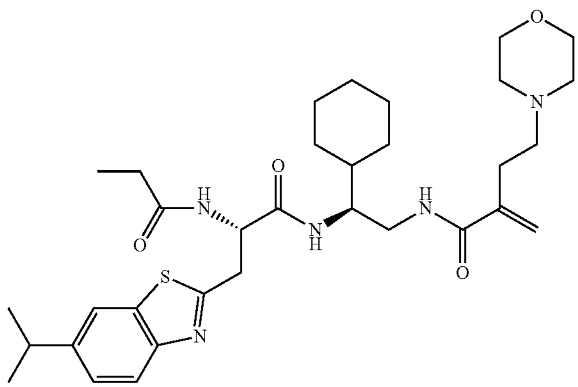 [SMILES: C=C(CCN1CCOCC1)C(=O)NC[C@@H](NC(=O)[C@H](Cc1nc2ccc(C(C)C)cc2s1)NC(=O)CC)C1CCCCC1] | ND |
| 11 | 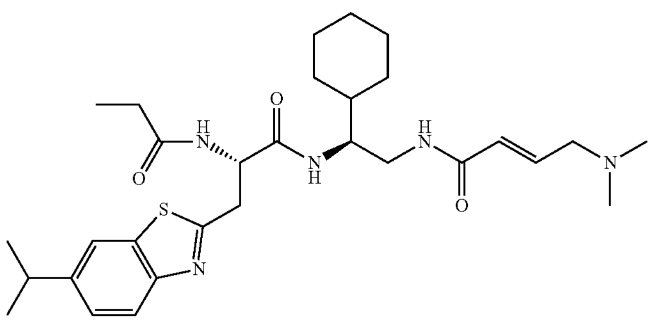 [SMILES: CCC(=O)N[C@@H](Cc1nc2ccc(C(C)C)cc2s1)C(=O)N[C@H](CNC(=O)/C=C/CN(C)C)C1CCCCC1] | ND |
| 12 | 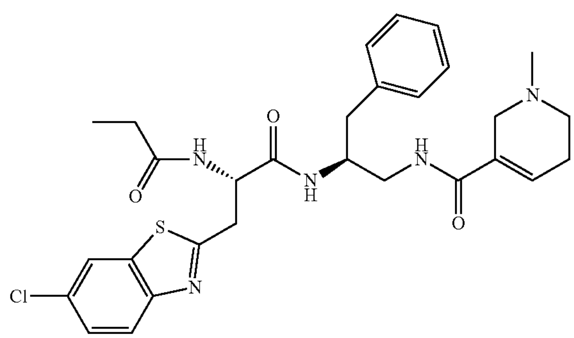 [SMILES: CCC(=O)N[C@@H](Cc1nc2ccc(Cl)cc2s1)C(=O)N[C@H](CNC(=O)C1=CCCN(C)C1)Cc1ccccc1] | 292 |
| 13 | 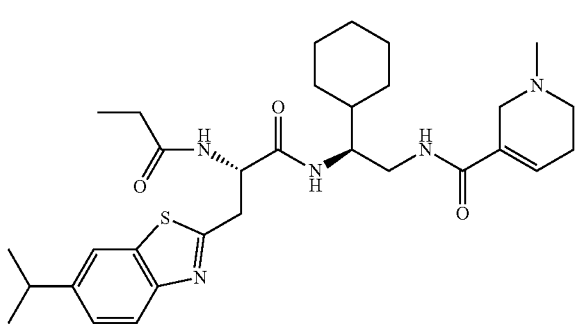 [SMILES: CCC(=O)N[C@@H](Cc1nc2ccc(C(C)C)cc2s1)C(=O)N[C@H](CNC(=O)C1=CCCN(C)C1)C1CCCCC1] | ND |

-continued

| Example | Structure | Binding affinity to DCN1 (IC$_{50}$, nM) |
|---|---|---|
| 14 | 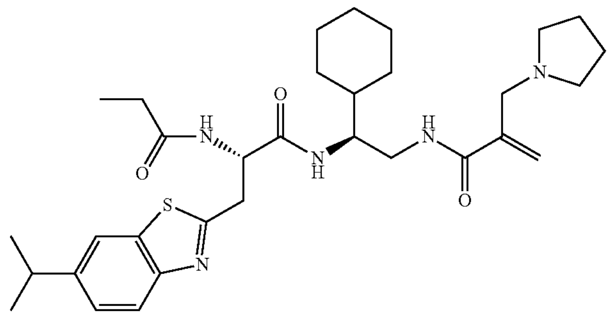 [SMILES: C=C(CN1CCCC1)C(=O)NC[C@@H](NC(=O)[C@H](Cc1nc2ccc(C(C)C)cc2s1)NC(=O)CC)C1CCCCC1] | ND |
| 15 | 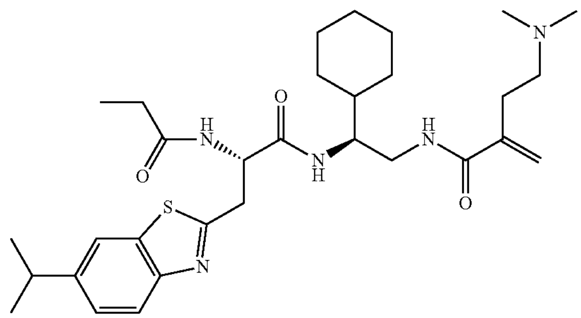 [SMILES: C=C(CCN(C)C)C(=O)NC[C@@H](NC(=O)[C@H](Cc1nc2ccc(C(C)C)cc2s1)NC(=O)CC)C1CCCCC1] | ND |
| 16 | 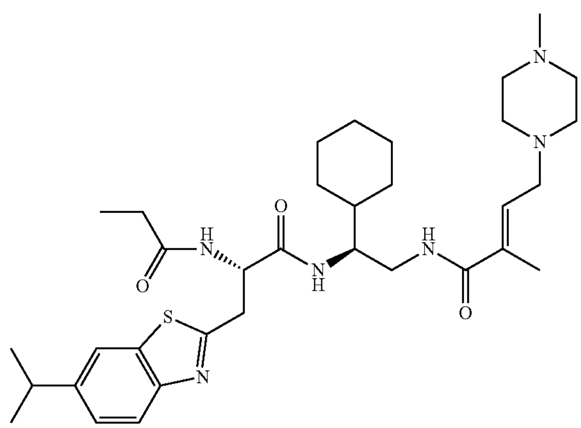 [SMILES: CCC(=O)N[C@@H](Cc1nc2ccc(C(C)C)cc2s1)C(=O)N[C@H](CNC(=O)/C(C)=C/CN1CCN(C)CC1)C1CCCCC1] | ND |
| 17 | 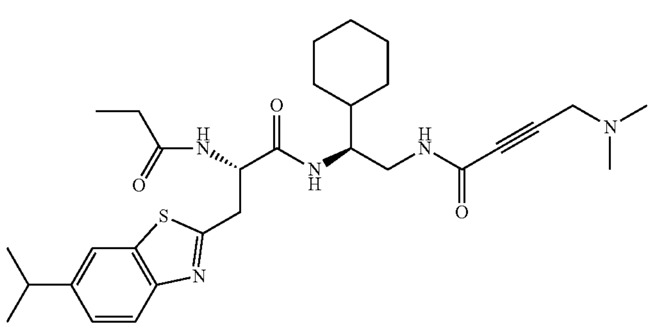 [SMILES: CCC(=O)N[C@@H](Cc1nc2ccc(C(C)C)cc2s1)C(=O)N[C@H](CNC(=O)C#CCN(C)C)C1CCCCC1] | ND |

-continued

| Example | Structure | Binding affinity to DCN1 (IC$_{50}$, nM) |
|---|---|---|
| 18 | 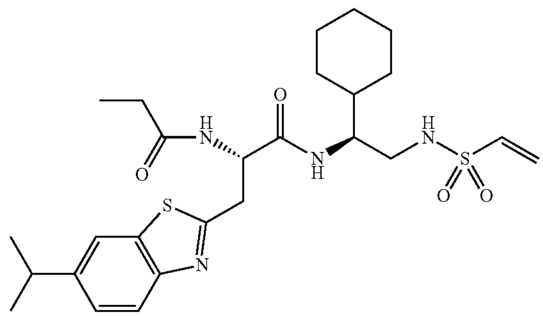 [SMILES: C=CS(=O)(=O)NC[C@@H](NC(=O)[C@H](Cc1nc2ccc(C(C)C)cc2s1)NC(=O)CC)C1CCCCC1] | ND |
| 19 | 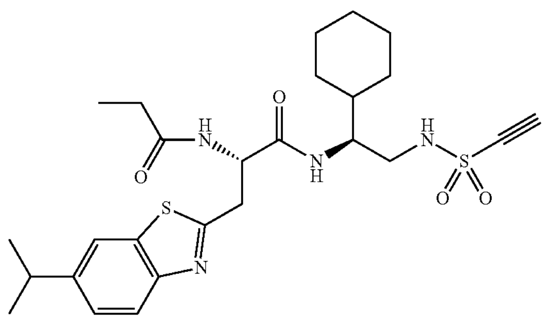 [SMILES: C#CS(=O)(=O)NC[C@@H](NC(=O)[C@H](Cc1nc2ccc(C(C)C)cc2s1)NC(=O)CC)C1CCCCC1] | ND |
| 20 | 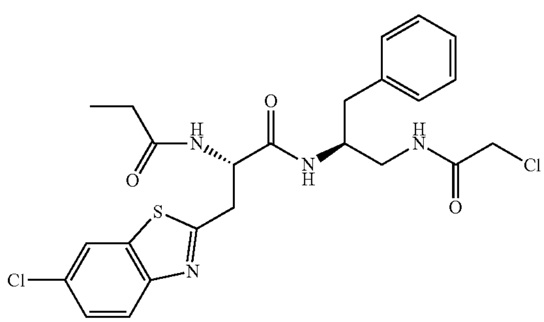 [SMILES: CCC(=O)N[C@@H](Cc1nc2ccc(Cl)cc2s1)C(=O)N[C@H](CNC(=O)CCl)Cc1ccccc1] | 360 |
| 21 | 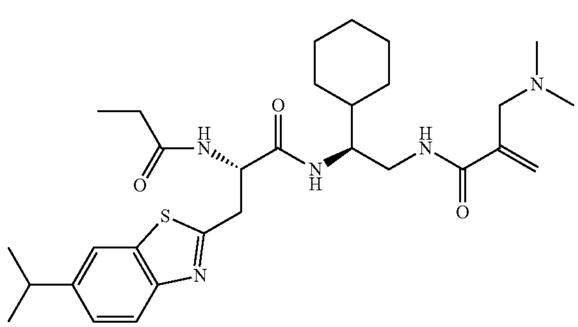 [SMILES: C=C(CN(C)C)C(=O)NC[C@@H](NC(=O)[C@H](Cc1nc2ccc(C(C)C)cc2s1)NC(=O)CC)C1CCCCC1] | <150 |

-continued

| Example | Structure | Binding affinity to DCN1 (IC$_{50}$, nM) |
|---|---|---|
| 22 | 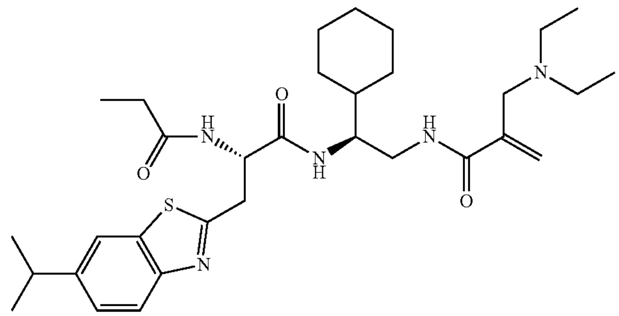 [SMILES: C=C(CN(CC)CC)C(=O)NC[C@@H](NC(=O)[C@H](Cc1nc2ccc(C(C)C)cc2s1)NC(=O)CC)C1CCCCC1] | <150 |
| 23 | 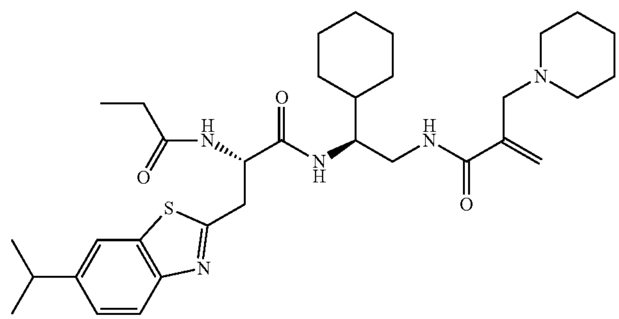 [SMILES: C=C(CN1CCCCC1)C(=O)NC[C@@H](NC(=O)[C@H](Cc1nc2ccc(C(C)C)cc2s1)NC(=O)CC)C1CCCCC1] | <150 |
| 24 | 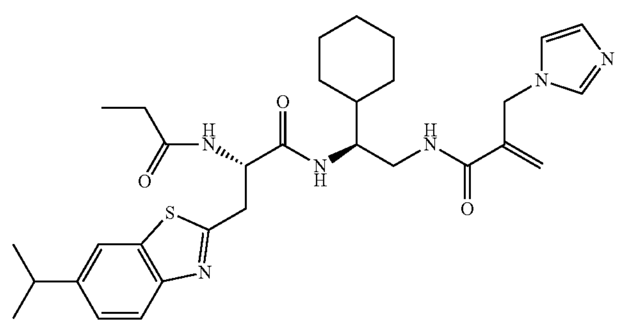 [SMILES: C=C(Cn1ccnc1)C(=O)NC[C@@H](NC(=O)[C@H](Cc1nc2ccc(C(C)C)cc2s1)NC(=O)CC)C1CCCCC1] | <150 |
| 25 | 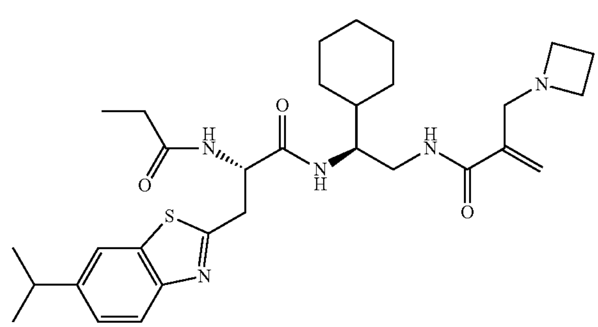 [SMILES: C=C(CN1CCC1)C(=O)NC[C@@H](NC(=O)[C@H](Cc1nc2ccc(C(C)C)cc2s1)NC(=O)CC)C1CCCCC1] | <150 |

-continued

| Example | Structure | Binding affinity to DCN1 (IC$_{50}$, nM) |
|---|---|---|
| 26 | 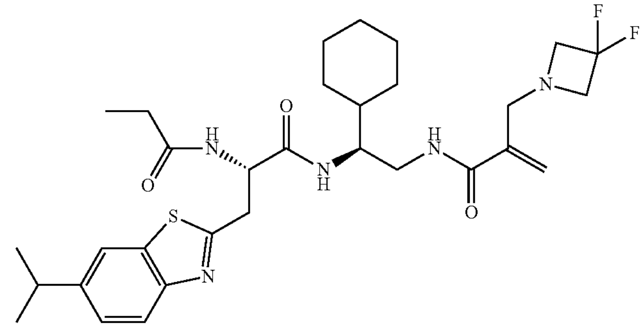 [SMILES: C=C(CN1CC(F)(F)C1)C(=O)NC[C@@H](NC(=O)[C@H](Cc1nc2ccc(C(C)C)cc2s1)NC(=O)CC)C1CCCCC1] | <150 |
| 27 | 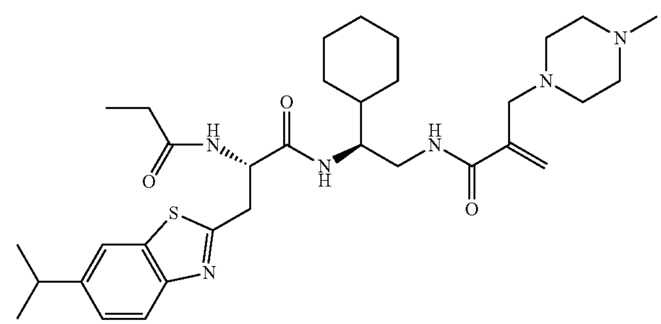 [SMILES: C=C(CN1CCN(C)CC1)C(=O)NC[C@@H](NC(=O)[C@H](Cc1nc2ccc(C(C)C)cc2s1)NC(=O)CC)C1CCCCC1] | <150 |
| 28 | 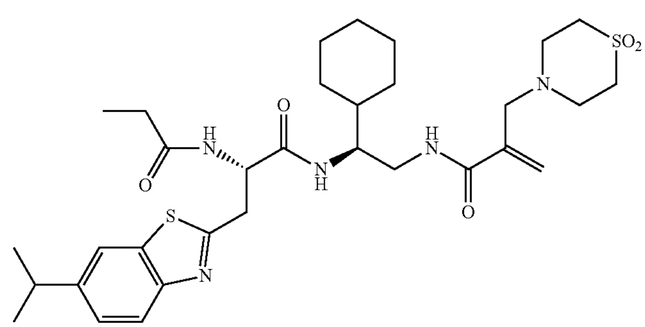 [SMILES: C=C(CN1CCS(=O)(=O)CC1)C(=O)NC[C@@H](NC(=O)[C@H](Cc1nc2ccc(C(C)C)cc2s1)NC(=O)CC)C1CCCCC1] | <150 |
| 29 | 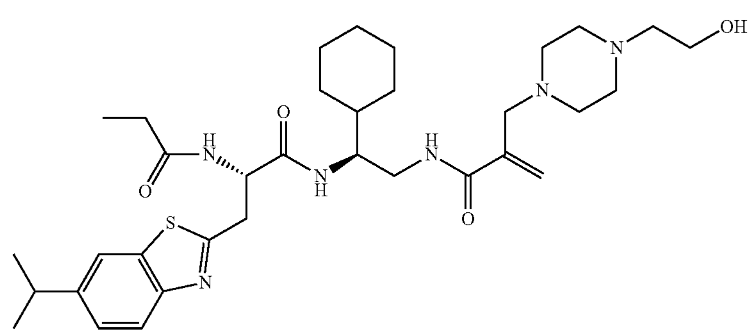 [SMILES: C=C(CN1CCN(CCO)CC1)C(=O)NC[C@@H](NC(=O)[C@H](Cc1nc2ccc(C(C)C)cc2s1)NC(=O)CC)C1CCCCC1] | <150 |

-continued

| Example | Structure | Binding affinity to DCN1 (IC$_{50}$, nM) |
| --- | --- | --- |
| 30 | 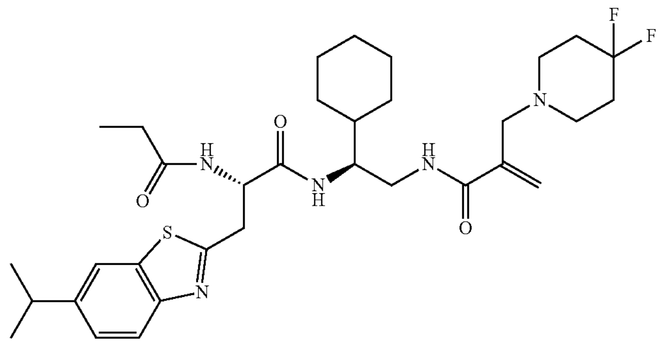 [SMILES: C=C(CN1CCC(F)(F)CC1)C(=O)NC[C@@H](NC(=O)[C@H](Cc1nc2ccc(C(C)C)cc2s1)NC(=O)CC)C1CCCCC1] | <150 |
| 31 | 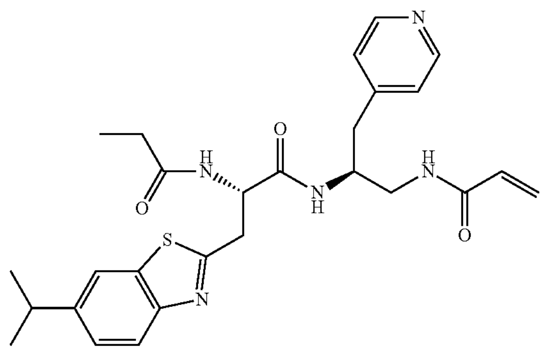 [SMILES: C=CC(=O)NC[C@H](Cc1ccncc1)NC(=O)[C@H](Cc1nc2ccc(C(C)C)cc2s1)NC(=O)CC] | <150 |
| 32 | 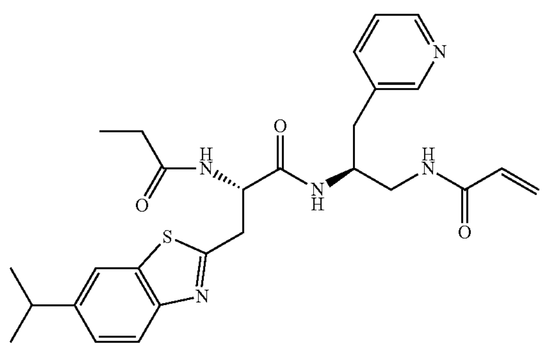 [SMILES: C=CC(=O)NC[C@H](Cc1cccnc1)NC(=O)[C@H](Cc1nc2ccc(C(C)C)cc2s1)NC(=O)CC] | <150 |
| 33 | 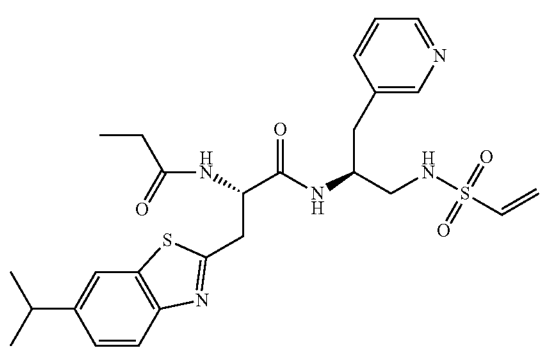 [SMILES: C=CS(=O)(=O)NC[C@H](Cc1cccnc1)NC(=O)[C@H](Cc1nc2ccc(C(C)C)cc2s1)NC(=O)CC] | <150 |

-continued

| Example | Structure | Binding affinity to DCN1 (IC$_{50}$, nM) |
|---|---|---|
| 34 | 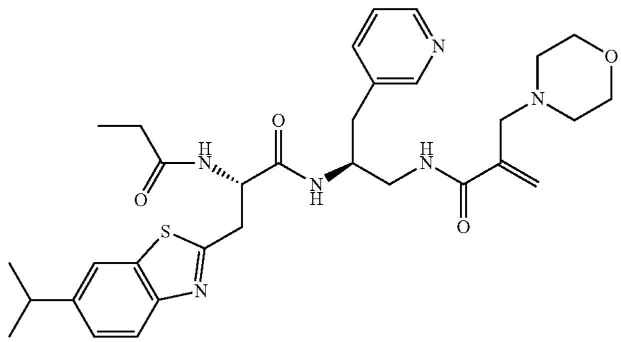 [SMILES: C=C(CN1CCOCC1)C(=O)NC[C@H](Cc1cccnc1)NC(=O)[C@H](Cc1nc2ccc(C(C)C)cc2s1)NC(=O)CC] | <150 |
| 35 | 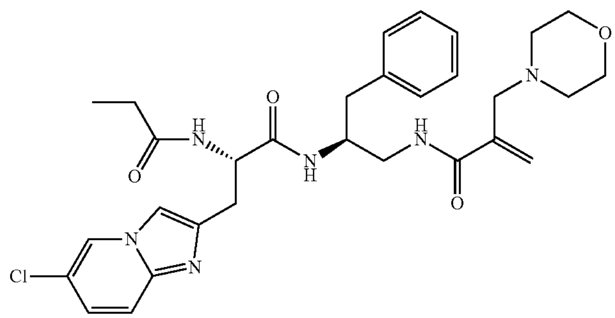 [SMILES: C=C(CN1CCOCC1)C(=O)NC[C@H](Cc1ccccc1)NC(=O)[C@H](Cc1cn2cc(Cl)ccc2n1)NC(=O)CC] | <300 |
| 36 | 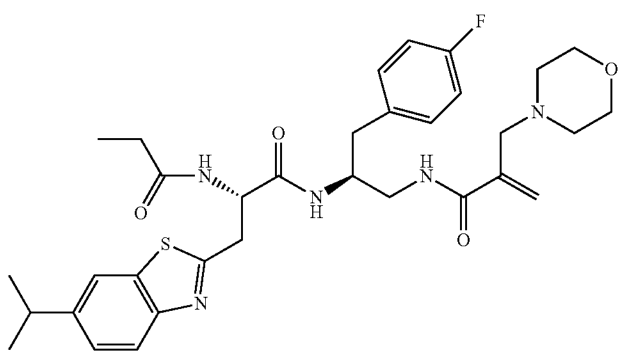 [SMILES: C=C(CN1CCOCC1)C(=O)NC[C@H](Cc1ccc(F)cc1)NC(=O)[C@H](Cc1nc2ccc(C(C)C)cc2s1)NC(=O)CC] | <150 |
| 37 | 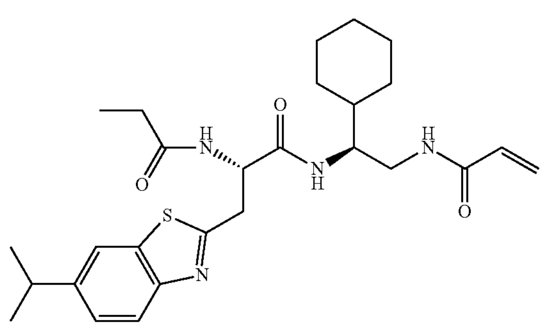 [SMILES: C=CC(=O)NC[C@@H](NC(=O)[C@H](Cc1nc2ccc(C(C)C)cc2s1)NC(=O)CC)C1CCCCC1] | <200 |

-continued
| Example | Structure | Binding affinity to DCN1 (IC$_{50}$, nM) |
|---|---|---|
| 38 | 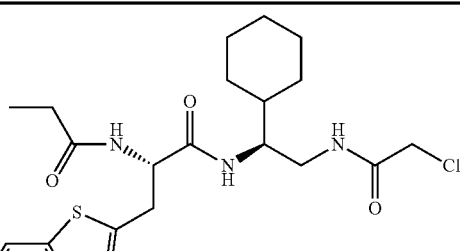 | <150 |
| 39 | 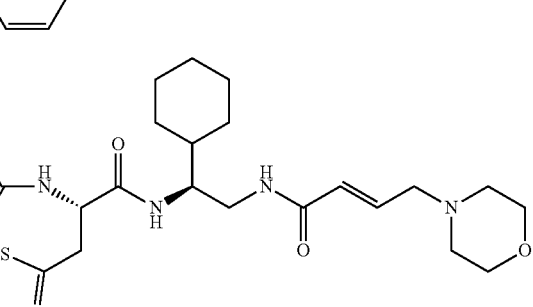 | <150 |
Representative compounds of the current invention include, but are not limited to the following.
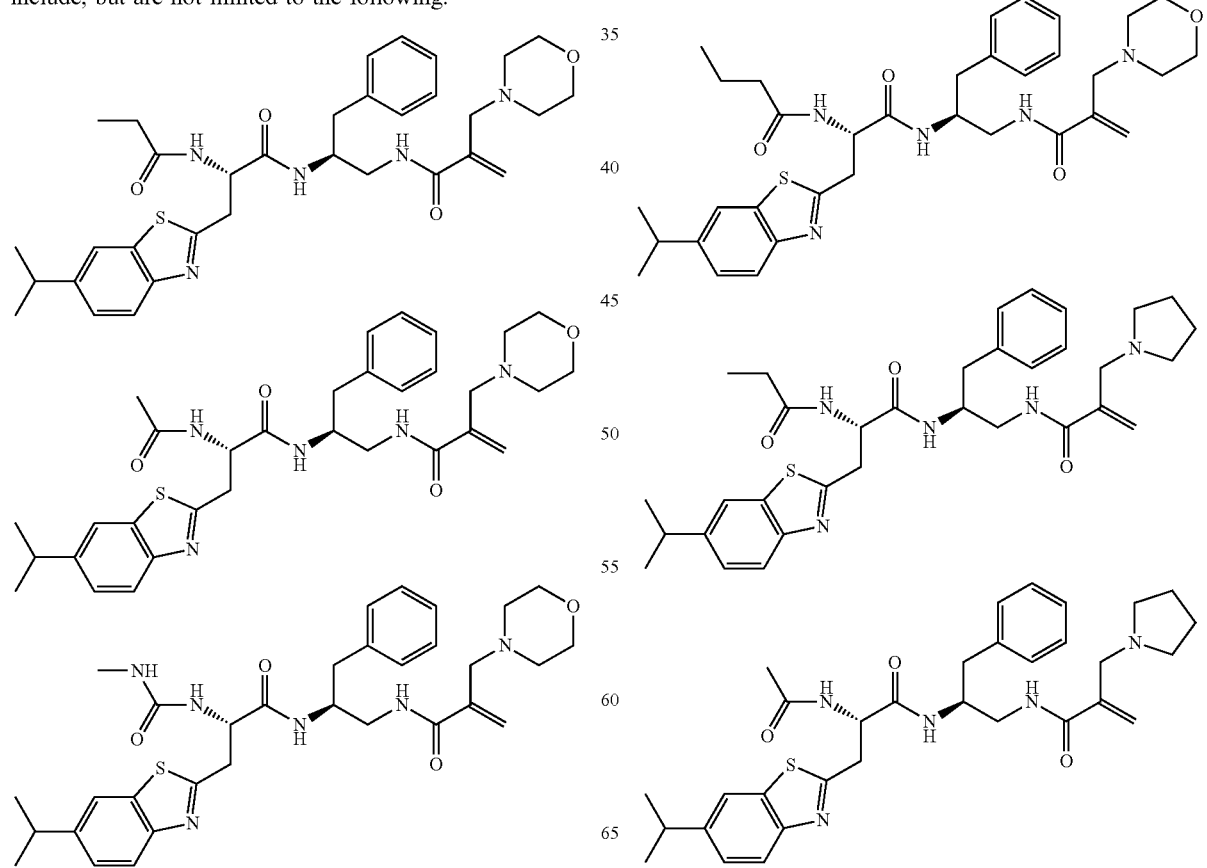

57
-continued
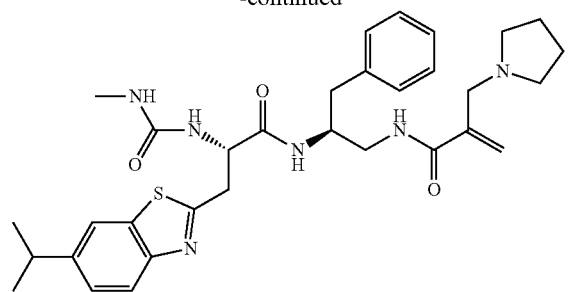
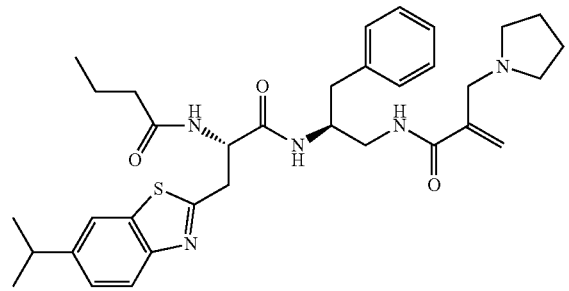
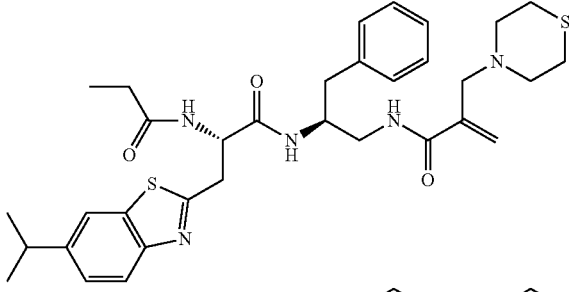
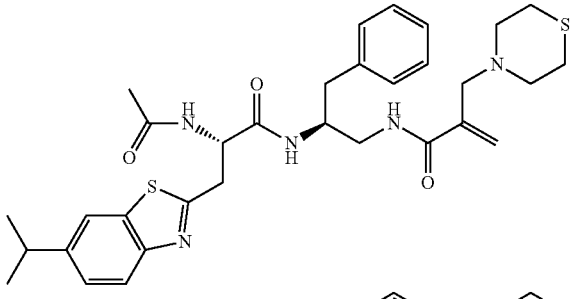
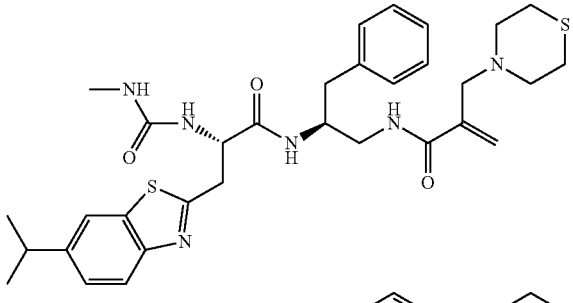
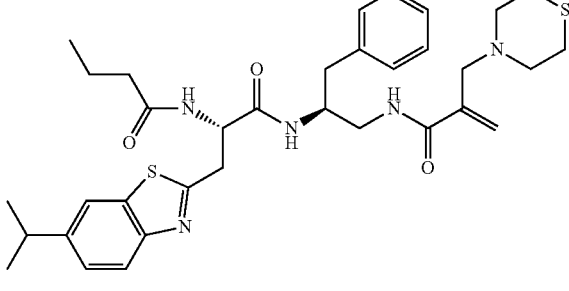
58
-continued
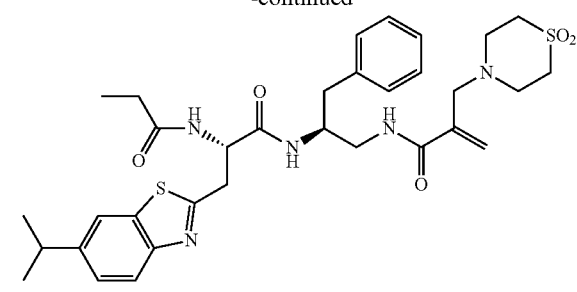
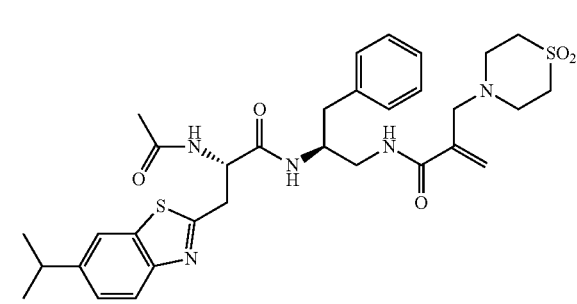
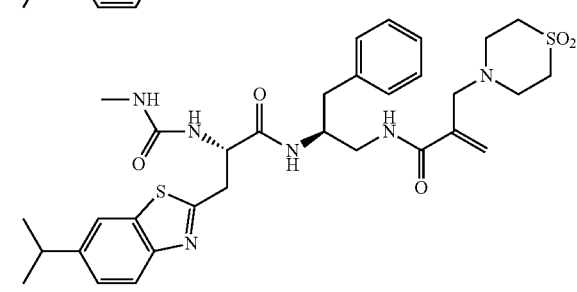
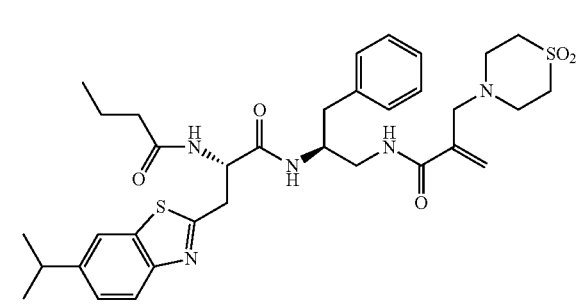
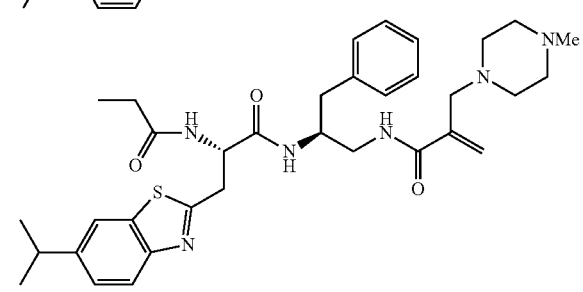
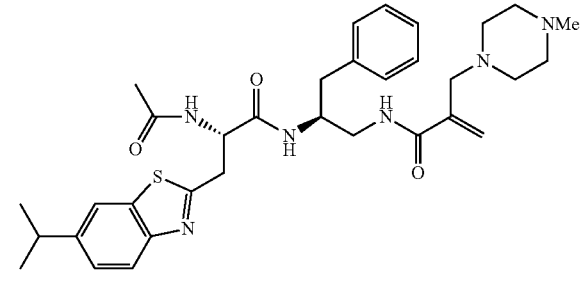

59
-continued
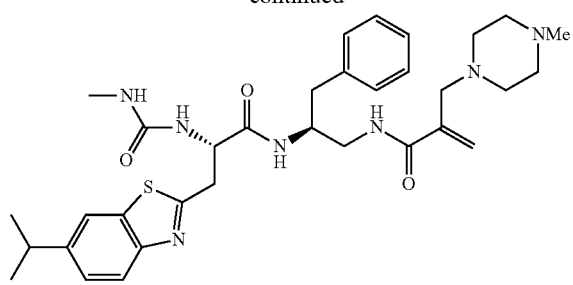
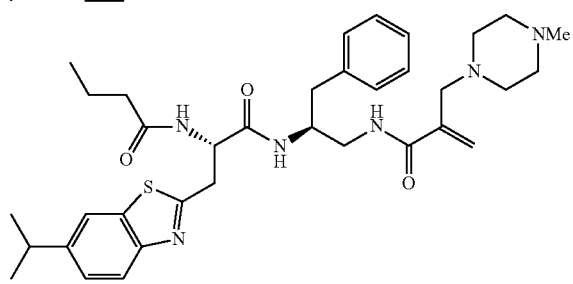
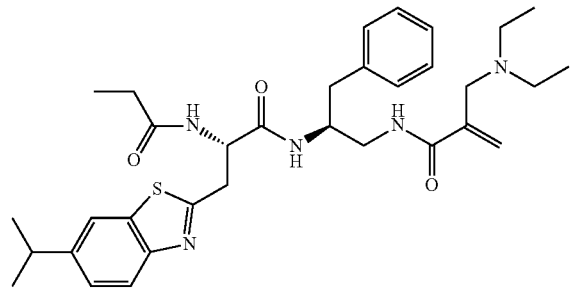
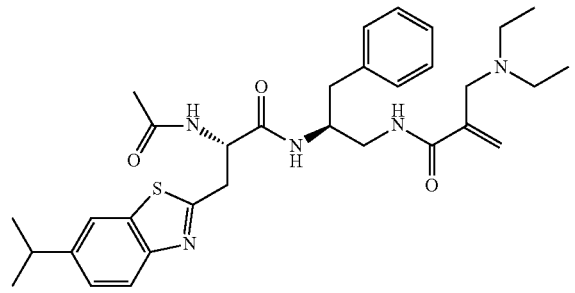
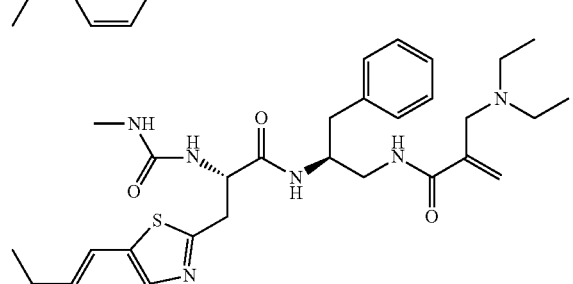
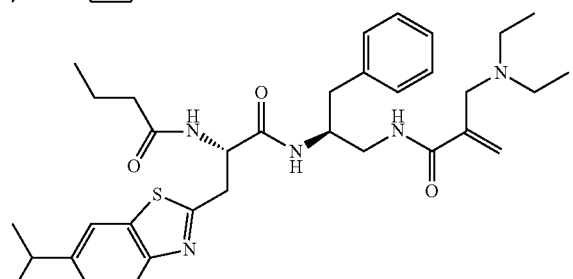
60
-continued
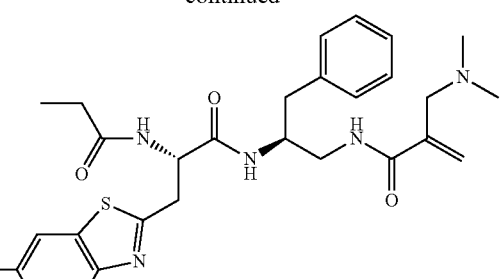

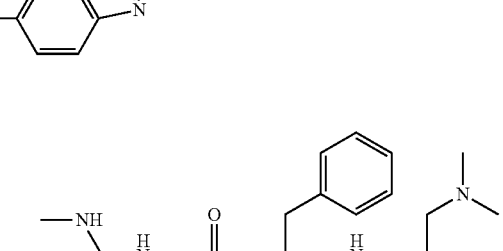
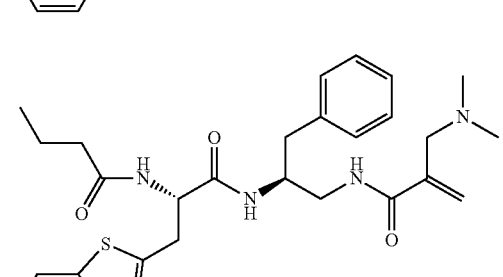
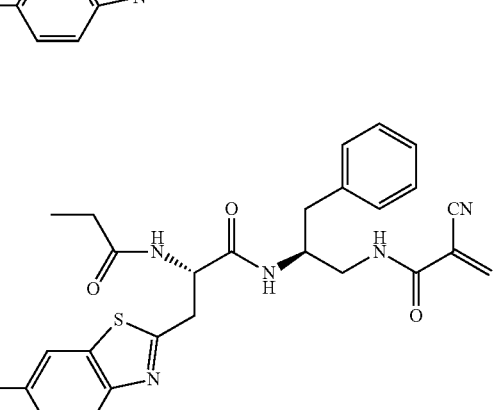

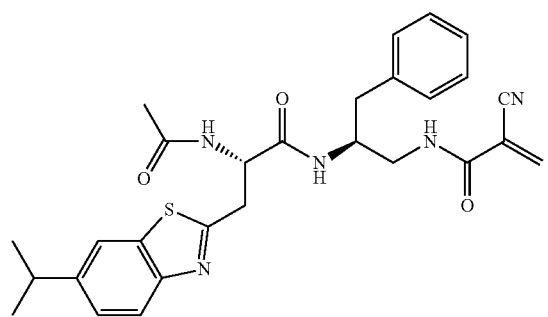
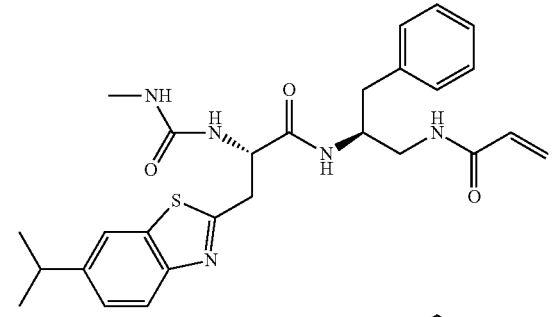

63
-continued
64
-continued
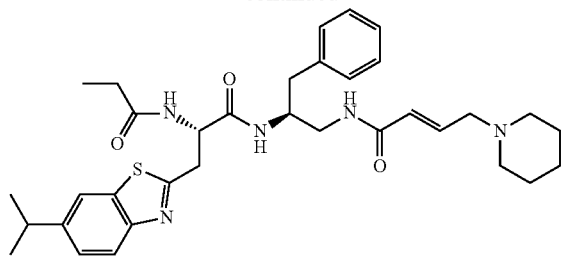
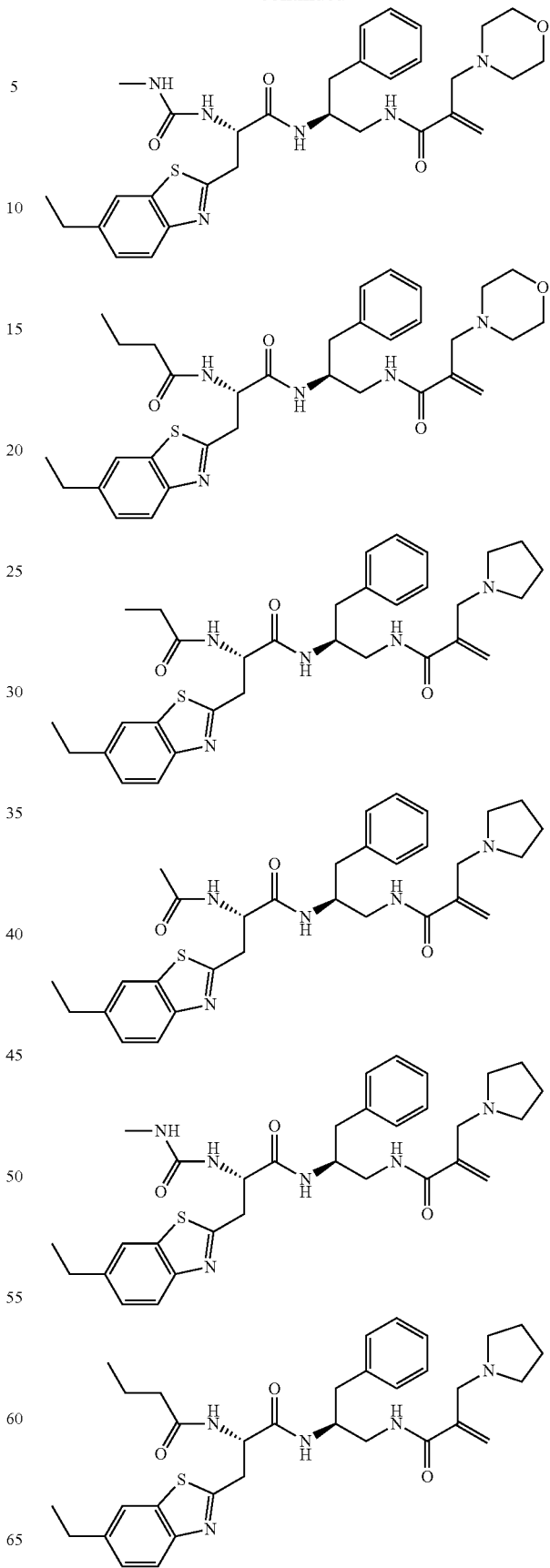

65
-continued
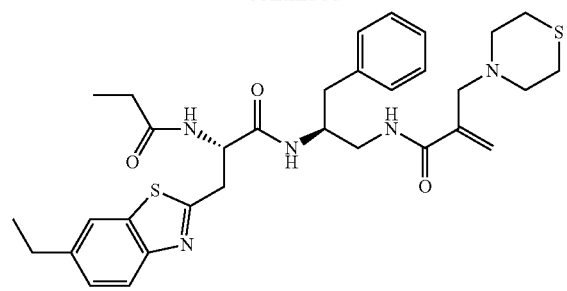
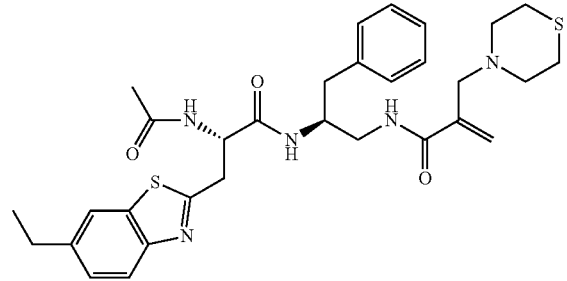
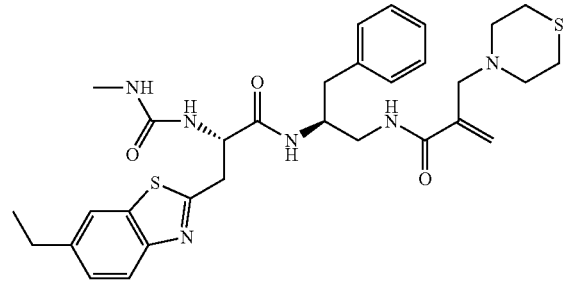
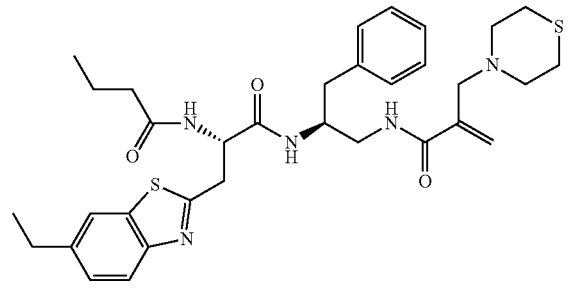
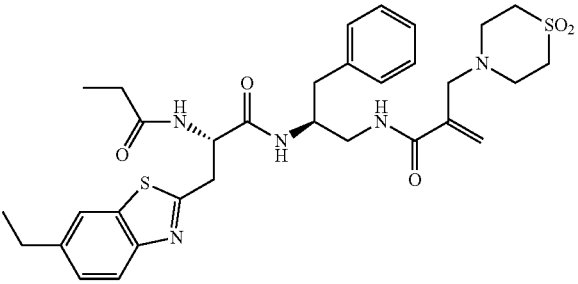
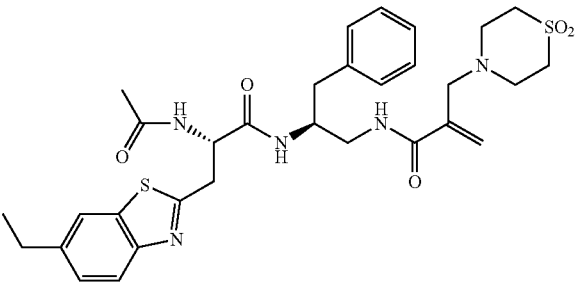
66
-continued
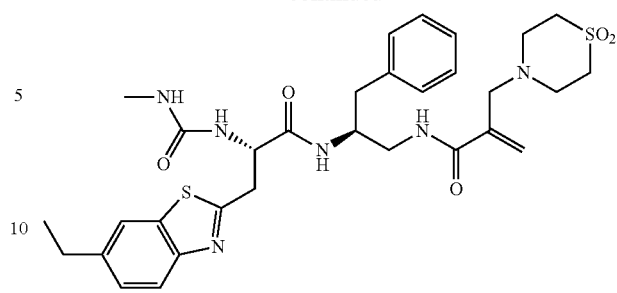

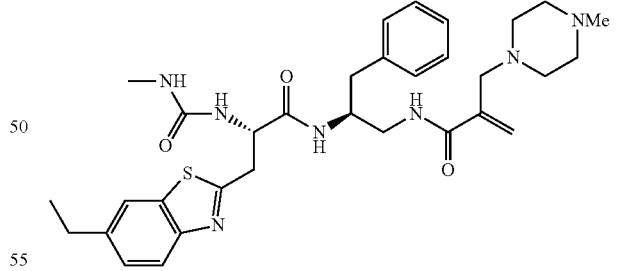
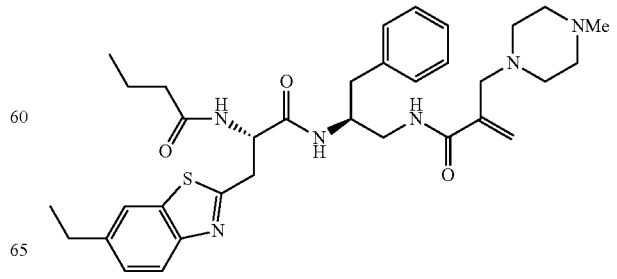

67
-continued
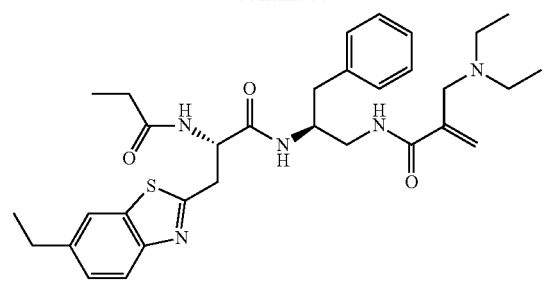
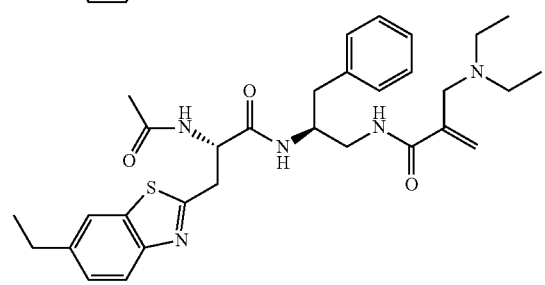
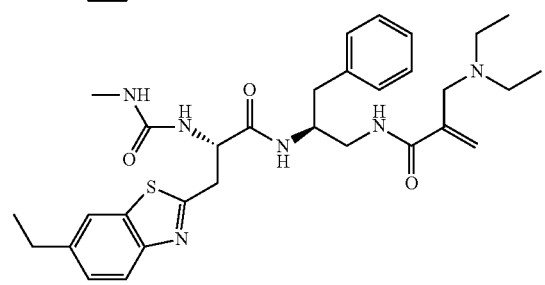
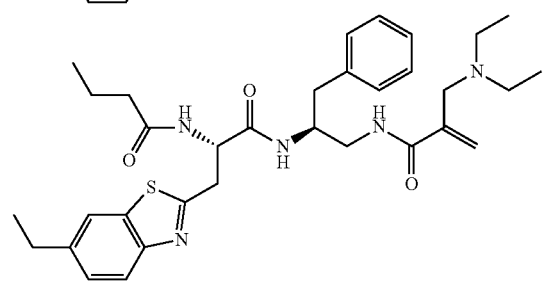
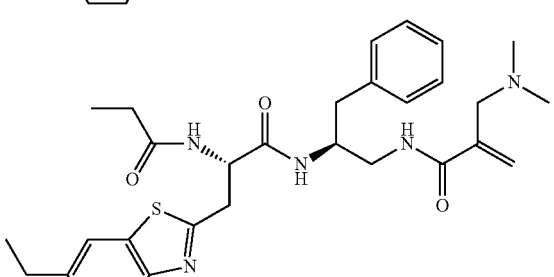
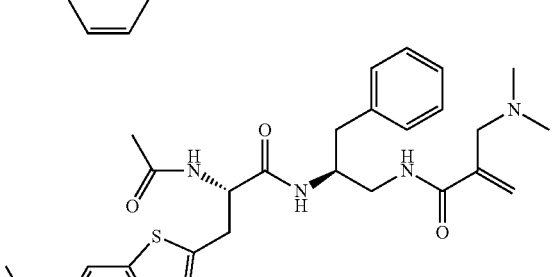
68
-continued
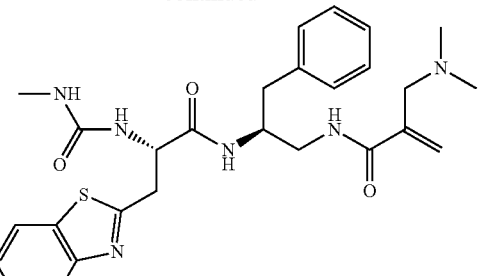
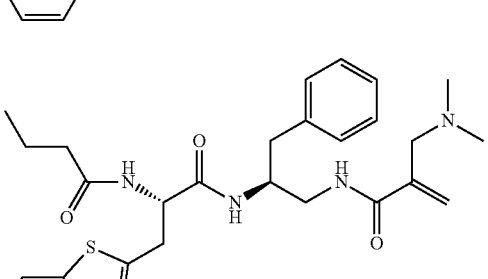
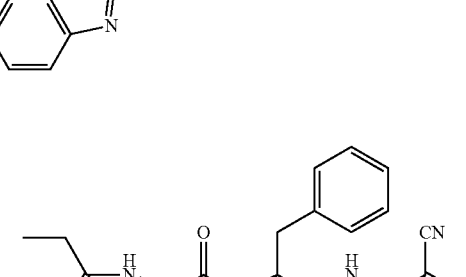
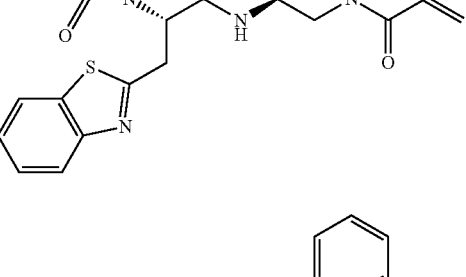
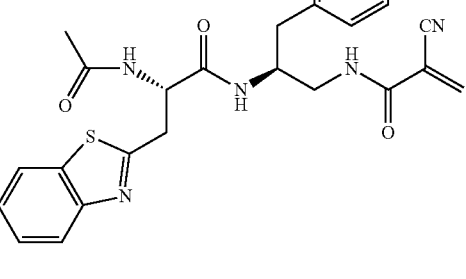
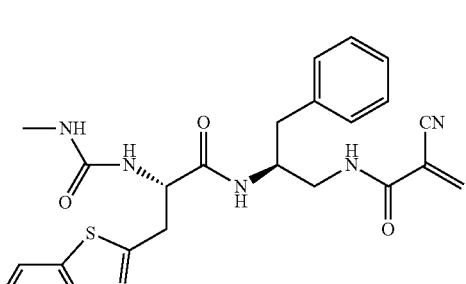

69
-continued
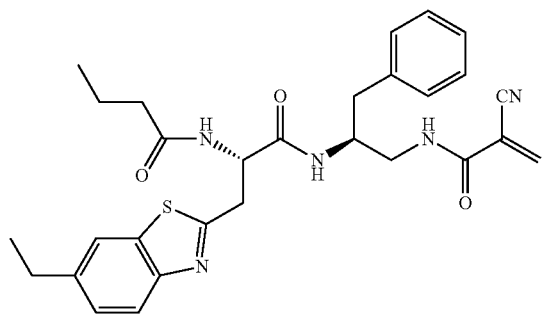
70
-continued
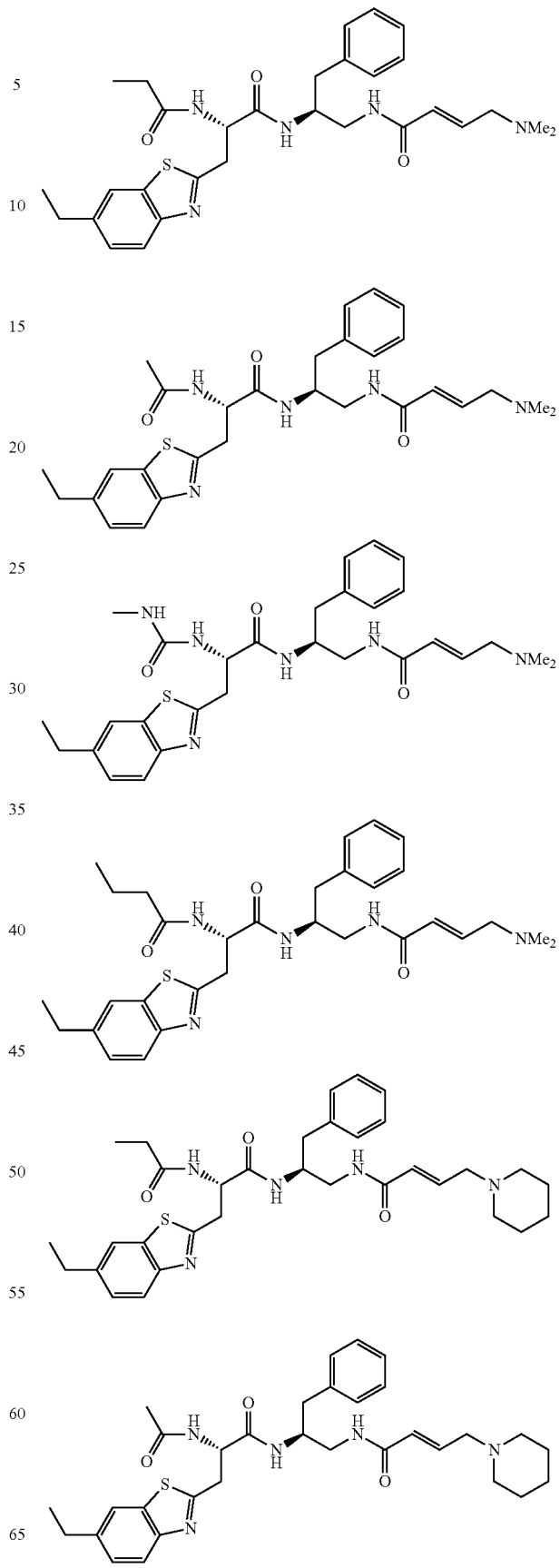

71
-continued
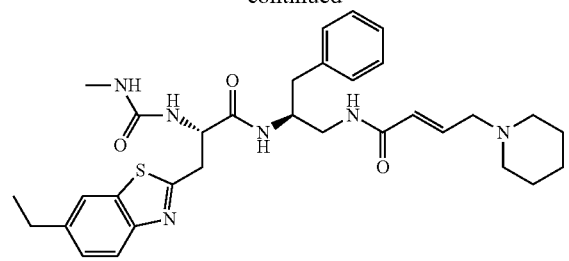
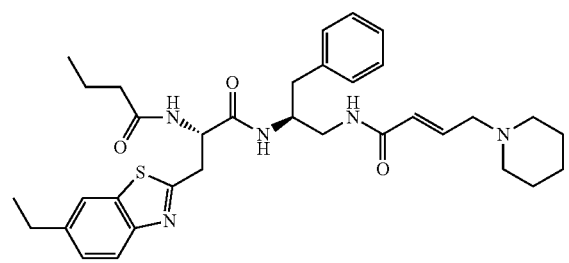
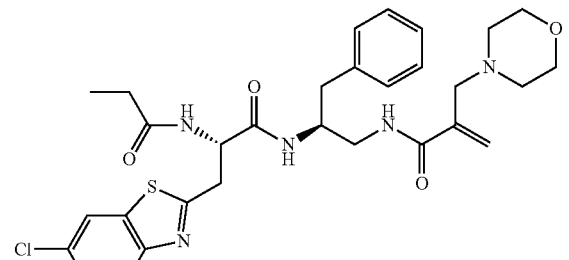
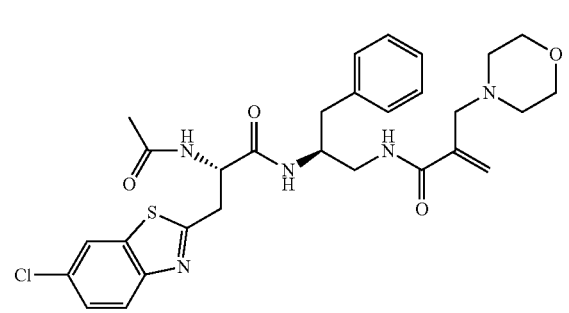
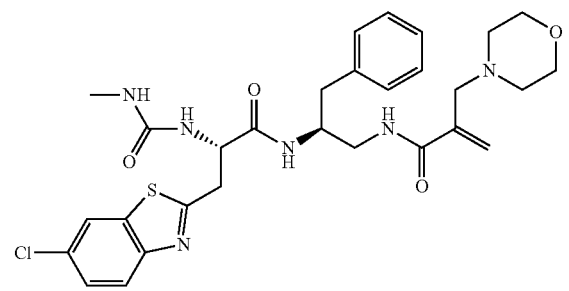
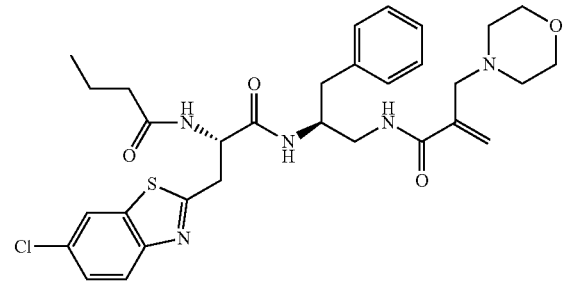
72
-continued
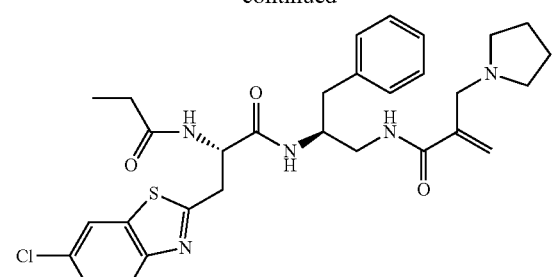
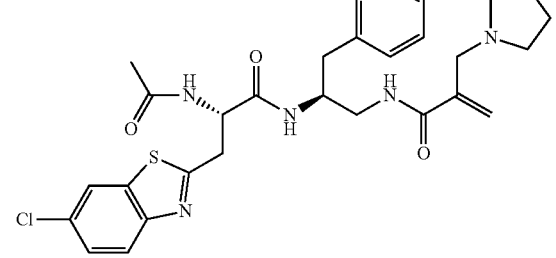
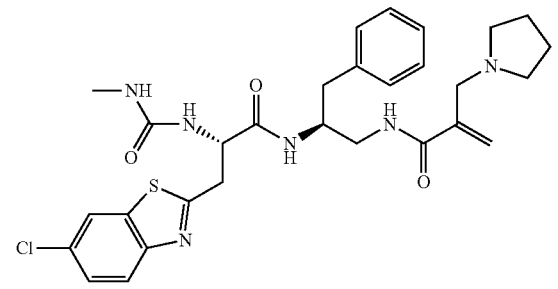
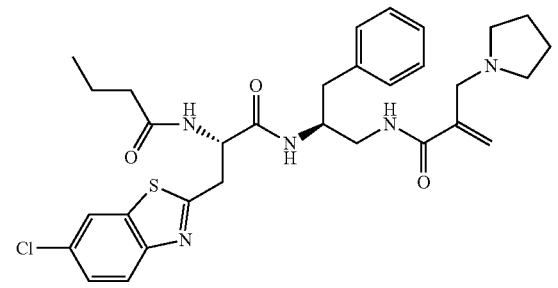
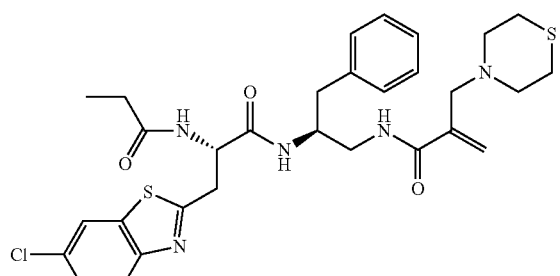
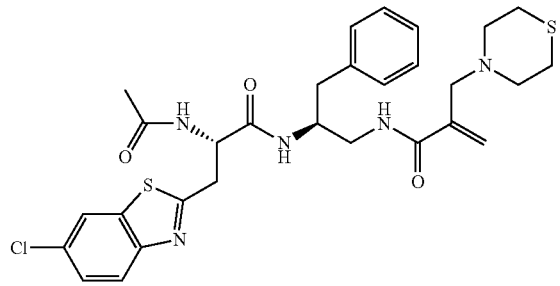

73
-continued
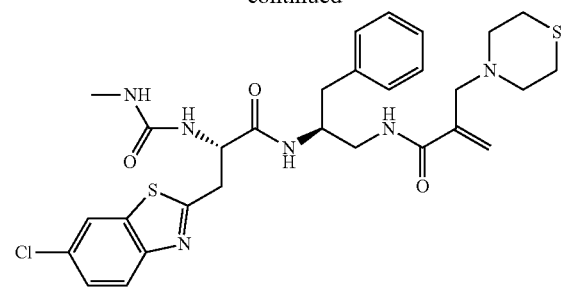
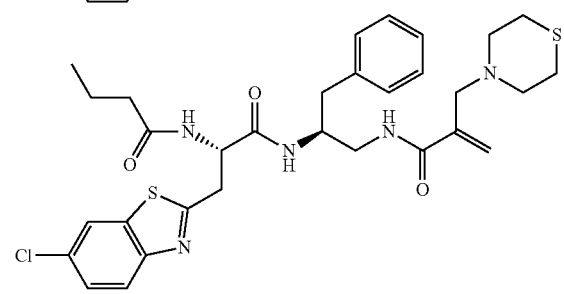
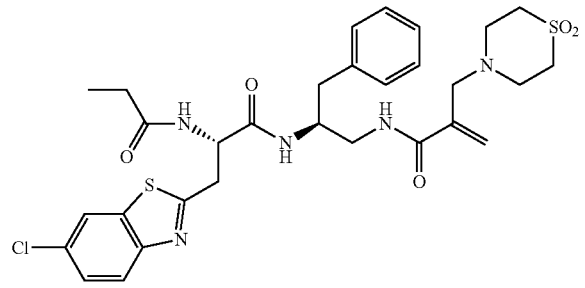
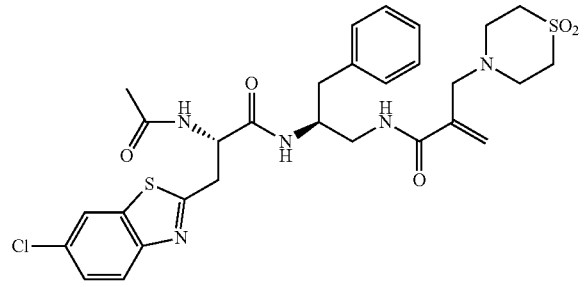
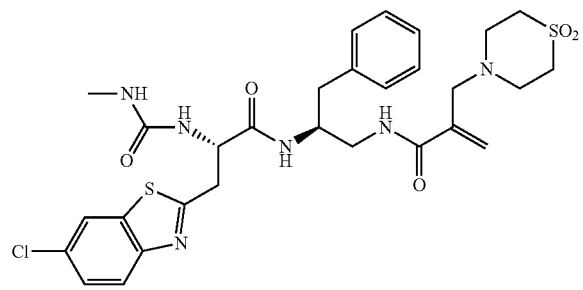
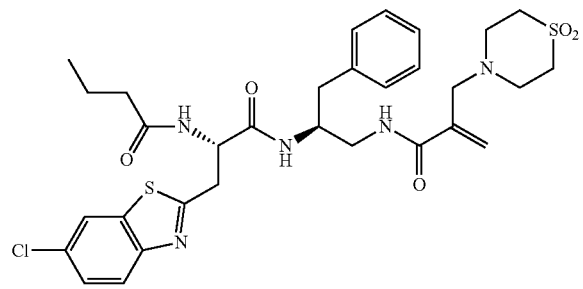
74
-continued
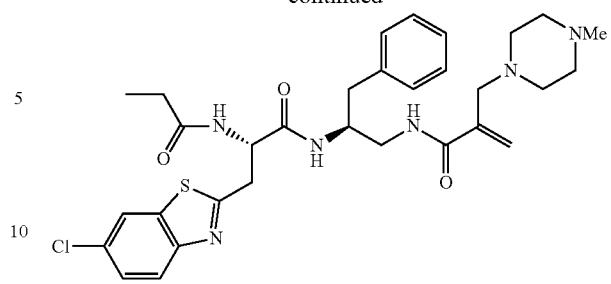
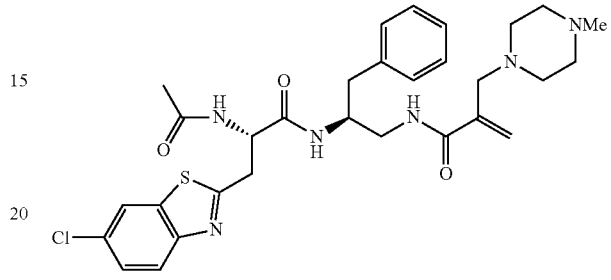

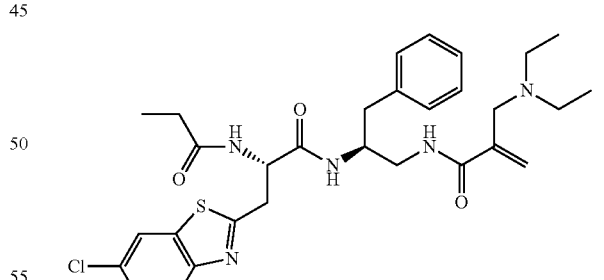
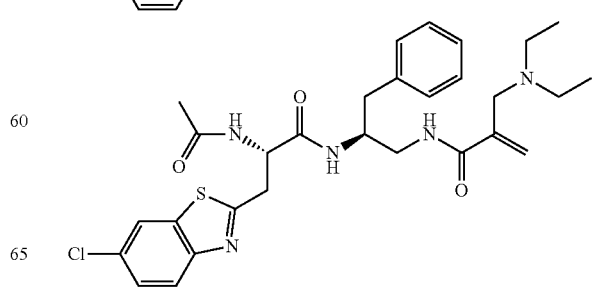

75
-continued
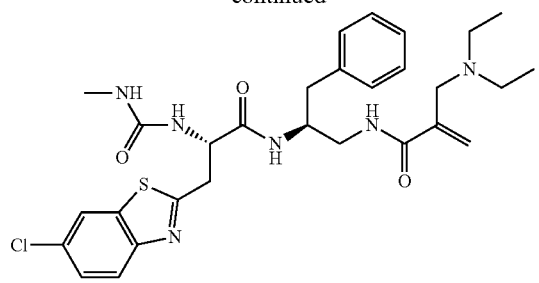
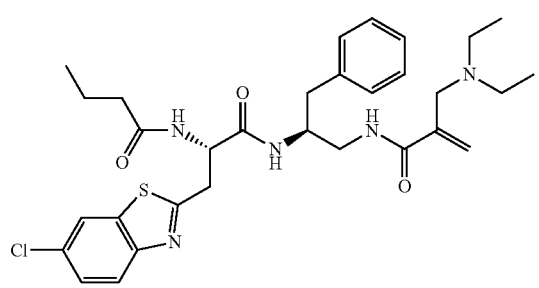
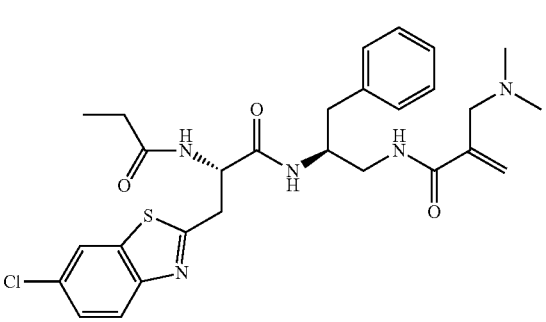
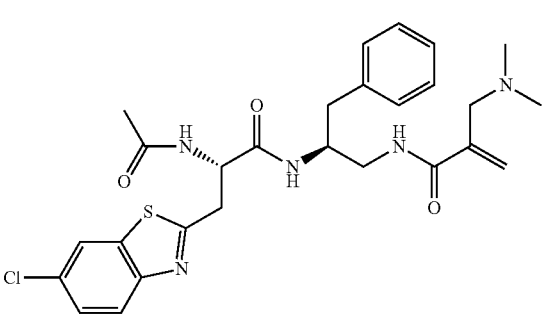
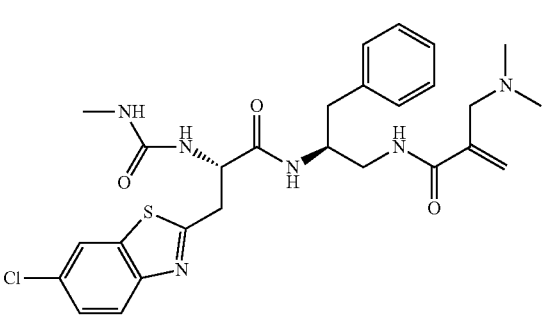
76
-continued
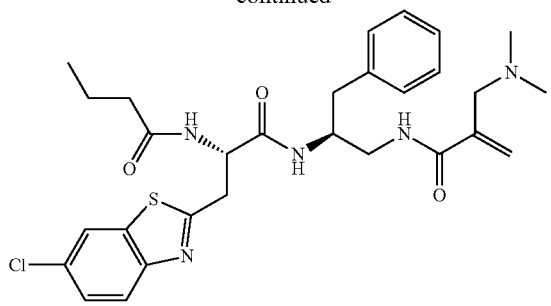
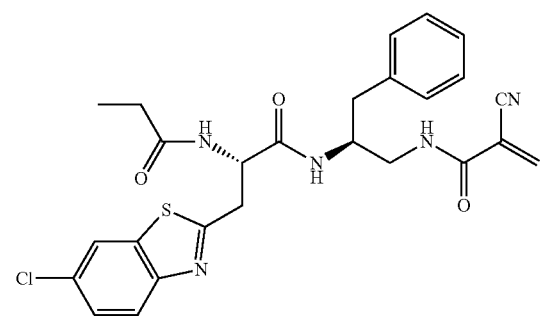
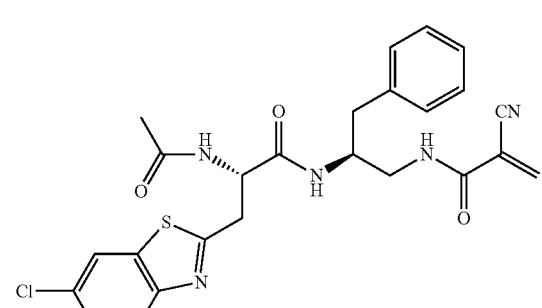
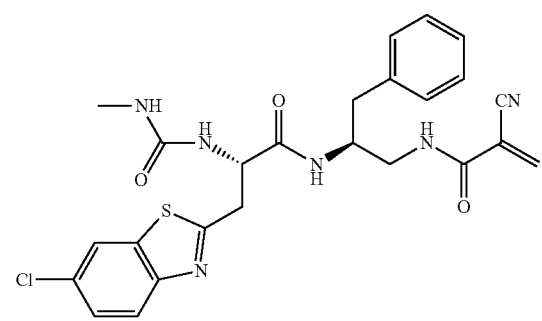
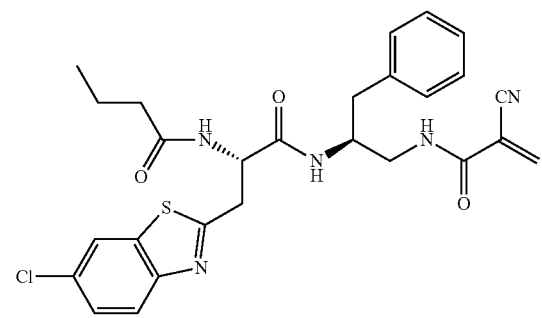

77
-continued
78
-continued
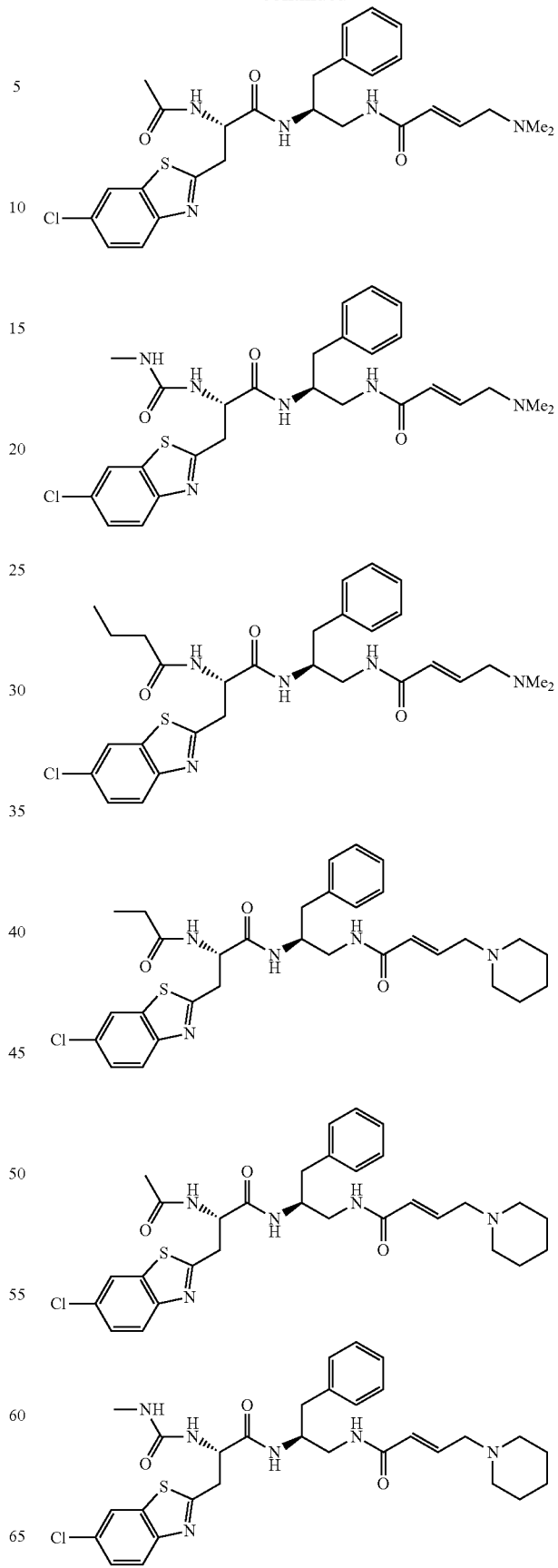

79
-continued
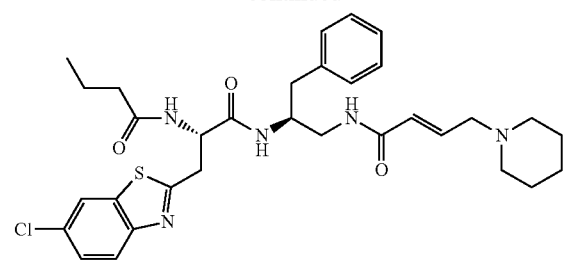
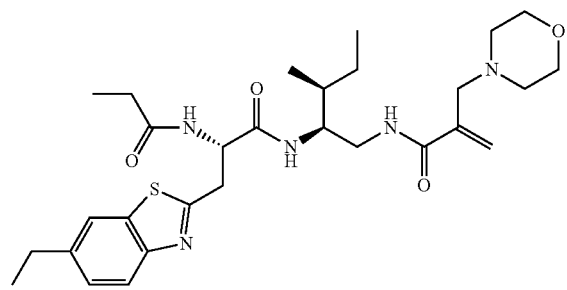
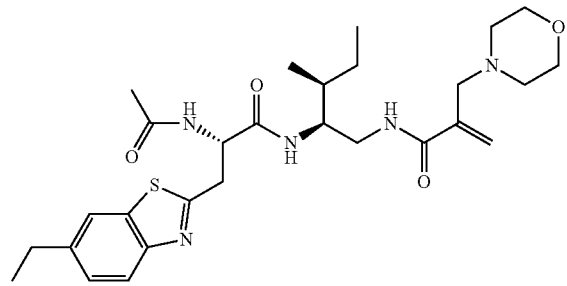
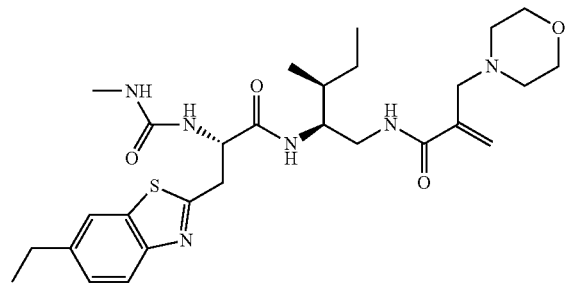
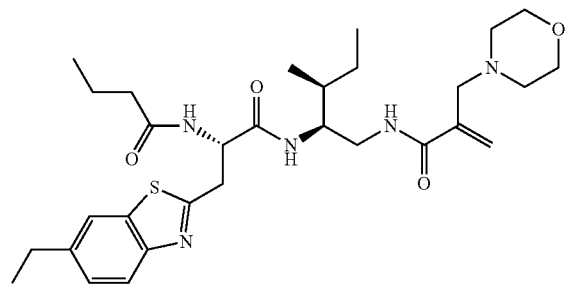
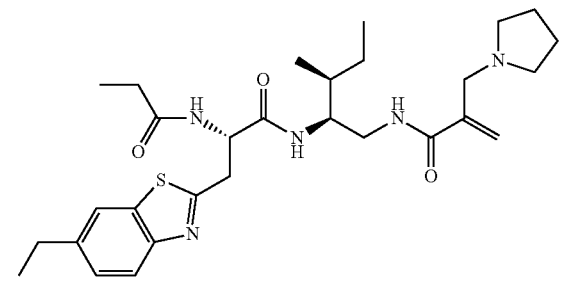
80
-continued
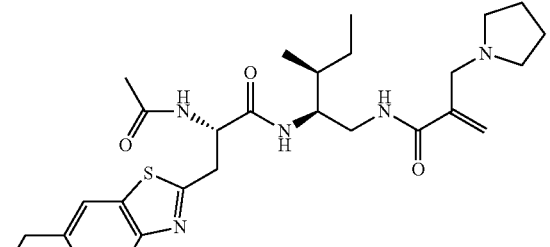
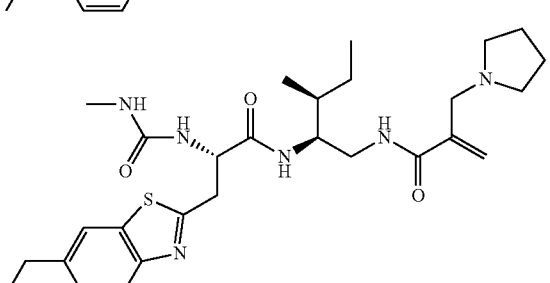
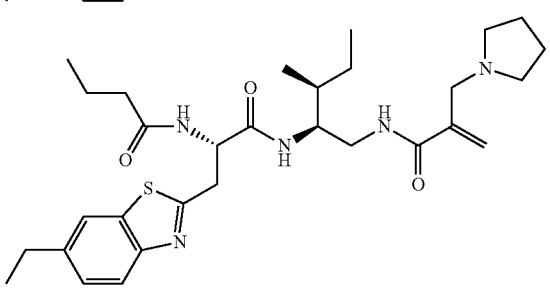
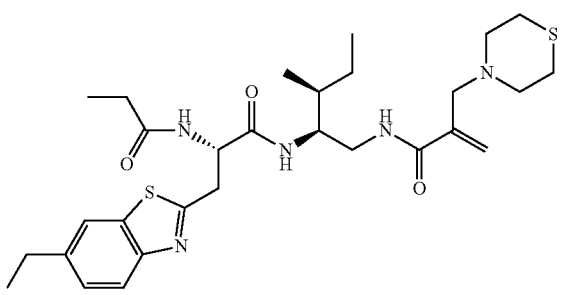
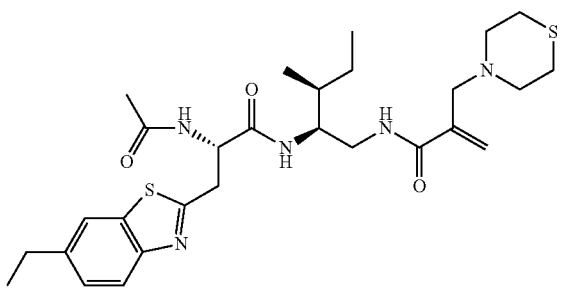
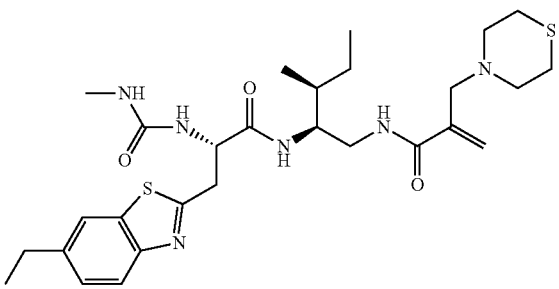

81
-continued
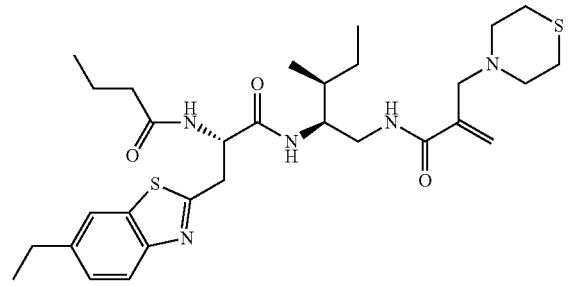
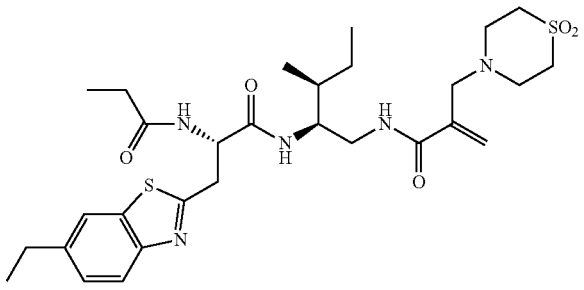
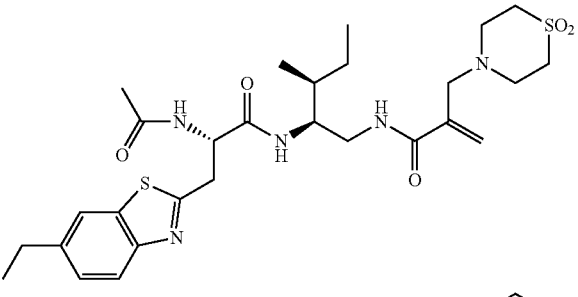
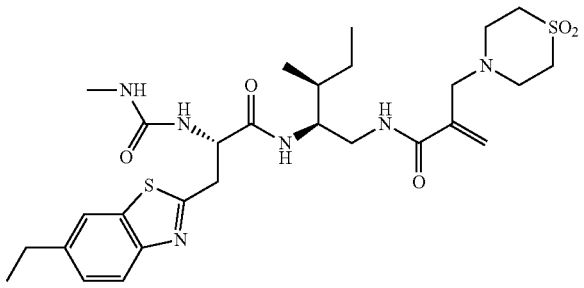
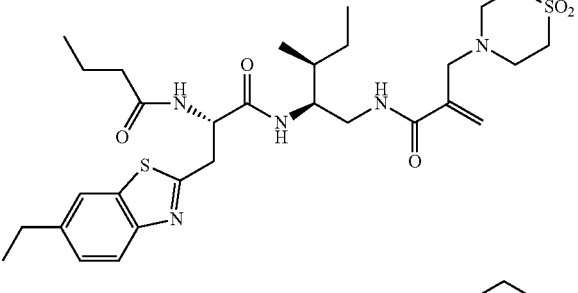
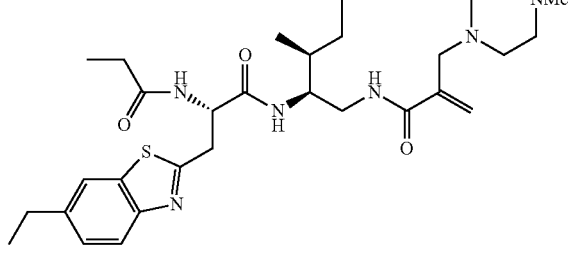
82
-continued
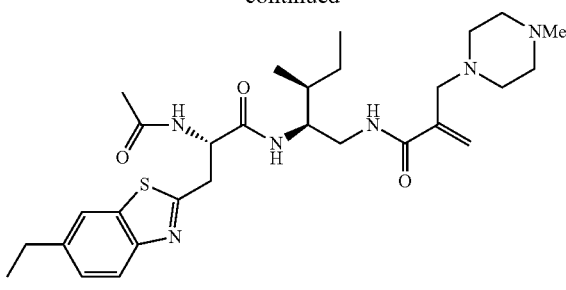
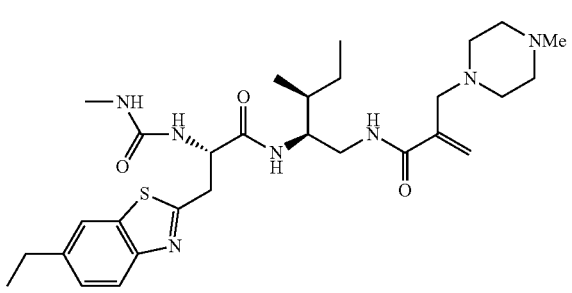
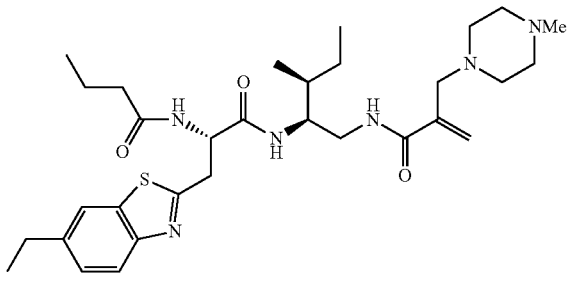
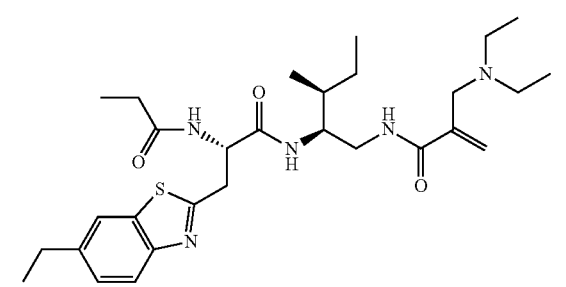
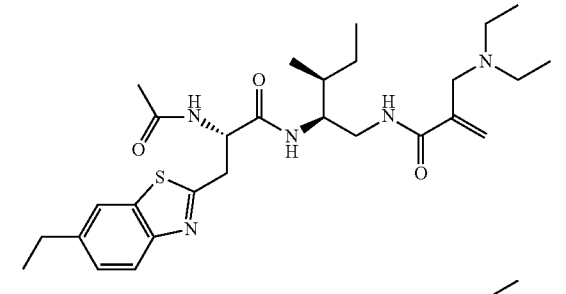
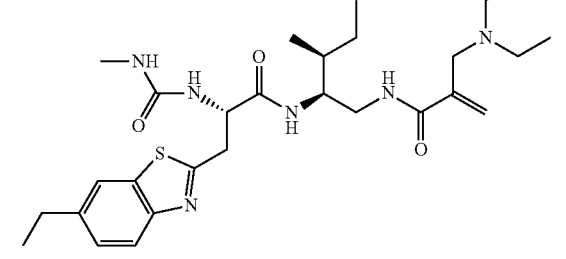

83
-continued
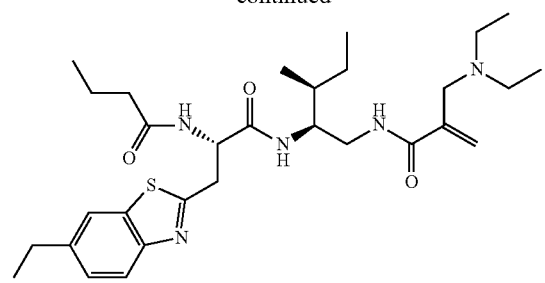
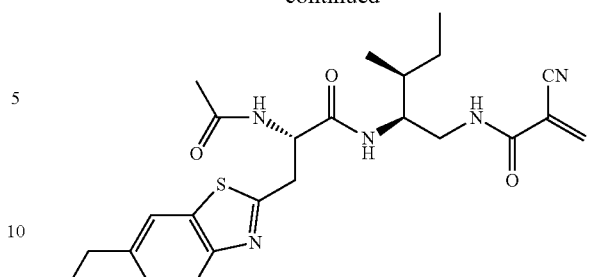
84
-continued
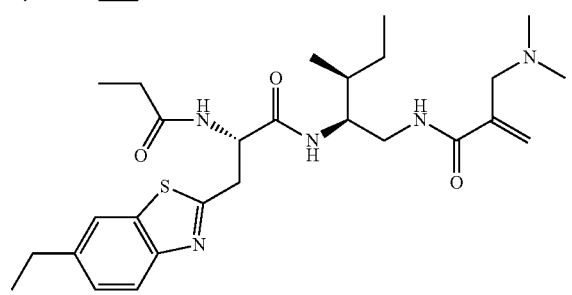
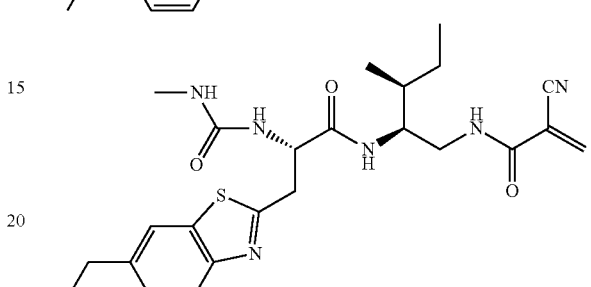
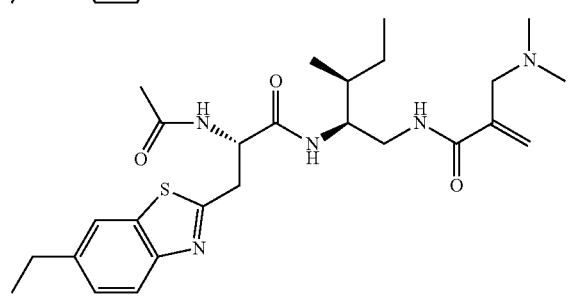
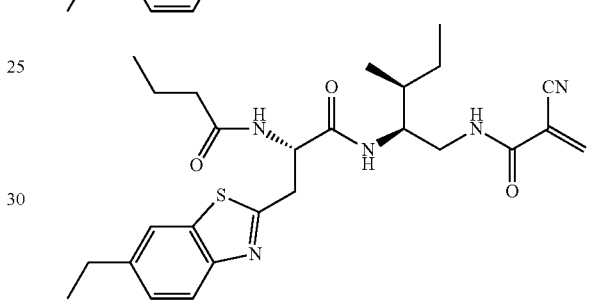
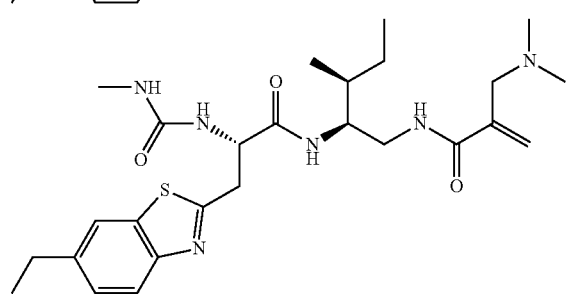
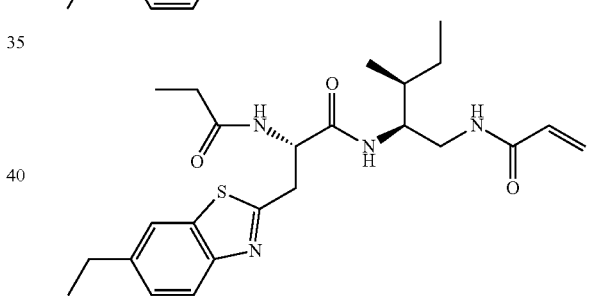
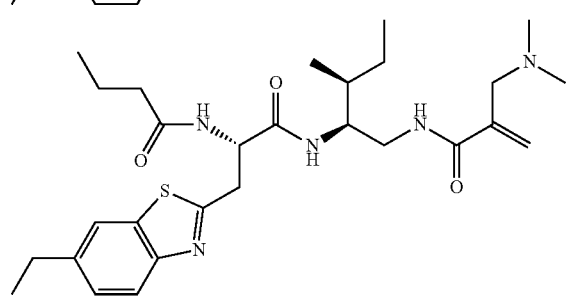
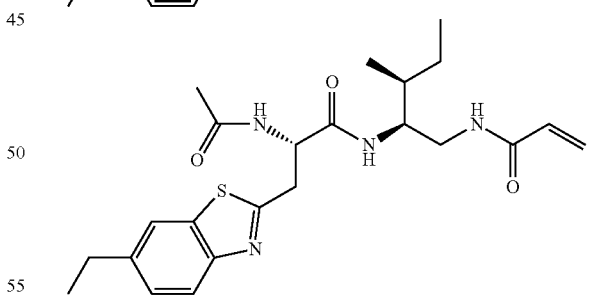
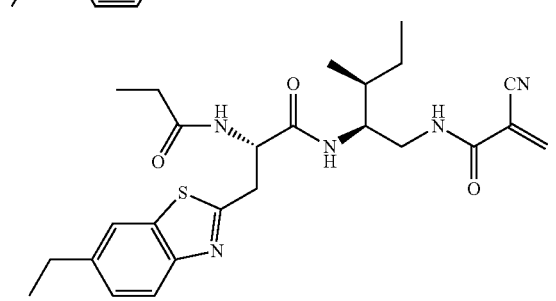
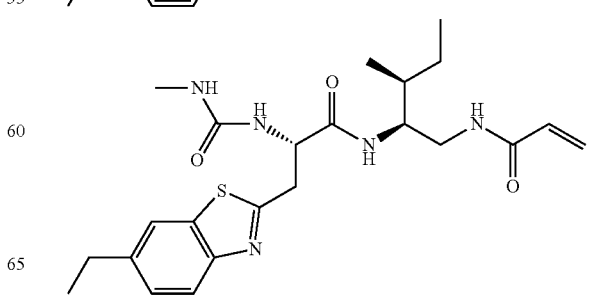

85
-continued
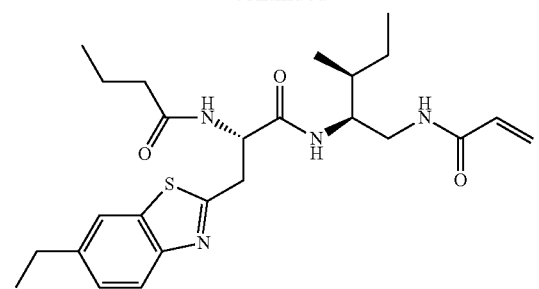
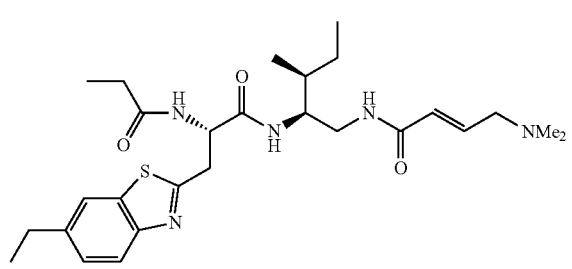
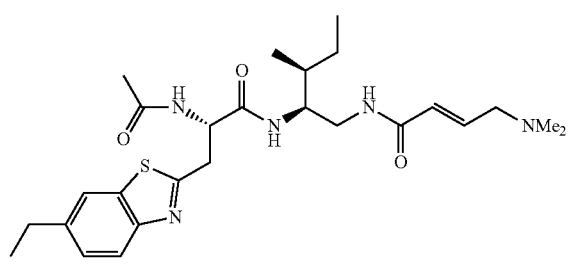
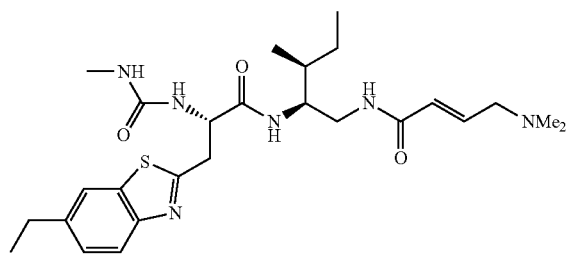
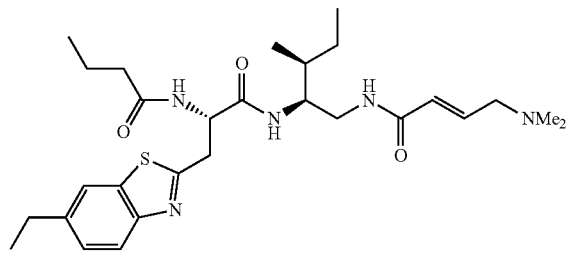
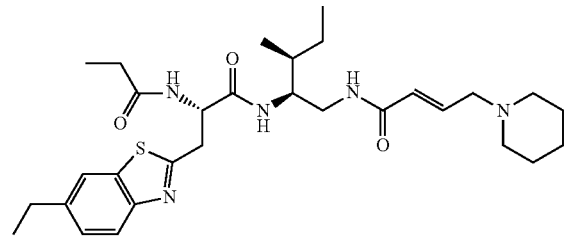
86
-continued
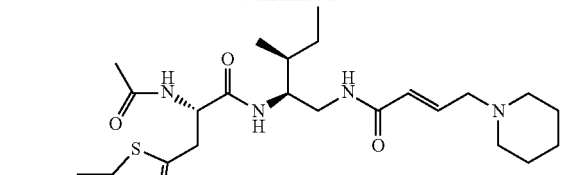
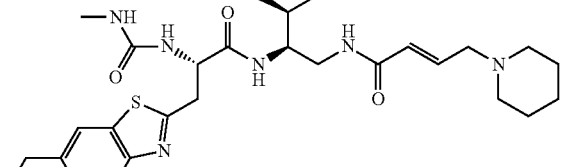
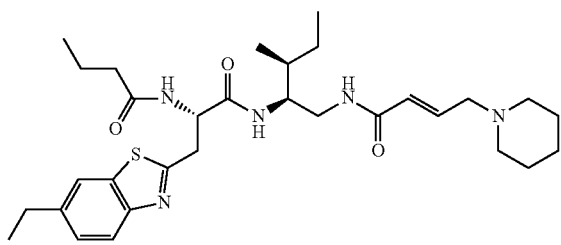
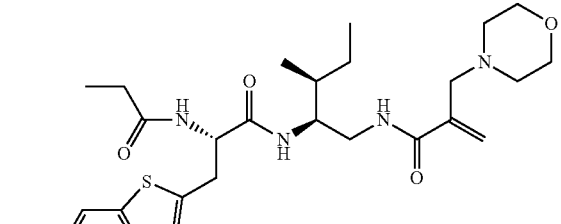
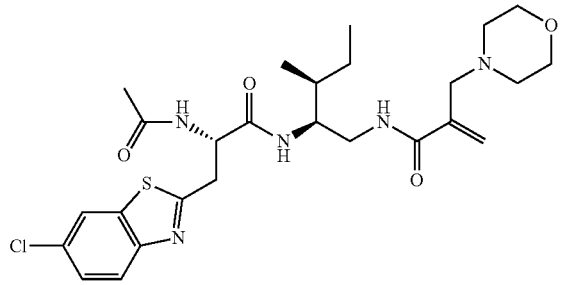
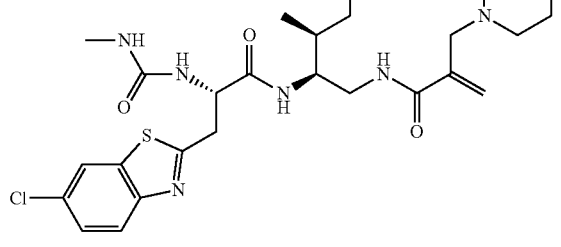

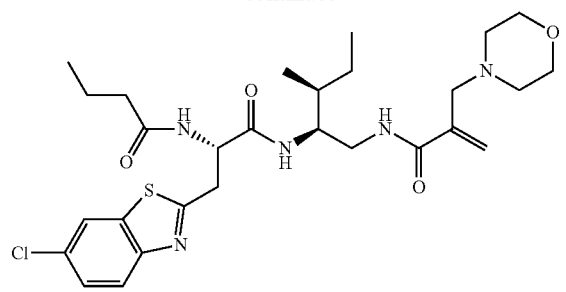
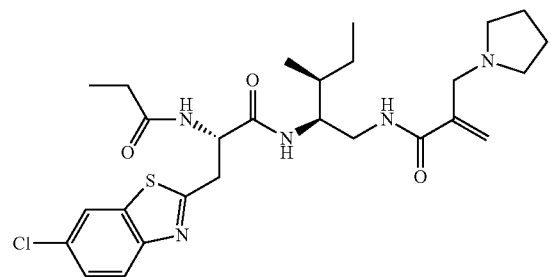
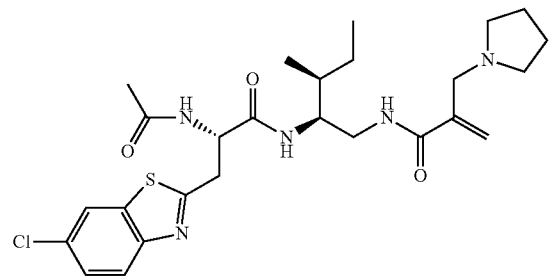
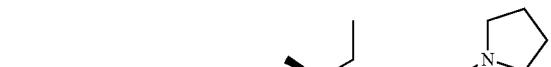
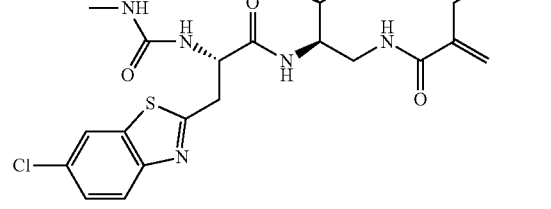
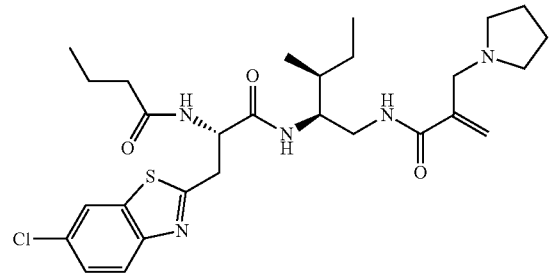
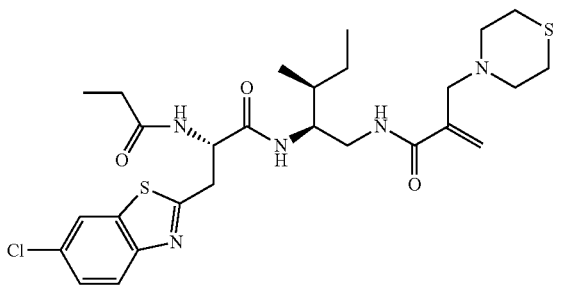
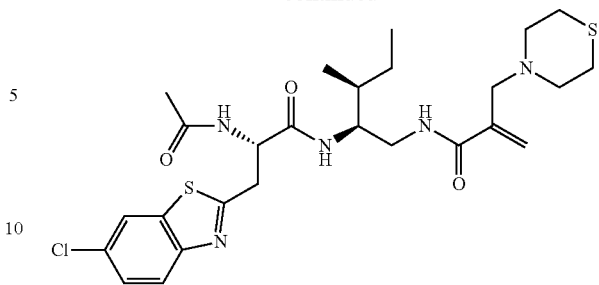
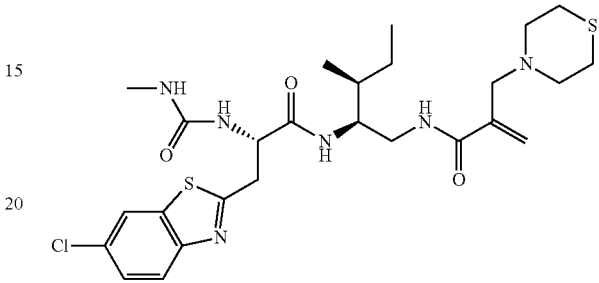
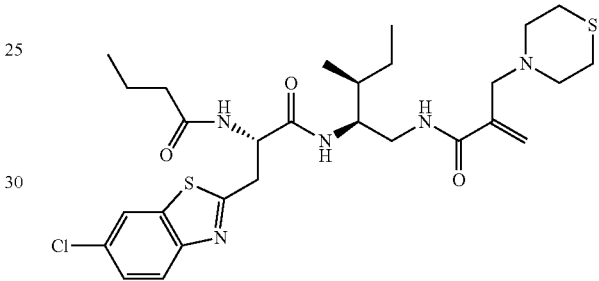
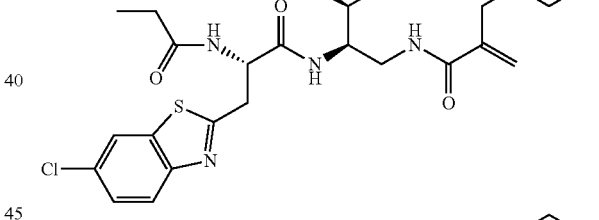
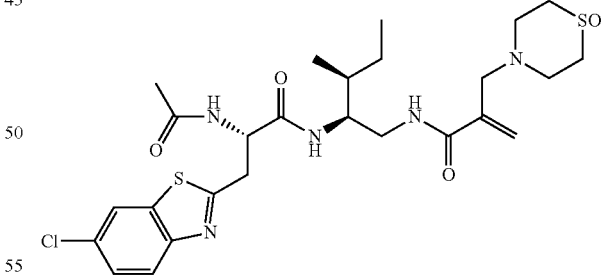
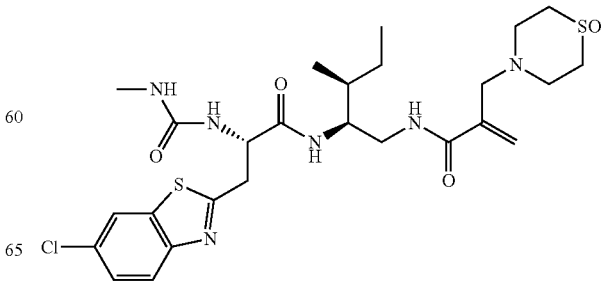

89
-continued
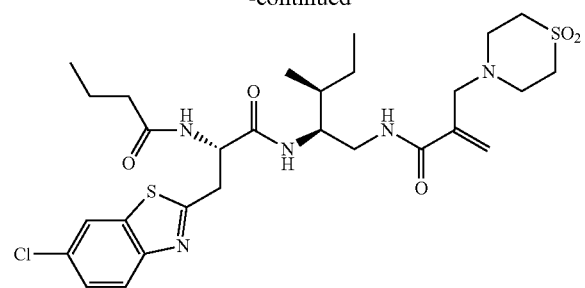
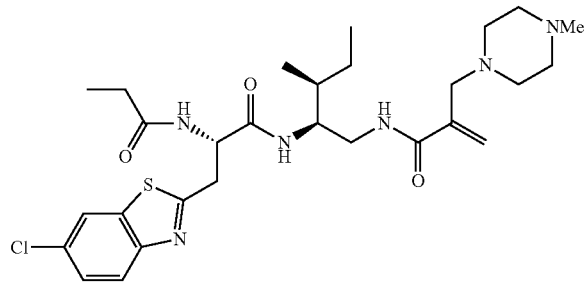
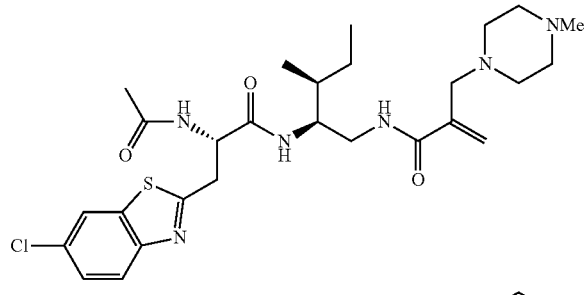
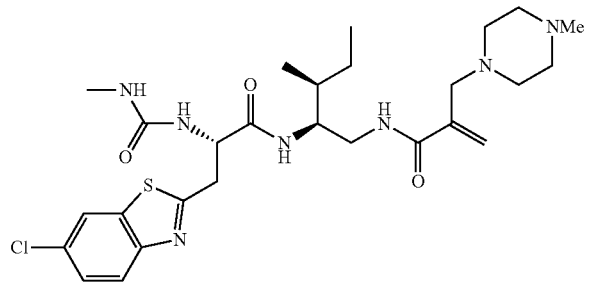
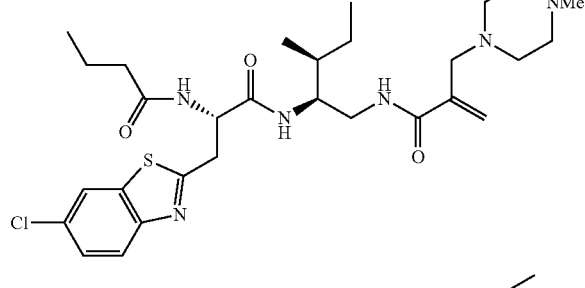
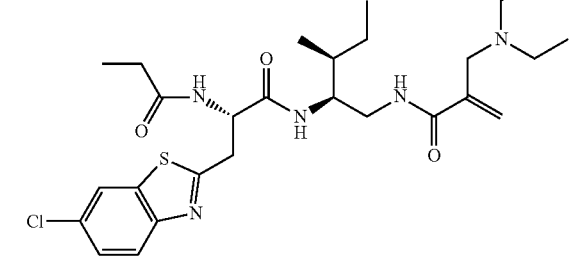
90
-continued
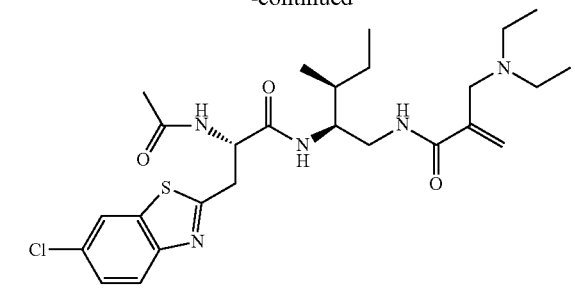
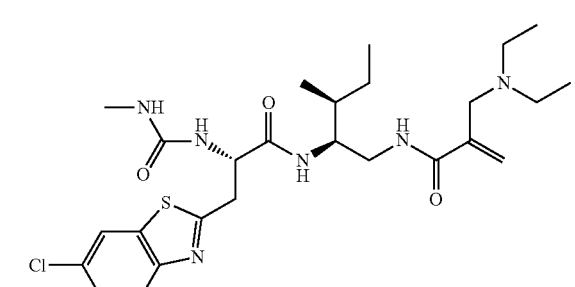
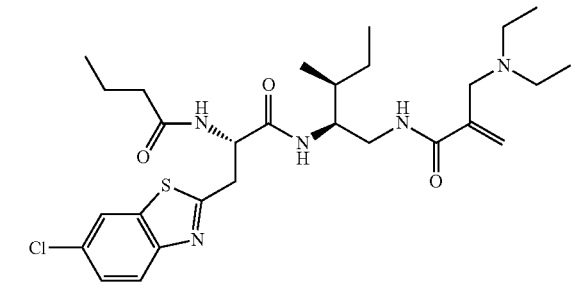
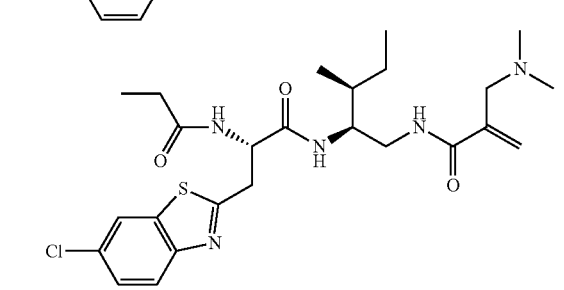
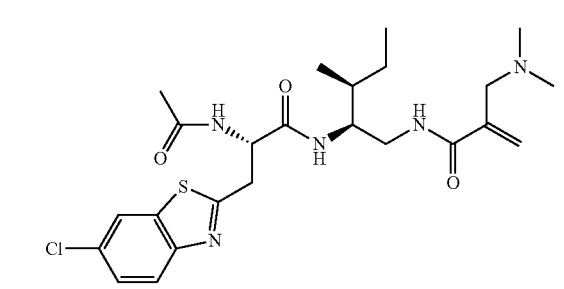
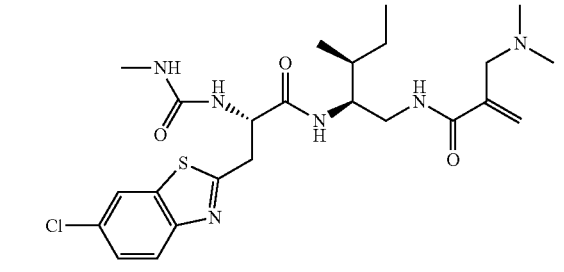

91
-continued
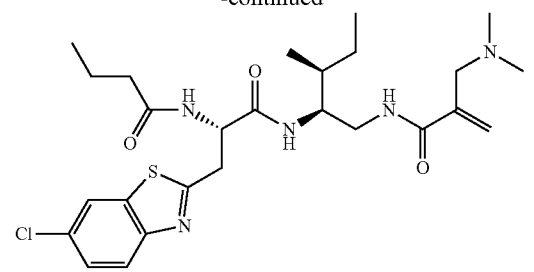
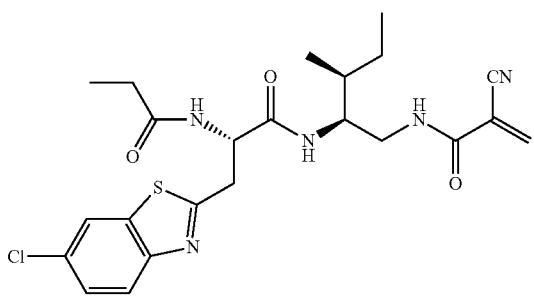
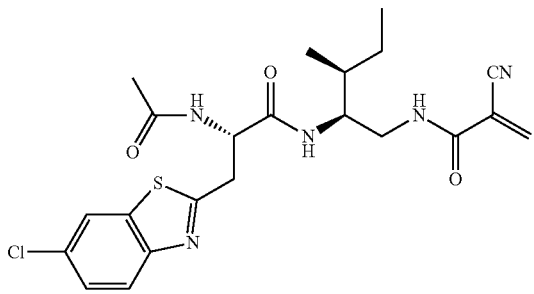
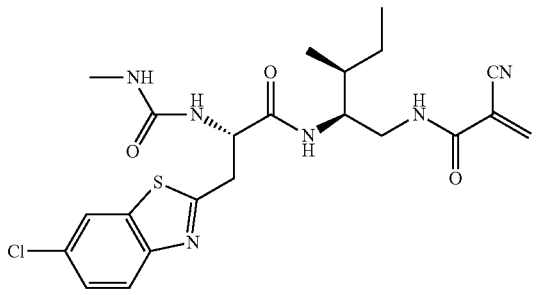
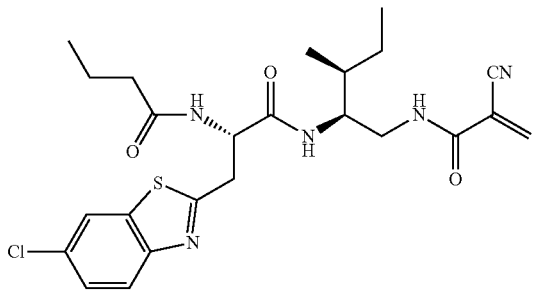
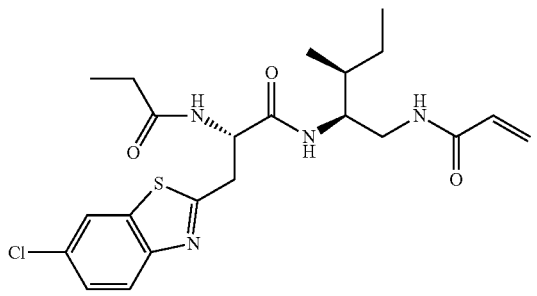
92
-continued
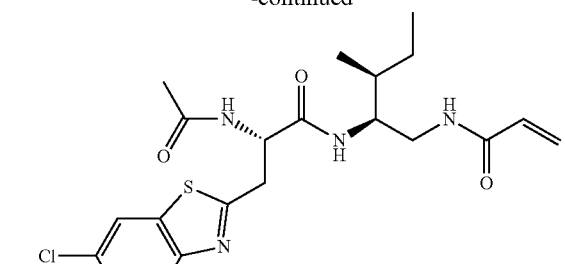
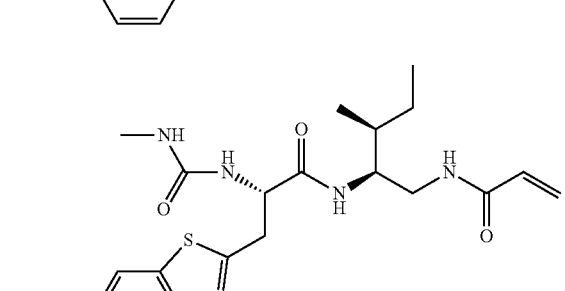
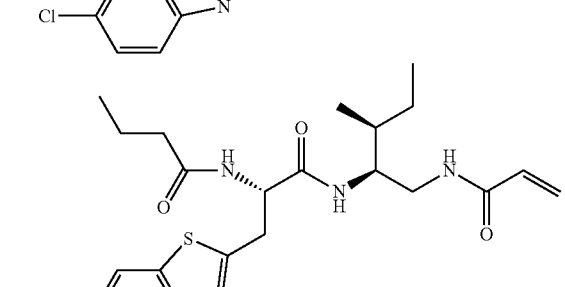
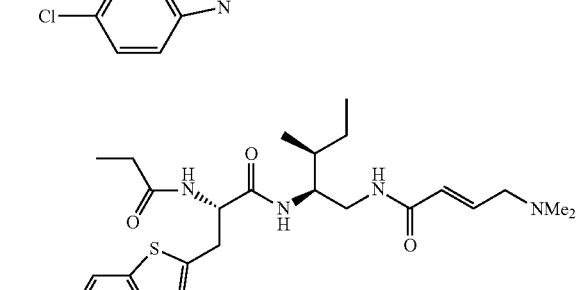
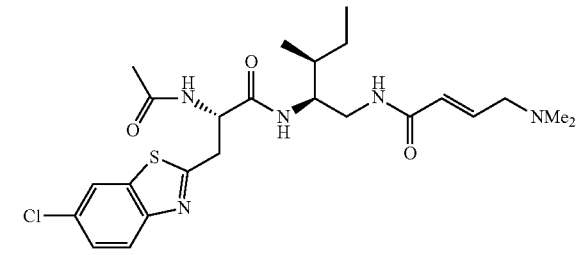
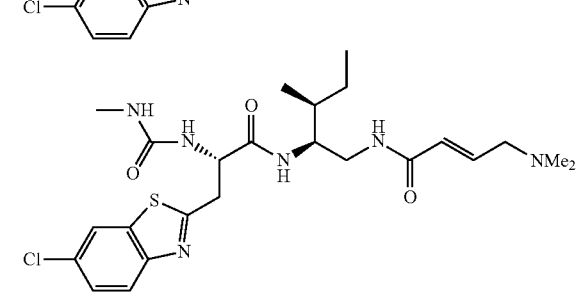

93
-continued
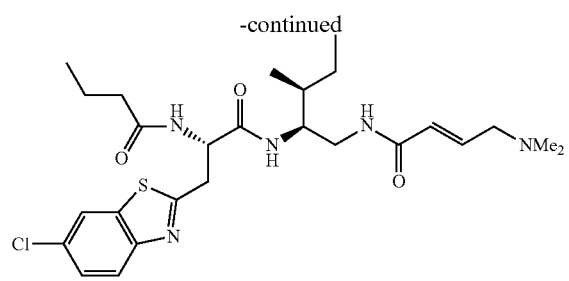
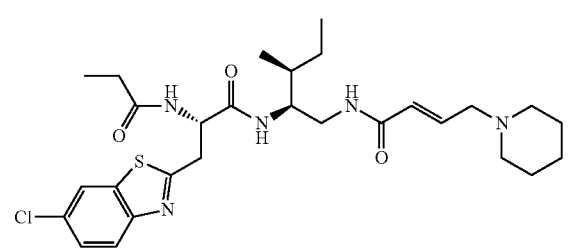
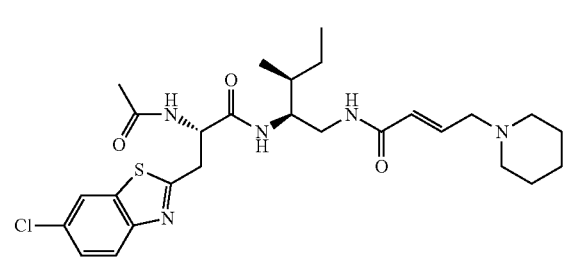
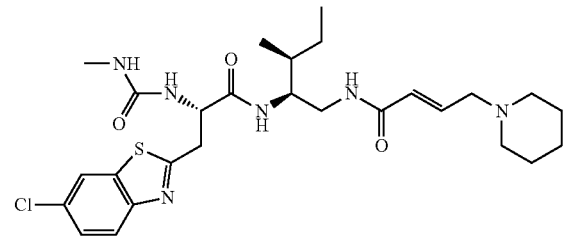
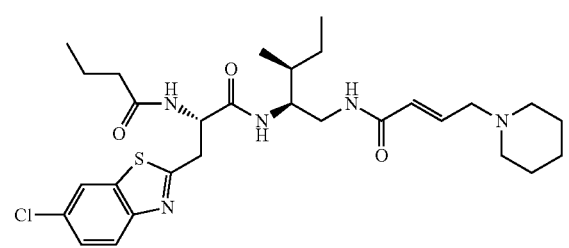
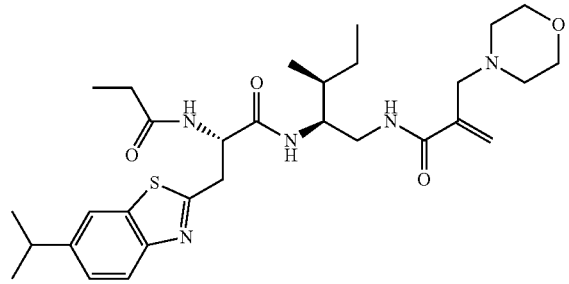
94
-continued
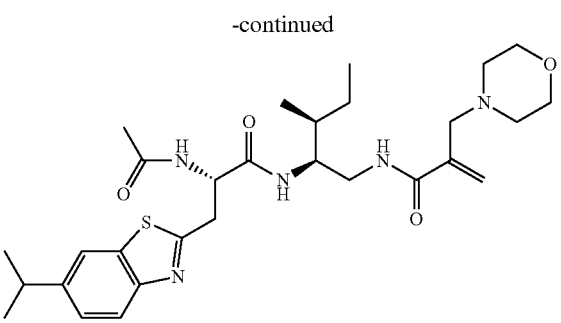
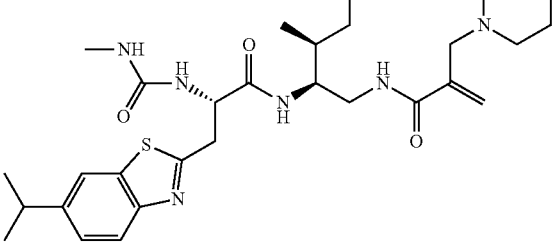
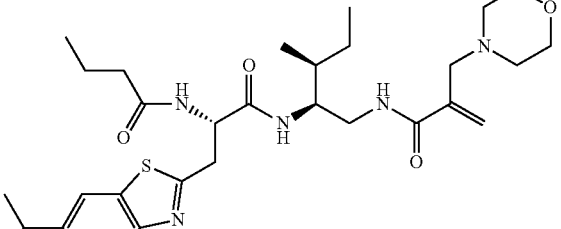
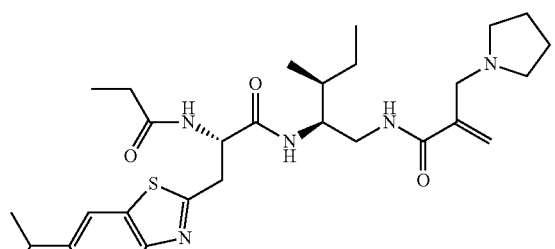
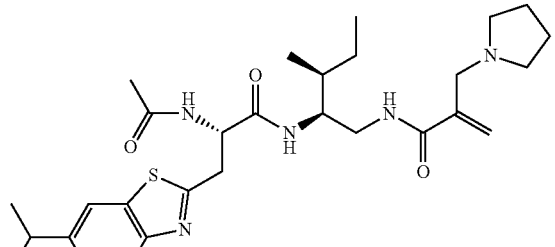
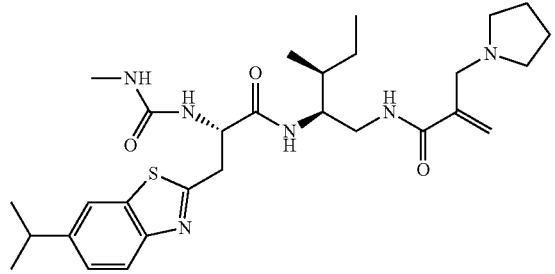

95
-continued
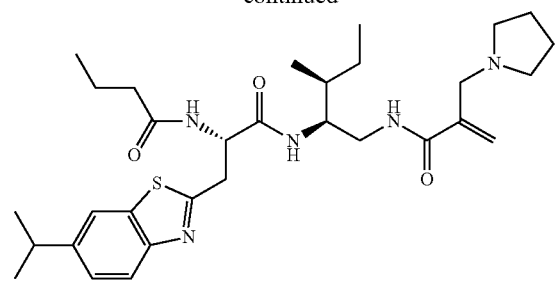
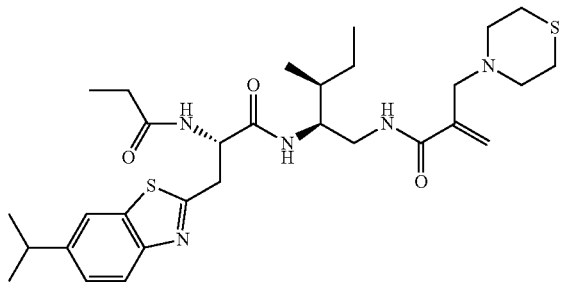
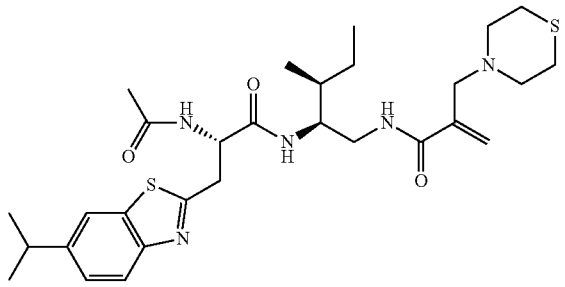
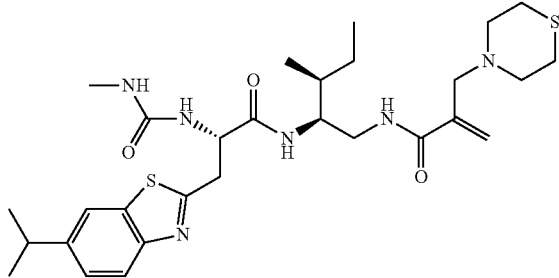
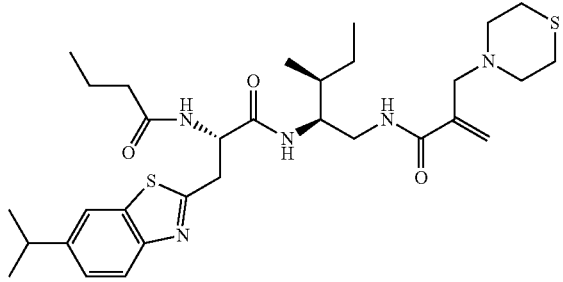
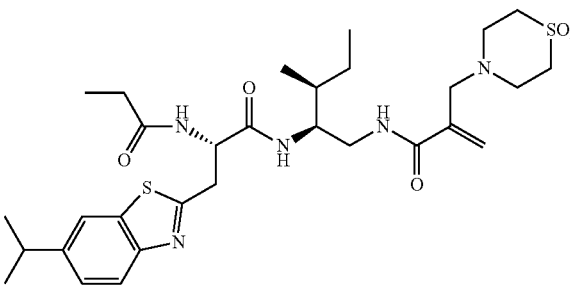
96
-continued
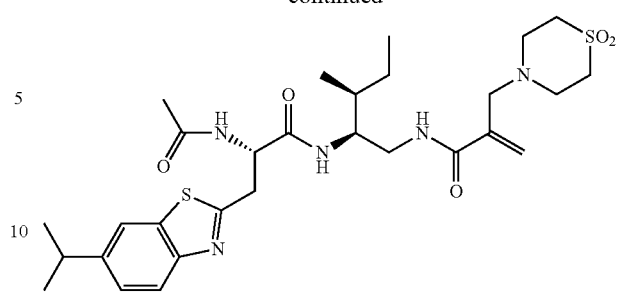
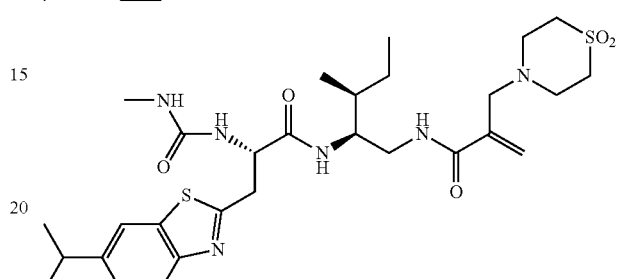

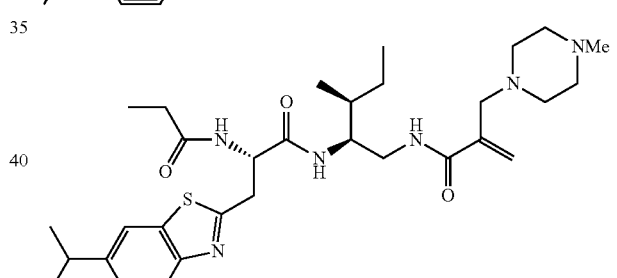
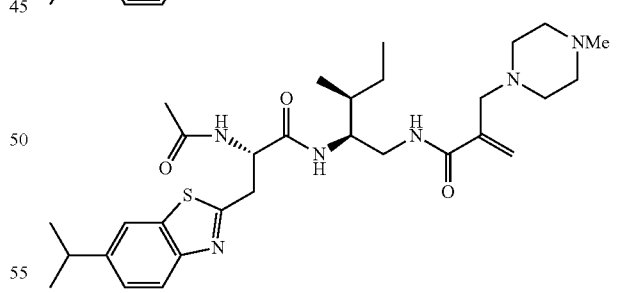
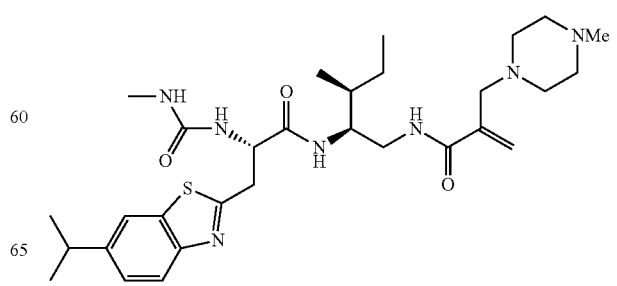

97
-continued
98
-continued
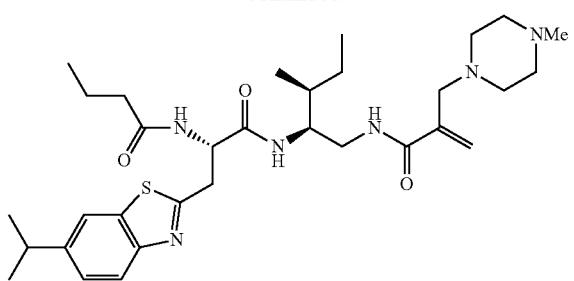
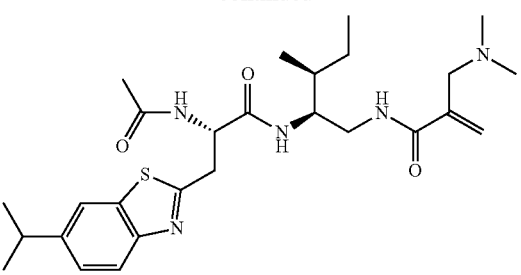
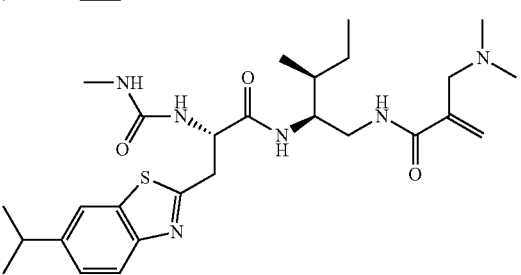
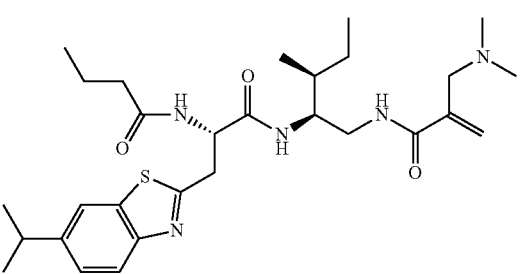
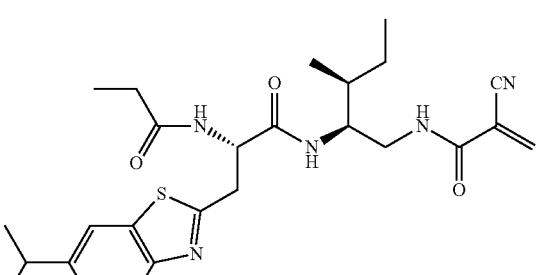
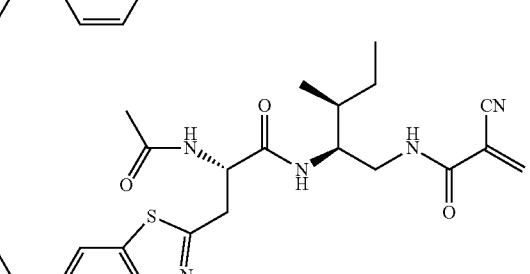
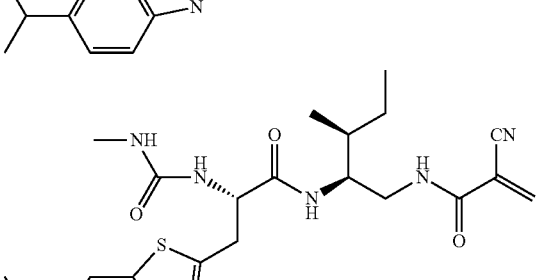

99
-continued
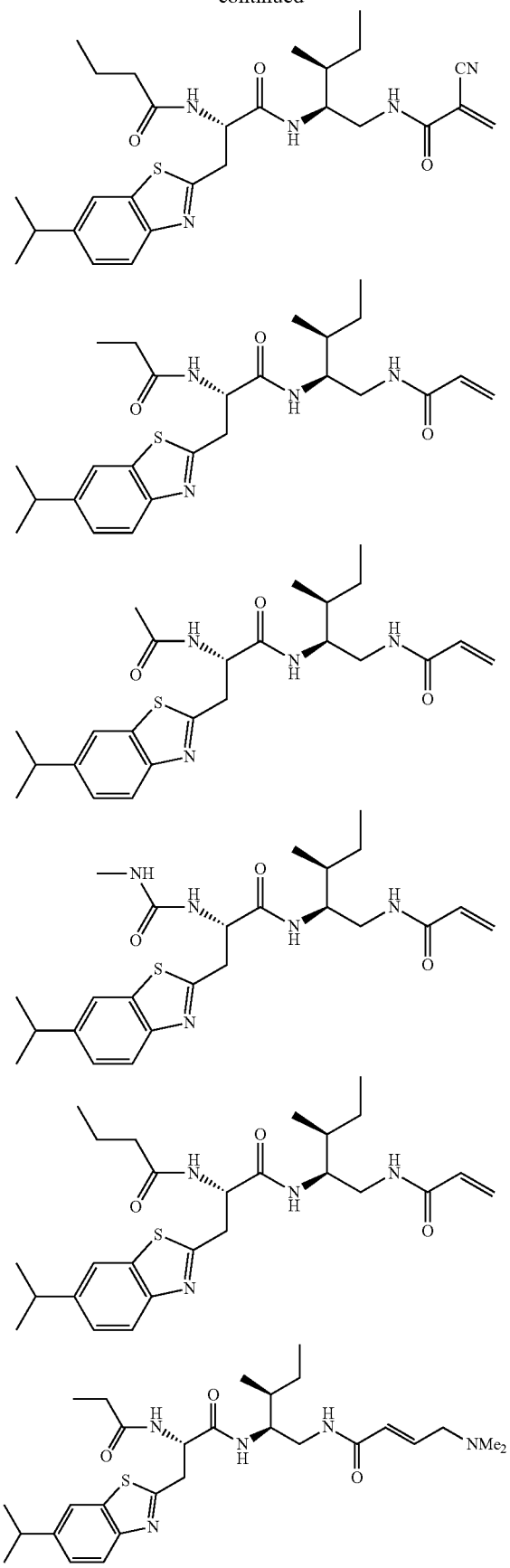
100
-continued
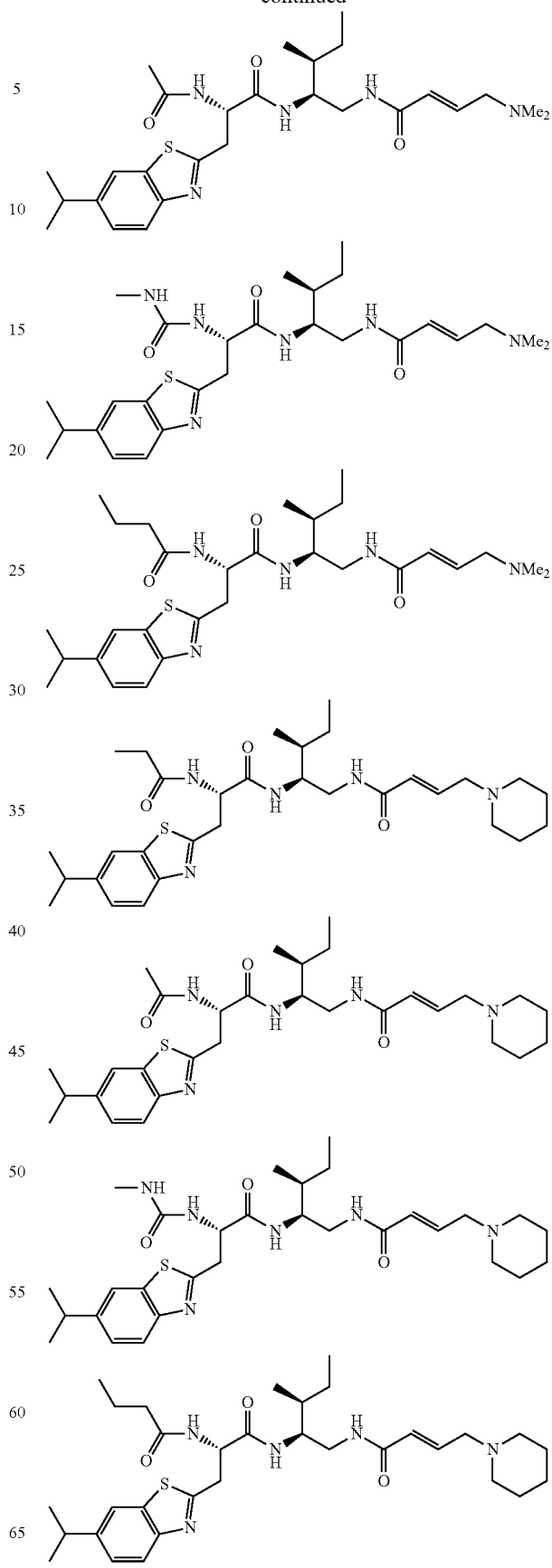

101
-continued
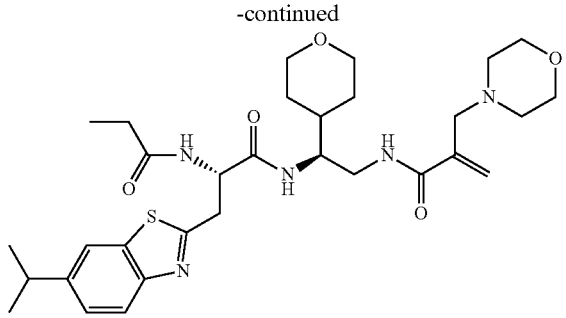
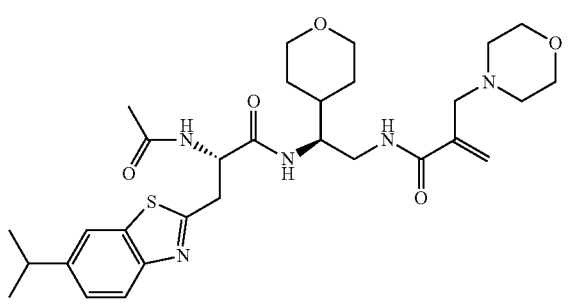
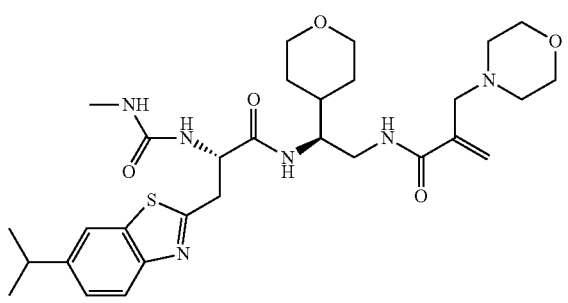
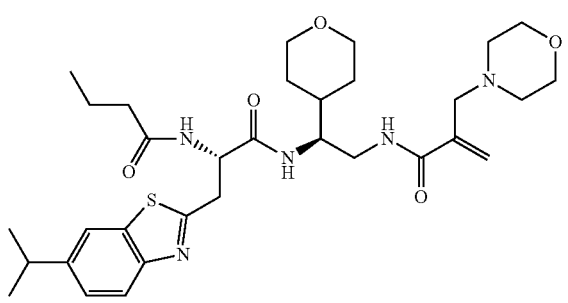
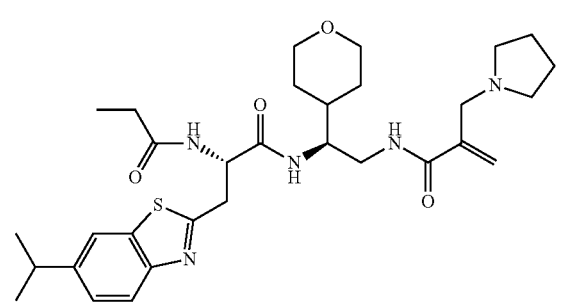
102
-continued
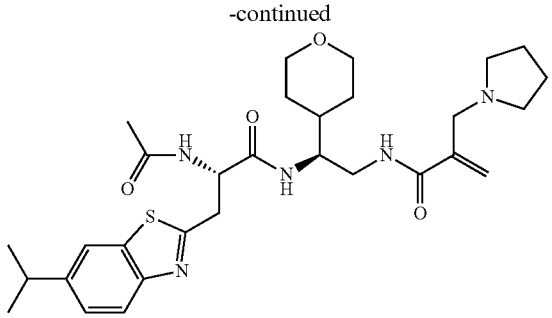
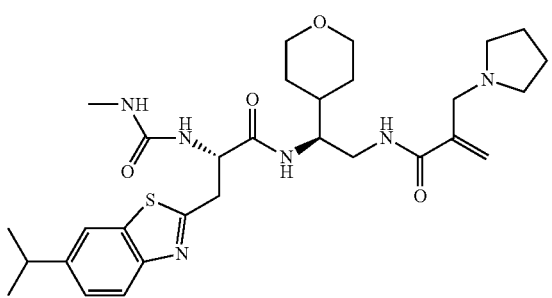
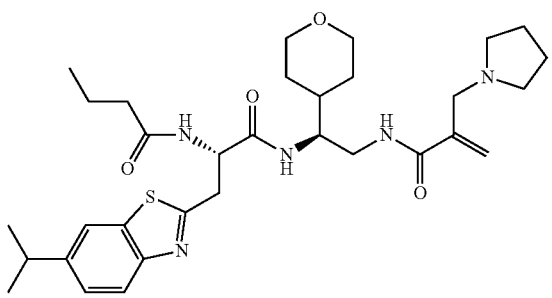
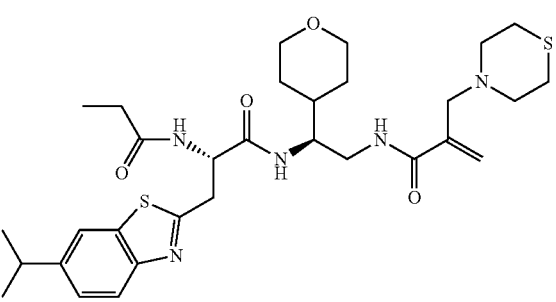
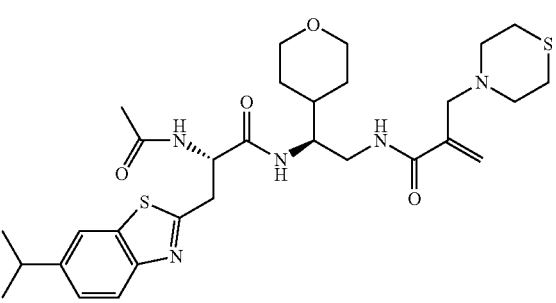

103
-continued
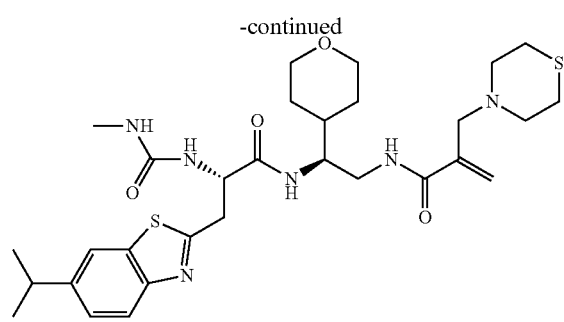
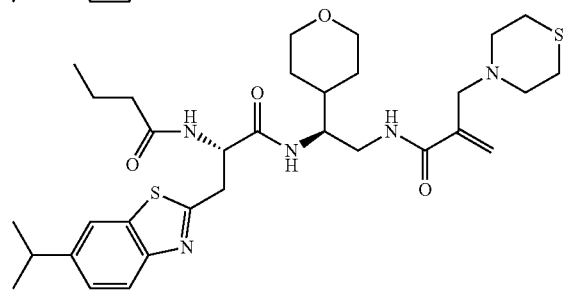
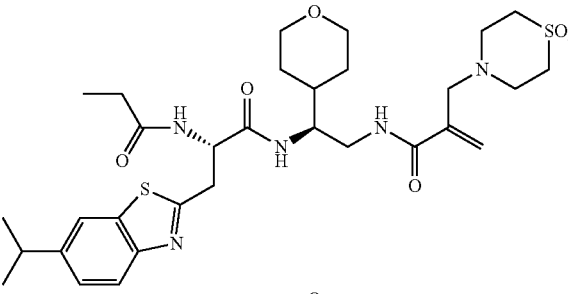
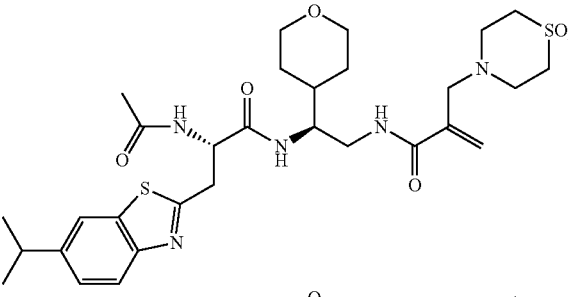
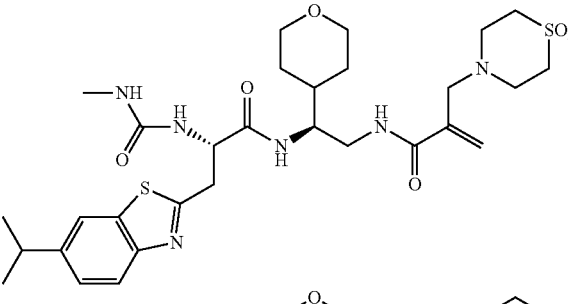
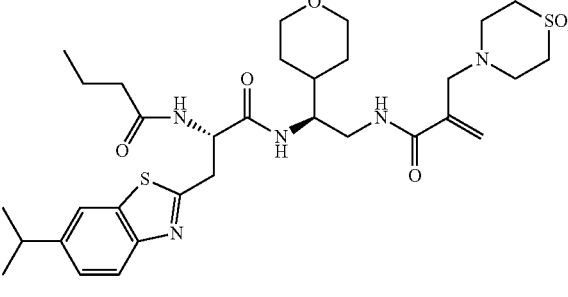
104
-continued
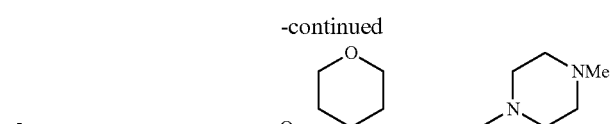

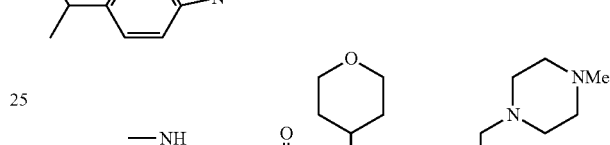

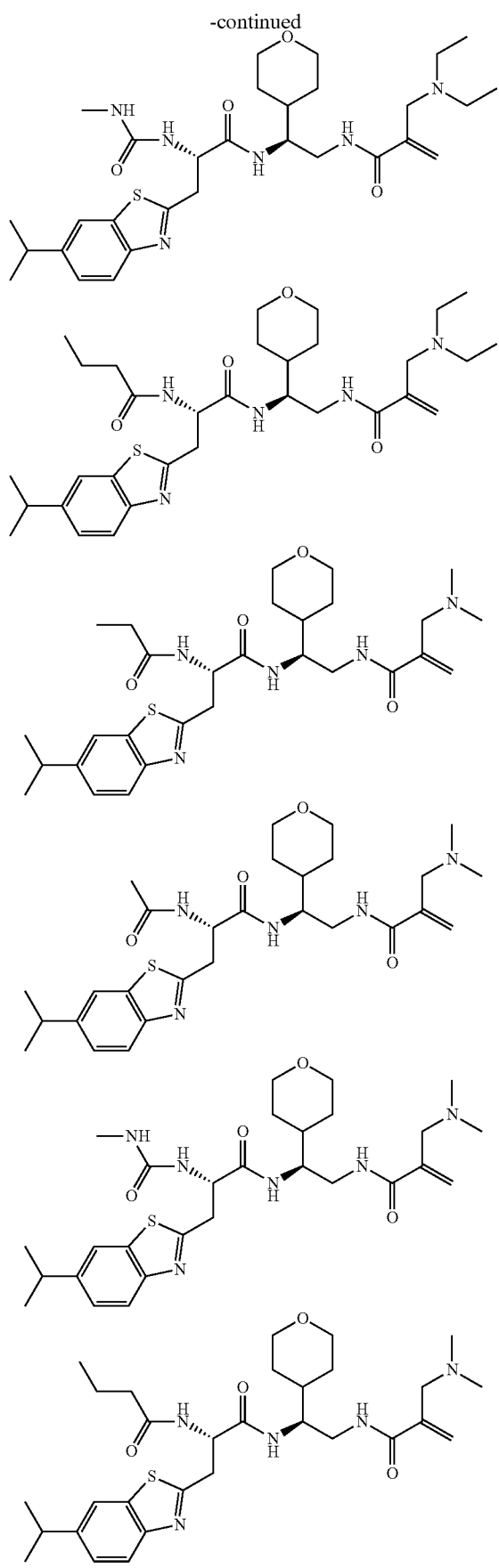
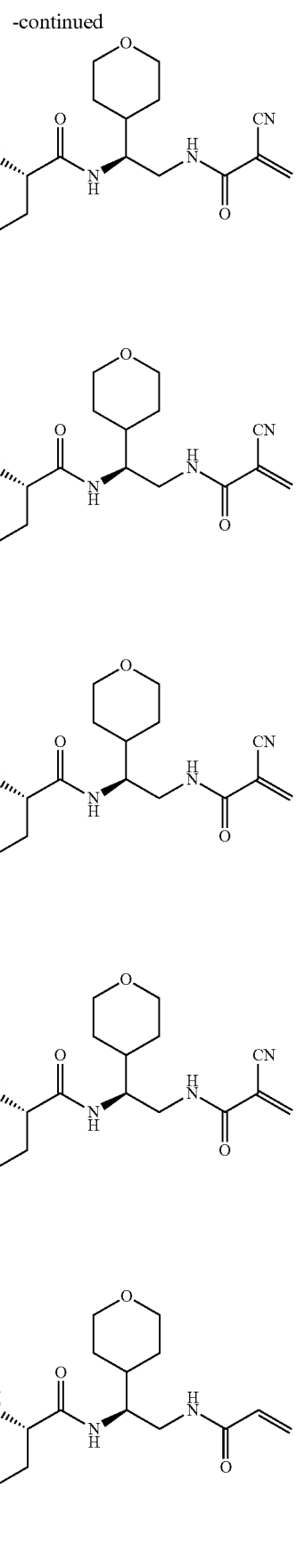

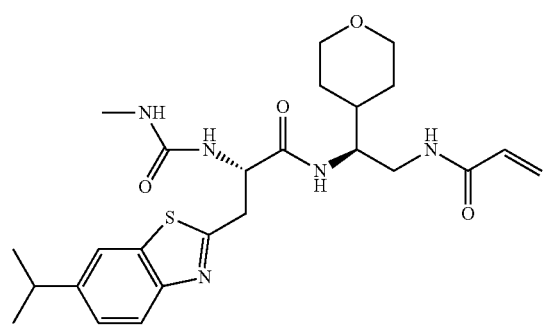
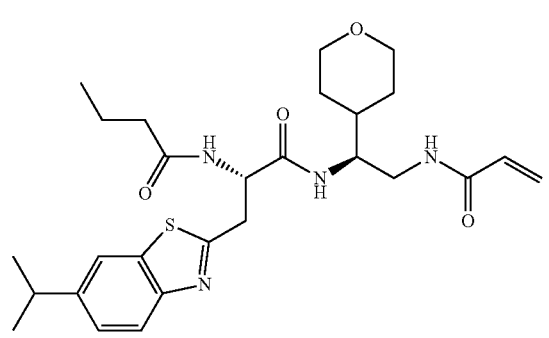
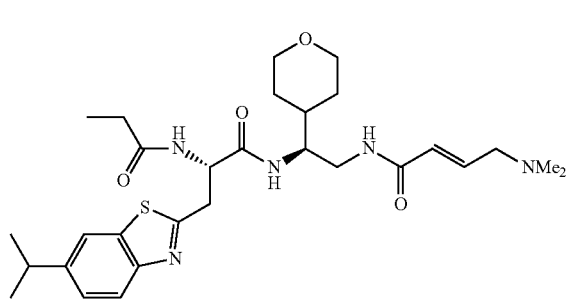
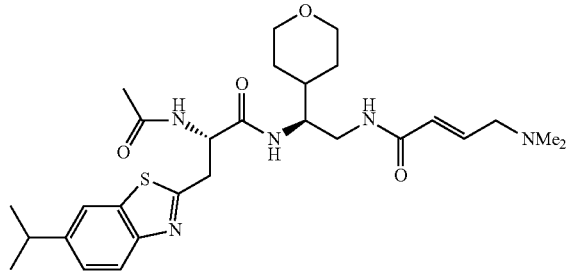
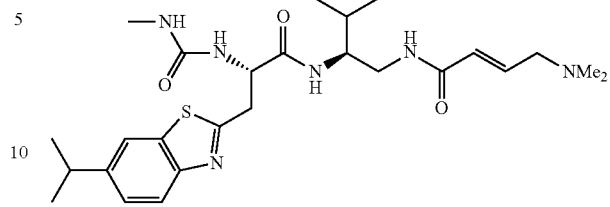
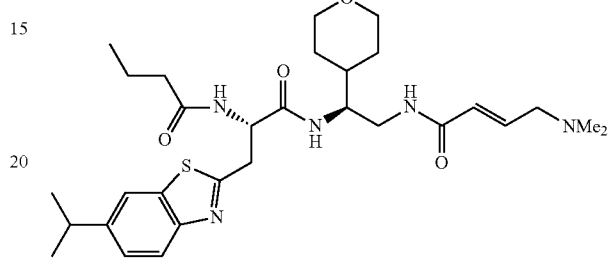
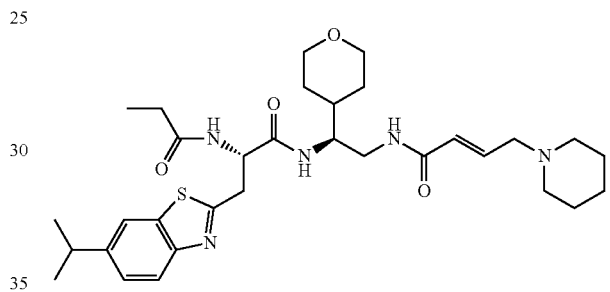
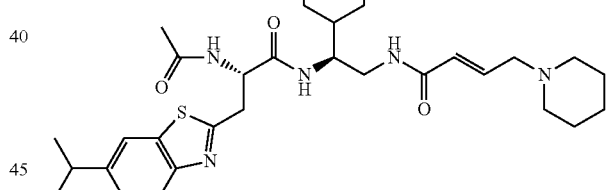
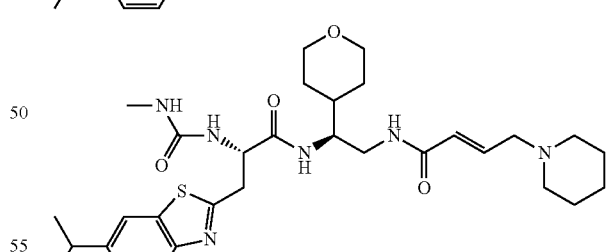
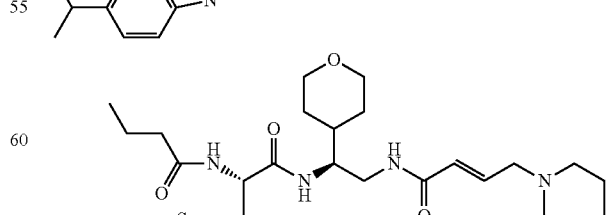
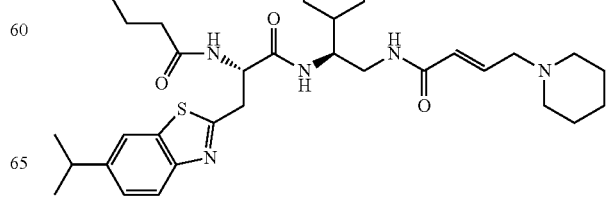

109
-continued
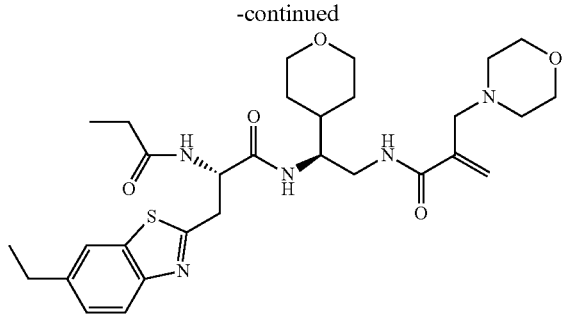
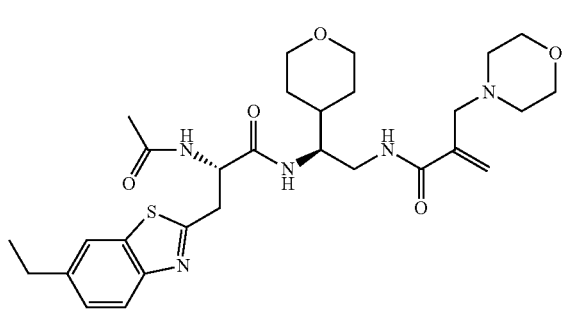
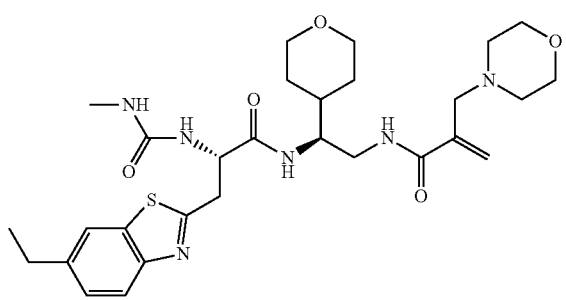
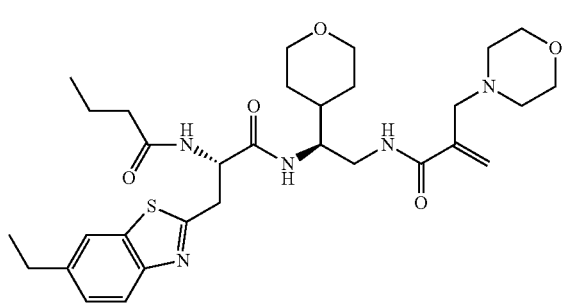
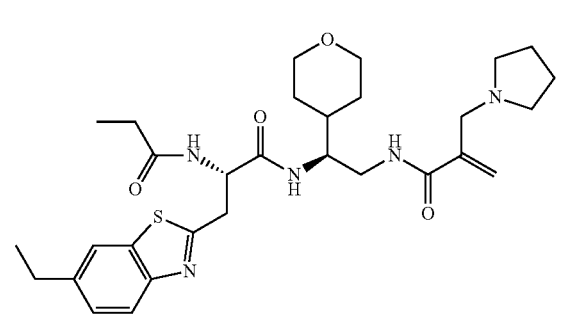
110
-continued
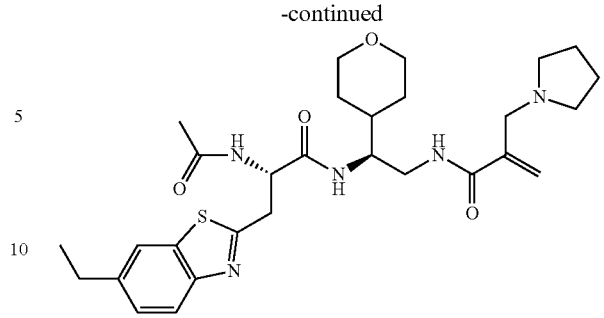
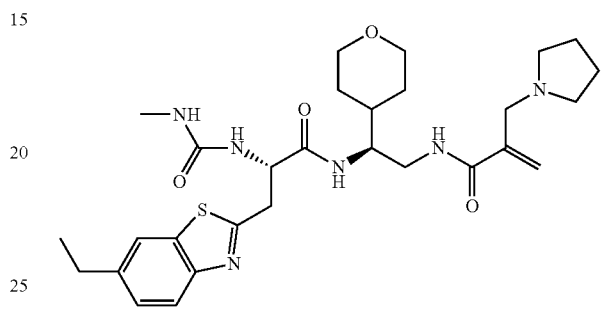
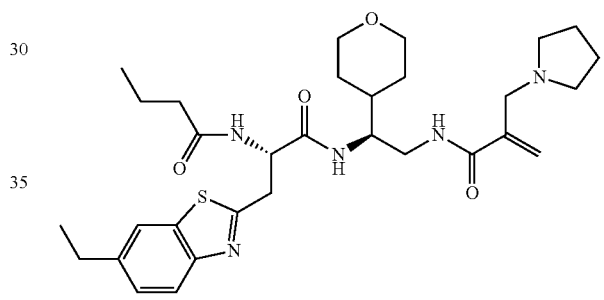
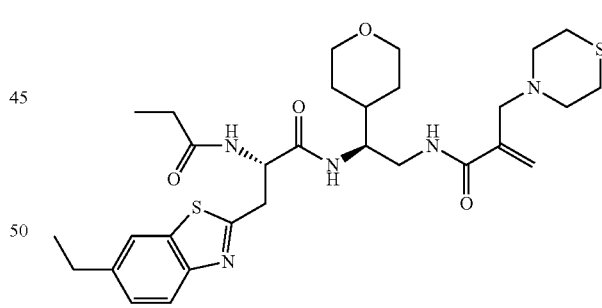
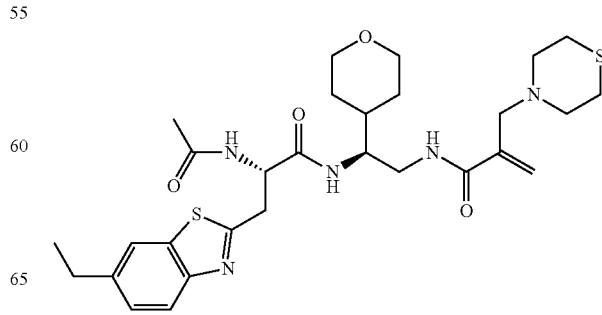

111
-continued
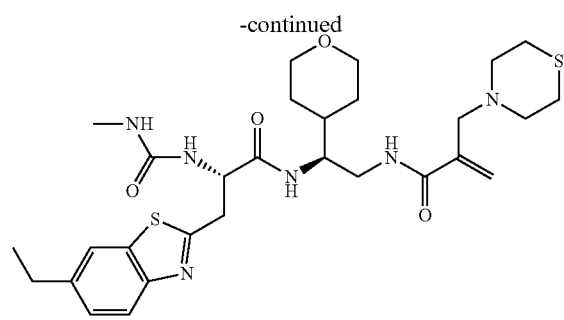
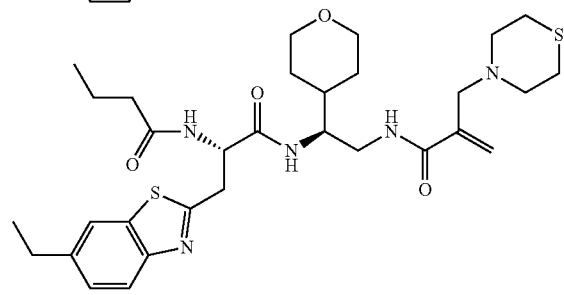
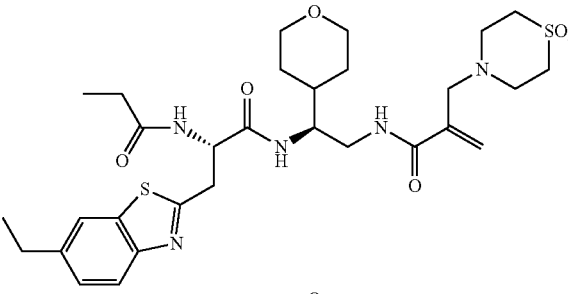
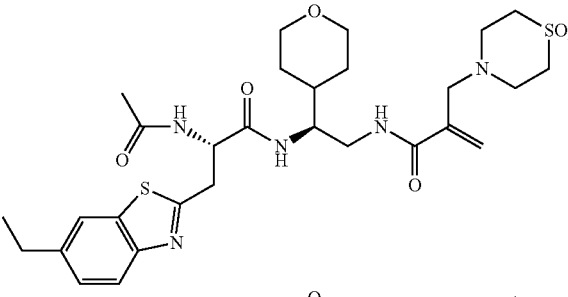
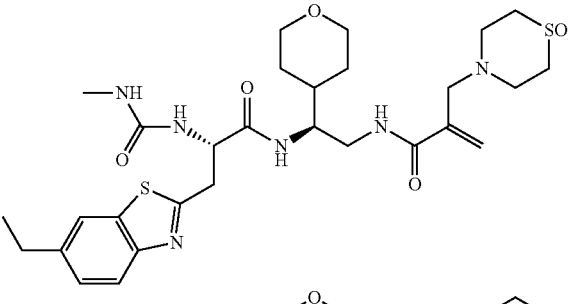
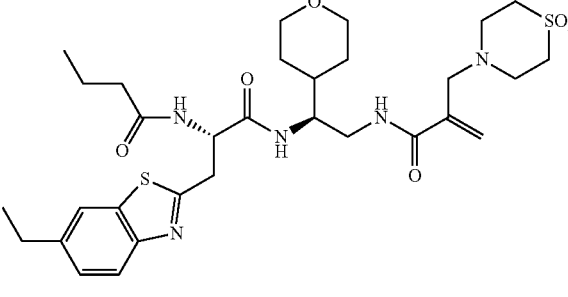
112
-continued
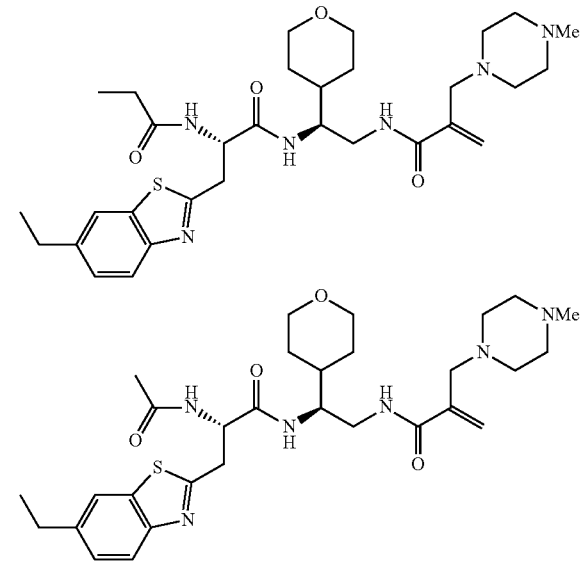
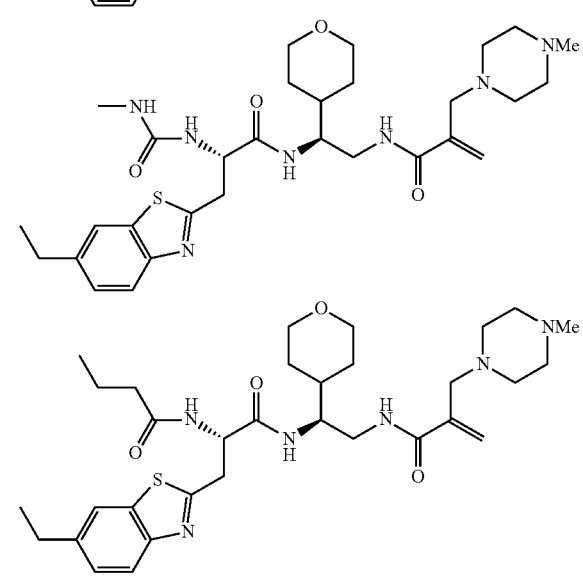
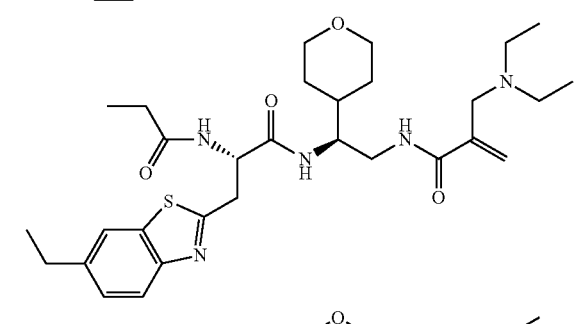
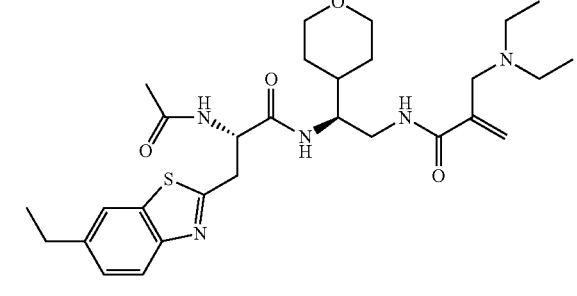

113
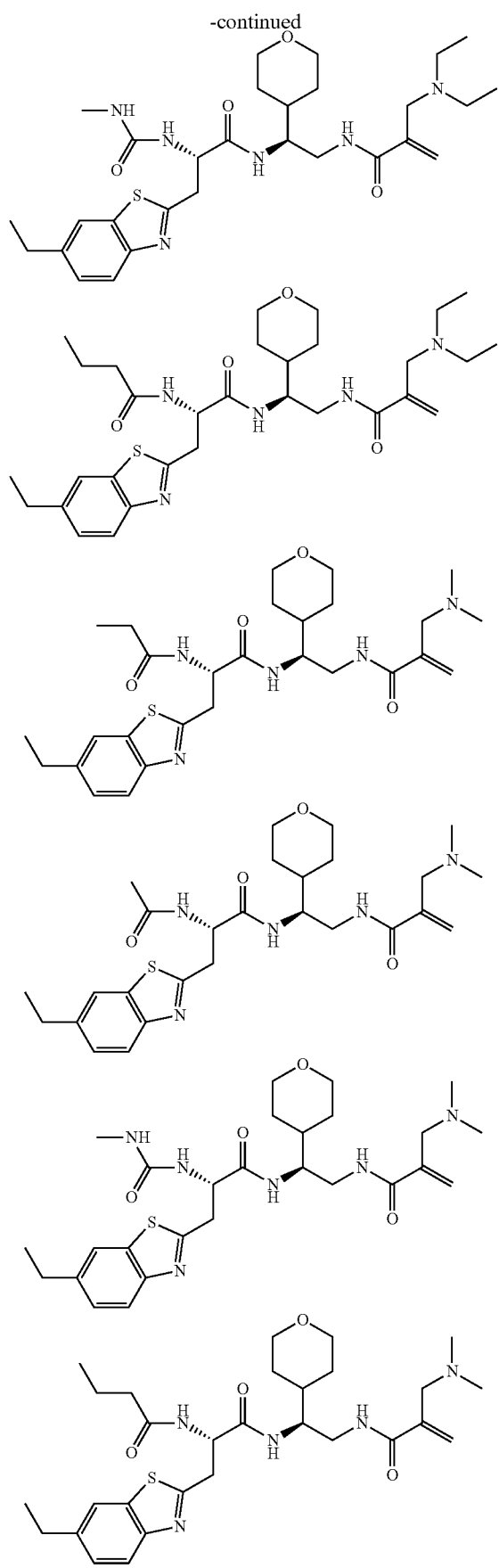
114
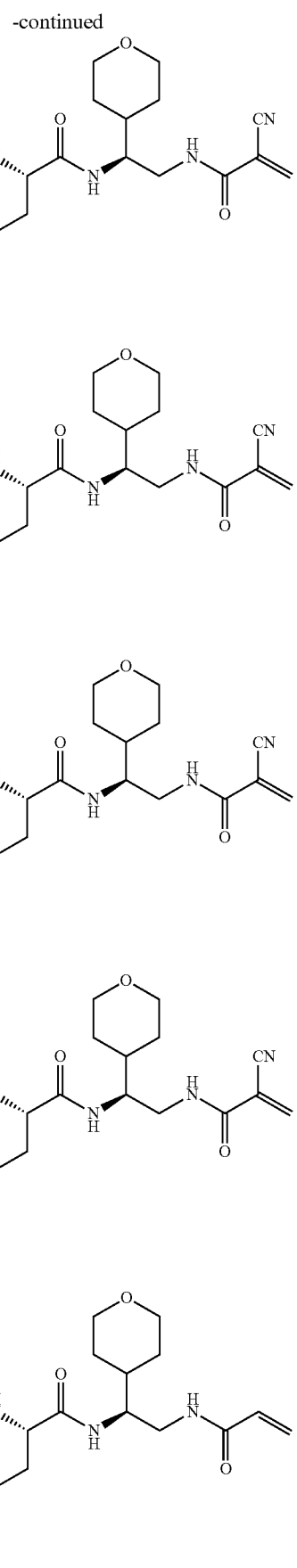

115
-continued
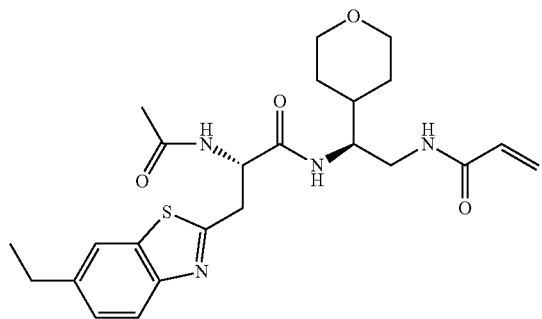
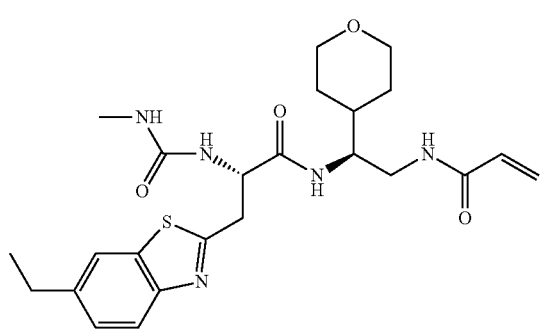
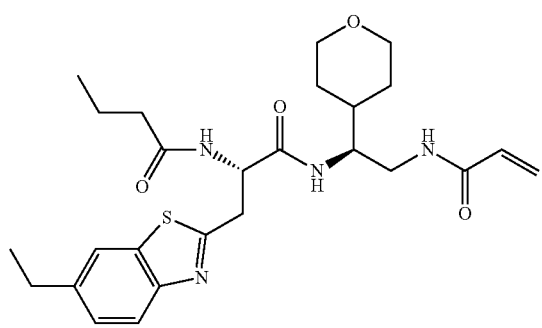
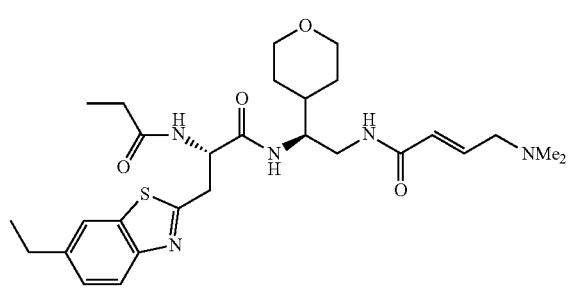
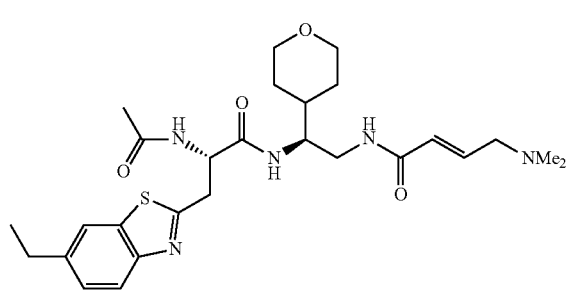
116
-continued
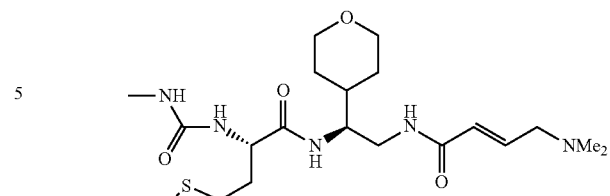
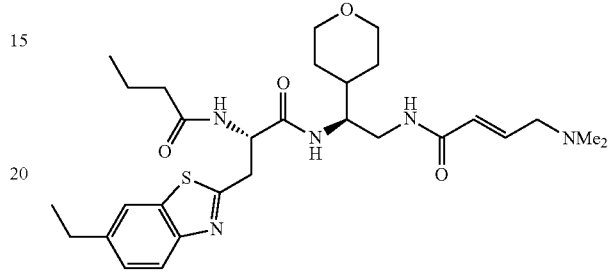
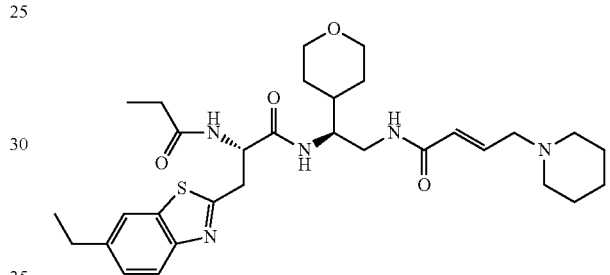
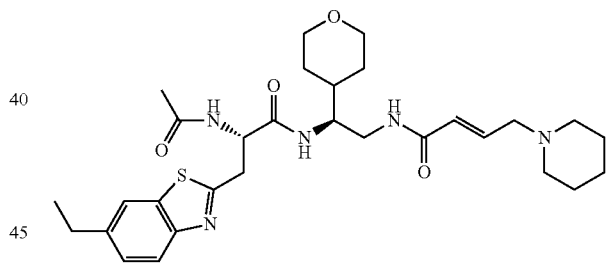
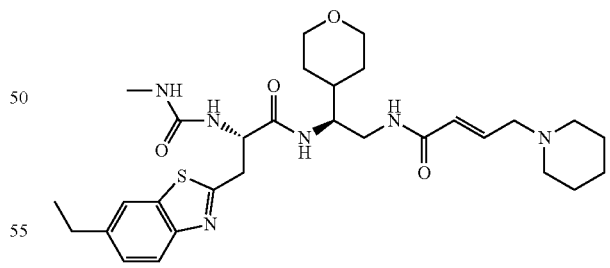

117
-continued

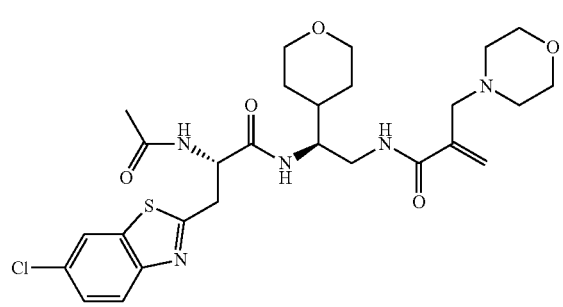
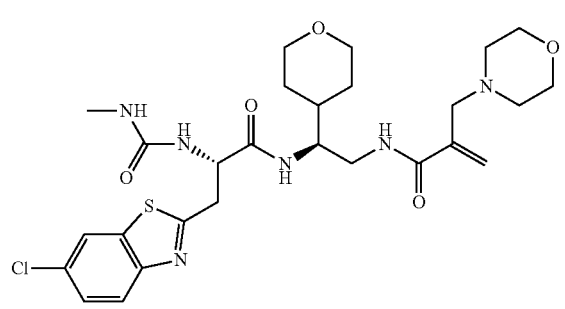
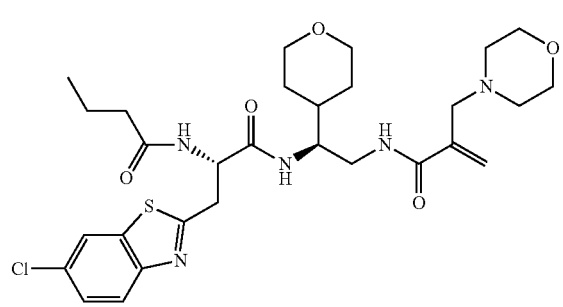
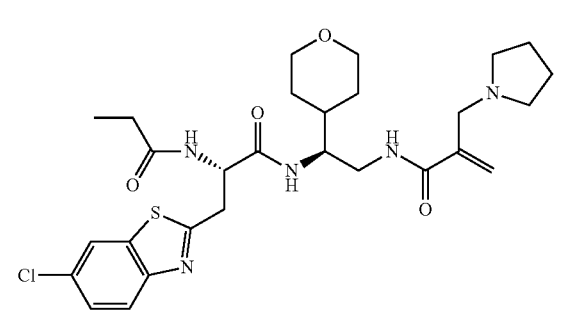
118
-continued
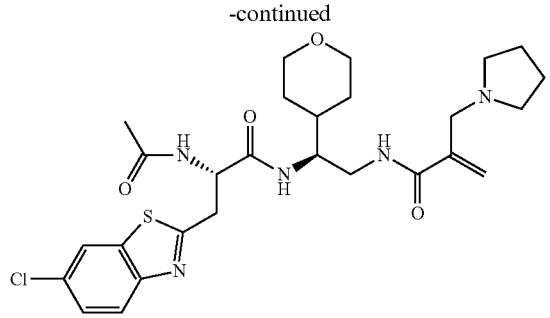
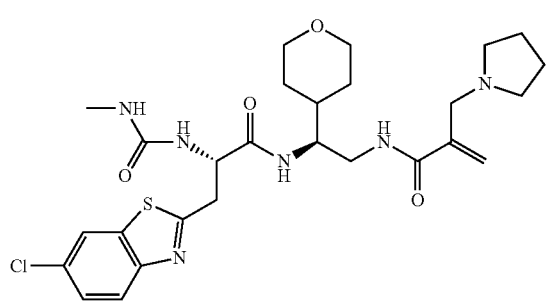
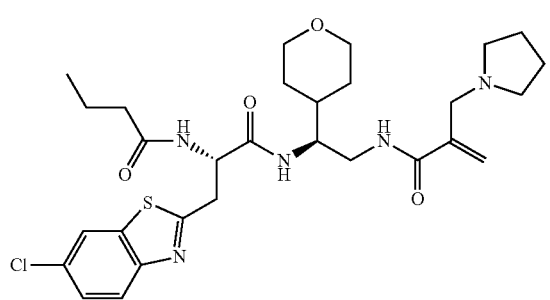
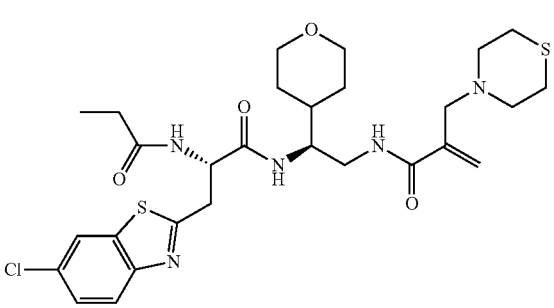
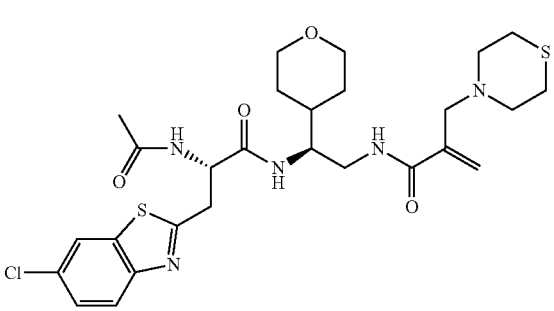

119
-continued
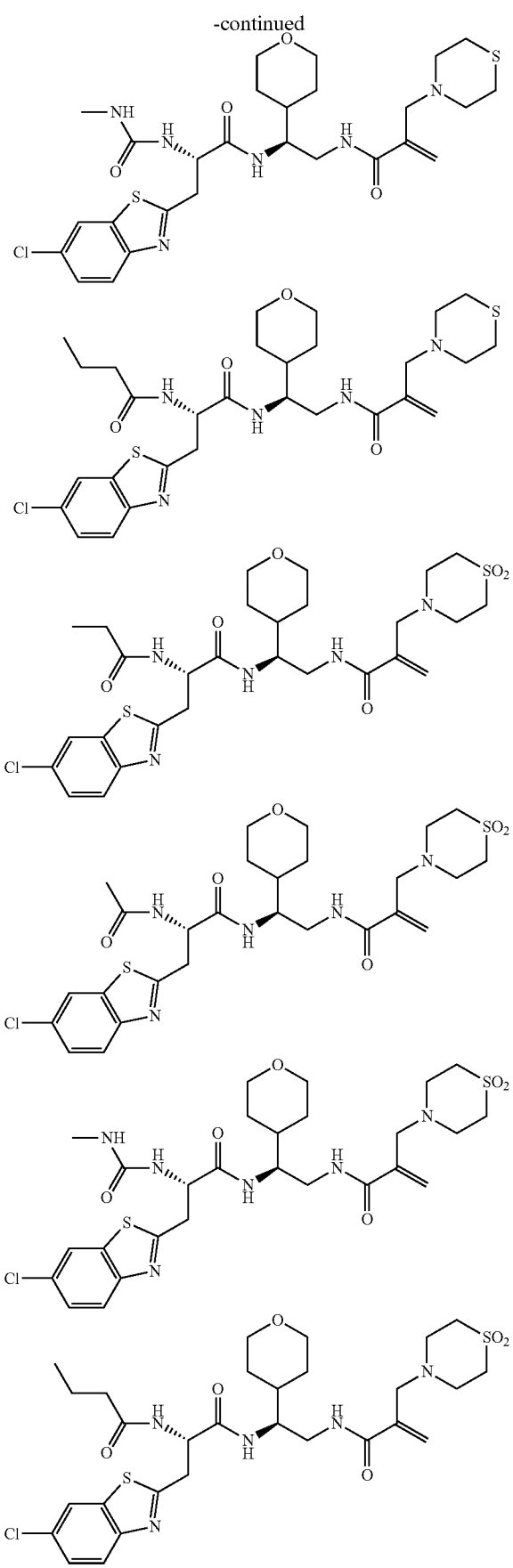
120
-continued
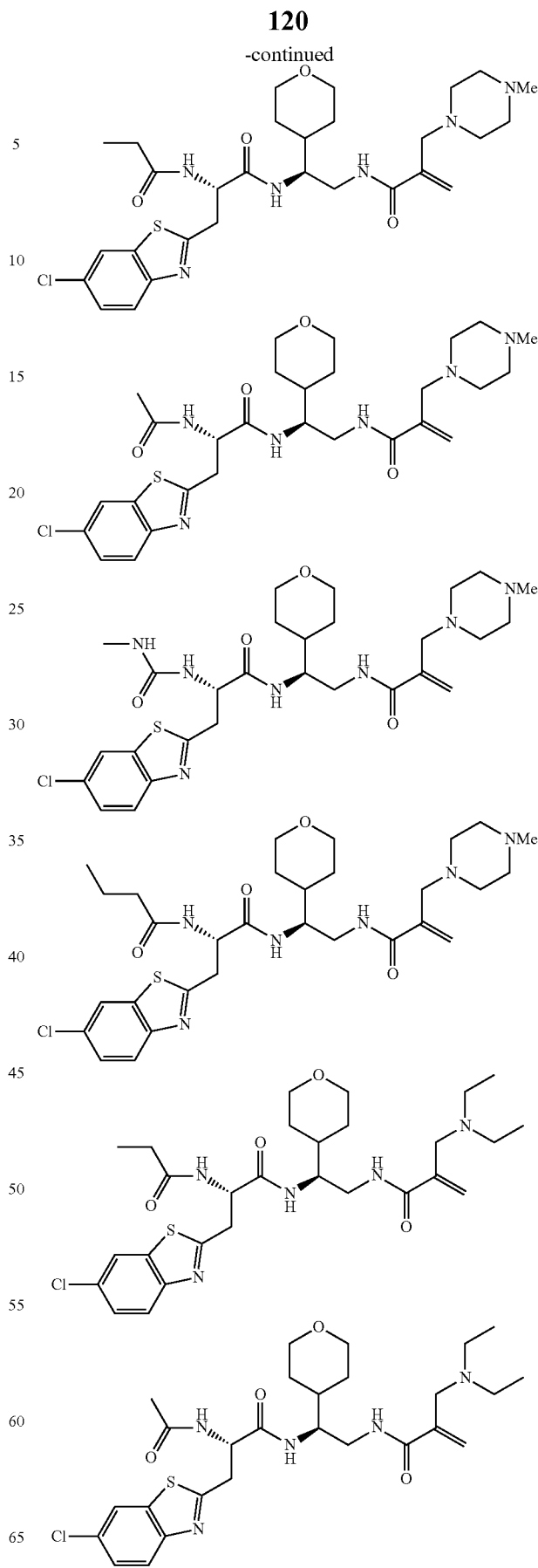

121
-continued
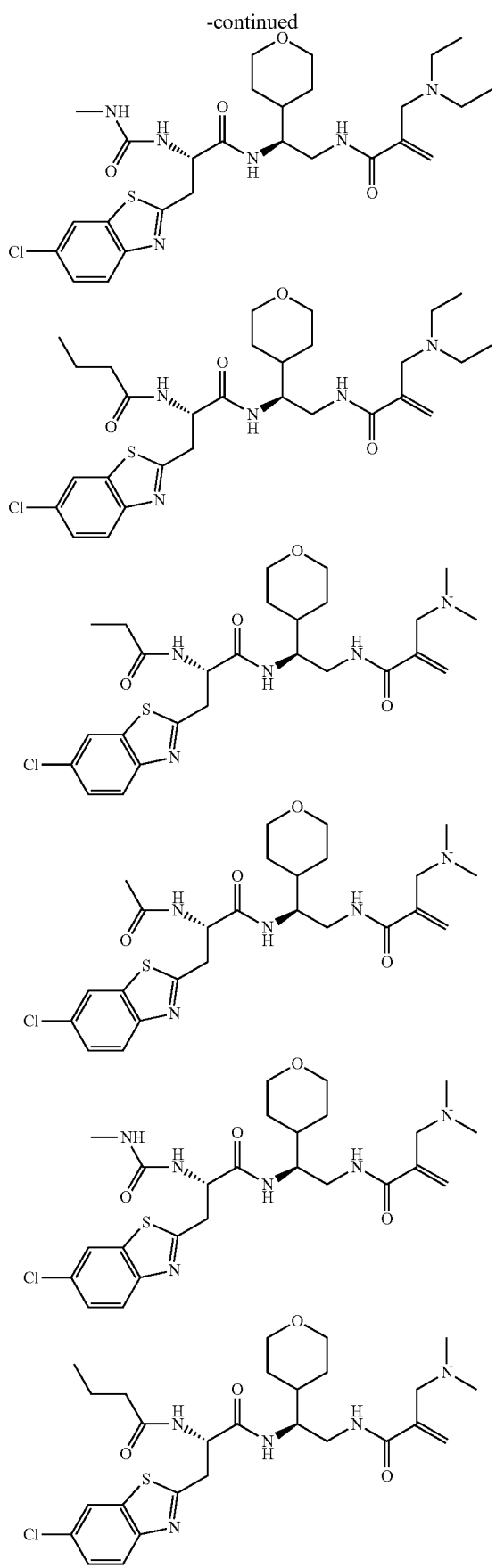
122
-continued
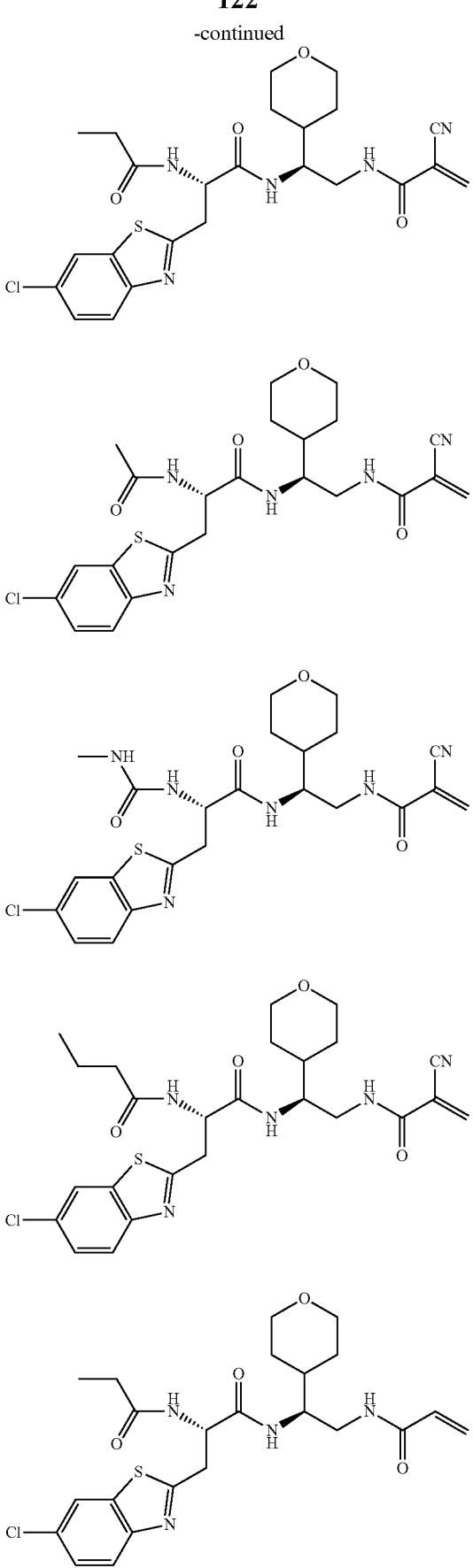

123
-continued
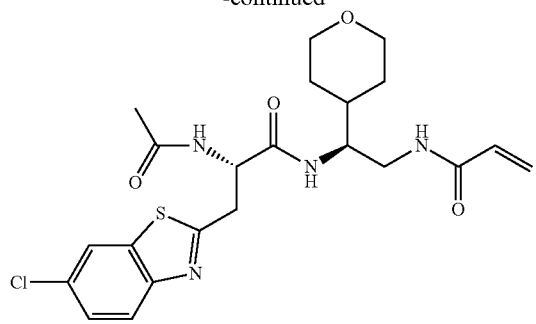
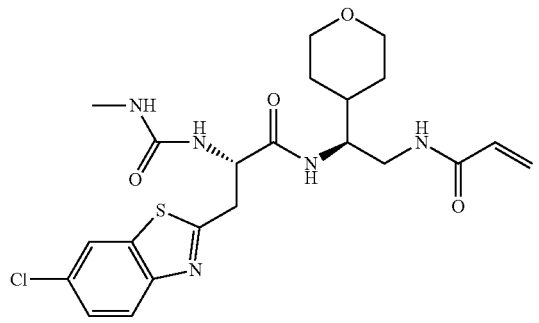
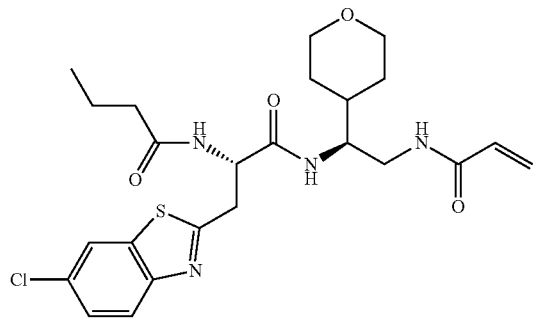
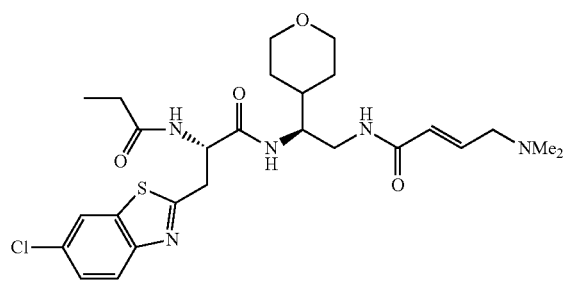
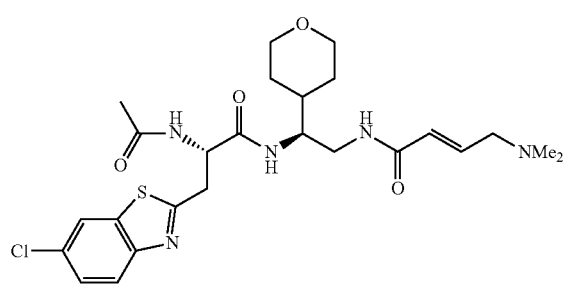
124
-continued
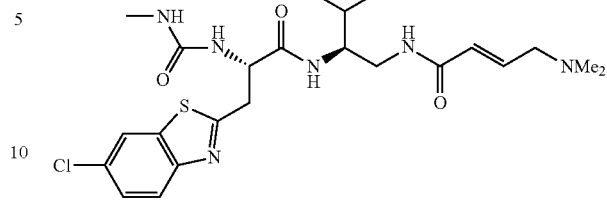
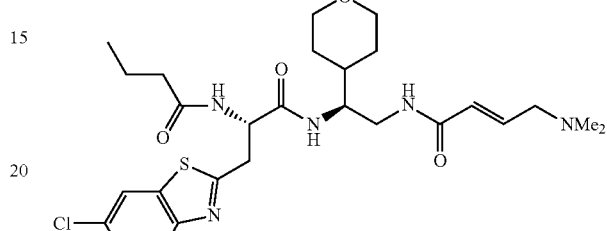
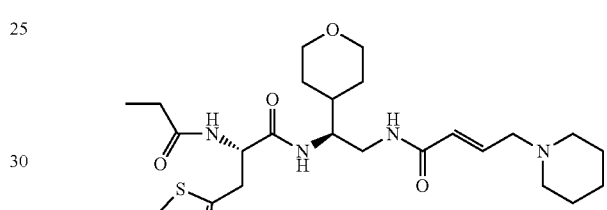
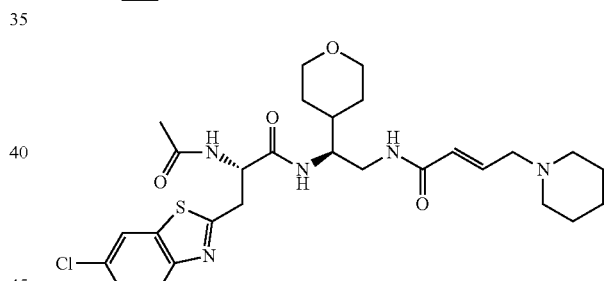
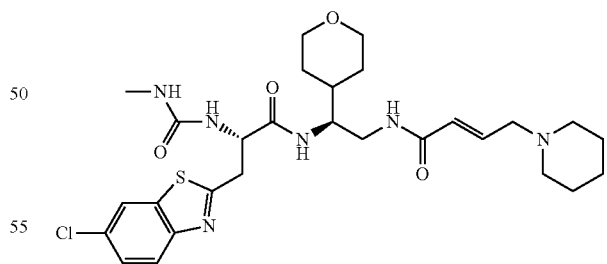
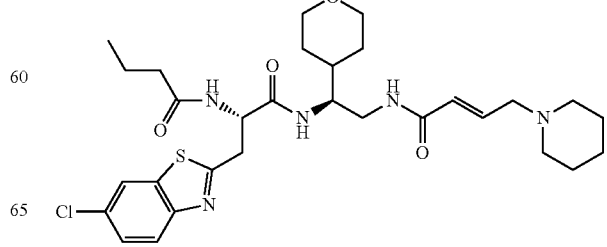

125
-continued
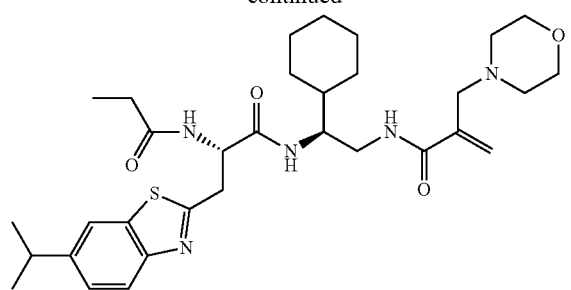
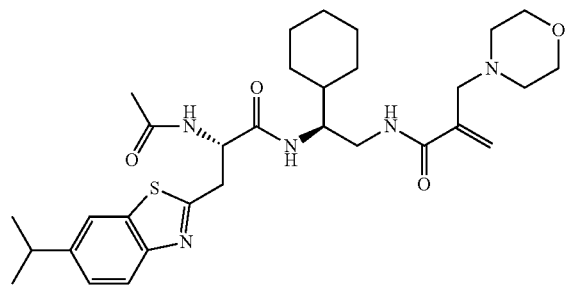
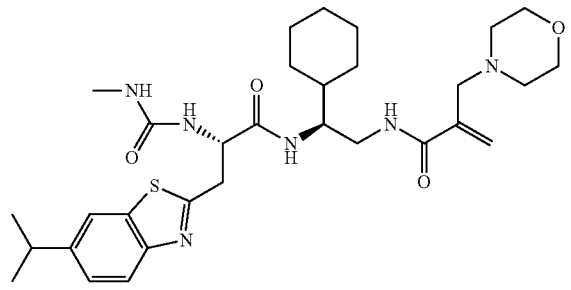
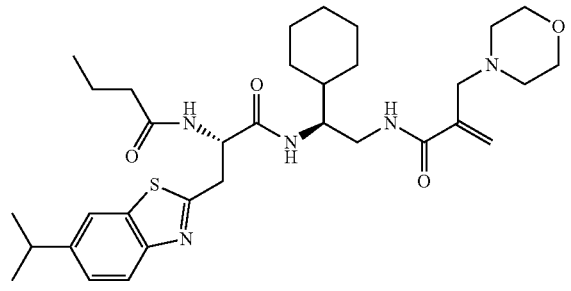
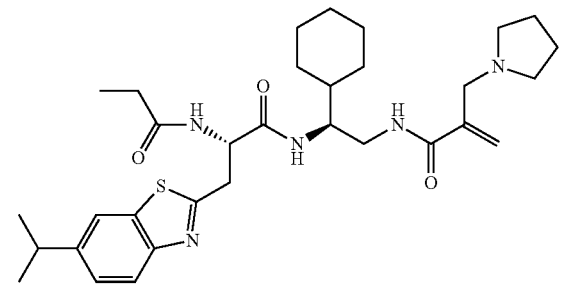
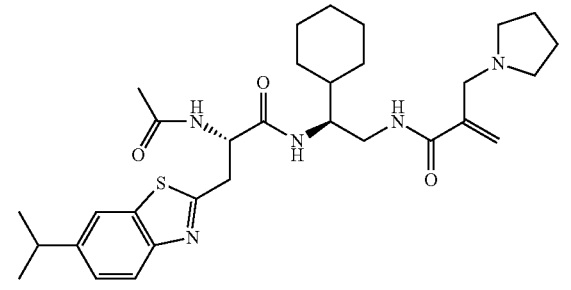
126
-continued
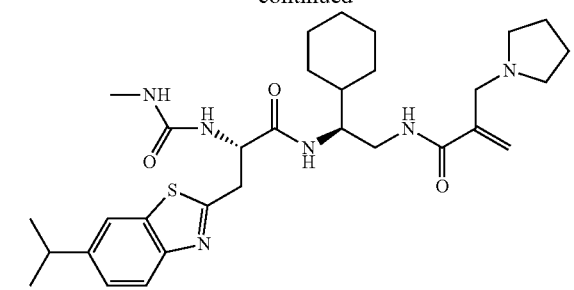
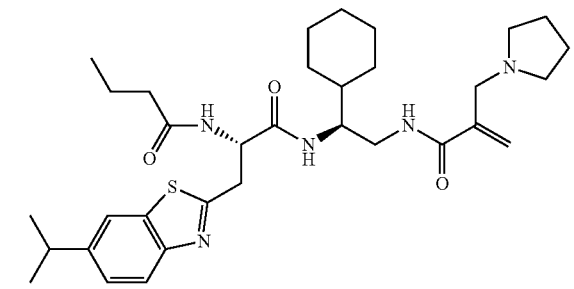
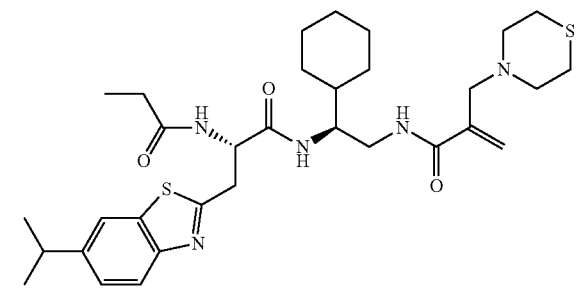
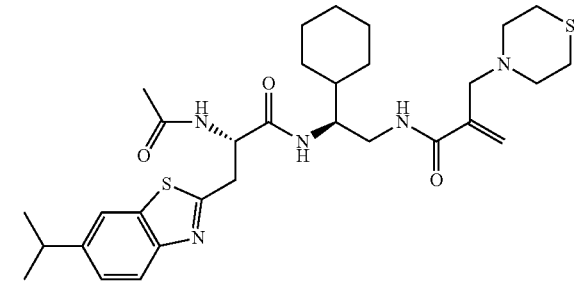
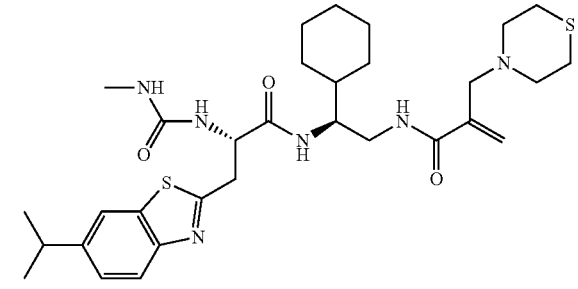
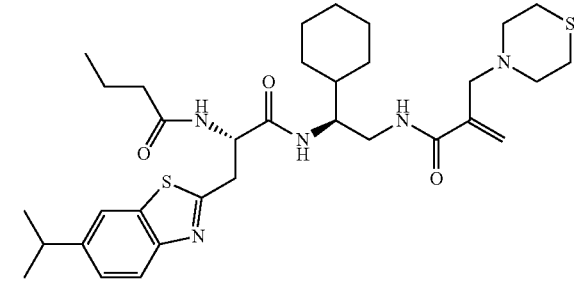

127
-continued
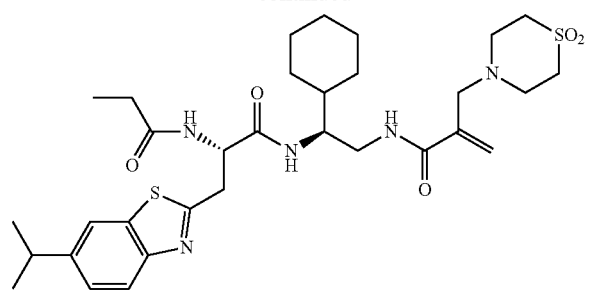
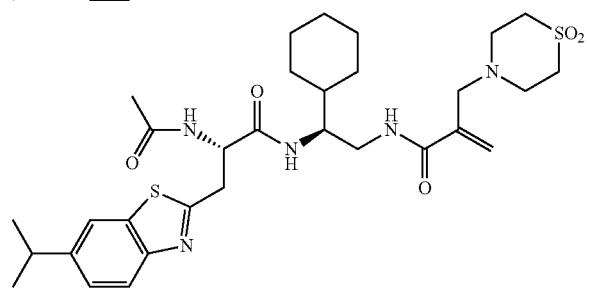
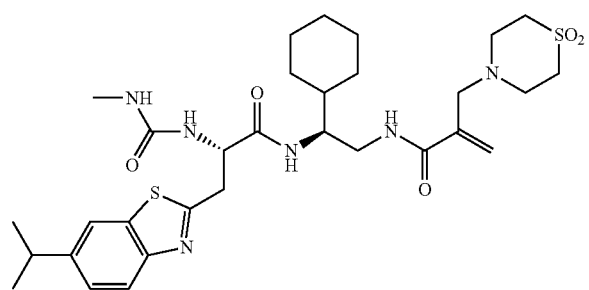
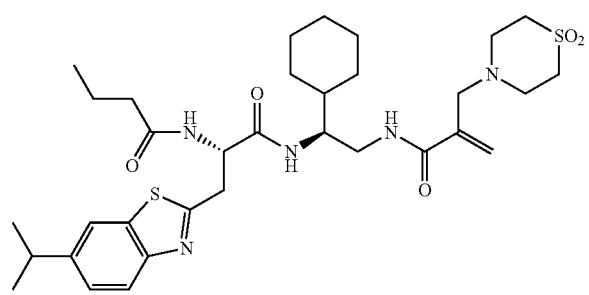
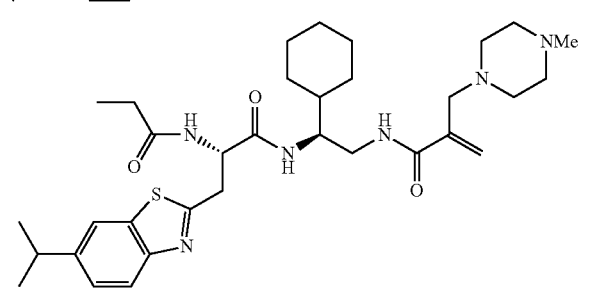
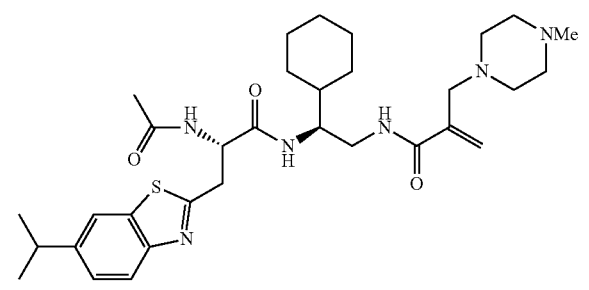
128
-continued
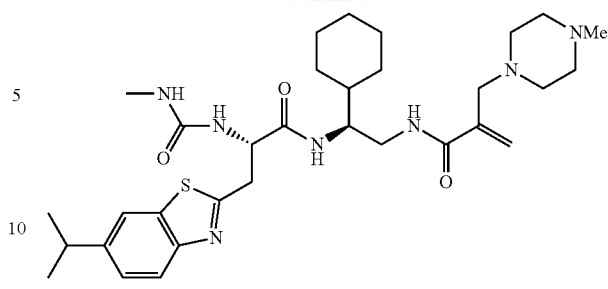
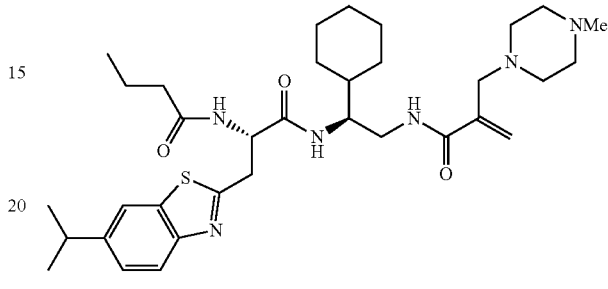
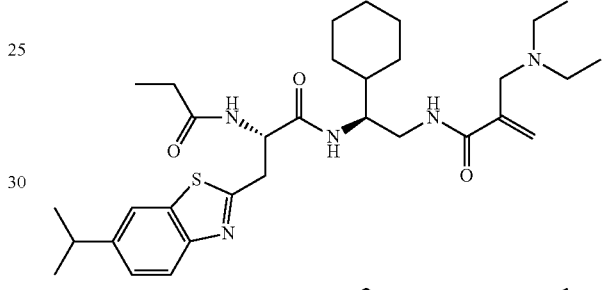
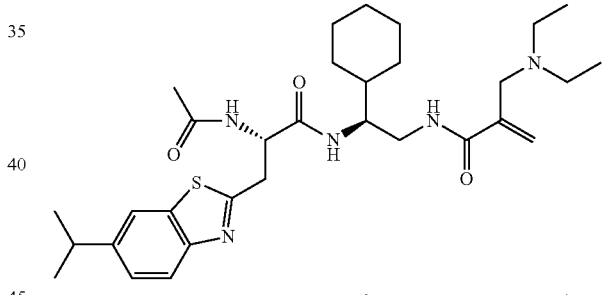
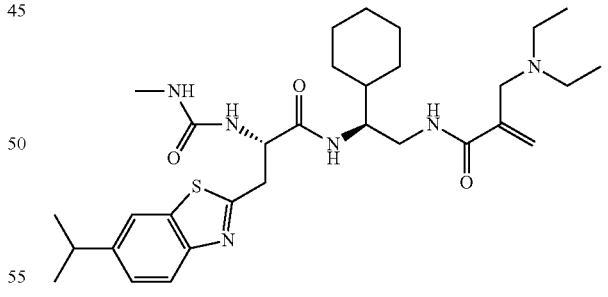
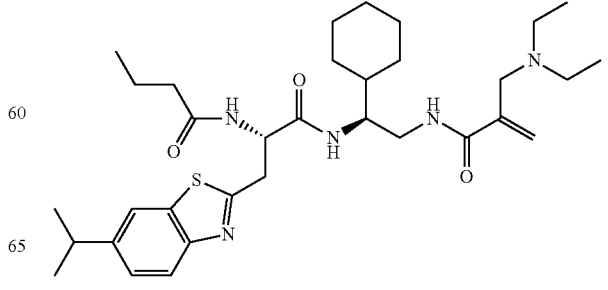

129
-continued
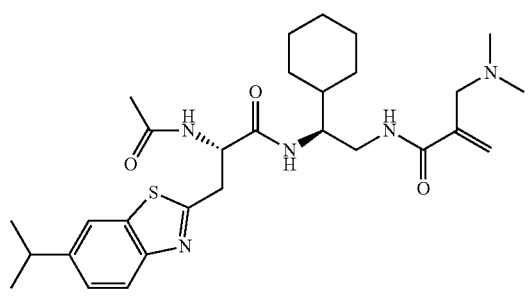
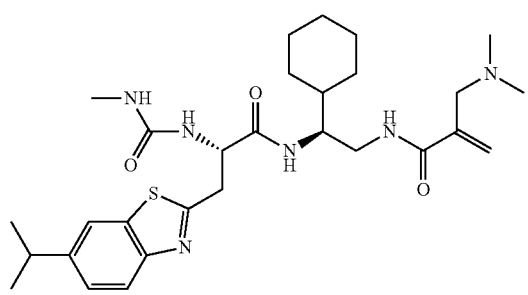
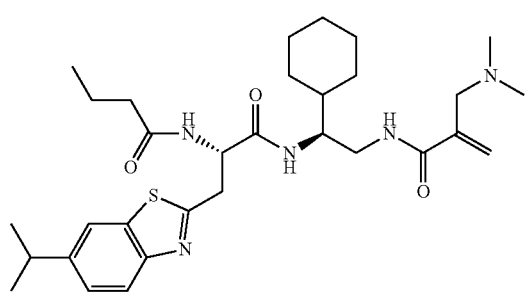
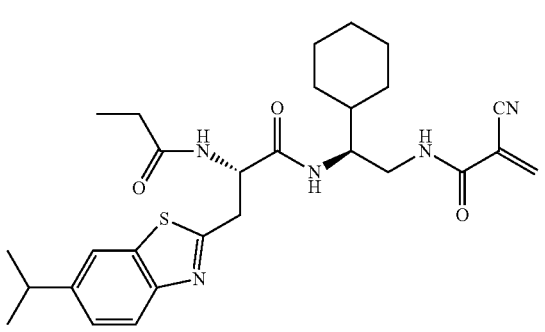
130
-continued
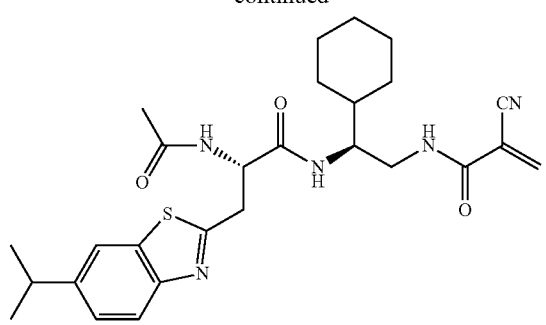
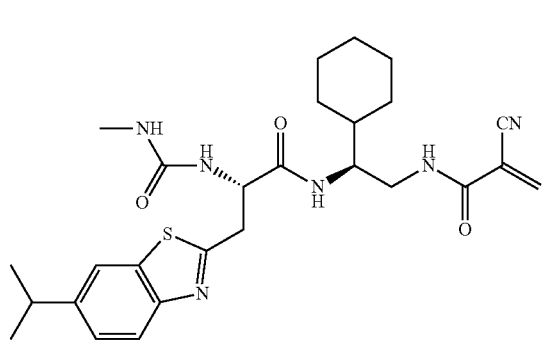
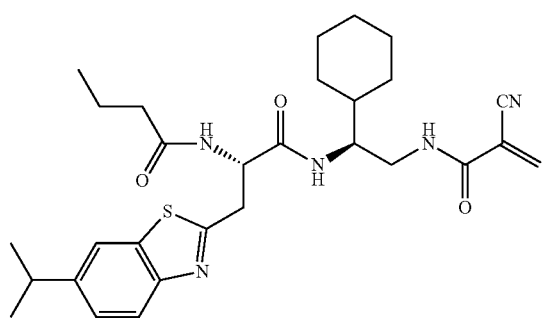
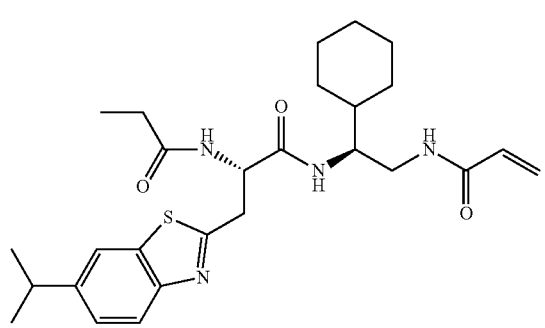
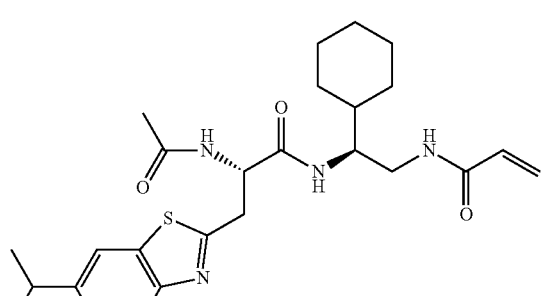

131
-continued
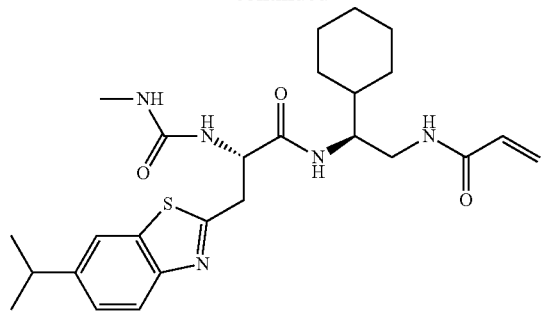
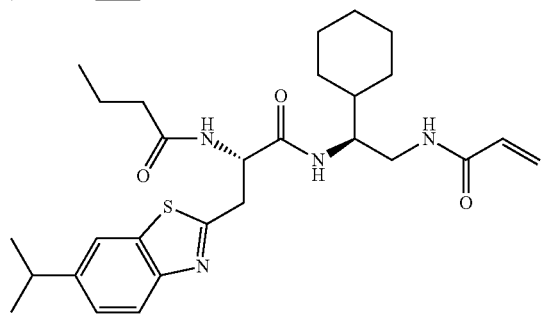
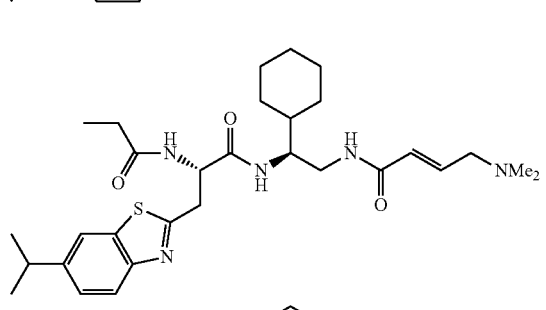
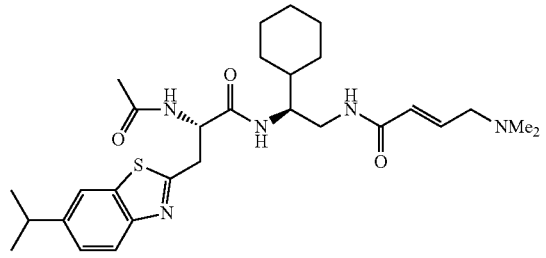
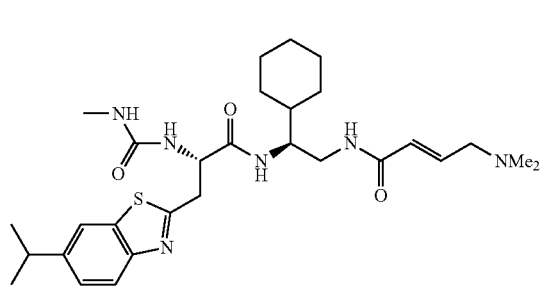
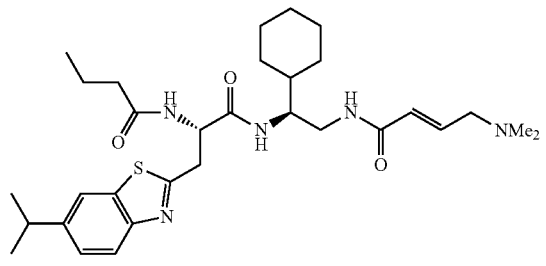
132
-continued
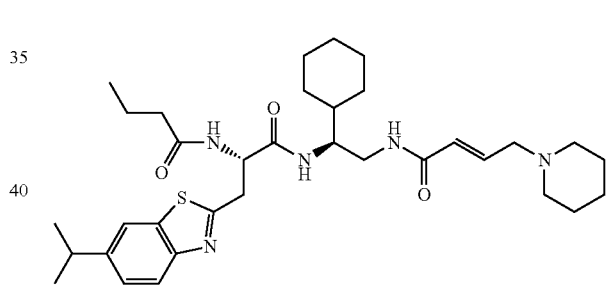
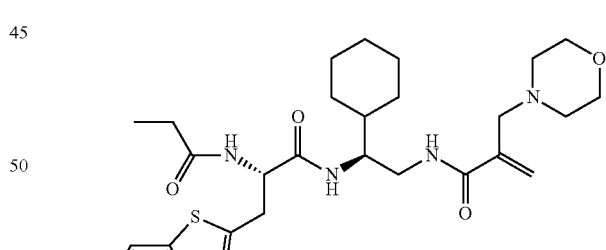
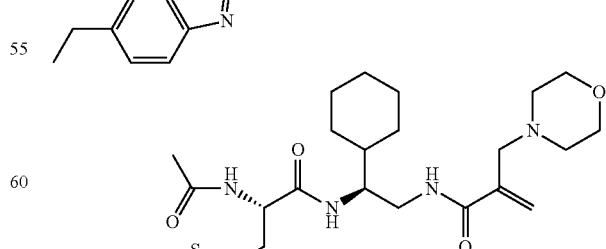
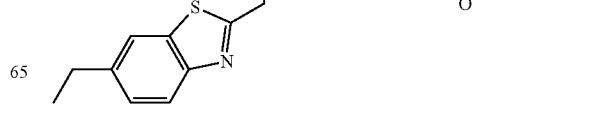

133
-continued
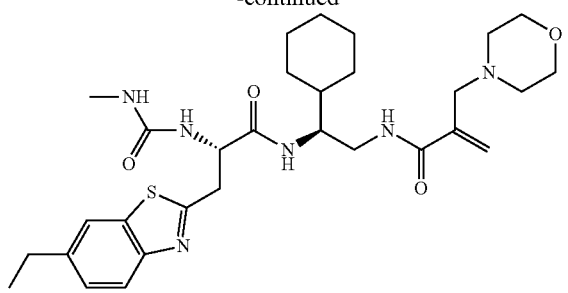
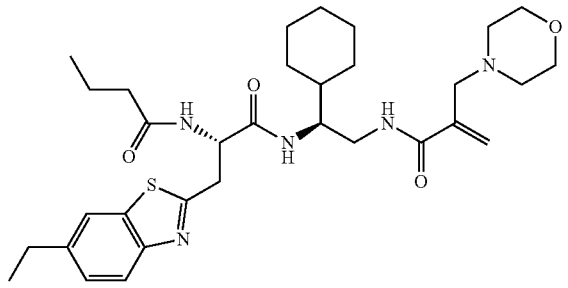
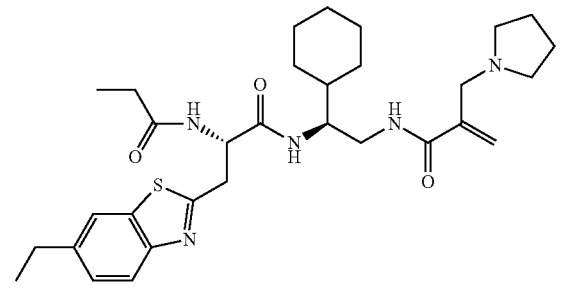
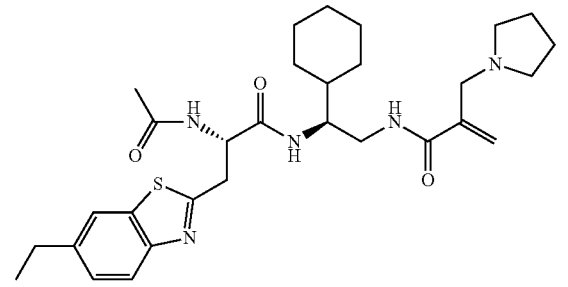
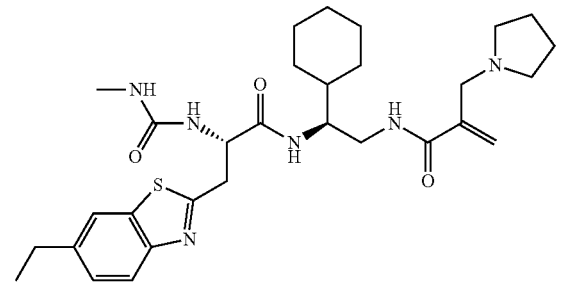
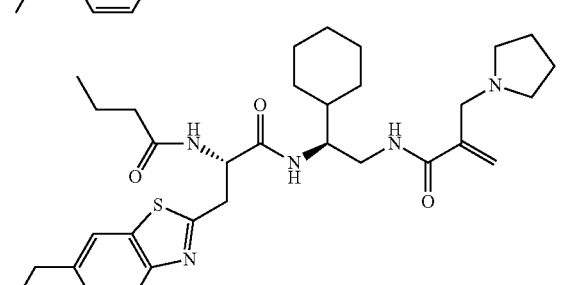
134
-continued
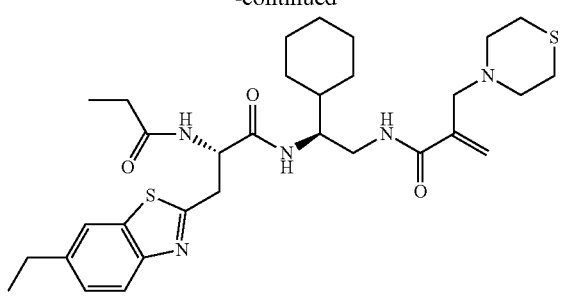
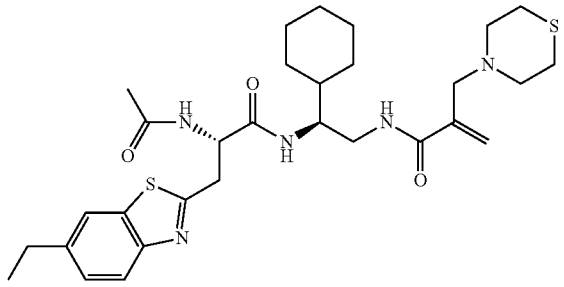
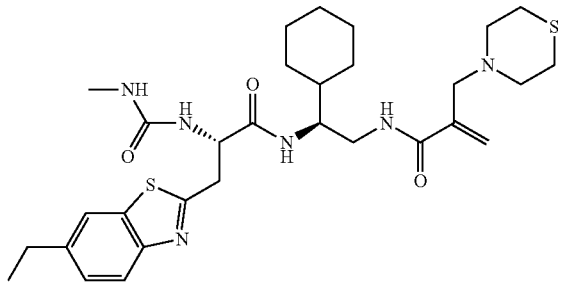
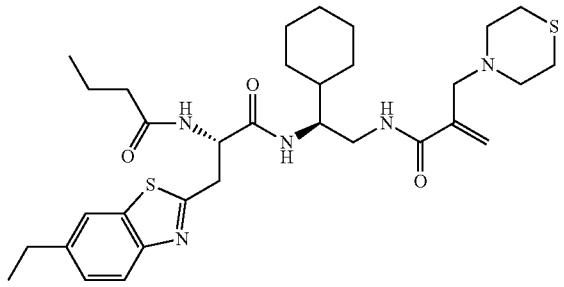
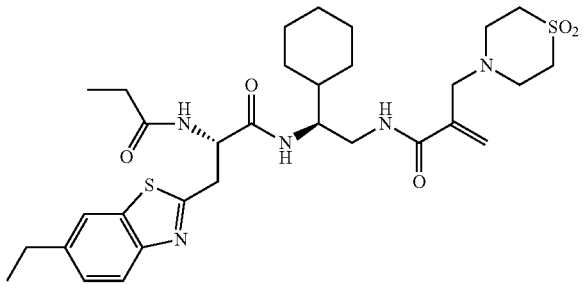
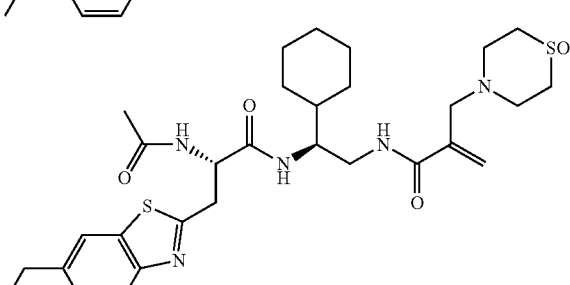

135
-continued
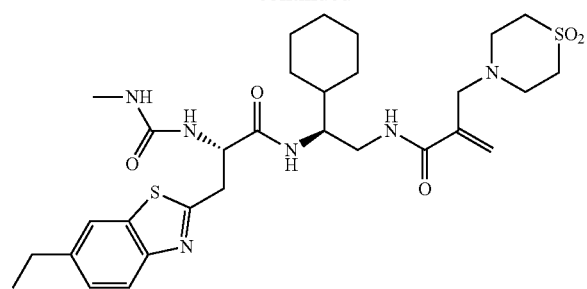
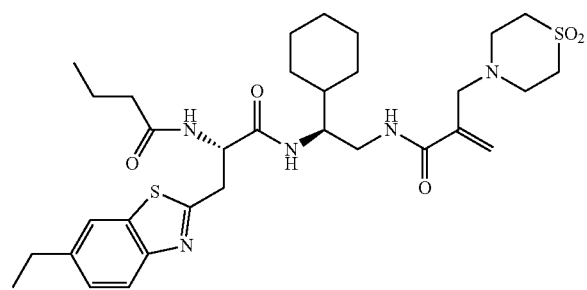
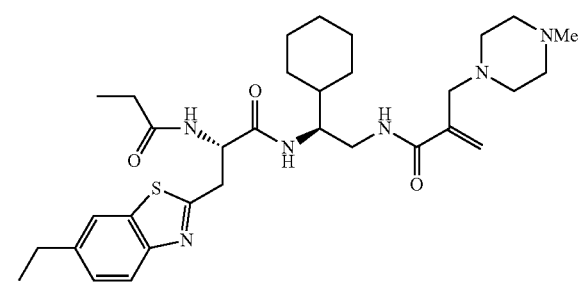
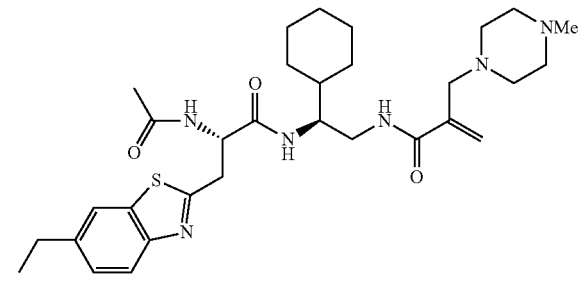
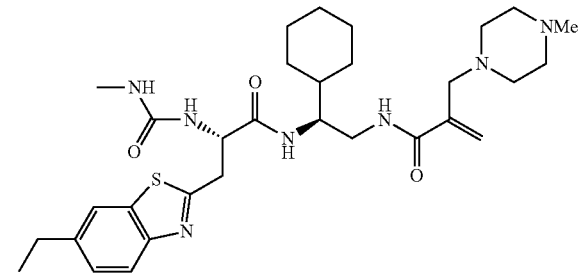
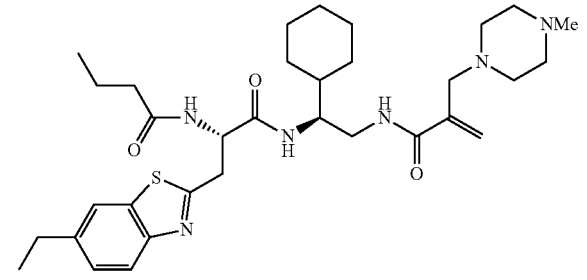
136
-continued
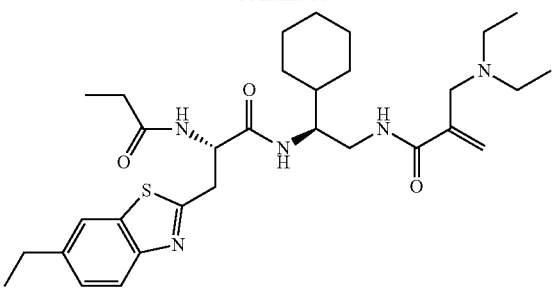
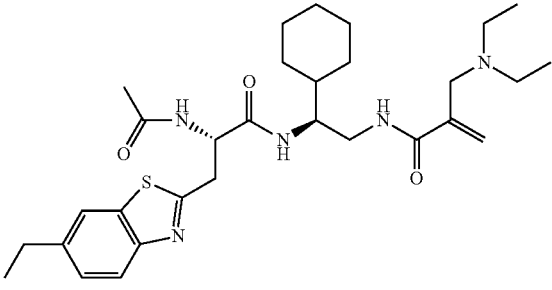
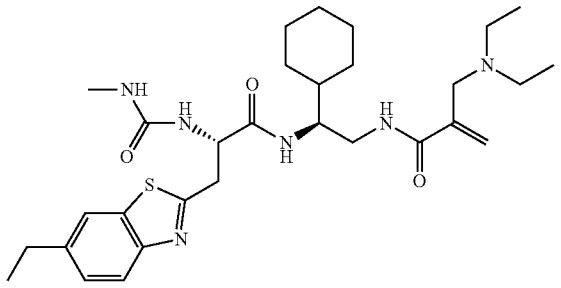
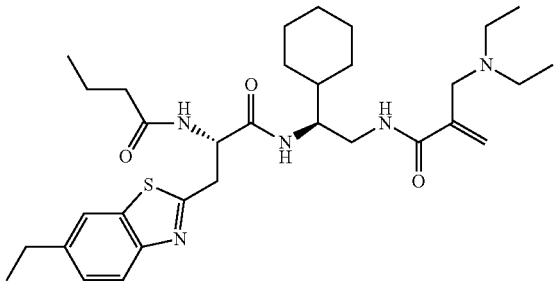
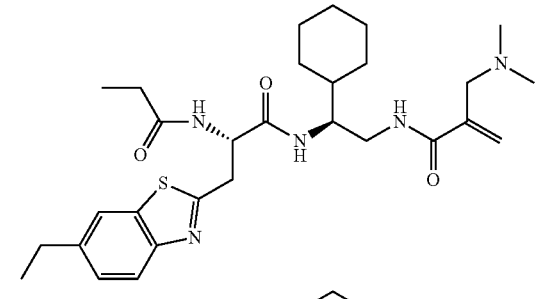
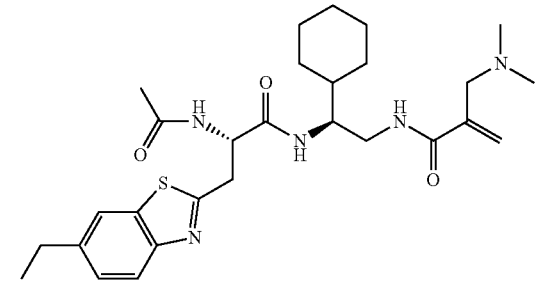

137
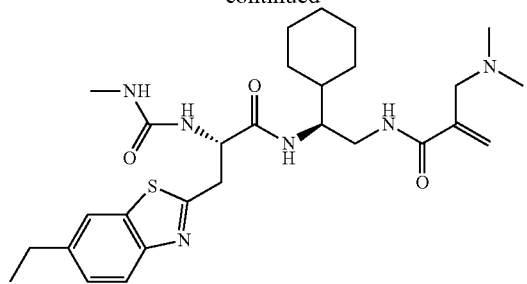
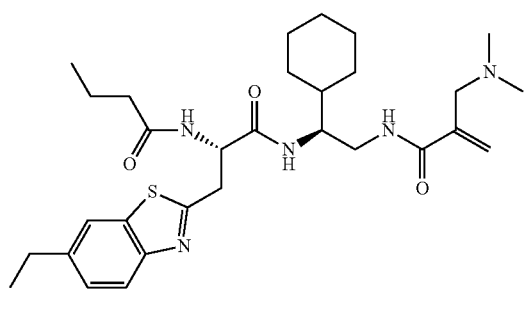
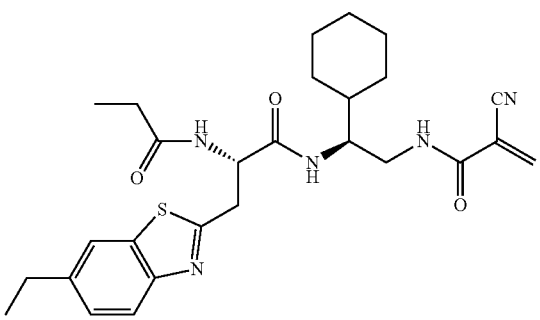
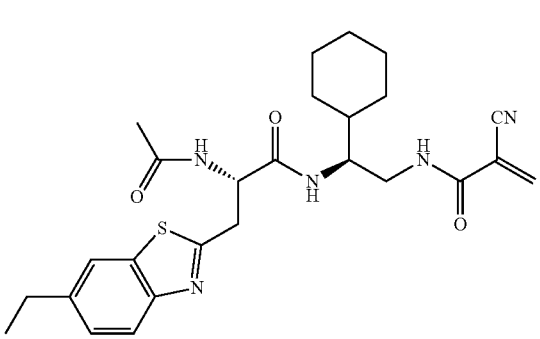
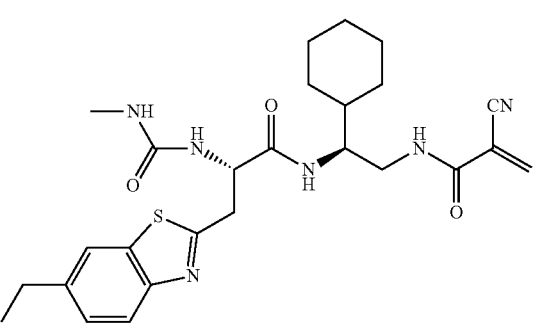
138
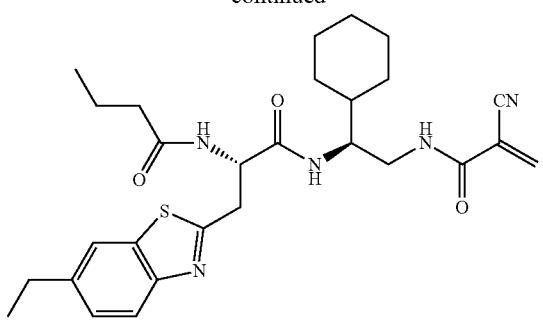
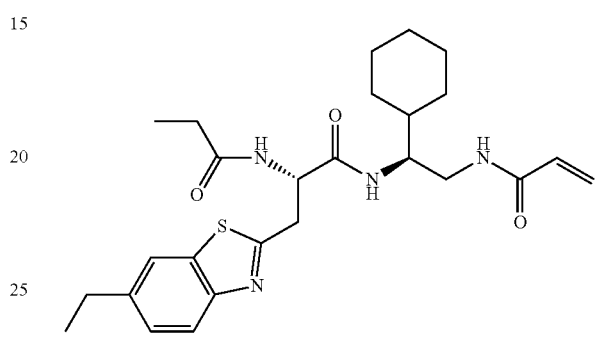
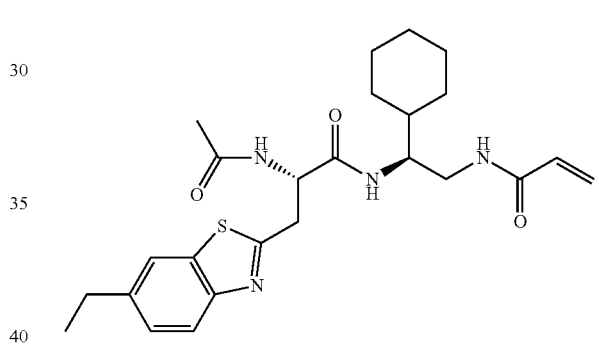
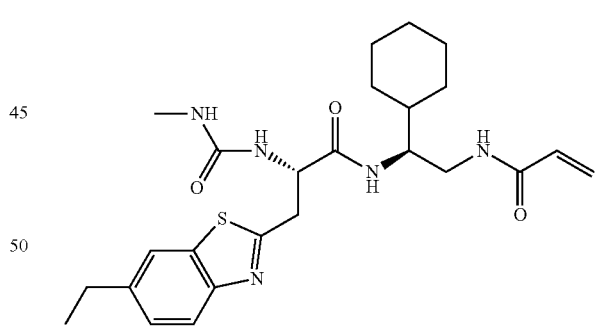
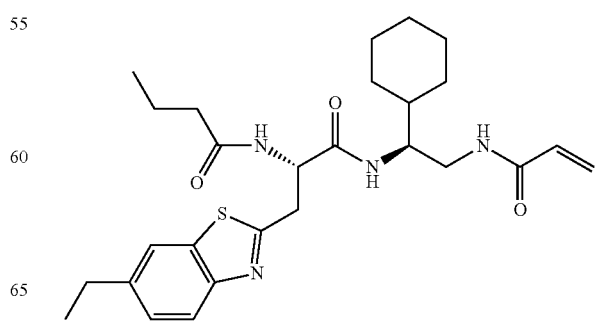

139
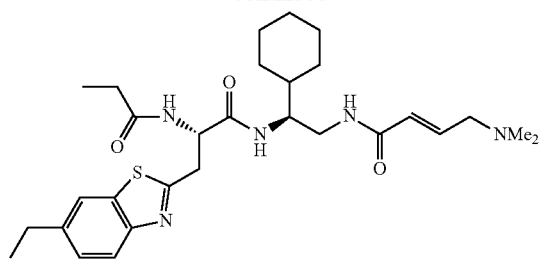
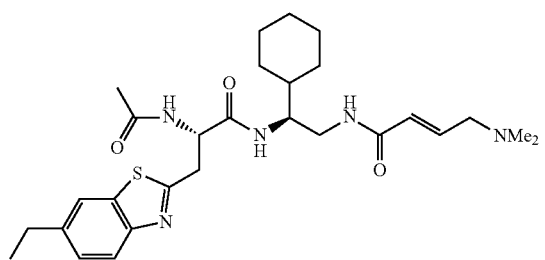
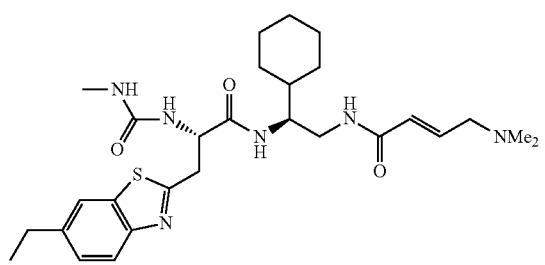
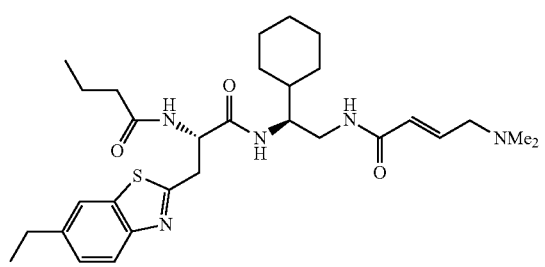
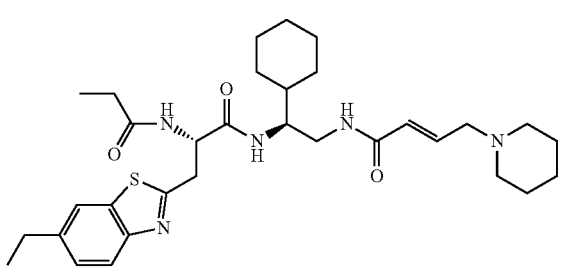
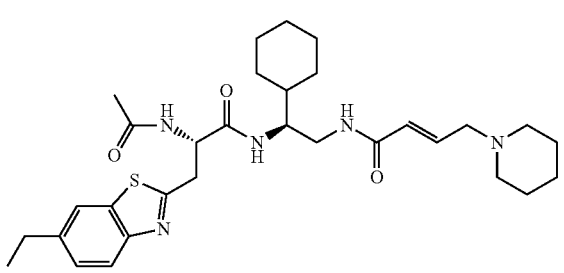
140
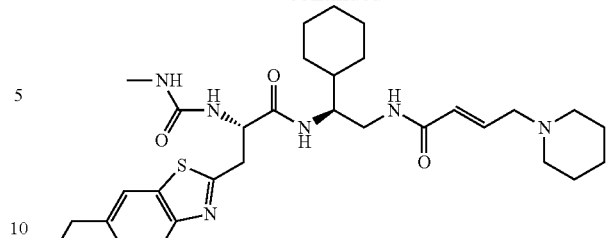
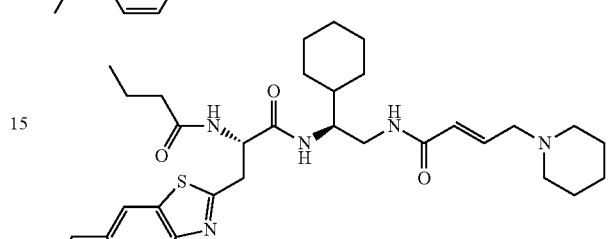
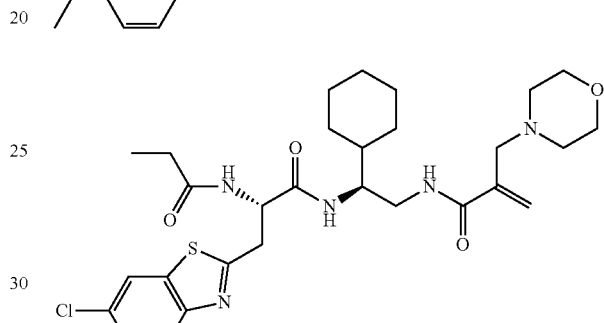

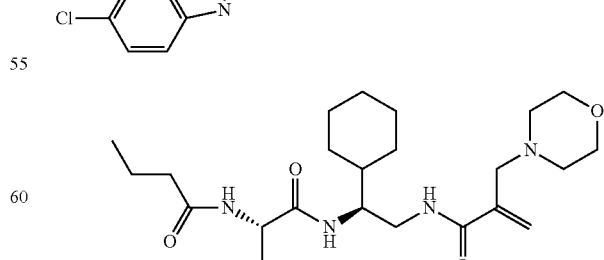
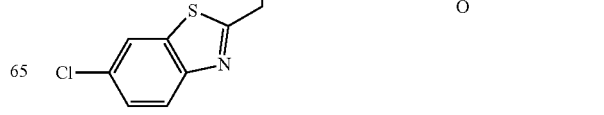

141
-continued
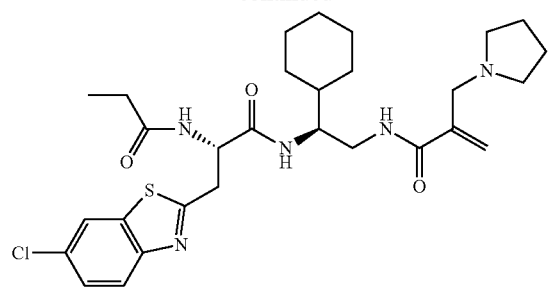
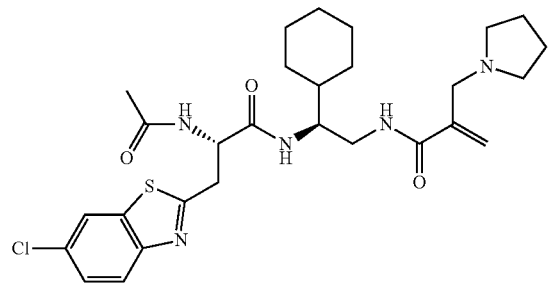
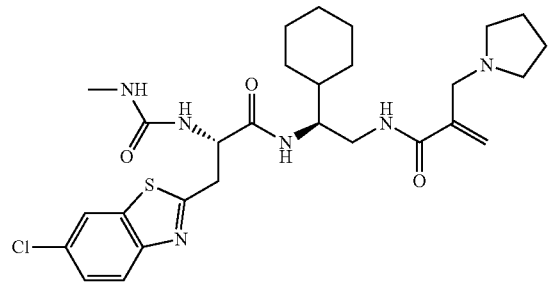
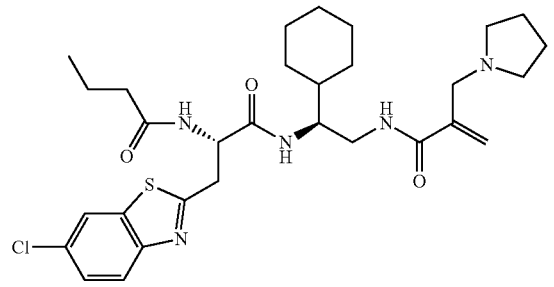
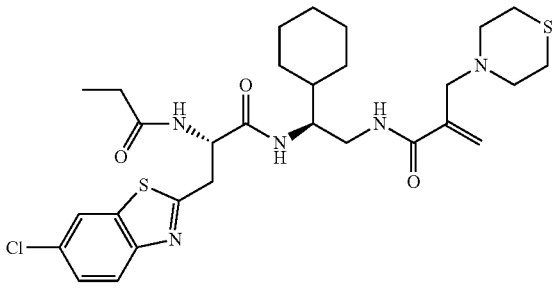
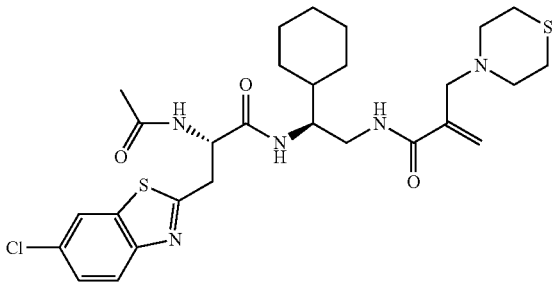
142
-continued
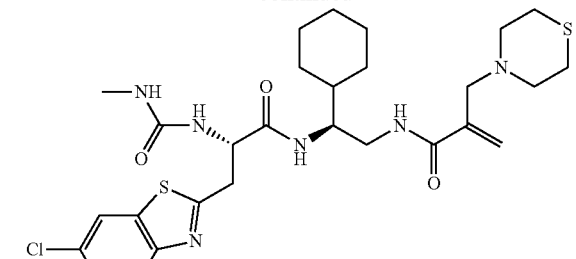
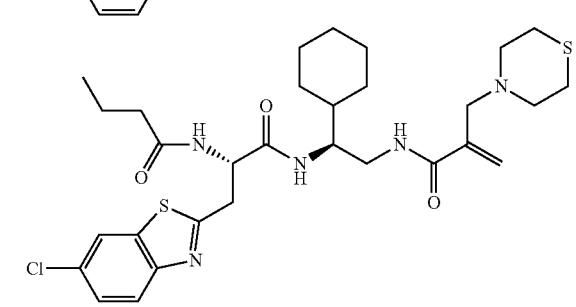
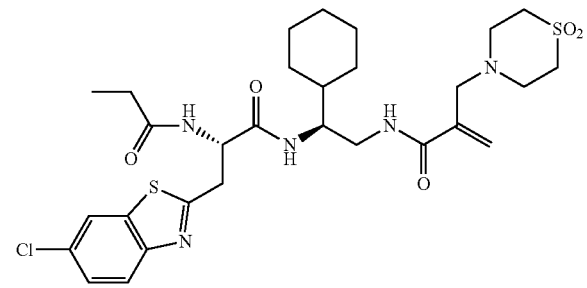
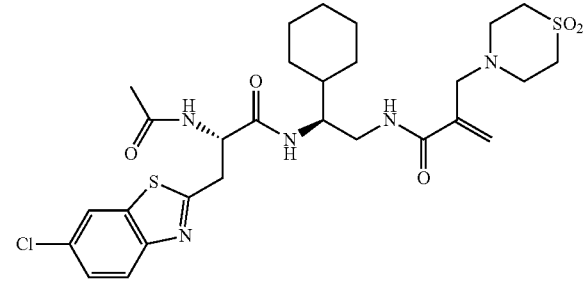
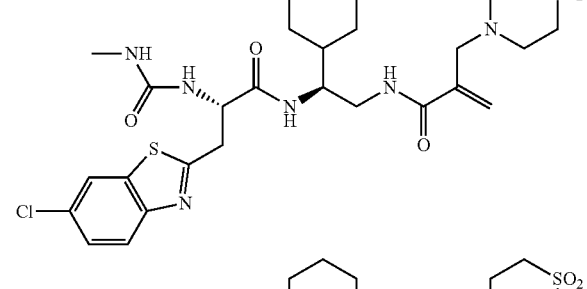
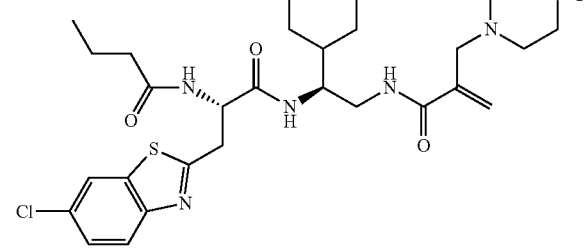

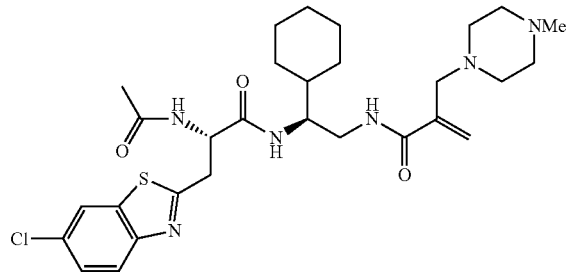
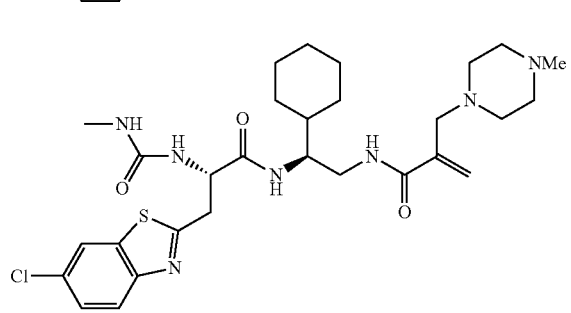
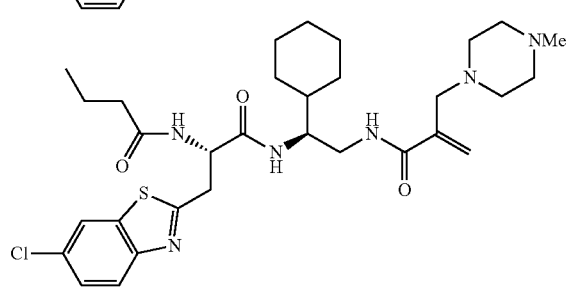
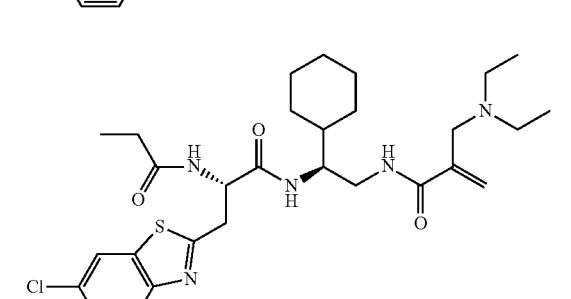
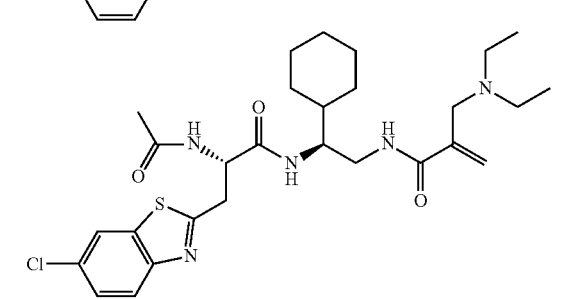
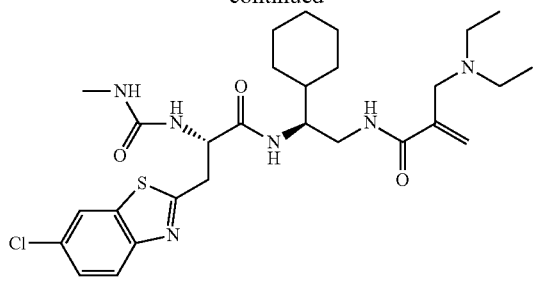
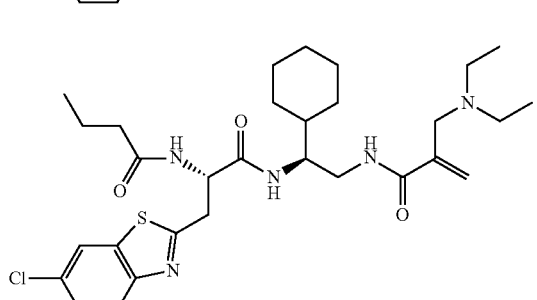
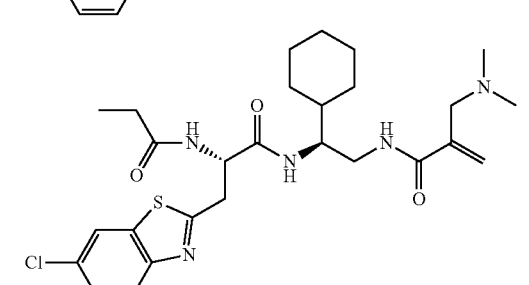
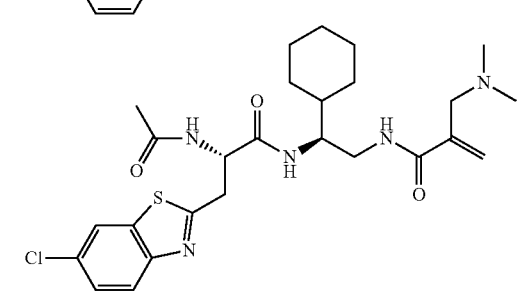
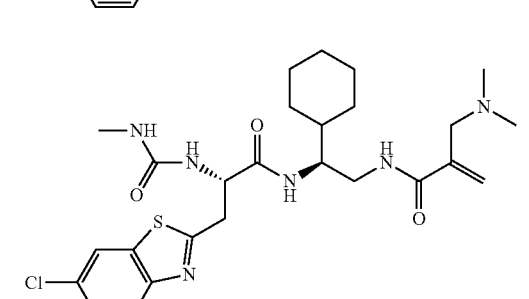
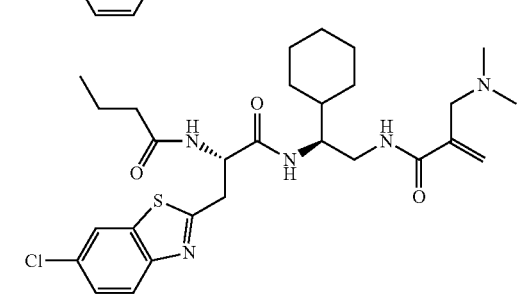

145
-continued
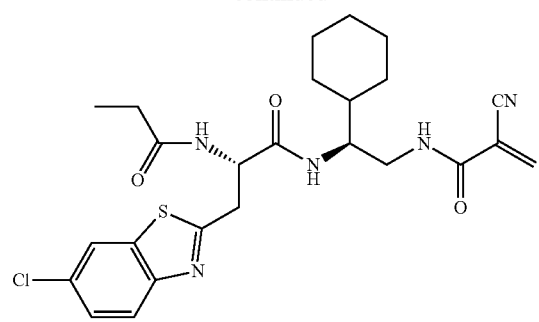
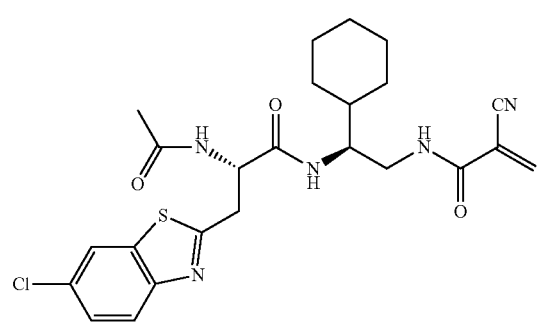
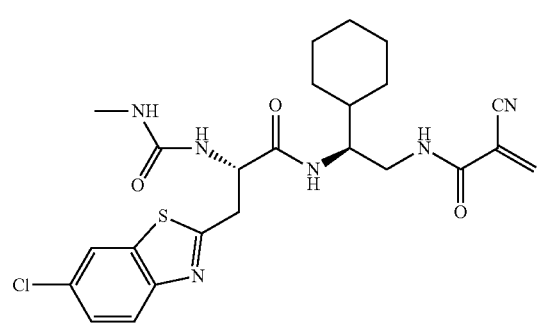
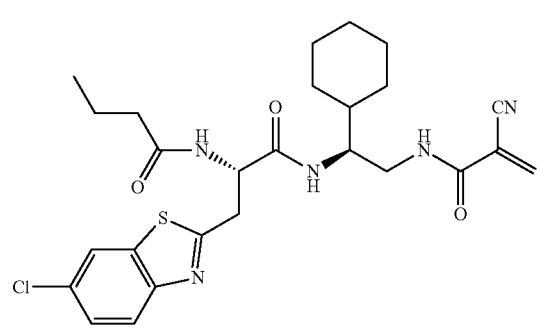
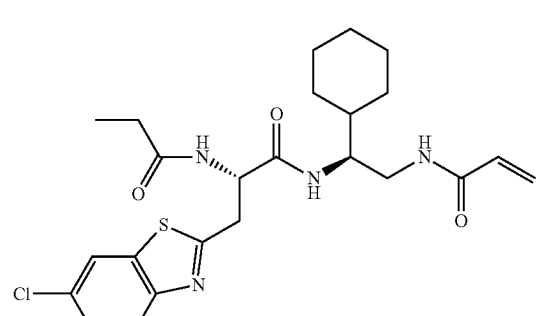
146
-continued
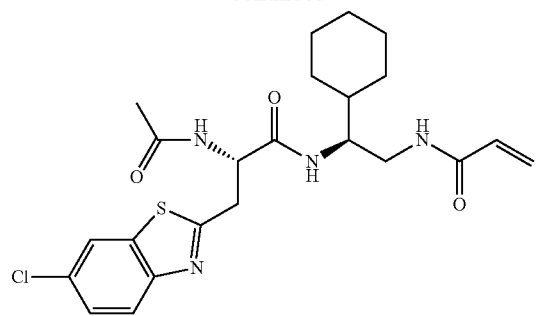
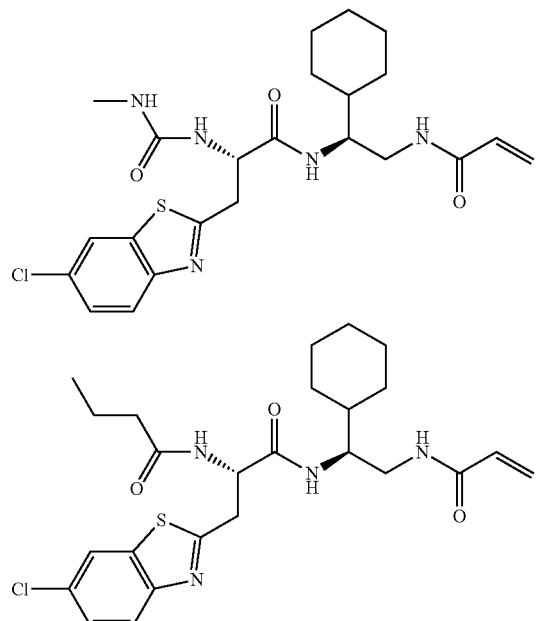
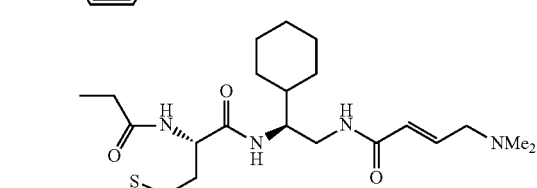
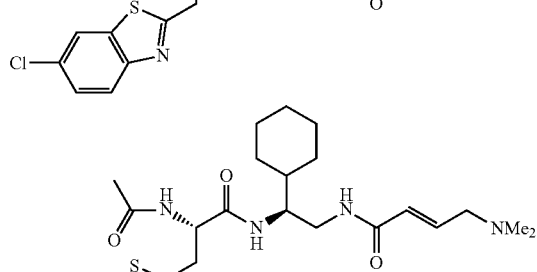
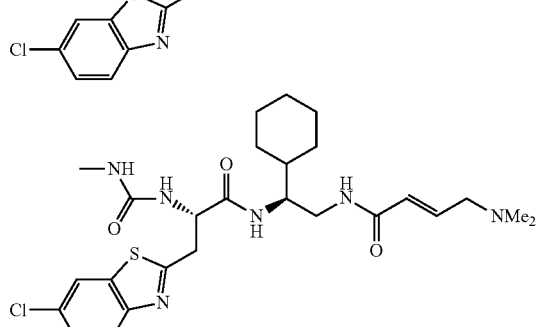

147
-continued
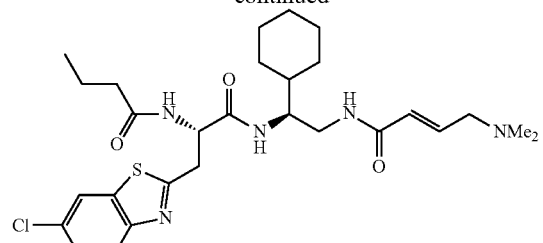
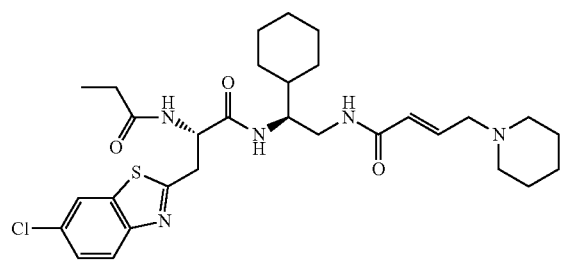 [SMILES: CCC(=O)N[C@@H](Cc1nc2ccc(C(C)C)cc2s1)C(=O)N[C@H](CNC(=O)/C=C/CN1CCOCC1)C1CCCCC1]
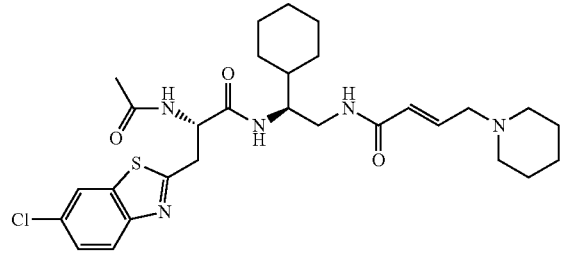
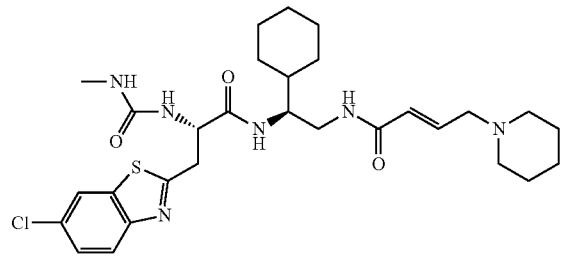
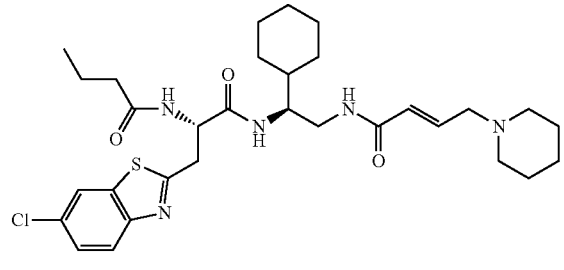
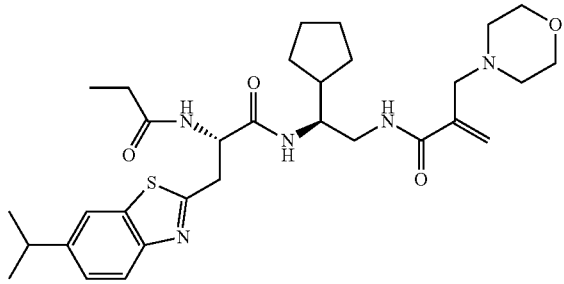
148
-continued
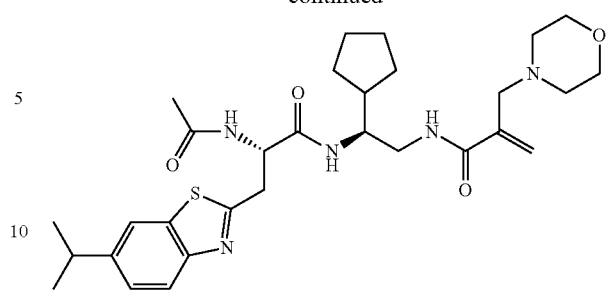
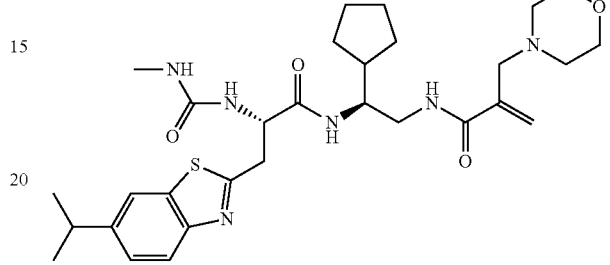
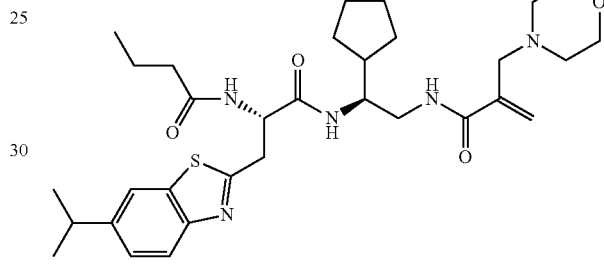

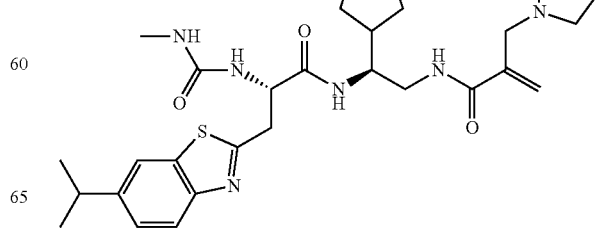

149
-continued
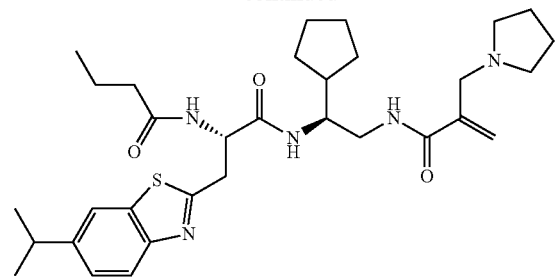
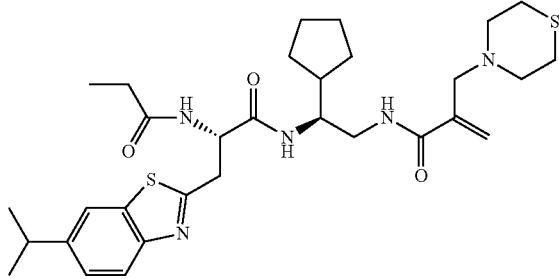
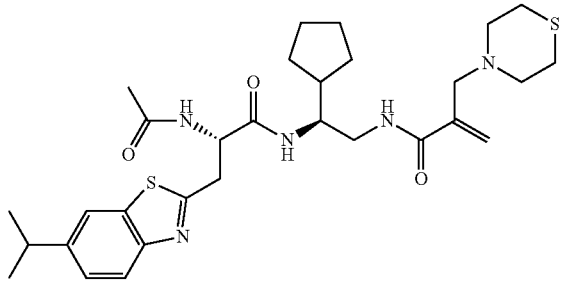
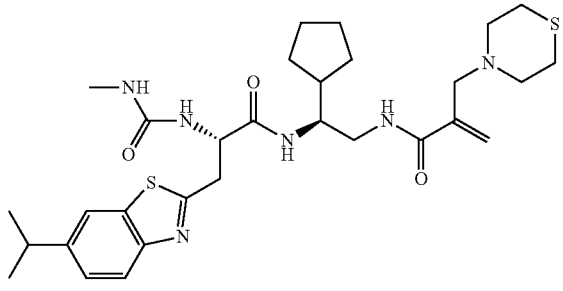
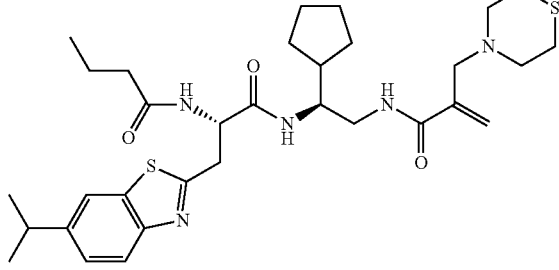
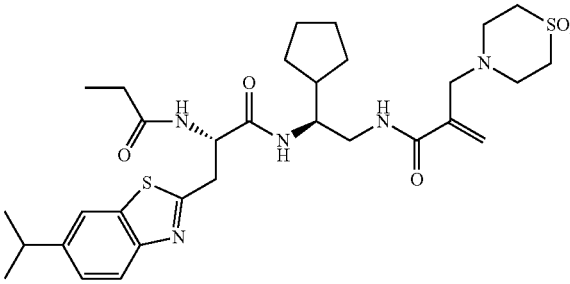
150
-continued
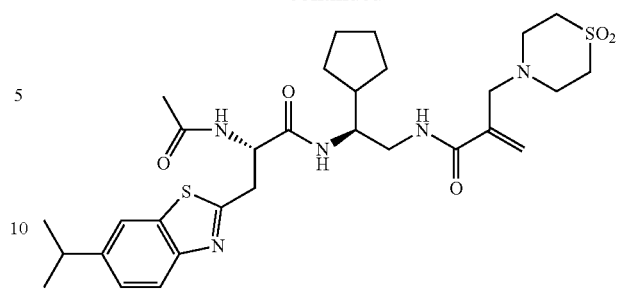
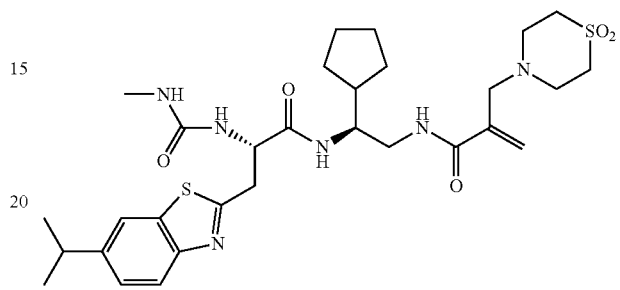
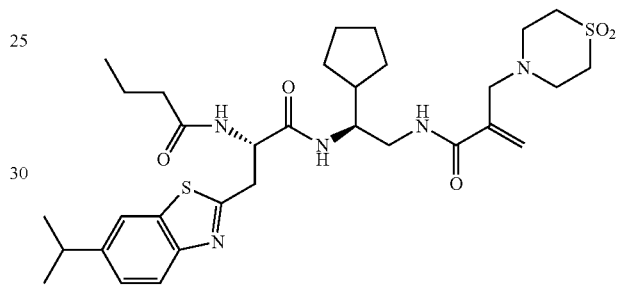
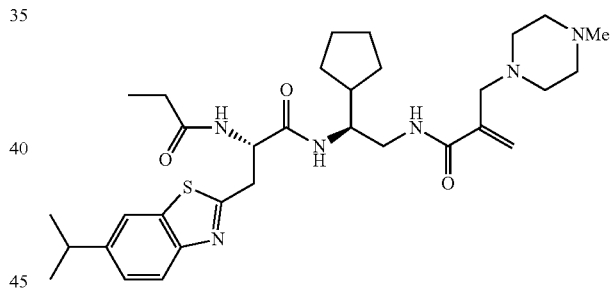
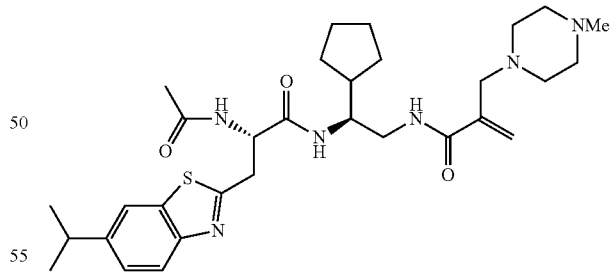
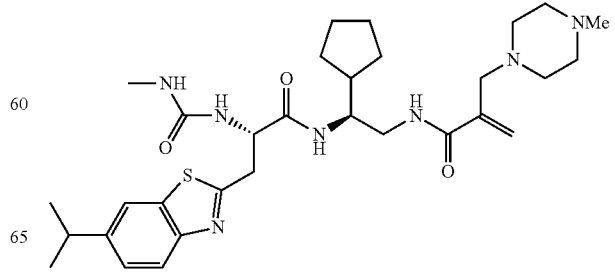

151
-continued
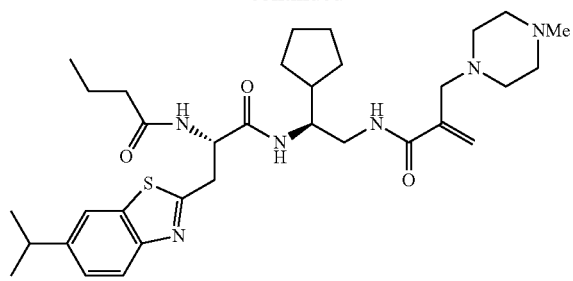
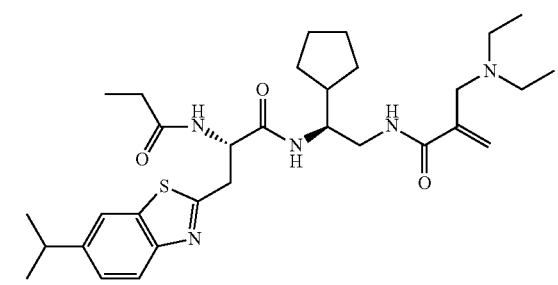
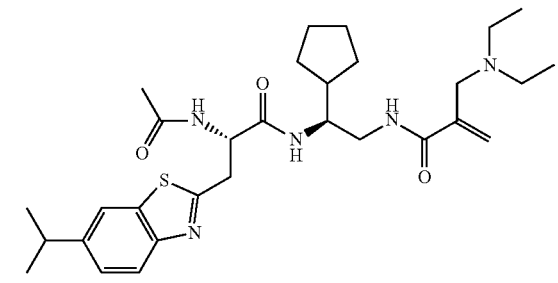
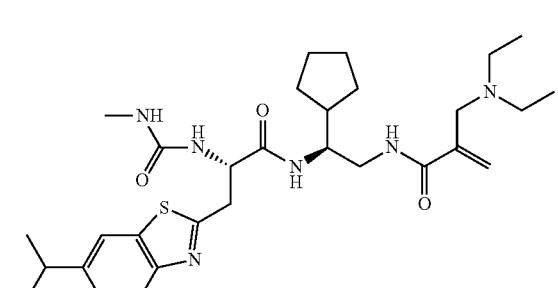
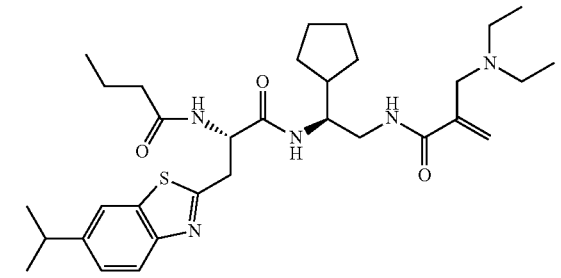
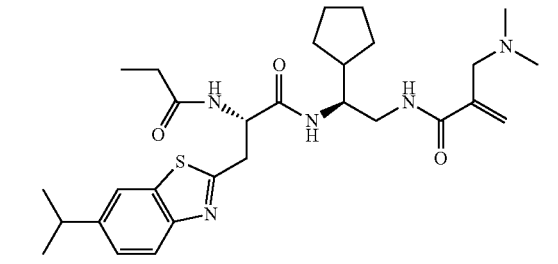
152
-continued
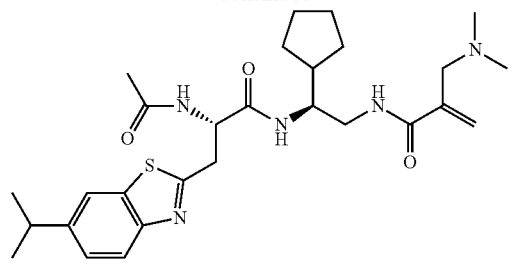
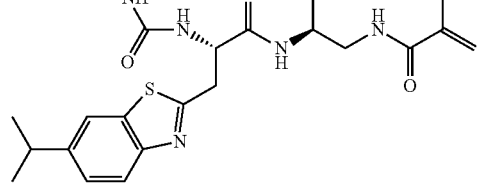
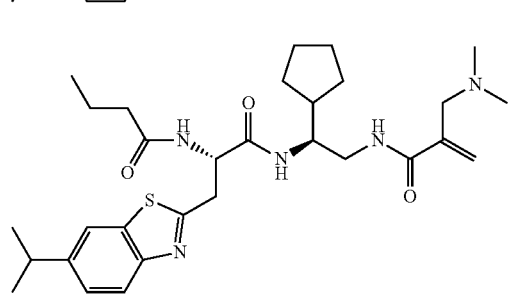
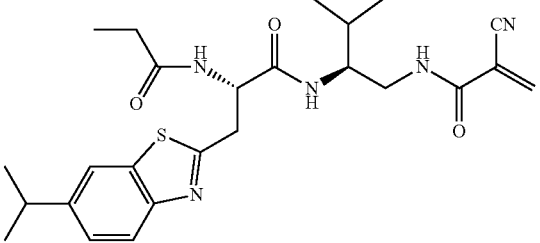
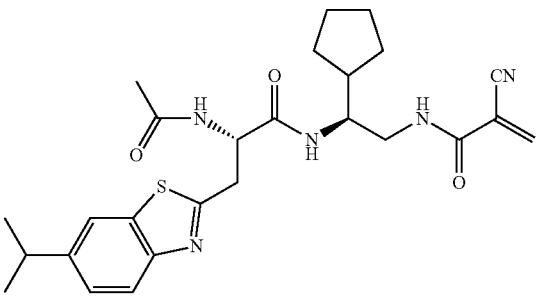
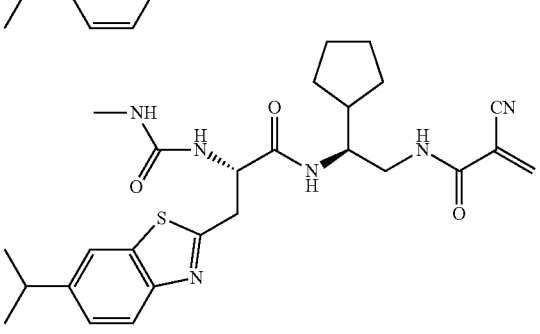

153
-continued

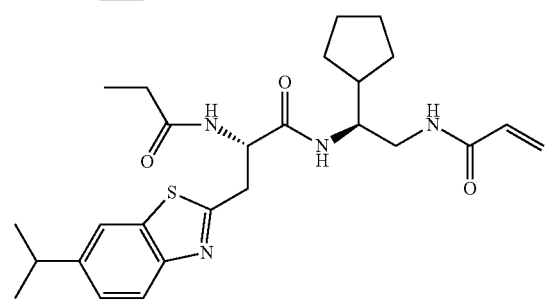
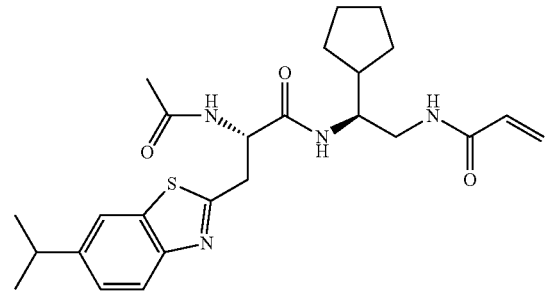
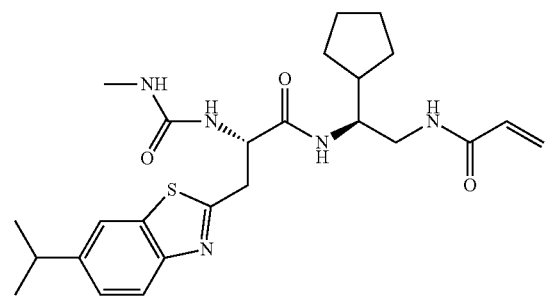
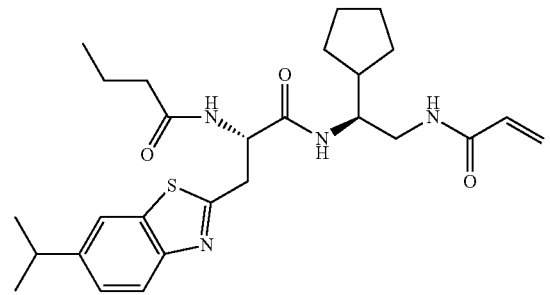
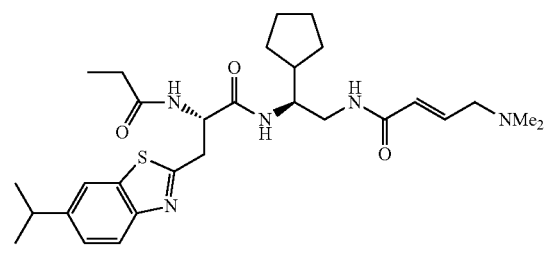
154
-continued

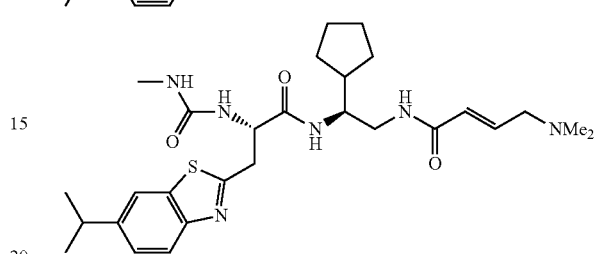

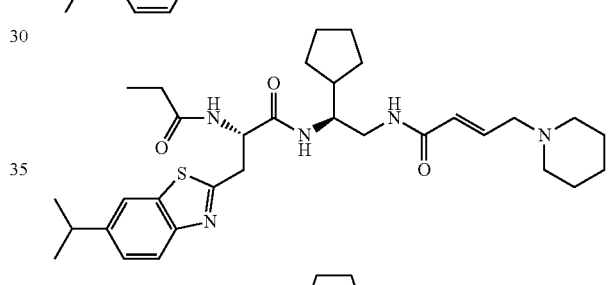
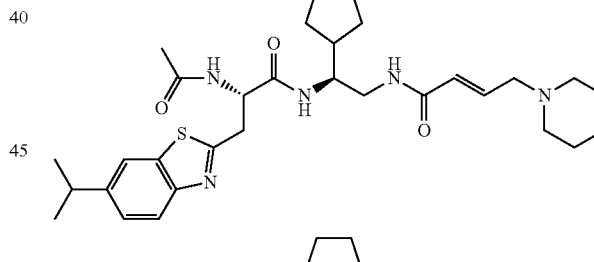
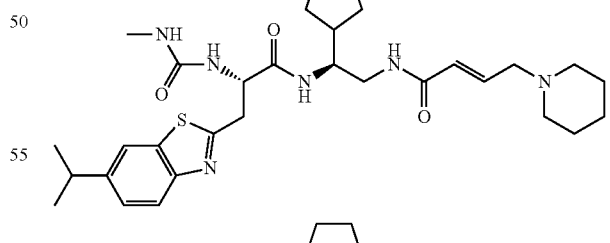
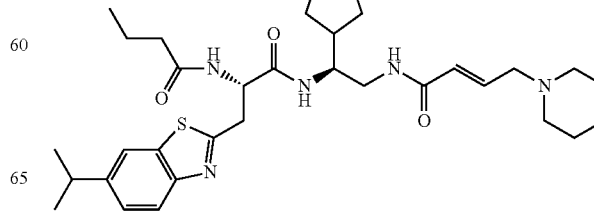

155
-continued
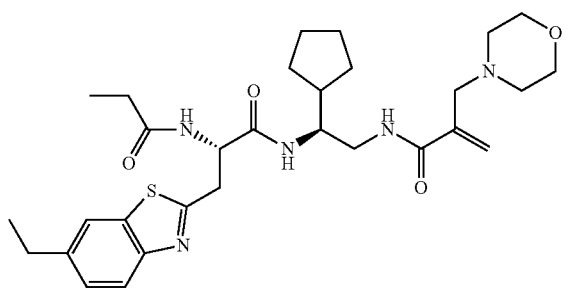
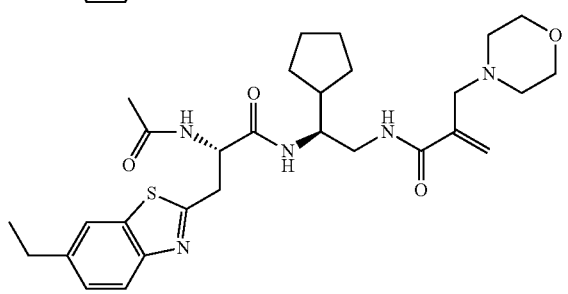
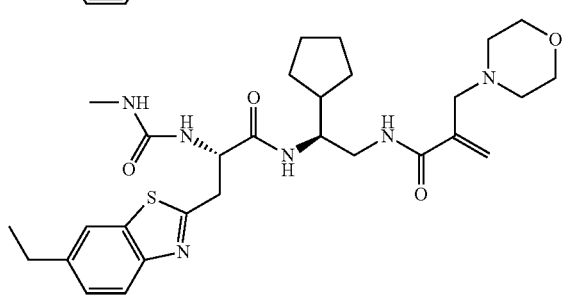
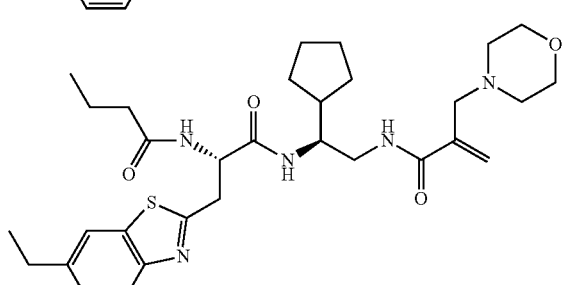
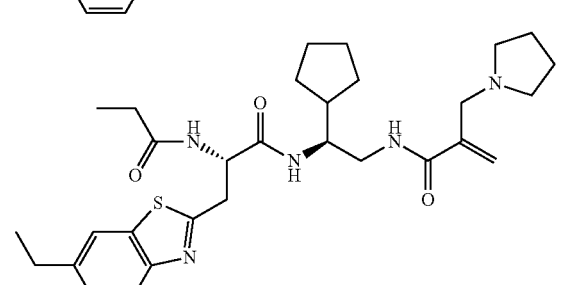
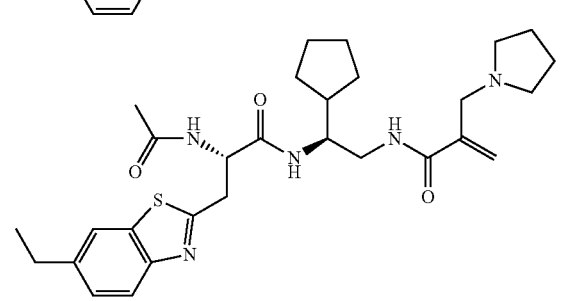
156
-continued
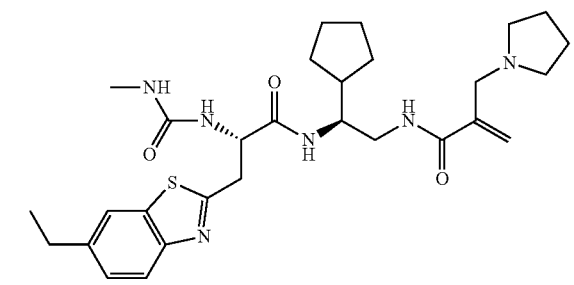
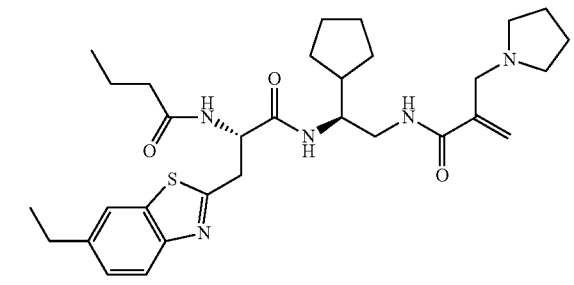
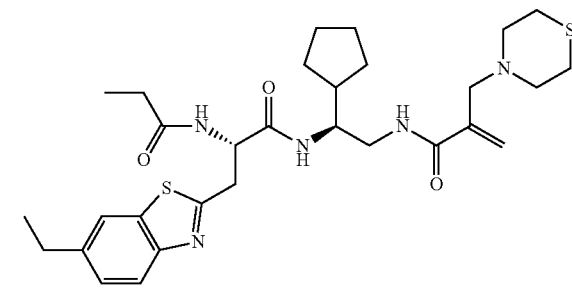
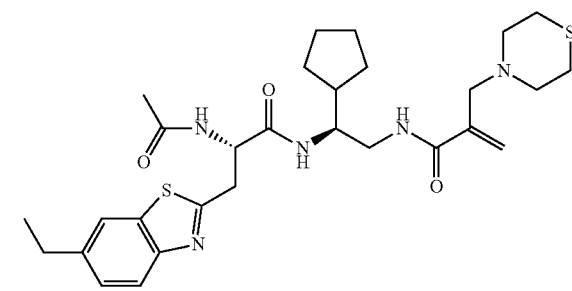
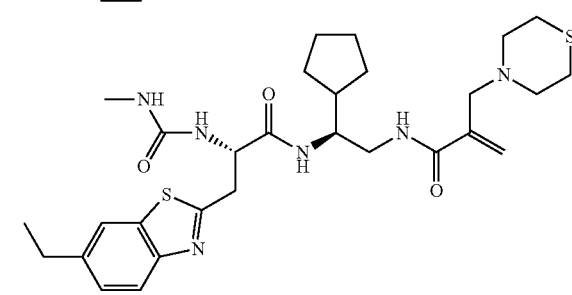
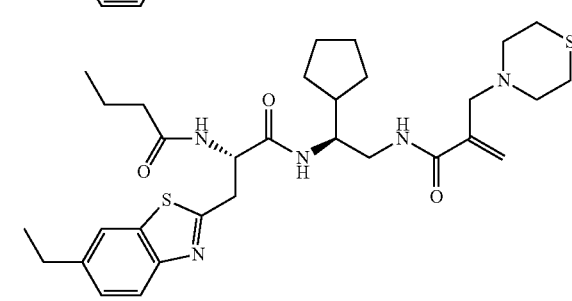

157
-continued
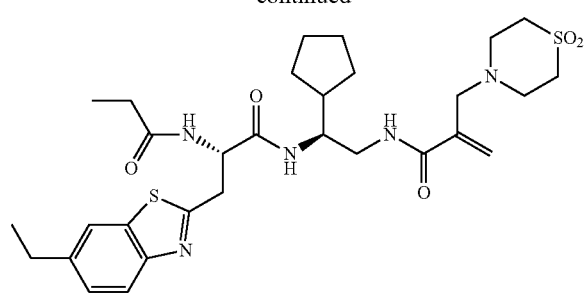
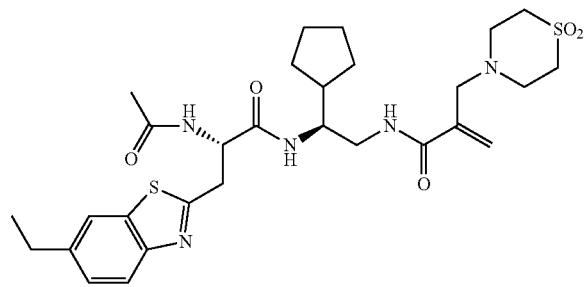
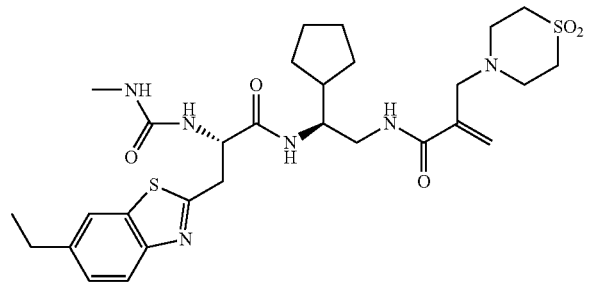
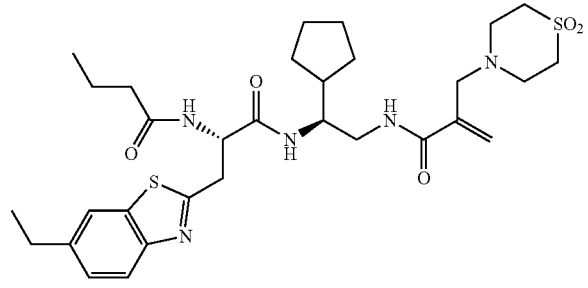
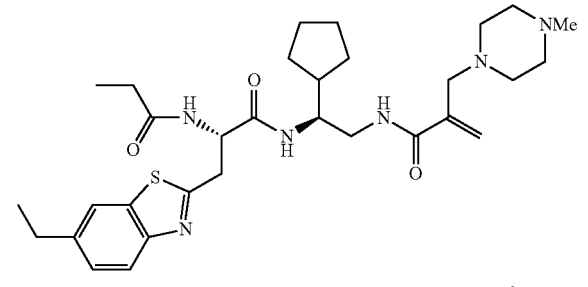
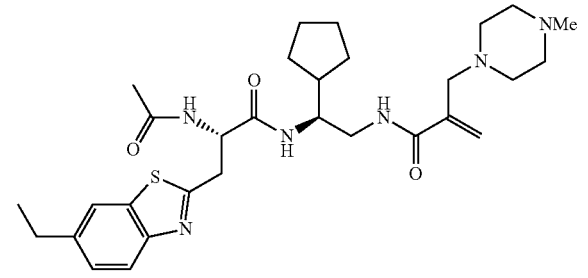
158
-continued
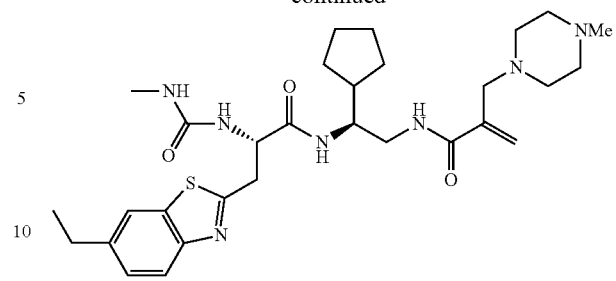
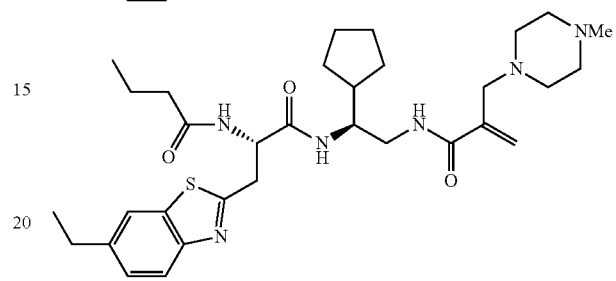
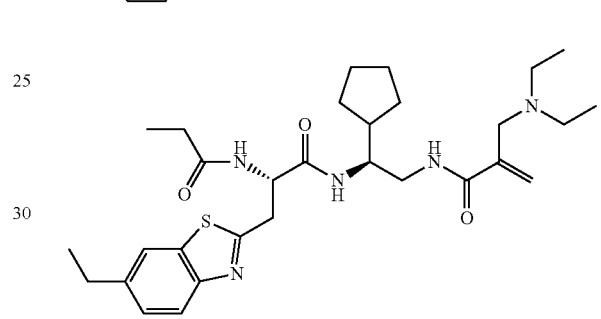
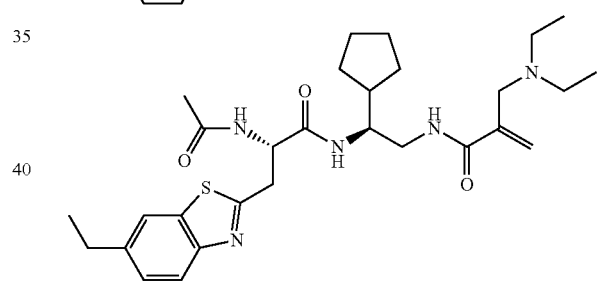
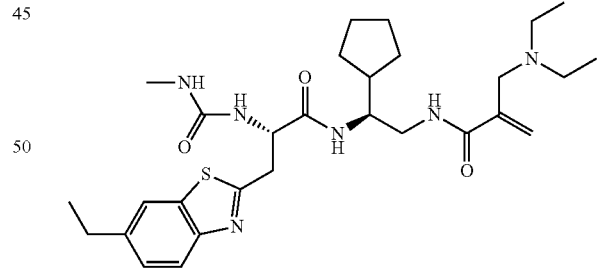
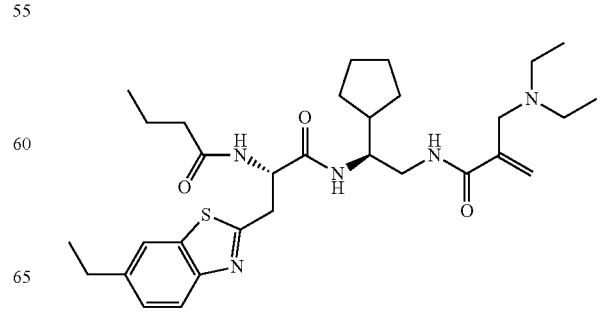

159
-continued
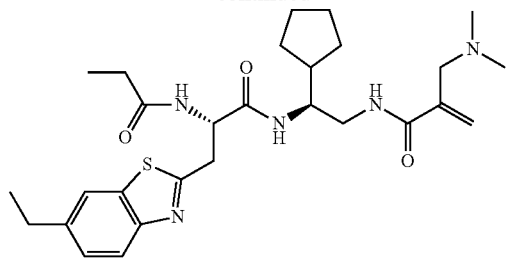
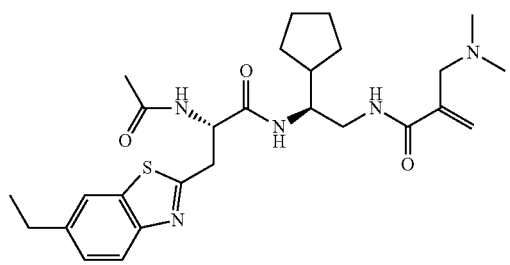
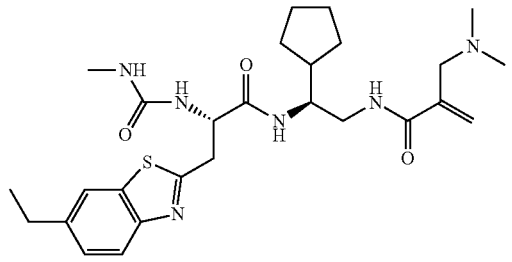
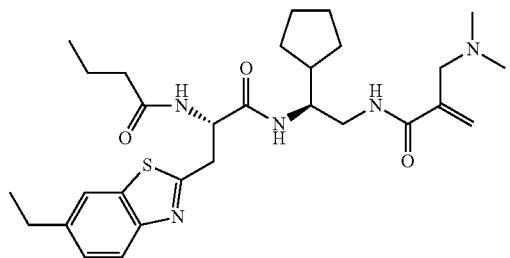
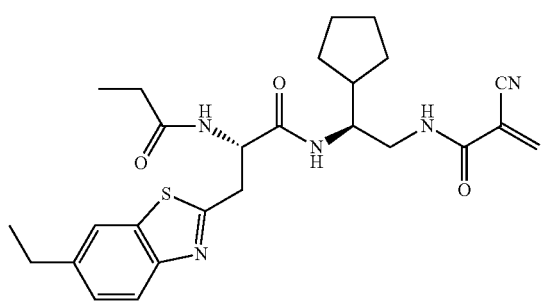
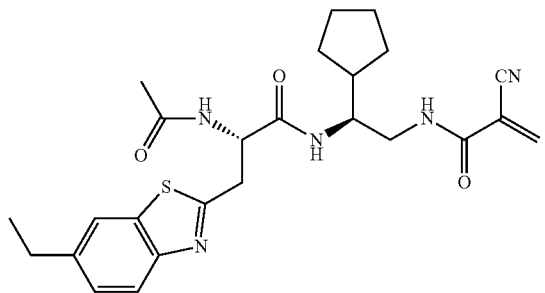
160
-continued
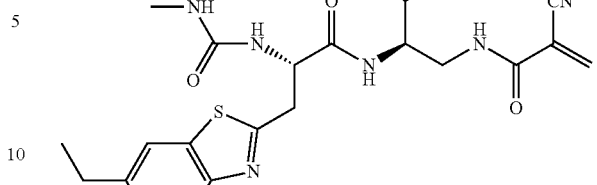
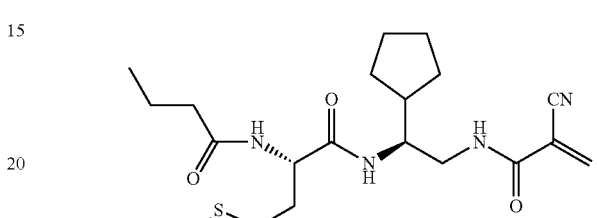
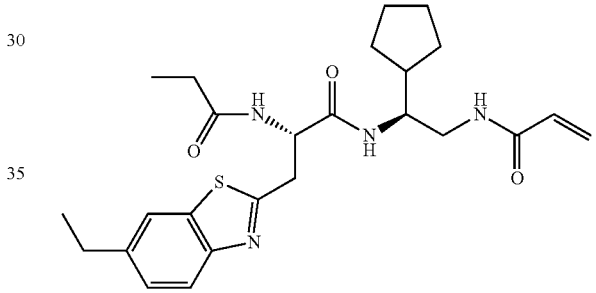
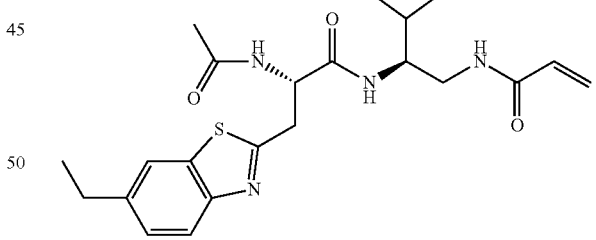
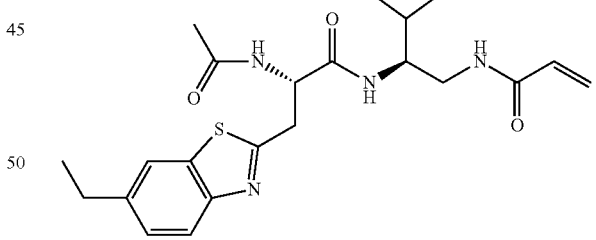
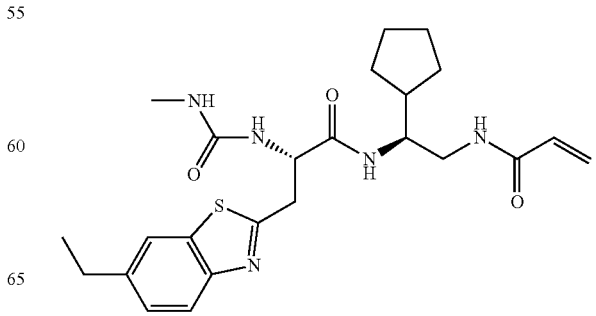

161
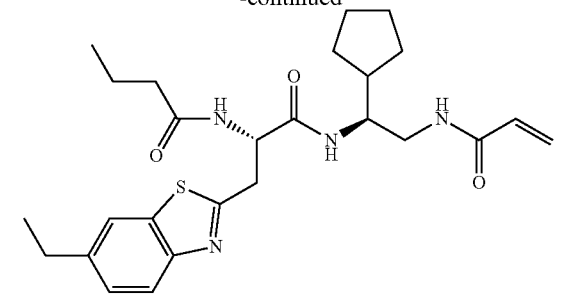
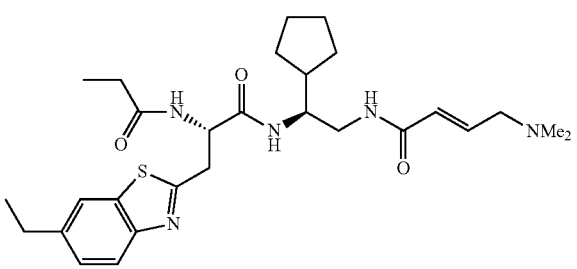
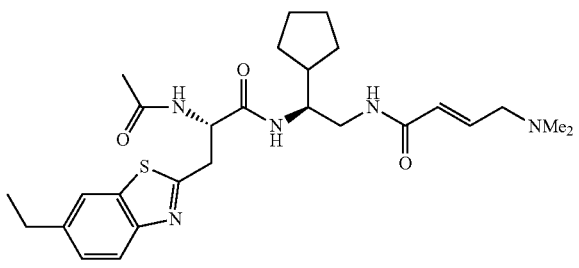
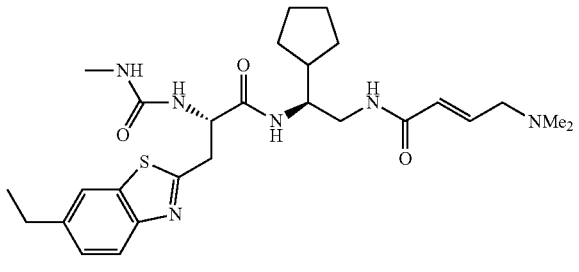
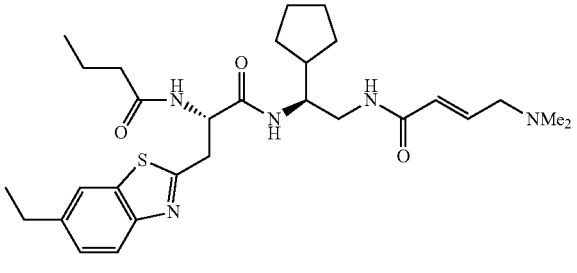
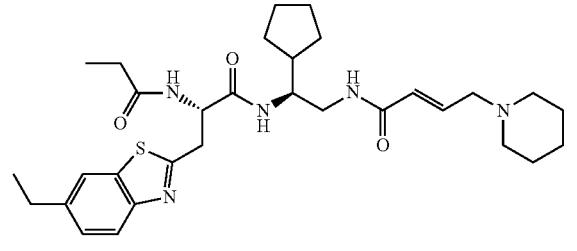
162
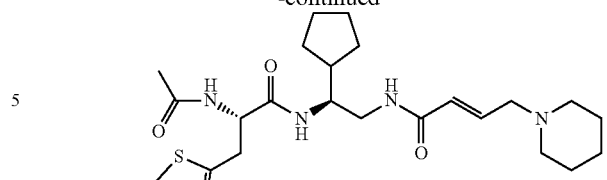
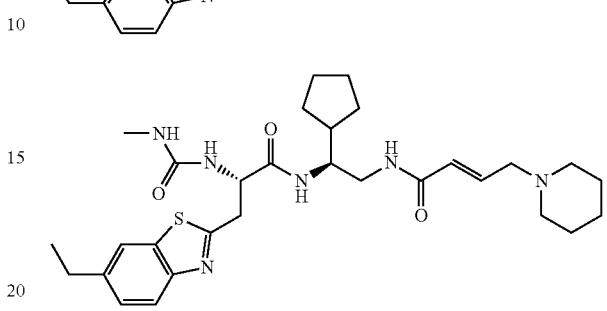
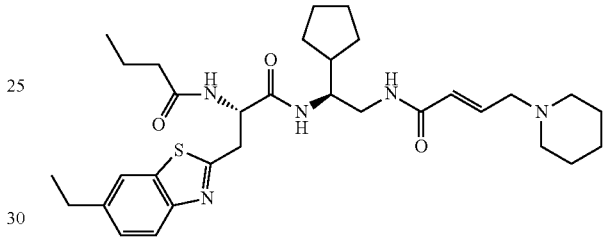

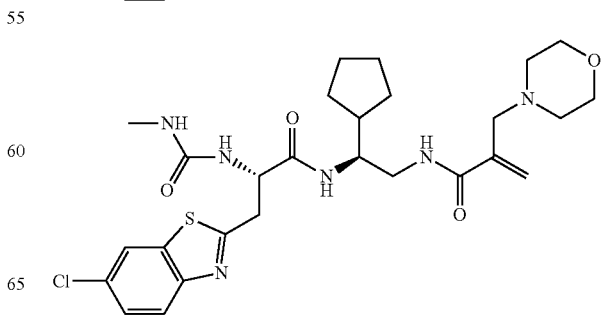

163
-continued
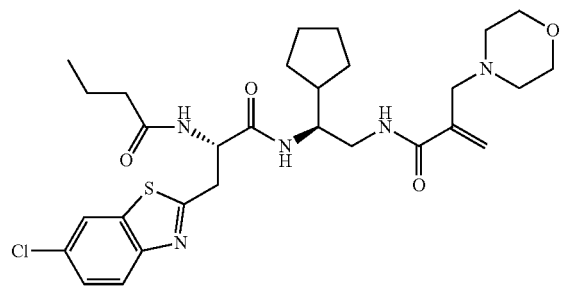
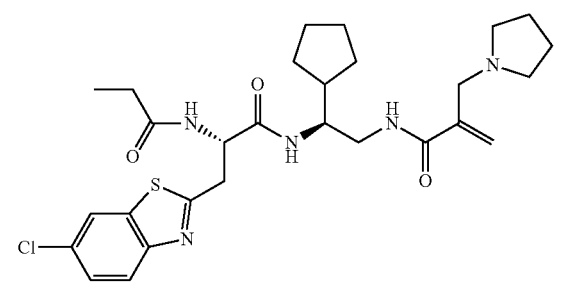
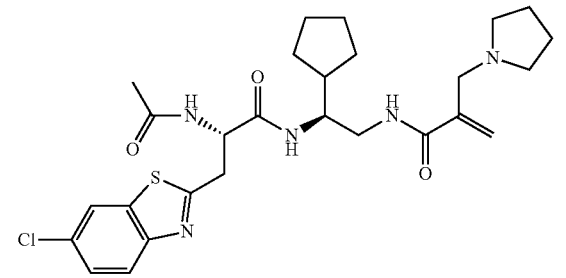
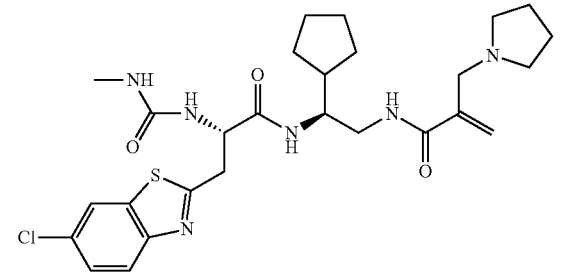
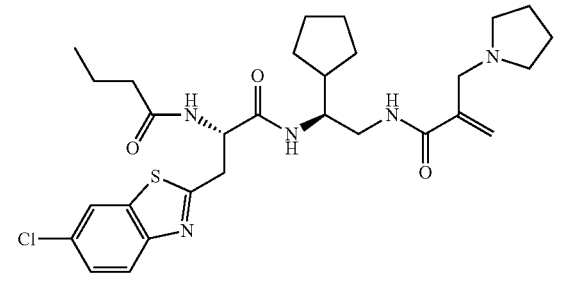
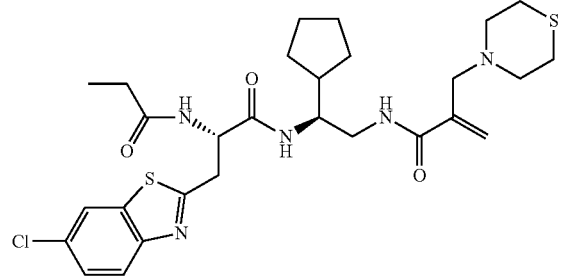
164
-continued
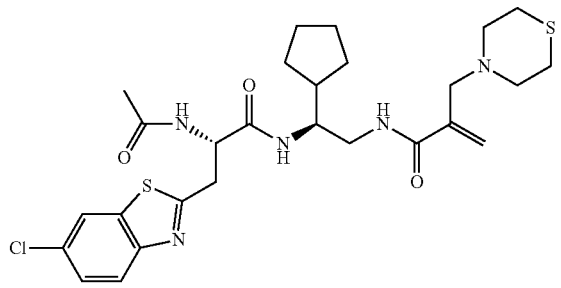
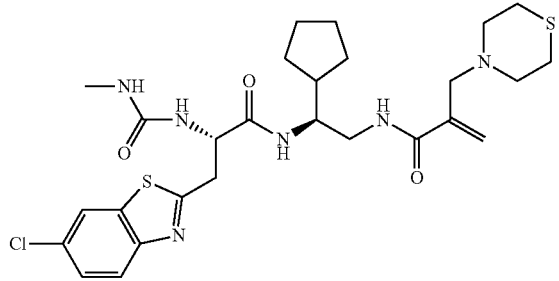
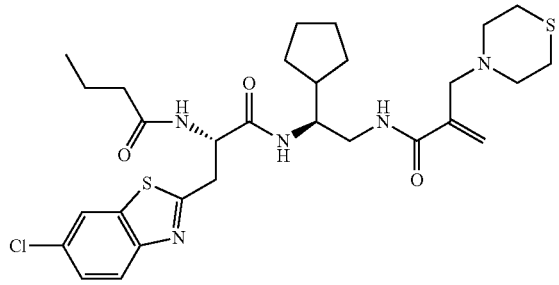
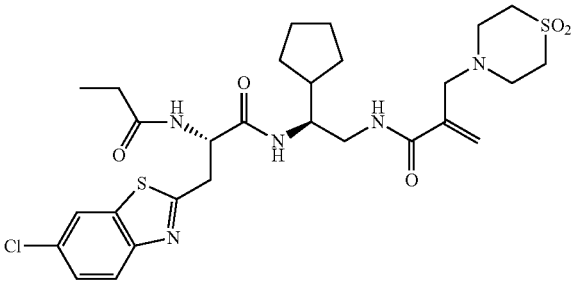
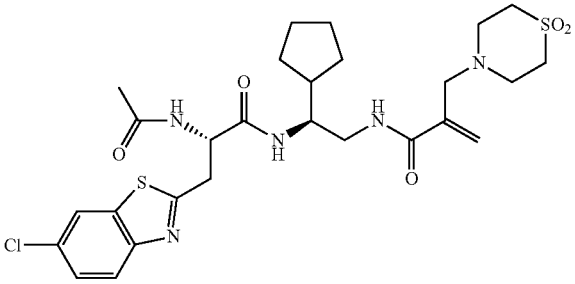
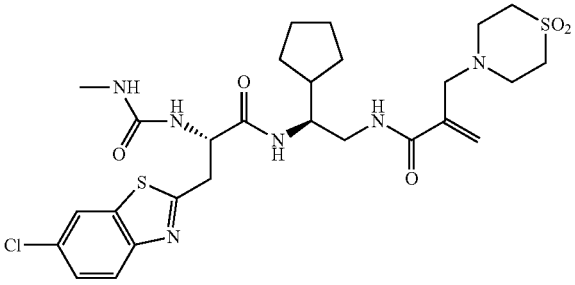

165
-continued
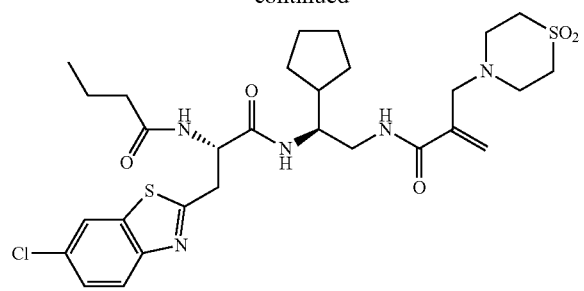
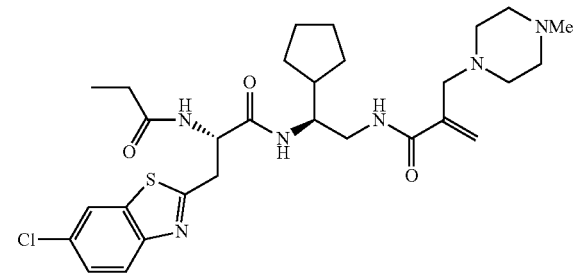
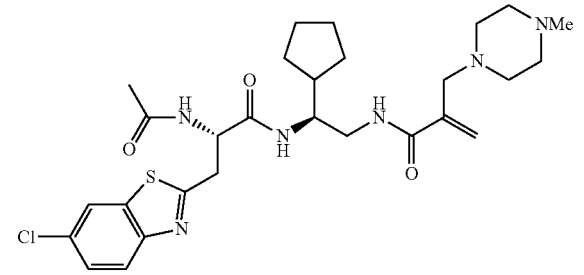
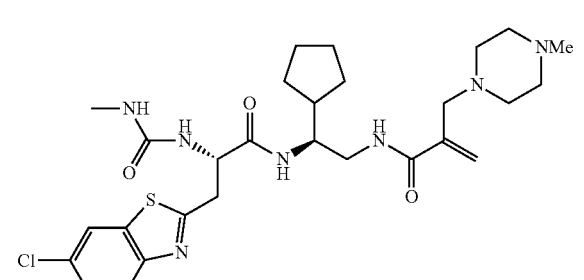
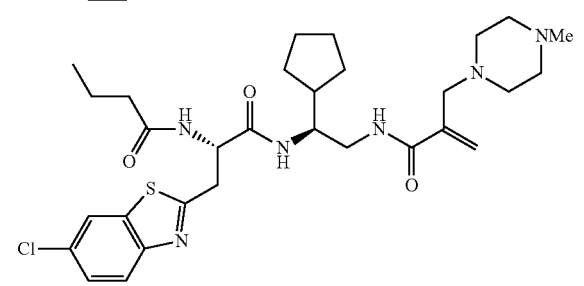
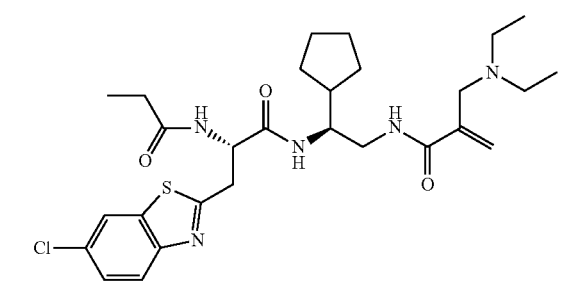
166
-continued
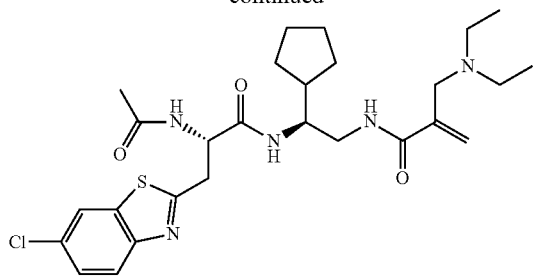
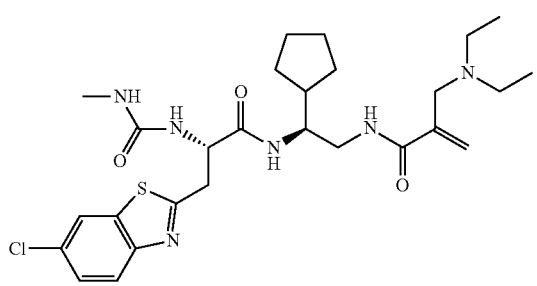
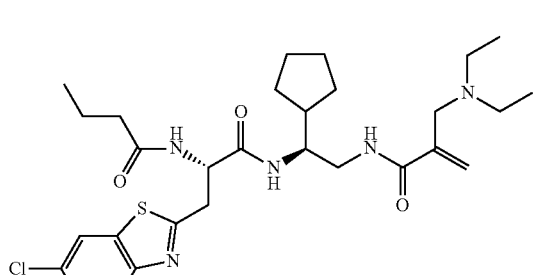
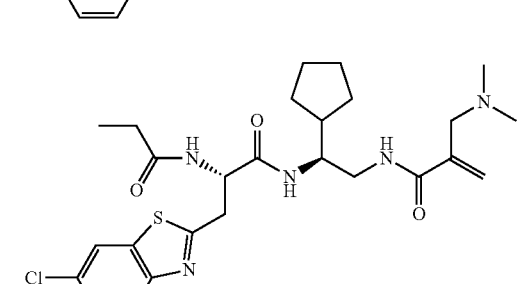
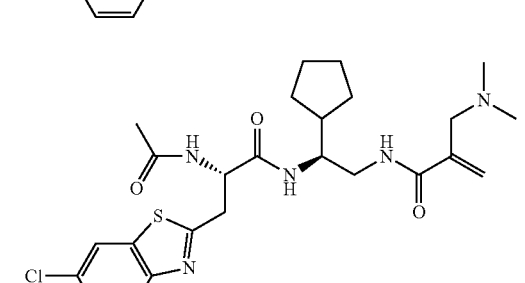
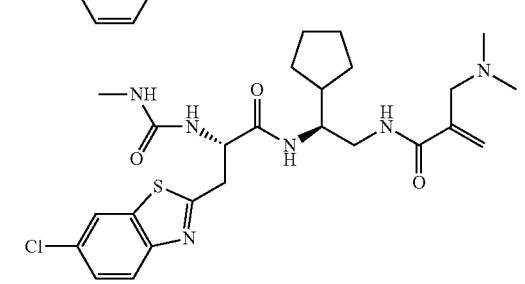

167
-continued

168
-continued


171
-continued
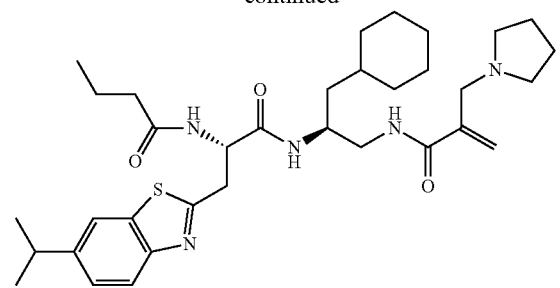
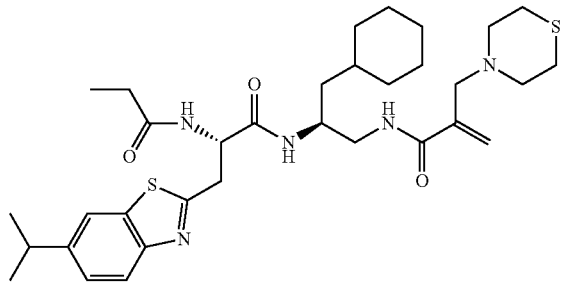
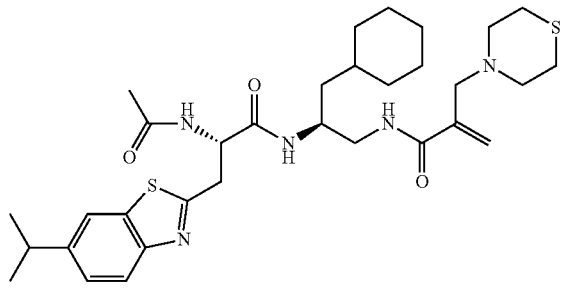
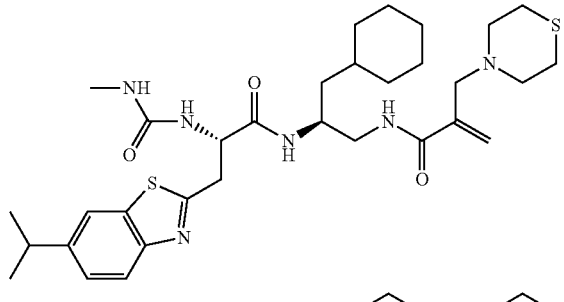
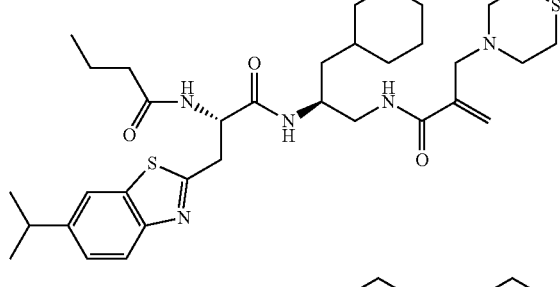
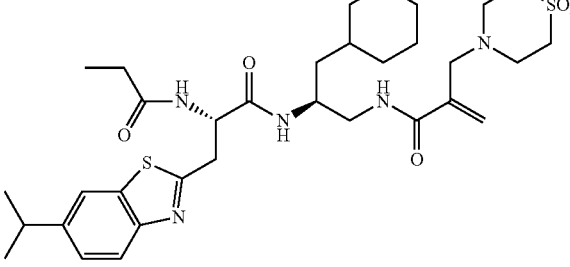
172
-continued
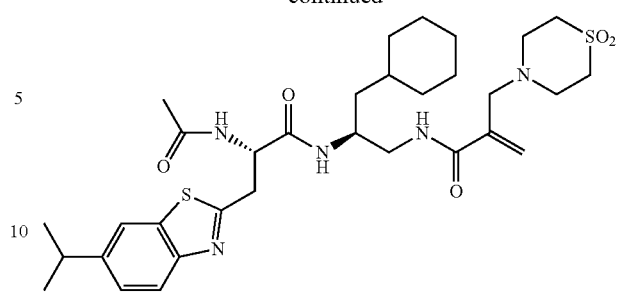

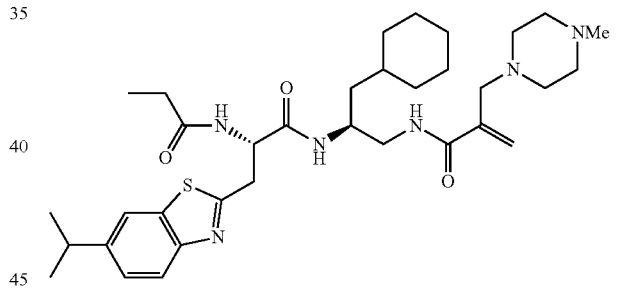
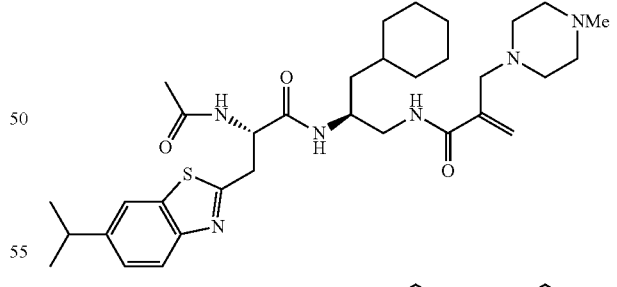
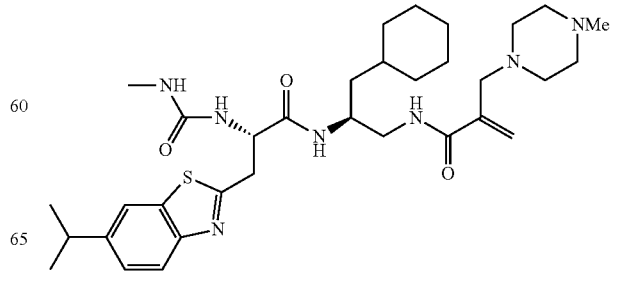

173
-continued
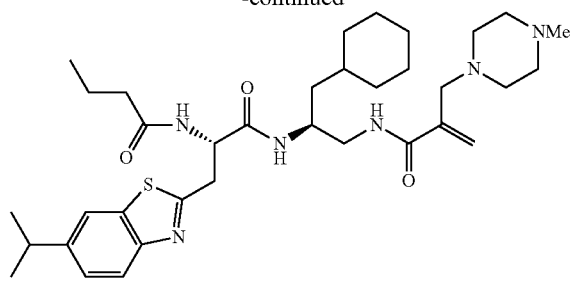
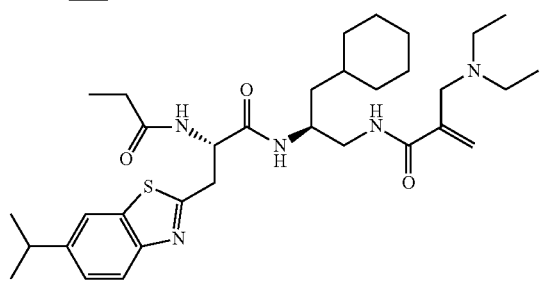
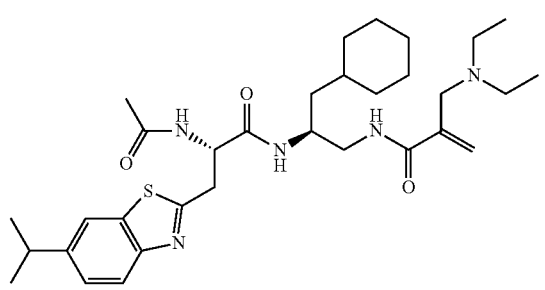
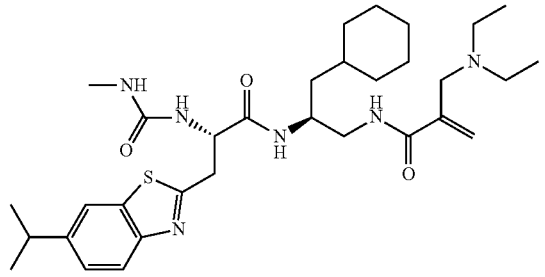
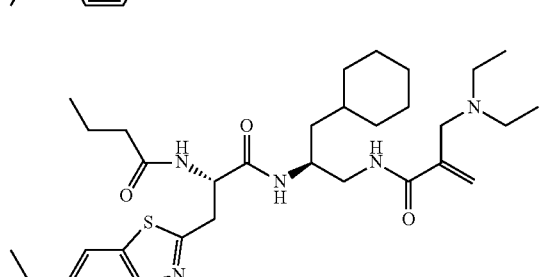
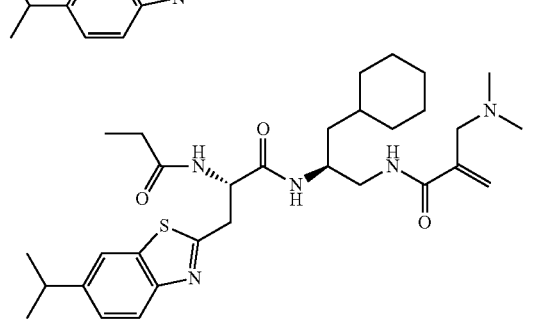
174
-continued
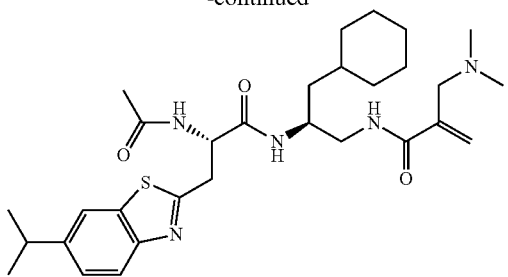
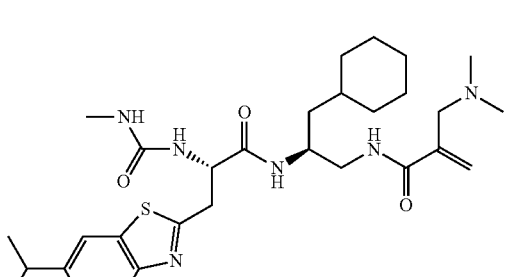
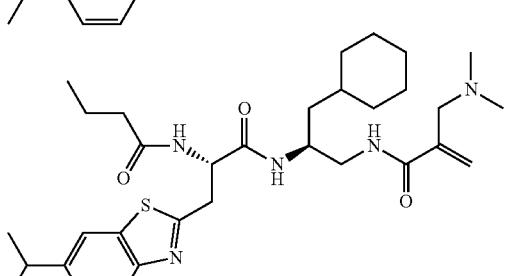
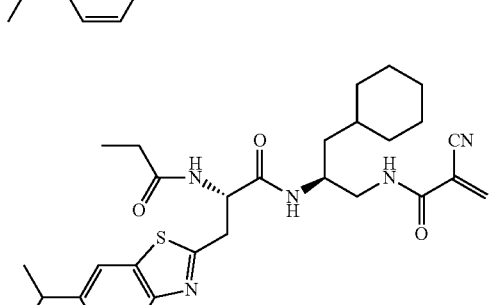
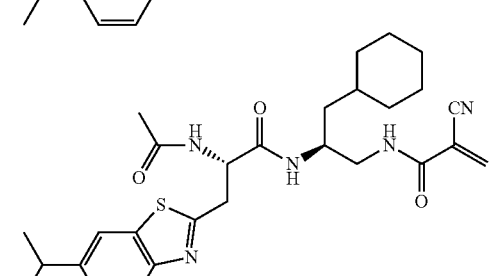
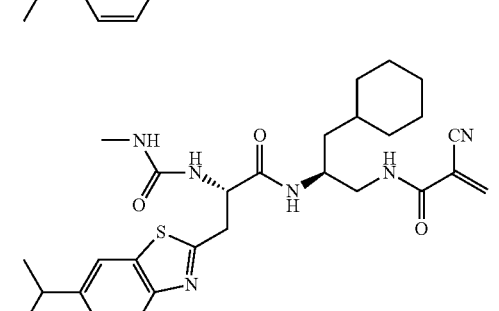

175
-continued
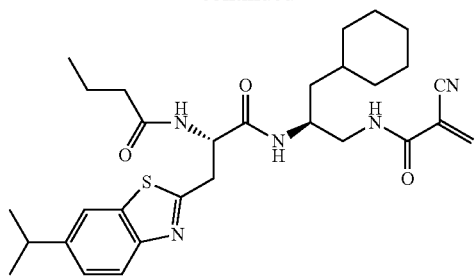
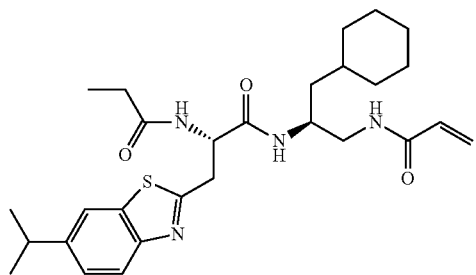
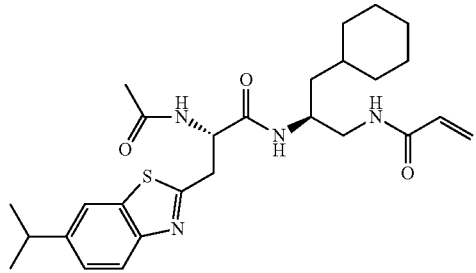
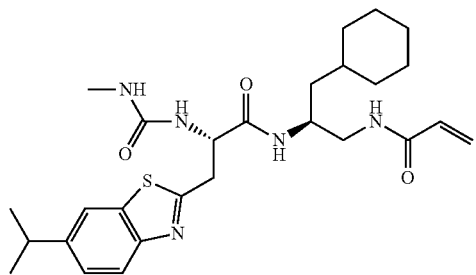
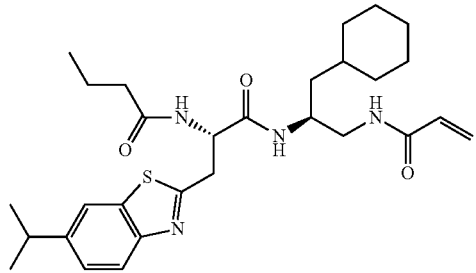
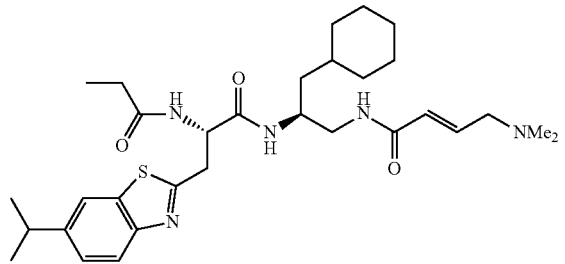
176
-continued
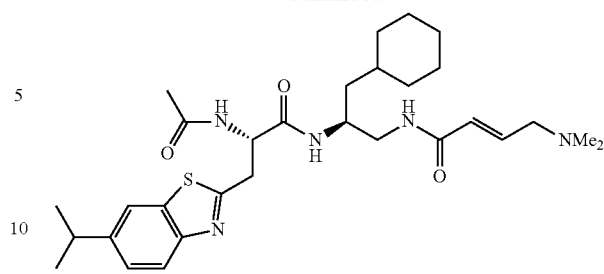
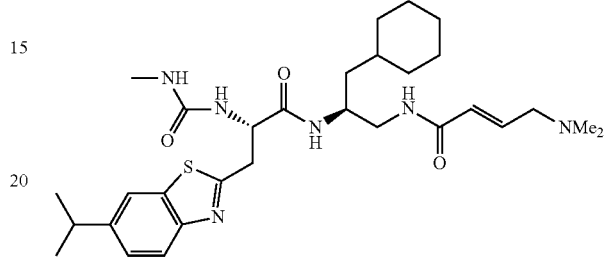
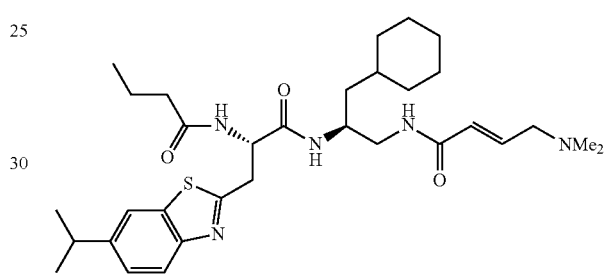
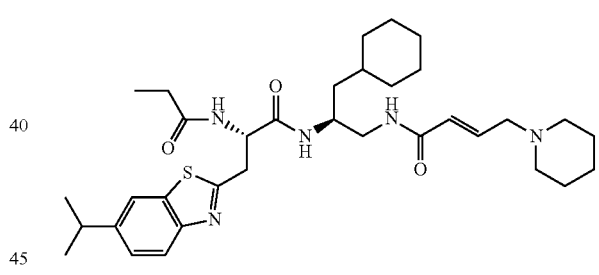
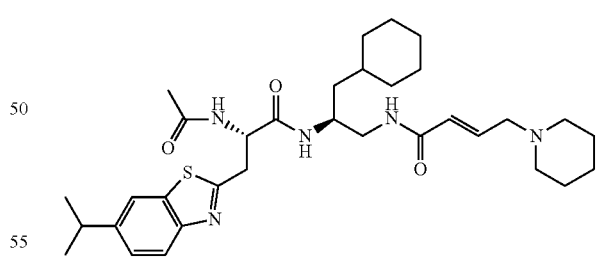
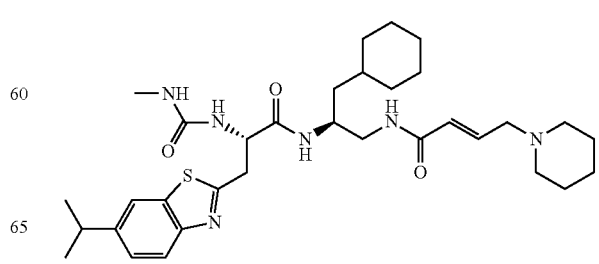

177
-continued
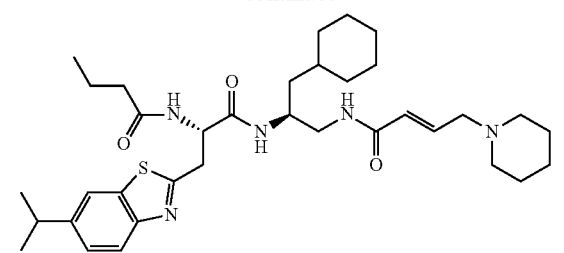
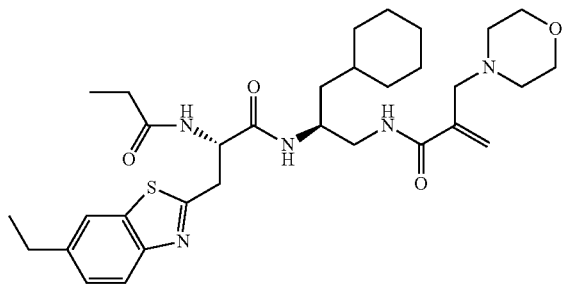
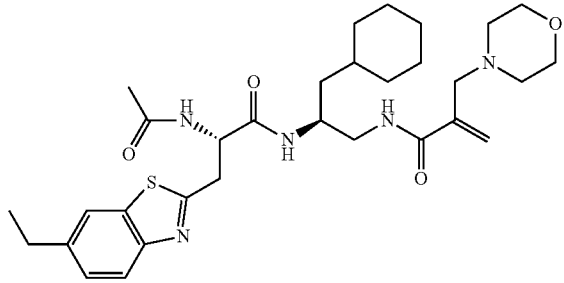
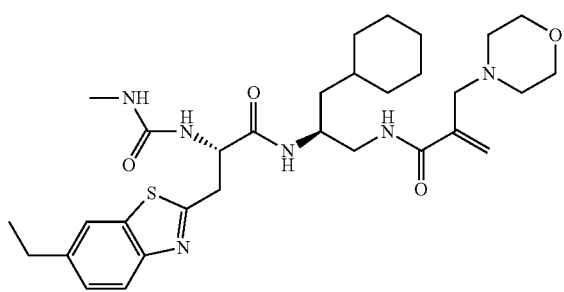
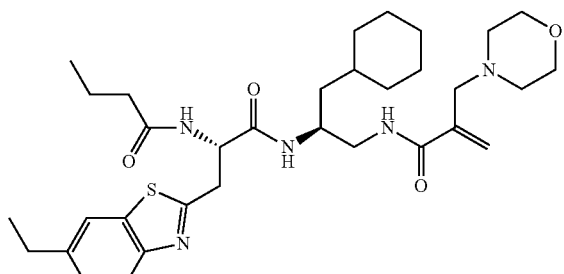
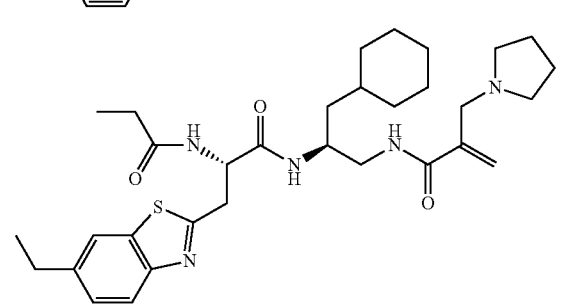
178
-continued
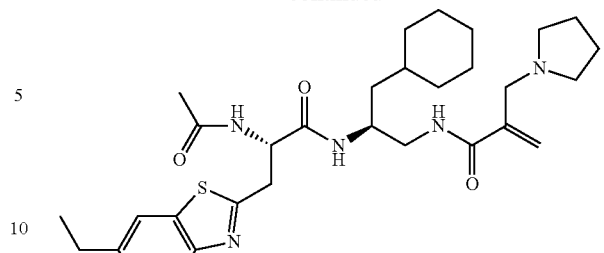
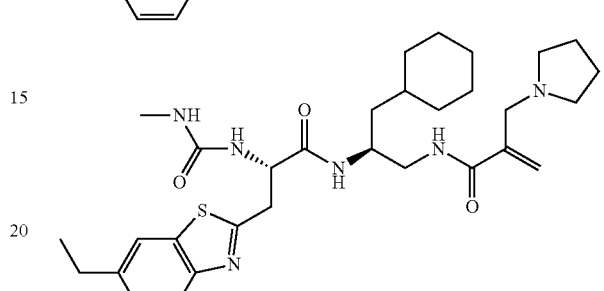
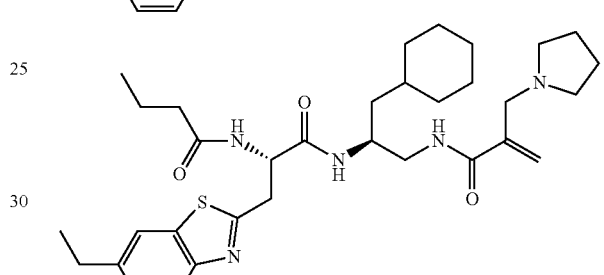
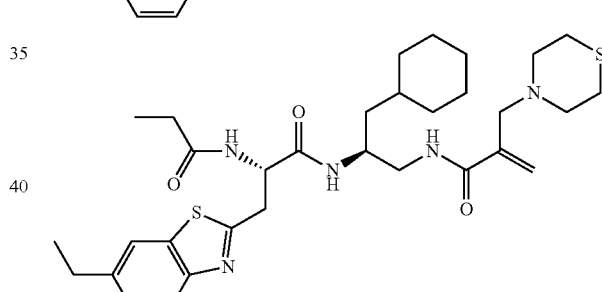
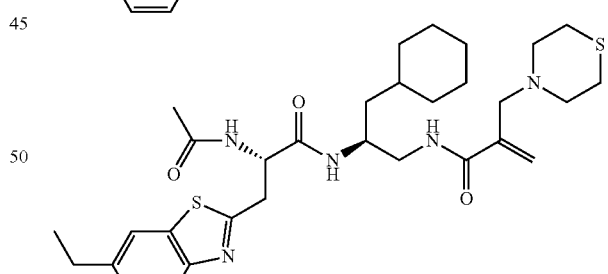
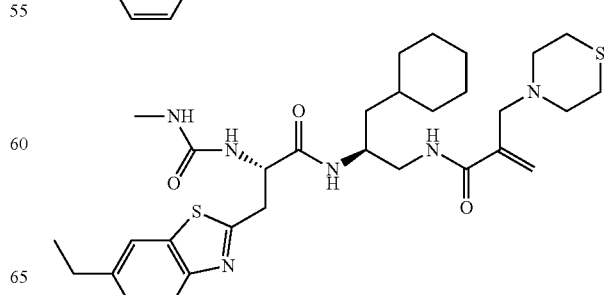

179
-continued
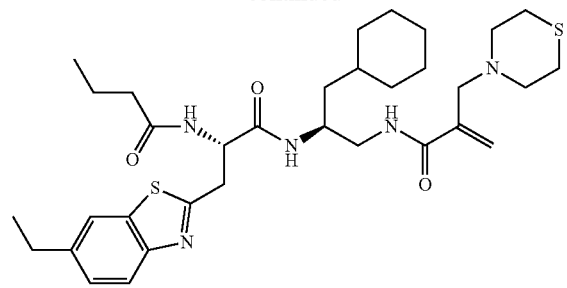
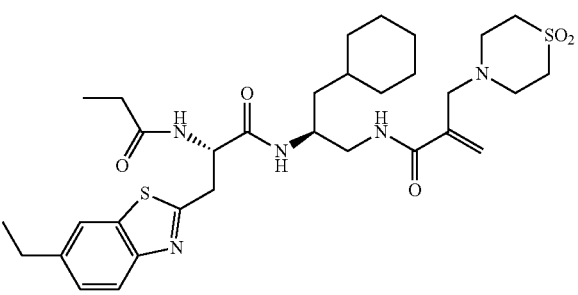
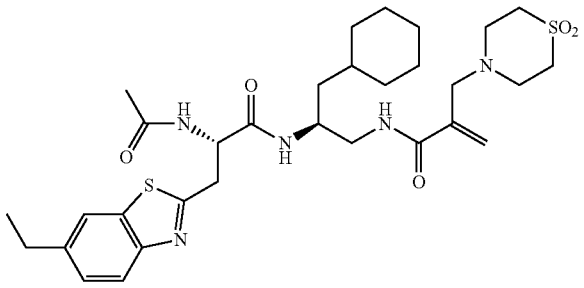
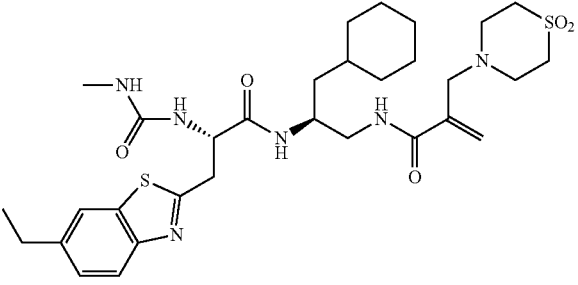
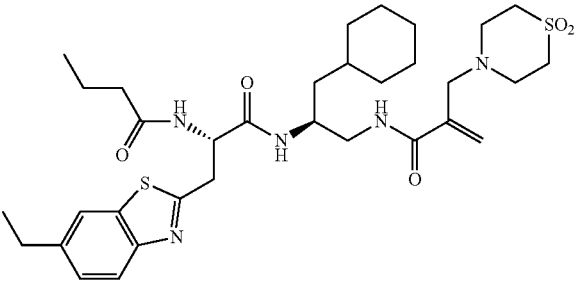
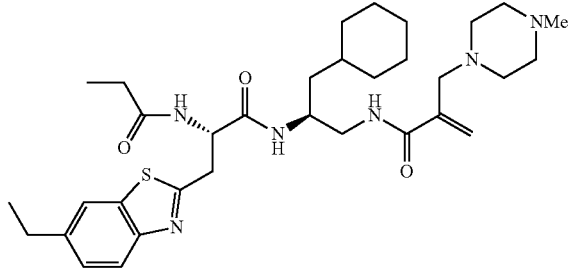
180
-continued

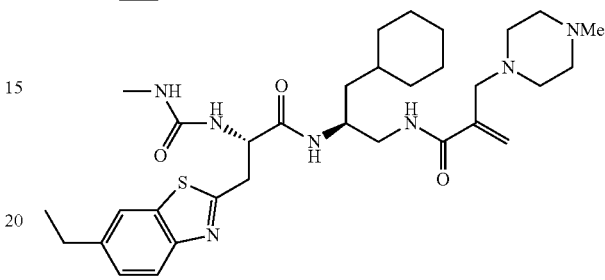
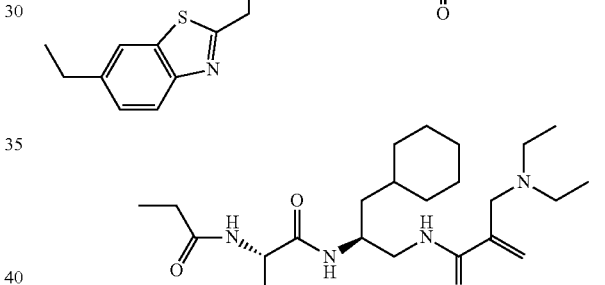
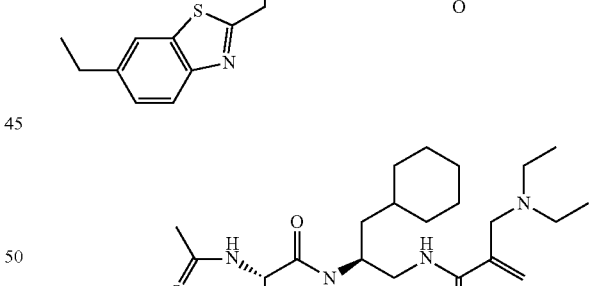
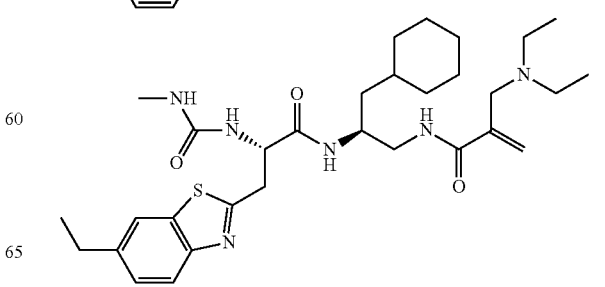

181
-continued
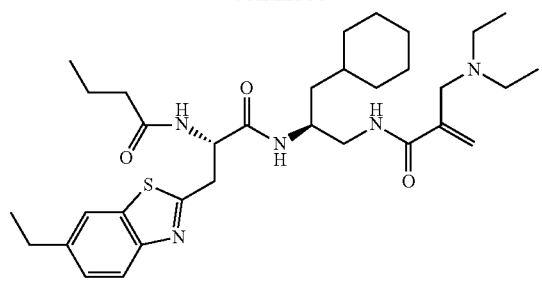
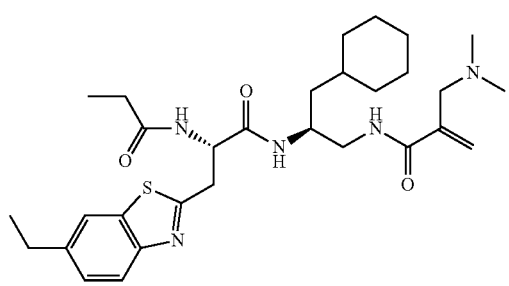
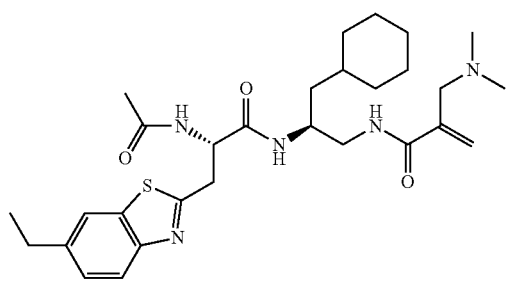
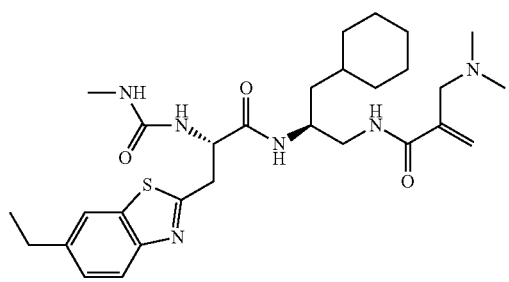
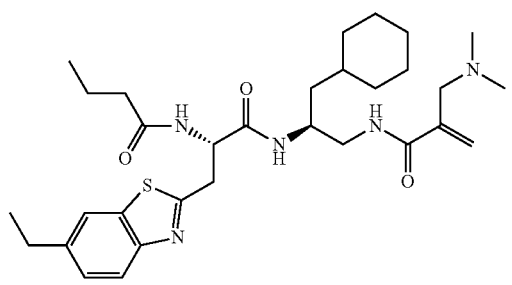
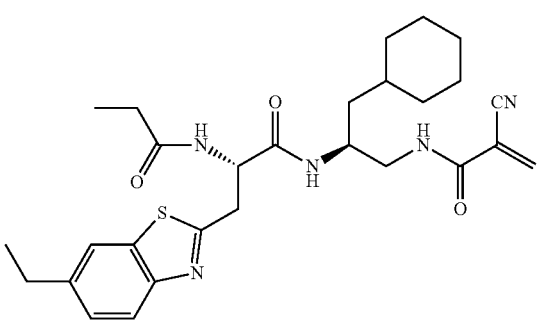
182
-continued
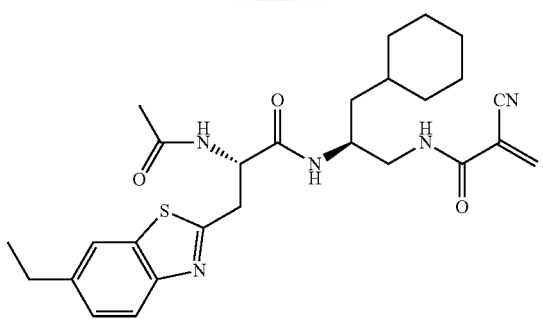
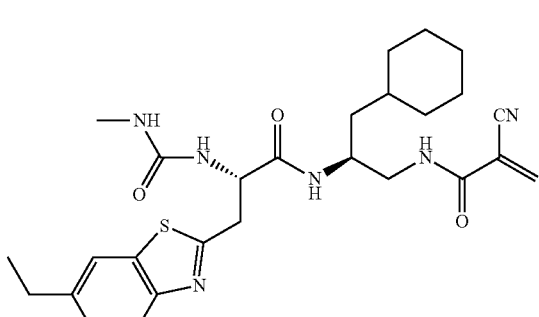
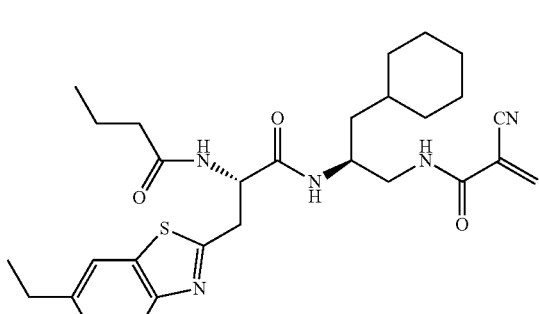
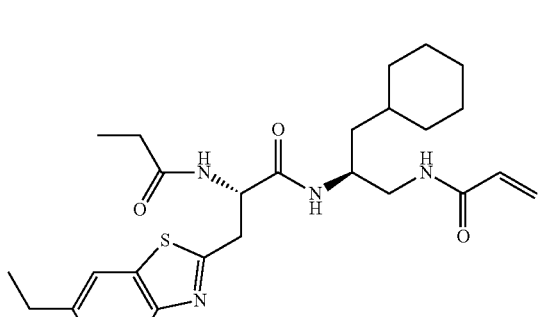
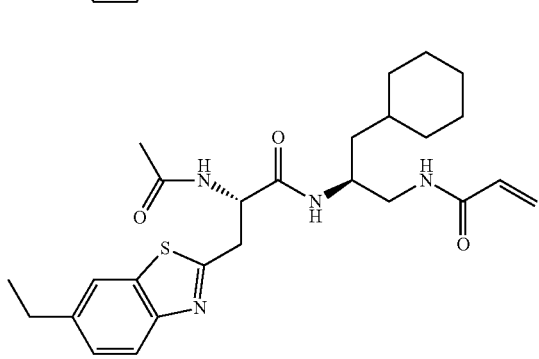

183
-continued
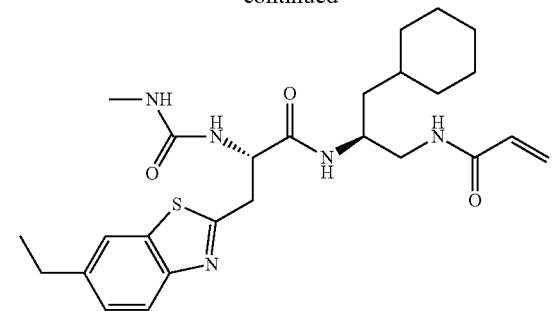
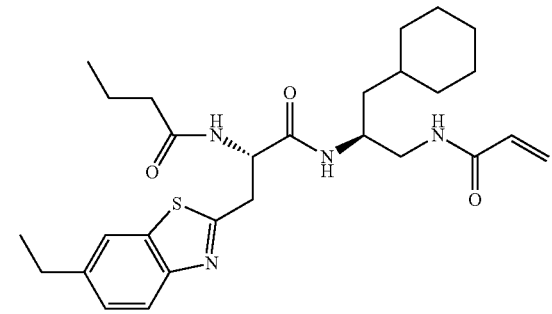
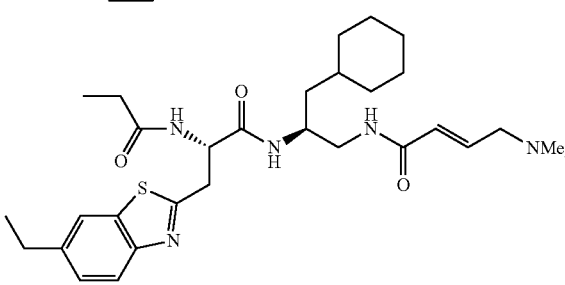
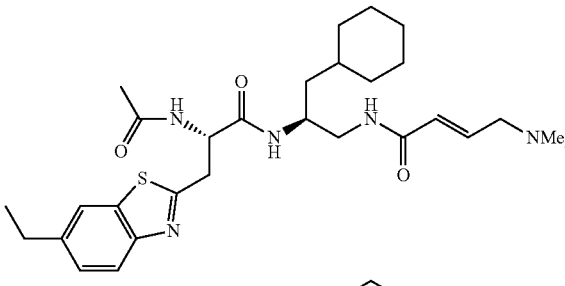
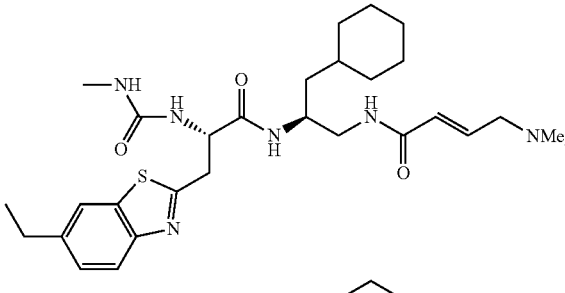
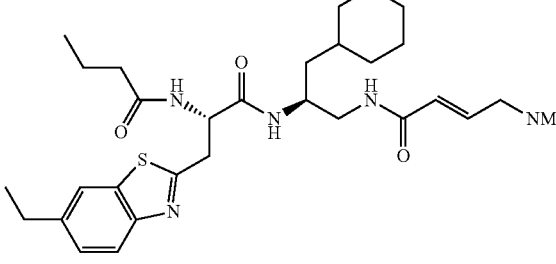
184
-continued
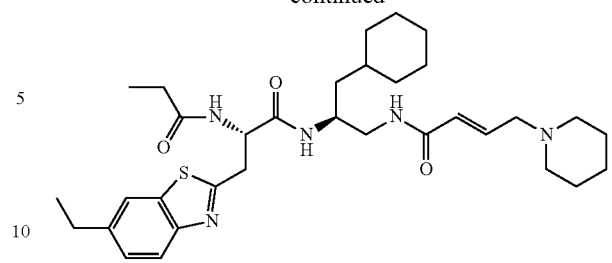
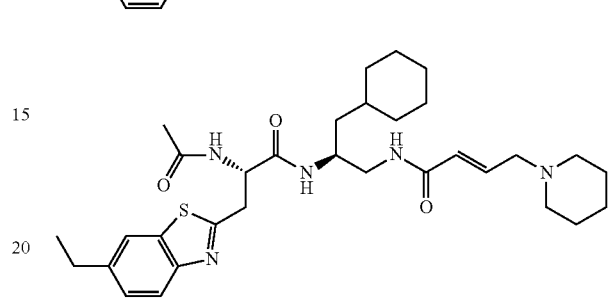
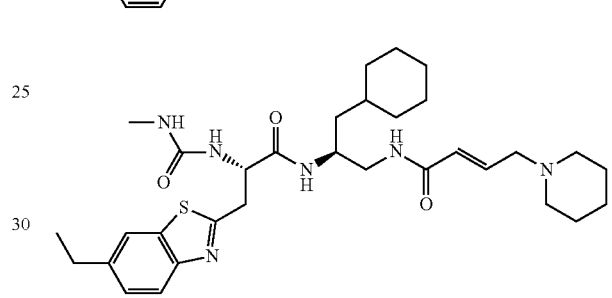
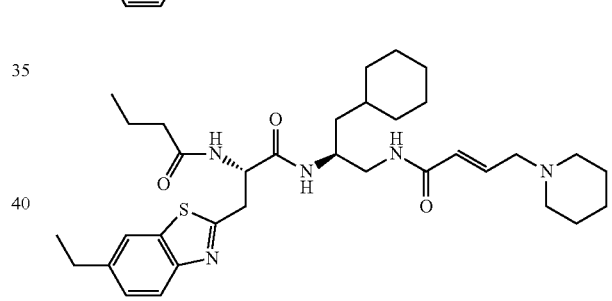
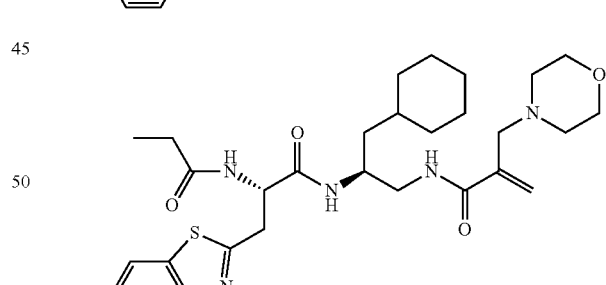
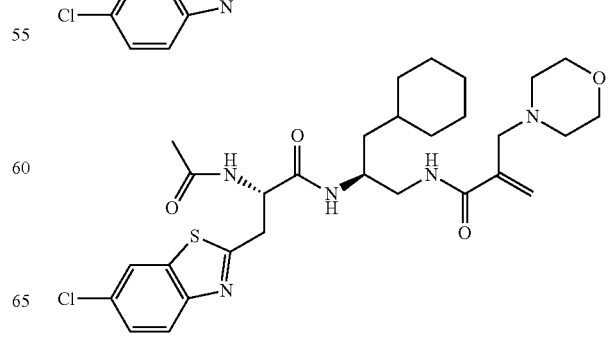

185
-continued
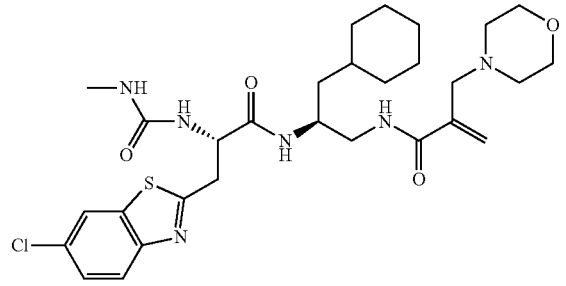
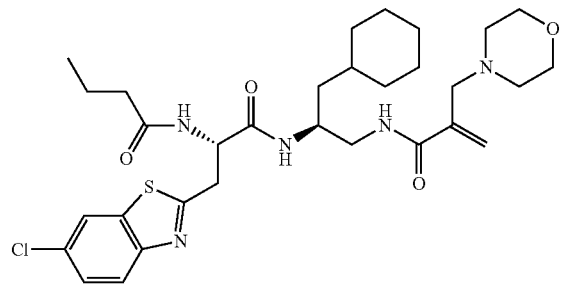
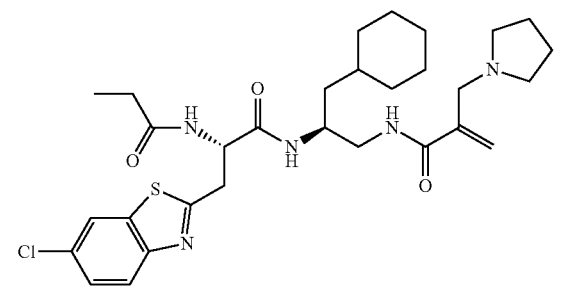
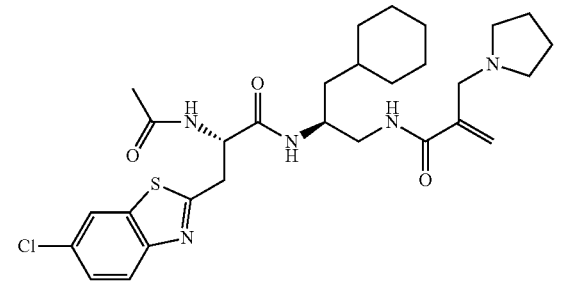
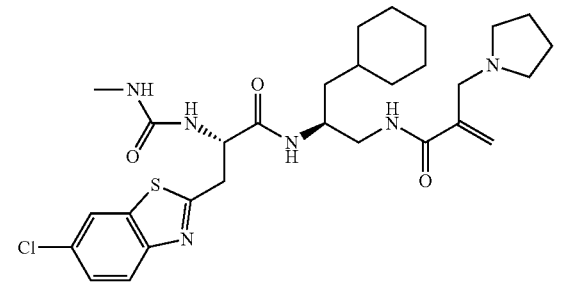
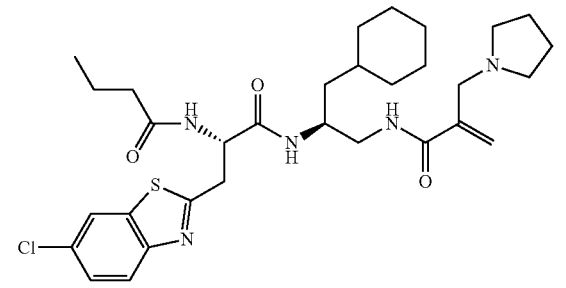
186
-continued
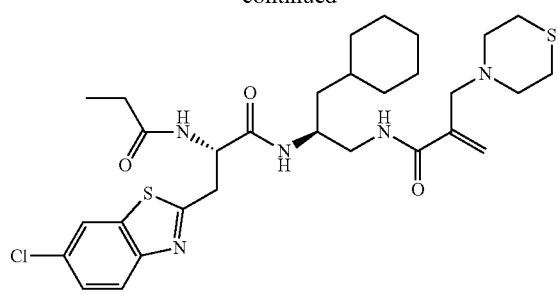
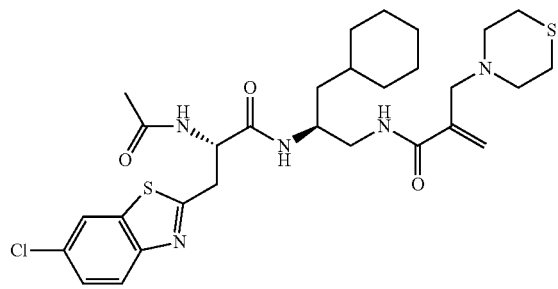
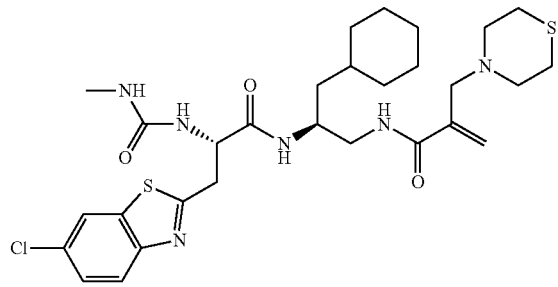
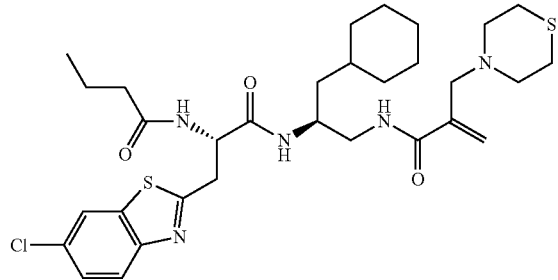
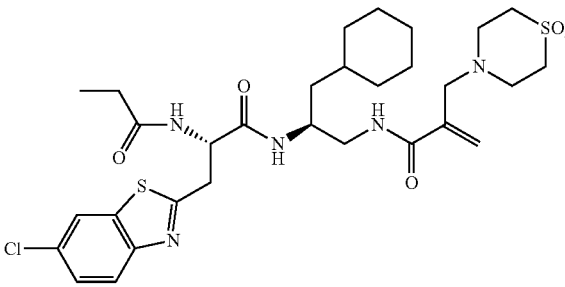
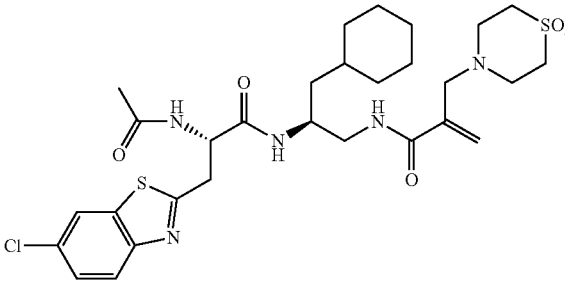

187
-continued
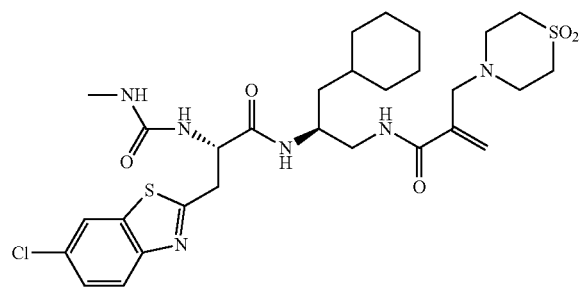
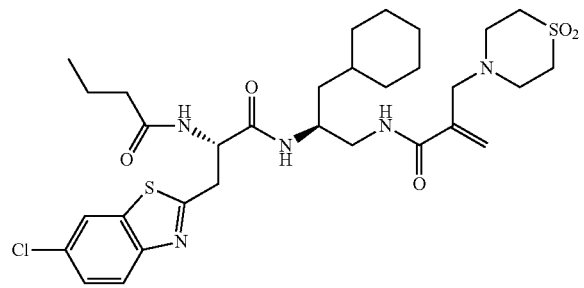
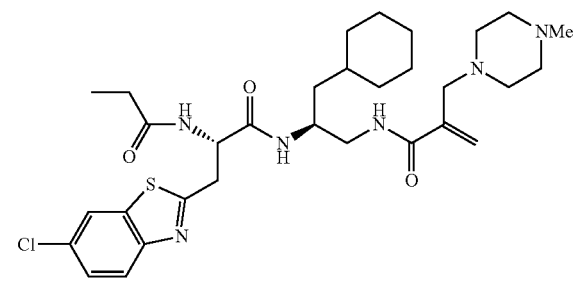
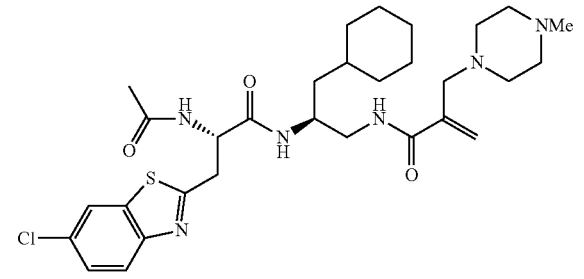
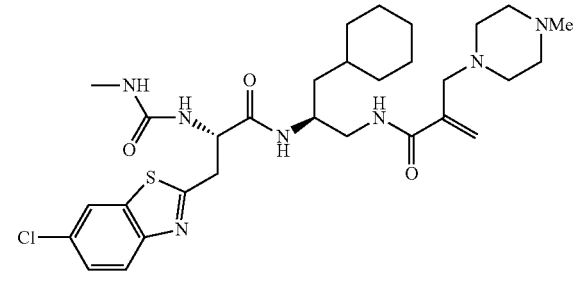
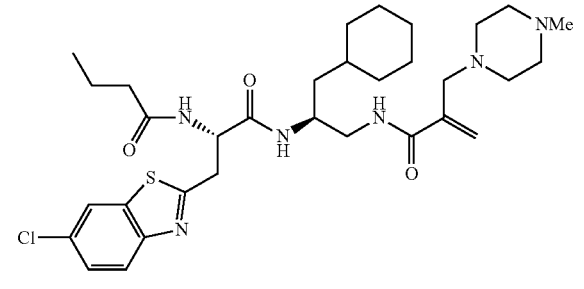
188
-continued
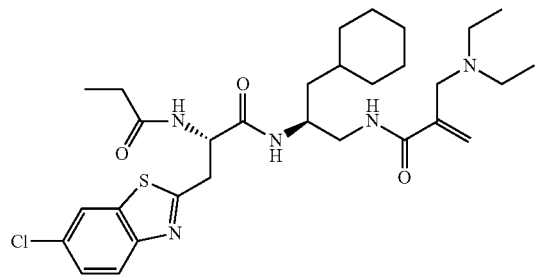
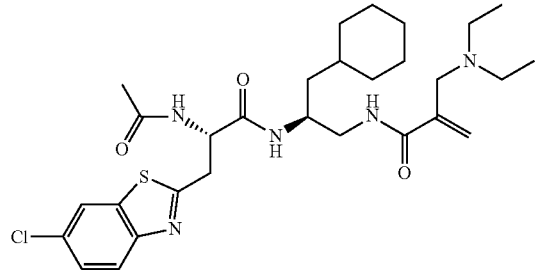
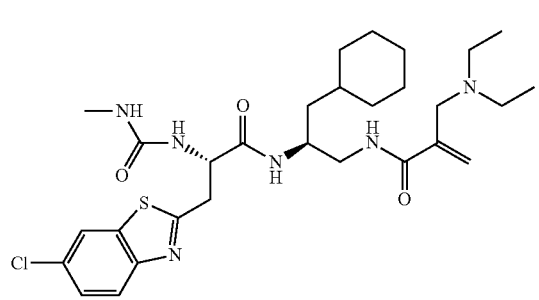
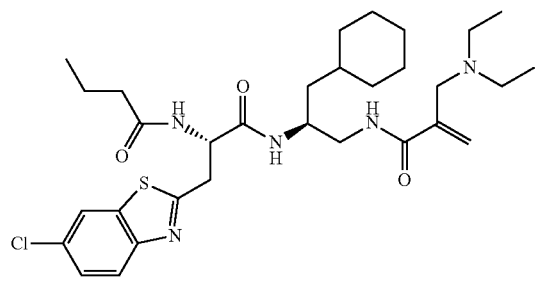
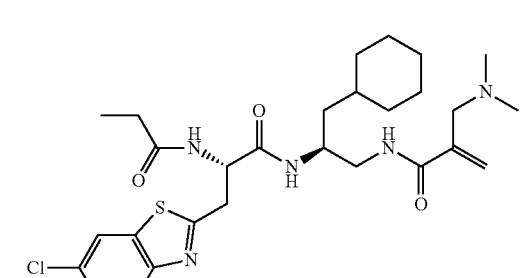
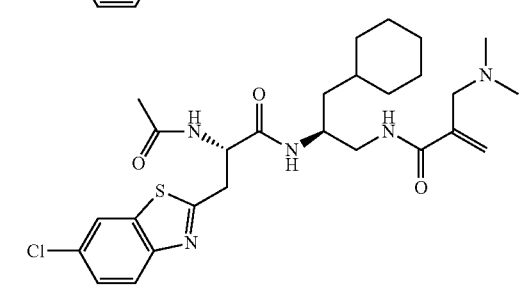

189
-continued
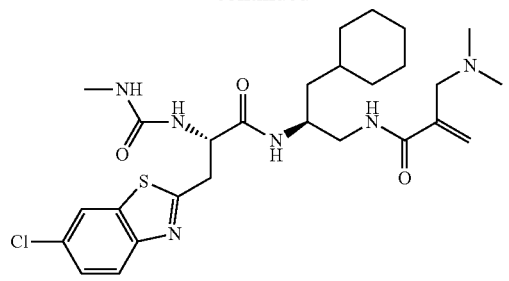
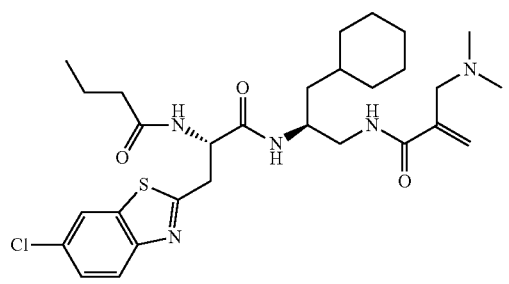
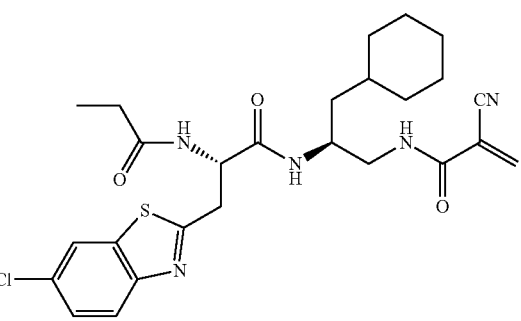
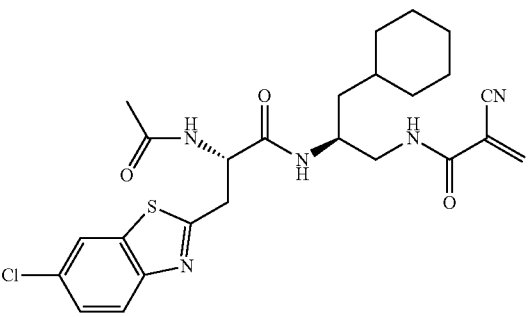
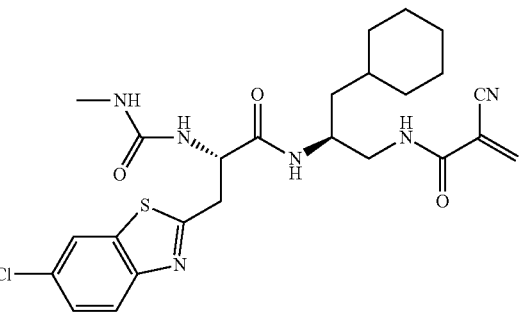
190
-continued
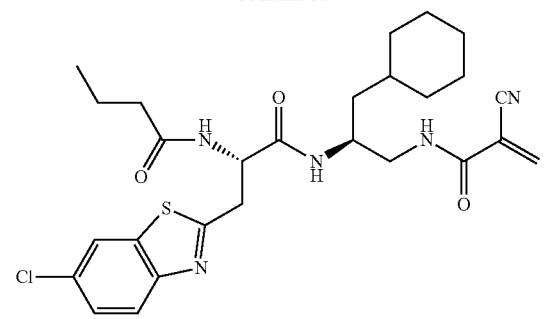
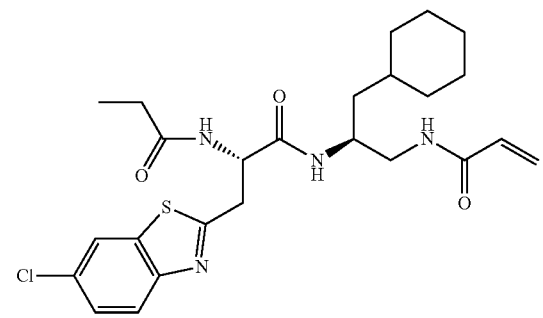
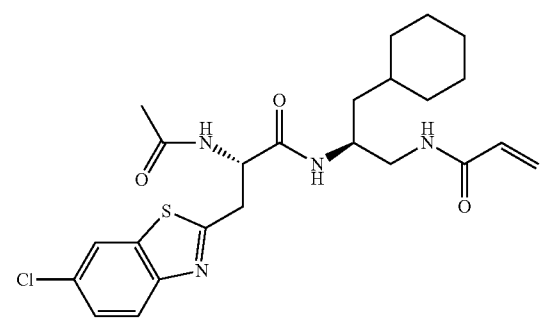
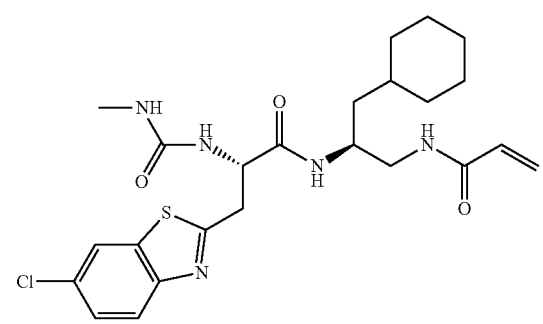
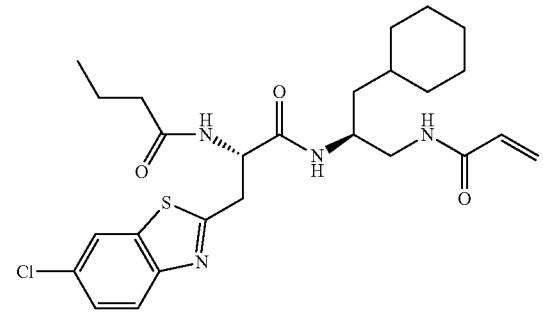

-continued

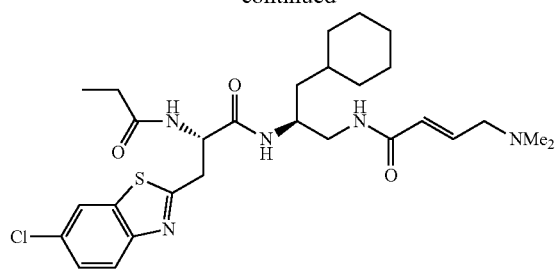

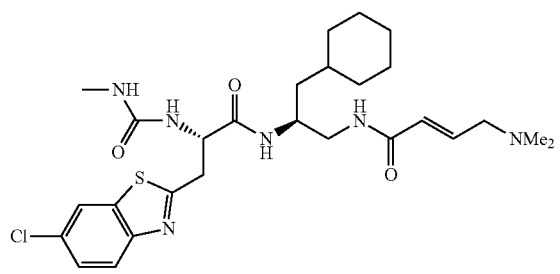

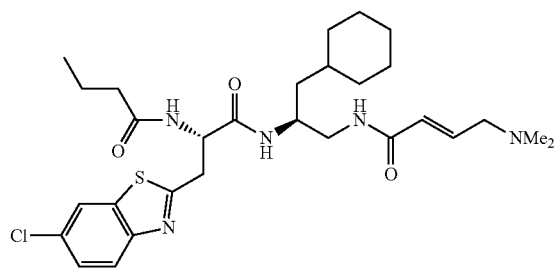

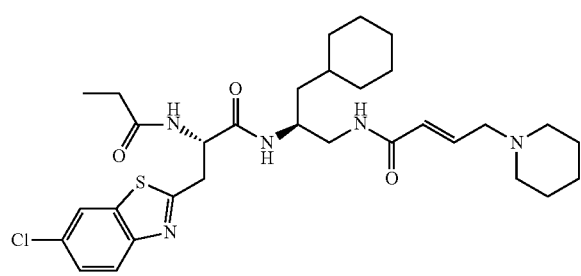

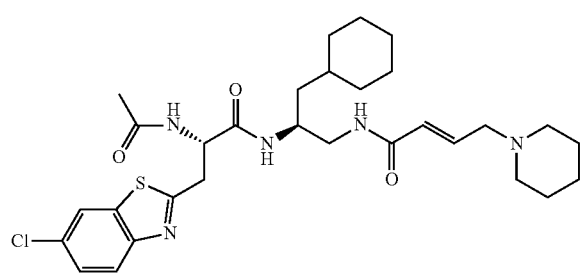

-continued

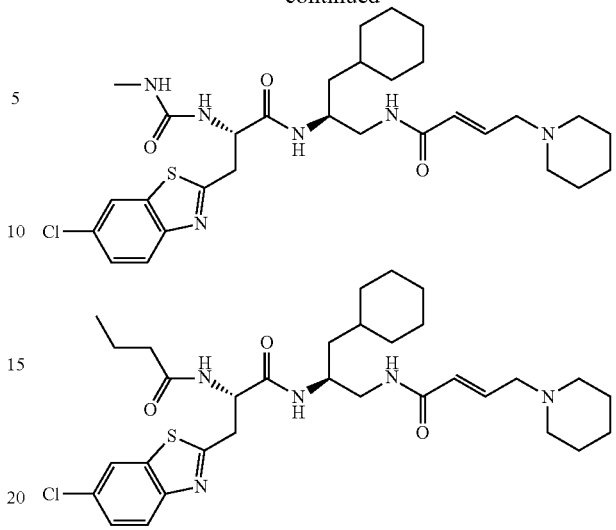

The present invention provides DCN1 inhibitors of structural formula (I) for the treatment of a variety of diseases and conditions wherein inhibition of DCN1 provides a beneficial effect. In one embodiment, the present invention relates to a method of treating an individual suffering from a disease or condition wherein inhibition of the DCN1 provides a benefit comprising administering a therapeutically effective amount of a compound of structural formula (I) to an individual in need thereof.

The method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of DCN1 provides a benefit, packaged separately or together, and an insert having instructions for using these active agents.

In many embodiments, a compound of structural formula (I) is administered in conjunction with a second therapeutic agent useful in the treatment of a disease or condition wherein inhibition of DCN1 provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, anticancer agents. It is envisioned that one or more dose of a DCN1 inhibitor of structural formula (I) and/or one or more dose of a second therapeutic agent can be administered.

A present DCN1 inhibitor can be used in the treatment of a variety of diseases and conditions, including for example, metabolic disorders, oxidative stress-related diseases, cardiovascular diseases, neurodegenerative diseases, viral infections, inflammation, acute lung injury, chronic obstructive pulmonary diseases, metabolic disorders, multiple sclerosis, inflammation, multiple myeloma, and autoimmune disease.

The diseases and conditions that can be treated in accordance to the invention include, for example, cancers. A variety of cancers can be treated including, but not limited to: carcinomas, including bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the DCN1 inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In the present method, a therapeutically effective amount of a compound of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the DCN1 inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present DCN1 inhibitor can be administered at a frequency of: one dose per day for 2 days with rest for 5 days for 2 weeks; one dose per day for 3 days with rest for 4 days for 3 weeks; weekly dosing for 2 weeks; weekly dosing for 4 weeks; or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a DCN1 inhibitor of structural formula (I) or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a compound of structural formula (I) can be administered with a chemotherapeutic agent and/or radiation.

Embodiments of the present invention employ electromagnetic radiation of: gamma-radiation (10-20 to 10-13 m), X-ray radiation (10-12 to 10-9 m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present DCN1 inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a DCN1 inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 1

| | |
|---|---|
| Alkylating agents | Natural products |
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| uracil mustard | vinorelbine |
| temozolomide | vindesine |
| Nitrosoureas | Taxotere ® (docetaxel) |
| carmustine (BCNU) | estramustine |
| lomustine (CCNU) | estramustine phosphate |

TABLE 1-continued

| | |
|---|---|
| semustine (methyl-CCNU) | Epipodophylotoxins |
| chlormethine | etoposide |
| streptozocin | teniposide |
| Ethylenimine/Methyl-melamine | Antibiotics |
| triethylenemelamine (TEM) | actimomycin D |
| triethylene thiophosphoramide (thiotepa) | daunomycin (rubidomycin) |
| | doxorubicin (adriamycin) |
| hexamethylmelamine (HMM, altretamine) | mitoxantroneidarubicin |
| | bleomycin |
| Alkyl sulfonates | splicamycin (mithramycin) |
| busulfan | mitromycin-C |
| pipobroman | dactinomycin |
| Triazines | aphidicolin |
| dacarbazine (DTIC) | epirubicin |
| Antimetabolites | idarubicin |
| Folic Acid analogs | daunorubicin |
| methotrexate | mithramycin |
| trimetrexate | deoxy co-formycin |
| pemetrexed (Multi-targeted antifolate) | Enzymes |
| | L-asparaginase |
| Pyrimidine analogs | L-arginase |
| 5-fluorouracil | Radiosensitizers |
| fluorodeoxyuridine | metronidazole |
| gemcitabine | misonidazole |
| cytosine arabinoside (AraC, cytarabine) | desmethylmisonidazole |
| | pimonidazole |
| 5-azacytidine | etanidazole |
| 2,2'-difluorodeoxy-cytidine | nimorazole |
| floxuridine | RSU 1069 |
| pentostatine | EO9 |
| Purine analogs | RB 6145 |
| 6-mercaptopurine | Nonsteroidal antiandrogens |
| 6-thioguanine | SR4233 |
| azathioprine | flutamide |
| 2'-deoxycoformycin (pentostatin) | nicotinamide |
| | 5-bromodeozyuridine |
| erythrohydroxynonyl-adenine (EHNA) | 5-iododeoxyuridine |
| | bromodeoxycytidine |
| fludarabine phosphate | Miscellaneous agents |
| 2-chlorodeoxyadenosine (cladribine, 2-CdA) | Platinium coordination complexes |
| Type I Topoisomerase Inhibitors | cisplatin |
| camptothecin | carboplatin |
| topotecan | oxaliplatin |
| irinotecan | anthracenedione |
| Biological response modifiers | mitoxantrone |
| G-CSF | Substituted urea |
| GM-CSF | hydroxyurea |
| Differentiation Agents | Methylhydrazine derivatives |
| retinoic acid derivatives | N-methylhydrazine (MIH) |
| Hormones and antagonists | procarbazine |
| Adrenocorticosteroids/antagonists | Adrenocortical suppressant |
| prednisone and equivalents | mitotane (o,p'-DDD) |
| dexamethasone | ainoglutethimide |
| ainoglutethimide | Cytokines |
| Progestins | interferon (α, β, γ) |
| hydroxyprogesterone caproate | interleukin-2 |
| medroxyprogesterone acetate | Photosensitizers |
| megestrol acetate | hematoporphyrin derivatives |
| Estrogens | PHOTOFRIN ® |
| diethylstilbestrol | benzoporphyrin derivatives |
| ethynyl estradiol/equivalents | Npe6 |
| Antiestrogen | tin etioporphyrin (SnET2) |
| tamoxifen | pheoboride-a |
| Androgens | bacteriochlorophyll-a |
| testosterone propionate | naphthalocyanines |
| fluoxymesterone/equivalents | phthalocyanines |
| Antiandrogens | zinc phthalocyanines |
| flutamide | Radiation |
| gonadotropin-releasing | X-ray |
| hormone analogs | ultraviolet light |
| leuprolide | gamma radiation |
| | visible light |
| | infrared radiation |
| | microwave radiation |

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792, trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 397:268-272; Vasquez (1997) Mol. Biol. Cell. 8:973-985; and Panda (1996) J. Biol. Chem. 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, and zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the DCN1 inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

In addition to its use in therapeutic medicine, compounds of structural formula (I), and pharmaceutically acceptable salts thereof, also are useful as pharmacological tools in the development and standardization of in vitro and in vivo test systems for the evaluation of the effects of inhibitors of DCN1 in laboratory animals, such as cats, dogs, rabbits, monkeys, rats, and mice, as part of the search for new therapeutic agents.

In accordance with an important feature of the present invention, compounds of structural formula (I) were synthesized and evaluated as inhibitors for DCN1. For example, compounds of the present invention typically have a binding affinity (IC50) to DCN1 of less than 500 nM.

Compounds of structural formula (I) were prepared using the following synthetic procedures.

A. Synthesis of Intermediate Amino Acids

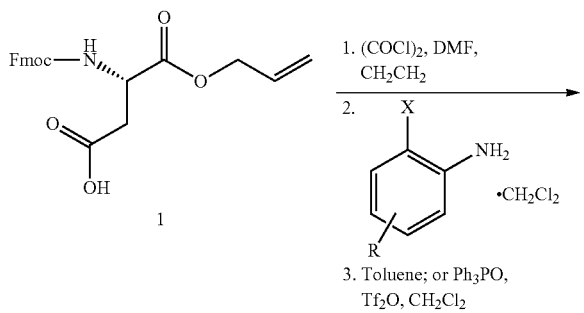

Scheme 1. Synthesis of intermediates amino acids 3.

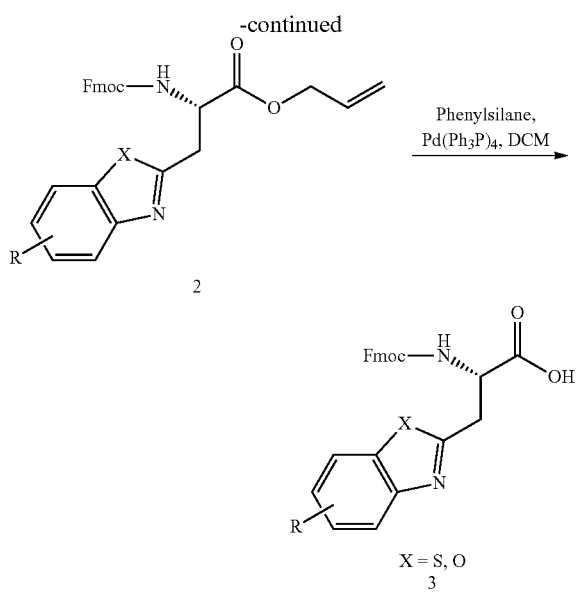

As shown in scheme 1, compounds 3 were afforded by transforming the carboxylic acid of compound 1 to benzothiazoles. A reported method[1] was employed for form the benzothiazole ring.

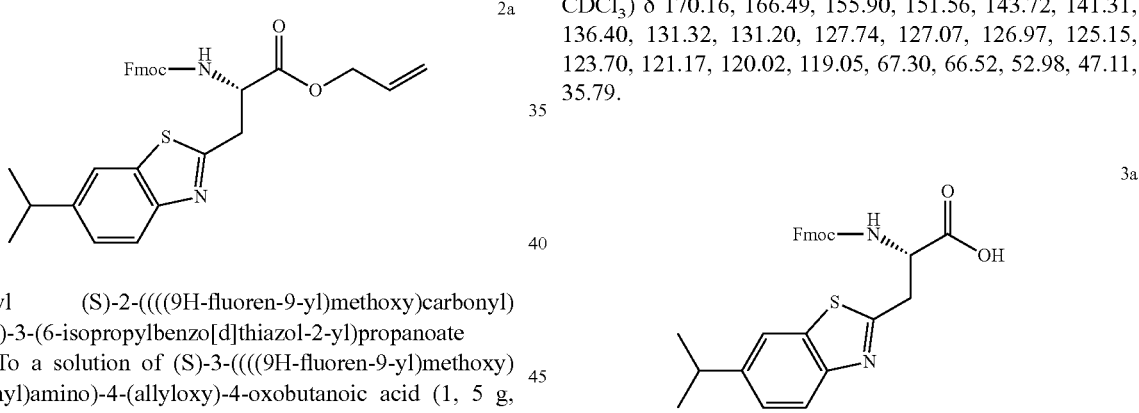

Allyl (S)-2-((((9H-fluoren-9-yl)methoxy)carbonyl)amino)-3-(6-isopropylbenzo[d]thiazol-2-yl)propanoate (2a): To a solution of (S)-3-((((9H-fluoren-9-yl)methoxy)carbonyl)amino)-4-(allyloxy)-4-oxobutanoic acid (1, 5 g, 12.6 mmol) in $CH_2Cl_2$ (300 mL) was added oxalyl chloride (3.3 mL, 38.0 mmol) and catalytic amount of DMF at 0° C. The reaction mixture was concentrated after being stirred for 0.5 h. The residue was suspended in toluene (250 mL) and treated with 2-amino-5-isopropylbenzenethiol (2.1 g, 12.6 mmol). The resultant mixture was stirred overnight at room temperature. The solution was diluted with EtOAc and washed with saturated sodium bicarbonate, 1.0 M HCl, brine and dried over sodium sulfate. The solvent was evaporated and the crude product was purified by flash chromatography on silica gel to afford intermediate 2a (3.5 g, 53%). $^1$H NMR (400 MHz, $CDCl_3$) δ 7.98 (d, J=8.4 Hz, 1H), 7.86-7.75 (m, 2H), 7.72 (s, 1H), 7.65 (t, J=7.1 Hz, 2H), 7.49-7.36 (m, 3H), 7.33-7.27 (m, 2H), 6.46 (d, J=8.5 Hz, 1H), 5.98-5.88 (m, 1H), 5.36 (d, J=17.2 Hz, 1H), 5.25 (dd, J=10.4, 0.8 Hz, 1H), 5.02 (dt, J=8.5, 5.3 Hz, 1H), 4.72 (d, J=4.9 Hz, 2H), 4.46 (d, J=7.3 Hz, 2H), 4.30 (t, J=7.3 Hz, 1H), 3.75 (qd, J=15.7, 5.3 Hz, 2H), 3.08 (dt, J=13.7, 6.9 Hz, 1H), 1.37 (d, J=6.9 Hz, 6H). $^{13}$C NMR (101 MHz, $CDCl_3$) δ 170.46, 165.13, 156.11, 151.53, 146.40, 143.98, 143.89, 141.35, 135.55, 131.60, 127.75, 127.14, 125.38, 125.30, 122.69, 120.04, 118.86, 118.74, 67.36, 66.42, 53.35, 47.19, 35.76, 34.30, 24.30. UPLC-MS (ESI-MS) m/z: calculated for $C_{31}H_{31}N_2O_4S^+$ 527.20, found 527.26 $[M+H]^+$.

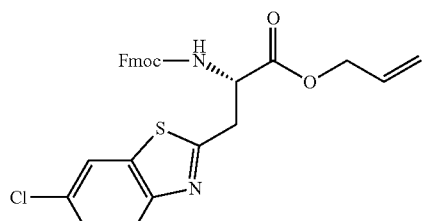

Allyl (S)-2-((((9H-fluoren-9-yl)methoxy)carbonyl)amino)-3-(6-chlorobenzo[d]thiazol-2-yl)propanoate (2b): Intermediate 2b was prepared in 46% yield by a similar procedure as that for 2a. $^1$H NMR (300 MHz, $CDCl_3$) δ 7.91 (d, J=8.7 Hz, 1H), 7.84 (d, J=1.4 Hz, 1H), 7.78 (d, J=7.3 Hz, 2H), 7.67-7.54 (m, 2H), 7.52-7.37 (m, 3H), 7.36-7.22 (m, 2H), 6.12 (d, J=8.1 Hz, 1H), 5.95-5.82 (m, 1H), 5.32 (d, J=17.3 Hz, 1H), 5.23 (d, J=10.3 Hz, 1H), 5.03-4.85 (m, 1H), 4.68 (d, J=5.1 Hz, 2H), 4.43 (d, J=7.1 Hz, 2H), 4.27 (t, J=7.0 Hz, 1H), 3.71 (qd, J=15.8, 4.9 Hz, 2H). $^{13}$C NMR (75 MHz, $CDCl_3$) δ 170.16, 166.49, 155.90, 151.56, 143.72, 141.31, 136.40, 131.32, 131.20, 127.74, 127.07, 126.97, 125.15, 123.70, 121.17, 120.02, 119.05, 67.30, 66.52, 52.98, 47.11, 35.79.

(S)-2-((((9H-fluoren-9-yl)methoxy)carbonyl)amino)-3-(6-isopropylbenzo[d]thiazol-2-yl)propanoic acid (3a): Phenylsilane (1.9 g, 17.1 mmol) was added to a solution of 2a (3.0 g, 5.7 mmol) and Tetrakis(triphenylphosphine)palladium(0) (658 mg, 0.57 mmol) in DCM. The resultant solution was stirred 1 h before being concentrated. The residue was purified by flash chromatography on silica gel to afford 3a (2.24 g, 81%). $^1$H NMR (400 MHz, DMSO) δ 8.01-7.82 (m, 5H), 7.64 (dd, J=11.7, 7.6 Hz, 2H), 7.41-7.37 (m, 3H), 7.29-7.25 (m, 1H), 7.23-7.13 (m, 1H), 4.57-4.51 (m, 1H), 4.30-4.16 (m, 3H), 3.60 (dd, J=15.1, 4.6 Hz, 1H), 3.44 (dd, J=15.0, 9.9 Hz, 1H), 3.03 (dt, J=13.7, 6.8 Hz, 1H), 1.26 (d, J=6.9 Hz, 6H). $^{13}$C NMR (101 MHz, DMSO) δ 172.71, 167.25, 156.39, 151.46, 146.13, 144.23, 144.14, 141.15, 135.65, 128.06, 127.49, 125.71, 125.65, 125.51, 122.45, 120.55, 119.48, 66.18, 54.10, 47.04, 35.53, 33.97, 24.55, 24.54. UPLC-MS (ESI-MS) m/z: calculated for $C_{28}H_{27}N_2O_4S^+$ 487.17, found 487.19 $[M+H]^+$.

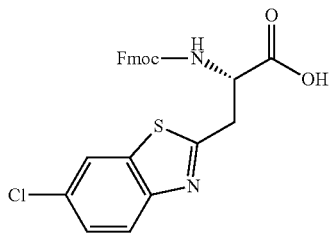

(S)-2-((((9H-fluoren-9-yl)methoxy)carbonyl)amino)-3-(6-chlorobenzo[d]thiazol-2-yl)propanoic acid (3b): Intermediate 3b was prepared from 2b in 79% yield by a similar procedure as that for 3a. $^1$H NMR (300 MHz, CD$_3$OD:CCl$_3$D=1:10) δ 7.84 (d, J=8.7 Hz, 1H), 7.78 (d, J=2.0 Hz, 1H), 7.72 (d, J=7.5 Hz, 2H), 7.57-7.54 (m, 2H), 7.43-7.30 (m, 3H), 7.24 (t, J=7.4 Hz, 2H), 4.95-4.66 (m, 1H), 4.45-4.25 (m, 2H), 4.19 (t, J=7.0 Hz, 1H), 3.67-3.64 (m, 2H). $^{13}$C NMR (75 MHz, CD$_3$OD:CCl$_3$D=1:10) δ 172.19, 167.48, 156.13, 151.13, 143.66, 141.24, 136.32, 131.19, 127.68, 127.02, 126.96, 125.06, 123.37, 121.15, 119.93, 67.15, 52.92, 47.03, 35.67. UPLC-MS (ESI-MS) m/z: calculated for C$_{25}$H$_{20}$ClN$_2$O$_4$S$^+$ 479.08, found 479.19 [M+H]$^+$.

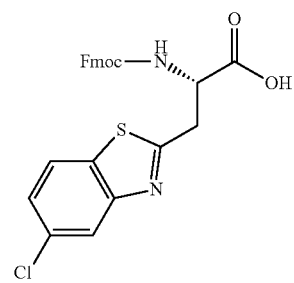

(S)-2-((((9H-fluoren-9-yl)methoxy)carbonyl)amino)-3-(5-chlorobenzo[d]thiazol-2-yl)propanoic acid (3c): Intermediate 3c was prepared from 1 in 41% yield in two steps using a similar procedure as that for 3a. $^1$H NMR (400 MHz, DMSO) δ 13.04 (br, 1H), 8.11 (d, J=8.6 Hz, 1H), 8.02 (d, J=1.9 Hz, 1H), 7.93 (d, J=8.6 Hz, 1H), 7.88 (d, J=7.5 Hz, 2H), 7.67-7.94 (m, 2H), 7.48 (dd, J=8.6, 2.0 Hz, 1H), 7.41-7.38 (m, 2H), 7.30-7.22 (m, 2H), 4.54 (td, J=9.5, 4.6 Hz, 1H), 4.29-4.27 (m, 2H), 4.20 (t, J=6.8 Hz, 1H), 3.63 (dd, J=15.2, 4.5 Hz, 1H), 3.47 (dd, J=15.1, 9.9 Hz, 1H). $^{13}$C NMR (101 MHz, DMSO) δ 172.59, 170.94, 156.41, 153.89, 144.21, 144.15, 141.17, 134.25, 131.33, 128.07, 127.48, 125.64, 125.57, 124.05, 122.28, 120.57, 66.15, 53.92, 47.05, 35.62. UPLC-MS (ESI-MS) m/z: calculated for C$_{25}$H$_{20}$ClN$_2$O$_4$S$^+$ 479.08, found 479.22[M+H]$^+$.

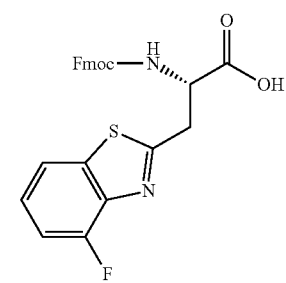

(S)-2-((((9H-fluoren-9-yl)methoxy)carbonyl)amino)-3-(4-fluorobenzo[d]thiazol-2-yl)propanoic acid (3d): Intermediate 3d was prepared from 1 in 36% yield in two steps using a similar procedure as that for 3a. $^1$H NMR (400 MHz, DMSO), δ 13.0 (br. 1H), 7.97-7.87 (m, 4H), 7.66-7.64 (m, 2H), 7.87 (d, J=7.5, 2H), 7.48-7.22 (m, 6H), 4.54 (dt, J=4.0, 8.8, 1H), 4.28 (d, J=6.3, 2H), 4.20 (t, J=6.8, 1H), 3.65 (dd, J=4.6, 15.1, 1H), 3.49 (dd, J=9.9, 15.1, 1H); $^{13}$C NMR (75 MHz, CD3OD).

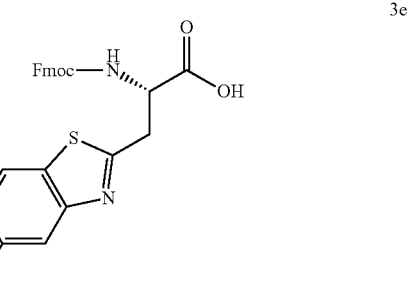

(S)-2-((((9H-fluoren-9-yl)methoxy)carbonyl)amino)-3-(5-fluorobenzo[d]thiazol-2-yl)propanoic acid (3e): Intermediate 3e was prepared from 1 in 39% yield in two steps using a similar procedure as that for 3a: $^1$H NMR (400 MHz, DMSO), δ 13.0 (br. 1H), 8.12-8.09 (m, 1H), 7.94 (d, J=8.6, 1H), 7.87 (d, J=7.5, 2H), 7.79 (dd, J=2.5, 9.9, 1H), 7.67-7.64 (m, 2H), 7.41-7.23 (m, 5H), 4.55 (dt, J=4.0, 9.4, 1H), 4.29 (d, J=6.7, 2H), 4.20 (t, J=6.8, 1H), 3.63 (dd, J=4.5, 15.1, 1H), 3.47 (dd, J=9.8, 15.1, 1H); $^{13}$C NMR (75 MHz, CD3OD).

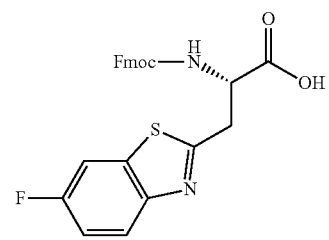

(S)-2-((((9H-fluoren-9-yl)methoxy)carbonyl)amino)-3-(6-fluorobenzo[d]thiazol-2-yl)propanoic acid (3f): Intermediate 3f was prepared from 1 in 32% yield in two steps using a similar procedure as that for 3a: $^1$H NMR (400 MHz, DMSO), δ 13.0 (br. 1H), 7.99-7.92 (m, 3H), 7.88 (d, J=7.5, 2H), 7.67-7.64 (m, 2H), 7.42-7.34 (m, 3H), 7.30-7.23 (m, 2H), 4.54 (dt, J=4.4, 8.6, 1H), 4.28 (d, J=7.0, 2H), 4.20 (t, J=6.8, 1H), 3.60 (dd, J=4.3, 15.1, 1H), 3.45 (dd, J=9.8, 15.1, 1H); $^{13}$C NMR (75 MHz, CD3OD).

(S)-2-((((9H-fluoren-9-yl)methoxy)carbonyl)amino)-3-(7-chlorobenzo[d]thiazol-2-yl)propanoic acid (3g): Intermediate 3g was prepared from 1 in 35% yield in two steps using a similar procedure as that for 3a. ESI-MS m/z: calculated for $C_{25}H_{20}ClN_2O_4S^+$ 479.1, found 479.4 [M+H]$^+$.

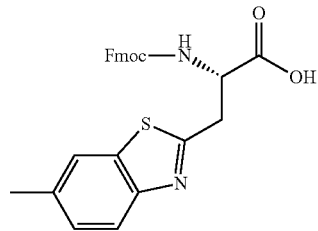

3h (S)-2-((((9H-fluoren-9-yl)methoxy)carbonyl)amino)-3-(6-methylbenzo[d]thiazol-2-yl)propanoic acid (3h): Intermediate 3h was prepared from 1 in two steps using a similar procedure as that for 3a. ESI-MS m/z: calculated for $C_{26}H_{23}N_2O_4S+$459.1, found 459.8 [M+H]$^+$.

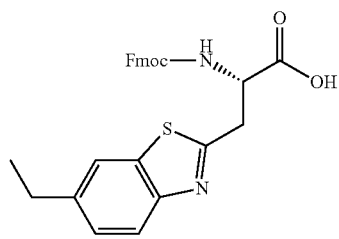

3i (S)-2-((((9H-fluoren-9-yl)methoxy)carbonyl)amino)-3-(6-ethylbenzo[d]thiazol-2-yl)propanoic acid (3i): Intermediate 3i was prepared from 1 in two steps using a similar procedure as that for 3a. ESI-MS m/z: calculated for $C_{27}H_{25}N_2O_4S+$ 473.2, found 473.5[M+H]$^+$.

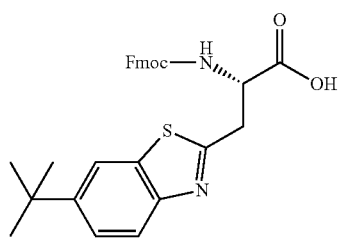

3j (S)-2-((((9H-fluoren-9-yl)methoxy)carbonyl)amino)-3-(6-(1,1-dimethylethyl)benzo[d]thiazol-2-yl)propanoic acid (3j): Intermediate 3j was prepared from 1 in two steps using a similar procedure as that for 3a. ESI-MS m/z: calculated for $C_{29}H_{29}N_2O_4S+$ 501.2, found 501.9 [M+H]$^+$.

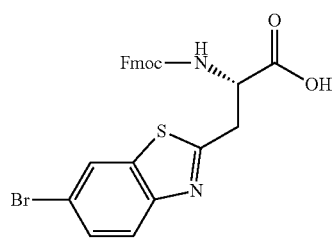

3k (S)-2-((((9H-fluoren-9-yl)methoxy)carbonyl)amino)-3-(6-bromobenzo[d]thiazol-2-yl)propanoic acid (3k): Intermediate 3k was prepared from 1 in two steps using a similar procedure as that for 3a. ESI-MS m/z: calculated for $C_{25}H_{20}BrN_2O_4S^+$ 523.0, found 523.6 [M+H]$^+$.

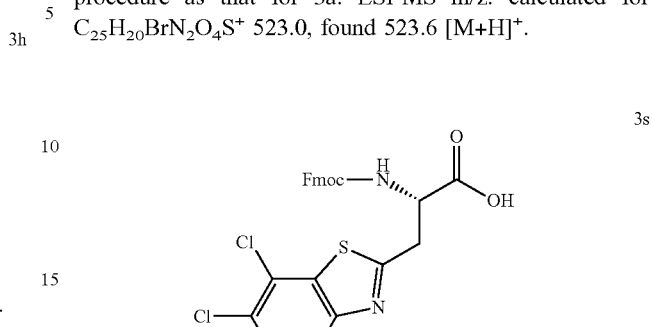

3s (S)-2-((((9H-fluoren-9-yl)methoxy)carbonyl)amino)-3-(6-methylbenzo[d]thiazol-2-yl)propanoic acid (3s): Intermediate 3s was prepared from 1 in two steps using a similar procedure as that for 3a. ESI-MS m/z: calculated for $C_{25}H_{18}C_{12}N_2O_4S^+$ 512.0, found 512.5 [M+H]$^+$.

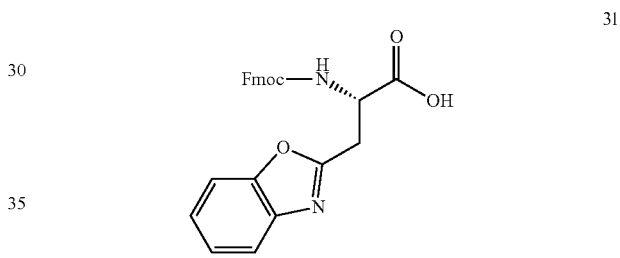

3l (S)-2-((((9H-fluoren-9-yl)methoxy)carbonyl)amino)-3-(benzo[d]oxazol-2-yl)propanoic acid (3l): To a solution of (S)-3-((((9H-fluoren-9-yl)methoxy)carbonyl)amino)-4-(allyloxy)-4-oxobutanoic acid (1, 5 g, 12.6 mmol) in $CH_2Cl_2$ (300 mL) was added oxalyl chloride (3.3 mL, 38.0 mmol) and catalytic amount of DMF at 0° C. The reaction mixture was concentrated after being stirred for 0.5 h. The residue was suspended in $CH_2Cl_2$ (250 mL) and treated with 2-amino-5-isopropylbenzenethiol (2.1 g, 12.6 mmol) and N,N-Diisopropylethylamine (5 mL). The resulting mixture was stirred for 3 h and treated with water. The separated organic phase was dried over $Na_2SO_4$ and concentrated to get 3l-1. Trifluoromethanesulfonic anhydride (3.2 ml, 18.9 mmol) was added slowly to a solution of triphenylphosphane oxide (10.5 g, 37.8 mmol) in dry $CH_2Cl_2$ (250 mL) at 0° C. After the mixture was stirred at 0° C. for 10 min, 3l-1 was then added at the same temperature. The reaction was allowed to warm to room temperature and stirred for 5 h. The reaction mixture was quenched with 10% aqueous $NaHCO_3$ solution. The aqueous layer was extracted with $CH_2Cl_2$, and the combined organic layers were dried over $Na_2SO_4$, filtered, and concentrated. The crude product was purified by flash chromatography on silica gel to afford 3l. ESI-MS m/z: calculated for $C_{25}H_{21}N_2O_5^+$ 429.1, found 429.6.

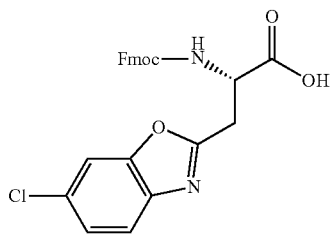

3m (S)-2-((((9H-fluoren-9-yl)methoxy)carbonyl)amino)-3-(6-chlorobenzo[d]oxazol-2-yl)propanoic acid (3m): Intermediate 3m was prepared from 1 in two steps using a similar procedure as that for 3l. ESI-MS m/z: calculated for $C_{25}H_{20}ClN_2O_5^+$ 463.1, found 463.0 [M+H]$^+$.

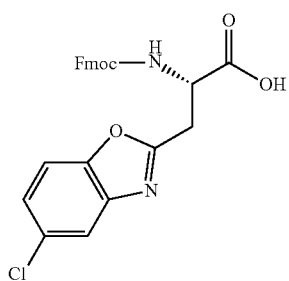

3n (S)-2-((((9H-fluoren-9-yl)methoxy)carbonyl)amino)-3-(5-chlorobenzo[d]oxazol-2-yl)propanoic acid (3n): Intermediate 3n was prepared from 1 in two steps using a similar procedure as that for 3l. ESI-MS m/z: calculated for $C_{25}H_{20}ClN_2O_5^+$ 463.1, found 463.2 [M+H]$^+$.

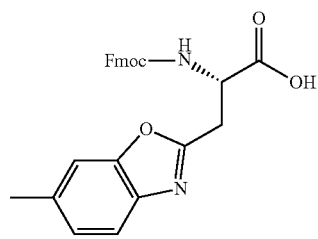

3o (S)-2-((((9H-fluoren-9-yl)methoxy)carbonyl)amino)-3-(6-methylbenzo[d]oxazol-2-yl)propanoic acid (3o): Intermediate 3o was prepared from 1 in two steps using a similar procedure as that for 3l. ESI-MS m/z: calculated for $C_{26}H_{23}N_2O_5^+$ 443.1, found 443.2 [M+H]$^+$.

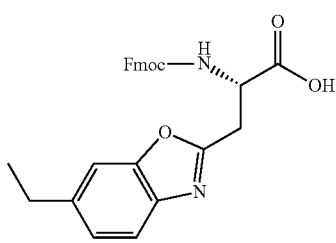

3p (S)-2-((((9H-fluoren-9-yl)methoxy)carbonyl)amino)-3-(6-ethylbenzo[d]oxazol-2-yl)propanoic acid (3p): Intermediate 3p was prepared from 1 in two steps using a similar procedure as that for 3l. ESI-MS m/z: calculated for $C_{27}H_{25}N_2O_5^+$ 457.2, found 457.4 [M+H]$^+$.

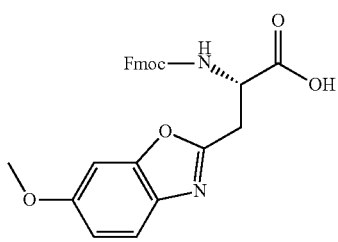

3q (S)-2-((((9H-fluoren-9-yl)methoxy)carbonyl)amino)-3-(6-methoxybenzo[d]oxazol-2-yl)propanoic acid (3q): Intermediate 3q was prepared from 1 in two steps using a similar procedure as that for 3l. ESI-MS m/z: calculated for $C_{26}H_{23}N_2O_6^+$ 459.2, found 459.2 [M+H]$^+$.

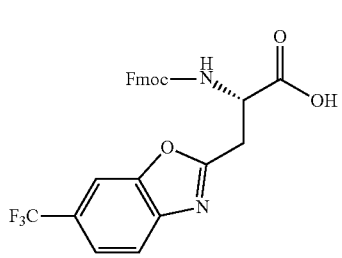

3r (S)-2-((((9H-fluoren-9-yl)methoxy)carbonyl)amino)-3-(6-trifluoromethylbenzo[d]oxazol-2-yl)propanoic acid (3r): Intermediate 3r was prepared from 1 in two steps using a similar procedure as that for 3l. ESI-MS m/z: calculated for $C_{26}H_{20}F_3N_2O_5^+$ 497.2, found 497.8 [M+H]$^+$.

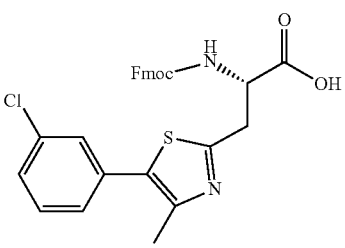

3s (S)-2-((((9H-Fluoren-9-yl)methoxy)carbonyl)amino)-3-(5-(3-chlorophenyl)-4-methylthiazol-2-yl)propanoic acid (3s): (S)-3-((((9H-fluoren-9-yl)methoxy)carbonyl)amino)-4-(allyloxy)-4-oxobutanoic acid (10.6 g, 27.3 mmol) was dissolved in dichloromethane then the solution was added ammonium carbonate (4.3 g, 54.6 mmol), HBTU (16.6 g, 43.68 mmol), HOBt (6.7 g, 43.68 mmol) and DIEA (14 ml, 81.9 mmol). The mixture was stirred at room temperature and monitored by TLC. After the reaction completed, the mixture was poured into saturated aqueous NaHCO$_3$ and extract with DCM. The organic layer was washed with brine and then evaporated for next reaction.

A solution of allyl (((9H-fluoren-9-yl)methoxy)carbonyl)-L-asparaginate (10 g, 28.6 mmol) and 2,4-bis(4-methoxyphenyl)-1,3-dithia-2,4-diphosphetane-2,4-disulfide (11.56 g, 28.6 mmol) in THF (500 mL) was stirred at room temperature for 18 h. The reaction mixture was then poured into saturated aqueous NaHCO3 (300 ml). The mixture was extracted with ethyl acetate (2×100 ml). The organic fractions were combined, dried over Na2SO4, filtered, and concentrated. The residue was purified by flash column chromatography. ESI-MS m/z: 411.7.

Allyl (S)-2-((((9H-fluoren-9-yl)methoxy)carbonyl)amino)-4-amino-4-thioxobutanoate (700 mg, 1.7 mmol) and Na2CO3 (550 mg, 5.1 mmol) were dissolved in DME under ice bath and N2 atmosphere. 1-bromo-1-(3-chlorophenyl)propan-2-one (500 mg, 3.4 mmol) was slowly to the mixture, and allowed to stir in ice bath for 10 mins, then slowly warm up to room temperature for 30 mins. Then TFAA (0.7 ml, 5.11 mmol) and 2,4,6-collidine (1.02 ml, 8.16 mmol) was added the white suspension mixture and stir for another 1 h in ice bath. The solution was added saturated sodium bicarbonate aqueous solution then extracted with ethyl acetate. The combined organic layer was evaporated and purified by flash column chromatography. ESI-MS m/z: 559.4.

Allyl (S)-2-((((9H-fluoren-9-yl)methoxy)carbonyl)amino)-3-(5-(3-chlorophenyl)-4-methylthiazol-2-yl)propanoate (100 mg, 0.178 mmol) was dissolved in dichloromethane in $N_2$ atmosphere. Tetrakis(triphenylphosphine)palladium(0) (31.6 mg, 0.026 mmol) and phenylsalen (0.09 ml, 0.715 mmol) was added subsequently to the solution. The solution was allowed to stir for 1 h in room temperature. The organic solvent was evaporated and concentrated to give crude (S)-2-((((9H-fluoren-9-yl)methoxy)carbonyl)amino)-3-(5-(3-chlorophenyl)-4-methylthiazol-2-yl)propanoic acid (3s) which was used for next reaction without purification. ESI-MS m/z: 519.3.

3t

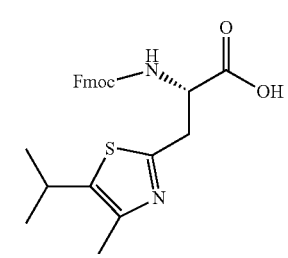

3u

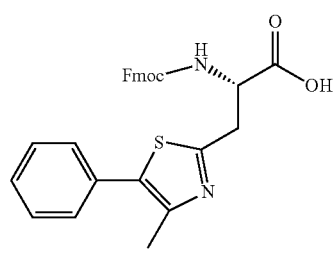

3v

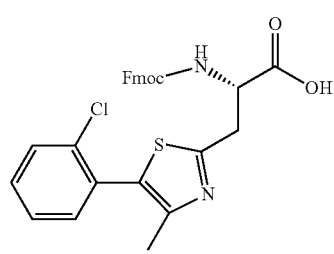

3w

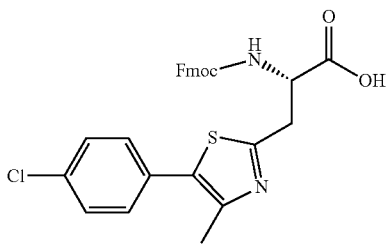

3x

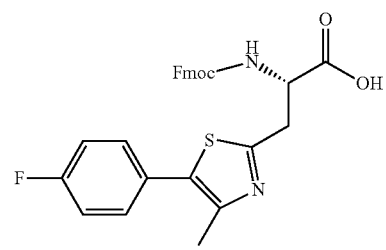

3y

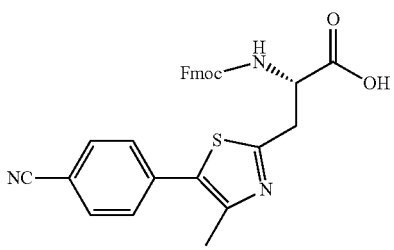

3z

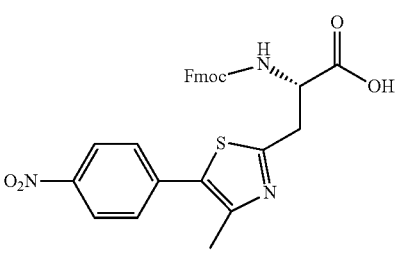

Using the appropriate bromoketones, readily obtained by thermodynamic bromination of the corresponding methylketones, the above 5-substituted thiazole amino acids (3t-3z) were also prepared using the above procedure.

A2. Synthesis of Azidoamines 10.

10CH tert-butyl (R)-(2-azido-1-cyclohexylethyl)carbamate, 10CH: 10CH was made by referring a reported method.[3] MsCl (710 mg, 6.2 mmol, 1.5 equiv.) was added dropwise to a solution of N-Boc-L-cyclohexylglycinol (1.00 g, 4.1 mmol, 1 equiv.) and $Et_3N$ (1.7 mL, 12.3 mmol, 3 equiv.) in $CH_2Cl_2$ (20 mL) at 0° C. The mixture was stirred 3 h at 0° C. and diluted with $CH_2Cl_2$. The mixture was washed with sat. aq $NaHCO_3$ (2×20 mL), IM HCl, and brine. The organic layer was dried ($Na_2SO_4$) and the solvent was removed in vacuo. The residue was dissolved in DMF and NaN₃ (802 mg, 12.3 mmol, 3 equiv.) was added. This reaction mixture was stirred at 60° C. for overnight and cooled to room temperature. EtOAc and H₂O were added to this mixture and the aqueous layer was extracted with EtOAc. The organic layer was washed with H₂O and brine. The organic layer was dried (Na₂SO₄) and the solvent was removed under vacuum. The crude product was purified by flash chromatography this gave 10CH (617 mg, 56% over two steps). ¹H NMR (400 MHz, CDCl₃) δ 4.60 (d, J=8.6 Hz, 1H), 3.63-3.29 (m, 3H), 1.79-1.65 (m, 5H), 1.54-1.36 (m, 11H), 1.33-0.86 (m, 6H). ¹³C NMR (101 MHz, CDCl₃) δ 155.57, 79.48, 54.82, 52.72, 39.31, 29.77, 28.86, 28.36, 28.29, 26.16, 25.97, 25.96. UPLC-MS (ESI-MS) m/z: calculated for $C_{13}H_{25}N_4O_2^+$ 269.20, found [M+H]⁺.

Other 2-azidoethylamines, 10 Il, 10CP, 10CHM 10Bn and 10No were made by analogous methods.

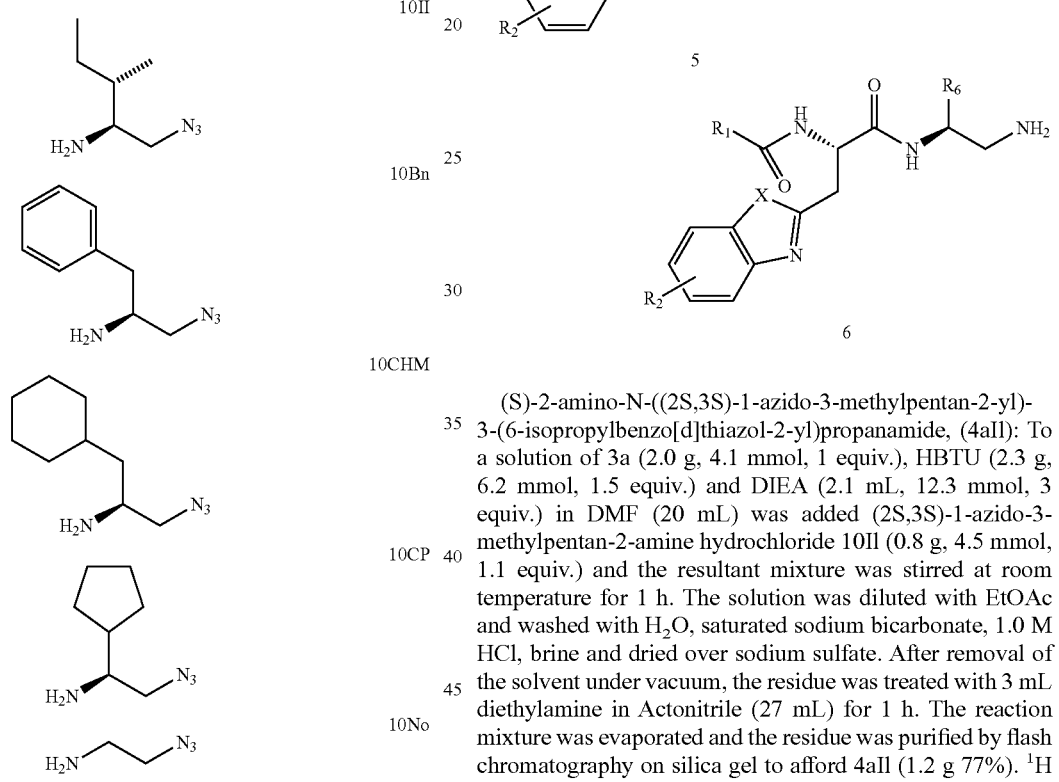

B. Synthesis of Dipeptide Intermediates

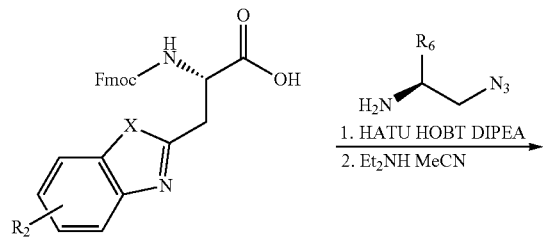

(S)-2-amino-N-((2S,3S)-1-azido-3-methylpentan-2-yl)-3-(6-isopropylbenzo[d]thiazol-2-yl)propanamide, (4aIl): To a solution of 3a (2.0 g, 4.1 mmol, 1 equiv.), HBTU (2.3 g, 6.2 mmol, 1.5 equiv.) and DIEA (2.1 mL, 12.3 mmol, 3 equiv.) in DMF (20 mL) was added (2S,3S)-1-azido-3-methylpentan-2-amine hydrochloride 10Il (0.8 g, 4.5 mmol, 1.1 equiv.) and the resultant mixture was stirred at room temperature for 1 h. The solution was diluted with EtOAc and washed with H₂O, saturated sodium bicarbonate, 1.0 M HCl, brine and dried over sodium sulfate. After removal of the solvent under vacuum, the residue was treated with 3 mL diethylamine in Actonitrile (27 mL) for 1 h. The reaction mixture was evaporated and the residue was purified by flash chromatography on silica gel to afford 4aIl (1.2 g 77%). ¹H NMR (400 MHz, MeOD) δ 7.94 (d, J=8.5 Hz, 1H), 7.84 (d, J=1.7 Hz, 1H), 7.44 (dd, J=8.5, 1.7 Hz, 1H), 4.57 (dd, J=7.8, 5.2 Hz, 1H), 3.87 (td, J=7.3, 3.8 Hz, 1H), 3.77 (dd, J=16.6, 5.2 Hz, 1H), 3.68 (dd, J=16.6, 7.8 Hz, 1H), 3.47 (dd, J=12.8, 3.9 Hz, 1H), 3.41-3.35 (m, 1H), 3.06 (dq, J=13.6, 6.8 Hz, 1H), 1.70-1.60 (m, 1H), 1.58-1.50 (m, 1H), 1.32 (d, J=6.9 Hz, 6H), 1.24-1.12 (m, 1H), 0.96-0.91 (m, 6H). ¹³C NMR (101 MHz, MeOD) δ 167.35, 164.24, 151.02, 146.98, 135.29, 125.36, 122.10, 118.60, 53.74, 52.01, 36.06, 34.11, 34.05, 24.98, 23.15, 14.16, 10.11. UPLC-MS (ESI-MS) m/z: calculated for $C_{19}H_{29}N_6OS^+$ 389.21, found 389.36[M+H]⁺.

(S)-2-acetamido-N-((2S,3S)-1-azido-3-methylpentan-2-yl)-3-(6-isopropylbenzo[d]thiazol-2-yl)propanamide, (5aIlAc): Acetic anhydride (46 mg, 0.45 mmoL, 2 equiv.) was added to a solution of 4aIl (87 mg, 0.22 mmoL, 1 equiv.) and DIEA (156 μL, 0.89 mmol, 4 equiv.) in DCM (10 mL). The resulting reaction mixture was stirred for half an hour and then was evaporated. The residue was purified by flash chromatography on silica gel to afford compounds (5aIlAc):

(89 mg, 92% yields). ¹H NMR (400 MHz, CDCl₃) δ 7.91 (d, J=8.5 Hz, 1H), 7.72 (d, J=1.6 Hz, 1H), 7.59 (d, J=9.1 Hz, 1H), 7.47-7.36 (m, 2H), 5.06 (q, J=6.4 Hz, 1H), 4.02-3.82 (m, 1H), 3.64 (d, J=6.3 Hz, 2H), 3.37 (qd, J=12.6, 5.3 Hz, 2H), 3.08 (dt, J=13.8, 6.9 Hz, 1H), 2.08 (s, 3H), 1.65-1.58 (m, 1H), 1.51-1.39 (m, 1H), 1.33 (d, J=6.9 Hz, 6H), 1.21-1.03 (m, 1H), 0.92 (d, J=6.8 Hz, 3H), 0.88 (t, J=7.4 Hz, 3H). ¹³C NMR (101 MHz, CDCl₃) δ 171.12, 169.86, 168.43, 148.60, 147.43, 134.34, 126.28, 121.25, 118.98, 53.54, 52.41, 52.37, 36.15, 35.62, 34.29, 25.06, 24.10, 22.97, 15.39, 11.19. UPLC-MS (ESI-MS) m/z: calculated for $C_{21}H_{31}N_6O_2S^+$ 431.22, found 431.36[M+H]⁺.

(S)-2-acetamido-N-((2S,3S)-1-amino-3-methylpentan-2-yl)-3-(6-isopropylbenzo[d]thiazol-2-yl)propanamide (6allAc): To a solution of compound 5allAc (45 mg, 0.11 mmol) in MeOH (10 mL) was added 10% Pd—C (20 mg). The solution was stirred under 1 atm of H₂ at room temperature for 3 hours before filtering through celite and being concentrated. The resulting amine was purified by HPLC to afford 6allAc (38 mg, 91%). ¹H NMR (400 MHz, MeOD) δ 7.92-7.77 (m, 2H), 7.49-7.36 (m, 1H), 4.87-4.85 (m, 1H), 4.01-3.96 (m, 1H), 3.69 (dd, J=15.2, 5.9 Hz, 1H), 3.55 (dd, J=15.2, 6.9 Hz, 1H), 3.30-3.19 (m, 1H), 3.08 (dt, J=13.8, 6.9 Hz, 1H), 2.97 (dd, J=12.6, 11.3 Hz, 1H), 2.03 (s, 3H), 1.68-1.54 (m, 1H), 1.48-1.41 (m, 1H), 1.33 (d, J=6.9 Hz, 6H), 1.21-1.06 (m, 1H), 0.94 (d, J=6.8 Hz, 3H), 0.86 (t, J=7.4 Hz, 3H). ¹³C NMR (101 MHz, MeOD) δ 172.45, 171.81, 167.06, 150.90, 146.80, 135.18, 125.31, 121.29, 118.67, 53.09, 52.09, 41.76, 36.51, 34.60, 34.08, 24.77, 23.14, 21.18, 14.22, 9.75. UPLC-MS (ESI-MS) m/z: calculated for $C_{21}H_{33}N_4O_2S^+$ 405.23, found 405.25[M+H]⁺.

(S)—N-((2S,3S)-1-azido-3-methylpentan-2-yl)-3-(6-isopropylbenzo[d]thiazol-2-yl)-2-propionamidopropanamide, 5allPr: Propionic anhydride (58 mg, 0.45 mmoL, 2 equiv.) was added to a solution of 4all (87 mg, 0.22 mmoL, 1 equiv.) and DIEA (156 µL, 0.89 mmol, 4 equiv.) in DCM (10 mL). The resulting reaction mixture was stirred for half an hour and then was evaporated. The residue was purified by flash chromatography on silica gel to afford compound 5allPr (86 mg, 89% yields). ¹H NMR (400 MHz, CDCl₃) δ 7.94 (d, J=8.5 Hz, 1H), 7.73 (d, J=1.0 Hz, 1H), 7.54 (d, J=9.0 Hz, 1H), 7.50 (d, J=7.0 Hz, 1H), 7.45 (dd, J=8.4, 1.5 Hz, 1H), 5.08 (dd, J=12.7, 6.8 Hz, 1H), 4.00-3.88 (m, 1H), 3.75 (dd, J=15.3, 5.3 Hz, 1H), 3.63 (dd, J=15.3, 7.2 Hz, 1H), 3.39 (qd, J=12.6, 5.4 Hz, 2H), 3.08 (dt, J=13.8, 6.9 Hz, 1H), 2.31 (q, J=7.6 Hz, 2H), 1.68-1.56 (m, 1H), 1.48-1.42 (m, 1H), 1.33 (d, J=6.9 Hz, 6H), 1.20-1.05 (m, 4H), 0.92 (d, J=6.8 Hz, 3H), 0.88 (t, J=7.4 Hz, 3H). ¹³C NMR (101 MHz, CDCl₃) δ 175.27, 169.85, 169.08, 147.86, 147.47, 133.89, 126.67, 120.89, 119.04, 53.65, 52.49, 52.36, 36.20, 35.35, 34.30, 29.42, 25.07, 24.05, 24.04, 15.32, 11.17, 9.61. UPLC-MS (ESI-MS) m/z: calculated for $C_{22}H_{33}N_6O_2S^+$ 445.24, found 445.37[M+H]⁺.

(S)—N-((2S,3S)-1-amino-3-methylpentan-2-yl)-3-(6-isopropylbenzo[d]thiazol-2-yl)-2-propionamidopropanamide (6allPr): To a solution of compound 5allPr (52 mg, 0.12 mmol) in MeOH (10 mL) was added 10% Pd—C (20 mg). The solution was stirred under 1 atm of H₂ at room temperature for 3 hours before filtering through celite and being concentrated. The resulting amine was purified by HPLC to afford 6allPr (36 mg, 86%). ¹H NMR (400 MHz, MeOD) δ 7.90-7.80 (m, 2H), 7.43 (dd, J=8.5, 1.7 Hz, 1H), 4.91-4.89 (m, 1H), 4.09-3.92 (m, 1H), 3.69 (dd, J=15.2, 5.9 Hz, 1H), 3.55 (dd, J=15.2, 7.0 Hz, 1H), 3.29-3.20 (m, 1H), 3.08 (dt, J=13.8, 6.9 Hz, 1H), 3.02-2.93 (m, 1H), 2.30 (q, J=7.6 Hz, 2H), 1.67-1.56 (m, 1H), 1.48-1.42 (m, 1H), 1.33 (d, J=6.9 Hz, 6H), 1.20-1.07 (m, 4H), 0.95 (d, J=6.8 Hz, 3H), 0.86 (t, J=7.4 Hz, 3H). ¹³C NMR (101 MHz, MeOD) δ 176.05, 171.86, 167.09, 150.90, 146.78, 135.16, 125.30, 121.28, 118.66, 52.92, 52.07, 41.77, 36.54, 34.55, 34.07, 28.54, 24.74, 23.14, 14.24, 9.76, 8.71. UPLC-MS (ESI-MS) m/z: calculated for $C_{22}H_{35}N_4O_2S^+$ 419.25, found 419.29 [M+H]⁺.

(S)—N-((2S,3S)-1-amino-3-methylpentan-2-yl)-2-formamido-3-(6-isopropylbenzo[d]thiazol-2-yl)propanamide (5allFo): 4all (100 mg, 0.26 mmol) was dissolved in a mixture of DIEA (1 mL) and Ethyl formate (5 mL) and the resulting reaction mixture was left stirring for 3 days. The solvents were removed in vacuo and the residue was dissolved in MeOH (10 ml). Then 10% Pd—C (20 mg) was added and the resulting reaction mixture was stirred under 1 atm of H₂ at room temperature for 3 hours before filtering through celite and being concentrated. The resulting amine was purified by HPLC to afford 5allFo (58 mg, 58%). ¹H NMR (400 MHz, MeOD) δ 8.18 (d, J=0.7 Hz, 1H), 7.87-7.81 (m, 2H), 7.43 (dd, J=8.5, 1.7 Hz, 1H), 4.99 (t, J=5.6 Hz, 1H), 4.04-3.98 (m, 1H), 3.69 (dd, J=15.3, 5.8 Hz, 1H), 3.63 (dd, J=15.3, 6.1 Hz, 1H), 3.27 (dd, J=12.9, 2.4 Hz, 1H), 3.08 (dt, J=13.8, 6.9 Hz, 1H), 2.98 (dd, J=12.9, 11.1 Hz, 1H), 1.68-1.55 (m, 1H), 1.48-1.42 (m, 1H), 1.33 (d, J=6.9 Hz, 6H), 1.21-1.08 (m, 1H), 0.94 (d, J=6.8 Hz, 3H), 0.85 (t, J=7.4 Hz, 3H). ¹³C NMR (101 MHz, MeOD) δ 171.17, 166.62, 162.68, 150.95, 146.81, 135.20, 125.30, 121.29, 118.67, 52.15, 52.06, 51.53, 41.84, 36.56, 34.73, 34.07, 24.76, 23.13, 14.20, 9.73. UPLC-MS (ESI-MS) m/z: calculated for $C_{20}H_{31}N_4O_2S^+$ 391.22, found 391.22 [M+H]⁺.

(S)—N-((2S,3S)-1-amino-3-methylpentan-2-yl)-2-isobutyramido-3-(6-isopropylbenzo[d]thiazol-2-yl)propanamide 6allIB: 6allIB was prepared from 4all in 72% yield over two steps by a similar procedure as that for compound 6allAc. ¹H NMR (400 MHz, MeOD) δ 8.33 (d, J=7.3 Hz, 1H), 7.99 (d, J=8.9 Hz, 1H), 7.85-7.83 (m, 2H), 7.43 (dd, J=8.6, 1.6 Hz, 1H), 4.91-4.88 (m, 1H), 4.09-3.90 (m, 1H), 3.69 (dd, J=15.2, 5.9 Hz, 1H), 3.55 (dd, J=15.2, 7.1 Hz, 1H), 3.26 (dd, J=13.4, 3.1 Hz, 1H), 3.08 (dt, J=13.8, 6.9 Hz, 1H), 3.02-2.93 (m, 1H), 2.53 (dt, J=13.7, 6.9 Hz, 1H), 1.68-1.57 (m, 1H), 1.50-1.42 (m, 1H), 1.33 (d, J=6.9 Hz, 6H), 1.23-1.04 (m, 7H), 0.95 (d, J=6.8 Hz, 3H), 0.88 (t, J=7.4 Hz, 3H). ¹³C NMR (101 MHz, MeOD) δ 179.04, 171.85, 167.11, 150.91, 146.78, 135.14, 125.30, 121.24, 118.67, 52.71, 52.02, 41.85, 36.59, 34.59, 34.45, 34.07, 24.69, 23.13, 18.48, 18.17, 14.25, 9.78. UPLC-MS (ESI-MS) m/z: calculated for $C_{23}H_{37}N_4O_2S^+$ 433.26, found 433.29 [M+H]⁺.

N—((S)-1-(((2S,3S)-1-amino-3-methylpentan-2-yl)amino)-3-(6-isopropylbenzo[d]thiazol-2-yl)-1-oxopropan-2-yl)butyramide 6allBu: 6allBu was prepared from 4all in 70% yield over two steps by a similar procedure as that for compound 6allAc. ¹H NMR (400 MHz, MeOD) δ 7.91-7.75 (m, 2H), 7.43 (dd, J=8.6, 1.6 Hz, 1H), 4.91-4.88 (m, 1H), 4.02-3.96 (m, 1H), 3.69 (dd, J=15.2, 5.9 Hz, 1H), 3.54 (dd, J=15.2, 7.2 Hz, 1H), 3.25 (dd, J=13.1, 3.1 Hz, 1H), 3.08 (dt, J=13.8, 6.9 Hz, 1H), 2.98 (dd, J=12.8, 11.1 Hz, 1H), 2.35-2.18 (m, 2H), 1.71-1.55 (m, 3H), 1.49-1.41 (m, 1H), 1.33 (d, J=6.9 Hz, 6H), 1.19-1.12 (m, 1H), 0.96-0.85 (m, 9H). ¹³C NMR (101 MHz, MeOD) δ 175.14, 171.86, 167.08, 150.93, 146.77, 135.17, 125.29, 121.28, 118.66, 52.90, 52.06, 41.78, 37.32, 36.56, 34.61, 34.07, 24.74, 23.14, 18.76, 14.23, 12.56, 9.78. UPLC-MS (ESI-MS) m/z: calculated for $C_{23}H_{37}N_4O_2S^+$ 433.26, found 433.29 [M+H]⁺.

(S)—N-((2S,3S)-1-amino-3-methylpentan-2-yl)-3-(6-isopropylbenzo[d]thiazol-2-yl)-2-(3-methylureido)propanamide 6allIC: Methyl isocyanate (18 mg, 0.31 mmol, 2 equiv.) was added to a solution of 4all (60 mg, 0.15 mmol, 1 equiv.) and DIEA (54 µL, 0.31 mmol, 2 equiv.) in CH$_2$Cl$_2$ (5 mL) and the resulting solution was stirred at room temperature for overnight. The reaction mixture was concentrated and the residue was dissolved in MeOH (10 ml). Then 10% Pd—C (20 mg) was added and the resulting reaction mixture was stirred under 1 atm of H$_2$ at room temperature for 3 hours before filtering through celite and being concentrated. The resulting amine was purified by HPLC to afford 6aIIIC (58 mg, 74%). 1H NMR (400 MHz, MeOD) δ 7.85 (d, J=8.5 Hz, 1H), 7.83 (d, J=1.7 Hz, 1H), 7.42 (dd, J=8.5, 1.7 Hz, 1H), 4.74 (t, J=5.8 Hz, 1H), 3.99-3.94 (m, 1H), 3.61 (d, J=5.8 Hz, 2H), 3.24 (dd, J=12.9, 3.0 Hz, 1H), 3.07 (dt, J=13.8, 6.9 Hz, 1H), 2.98 (dd, J=12.8, 11.3 Hz, 1H), 2.74 (s, 3H), 1.58 (dtd, J=8.8, 7.3, 3.7 Hz, 1H), 1.44-1.35 (m, 1H), 1.32 (d, J=6.9 Hz, 6H), 1.12-1.04 (m, 1H), 0.91 (d, J=6.8 Hz, 3H), 0.79 (t, J=7.4 Hz, 3H). $^{13}$C NMR (101 MHz, MeOD) δ 172.94, 167.09, 159.77, 150.97, 146.68, 135.23, 125.18, 121.40, 118.59, 53.78, 52.00, 41.73, 36.52, 35.24, 34.07, 25.54, 24.79, 23.15, 14.24, 9.70. UPLC-MS (ESI-MS) m/z: calculated for C$_{21}$H$_{34}$N$_5$O$_2$S$^+$ 420.24, found 419.29 [M+H]$^+$.

(S)—N—((S)-2-azido-1-cyclohexylethyl)-3-(6-isopropylbenzo[d]thiazol-2-yl)-2-propionamidopropanamide, 5aCHPr: Compound 5aCHPr was prepared from 3a and 10CH in 65% yield in three steps by a similar procedure as that for compound 5aIIPr. $^1$H NMR (400 MHz, CDCl$_3$) δ 7.84 (d, J=8.4 Hz, 1H), 7.69 (d, J=1.7 Hz, 1H), 7.50 (d, J=9.1 Hz, 1H), 7.39 (d, J=7.1 Hz, 1H), 7.34 (dd, J=8.5, 1.7 Hz, 1H), 5.04 (td, J=7.0, 4.8 Hz, 1H), 3.91-3.76 (m, 1H), 3.66 (dd, J=15.9, 4.7 Hz, 1H), 3.43 (dd, J=15.9, 7.0 Hz, 1H), 3.35 (dd, J=5.0, 1.1 Hz, 2H), 3.04 (dt, J=13.8, 6.9 Hz, 1H), 2.32 (q, J=7.6 Hz, 2H), 1.70-1.60 (dd, J=28.1, 15.3 Hz, 6H), 1.52-1.41 (m, 1H), 1.32-0.87 (m, 14H). $^{13}$C NMR (101 MHz, CDCl$_3$) δ 174.11, 170.30, 167.09, 150.97, 146.46, 135.25, 125.39, 121.98, 118.79, 53.54, 52.31, 51.92, 38.95, 35.50, 34.24, 29.69, 29.65, 28.51, 26.09, 25.91, 25.85, 24.18, 9.68. UPLC-MS (ESI-MS) m/z: calculated for C$_{24}$H$_{35}$N$_6$O$_2$S$^+$ 471.25, found 471.27 [M+H]$^+$.

(S)—N—((S)-2-amino-1-cyclohexylethyl)-3-(6-isopropylbenzo[d]thiazol-2-yl)-2-propionamidopropanamide: Compound 6aCHPr was prepared from 6aCHPr in 88% yield by a similar procedure as that for 6aIIPr. $^1$H NMR (400 MHz, MeOD) δ 7.99 (d, J=8.9 Hz, 1H), 7.86-7.84 (m, 2H), 7.43 (d, J=8.5 Hz, 1H), 4.87-4.84 (m, 1H), 3.94-3.90 (m, 1H), 3.68 (dd, J=15.3, 5.8 Hz, 1H), 3.56 (dd, J=15.2, 6.9 Hz, 1H), 3.29-3.20 (m, 1H), 3.12-2.91 (m, 2H), 2.31 (q, J=7.6 Hz, 2H), 1.75-1.63 (m, 5H), 1.54-1.46 (m, 1H), 1.36-0.90 (m, 14H). $^{13}$C NMR (101 MHz, MeOD) δ 176.08, 171.86, 167.03, 150.94, 146.76, 135.15, 125.30, 121.33, 118.65, 52.99, 52.48, 41.73, 39.59, 34.51, 34.08, 29.39, 28.57, 28.25, 25.70, 25.50, 25.43, 23.14, 8.70. UPLC-MS (ESI-MS) m/z: calculated for C$_{24}$H$_{37}$N$_4$O$_2$S$^+$ 445.26, found 445.27 [M+H]$^+$.

(S)—N—((S)-2-amino-1-cyclopentylethyl)-3-(6-chlorobenzo[d]thiazol-2-yl)-2-propionamidopropanamide 6bCPPr: Compound 6bCPPr was prepared from 3b and 10CP by a similar procedure as that for 6aIIPr. MS found: 423.3.

(S)—N—((S)-2-amino-1-cyclohexylethyl)-3-(6-chlorobenzo[d]thiazol-2-yl)-2-propionamidopropanamide 6bCHPr: Compound 6bCHPr was prepared from 3b and 10CH by a similar procedure as that for 6aIIPr. $^1$H NMR (400 MHz, MeOD) δ 8.02 (d, J=1.9 Hz, 1H), 7.90 (d, J=8.7 Hz, 1H), 7.51 (dd, J=8.7, 2.1 Hz, 1H), 4.94-4.90 (m, 1H), 3.95-3.90 (m, 1H), 3.71 (dd, J=15.4, 5.6 Hz, 1H), 3.57 (dd, J=15.4, 7.5 Hz, 1H), 3.24 (dd, J=13.0, 3.2 Hz, 1H), 3.05-2.93 (m, 1H), 2.30 (q, J=7.6 Hz, 2H), 1.82-1.60 (m, 5H), 1.58-1.45 (m, 1H), 1.37-0.84 (m, 8H). $^{13}$C NMR (101 MHz, MeOD) δ 176.15, 171.83, 168.87, 151.32, 136.44, 130.95, 126.73, 122.77, 121.21, 52.90, 52.51, 41.57, 39.61, 34.53, 29.40, 28.56, 28.24, 25.73, 25.51, 25.46, 8.71.

(S)—N—((S)-3-amino-1-cyclohexylprop-2-yl)-3-(6-chlorobenzo[d]thiazol-2-yl)-2-propionamidopropanamide 6bCHMPr: Compound 6bCHMPr was prepared from 3b and 10CHM by a similar procedure as that for 6aIIPr. MS found: 451.5

((S)—N—((S)-3-amino-1-phenylprop-2-yl)-3-(6-chlorobenzo[d]thiazol-2-yl)-2-propionamidopropanamide 6bBnPr: Compound 6bBnPr was prepared from 3b and 10Bn by a similar procedure as that for 6aIIPr. $^1$H NMR (400 MHz, MeOD) δ 8.02 (d, J=2.0 Hz, 1H), 7.88 (d, J=8.7 Hz, 1H), 7.51 (dd, J=8.7, 2.1 Hz, 1H), 7.38-7.14 (m, 5H), 4.84-4.82 (m, 1H), 4.46-4.32 (m, 1H), 3.59 (dd, J=15.4, 5.3 Hz, 1H), 3.43 (dd, J=15.4, 8.1 Hz, 1H), 3.17 (dd, J=13.0, 3.8 Hz, 1H), 3.08 (dd, J=12.9, 10.2 Hz, 1H), 2.98-2.79 (m, 2H), 2.24 (q, J=7.6 Hz, 2H), 1.07 (t, J=7.6 Hz, 3H). $^{13}$C NMR (101 MHz, MeOD) δ 176.05 (s), 171.66 (s), 168.80 (s), 151.27 (s), 136.79 (s), 136.46 (s), 130.93 (s), 128.79 (s), 128.31 (s), 126.65 (d, J=13.1 Hz), 122.76 (s), 121.21 (s), 52.76 (s), 49.42 (s), 42.95 (s), 37.43 (s), 34.72 (s), 28.50 (s), 8.59 (s).

(S)—N-(1-aminoeth-2-yl)-2-isobutyramido-3-(6-isopropylbenzo[d]thiazol-2-yl)propanamide 6aNoIB: Compound 6aNoIB was prepared from 3a and 10No by a similar procedure as that for 6aIIPr.

1H NMR (400 MHz, MeOD) δ 7.85 (d, J=8.5 Hz, 1H), 7.83 (s, 1H), 7.42 (d, J=8.5 Hz, 1H), 4.84-4.77 (m, 1H), 3.66 (dd, J=15.0, 5.3 Hz, 1H), 3.51 (dd, J=13.8, 8.0 Hz, 3H), 3.17-2.99 (m, 3H), 2.52 (dt, J=13.7, 6.8 Hz, 1H), 1.40-1.27 (m, 6H), 1.16-0.99 (m, 6H).

(S)—N—((S)-1-amino-3-phenylpropan-2-yl)-3-(6-isopropylbenzo[d]thiazol-2-yl)-2-propionamidopropanamide, 6aBnPr. Compound 6aBnPr was prepared from 3a and 10Bn in 53% yield over four steps by a similar procedure as that for compound 6aIIAc. $^1$H NMR (400 MHz, MeOD) δ 7.86-7.80 (m, 2H), 7.42 (dd, J=8.5, 1.6 Hz, 1H), 7.33-7.18 (m, 5H), 4.81 (dd, J=7.6, 5.5 Hz, 1H), 4.47-4.32 (m, 1H), 3.58 (dd, J=15.2, 5.5 Hz, 1H), 3.42 (dd, J=15.2, 7.6 Hz, 1H), 3.18 (dd, J=13.0, 3.6 Hz, 1H), 3.10-3.04 (m, 2H), 2.93-2.84 (m, 2H), 2.24 (q, J=7.6 Hz, 2H), 1.32 (d, J=6.9 Hz, 6H), 1.08 (t, J=7.6 Hz, 3H). $^{13}$C NMR (101 MHz, MeOD) δ 175.96, 171.68, 167.04, 150.86, 146.74, 136.78, 135.18, 128.77, 128.31, 126.58, 125.27, 121.31, 118.64, 52.86, 49.38, 43.08, 37.43, 34.73, 34.07, 28.49, 23.14, 8.60. UPLC-MS (ESI-MS) m/z: calculated for C$_{25}$H$_{33}$N$_4$O$_2$S$^+$ 453.23, found 453.24 [M+H]$^+$.

(S)—N-(1-aminoeth-2-yl)-2-isobutyramido-3-(6-isopropylbenzo[d]thiazol-2-yl)propanamide 6aNoCPR: Compound 6aNoCPR was prepared from 3a and 10No by a similar procedure as that for 6aIIPr. $^1$H NMR (400 MHz, MeOD) δ 8.41 (t, J=5.5 Hz, 1H), 7.86 (d, J=8.5 Hz, 1H), 7.83 (s, 1H), 7.42 (d, J=8.5 Hz, 1H), 4.82 (dd, J=7.8, 5.8 Hz, 1H), 3.66 (dd, J=15.1, 5.8 Hz, 1H), 3.55-3.47 (m, 3H), 3.17-2.97 (m, 3H), 1.80-1.59 (m, 1H), 1.33 (d, J=6.9 Hz, 6H), 0.95-0.73 (m, 4H).

Scheme 3. Alternative Synthesis 1 of Intermediate Diamido amines 6.

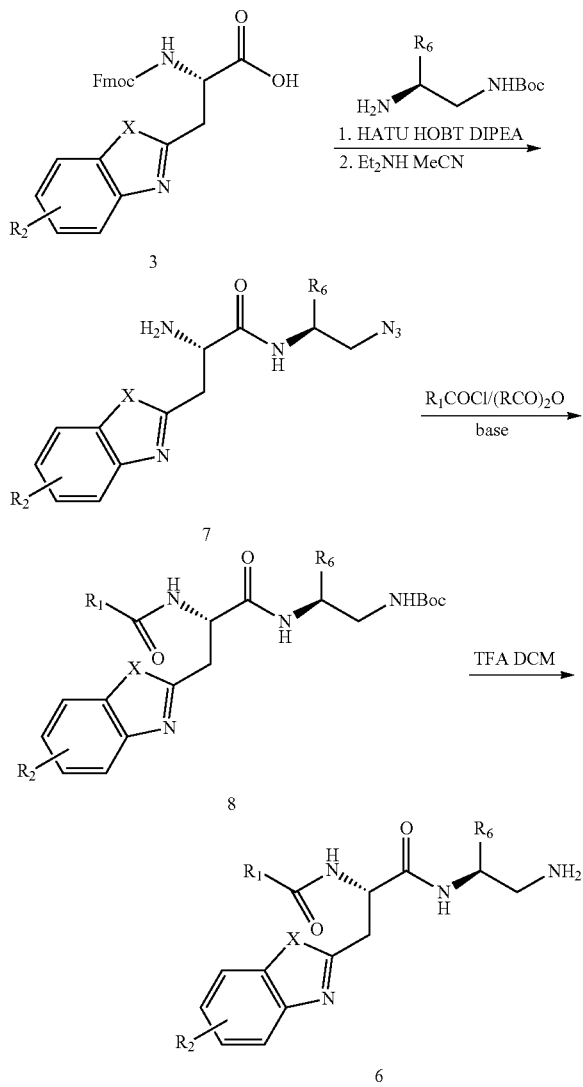

(S)—N-(2-aminoethyl)-3-(6-isopropylbenzo[d]thiazol-2-yl)-2-propionamidopropanamide (6aNoPr): To a solution of the 3a (120 mg, 0.25 mmol, 1 equiv.), HBTU (140 mg, 0.37 mmol, 1.5 equiv.) and DIEA (129 µL, 0.74 mmol, 3 equiv.) in DMF (5 mL) was added tert-butyl (2-aminoethyl)carbamate (43 mg, 0.27 mmol, 1.1 equiv.) and the resultant mixture was stirred at room temperature for 1 h. The solution was diluted with EtOAc and washed with H₂O, saturated sodium bicarbonate, 1.0 M HCl, brine and dried over sodium sulfate. After removal of the solvent under vacuum, the residue was treated with 1 mL diethylamine in Acetonitrile (9 mL) for 1 h. The reaction mixture was evaporated and dissolved in DCM (5 mL). This solution was treated with propionic anhydride (64 mg, 0.49 mmoL, 2 equiv.) and DIEA (171 µL, 0.99 mmol, 4 equiv.). The resulting reaction mixture was stirred for half an hour and then was evaporated. The residue was treated with TFA (1 ml) in DCM (5 mL) and stirred for 5 h. This reaction mixture was concentrated and purified by HPLC to afford 6aNoPr (54 mg, 61%). ¹H NMR (400 MHz, MeOD) δ 7.86 (d, J=8.5 Hz, 1H), 7.82 (d, J=1.7 Hz, 1H), 7.42 (dd, J=8.5, 1.7 Hz, 1H), 4.83 (dd, J=8.2, 5.5 Hz, 1H), 3.67 (dd, J=15.1, 5.5 Hz, 1H), 3.56-3.43 (m, 3H), 3.10-3.03 (m, 3H), 2.28 (q, J=7.6 Hz, 2H), 1.32 (d, J=6.9 Hz, 6H), 1.09 (t, J=7.6 Hz, 3H). ¹³C NMR (101 MHz, MeOD) δ 176.04, 172.38, 166.94, 150.80, 146.73, 135.22, 125.26, 121.46, 118.60, 53.15, 39.46, 36.83, 34.93, 34.07, 28.50, 23.14, 8.56. UPLC-MS (ESI-MS) m/z: calculated for $C_{18}H_{27}N_4O_2S^+$ 363.18, found 363.18 [M+H]⁺.

(S)—N—((S)-1-aminopropan-2-yl)-3-(6-isopropylbenzo[d]thiazol-2-yl)-2-propionamidopropanamide 6aMePr: 6aMePr was prepared from 3a in 57% yield over four steps by a similar procedure as that for compound 6aNoPr ¹H NMR (400 MHz, MeOD) δ 7.86-7.83 (m, 2H), 7.42 (dd, J=8.5, 1.7 Hz, 1H), 4.84 (dd, J=7.1, 5.8 Hz, 1H), 4.31-4.15 (m, 1H), 3.69 (dd, J=15.0, 5.8 Hz, 1H), 3.51 (dd, J=15.0, 7.2 Hz, 1H), 3.17-2.91 (m, 3H), 2.28 (q, J=7.6 Hz, 2H), 1.32 (d, J=6.9 Hz, 6H), 1.25 (d, J=6.9 Hz, 3H), 1.10 (t, J=7.6 Hz, 3H). ¹³C NMR (101 MHz, MeOD) δ 175.90, 171.51, 166.97, 150.86, 146.75, 135.21, 125.29, 121.29, 118.65, 52.91, 44.65, 43.71, 35.02, 34.07, 28.52, 23.14, 16.39, 8.65. UPLC-MS (ESI-MS) m/z: calculated for $C_{19}H_{29}N_4O_2S^+$ 377.20, found 377.23 [M+H]⁺.

(S)—N—((S)-1-amino-3-phenylpropan-2-yl)-3-(6-isopropylbenzo[d]thiazol-2-yl)-2-propionamidopropanamide 6aBnPr: 6aBnPr was prepared from 3a in 53% yield over four steps by a similar procedure as that for 6aNoPr. ¹H NMR (400 MHz, MeOD) δ 7.86-7.80 (m, 2H), 7.42 (dd, J=8.5, 1.6 Hz, 1H), 7.33-7.18 (m, 5H), 4.81 (dd, J=7.6, 5.5 Hz, 1H), 4.47-4.32 (m, 1H), 3.58 (dd, J=15.2, 5.5 Hz, 1H), 3.42 (dd, J=15.2, 7.6 Hz, 1H), 3.18 (dd, J=13.0, 3.6 Hz, 1H), 3.10-3.04 (m, 2H), 2.93-2.84 (m, 2H), 2.24 (q, J=7.6 Hz, 2H), 1.32 (d, J=6.9 Hz, 6H), 1.08 (t, J=7.6 Hz, 3H). ¹³C NMR (101 MHz, MeOD) δ 175.96, 171.68, 167.04, 150.86, 146.74, 136.78, 135.18, 128.77, 128.31, 126.58, 125.27, 121.31, 118.64, 52.86, 49.38, 43.08, 37.43, 34.73, 34.07, 28.49, 23.14, 8.60. UPLC-MS (ESI-MS) m/z: calculated for $C_{25}H_{33}N_4O_2S^+$ 453.23, found 453.24 [M+H]⁺.

Using methods described above, and the intermediate Fmoc-protected amino acids and 2-azidoethylamines described above, the following compounds were also synthesized.

(S)—N—((S)-1-amino-2-cyclopentylethyl)-3-(6-chlorobenzo[d]thiazol-2-yl)-2-propionamidopropanamide 6bCPPr: MS found: 423.3.

(S)—N—((S)-1-amino-2-cyclohexylethyl)-3-(6-chlorobenzo[d]thiazol-2-yl)-2-propionamidopropanamide 6bCHPr: 1H NMR (400 MHz, MeOD) δ 8.02 (d, J=1.9 Hz, 1H), 7.90 (d, J=8.7 Hz, 1H), 7.51 (dd, J=8.7, 2.1 Hz, 1H), 4.94-4.90 (m, 1H), 3.95-3.90 (m, 1H), 3.71 (dd, J=15.4, 5.6 Hz, 1H), 3.57 (dd, J=15.4, 7.5 Hz, 1H), 3.24 (dd, J=13.0, 3.2 Hz, 1H), 3.05-2.93 (m, 1H), 2.30 (q, J=7.6 Hz, 2H), 1.82-1.60 (m, 5H), 1.58-1.45 (m, 1H), 1.37-0.84 (m, 8H).
¹³C NMR (101 MHz, MeOD) δ 176.15, 171.83, 168.87, 151.32, 136.44, 130.95, 126.73, 122.77, 121.21, 52.90, 52.51, 41.57, 39.61, 34.53, 29.40, 28.56, 28.24, 25.73, 25.51, 25.46, 8.71.

(S)—N—((S)-1-amino-3-cyclohexylpropan-1-yl)-3-(6-chlorobenzo[d]thiazol-2-yl)-2-propionamidopropanamide 6bCHMPr: MS found: 451.5.

(S)—N—((S)-1-amino-3-phenylpropan-1-yl)-3-(6-chlorobenzo[d]thiazol-2-yl)-2-propionamidopropanamide 6bBnPr: 1H NMR (400 MHz, MeOD) δ 8.02 (d, J=2.0 Hz, 1H), 7.88 (d, J=8.7 Hz, 1H), 7.51 (dd, J=8.7, 2.1 Hz, 1H), 7.38-7.14 (m, 5H), 4.84-4.82 (m, 1H), 4.46-4.32 (m, 1H), 3.59 (dd, J=15.4, 5.3 Hz, 1H), 3.43 (dd, J=15.4, 8.1 Hz, 1H), 3.17 (dd, J=13.0, 3.8 Hz, 1H), 3.08 (dd, J=12.9, 10.2 Hz, 1H), 2.98-2.79 (m, 2H), 2.24 (q, J=7.6 Hz, 2H), 1.07 (t, J=7.6 Hz, 3H). ¹³C NMR (101 MHz, MeOD) δ 176.05 (s), 171.66 (s), 168.80 (s), 151.27 (s), 136.79 (s), 136.46 (s), 130.93 (s), 128.79 (s), 128.31 (s), 126.65 (d, J=13.1 Hz), 122.76 (s), 121.21 (s), 52.76 (s), 49.42 (s), 42.95 (s), 37.43 (s), 34.72 (s), 28.50 (s), 8.59 (s).

(S)—N—((S)-1-amino-2-cyclohexylethyl)-3-(6-chlorobenzo[d]thiazol-2-yl)-2-isobutanamidopropanamide 6bNoIB: 1H NMR (400 MHz, MeOD) δ 7.85 (d, J=8.5 Hz, 1H), 7.83 (s, 1H), 7.42 (d, J=8.5 Hz, 1H), 4.84-4.77 (m, 1H), 3.66 (dd, J=15.0, 5.3 Hz, 1H), 3.51 (dd, J=13.8, 8.0 Hz, 3H), 3.17-2.99 (m, 3H), 2.52 (dt, J=13.7, 6.8 Hz, 1H), 1.40-1.27 (m, 6H), 1.16-0.99 (m, 6H).

(S)—N—((S)-1-amino-2-cyclohexylethyl)-3-(6-chlorobenzo[d]thiazol-2-yl)-2-cyclopropylcarboxamidopropanamide 6bNoCPr: 1H NMR (400 MHz, MeOD) δ 8.41 (t, J=5.5 Hz, 1H), 7.86 (d, J=8.5 Hz, 1H), 7.83 (s, 1H), 7.42 (d, J=8.5 Hz, 1H), 4.82 (dd, J=7.8, 5.8 Hz, 1H), 3.66 (dd, J=15.1, 5.8 Hz, 1H), 3.55-3.47 (m, 3H), 3.17-2.97 (m, 3H), 1.80-1.59 (m, 1H), 1.33 (d, J=6.9 Hz, 6H), 0.95-0.73 (m, 4H).

(S)—N—((S)-1-amino-3-phenylpropan-2-yl)-3-(5-isopropyl-4-methylthiazol-2-yl)-2-propionamidopropanamide. 6tBnPr: 1H NMR (400 MHz, MeOD) δ 7.36-7.29 (m, 2H), 7.28-7.21 (m, 3H), 4.64 (dd, J=8.0, 5.1 Hz, 1H), 4.47-4.26 (m, 1H), 3.44 (dd, J=15.1, 5.1 Hz, 1H), 3.28-3.22 (m, 2H), 3.16 (dd, J=13.0, 3.6 Hz, 1H), 3.06 (dd, J=12.9, 10.4 Hz, 1H), 2.90 (dd, J=7.4, 3.4 Hz, 2H), 2.34 (d, J=6.4 Hz, 3H), 2.23 (q, J=7.6 Hz, 2H), 1.28 (dd, J=6.8, 2.0 Hz, 6H), 1.09 (t, J=7.6 Hz, 3H).

(S)—N—((S)-1-amino-3-phenylpropan-2-yl)-3-(5-(4-fluorophenyl)-4-methylthiazol-2-yl)-2-propionamidopropanamide. 6xBnPr: 1H NMR (400 MHz, MeOD) δ 7.54-7.39 (m, 2H), 7.34-7.30 (m, 2H), 7.27-7.19 (m, 5H), 4.69 (dd, J=7.9, 5.2 Hz, 1H), 4.51-4.30 (m, 1H), 3.45 (dd, J=15.1, 5.1 Hz, 1H), 3.28 (dd, J=15.1, 7.9 Hz, 1H), 3.18 (dd, J=13.0, 3.6 Hz, 1H), 3.12-3.01 (m, 1H), 2.91 (dd, J=7.4, 3.9 Hz, 2H), 2.40 (s, 3H), 2.26 (q, J=7.4 Hz, 2H), 1.10 (t, J=7.6 Hz, 3H).

(S)—N—((S)-1-amino-3-phenylpropan-2-yl)-3-(5-phenyl-4-methylthiazol-2-yl)-2-propionamidopropanamide. 6uBnPr: 1H NMR (400 MHz, MeOD) δ 7.50-7.37 (m, 5H), 7.34-7.28 (m, 2H), 7.28-7.17 (m, 3H), 4.70 (dd, J=7.8, 5.2 Hz, 1H), 4.48-4.33 (m, 1H), 3.47 (dd, J=15.1, 5.2 Hz, 1H), 3.32-3.25 (m, 1H), 3.18 (dd, J=13.0, 3.6 Hz, 1H), 3.09 (dd, J=12.9, 10.4 Hz, 1H), 2.91 (dd, J=7.4, 3.3 Hz, 2H), 2.43 (s, 3H), 2.26 (dt, J=15.0, 7.4 Hz, 2H), 1.10 (t, J=7.6 Hz, 3H).

(S)—N—((S)-1-amino-3-phenylpropan-2-yl)-3-(5-(4-chlorophenyl)-4-methylthiazol-2-yl)-2-propionamidopropanamide. 6wBnPr: 1H NMR (400 MHz, MeOD) δ 7.54-7.45 (m, 2H), 7.44-7.39 (m, 2H), 7.35-7.28 (m, 2H), 7.28-7.18 (m, 3H), 4.69 (dd, J=7.9, 5.2 Hz, 1H), 4.48-4.32 (m, 1H), 3.45 (dd, J=15.1, 5.1 Hz, 1H), 3.28 (dd, J=15.1, 7.9 Hz, 1H), 3.18 (dd, J=13.0, 3.6 Hz, 1H), 3.08 (dd, J=12.9, 10.4 Hz, 1H), 2.91 (dd, J=7.4, 3.7 Hz, 2H), 2.42 (s, 3H), 2.25 (q, J=7.5 Hz, 2H), 1.10 (t, J=7.6 Hz, 3H).

(S)—N—((S)-1-amino-3-phenylpropan-2-yl)-3-(5-(3-chlorophenyl)-4-methylthiazol-2-yl)-2-propionamidopropanamide. 6sBnPr: 1H NMR (400 MHz, MeOD) δ 7.54-7.40 (m, 3H), 7.39-7.29 (m, 3H), 7.28-7.15 (m, 3H), 4.70 (dd, J=7.8, 5.2 Hz, 1H), 4.42-4.39 (m, 1H), 3.45 (dd, J=15.1, 5.2 Hz, 1H), 3.31-3.23 (m, 1H), 3.18 (dd, J=13.0, 3.4 Hz, 1H), 3.07 (dd, J=15.8, 7.6 Hz, 1H), 2.98-2.84 (m, 2H), 2.43 (s, 3H), 2.26 (q, J=7.6 Hz, 2H), 1.10 (t, J=7.6 Hz, 3H).

(S)—N—((S)-1-amino-3-phenylpropan-2-yl)-3-(5-(2-chlorophenyl)-4-methylthiazol-2-yl)-2-propionamidopropanamide. 6vBnPr: 1H NMR (400 MHz, MeOD) δ 7.59-7.53 (m, 1H), 7.48-7.37 (m, 3H), 7.35-7.19 (m, 5H), 4.59 (dd, J=8.5, 5.8 Hz, 1H), 4.49-4.32 (m, 3H), 3.22-3.09 (m, 3H), 3.00 (dd, J=12.9, 10.6 Hz, 1H), 2.92 (dd, J=13.9, 6.4 Hz, 1H), 2.82 (dd, J=13.9, 8.7 Hz, 1H), 2.34-2.16 (m, 5H), 1.10 (t, J=7.6 Hz, 3H).

(S)—N—((S)-1-amino-3-phenylpropan-2-yl)-3-(5-(4-cyanophenyl)-4-methylthiazol-2-yl)-2-propionamidopropanamide. 6yBnPr: 1H NMR (400 MHz, MeOD) δ 7.92-7.78 (m, 2H), 7.68-7.59 (m, 2H), 7.37-7.28 (m, 2H), 7.28-7.18 (m, 3H), 4.71 (dd, J=8.1, 5.1 Hz, 1H), 4.41-4.38 (m, 1H), 3.46 (dd, J=15.2, 5.1 Hz, 1H), 3.31-3.25 (m, 1H), 3.18 (dd, J=13.1, 3.7 Hz, 1H), 3.11-3.02 (m, 1H), 2.92-2.90 (m, 2H), 2.47 (s, 3H), 2.25 (q, J=7.5 Hz, 2H), 1.10 (t, J=7.6 Hz, 3H).

(S)—N—((S)-1-amino-3-phenylpropan-2-yl)-3-(5-(4-nitrophenyl)-4-methylthiazol-2-yl)-2-propionamidopropanamide. 6zBnPr: 1H NMR (400 MHz, MeOD) δ 8.47-8.26 (m, 2H), 7.79-7.56 (m, 2H), 7.38-7.29 (m, 2H), 7.25 (dd, J=7.5, 4.2 Hz, 2H), 4.72 (dd, J=8.1, 5.1 Hz, 1H), 4.40 (d, J=6.9 Hz, 1H), 3.47 (dd, J=15.2, 5.1 Hz, 1H), 3.32-3.26 (m, 1H), 3.18 (dd, J=13.0, 3.6 Hz, 1H), 3.13-3.03 (m, 1H), 2.91 (dd, J=7.4, 3.8 Hz, 2H), 2.49 (s, 3H), 2.26 (q, J=7.6 Hz, 2H), 1.10 (t, J=7.6 Hz, 3H).

(S)—N—((S)-1-amino-2-cyclohexylethyl)-3-(5-(3-chlorophenyl)-4-methylthiazol-2-yl)-2-propionamidopropanamide. 6sCHPr: 1H NMR (400 MHz, MeOD) δ 7.52-7.33 (m, 4H), 4.82-4.81 (m, 1H), 3.75-3.68 (m, 1H), 3.61-3.58 (m, 2H), 3.51 (dd, J=15.0, 5.6 Hz, 1H), 3.38-3.36 (m, 1H), 2.45 (s, 3H), 2.29 (q, J=7.6 Hz, 2H), 1.81-1.55 (m, 6H), 1.31-0.98 (m, 8H).

13C NMR (101 MHz, MeOD) δ 175.58, 170.92, 164.54, 147.55, 134.34, 133.56, 130.71, 130.08, 128.54, 127.77, 127.24, 61.30, 56.07, 53.03, 38.27, 34.52, 29.68, 28.64, 28.51, 26.04, 25.85, 14.43, 8.88.

Synthesis of Imidazolo[1,2-a]pyridine-2-yl Derivatives

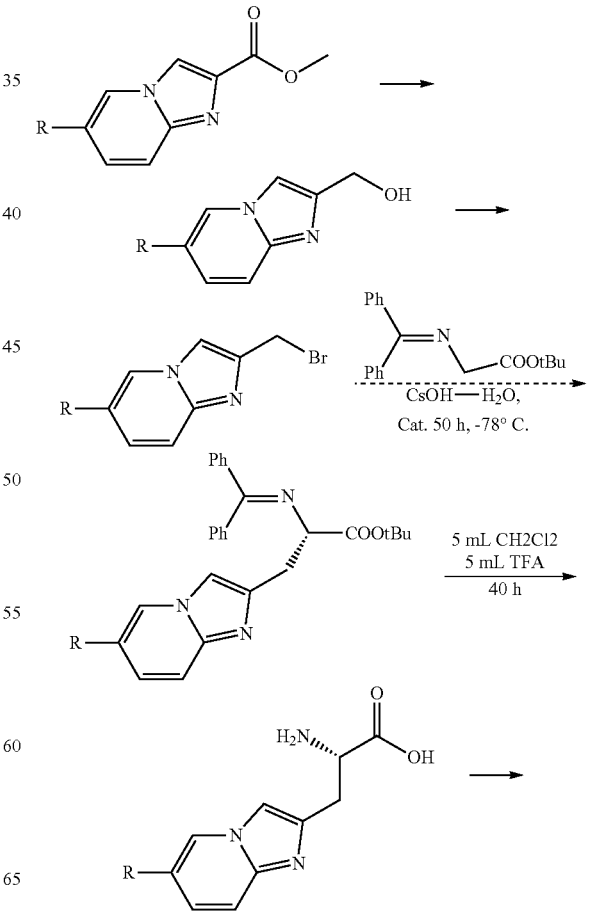

-continued

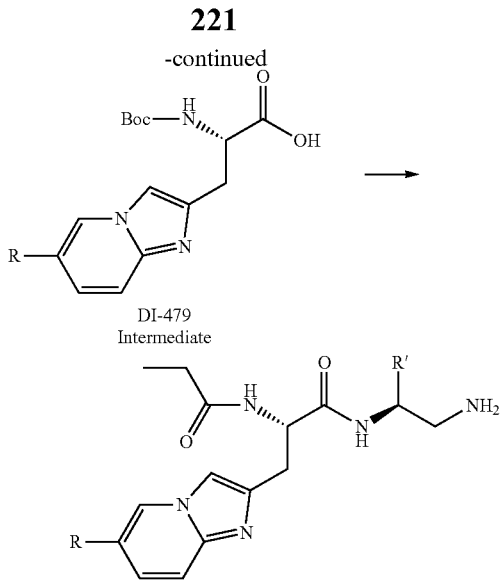

DI-479 Intermediate

These compounds were synthesized using the synthetic route shown above, and a representative example is described below.

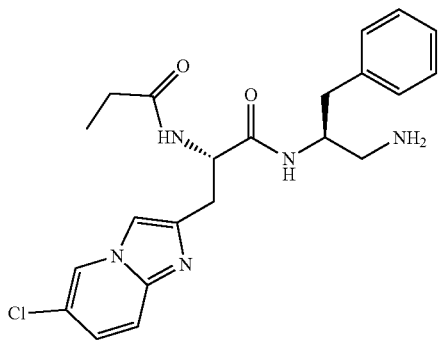 [SMILES: CCC(=O)N[C@@H](Cc1cn2cc(Cl)ccc2n1)C(=O)N[C@H](CN)Cc1ccccc1]

(S)—N—((S)-1-amino-3-phenylpropan-2-yl)-3-(5-chloroimidazolo[1,2-a]pyrid-2-yl)-2-propionamidopropanamide: $^1$H NMR (400 MHz, MeOD) δ 8.89 (d, J=0.8 Hz, 1H), 7.87-7.84 (m, 3H), 7.35-7.16 (m, 5H), 4.70 (dd, J=8.4, 5.4 Hz, 1H), 4.42-4.35 (m, 1H), 3.24-2.99 (m, 4H), 2.91 (d, J=7.5 Hz, 2H), 2.22 (q, J=7.6 Hz, 2H), 1.05 (td, J=7.5, 0.6 Hz, 3H). $^{13}$C NMR (101 MHz, MeOD) δ 176.06, 171.65, 139.36, 136.91, 136.30, 132.72, 128.84, 128.27, 126.54, 126.31, 124.21, 113.31, 112.91, 52.51, 49.47, 42.73, 37.41, 28.35, 27.52, 8.50.

Scheme 4. Synthetic Scheme for Cyclic linker Tripeptide amines.

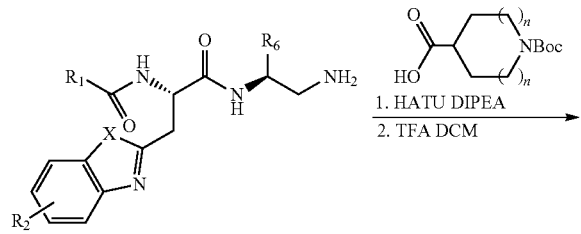

-continued

N—((S)-2-cyclohexyl-2-((S)-3-(6-isopropylbenzo[d]thiazol-2-yl)-2-propionamidopropanamido)ethyl) piperidine-4-carboxamide 9aCHPr46: Compound 6aCHPr (150 mg, 0.34 mmol, 1 equiv.) was added to a solution of the 1-(tert-butoxycarbonyl)piperidine-4-carboxylic acid (93 mg, 0.40 mmol, 1.2 equiv.), HBTU (192 mg, 0.51 mmol, 1.5 equiv.) and DIEA (176 µL, 1.01 mmol, 3 equiv.) in DCM (10 mL). The resultant mixture was stirred at room temperature for 1 h and concentrated. The residue was dissolve in EtOAc and washed with H$_2$O, saturated sodium bicarbonate, 1.0 M HCl, brine and dried over sodium sulfate. After removal of the solvent under vacuum, the residue was treated with TFA (2 ml) in DCM (10 mL) and stirred for 5 h. This reaction mixture was concentrated and purified by HPLC to afford 9aCHPr46 (139 mg, 74%). $^1$H NMR (400 MHz, MeOD) δ 7.87 (d, J=8.5 Hz, 1H), 7.83 (s, 1H), 7.42 (dd, J=8.5, 1.5 Hz, 1H), 4.89 (dd, J=7.8, 5.4 Hz, 1H), 3.80 (ddd, J=10.2, 7.0, 3.5 Hz, 1H), 3.63 (dd, J=15.4, 5.5 Hz, 1H), 3.53-3.36 (m, 4H), 3.12-3.04 (m, 2H), 2.98-2.90 (m, 2H), 2.49-2.38 (m, 1H), 2.32 (q, J=7.6 Hz, 2H), 1.98-1.81 (m, 4H), 1.72-1.62 (m, 5H), 1.39-0.92 (m, 15H). $^{13}$C NMR (101 MHz, MeOD) δ 175.87, 174.55, 171.35, 167.22, 150.93, 146.73, 135.21, 125.25, 121.57, 118.63, 54.31, 53.02, 42.89, 40.66, 39.79, 39.39, 34.95, 34.08, 29.54, 28.66, 28.32, 25.89, 25.72, 25.66, 25.14, 25.08, 23.16, 8.70. UPLC-MS (ESI-MS) m/z: calculated for $C_{30}H_{46}N_5O_3S^+$ 556.33, found 556.22 [M+H]$^+$.

N—((S)-2-cyclohexyl-2-((S)-3-(6-isopropylbenzo[d]thiazol-2-yl)-2-propionamidopropanamido)ethyl) azetidine-3-carboxamide 9aCHPr34: Compound 9aCHPr34 was made from compound 6aCHPr and 1-(tert-butoxycarbonyl)azetidine-4-carboxylic acid as described above for compound 9aCHPr46. $^1$H NMR (400 MHz, MeOD) δ 7.86 (d, J=8.4 Hz, 1H), 7.82 (d, J=0.5 Hz, 1H), 7.42 (dd, J=8.4, 0.5 Hz, 1H), 4.85 (dd, J=7.7, 5.3 Hz, 1H), 4.31-4.11 (m, 4H), 3.87-3.76 (m, 1H), 3.67-3.55 (m, 2H), 3.53-3.46 (m, 2H), 3.15 (dd, J=13.7, 10.0 Hz, 1H), 3.06 (dt, J=13.8, 6.9 Hz, 1H), 2.34 (dt, J=15.0, 4.2 Hz, 2H), 1.71-1.60 (m, 5H), 1.38-0.88 (m, 15H).

N—((S)-2-cyclohexyl-2-((S)-3-(6-isopropylbenzo[d]thiazol-2-yl)-2-propionamidopropanamido)ethyl) piperidine-4-sulfonamide 9aCHPrS46: Compound 9aCHPrS46 was made from Compound 6aCHPr and 1-(tert-butoxycarbonyl)piperidine-4-sulfonyl chloride in the presence of DIPEA, followed by TFA/DCM deprotection and HPLC purification. $^1$H NMR (400 MHz, MeOD) δ 7.89 (d, J=8.5 Hz, 1H), 7.82 (d, J=0.6 Hz, 1H), 7.79 (d, J=9.4 Hz, 1H), 7.41 (dd, J=8.4, 1.4 Hz, 1H), 4.94-4.90 (m, 1H), 3.78-3.65 (m, 2H), 3.54-3.46 (m, 3H), 3.39-3.35 (m, 2H), 3.29-3.22 (m, 1H), 3.16-3.02 (m, 4H), 2.37-2.23 (m, 4H), 1.99-1.91 (m, 2H), 1.69 (dd, J=25.9, 10.8 Hz, 6H), 1.35-0.94 (m, 15H). Not in DB but I added it at end.

N—((S)-2-cyclohexyl-2-((S)-3-(6-isopropylbenzo[d]thiazol-2-yl)-2-propionamidopropanamido)ethyl)-N'-piperidin-4-yl urea 9aCHPrU46. Compound 9aCHPrU46 was made from Compound 6aCHPr and 1-(tert-butoxycarbonyl)piperidin-4-yl isocyanate, followed by TFA/DCM deprotection and HPLC purification. $^1$H NMR (400 MHz, MeOD) δ 7.86 (d, J=8.5 Hz, 1H), 7.82 (d, J=1.6 Hz, 1H), 7.41 (dd, J=8.5, 1.7 Hz, 1H), 4.94-4.90 (m, 1H), 3.80-3.69 (m, 2H), 3.61 (dd, J=15.3, 4.9 Hz, 1H), 3.48 (dd, J=15.3, 8.5 Hz, 1H), 3.42-3.34 (m, 3H), 3.18-2.99 (m, 4H), 2.30 (q, J=7.5 Hz, 2H), 2.14-2.08 (m, 2H), 1.78-1.54 (m, 7H), 1.41-0.93 (m, 15H).

N1-((S)-2-cyclohexyl-2-((S)-3-(6-isopropylbenzo[d]thiazol-2-yl)-2-propionamidopropanamido)ethyl)-1,2,3-triazol-4-ylmethylamine 9aCHPrTZ. Compound 9aCHPrTZ was made from Compound 5aCHPr and N-(tert-butoxycarbonyl) propargylamine in presence of $Cu^I$ catalyst, followed by TFA/DCM deprotection and HPLC purification. 1H NMR (400 MHz, MeOD) δ 7.97 (s, 1H), 7.86 (d, J=8.5 Hz, 1H), 7.82 (d, J=1.5 Hz, 1H), 7.42 (dd, J=8.5, 1.6 Hz, 1H), 4.75 (dd, J=8.8, 4.6 Hz, 1H), 4.69 (dd, J=14.0, 3.9 Hz, 1H), 4.45 (dd, J=14.0, 10.1 Hz, 1H), 4.23 (s, 2H), 4.16-4.12 (m, 1H), 3.46 (dd, J=15.5, 4.6 Hz, 1H), 3.41-3.34 (m, 1H), 3.07 (dt, J=13.8, 6.9 Hz, 1H), 2.37-2.23 (m, 2H), 1.85-1.61 (m, 5H), 1.55-1.47 (m, 1H), 1.37-0.94 (m, 15H).

C. Synthesis of Final Compounds

Example 1

N—((S)-2-((S)-3-(6-chlorobenzo[d]thiazol-2-yl)-2-propionamidopropanamido)-3-phenylpropyl)acrylamide: Compound 6bBnPr (40 mg, 0.09 mmol, 1 equiv.) was added to a solution of acrylic acid (8 mg, 0.11 mmol, 1.2 equiv.), HBTU (51 mg, 0.13 mmol, 1.5 equiv.) and DIEA (47 µL, 0.27 mmol, 3 equiv.) in DCM (5 mL). The resultant mixture was stirred at room temperature for 1 h and concentrated. The residue was purified by HPLC to afford Example 1 (37 mg, 81%). $^1$H NMR (400 MHz, MeOD:CCl3D=1:1) δ 7.88 (d, J=1.8 Hz, 1H), 7.82 (d, J=8.7 Hz, 1H), 7.44 (dd, J=8.7, 2.1 Hz, 1H), 7.29-7.11 (m, 5H), 6.21-6.08 (m, 2H), 5.59 (dd, J=9.7, 2.2 Hz, 1H), 4.80 (dd, J=7.5, 5.6 Hz, 1H), 4.22-4.15 (m, 1H), 3.53 (dd, J=15.2, 5.6 Hz, 1H), 3.44-3.34 (m, 3H), 2.80 (d, J=7.1 Hz, 2H), 2.22 (q, J=7.6 Hz, 2H), 1.07 (t, J=7.6 Hz, 3H).

Example 2

(E)-N—((S)-2-((S)-3-(6-chlorobenzo[d]thiazol-2-yl)-2-propionamidopropanamido)-3-phenylpropyl)-4-(dimethylamino)but-2-enamide. Example 2 was prepared from Compound 6bBnPr by a similar procedure as that described for Example 1. $^1$H NMR (400 MHz, MeOD) δ 8.01 (d, J=2.0 Hz, 1H), 7.89 (d, J=8.7 Hz, 1H), 7.50 (dd, J=8.7, 2.1 Hz, 1H), 7.35-7.11 (m, 5H), 6.69 (dt, J=14.9, 7.3 Hz, 1H), 6.33 (d, J=15.3 Hz, 1H), 4.82 (dd, J=8.8, 5.1 Hz, 1H), 4.37-4.17 (m, 1H), 3.90 (d, J=6.9 Hz, 2H), 3.53 (dd, J=15.3, 5.1 Hz, 1H), 3.47 (dd, J=13.7, 4.6 Hz, 1H), 3.40-3.34 (m, 2H), 2.90 (s, 6H), 2.88-2.74 (m, 2H), 2.25 (q, J=7.6 Hz, 2H), 1.06 (t, J=7.6 Hz, 3H).

Example 3

N—((S)-2-((S)-3-(6-chlorobenzo[d]thiazol-2-yl)-2-propionamidopropanamido)-3-phenylpropyl)-2-(morpholinomethyl)acrylamide: Example 3 was prepared from Compound 6bBnPr by a similar procedure as that described for Example 1. $^1$H NMR (400 MHz, MeOD) δ 8.01 (d, J=1.8 Hz, 1H), 7.88 (d, J=8.7 Hz, 1H), 7.51 (dd, J=8.7, 2.1 Hz, 1H), 7.35-7.08 (m, 5H), 6.18 (s, 1H), 5.96 (s, 1H), 4.81 (dd, J=8.6, 5.3 Hz, 1H), 4.43-4.30 (m, 1H), 4.12-3.73 (m, 6H), 3.62-3.34 (m, 5H), 3.32-3.03 (m, 3H), 2.89-2.78 (m, 2H), 2.29 (tt, J=7.7, 4.0 Hz, 2H), 1.08 (t, J=7.6 Hz, 3H). $^{13}$C NMR (101 MHz, MeOD) δ 175.95, 171.33, 171.25, 168.78, 167.42, 151.30, 137.72, 136.48, 132.70, 130.89, 128.94, 128.82, 128.11, 126.70, 126.22, 122.91, 121.19, 63.47, 58.50, 52.95, 51.80, 51.18, 43.00, 37.76, 34.91, 28.63, 8.66.

Example 4

N—((S)-2-((S)-3-(6-chlorobenzo[d]thiazol-2-yl)-2-propionamidopropanamido)-2-cyclohexylethyl)-2-(morpholinomethyl)acrylamide: Example 4 was prepared from Compound 6bCHPr by a similar procedure as that described for Example 1. $^1$H NMR (400 MHz, MeOD) δ 8.04 (d, J=1.9 Hz, 1H), 7.91 (d, J=8.7 Hz, 1H), 7.52 (dd, J=8.7, 2.1 Hz, 1H), 6.19 (s, 1H), 5.96 (s, 1H), 4.90-4.88 (m, 1H), 4.24-3.74 (m, 6H), 3.64 (dd, J=15.5, 5.4 Hz, 1H), 3.60-3.34 (m, 6H), 3.30-3.00 (m, 3H), 2.34 (qd, J=7.6, 1.4 Hz, 2H), 1.75-1.65 (m, 5H), 1.50-1.39 (m, 1H), 1.36-0.80 (m, 8H).

Example 5

N—((S)-2-((S)-3-(6-chlorobenzo[d]thiazol-2-yl)-2-propionamidopropanamido)-3-cyclohexylpropyl)-2-(morpholinomethyl)acrylamide: Example 5 was prepared from Compound 6bCHMPr by a similar procedure as that described for Example 1. $^1$H NMR (400 MHz, MeOD) δ 8.04 (d, J=1.8 Hz, 1H), 7.91 (d, J=8.7 Hz, 1H), 7.52 (dd, J=8.7, 2.1 Hz, 1H), 6.20 (s, 1H), 5.96 (s, 1H), 4.85-4.79 (m, 1H), 4.25-4.18 (m, 1H), 4.06-3.87 (m, 5H), 3.65-3.35 (m, 7H), 3.17-3.11 (m, 3H), 2.33 (qd, J=7.6, 1.2 Hz, 2H), 1.79-1.60 (m, 5H), 1.50-0.62 (m, 11H).

Example 6

N—((S)-2-((S)-3-(6-chlorobenzo[d]thiazol-2-yl)-2-propionamidopropanamido)-2-cyclopentylethyl)-2-(morpholinomethyl)acrylamide: Example 6 was prepared from Compound 6bCPPr by a similar procedure as that described for Example 1. 1H NMR (400 MHz, MeOD) δ 8.04 (d, J=2.1 Hz, 1H), 7.90 (d, J=8.7 Hz, 1H), 7.52 (dd, J=8.7, 2.1 Hz, 1H), 6.18 (s, 1H), 5.94 (s, 1H), 4.94-4.92 (m, 1H), 4.25-3.74 (m, 6H), 3.64 (dd, J=15.4, 5.5 Hz, 1H), 3.56-3.36 (m, 6H), 3.24-3.15 (m, 3H), 2.42-2.24 (m, 2H), 2.01-1.90 (m, 1H), 1.88-1.77 (m, 1H), 1.74-1.44 (m, 4H), 1.43-1.03 (m, 6H).

Example 7

N—((S)-2-((S)-3-(6-prop-2-ylbenzo[d]thiazol-2-yl)-2-propionamidopropanamido)-3-phenylpropyl)-2-(morpholinomethyl)acrylamide: Example 7 was prepared from Compound 6aBnPr by a similar procedure as that described for Example 1. 1H NMR (400 MHz, MeOD) δ 7.84 (d, J=8.5 Hz, 1H), 7.82 (d, J=1.7 Hz, 1H), 7.42 (dd, J=8.5, 1.6 Hz, 1H), 7.35-7.03 (m, 5H), 6.19 (s, 1H), 5.95 (s, 1H), 4.78 (dd, J=8.5, 5.4 Hz, 1H), 4.45-4.28 (m, 1H), 4.18-3.67 (m, 6H), 3.56-3.38 (m, 4H), 3.31-3.23 (m, 2H), 3.21-2.98 (m, 3H), 2.90-2.73 (m, 2H), 2.28 (q, J=7.6 Hz, 2H), 1.33 (d, J=6.9 Hz, 6H), 1.09 (t, J=7.6 Hz, 3H). $^{13}$C NMR (101 MHz, MeOD) δ 175.91, 171.34, 167.40, 167.05, 150.91, 146.70, 137.72, 135.22, 132.71, 128.97, 128.82, 128.10, 126.21, 125.22, 121.53, 118.61, 63.44, 58.47, 53.16, 51.80, 51.14, 43.04, 37.76, 34.91, 34.08, 28.63, 23.16, 8.65.

Example 8

N—((S)-2-((S)-3-(6-ethylbenzo[d]thiazol-2-yl)-2-propionamidopropanamido)-3-phenylpropyl)-2-(morpholinomethyl)acrylamide: Example 8 was prepared from Compound 6iBnPr by a similar procedure as that described for Example 1. 1H NMR (400 MHz, MeOD) δ 7.83 (d, J=8.4 Hz, 1H), 7.78 (s, 1H), 7.38 (dd, J=8.4, 1.6 Hz, 1H), 7.32-7.17 (m, 4H), 6.18 (s, 1H), 5.94 (s, 1H), 4.78 (dd, J=8.5, 5.5 Hz, 1H), 4.38-4.35 (m, 1H), 4.18-3.65 (m, 6H), 3.56-3.39 (m, 3H), 3.31-2.99 (m, 6H), 2.91-2.75 (m, 3H), 2.28 (q, J=7.6 Hz, 2H), 1.31 (t, J=7.6 Hz, 3H), 1.09 (t, J=7.6 Hz, 3H).

Example 9

(DI-1548). N—((S)-2-((S)-3-(6-prop-2-ypbenzo[d]thiazol-2-yl)-2-propionamidopropanamido)-2-cyclohexylethyl)-2-(morpholinomethyl)acrylamide: Example 9 was prepared from Compound 6aCHPr by a similar procedure as that described for Example 1. $^1$H NMR (400 MHz, MeOD) δ 7.85 (d, J=8.5 Hz, 1H), 7.82 (d, J=1.7 Hz, 1H), 7.42 (dd, J=8.5, 1.7 Hz, 1H), 6.20 (s, 1H), 5.96 (s, 1H), 4.85 (dd, J=7.7, 5.5 Hz, 1H), 4.16-3.73 (m, 7H), 3.62 (dd, J=15.3, 5.5 Hz, 1H), 3.54-3.43 (m, 4H), 3.29-2.95 (m, 4H), 2.34 (qd, J=7.6, 0.9 Hz, 2H), 2.34 (q, J=7.6, 0.9 Hz, 2H), 1.72 (t, J=12.5 Hz, 2H), $^1$H NMR (400 MHz, MeOD) δ 7.85 (d, J=8.5 Hz, 1H), 7.82 (d, J=1.7 Hz, 1H), 7.42 (dd, J=8.5, 1.7 Hz, 1H), 6.20 (s, 1H), 5.96 (s, 1H), 4.85 (dd, J=7.7, 5.5 Hz, 1H), 4.16-3.73 (m, 7H), 3.62 (dd, J=15.3, 5.5 Hz, 1H), 3.54-3.43 (m, 4H), 3.29-2.95 (m, 4H), 2.34 (qd, J=7.6, 0.9 Hz, 2H), 1.80-1.56 (m, 5H), 1.53-1.36 (m, 1H), 1.32 (d, J=6.9 Hz, 6H), 1.26-0.80 (m, 8H).

Example 10

N—((S)-2-((S)-3-(6-prop-2-ypbenzo[d]thiazol-2-yl)-2-propionamidopropanamido)-2-cyclohexylethyl)-2-(2-morpholinoethyl)acrylamide: Example 10 was prepared from Compound 6aCHPr by a similar procedure as that described for Example 1.1H NMR (400 MHz, MeOD) δ 7.85 (d, J=8.5 Hz, 1H), 7.83 (d, J=1.7 Hz, 1H), 7.42 (dd, J=8.5, 1.7 Hz, 1H), 5.77 (s, 1H), 5.53 (s, 1H), 4.86 (dd, J=7.7, 5.9 Hz, 1H), 4.09-4.05 (m, 2H), 3.96-3.91 (m, 1H), 3.78 (t, J=12.5 Hz, 2H), 3.68-3.49 (m, 4H), 3.43 (dd, J=15.3, 7.8 Hz, 1H), 3.24 (t, J=7.0 Hz, 2H), 3.19-2.99 (m, 4H), 2.76-2.69 (dt, J=13.9, 6.8 Hz, 1H), 2.67-2.54 (m, 1H), 2.30 (q, J=7.6 Hz, 2H), 1.82-1.58 (m, 5H), 1.51-1.39 (m, 1H), 1.33 (d, J=6.9 Hz, 6H), 1.27-0.87 (m, 8H).

Example 11

(E)-N—((S)-2-((S)-3-(6-prop-2-ylbenzo[d]thiazol-2-yl)-2-propionamidopropanamido)-3-phenylpropyl)-4-(dimethylamino)but-2-enamide. Example 11 was prepared from Compound 6aCHPr by a similar procedure as that described for Example 11H NMR (400 MHz, MeOD) δ 7.85 (d, J=8.5 Hz, 1H), 7.82 (d, J=1.7 Hz, 1H), 7.42 (dd, J=8.5, 1.7 Hz, 1H), 6.75-6.63 (m, 1H), 6.35 (dt, J=15.3, 1.1 Hz, 1H), 4.86-4.82 (m, 1H), 3.90 (dd, J=7.3, 1.2 Hz, 2H), 3.85-3.80 (m, 1H), 3.59 (dd, J=15.3, 5.1 Hz, 1H), 3.53 (d, J=13.7, 4.0 Hz, 1H), 3.46 (d, J=15.3, 8.2 Hz, 1H), 3.32-3.24 (m, 1H), 3.11-3.04 (m, 1H), 2.90 (s, 6H), 2.37-2.26 (m, 2H), 1.79-1.57 (m, 5H), 1.47-1.41 (m, 1H), 1.32 (d, J=6.9 Hz, 6H), 1.28-0.88 (m, 8H).

Example 12

N—((S)-2-((S)-3-(6-chlorobenzo[d]thiazol-2-yl)-2-propionamidopropanamido)-3-phenylpropyl)-1-methyl-1,2,5,6-tetrahydropyridine-3-carboxamide: Example 12 was prepared from Compound 6bBnPr by a similar procedure as that described for Example 1. $^1$H NMR (400 MHz, MeOD) δ 8.08-7.98 (m, 1H), 7.94-7.84 (m, 1H), 7.51 (dd, J=8.7, 2.1 Hz, 1H), 7.33-7.11 (m, 5H), 6.67 (s, 1H), 4.82 (dd, J=8.7, 5.2 Hz, 1H), 4.32-4.25 (m, 1H), 3.83-3.33 (m, 7H), 3.24-3.07 (m, 1H), 3.00 (s, 3H), 2.89-2.75 (m, 2H), 2.59 (s, 2H), 2.25 (q, J=7.6 Hz, 2H), 1.07 (t, J=7.6 Hz, 3H).

Example 13

N—((S)-2-((S)-3-(6-prop-2-ylbenzo[d]thiazol-2-yl)-2-propionamidopropanamido)-3-phenylpropyl)-1-methyl-1,2,5,6-tetrahydropyridine-3-carboxamide: Example 13 was prepared from Compound 6aCHPr by a similar procedure as that described for Example 1. 1H NMR (400 MHz, MeOD) δ 7.85 (d, J=8.5 Hz, 1H), 7.83 (d, J=1.7 Hz, 1H), 7.42 (dd, J=8.5, 1.7 Hz, 1H), 6.67 (s, 1H), 4.86-4.84 (m, 1H), 4.23-4.15 (m, 1H), 3.89-3.39 (m, 6H), 3.30-3.03 (m, 3H), 2.99 (s, 3H), 2.66-2.52 (m, 2H), 2.32 (qd, J=7.6, 1.0 Hz, 2H), 1.71-1.63 (m, 5H), 1.47-1.39 (m, 1H), 1.33 (d, J=6.9 Hz, 6H), 1.26-0.83 (m, 8H).

Example 14

N—((S)-2-((S)-3-(6-prop-2-ypbenzo[d]thiazol-2-yl)-2-propionamidopropanamido)-2-cyclohexylethyl)-2-(pyrrolidin-1-ylmethyl)acrylamide: Example 14 was prepared from Compound 6aCHPr by a similar procedure as that described for Example 1. 1H NMR (400 MHz, MeOD) δ 7.85 (d, J=8.5 Hz, 1H), 7.82 (d, J=1.7 Hz, 1H), 7.42 (dd, J=8.5, 1.7 Hz, 1H), 6.13 (s, 1H), 5.93 (s, 1H), 4.85 (dd, J=7.7, 5.5 Hz, 1H), 3.98 (d, J=1.7 Hz, 2H), 3.89-3.84 (m, 1H), 3.68-3.56 (m, 3H), 3.53-3.40 (m, 2H), 3.25 (dd, J=13.7, 10.4 Hz, 1H), 3.17-3.00 (m, 3H), 2.34 (qd, J=7.6, 1.7 Hz, 2H), 2.20-1.99 (m, 4H), 1.78-1.56 (m, 5H), 1.48-1.38 (m, 1H), 1.32 (d, J=6.9 Hz, 6H), 1.24-0.89 (m, 8H).

Example 15

N—((S)-2-((S)-3-(6-prop-2-ypbenzo[d]thiazol-2-yl)-2-propionamidopropanamido)-2-cyclohexylethyl)-2-(2-(dimethylamino)ethyl)acrylamide: Example 15 was prepared from Compound 6aCHPr by a similar procedure as that described for Example 1. $^1$H NMR (400 MHz, MeOD) δ 7.85 (d, J=8.5 Hz, 1H), 7.82 (d, J=1.7 Hz, 1H), 7.42 (dd, J=8.5, 1.7 Hz, 1H), 5.76 (s, 1H), 5.52 (s, 1H), 4.87-4.84 (m, 1H), 3.92-3.87 (m, 1H), 3.65-3.52 (m, 2H), 3.44 (dd, J=15.3, 7.8 Hz, 1H), 3.23 (t, J=7.2 Hz, 2H), 3.18-3.01 (m, 2H), 2.93 (s, 6H), 2.77-2.55 (m, 2H), 2.31 (q, J=7.6 Hz, 2H), 1.79-1.58 (m, 5H), 1.49-1.38 (m, 1H), 1.32 (d, J=6.9 Hz, 6H), 1.27-0.87 (m, 8H).

Example 16

(E)-N—((S)-2-cyclohexyl-2-((S)-3-(6-isopropylbenzo[d]thiazol-2-yl)-2-propionamidopropanamido)ethyl)-2-methyl-4-(4-methylpiperidin-1-yl)but-2-enamide: Example 16 was prepared from Compound 6aCHPr by a similar procedure as that described for Example 1. $^1$H NMR (400 MHz, MeOD) δ 7.86-7.83 (m, 2H), 7.42 (dd, J=8.5, 1.7 Hz, 1H), 6.23 (td, J=7.0, 1.4 Hz, 1H), 4.86-4.83 (m, 1H), 3.87-3.82 (m, 1H), 3.63-3.56 (m, 3H), 3.53-3.41 (m, 6H), 3.28-3.22 (m, 5H), 3.07 (dt, J=13.8, 6.9 Hz, 1H), 2.91 (s, 3H), 2.34-2.28 (m, 2H), 1.89 (d, J=1.2 Hz, 3H), 1.80-1.58 (m, 5H), 1.49-1.40 (m, 1H), 1.33 (d, J=6.9 Hz, 6H), 1.25-0.91 (m, 8H).

Example 17

N—((S)-2-((S)-3-(6-prop-2-ylbenzo[d]thiazol-2-yl)-2-propionamidopropanamido)-3-phenylpropyl)-4-(dimethylamino)but-2-ynamide: Example 17 was prepared from Compound 6aCHPr by a similar procedure as that described for Example 1. ESI-MS m/z: calculated for $C_{30}H_{44}N_5O_3S+$ 554.3, found 554.5 [M+H]+.

Example 18

(S)—N—((S)-1-cyclohexyl-2-(vinylsulfonamido)ethyl)-3-(6-isopropylbenzo[d]thiazol-2-yl)-2-propionamidopropanamide: To a mixture of 6aCHPr (45 mg, 0.1 mmol) and DIEA (47 µL) in DCM (5 mL) was added ethenesulfonyl chloride (15 mg, 0.12 mmol) at 0° C. The resulting mixture was stirred at room temperature for 1 h and concentrated. The residue was purified by HPLC to yield Example 18. ESI-MS m/z: calculated for $C_{26}H_{39}N_4O_4S_2+$ 535.2, found 535.3 [M+H]+.

Example 19

(S)—N—((S)-1-cyclohexyl-2-(ethynylsulfonamido)ethyl)-3-(6-isopropylbenzo[d]thiazol-2-yl)-2-propionamidopropanamide: Example 19 was prepared from 6aCHPr by a similar procedure as that for Example 18. ESI-MS m/z: calculated for $C_{26}H_{37}N_4O_4S_2+$ 533.2, found 533.7 [M+H]+.

Example 20

(S)—N—((S)-1-(2-chloroacetamido)-3-phenylpropan-2-yl)-3-(6-chlorobenzo[d]thiazol-2-yl)-2-propionamidopropanamide: Example 20 was prepared from Compound 6bBnPr by a similar procedure as that described for Example 1. 1H NMR (400 MHz, MeOD:CCl3D=1:1) δ 7.86 (d, J=1.8 Hz, 1H), 7.83 (d, J=8.7 Hz, 1H), 7.44 (dd, J=8.7, 2.0 Hz, 1H), 7.25-7.15 (m, 5H), 4.85-4.75 (m, 1H), 4.28-4.14 (m, 1H), 3.94 (s, 2H), 3.52 (dd, J=15.3, 5.6 Hz, 1H), 3.44-3.36 (m, 2H), 3.31-3.23 (m, 1H), 2.78 (d, J=7.1 Hz, 2H), 2.22 (q, J=7.6 Hz, 2H), 1.07 (t, J=7.6 Hz, 3H).

Example 21

(DI-1859): N—((S)-2-cyclohexyl-2-((S)-3-(6-isopropylbenzo[d]thiazol-2-yl)-2-propionamidopropanamido)ethyl)-2-((dimethylamino)methyl)acrylamide. Example 21 was prepared from Compound 6aCHPr by a similar procedure as that described for Example 1. $^1$H NMR (400 MHz, MeOD) δ 7.85 (d, J=8.5 Hz, 1H), 7.82 (d, J=1.7 Hz, 1H), 7.41 (dd, J=8.5, 1.7 Hz, 1H), 6.18 (s, 1H), 5.93 (s, 1H), 4.86 (dd, J=7.7, 5.5 Hz, 1H), 3.99-3.82 (m, 3H), 3.62 (dd, J=15.3, 5.5 Hz, 1H), 3.53-3.43 (m, 2H), 3.24 (dd, J=13.7, 10.3 Hz, 1H), 3.07 (dt, J=13.8, 6.9 Hz, 1H), 2.88 (s, 6H), 2.34 (qd, J=7.6, 1.5 Hz, 2H), 1.79-1.57 (m, 5H), 1.47-1.38 (m, 1H), 1.32 (d, J=6.9 Hz, 6H), 1.24-0.88 (m, 8H). $^{13}$C NMR (101 MHz, DMSO) δ 175.17, 170.62, 166.49, 166.30, 150.15, 145.89, 134.37, 132.78, 127.28, 124.44, 120.76, 117.80, 58.60, 53.62, 52.26, 41.33, 40.31, 38.94, 34.00, 33.28, 28.79, 27.89, 27.61, 25.07, 24.86, 24.78, 22.36, 7.89. HRMS (ESI-MS) m/z: calculated for $C_{30}H_{46}N_5O_3S^+$ 556.3316, found 556.3321 [M+H]+.

Example 22

(DI-1860): N—((S)-2-cyclohexyl-2-((S)-3-(6-isopropylbenzo[d]thiazol-2-yl)-2-propionamidopropanamido)ethyl)-2-((diethylamino)methyl)acrylamide. Example 22 was prepared from Compound 6aCHPr by a similar procedure as that described for Example 1. ESI-MS m/z: calculated for $C_{32}H_{50}N_5O_3S^+$ 584.4, found 584.7 [M+H]+.

Example 23

N—((S)-2-cyclohexyl-2-((S)-3-(6-isopropylbenzo[d]thiazol-2-yl)-2-propionamidopropanamido)ethyl)-2-(piperidin-1-ylmethyl)acrylamide. Example 23 was prepared from Compound 6aCHPr by a similar procedure as that described for Example 1. ESI-MS m/z: calculated for $C_{33}H_{50}N_5O_3S^+$ 596.4, found 596.5 [M+H]+.

Example 24

2-((1H-imidazol-1-yl)methyl)-N—((S)-2-cyclohexyl-2-((S)-3-(6-isopropylbenzo[d]thiazol-2-yl)-2-propionamidopropanamido)ethyl)acrylamide. Example 24 was prepared from Compound 6aCHPr by a similar procedure as that described for Example 1. $^1$H NMR (400 MHz, MeOD) δ 8.94 (t, J=1.4 Hz, 1H), 7.91-7.75 (m, 2H), 7.62-7.56 (m, 1H), 7.56-7.50 (m, 1H), 7.46-7.37 (m, 1H), 6.04 (s, 1H), 5.78 (s, 1H), 5.06 (q, J=14.7 Hz, 2H), 4.85-4.83 (m, 1H), 3.83-3.78 (m, 1H), 3.58 (dd, J=15.2, 5.8 Hz, 1H), 3.50 (dd, J=13.7, 3.7 Hz, 1H), 3.42 (dd, J=15.2, 7.8 Hz, 1H), 3.20-3.02 (m, 2H), 2.30 (q, J=7.6 Hz, 2H), 1.80-1.54 (m, 5H), 1.42-1.35 (m, 1H), 1.33 (d, J=6.9 Hz, 6H), 1.26-0.84 (m, 8H). $^{13}$C NMR (101 MHz, MeOD) δ 175.77, 171.34, 167.08, 166.67, 150.97, 146.69, 137.93, 135.70, 135.23, 125.21, 124.17, 122.01, 121.55, 119.66, 118.61, 54.22, 52.98, 50.10, 41.11, 39.69, 34.91, 34.09, 29.56, 28.63, 28.31, 25.89, 25.71, 25.65, 23.17, 23.15, 8.73. HRMS (ESI-MS) m/z: calculated for $C_{31}H_{43}N_6O_3S^+$ 579.3112, found 579.3112 [M+H]+.

Example 25

2-(azetidin-1-ylmethyl)-N—((S)-2-cyclohexyl-2-((S)-3-(6-isopropylbenzo[d]thiazol-2-yl)-2-propionamidopropanamido)ethyl)acrylamide. Example 25 was prepared from Compound 6aCHPr by a similar procedure as that described for Example 1. ESI-MS m/z: calculated for $C_{31}H_{46}N_5O_3S^+$ 568.3, found 568.9 [M+H]+.

Example 26

N—((S)-2-cyclohexyl-2-((S)-3-(6-isopropylbenzo[d]thiazol-2-yl)-2-propionamidopropanamido)ethyl)-2-((3,3-difluoroazetidin-1-yl)methyl)acrylamide. Example 26 was prepared from Compound 6aCHPr by a similar procedure as that described for Example 1. ESI-MS m/z: calculated for $C_{31}H_{44}F_2N_5O_3S^+$ 604.3, found 604.4 [M+H]+.

Example 27

N—((S)-2-cyclohexyl-2-((S)-3-(6-isopropylbenzo[d]thiazol-2-yl)-2-propionamidopropanamido)ethyl)-2-((4-methylpiperazin-1-yl)methyl)acrylamide. Example 27 was prepared from Compound 6aCHPr by a similar procedure as that described for Example 1. ESI-MS m/z: calculated for $C_{31}H_{51}N_6O_3S^+$ 611.4, found 611.8 [M+H]+.

Example 28

N—((S)-2-cyclohexyl-2-((S)-3-(6-isopropylbenzo[d]thiazol-2-yl)-2-propionamidopropanamido)ethyl)-2-((1,1-dioxidothiomorpholino)methyl)acrylamide. Example 28 was prepared from Compound 6aCHPr by a similar procedure as that described for Example 1. ESI-MS m/z: calculated for $C_{32}H_{48}N_5O_5S_2^+$ 646.3, found 646.5 [M+H]$^+$.

Example 29

N—((S)-2-cyclohexyl-2-((S)-3-(6-isopropylbenzo[d]thiazol-2-yl)-2-propionamidopropanamido)ethyl)-2-((4-(2-hydroxyethyl)piperazin-1-yl)methyl)acrylamide. Example 29 was prepared from Compound 6aCHPr by a similar procedure as that described for Example 1. ESI-MS m/z: calculated for $C_{34}H_{53}N_6O_4S^+$ 641.4, found 641.4 [M+H]$^+$.

Example 30. N—((S)-2-cyclohexyl-2-((S)-3-(6-isopropylbenzo[d]thiazol-2-yl)-2-propionamidopropanamido)ethyl)-2-((4,4-difluoropiperidin-1-yl)methyl)acrylamide Example 30 was prepared from Compound 6aCHPr by a similar procedure as that described for Example 1. ESI-MS m/z: calculated for $C_{33}H_{48}F_2N_5O_3S^+$ 632.3, found 632.6 [M+H]$^+$.

Example 31. N—((S)-2-((S)-3-(6-isopropylbenzo[d]thiazol-2-yl)-2-propionamidopropanamido)-3-(pyridin-4-yl)propyl)acrylamide Example 31 was prepared from by a similar procedure as that described for Example 1. ESI-MS m/z: calculated for $C_{27}H_{34}N_5O_3S^+$ 508.2, found 508.4 [M+H]$^+$.

Example 32. N—((S)-2-((S)-3-(6-isopropylbenzo[d]thiazol-2-yl)-2-propionamidopropanamido)-3-(pyridin-3-yl)propyl)acrylamide Example 32 was prepared from by a similar procedure as that described for Example 1. ESI-MS m/z: calculated for $C_{27}H_{34}N_5O_3S^+$ 508.2, found 508.3 [M+H]$^+$.

Example 33

(S)-3-(6-isopropylbenzo[d]thiazol-2-yl)-2-propionamido-N—((S)-1-(pyridin-3-yl)-3-(vinylsulfonamido)propan-2-yl)propanamide. Example 33 was prepared from by a similar procedure as that described for Example 1. ESI-MS m/z: calculated for $C_{26}H_{34}N_5O_4S_2^+$ 544.2, found 544.3 [M+H]$^+$.

Example 34

N—((S)-2-((S)-3-(6-isopropylbenzo[d]thiazol-2-yl)-2-propionamidopropanamido)-3-(pyridin-3-yl)propyl)-2-(morpholinomethyl)acrylamide. Example 34 was prepared from by a similar procedure as that described for Example 1. ESI-MS m/z: calculated for $C_{32}H_{43}N_6O_4S^+$ 607.3, found 607.7 [M+H]$^+$.

Example 35

N—((S)-2-((S)-3-(6-chloroimidazo[1,2-a]pyridin-2-yl)-2-propionamidopropanamido)-3-phenylpropyl)-2-(morpholinomethyl)acrylamide. Example 35 was prepared from by a similar procedure as that described for Example 1. ESI-MS m/z: calculated for $C_{30}H_{38}ClN_6O_4^+$ 581.3, found 581.5 [M+H]$^+$.

Example 36

N—((S)-3-(4-fluorophenyl)-2-((S)-3-(6-isopropylbenzo[d]thiazol-2-yl)-2-propionamidopropanamido)propyl)-2-(morpholinomethyl)acrylamide. Example 36 was prepared from by a similar procedure as that described for Example 1. ESI-MS m/z: calculated for $C_{33}H_{43}FN_5O_4S^+$ 624.3.3, found 624.7 [M+H]$^+$.

Example 37

N—((S)-2-cyclohexyl-2-((S)-3-(6-isopropylbenzo[d]thiazol-2-yl)-2-propionamidopropanamido)ethyl)acrylamide. Example 37 was prepared from Compound 6aCHPr by a similar procedure as that described for Example 1. $^1$H NMR (400 MHz, CDCl$_3$) δ 7.85 (d, J=8.4 Hz, 1H), 7.71 (d, J=1.2 Hz, 1H), 7.50-7.31 (m, 2H), 6.96-6.94 (m, 2H), 6.24 (dd, J=17.0, 1.3 Hz, 1H), 6.09 (dd, J=17.0, 10.2 Hz, 1H), 5.58 (dd, J=10.2, 1.2 Hz, 1H), 4.94-4.90 (m, 1H), 3.94-3.76 (m, 1H), 3.64 (dd, J=15.3, 4.8 Hz, 1H), 3.57-3.42 (m, 2H), 3.39-3.22 (m, 1H), 3.06 (dt, J=13.8, 6.9 Hz, 1H), 2.36 (q, J=7.6 Hz, 2H), 1.66-1.61 (m, 5H), 1.45-1.27 (m, 7H), 1.25-0.83 (m, 8H). $^{13}$C NMR (101 MHz, CDCl$_3$) δ 174.43, 170.68, 166.83, 166.52, 150.40, 146.95, 134.95, 130.71, 126.46, 125.82, 121.80, 118.87, 54.66, 52.63, 41.77, 40.08, 35.45, 34.27, 29.62, 29.52, 28.58, 26.07, 25.95, 25.89, 24.16, 9.61. HRMS (ESI-MS) m/z: calculated for $C_{27}H39N_4O_3S^+$ 499.2737, found 499.2741 [M+H]$^+$.

Example 38

(S)—N—((S)-2-(2-chloroacetamido)-1-cyclohexylethyl)-3-(6-isopropylbenzo[d]thiazol-2-yl)-2-propionamidopropanamide. Example 38 was prepared from Compound 6aCHPr by a similar procedure as that described for Example 1. $^1$H NMR (400 MHz, CDCl$_3$) δ 7.85 (d, J=8.4 Hz, 1H), 7.70 (s, 1H), 7.45 (d, J=7.0 Hz, 1H), 7.37 (dd, J=8.4, 1.2 Hz, 1H), 7.23-=7.14 (m, 1H), 7.02 (d, J=8.8 Hz, 1H), 4.95 (dd, J=11.3, 6.3 Hz, 1H), 4.06 (d, J=14.9 Hz, 1H), 3.94 (d, J=15.0 Hz, 1H), 3.90-3.79 (m, 1H), 3.69 (dd, J=15.6, 4.5 Hz, 1H), 3.48-3.28 (m, 3H), 3.06 (dt, J=13.7, 6.8 Hz, 1H), 2.38 (q, J=7.5 Hz, 2H), 1.69-1.47 (m, 5H), 1.39-1.28 (m, 7H), 1.22 (t, J=7.6 Hz, 3H), 1.15-0.77 (m, 5H). $^{13}$C NMR (101 MHz, CDCl$_3$) δ 174.27, 170.85, 167.29, 166.83, 150.82, 146.74, 135.05, 125.62, 121.92, 118.83, 54.44, 52.24, 42.52, 41.72, 40.21, 35.32, 34.26, 29.66, 29.44, 28.39, 26.02, 25.95, 25.87, 24.17, 9.53. HRMS (ESI-MS) m/z: calculated for $C_{26}H_{38}ClN_4O_3S^+$ 521.2348, found 521.2350 [M+H]$^+$.

Example 39

(E)-N—((S)-2-cyclohexyl-2-((S)-3-(6-isopropylbenzo[d]thiazol-2-yl)-2-propionamidopropanamido)ethyl)-4-morpholinobut-2-enamide. Example 39 was prepared from Compound 6aCHPr by a similar procedure as that described for Example 1. $^1$H NMR (400 MHz, MeOD) δ 7.86 (d, J=8.5 Hz, 1H), 7.82 (d, J=1.6 Hz, 1H), 7.42 (dd, J=8.5, 1.7 Hz, 1H), 6.70 (dt, J=15.0, 7.4 Hz, 1H), 6.37 (d, J=15.3 Hz, 1H), 4.85 (dd, J=8.2, 5.1 Hz, 1H), 4.16-3.91 (m, 4H), 3.85-3.76 (m, 3H), 3.59 (dd, J=15.3, 5.1 Hz, 1H), 3.54-3.43 (m, 4H), 3.31-3.01 (m, 4H), 2.31 (q, J=7.6 Hz, 2H), 1.73-1.61 (m, 5H), 1.49-1.39 (m, 1H), 1.32 (d, J=6.9 Hz, 6H), 1.25-0.90

(m, 8H). $^{13}$C NMR (101 MHz, MeOD) δ 175.78, 171.38, 167.09, 165.21, 150.95, 146.70, 135.23, 132.88, 129.03, 125.23, 121.57, 118.61, 63.70, 56.84, 54.48, 53.08, 51.58, 40.53, 39.81, 35.10, 34.08, 29.52, 28.68, 28.34, 25.89, 25.73, 25.67, 23.17, 23.15, 8.73. HRMS (ESI-MS) m/z: calculated for $C_{32}H_{48}N_5O_4S^+$ 598.3422, found 598.3425 $[M+H]^+$.

EXPERIMENTAL PROCEDURES

Competitive FP Binding Assay

The Fluorescence Polarization (FP) competitive binding assays were performed to accurately determine the binding affinities of our DCN1 inhibitors. A novel FAM labeled fluorescent probe compound (46) was designed and synthesized based on one of our potent small molecule DCN1 inhibitors. Equilibrium dissociation constants ($K_d$) values of 46 to both DCN1 and DCN2 proteins were determined from protein saturation experiments by monitoring the total FP values of mixtures composed with the fluorescent probe at a fixed concentration and proteins with increasing concentrations up to full saturation. Serial dilutions of proteins were mixed with 46 to a final volume of 200 μl in the assay buffer (100 mM phosphate buffer, pH=6.5, with 0.02% Tween-20 and 2% DMSO). Final probe concentration was 5 nM for both assays. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, round-bottom plates (Thermo Scientific, Waltham, Mass.) at an excitation wavelength of 485 nm and an emission wavelength of 530 nm. $K_d$ values of 46 were calculated by fitting the sigmoidal dose-dependent FP increases as a function of protein concentrations using Graphpad Prism 6.0 software (Graphpad Software, San Diego, Calif.).

Cloning and Purification of DCN Proteins

Human DCN1 (residues 58-259) were cloned into a pDEST17 plasmid containing an N-terminal His$_6$ tag. DCN2 (residues 62-259), DCN3 (residues 86-304), DCN4 (residues 102-292) and DCN5 (residues 47-237) were cloned into an N-terminal His$_6$-TEV expression vector. Pure proteins were derived from the same expression and purification protocols. Plasmids were transformed into Rosetta2 cells, the cells were grown in Terrific Broth at 37° C. to an O.D.$_{600}$>1.0 and induced with 0.4 mM Isopropyl β-D-1-thiogalactopyranoside overnight at 20° C. The pelleted cells were resuspended in lysis buffer containing 25 mM Tris-HCl, pH 7.5, 200 mM NaCl and protease inhibitors, sonicated and centrifuged at 34,000×g for 45 minutes to remove debris. Cleared lysate was incubated with Ni-NTA resin (Qiagen) prewashed with lysis buffer, for 1 hr at 4° C. The matrix was loaded into a column then washed with 25 mM Tris-HCl, pH 7.5, 200 mM NaCl and 10 mM imidazole. Protein was eluted with 25 mM Tris-HCl, pH 7.5, 200 mM NaCl and 300 mM imidazole, concentrated and applied to a Superdex 75 (GE Healthcare) column pre-equilibrated with 25 mM Tris pH 7.5, 200 mM NaCl and 1 mM DTT. For DCN2-5, the N-terminal His$_6$ tag was removed prior to gel filtration. Tag removal was achieved through incubation with TEV protease during overnight dialysis against 25 mM Tris pH 7.5, 200 mM NaCl and 1 mM DTT and a second Ni-NTA column. DCN2-5 proteins were stored at −80° C. in 1 mg/mL fractions containing 5% glycerol. The uncleaved DCN1 protein was stored at −80° C. without glycerol.

Cell Lines and Culture Conditions

Immortalized liver THLE2 (ATCC® CRL-2706™) cell lines was purchased from the ATCC (Rockville, Md.). The cell line was maintained in BEGM Bronchial Epithelial Cell Growth Medium from Lonza/Clonetics Corporation (CC3170, Walkersville, Md.) supplemented with 10% FBS and pen-strep at 37° C. in a humidified incubator with 5% $CO_2$. Esophageal cancer KYSE140 cell line (ACC 348) was purchased from DSMZ (Braunschweig, Germany). The cell line was maintained RPMI1640 supplemented with 10% FBS and pen-strep at 37° C. in a humidified incubator with 5% $CO_2$.

Western Blotting Analysis and Antibodies

Treated cells were lysed by RIPA buffer supplemented with protease inhibitor. The expression level of indicated proteins was examined by western blotting analysis. GAPDH was used as a loading control. Antibodies were purchased: Cullin 1 (sc-11384), Cullin2 (sc-10781), Cullin5 (sc-13014) and Cullin7 (sc-134565) from Santa Cruz Biotech. (Santa Cruz, Calif.); Cullin 4A (PA5-14542), Cullin 4B (PA5-35239), Cullin9 (PA5-20277), DCN2 (DCUNID2, PA5-31607) and DCN3 (DCUNID3, PA5-44000) from ThermoFisher Scientific (Wayne, Mich.); Cullin 3 (2759), NRF2 (12721), HO-1 (70081), NQO1 (3187), Cyclin E (4129), Bim (2819), Keap1 (8047) and UBC12 (4913) from Cell Signaling Technology (Boston, Mass.); DCN1 (GWB-E3D700) from GenWay Biotech (San Diego, Calif.). Results are representative of three independent experiments.

Mass Spectroscopy of DCN1 Protein Incubations

Recombinant DCN1 protein (380 μM) in 25 mM Tris 7.5, 200 mM NaCl, 1 mM DTT buffer was incubated with a 1.2 fold excess of selected DCN1 inhibitors at 4° C. for overnight. The reaction mixture was diluted with tenfold with water, and the protein was analyzed by Q-TOF mass spectroscopy. DCN1 untreated, or treated with previously described non-covalent inhibitors produced an isotope deconvoluted peak at 26.085.75 amus. Incubation under the described conditions with Examples 4, 7 and 9 led to 95-99% ablation of the parent peak in the mass spectrum, with a major (>90%) new peak appearing at 26588.96 amu (Dalton) for Example 4, 26604.34 amu for Example 7, and 26596.18 amu for Example 9. In each case this corresponds to addition of the inhibitor to the protein, coupled with the loss of the morpholinyl group, from the initial Michael adduct between the protein and the small molecule. The data are further shown in FIG. 2.

Figure 2A:
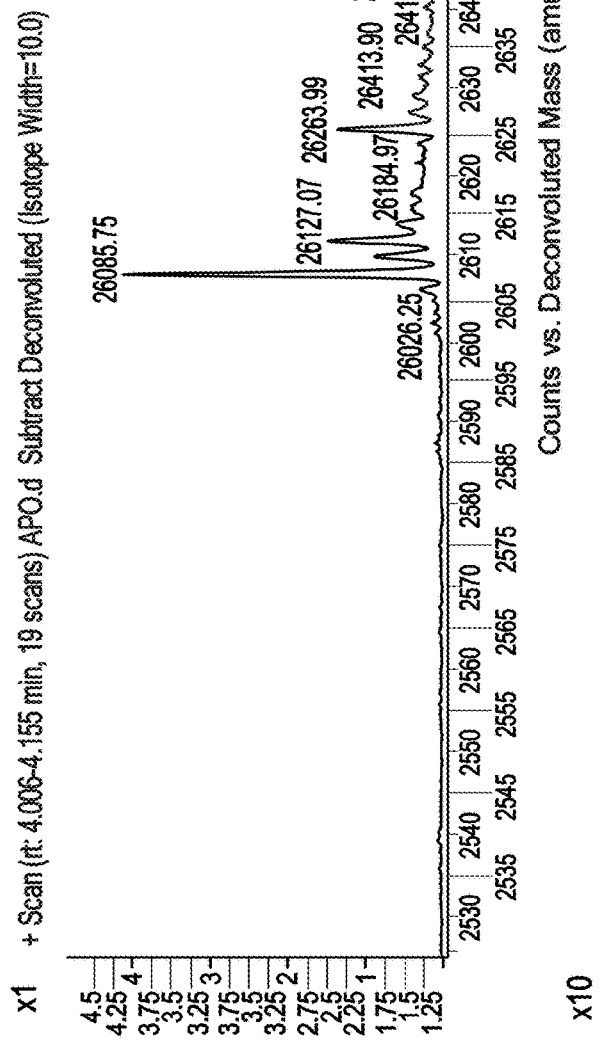
FIG. 2A shows the mass-spectroscopic analyses of DCN1 apo-protein.

FIG. 2A shows DCN1 Apo-protein Mass is 26085.75 Da. The calculated mass from protein sequence is 26.2 kDa.

Figure 2B:
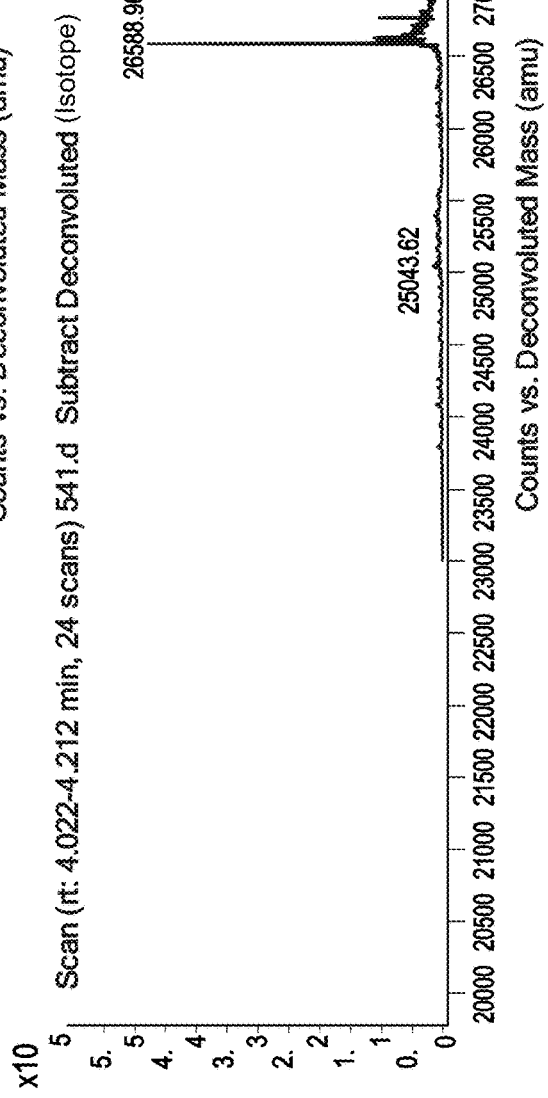
FIG. 2B shows DCN1 apo-protein incubated with covalent DCN1 inhibitor Example 4.

FIG. 2B shows Apo-DCN1 plus Example 4 Mass is 26588.96 Da. The difference from DCN1 Apo-protein is 503.21 Da. The calculated molecular mass for Example 4 is 589.25 Da. The difference in compound mass is 86.04 Da. The calculated molecular mass for the Morpholino group is 87.07 Da.

Figure 2C:
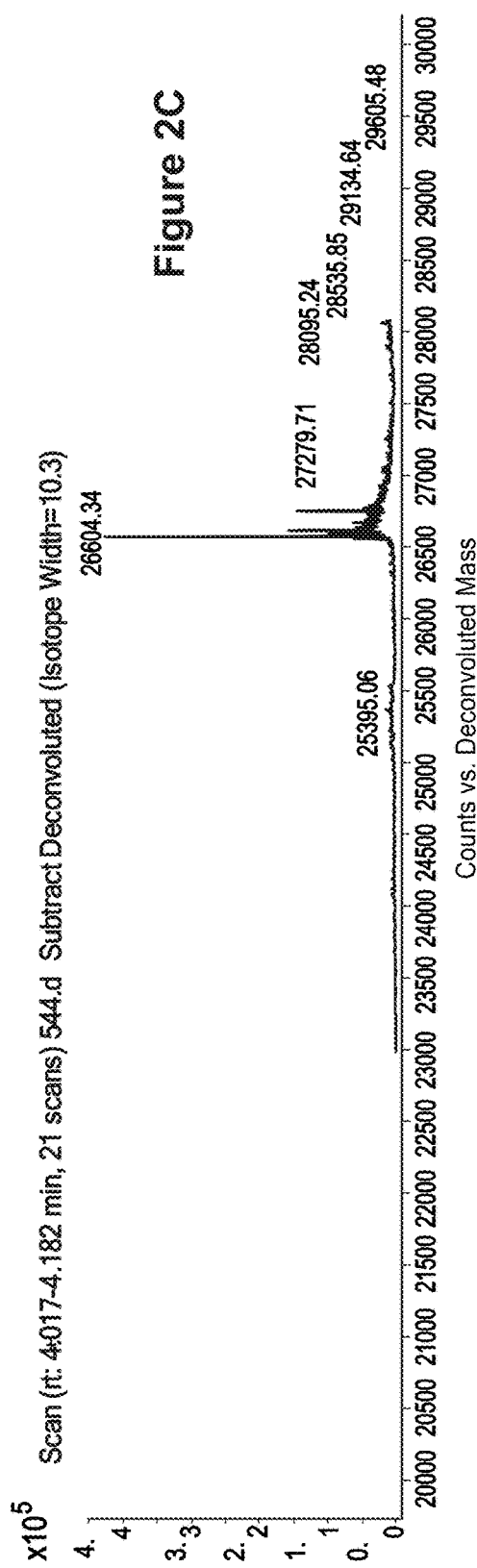
FIG. 2C is Example 7.

FIG. 2C shows DCN1 plus Example 7 mass is 26604.34 Da. The difference from DCN1 Apo-protein is 518.59 Da. The calculated molecular mass for Example is 7605.3 Da. The difference in compound mass is 86.71 Da. The calculated molecular mass for Morpholino group is 87.07 Da.

Figure 2D:
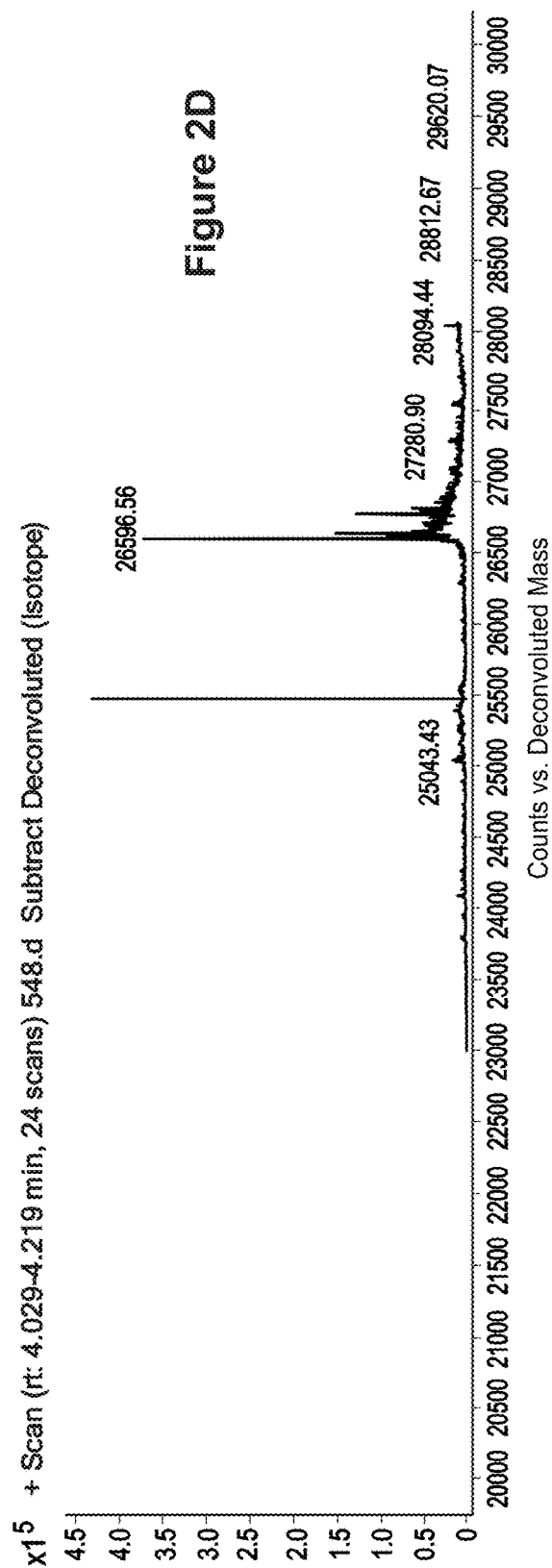
FIG. 2D is Example 9. The data showed the formation of a covalent bond between DCN1 protein and each of these three representative covalent inhibitors.
Figure 3:
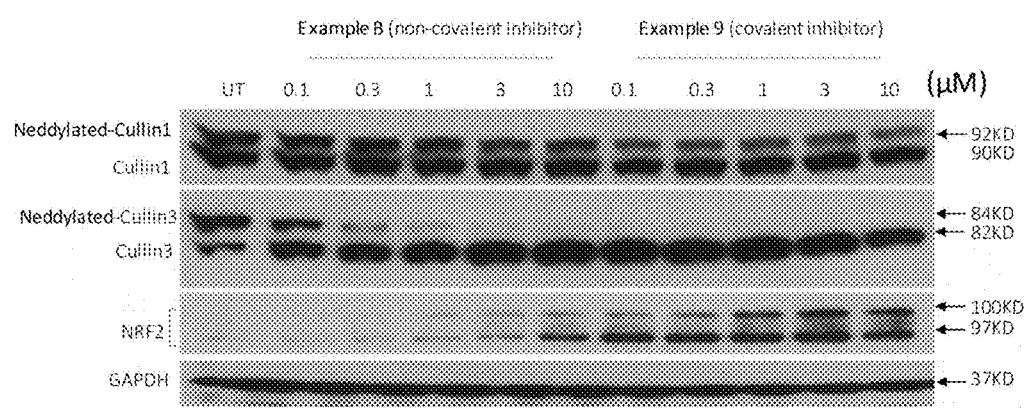
FIG. 3 shows the effect of covalent inhibitor Example 9 (see FIG. 1) and non-covalent inhibitor B (see FIG. 1) on neddylation of cullin 1 and cullin 3 and on the protein level of NRF2 in HepG2 cells. HepG2 cells were treated as indicated concentrations for 20 h, NRF2, Cullin 1, and Cullin 3 proteins were examined by western blotting. GAPDH was used as a loading control. The data showed that the representative covalent inhibitor Example 9 has a much stronger biological activity in inhibition of neddylation of cullin 3 and in increasing the level of NRF2 protein than the representative non-covalent inhibitor Example B.
Figure 4:
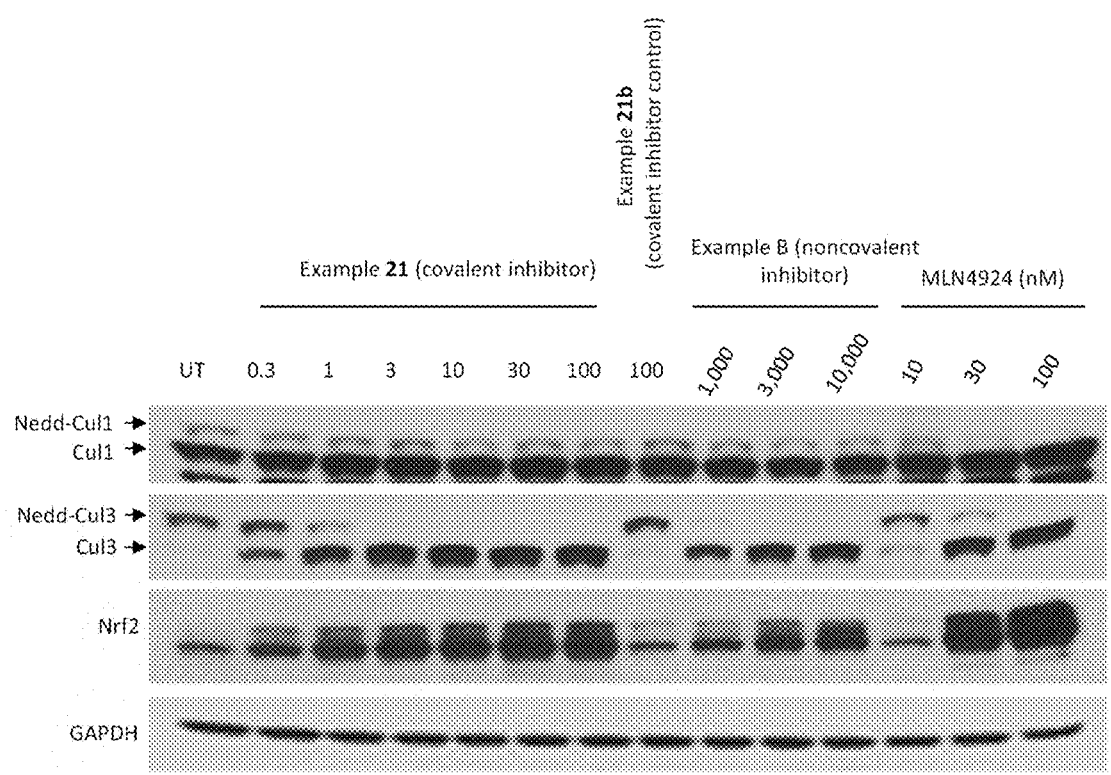
FIG. 4 shows the effect of covalent inhibitor Example 21 (see FIG. 1), a covalent, control compound 21b (DI-1859DD, see FIG. 1), and non-covalent inhibitor B (see FIG. 1) on neddylation of cullin 1 and cullin 3 and on the protein level of NRF2 in immortalized liver THLE2 cell line cells. Immortalized liver THLE2 cell line was treated by dose-ranges of covalent DCN1 inhibitor Examples 21 (DI-1859), 21b (DI-1859DD), non-covalent example B (DI-591), a neddylation pan-inhibitor MLN4924 for 24 h. The protein levels of neddylated and un-neddylated cullin3, cullin1 and the NRF2 level were examined by western blotting analysis. GAPDH was used as a loading control.

FIG. 2D shows DCN1 plus Example 9 mass is 26596.56 Da. The difference from DCN1 apo-protein is 510.81 Da.

The calculated molecular mass for Example 9 is 597.33 Da. The difference in compound mass is 86.52 Da. The calculated molecular mass for Morpholino group is 87.07 Da.

Analysis of the Effect of Covalent DCN1 Inhibitors in Mice

Figure 5:
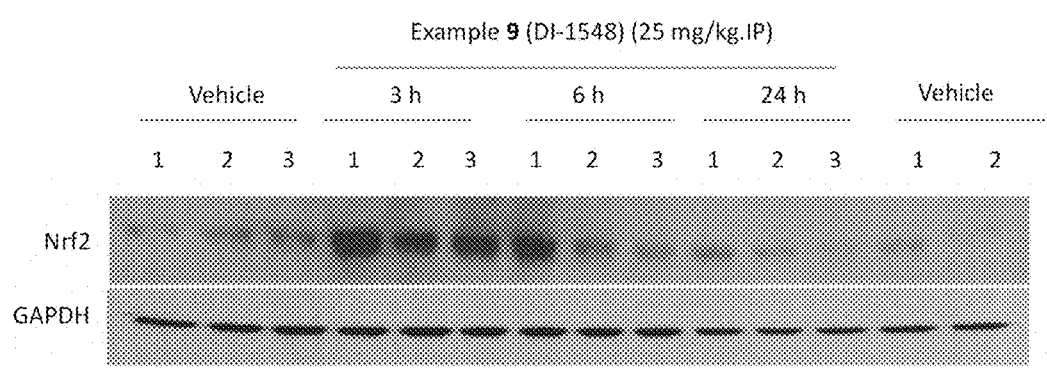
FIG. 5 shows the effect of covalent inhibitor Example 9 (DI-1548) (see FIG. 1) on the level of Nrf2 protein in mouse liver tissue. Liver tissues harvested from C57BL/6 male mice treated with Example 9 (DI-1548) at 25 mg/kg via intraperitoneal (IP) injection were lysed with RIAP buffer. The expression level of Nrf2 protein was examined by western blotting. GAPDH was used a loading control. A single dose of Example 9 (DI-1548) effectively increases the level of Nrf2 protein in the liver tissue.
Figure 6:
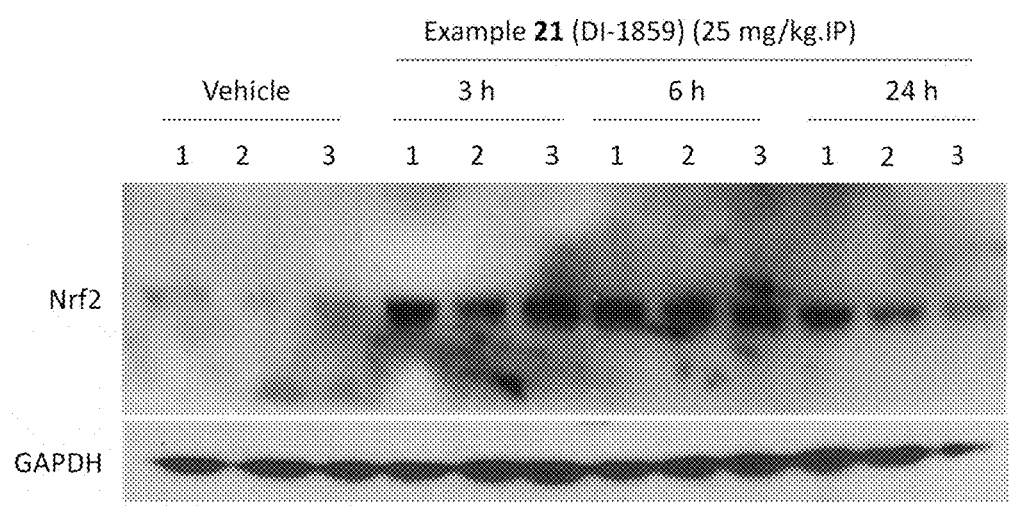
FIG. 6 shows the effect of covalent inhibitor Example 21 (DI-1859) (see FIG. 1) on the level of Nrf2 protein in mouse liver tissue. Liver tissues harvested from C57BL/6 male mice treated with Example 21 (DI-1859) at 25 mg/kg via intraperitoneal (IP) injection were lysed with RIAP buffer. The expression level of Nrf2 protein was examined by western blotting. GAPDH was used a loading control. A single dose of Example 21 (DI-1859) effectively increases the level of Nrf2 protein in the liver tissue.
Figure 7:
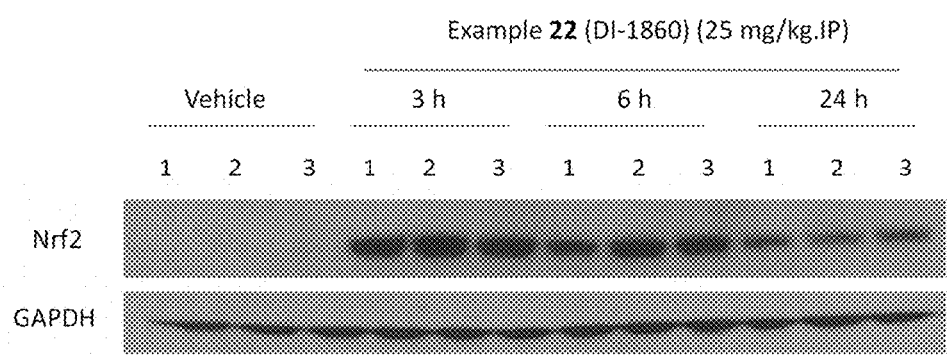
FIG. 7 shows the effect of covalent inhibitor Example 22 (DI-1860) (see FIG. 1) on the level of Nrf2 protein in mouse liver tissue. Liver tissues harvested from C57BL/6 male mice treated with Example 22 (DI-1860) at 25 mg/kg via intraperitoneal (IP) injection were lysed with RIAP buffer. The expression level of Nrf2 protein was examined by western blotting. GAPDH was used a loading control. A single dose of Example 22 (DI-1860) effectively increases the level of Nrf2 protein in the liver tissue.

The effect of several representative covalent DCN1 inhibitors (Examples 9, 21 and 22) on the level of Nrf2 protein in mouse liver was examined. Mice were administered with a single dose of Example 9 (DI-1548), Example 21 (DI-1859) or Example 22 (DI-1860) at 25 mg/kg, or phosphate-buffered saline (PBS), all via intraperitoneal (IP) injection. Mice were sacrificed at different time points and liver tissues were harvested for western blotting analysis for Nrf2 protein level. The data are shown in FIGS. 5, 6 and 7, respectively. The data demonstrate that a single dose of Example 9 (DI-1548), Example 21 (DI-1859) or Example 22 (DI-1860) effectively increases the level of Nrf2 protein in mouse liver tissue.

Analysis of the Effect of Covalent DCN1 Inhibitor Example 21 (DI-1859) in Protection of Mice from Acetaminophen-Induced Liver Injury Drug-induced liver injury remains an important clinical problem globally. In the United States, acetaminophen (APAP, or Tylenol) overdose is responsible for more than 50% of overdose-related acute liver failure and approximately 20% of the liver transplant cases (Yoon, et al. 2016). Example 21 (DI-1859) effectively induces upregulation of NRF2 protein in mouse liver. One of the potential therapeutic applications through upregulation of NRF2 is protection of tissue damage induced by acetaminophen (APAP). Accordingly, Example 21 (DI-1859) was evaluated for its ability to protect or reduce APAP-induced liver injury in mice, with the data summarized in FIG. 8.

To induce acute liver injury, mice were administered a large dose (400 mg/kg) of APAP via intraperitoneal (I.P.) injection and were sacrificed 48 hr later. To examine the protective effect of DI-1859 (pretreatment), animals were I.P. injected with DI-1859 for three consecutive days (one day before APAP injection, three hours before APAP injection and a third dose on the next day after APAP injection). To examine the restorative effect of DI-1859 (post-treatment), mice were treated with DI-1859 three hours after APAP administration followed by two additional doses on the following two days. Two control groups of mice were treated with phosphate-buffered saline (PBS) or DI-1859, respectively. Blood sample collection was performed on each day.

Figure 8:
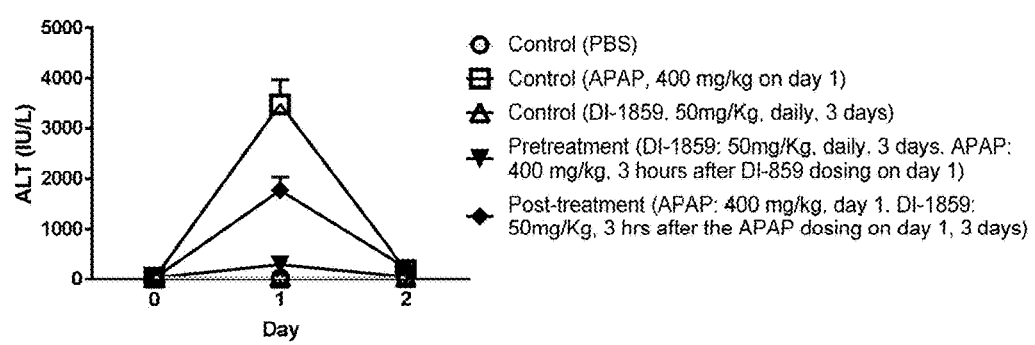
FIG. 8 shows the effect of covalent inhibitor Example 21 (DI-1859) (see FIG. 1) in effectively reducing the liver tissue damage induced by acetaminophen (APAP) in mice. Mice were treated with APAP, DI-1859, phosphate-buffered saline (PBS), pretreatment with DI-1859, followed with APAP, or APAP, followed by post-treatment with DI-1859. The serum level of alanine transaminase (ALT) was determined for each group of mice. The data show that DI-1859 effectively blocks or reduces APAP-induced alanine aminotransferase (ALT) increase in mice, indicating that DI-1859 effectively blocks or reduces the liver tissue damage induced by APAP.

The activity of alanine aminotransferase (ALT) in blood is a commonly used measurement clinically as a part of a diagnostic evaluation of liver injury, to determine liver health. Therefore, the blood ALT activity was measured using an ALT reagent set (Pointe Scientific Inc., Canton, Mich.). The data showed that pretreatment with DI-1859 effectively reduces the dramatically elevated levels of alanine aminotransferase (ALT) activity induced by APAP in a dose-dependent manner (FIG. 8). DI-1859 at 50 mg/kg completely prevents the elevation of ALT activity by APAP. Furthermore, post-treatment of APAP with DI-1859 at 50 mg/kg reduces the APAP-induced elevated ALT level by approximately 50%. These data (FIG. 8) demonstrate that DI-1859 is very effective in reducing the APAP-induced liver tissue damage in either prevention or treatment setting.

REFERENCES

1 Ciechanover, A. & Schwartz, A. L. The ubiquitin-proteasome pathway: the complexity and myriad functions of proteins death. *Proc Natl Acad Sci USA* 95, 2727-2730 (1998).

2 Hershko, A. The ubiquitin system for protein degradation and some of its roles in the control of the cell division cycle. Cell Death and Differentiation 12, 1191-1197, doi:10.1038/sj.cdd.4401702 (2005).

3 Bedford, L., Lowe, J., Dick, L. R., Mayer, R. J. & Brownell, J. E. Ubiquitin-like protein conjugation and the ubiquitin-proteasome system as drug targets. *Nat. Rev. Drug Discov.* 10, 29-46, doi:10.1038/nrd3321 (2011).

4 Nalepa, G., Rolfe, M. & Harper, J. W. Drug discovery in the ubiquitin-proteasome system. *Nat. Rev. Drug Discov.* 5, 596-613, doi:10.1038/nrd2056 (2006).

5 Kane, R. C., Bross, P. F., Farrell, A. T. & Pazdur, R. Velcade®: USFDA approval for the treatment of multiple myeloma progressing on prior therapy. *Oncologist* 8, 508-513, doi:DOI 10.1634/theoncologist.8-6-508 (2003).

6 Kane, R. C. et al. Bortezomib for the treatment of mantle cell lymphoma. *Clinical Cancer Research* 13, 5291-5294, doi:10.1158/1078-0432.CCR-07-0871 (2007).

7 McCormack, P. L. Carfilzomib: in relapsed, or refractory, multiple myeloma. *Drugs* 72, 2023-2032, doi:10.2165/11209010-000000000-00000 (2012).

8 Petroski, M. D. & Deshaies, R. J. Function and regulation of cullin-RING ubiquitin ligases. *Nat Rev Mol Cell Biol* 6, 9-20, doi:10.1038/nrm1547 (2005).

9 Gong, L. M. & Yeh, E. T. H. Identification of the activating and conjugating enzymes of the NEDD8 conjugation pathway. *J. Biol. Chem.* 274, 12036-12042, doi:DOI 10.1074/jbc.274.17.12036 (1999).

10 Deshaies, R. J., Emberley, E. D. & Saha, A. Control of Cullin-Ring Ubiquitin Ligase Activity by Nedd8. *Conjugation and Deconjugation of Ubiquitin Family Modifiers* 54, 41-56, doi:Book_Doi 10.1007/978-1-4419-6676-6 (2010).

11 Bulatov, E. & Ciulli, A. Targeting Cullin-RING E3 ubiquitin ligases for drug discovery: structure, assembly and small-molecule modulation. *Biochem J* 467, 365-386, doi:10.1042/BJ20141450 (2015).

12 Duda, D. M. et al. Structural insights into NEDD8 activation of Cullin-RING ligases: Conformational control of conjugation. *Cell* 134, 995-1006, doi:10.1016/j.cell.2008.07.022 (2008).

13 Scott, D. C. et al. A Dual E3 Mechanism for Rub1 Ligation to Cdc53. *Molecular Cell* 39, 784-796, doi:10.1016/j.molcel.2010.08.030 (2010).

14 Soucy, T. A., Dick, L. R., Smith, P. G., Milhollen, M. A. & Brownell, J. E. The NEDD8 Conjugation Pathway and Its Relevance in Cancer Biology and Therapy. *Genes Cancer* 1, 708-716, doi:10.1177/1947601910382898 (2010).

15 Watson, I. R., Irwin, M. S. & Ohh, M. NEDD8 Pathways in Cancer, Sine Quibus Non. *Cancer Cell* 19, 168-176, doi:10.1016/j.ccr.2011.01.002 (2011).

16 Zhao, Y. C. & Sun, Y. Cullin-RING Ligases as Attractive Anti-cancer Targets. *Curr Pharm Design* 19, 3215-3225 (2013).

17 Zhao, Y. C., Morgan, M. A. & Sun, Y. Targeting Neddylation Pathways to Inactivate Cullin-RING Ligases for Anticancer Therapy. *Antioxid Redox Sign* 21, 2383-2400, doi:10.1089/ars.2013.5795 (2014).

18 Soucy, T. A. et al. An inhibitor of NEDD8-activating enzyme as a new approach to treat cancer. *Nature* 458, 732-U767, doi:10.1038/nature07884 (2009).

19 Brownell, J. E. et al. Substrate-Assisted Inhibition of Ubiquitin-like Protein-Activating Enzymes: The NEDD8 E1 Inhibitor MLN4924 Forms a NEDD8-AMP Mimetic In Situ. *Molecular Cell* 37, 102-111, doi:10.1016/j.molcel.2009.12.024 (2010).

20 Soucy, T. A., Smith, P. G. & Rolfe, M. Targeting NEDD8-Activated Cullin-RING Ligases for the Treatment of Cancer. *Clinical Cancer Research* 15, 3912-3916, doi:10.1158/1078-0432.CCR-09-0343 (2009).

21 Huang, D. T. et al. A unique E1-E2 interaction required for optimal conjugation of the ubiquitin-like protein NEDD8. *Nature Structural & Molecular Biology* 11, 927-935, doi:10.1038/nsmb826 (2004).

22 Scott, D. C., Monda, J. K., Bennett, E. J., Harper, J. W. & Schulman, B. A. N-Terminal Acetylation Acts as an Avidity Enhancer Within an Interconnected Multiprotein Complex. *Science* 334, 674-678, doi:10.1126/science.1209307 (2011).

23 Scott, D. C. et al. Structure of a RING E3 Trapped in Action Reveals Ligation Mechanism for the Ubiquitin-like Protein NEDD8. *Cell* 157, 1671-1684, doi:10.1016/j.cell.2014.04.037 (2014).

24 Yang, C. Y. & Wang, S. M. Computational Analysis of Protein Hotspots. *ACS Med. Chem. Lett.* 1, 125-129, doi:10.1021/ml100026a (2010).

25 Yang, C. Y. & Wang, S. M. Hydrophobic Binding Hot Spots of Bcl-xL Protein-Protein Interfaces by Cosolvent Molecular Dynamics Simulation. *ACS Med. Chem. Lett.* 2, 280-284, doi:10.1021/ml100276b (2011).

26 Yang, C. Y. & Wang, S. M. Analysis of Flexibility and Hotspots in Bcl-xL and Mcl-1 Proteins for the Design of Selective Small-Molecule Inhibitors. *ACS Med. Chem. Lett.* 3, 308-312, doi:10.1021/ml200301w (2012).

27 Monda, J. K. et al. Structural Conservation of Distinctive N-terminal Acetylation-Dependent Interactions across a Family of Mammalian NEDD8 Ligation Enzymes. *Structure* 21, 42-53, doi:10.1016/j.str.2012.10.013 (2013).

28 Keuss, M. J. et al. Characterization of the mammalian family of DCN-type NEDD8 E3 ligases. *J Cell Sci* 129, 1441-1454, doi:10.1242/jcs.181784 (2016).

29 Molina, D. M. et al. Monitoring Drug Target Engagement in Cells and Tissues Using the Cellular Thermal Shift Assay. *Science* 341, 84-87, doi:10.1126/science.1233606 (2013).

30 Kim, A. Y. et al. SCCRO (DCUN1D1) Is an Essential Component of the E3 Complex for Neddylation. *J. Biol. Chem.* 283, 33211-33220, doi:10.1074/jbc.M804440200 (2008).

31 Kurz, T. et al. Dcn1 functions as a scaffold-type E3 ligase for cullin neddylation. *Molecular Cell* 29, 23-35, doi: 10.1016/j.molcel.2007.12.012 (2008).

32 Kobayashi, A. et al. Oxidative stress sensor Keap1 functions as an adaptor for Cul3-based E3 ligase to regulate for proteasomal degradation of Nrf2. *Molecular and Cellular Biology* 24, 7130-7139, doi:10.1128/Mcb.24.16.7130-7139.2004 (2004).

33 Cullinan, S. B., Gordan, J. D., Jin, J. O., Harper, J. W. & Diehl, J. A. The Keap1-BTB protein is an adaptor that bridges Nrf2 to a Cul3-based E3 ligase: Oxidative stress sensing by a Cul3-Keap1 ligase. *Molecular and Cellular Biology* 24, 8477-8486, doi:10.1128/Mcb.24.19.8477-8486.2004 (2004).

34 Venugopal, R. & Jaiswal, A. K. Nrf2 and Nrf1 in association with Jun proteins regulate antioxidant response element-mediated expression and coordinated induction of genes encoding detoxifying enzymes. *Oncogene* 17, 3145-3156, doi:DOI 10.1038/sj.onc.1202237 (1998).

35 Nishitani, H. et al. Two E3 ubiquitin ligases, SCF-Skp2 and DDB1-Cul4, target human Cdt1 for proteolysis. *EMBO J* 25, 1126-1136, doi:10.1038/sj.emboj.7601002 (2006).

36 Gorrini, C., Harris, I. S. & Mak, T. W. Modulation of oxidative stress as an anticancer strategy. *Nat. Rev. Drug Discov.* 12, 931-947, doi:10.1038/nrd4002 (2013).

37 Ma, Q. Role of Nrf2 in Oxidative Stress and Toxicity. *Annu Rev Pharmacol* 53, 401-+, doi:10.1146/annurev-pharmtox-011112-140320 (2013).

38 Bomprezzi, R. Dimethyl fumarate in the treatment of relapsing-remitting multiple sclerosis: an overview. *Ther Adv Neurol Diso* 8, 20-30, doi:10.1177/1756285614564152 (2015).

39 Liby, K. T. & Sporn, M. B. Synthetic Oleanane Triterpenoids: Multifunctional Drugs with a Broad Range of Applications for Prevention and Treatment of Chronic Disease. *Pharmacol Rev* 64, 972-1003, doi:10.1124/pr.111.004846 (2012).

40 de Zeeuw, D. et al. Bardoxolone Methyl in Type 2 Diabetes and Stage 4 Chronic Kidney Disease. *New Engl J Med* 369, 2492-2503, doi:10.1056/Nejmoa1306033 (2013).

41 Buendia, I. et al. Nrf2-ARE pathway: An emerging target against oxidative stress and neuroinflammation in neurodegenerative diseases. *Pharmacol Therapeut* 157, 84-104, doi:10.1016/j.pharmthera.2015.11.003 (2016).

42 Genschik, P., Sumara, I. & Lechner, E. The emerging family of CULLIN 3-RING ubiquitin ligases (CRL3s): cellular functions and disease implications. *EMBO J.* 32, 2307-2320, doi:10.1038/emboj.2013.173 (2013).

43 Anderica-Romero, A. C., Gonzalez-Herrera, I. G., Santamaria, A. & Pedraza-Chaverri, J. Cullin 3 as a novel target in diverse pathologies. *Redox Biology* 1, 366-372, doi:10.1016/j.redox.2013.07.003 (2013).

44 Canning, P. & Bullock, A. N. New strategies to inhibit KEAP1 and the Cul3-based E3 ubiquitin ligases. *Biochem Soc Trans* 42, 103-107, doi:10.1042/BST20130215 (2014).

45 Hayes, J. D. & Dinkova-Kostova, A. T. The Nrf2 regulatory network provides an interface between redox and intermediary metabolism. *Trends Biochem. Sci* 39, 199-218 (2014).

46 Suzuki, T., Motohashi, H. & Yamamoto, M. Toward clinical application of the Keap1-Nrf2 pathway. *Trends in Pharmacological Sciences* 34, 340-346, doi:10.1016/j.tips.2013.04.005 (2013).

47 Sporn, M. B. & Liby, K. T. NRF2 and cancer: the good, the bad and the importance of context. *Nat. Rev. Cancer* 12, 564-571, doi:10.1038/nrc3278 (2012).

48. Yoon, E.; Babar, A.; Choudhary, M.; Kutner, M.; Pyrsopoulos, N., Acetaminophen-Induced Hepatotoxicity: A Comprehensive Update. *J Clin Transl Hepatol* 2016, 4 (2), 131-42.

The invention claimed is:

1. A compound having a structural formula (I)

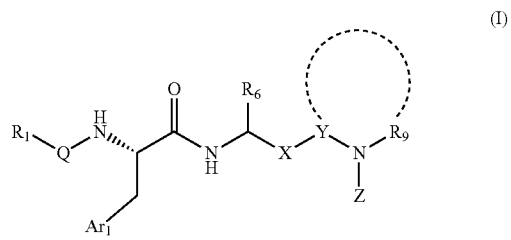

wherein;

Q is C=O, C=S or $SO_2$;

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

T is halogen, SS—$C_{1-6}$ lower alkyl, pentafluorophenoxy, tetrafluorophenoxy:

X is selected from a bond, $CR_7R_8$, $CR_7R_8NR_{12}$, $CR_7R_8NR_{12}CO$, $CR_7R_8NR_{12}CONR_{12}$, $CR_7R_8NR_{12}SO_2$, $CR_7R_8O$, $CR_7R_8S(O)x$ $CONR_{12}$;

Y is selected from $C_{1-6}$ alkylidyl, $C_{3-6}$ cycloalkylidyl, $C_{4-7}$ heterocloalkylidyl, arylene, heteroarylene, aryl(m)ethylene, heteroaryl(m)ethylene, fused $C_{5-8}$ bicycloalkylidyl or $C_{5-9}$ spirocycloalkylidyl;

or Y and $R_9$ are taken together with the nitrogen atom to which they are attached to form a heterocyclic or heteroaryl ring of four to seven members, optionally including any chemically stable combination of one to three groups selected from O, C=O, N, $NR_5$ and S;

Z is

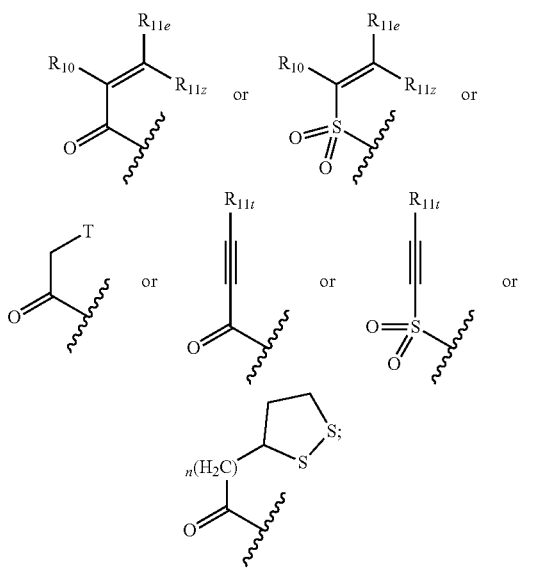

$R_1$ is selected from the group consisting of H, $C_{1-6}$ alkyl, $C_{3-6}$ cycloalkyl, $C_{3-6}$ cycloalkylmethylene, NHMe, N(Me)$_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_7$ and $R_8$ may be independently H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, or taken together with the C atom to which they are attached, form a carbonyl group, a thionyl group, an oxime, a hydrazone, $C_{3-6}$ cycloalkyl, substituted $C_{3-6}$ cycloalkyl, $C_{4-6}$ cycloalkenyl substituted $C_{4-6}$ cycloalkenyl or $C_{4-7}$ heterocycloalkyl:

$R_9$ is selected from the group consisting of H, $C_{1-6}$ alkyl, substituted $C_{1-6}$ alkyl, $C_{3-6}$ alkenyl, substituted $C_{3-6}$ alkenyl, $C_{3-6}$ alkynyl, substituted $C_{3-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl or $C_{4-7}$ heterocycloalkyl:

$R_{10}$ is H, F, Cl, $CF_3$, $CHF_2$, $(CH_2)_nNR_3R_4$, $CH_2SO_2R_{12}$, $CH_2OCOR_{12}$, CN or $R_{12}$;

$R_{11e}$ is H, $R_{12}$, $(CH_2)_nR_2$, $CF_2(CH_2)_xR_2$, $COR_5$, $CO_2R_5$ or $CONR_3R_4$;

$R_{11z}$ is H, F, Cl, $CF_3$, $CHF_2$, $CF_2R_{12}$ or $R_{12}$;

or $R_{11e}$ and $R_{11z}$ may be taken together with the sp$^2$ carbon atom to which both are bonded to form an alicyclic ring of 4 to 7 members where one of the ring atoms may be $NR_{12}$, O, or $S(O)_x$, optionally substituted with halogen, oxo, OH, $OR_5$, $NR_3R_4$;

or $R_{11e}$ and $R_{11z}$ taken together may be $R_{11e}R_{11z}C=$, forming an allenyl group;

or $R_{10}$ and $R_{11e}$ may be taken together with the sp$^2$ C atoms to which they are attached to form a partially saturated carbocyclic or heterocyclic ring of 5-7 atoms, with up to two of the ring atoms being O, $S(O)_x$, $NR_{12}$, and said ring may be substituted with hydroxy, oxo, $C_{1-6}$ alkoxy, $R_{11t}$ is $C_{1-6}$ alkyl, $C_{3-6}$ cycloalkyl, aryl, heteroaryl, $C_{4-7}$ heterocycloalkyl, $CH_2NR_3R_4$;

$R_{12}$ is H or $C_{1-6}$ alkyl, either straight chain or branched;

n is 1, 2 or 3;

x is 0, 1, or 2;

or a pharmaceutically acceptable salt, hydrate, or solvate thereof.

2. The compound of claim 1

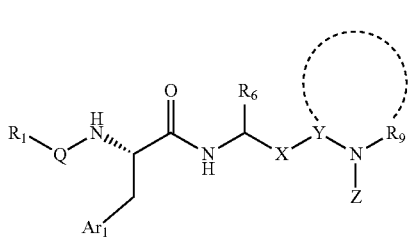

(I)

wherein;

Q is C=O;

Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substituents;

T is halogen:

X is selected from a bond, CR$_7$R$_8$, CR$_7$R$_8$NR$_{12}$, CR$_7$R$_8$NR$_{12}$CO, CR$_7$R$_8$NR$_{12}$CONR$_{12}$, CR$_7$R$_8$NR$_{12}$SO$_2$, CR$_7$R$_8$O, CR$_7$R$_8$S(O)x CONR$_{12}$;

Y is selected from C$_{1-6}$ alkylidyl, C$_{3-6}$ cycloalkylidyl, C$_{4-7}$ heterocloalkylidyl, arylene, heteroarylene, aryl(m)ethylene, heteroaryl(m)ethylene;

or Y and R$_9$ are taken together with the nitrogen atom to which they are attached to form a heterocyclic or heteroaryl ring of four to seven members, optionally including any chemically stable combination of one to three groups selected from O, C=O, N, NR$_5$ and S;

Z is

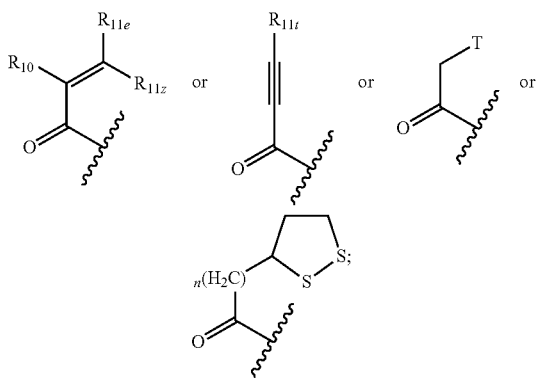

R$_1$ is selected from the group consisting of H, C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, C$_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-7}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;

R$_5$ is selected from the group consisting of hydrogen, CF$_3$, CHF$_2$, C$_{1-6}$ alkyl, allyl, propargyl, C$_{3-6}$ cycloalkyl, C$_{1-6}$ alkyl-C$_{4-6}$ cycloalkenyl, C$_{4-7}$ heterocycloalkyl, aryl, heteroaryl, C$_{1-6}$ alkyl-C$_{3-6}$ cycloalkyl, C$_{1-6}$ alkyl-C$_{4-7}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-7}$ heterocycloalkyl, aryl, and heteroaryl;

R$_6$ is selected from the group consisting of C$_{1-6}$ alkyl, C$_{3-6}$ cycloalkyl, C$_{2-6}$ alkenyl, C$_{4-6}$ cycloalkenyl, C$_{4-7}$ heterocycloalkyl, C$_{2-6}$ alkynyl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-7}$ heterocycloalkyl, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;

R$_7$ and R$_8$ may be independently H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, or taken together with the C atom to which they are attached, form a carbonyl group, a thionyl group, an oxime, a hydrazone, C$_{3-6}$ cycloalkyl, substituted C$_{3-6}$ cycloalkyl, C$_{4-6}$ cycloalkenyl substituted C$_{4-6}$ cycloalkenyl or C$_{4-7}$ heterocycloalkyl:

R$_9$ is selected from the group consisting of H, C$_{1-6}$ alkyl, substituted C$_{1-6}$ alkyl, C$_{3-6}$ alkenyl, substituted C$_{3-6}$ alkenyl, C$_{3-6}$ alkynyl, substituted C$_{3-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl or C$_{4-7}$ heterocycloalkyl:

R$_{10}$ is H, F, CF$_3$, CHF$_2$, (CH$_2$)$_n$NR$_3$R$_4$, CN or R$_{12}$;

R$_{11e}$ is H, R$_{12}$, (CH$_2$)$_n$R$_2$, CF$_2$(CH$_2$)$_x$R$_2$, COR$_5$, CO$_2$R$_5$ or CONR$_3$R$_4$;

R$_{11z}$ is H, F, Cl, CF$_3$, CHF$_2$;

Or R$_{11e}$ and R$_{11z}$ may be taken together with the sp$^2$ carbon atom to which both are bonded to form an alicyclic ring of 4 to 7 members where one of the ring atoms may be NR$_{12}$, O, or S(O)$_x$, optionally substituted with halogen, oxo, OH, OR$_5$, NR$_3$R$_4$;

or R$_{10}$ and R$_{11e}$ may be taken together with the sp$^2$ C atoms to which they are attached to form a partially saturated carbocyclic or heterocyclic ring of 5-7 atoms, with up to two of the ring atoms being O, S(O)$_x$, NR$_{12}$, and said ring may be substituted with hydroxy, oxo, C$_{1-6}$ alkoxy, R$_{11t}$ is C$_{1-6}$ alkyl, C$_{3-6}$ cycloalkyl, C$_{4-7}$ heterocycloalkyl, CH$_2$NR$_3$R$_4$;

R$_{12}$ is H or C$_{1-6}$ alkyl, either straight chain or branched;

n is 1, 2 or 3;

x is 0, 1, or 2;

or a pharmaceutically acceptable salt, hydrate, or solvate thereof.

3. The compound of claim 1

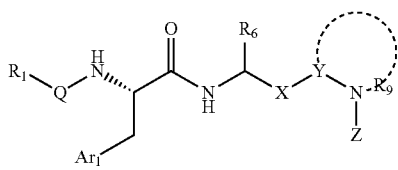
(I)

wherein;
Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substituents;
T is halogen:
X—Y is selected from the group consisting of:

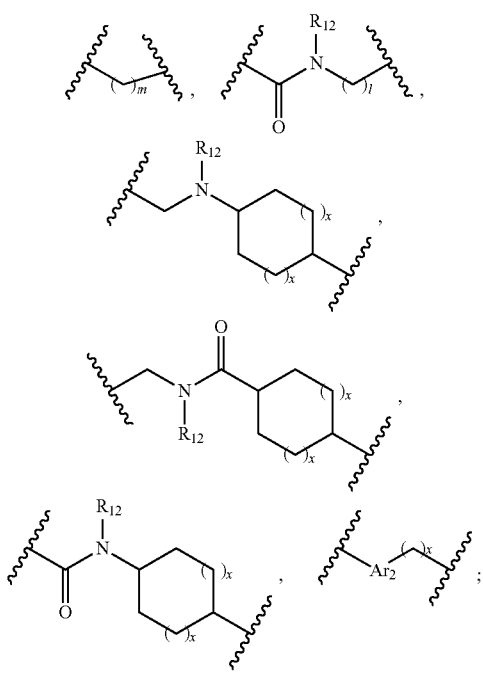

such that Ar$_2$ is monocyclic arylene or heteroarylene;
Z is

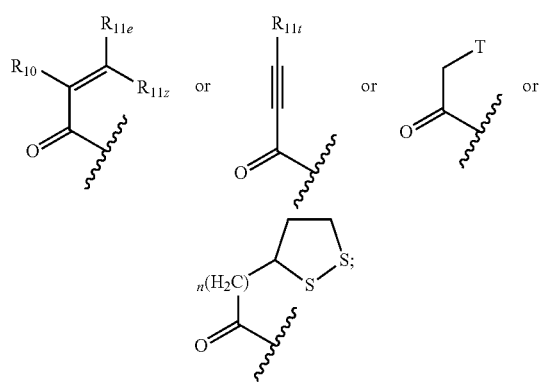

R$_1$ is selected from the group consisting of H, C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;
R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, C$_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;
R$_3$ and R$_4$, independently, are selected from the group consisting of hydrogen, C$_{1-6}$ alkyl, allyl, C$_{3-6}$ cycloalkyl, C$_{4-7}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;
R$_5$ is selected from the group consisting of hydrogen, CF$_3$, CHF$_2$, C$_{1-6}$ alkyl, allyl, propargyl, C$_{3-6}$ cycloalkyl, C$_{1-6}$ alkyl-C$_{4-6}$ cycloalkenyl, C$_{4-7}$ heterocycloalkyl, aryl, heteroaryl, C$_{1-6}$ alkyl-C$_{3-6}$ cycloalkyl, C$_{1-6}$ alkyl-C$_{4-7}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-7}$ heterocycloalkyl, aryl, and heteroaryl;
R$_6$ is selected from the group consisting of C$_{1-6}$ alkyl, C$_{3-6}$ cycloalkyl, C$_{2-6}$ alkenyl, C$_{4-6}$ cycloalkenyl, C$_{4-7}$ heterocycloalkyl, C$_{2-6}$ alkynyl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-7}$ heterocycloalkyl, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;
R$_9$ is selected from the group consisting of H, C$_{1-6}$ alkyl, substituted C$_{1-6}$ alkyl, C$_{3-6}$ alkenyl, substituted C$_{3-6}$ alkenyl, C$_{3-6}$ alkynyl, substituted C$_{3-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl or C$_{4-7}$ heterocycloalkyl:
R$_{10}$ is H, (CH$_2$)$_n$NR$_3$R$_4$, CN or R$_{12}$;
R$_{11e}$ is H, R$_{12}$, or (CH$_2$)$_n$NR$_3$R$_4$;
R$_{11z}$ is H, F, Cl, CF$_3$, CHF$_2$;
Or R$_{10}$ and R$_{11e}$ may be taken together with the sp$^2$ C atoms to which they are attached to form a partially saturated carbocyclic or heterocyclic ring of 5-7 atoms, with up to two of the ring atoms being O, S(O)$_x$, NR$_{12}$, and said ring may be substituted with hydroxy, oxo, C$_{1-6}$ alkoxy,
R$_{11t}$ is C$_{1-6}$ alkyl, C$_{3-6}$ cycloalkyl, C$_{4-7}$ heterocycloalkyl, CH$_2$NR$_3$R$_4$;
R$_{12}$ is H or C$_{1-6}$ alkyl, either straight chain or branched;
l is 2-4;
m is 2-6;
n is 1, 2 or 3;
x is independently 0, 1, or 2;

or a pharmaceutically acceptable salt, hydrate, or solvate thereof.

4. The compound of claim 1

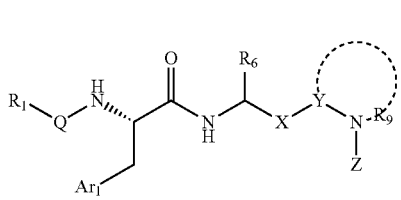

wherein;

Q is C=O;

$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

T is halogen:

X, Y and $R_9$ are taken together with the nitrogen atom to which they are attached to form a ring which selected from the group consisting of:

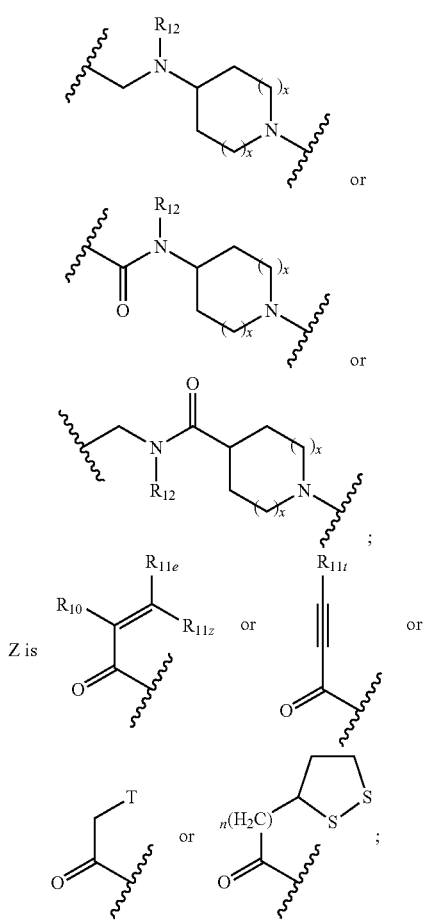

$R_1$ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_{10}$ is H, $(CH_2)_nNR_3R_4$, CN or $R_{12}$;

$R_{11e}$ is H, $R_{12}$, or $(CH_2)_nNR_3R_4$;

$R_{11z}$ is H, F, Cl, $CF_3$, $CHF_2$;

or $R_{10}$ and $R_{11e}$ may be taken together with the sp$^2$ C atoms to which they are attached to form a partially saturated carbocyclic or heterocyclic ring of 5-7 atoms, with up to two of the ring atoms being O, $S(O)_x$, $NR_{12}$, and said ring may be substituted with hydroxy, oxo, $C_{1-6}$ alkoxy, $R_{11t}$ is $C_{1-6}$ alkyl, $C_{3-6}$ cycloalkyl, $C_{4-7}$ heterocycloalkyl, $CH_2NR_3R_4$;

$R_{12}$ is H or $C_{1-6}$ alkyl, either straight chain or branched;

m is 2-6;

n is 1, 2 or 3;

x is independently 0, 1, or 2;

or a pharmaceutically acceptable salt, hydrate, or solvate thereof.

5. The compound of claim 1

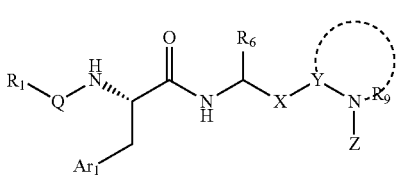

wherein;
Q is C=O;
Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substituents;
X—Y is selected from the group consisting of:

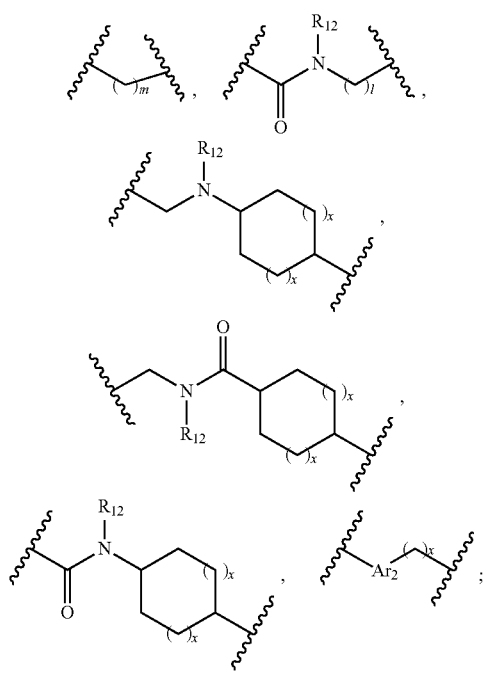

such that Ar$_2$ is monocyclic arylene or heteroarylene;
Z is

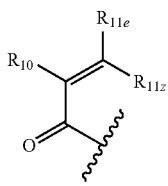

R$_1$ is selected from the group consisting of H, C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;
R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, C$_{4-7}$ heterocycloalkyl, phenyl, substituted phenyl, monocyclic heteroaryl, substituted monocyclic heteroaryl, OR$_5$, NR$_3$R$_4$, COOR$_5$, CONR$_3$R$_4$;
R$_3$ and R$_4$, independently, are selected from the group consisting of hydrogen, C$_{1-6}$ alkyl, allyl, C$_{3-6}$ cycloalkyl, C$_{4-7}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, NR$_5$ and S;
R$_5$ is selected from the group consisting of hydrogen, CF$_3$, CHF$_2$, C$_{1-6}$ alkyl, allyl, propargyl, C$_{3-6}$ cycloalkyl, C$_{1-6}$ alkyl-C$_{4-6}$ cycloalkenyl, C$_{4-7}$ heterocycloalkyl, aryl, heteroaryl, C$_{1-6}$ alkyl-C$_{3-6}$ cycloalkyl, C$_{1-6}$ alkyl-C$_{4-7}$ heterocycloalkyl, C$_{1-6}$ alkaryl, C$_{1-6}$ alkyl-heteroaryl, C$_{1-6}$ acyl, C$_{3-6}$ cycloalkylcarbonyl, C$_{4-7}$ heterocycloalkylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-7}$ heterocycloalkyl, aryl, and heteroaryl;
R$_6$ is selected from the group consisting of C$_{1-6}$ alkyl, C$_{3-6}$ cycloalkyl, C$_{2-6}$ alkenyl, C$_{4-6}$ cycloalkenyl, C$_{4-7}$ heterocycloalkyl, C$_{2-6}$ alkynyl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-7}$ heterocycloalkyl, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;
R$_9$ is H; or
R$_{10}$ is H, CN or CH$_2$NR$_3$R$_4$;
R$_{11e}$ and R$_{11z}$ are H or one may be R$_{12}$;
R$_{12}$ is H or C$_{1-6}$ alkyl, either straight chain or branched;
l is 2-4;
m is 2-6;
n is 1, 2 or 3;
x is independently 0, 1, or 2;
or a pharmaceutically acceptable salt, hydrate, or solvate thereof.
6. The compound of claim 1

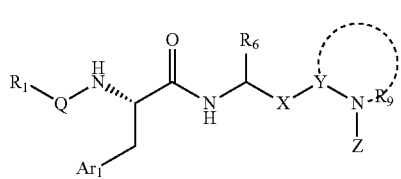

wherein;
Q is C=O;
Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substituents;
X, Y and R$_9$ are taken together with the nitrogen atom to which they are attached to form a ring which selected from the group consisting of:

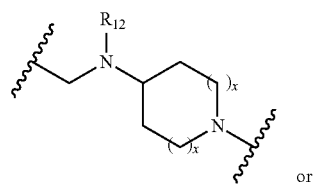

or

-continued

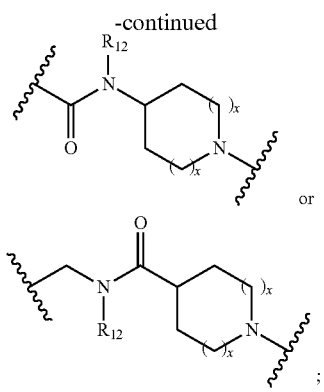

Z is

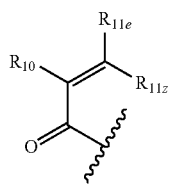

R₁ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

R₂ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

R₃ and R₄, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

R₅ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

R₆ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

R₁₀ is H, CN or $CH_2NR_3R_4$;

$R_{11e}$ and $R_{11z}$ are H or one may be $R_{12}$;

R₁₂ is H or $C_{1-6}$ alkyl, either straight chain or branched;

m is 2-6;

n is 1, 2 or 3;

x is independently 0, 1, or 2;

or a pharmaceutically acceptable salt, hydrate, or solvate thereof.

7. The compound of claim 1 of Formula (II)

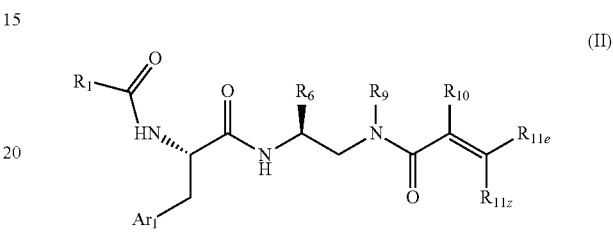

(II)

wherein:

Ar₁ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R₂ substituents;

R₁ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

R₂ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

R₃ and R₄, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

R₅ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_9$ is selected from the group consisting of H, $C_{1-6}$ alkyl, substituted $C_{1-6}$ alkyl, $C_{3-6}$ alkenyl, substituted $C_{3-6}$ alkenyl, $C_{3-6}$ alkynyl, substituted $C_{3-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl or $C_{4-7}$ heterocycloalkyl:

$R_{10}$ is H, F, Cl, $CF_3$, $CHF_2$, $(CH_2)_n NR_3R_4$, $CH_2SO_2R_{12}$, $CH_2OCOR_{12}$, CN or $R_{12}$;

$R_{11e}$ is H, $R_{12}$, $(CH_2)_n R_2$, $CF_2(CH_2)_x R_2$, $COR_5$, $CO_2R_5$ or $CONR_3R_4$;

$R_{11z}$ is H, F, Cl, $CF_3$, $CHF_2$, $CF_2R_{12}$ or $R_{12}$;

Or $R_{11e}$ and $R_{11z}$ may be taken together with the $sp^2$ carbon atom to which both are bonded to form an alicyclic ring of 4 to 7 members where one of the ring atoms may be $NR_{12}$, O, or $S(O)_x$, optionally substituted with halogen, oxo, OH, $OR_5$, $NR_3R_4$;

or $R_{11e}$ and $R_{11z}$ taken together may be $R_{11e}R_{11z}C=$, forming an allenyl group;

or $R_{10}$ and $R_{11e}$ may be taken together with the $sp^2$ C atoms to which they are attached to form a partially saturated carbocyclic or heterocyclic ring of 5-7 atoms, with up to two of the ring atoms being O, $S(O)_x$, $NR_{12}$, and said ring may be substituted with hydroxy, oxo, $C_{1-6}$ alkoxy, $R_{11z}$ is $C_{1-6}$ alkyl, $C_{3-6}$ cycloalkyl, aryl, heteroaryl, $C_{4-7}$ heterocycloalkyl, $CH_2NR_3R_4$;

$R_{12}$ is H or $C_{1-6}$ alkyl, either straight chain or branched;

n is 1, 2 or 3;

x is 0, 1, or 2;

or a pharmaceutically acceptable salt, hydrate, or solvate thereof.

8. The compound of claim 1 of Formula (III)

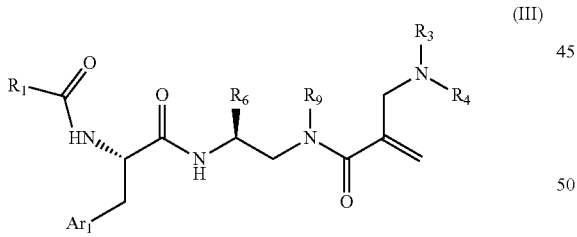

(III)

wherein:
$Ar_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four $R_2$ substituents;

$R_1$ is selected from the group consisting of H, $C_{1-6}$ alkyl, $C_{3-6}$ cycloalkyl, $C_{3-6}$ cycloalkylmethylene, NHMe, $N(Me)_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, $C_{4-7}$ heterocycloalkyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-7}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, or are taken together with the nitrogen atom to which they are attached to form a ring of four to seven members, optionally including any chemically stable combination of one to three O, C=O, $NR_5$ and S;

$R_5$ is selected from the group consisting of hydrogen, $CF_3$, $CHF_2$, $C_{1-6}$ alkyl, allyl, propargyl, $C_{3-6}$ cycloalkyl, $C_{1-6}$ alkyl-$C_{4-6}$ cycloalkenyl, $C_{4-7}$ heterocycloalkyl, aryl, heteroaryl, $C_{1-6}$ alkyl-$C_{3-6}$ cycloalkyl, $C_{1-6}$ alkyl-$C_{4-7}$ heterocycloalkyl, $C_{1-6}$ alkaryl, $C_{1-6}$ alkyl-heteroaryl, $C_{1-6}$ acyl, $C_{3-6}$ cycloalkylcarbonyl, $C_{4-7}$ heterocycloalkylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-7}$ heterocycloalkyl, aryl, and heteroaryl;

$R_6$ is selected from the group consisting of $C_{1-6}$ alkyl, $C_{3-6}$ cycloalkyl, $C_{2-6}$ alkenyl, $C_{4-6}$ cycloalkenyl, $C_{4-7}$ heterocycloalkyl, $C_{2-6}$ alkynyl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-7}$ heterocycloalkyl, aryl, $C_{1-6}$ alkylaryl, heteroaryl, $C_{1-6}$ alkyl-heteroaryl, $C_{5-10}$ bicycloalkyl and $C_{1-6}$ alkyl-$C_{5-10}$ bicycloalkyl;

$R_9$ is selected from the group consisting of H, $C_{1-6}$ alkyl, substituted $C_{1-6}$ alkyl, $C_{3-6}$ alkenyl, substituted $C_{3-6}$ alkenyl, $C_{3-6}$ alkynyl, substituted $C_{3-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl or $C_{4-7}$ heterocycloalkyl:

n is 1, 2 or 3;

x is 0, 1, or 2;

or a pharmaceutically acceptable salt, hydrate, or solvate thereof.

9. The compound of claim 8 of Formula (III)

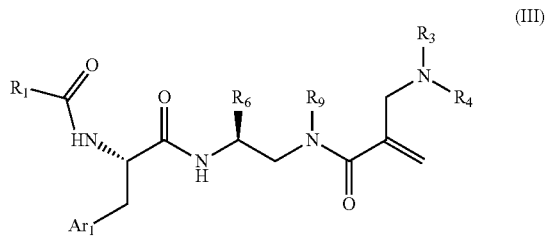

(III)

wherein:
$Ar_1$ is benzothiazol-2-yl, benzoxazol-2-yl, naphth-2-yl, 4-methyl-5-phenylthiazole, 4-methyl-5-phenyloxazole and imidazo[1,2-a]pyrid-2-yl, whereby each 6-membered aromatic ring in may be substituted with up to two $R_2$ substituents selected from $C_{1-6}$ lower alkyl, $CF_3$, and halogen;

R₁ is methyl, ethyl, methylamino, cyclopropyl, isopropyl or n-propyl;

R₃ and R₄, independently, are selected from the group consisting of $C_{1-6}$ alkyl, allyl, $C_{3-6}$ cycloalkyl, $C_{4-7}$ heterocyclyl, or are taken together with the nitrogen atom to which they are attached to form a ring of four to seven members, optionally including any chemically stable combination of one to three O, C=O, NR₅ and S;

R₅ is $C_{1-4}$ alkyl, $C_{1-4}$ acyl, $C_{2-4}$ hydroxyalkyl, $C_{1-2}$ alkoxy-$C_{2-4}$ alkyl, oxetan-3-yl, oxolan-3-yl, oxan-4-yl, N-methylazetidin-3-yl, N-methylpyrrolidin-3-yl or N-methylpiperidin-4-yl;

R₆ is benzyl, isopropyl, [R]- or [S]-2-butyl, 3-pentyl, cyclopentyl, cyclohexyl, cyclohexylmethyl, cyclpentylmethyl, 4-tetrahydrofuranyl or isopropyl;

R₉ is H, $C_{1-4}$ alkyl, $C_{2-4}$ hydroxyalkyl, $C_{1-2}$ alkoxy-$C_{2-4}$ alkyl, oxetan-3-yl, oxolan-3-yl, oxan-4-yl, N-methylazetidin-3-yl, N-methylpyrrolidin-3-yl or N-methylpiperidin-4-yl.

10. The compound of claim 1 wherein Ar₁ is selected from benzothiazol-2-yl, benzoxazol-2-yl, naphtha-2-yl, 4-methyl-5-phenylthiazole, 4-methyl-5-phenyloxazole, imidazo[1,2-a]pyrid-2-yl, whereby each 6-membered aromatic ring may be substituted with up to two R₂ substituents selected from $C_{1-6}$ lower alkyl, CF₃ and halogen.

11. The compound of claim 5 wherein Ar₁ is selected from benzothiazol-2-yl, benzoxazol-2-yl, naphtha-2-yl, 4-methyl-5-phenylthiazole, 4-methyl-5-phenyloxazole, imidazo[1,2-a]pyrid-2-yl whereby each 6-membered aromatic ring may be substituted with up to two R₂ substituents selected from $C_{1-6}$ lower alkyl, CF₃ and halogen.

12. The compound of claim 6 wherein Ar₁ is selected from benzothiazol-2-yl, benzoxazol-2-yl, naphtha-2-yl, 4-methyl-5-phenylthiazole, 4-methyl-5-phenyloxazole, imidazo[1,2-a]pyrid-2-yl whereby each 6-membered aromatic ring may be substituted with up to two R₂ substituents selected from $C_{1-6}$ lower alkyl, CF₃ and halogen.

13. The compound of claim 1 wherein Z is acryloyl, or 2-(aminomethyl)acryloyl, such that the amine is substituted with R₃ and R₄, and neither is hydrogen.

14. The compound of claim 5 wherein Z is acryloyl, or 2-(aminomethyl)acryloyl, such that the amine is substituted with R₃ and R₄, and neither is hydrogen.

15. The compound of claim 6 wherein Z is acryloyl, or 2-(aminomethyl)acryloyl, such that the amine is substituted with R₃ and R₄, and neither is hydrogen.

16. The following compounds of claim 1:

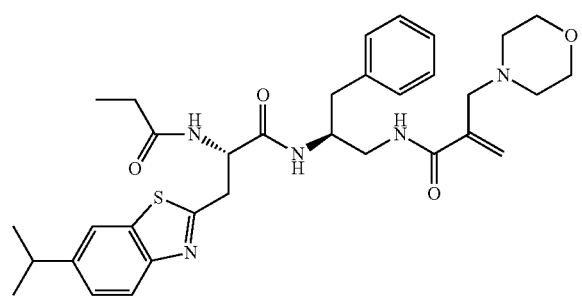

-continued

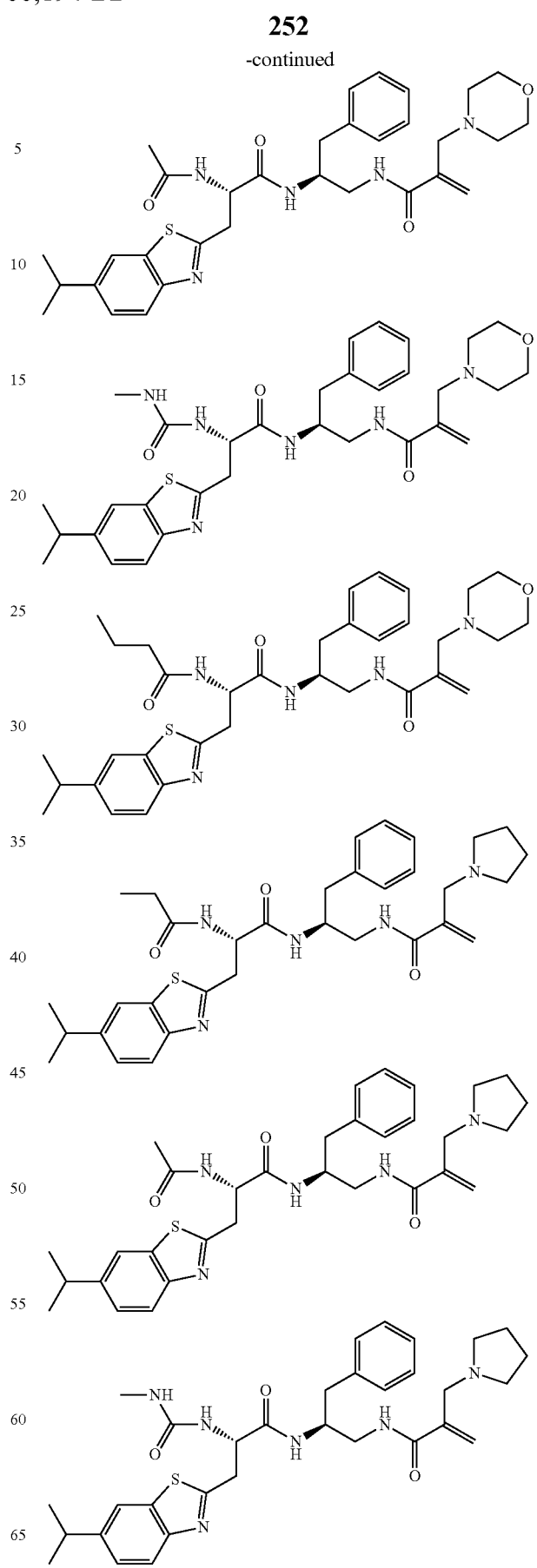

253
-continued
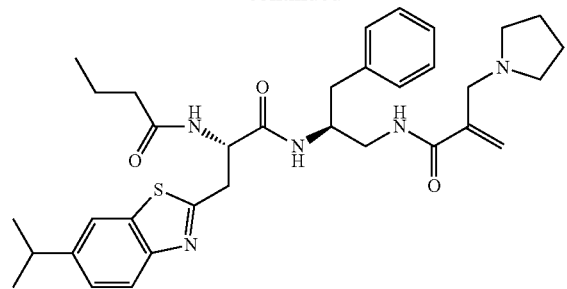
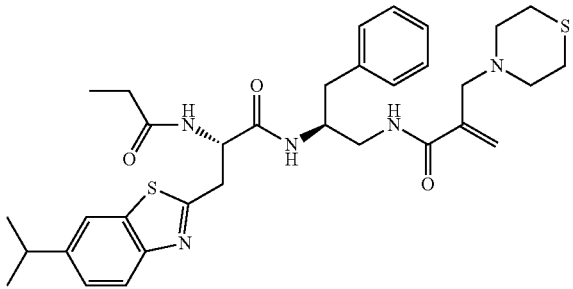
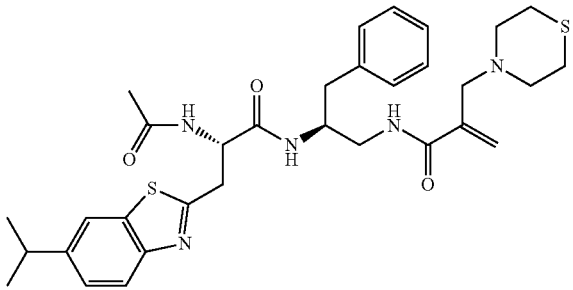
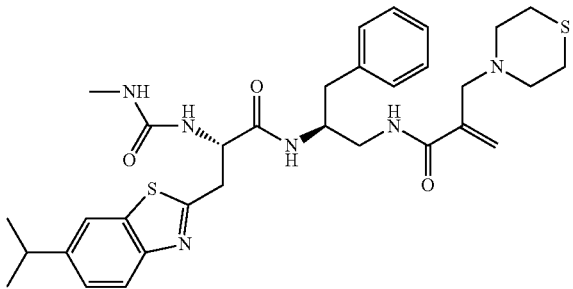
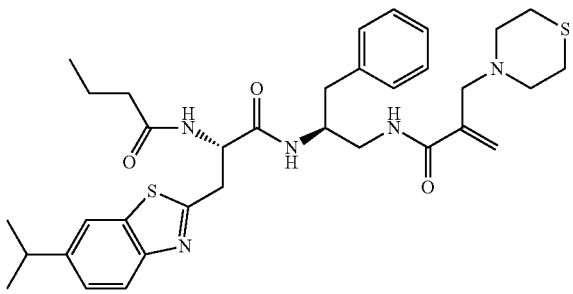
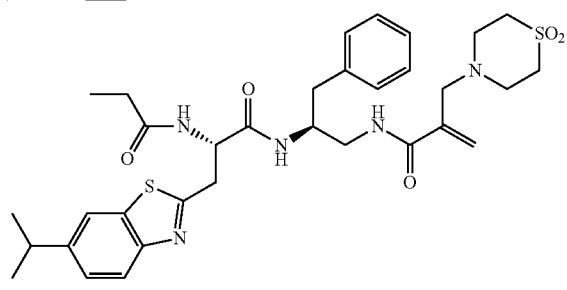
254
-continued
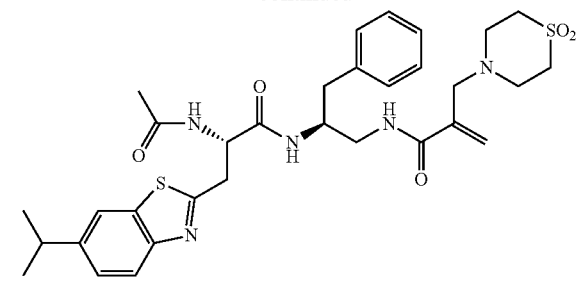
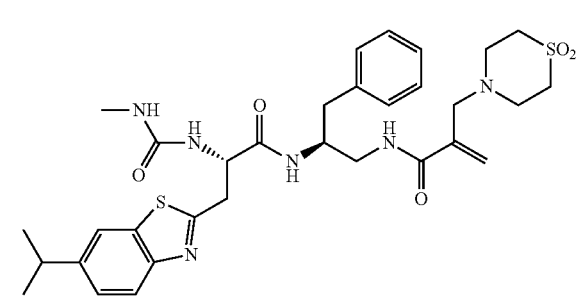
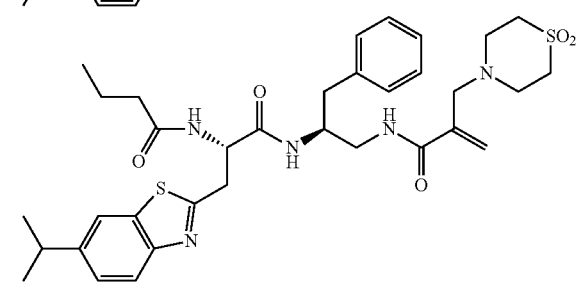
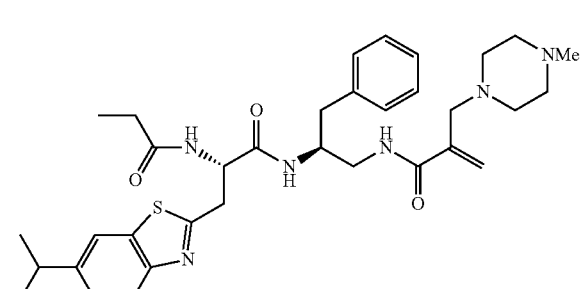
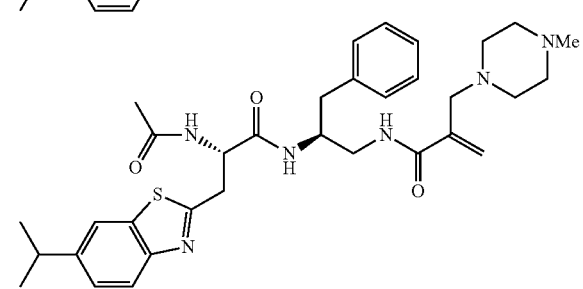
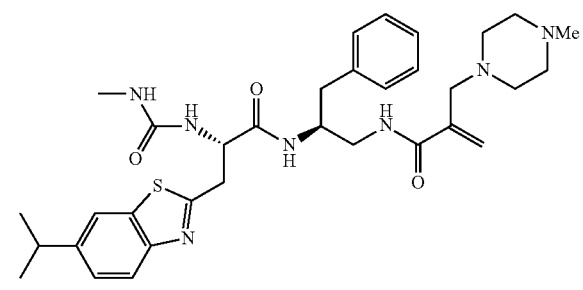

255
-continued
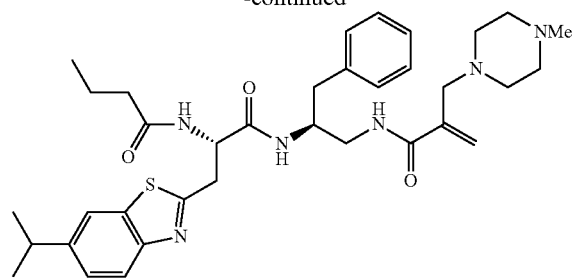
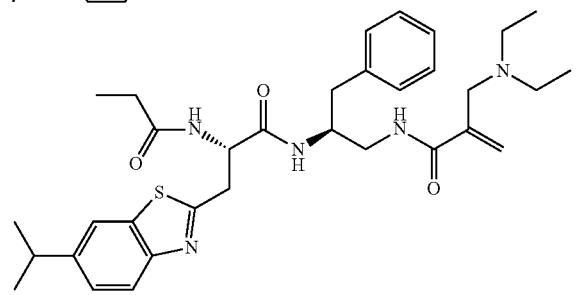
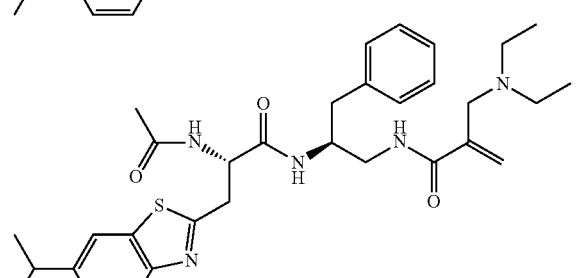
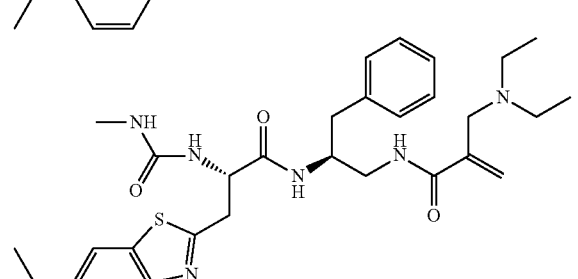
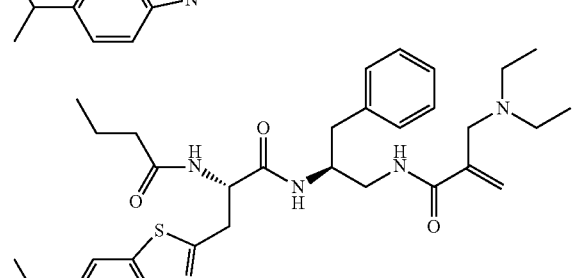
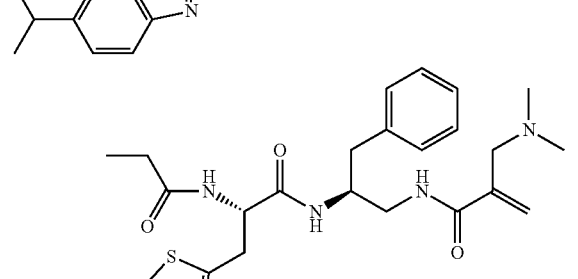
256
-continued
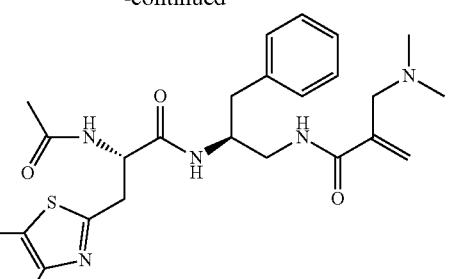
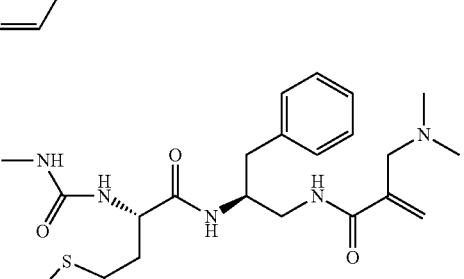
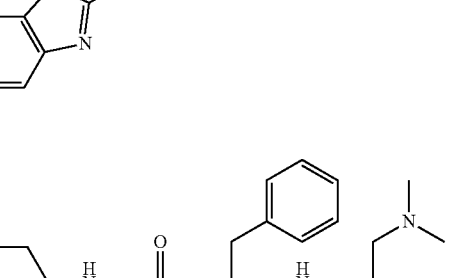
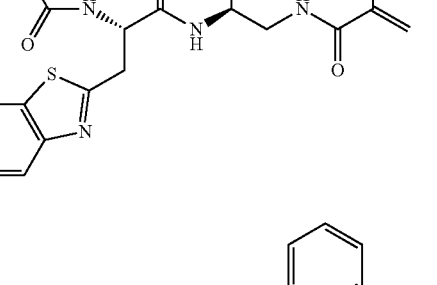
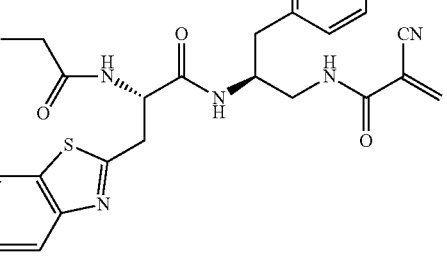
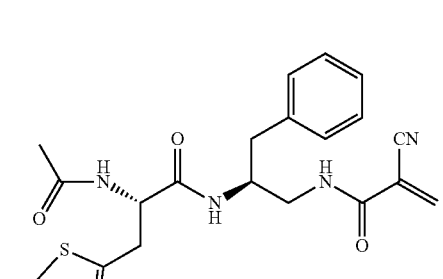

257
-continued
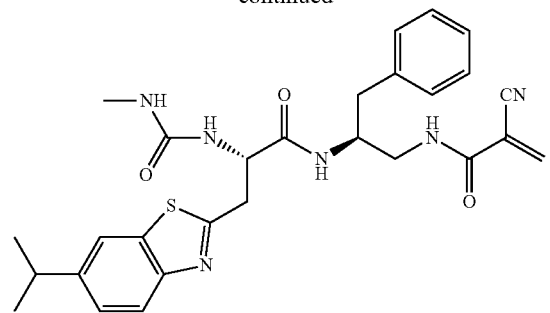
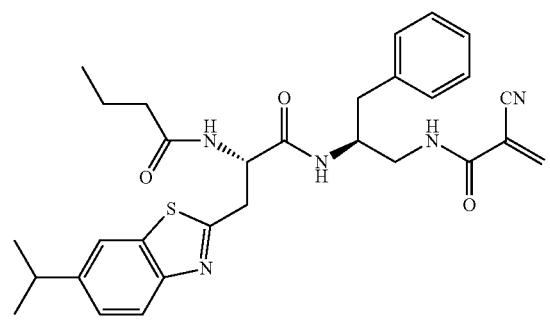
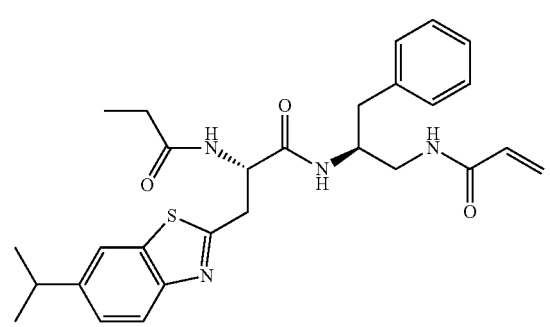
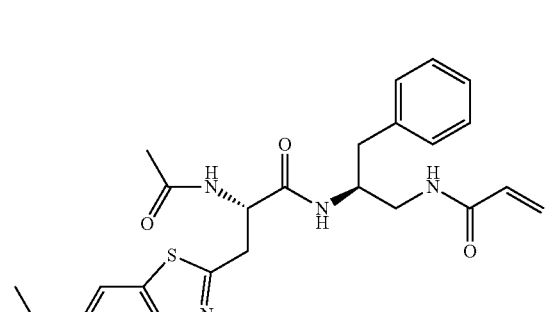
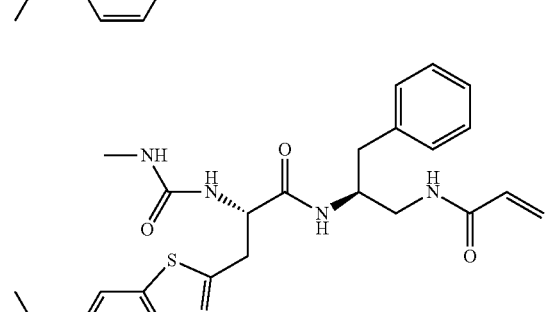
258
-continued
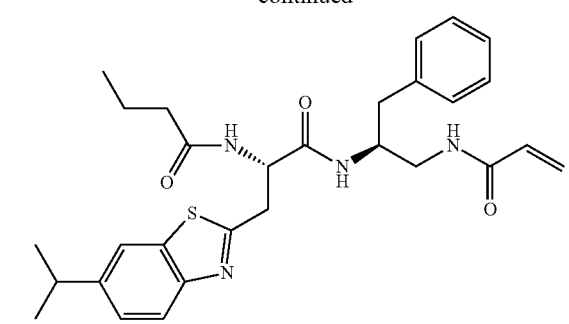
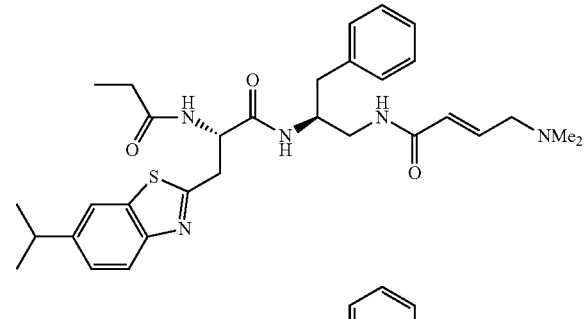
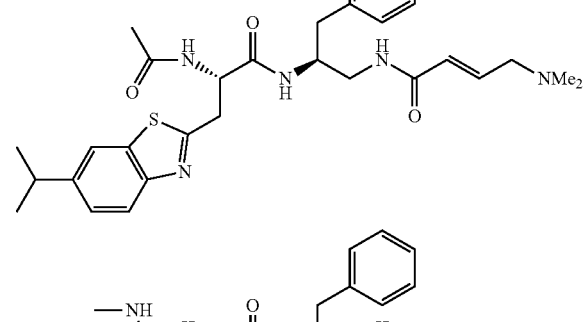
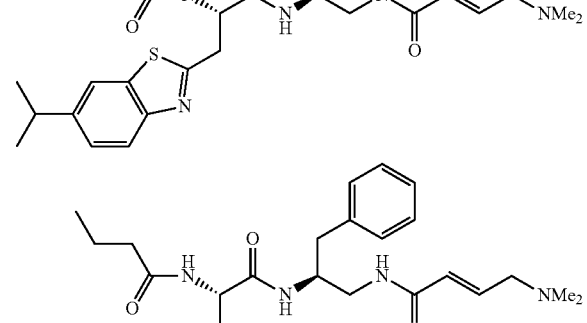
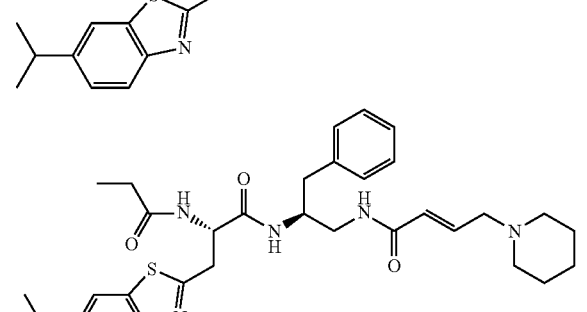

259
-continued
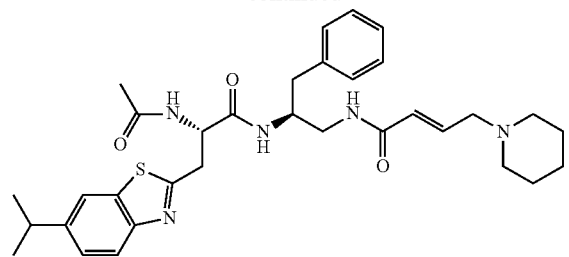
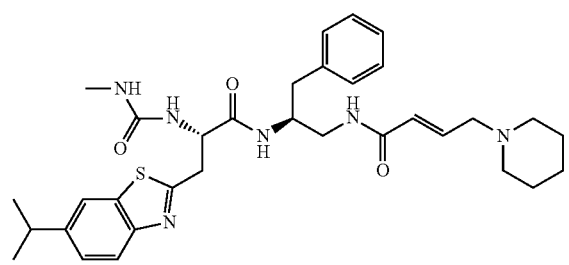
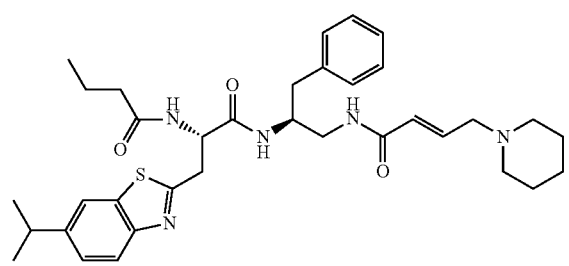
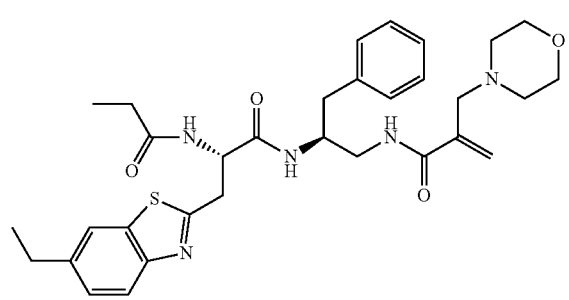
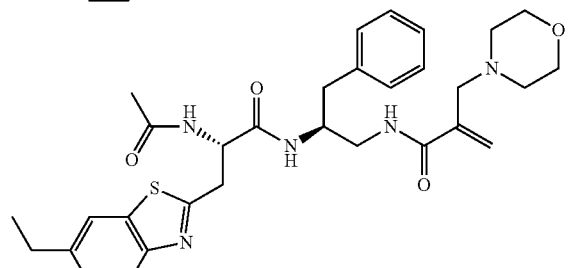
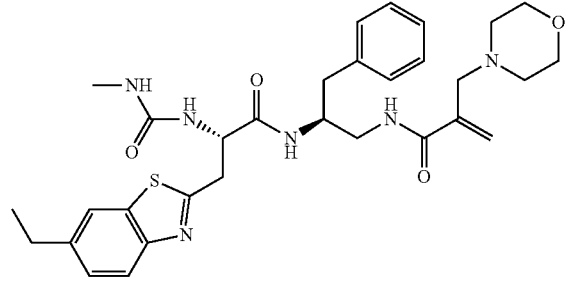
260
-continued
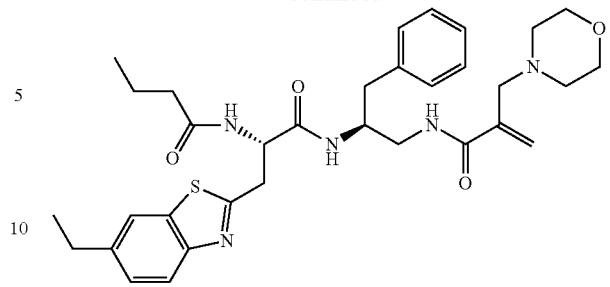
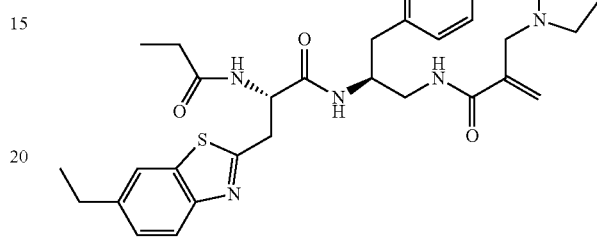
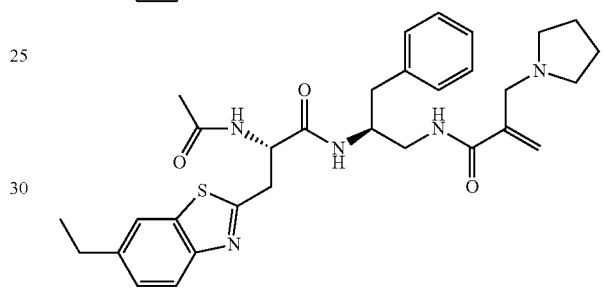
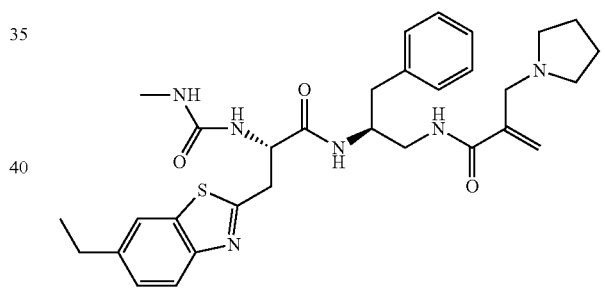
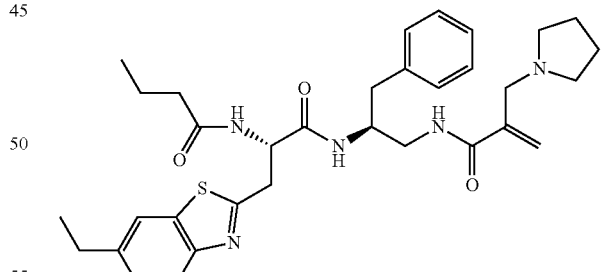
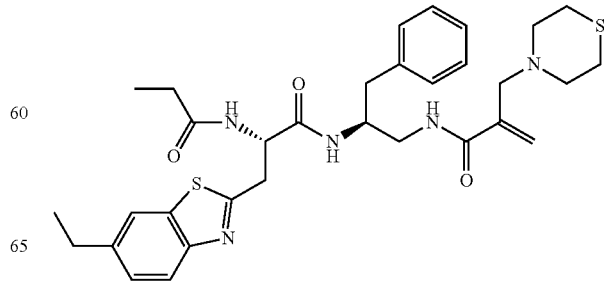

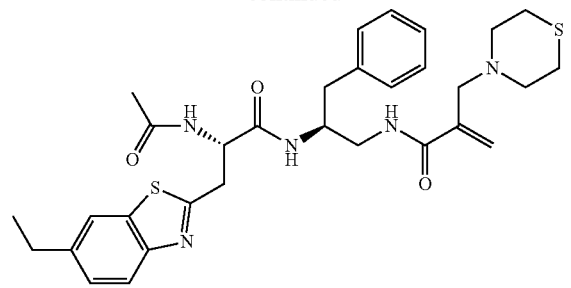
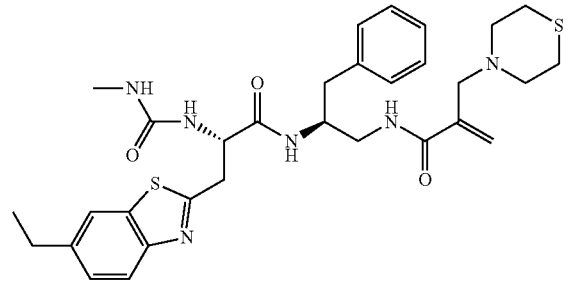
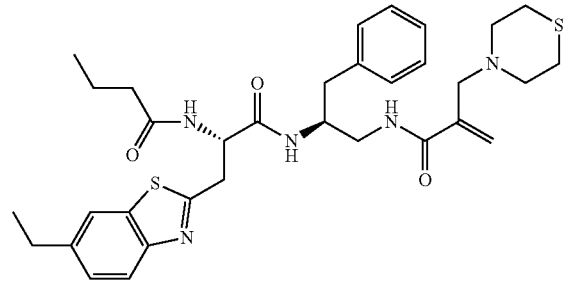
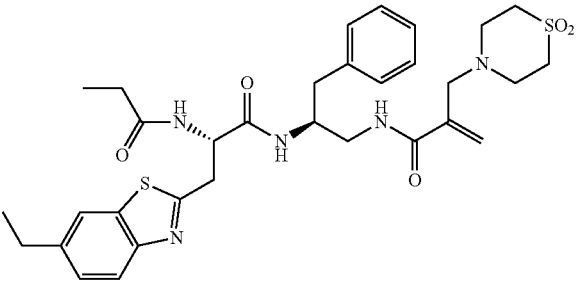
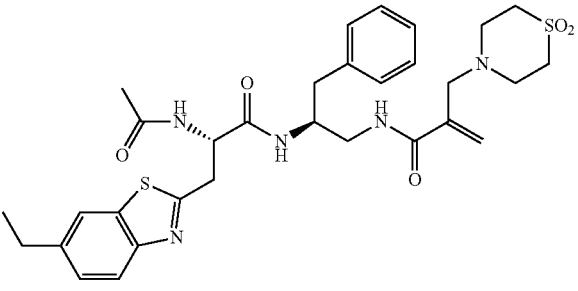
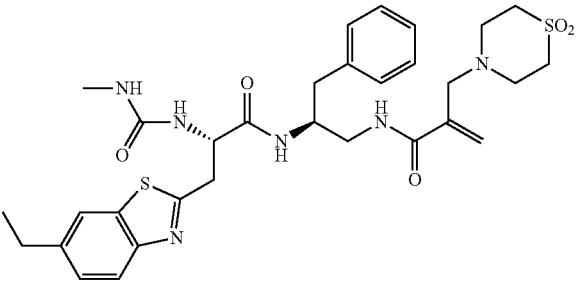
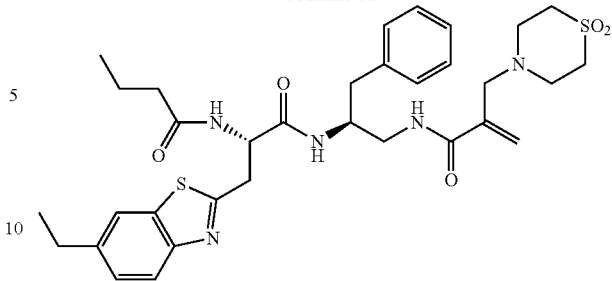
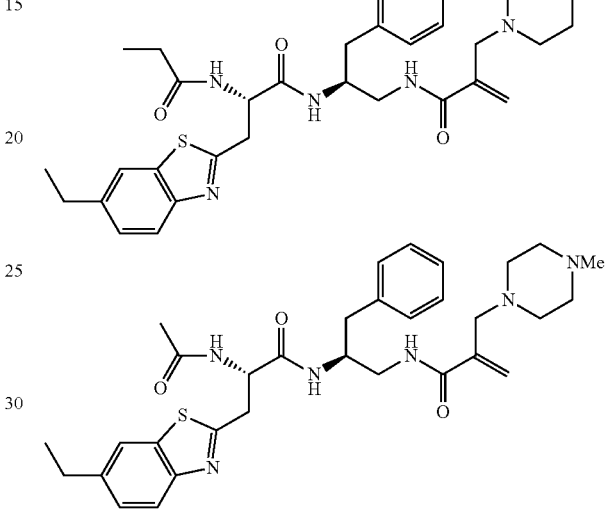
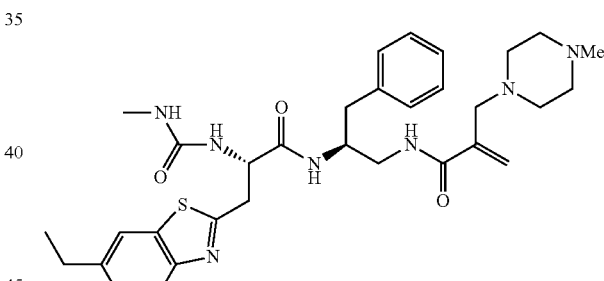
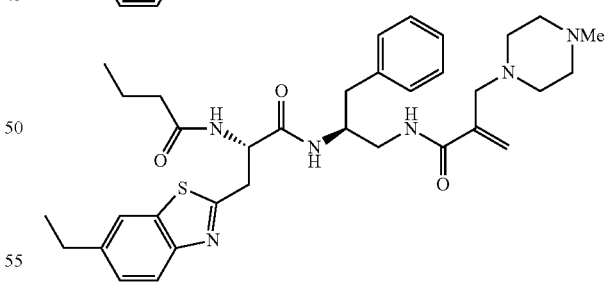
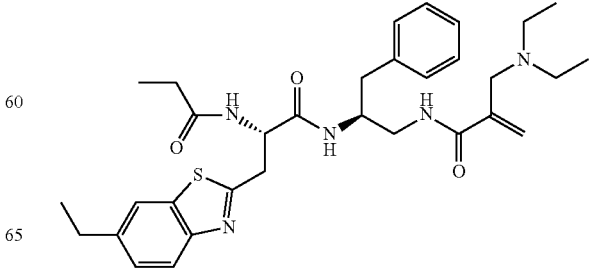

263
-continued
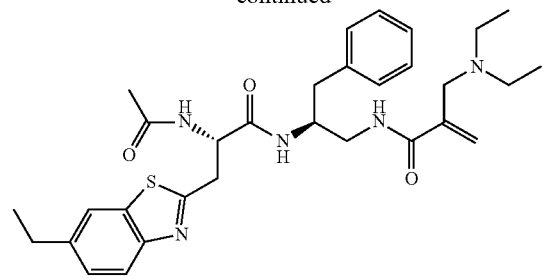
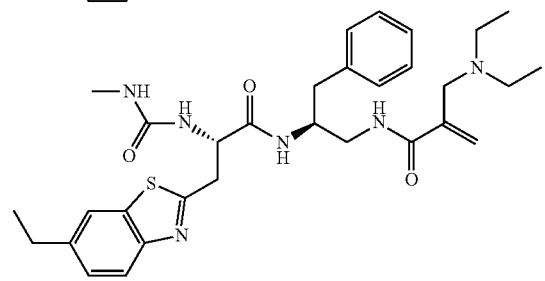
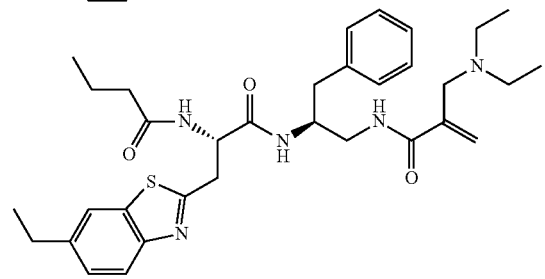
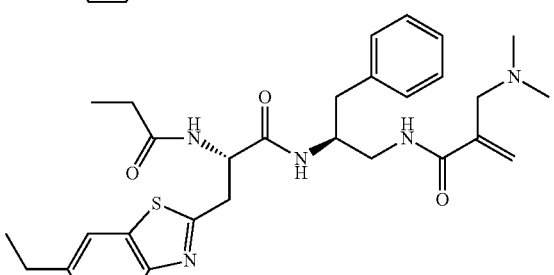
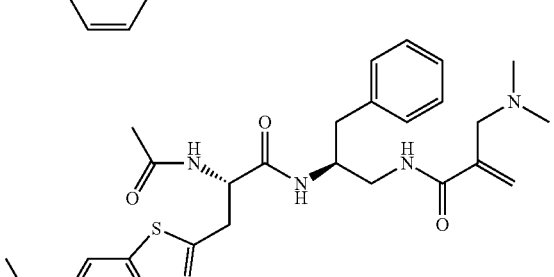
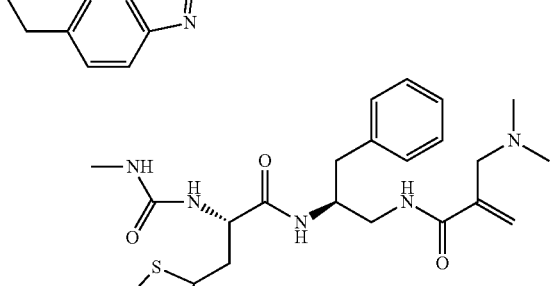
264
-continued
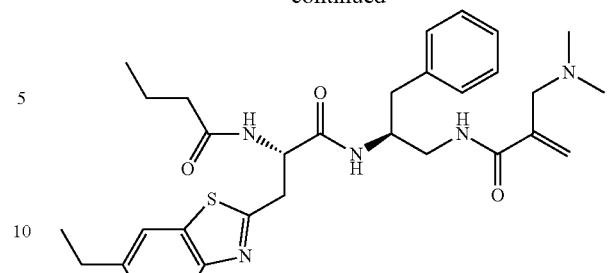
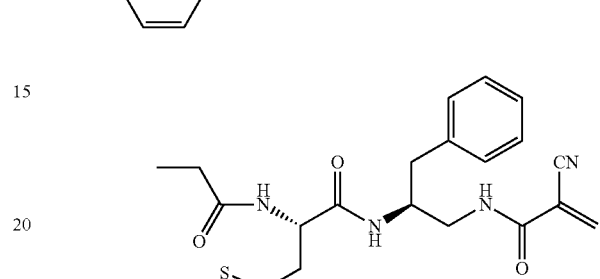
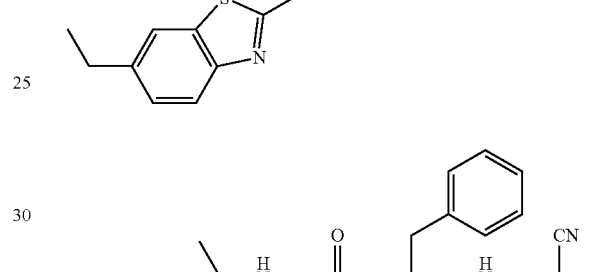
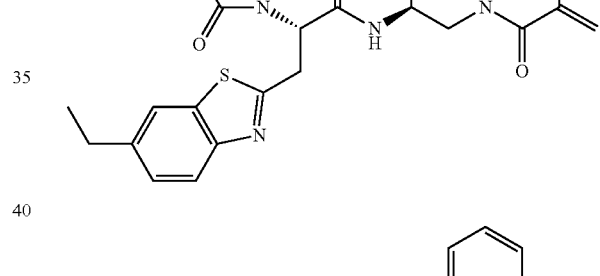
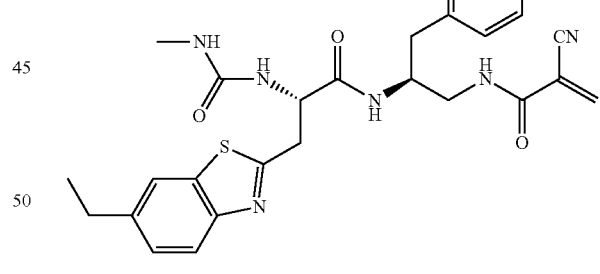
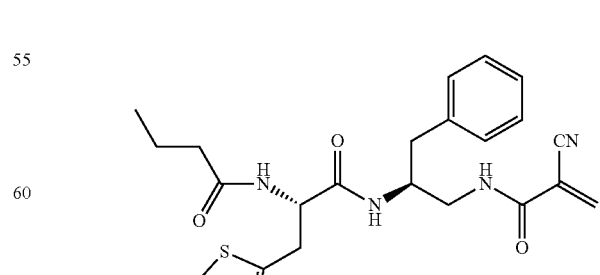

265
-continued
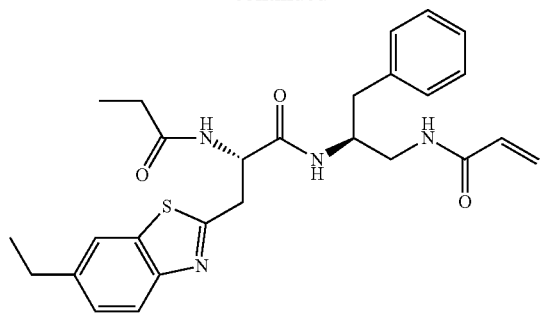
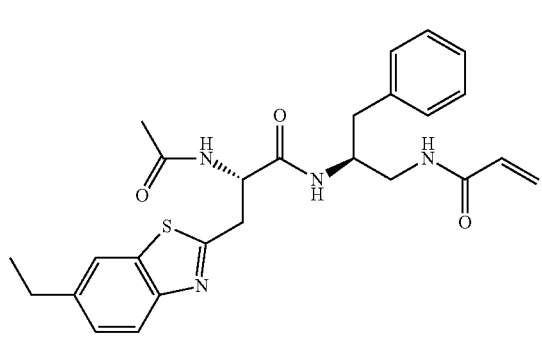
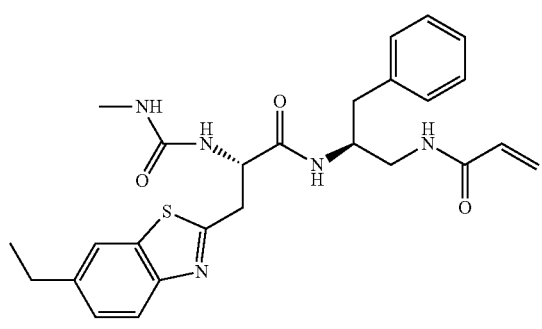
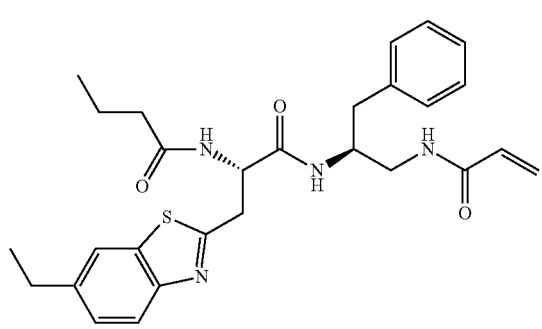
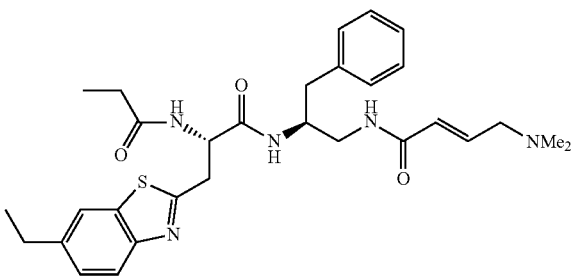
266
-continued
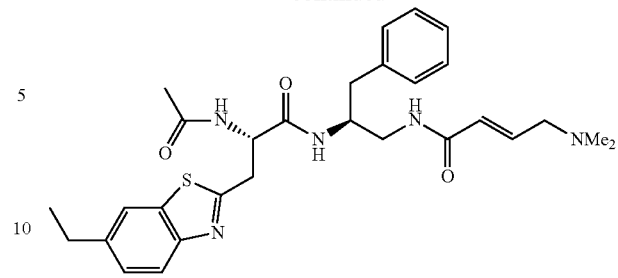
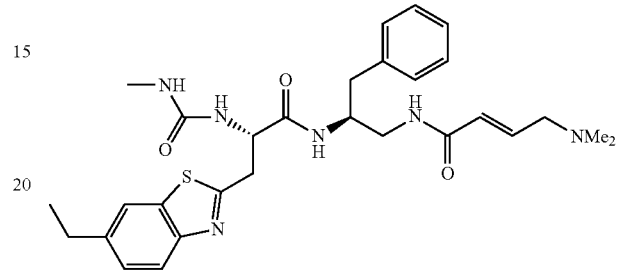
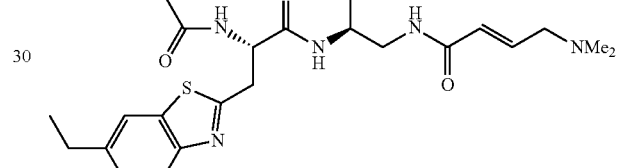
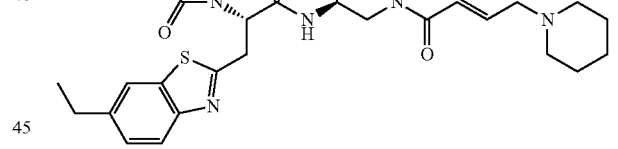
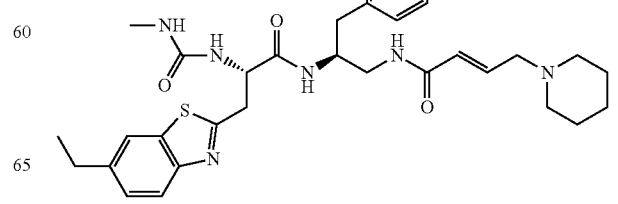

267
-continued
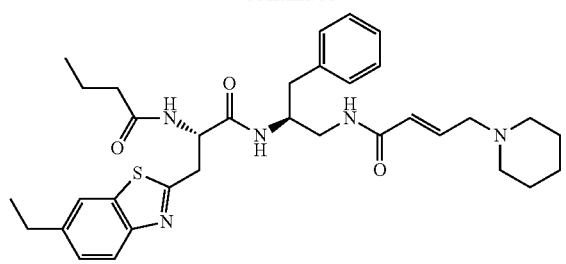
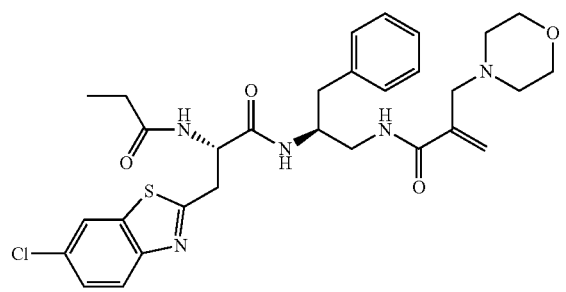
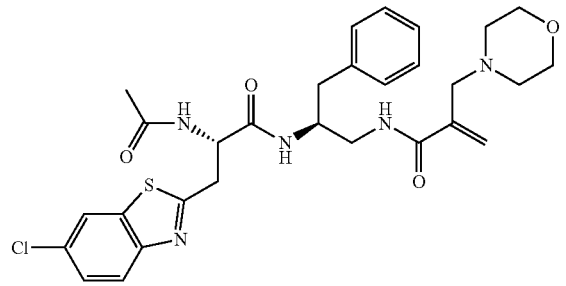
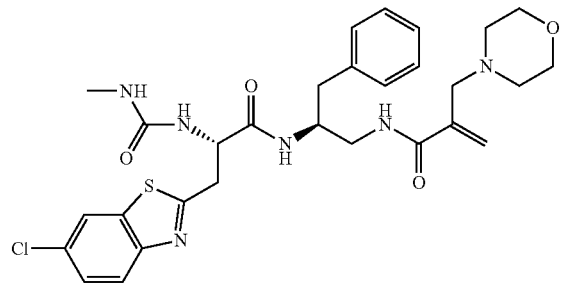
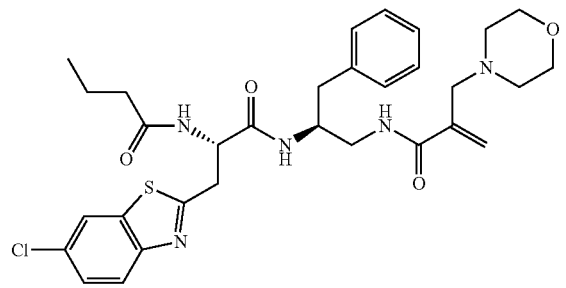
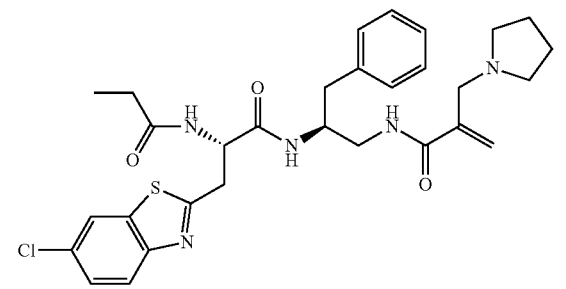
268
-continued
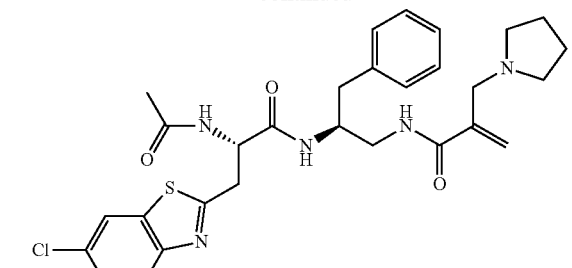
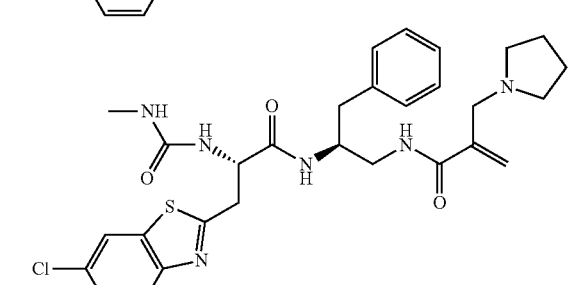
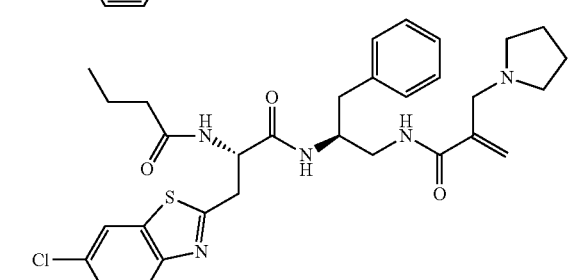
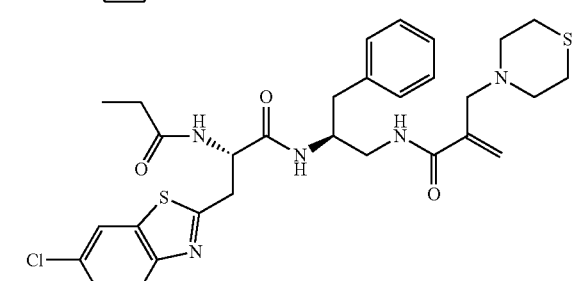
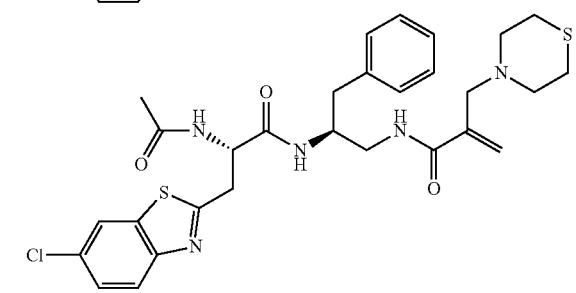
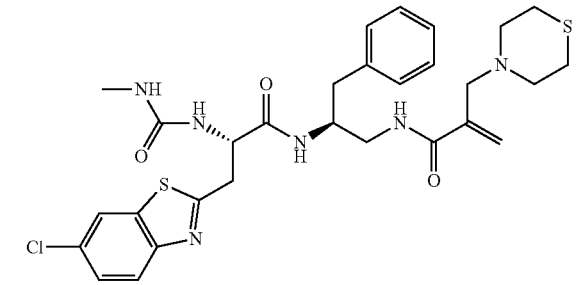

269
-continued
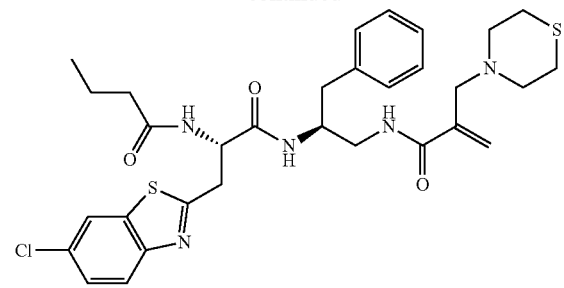
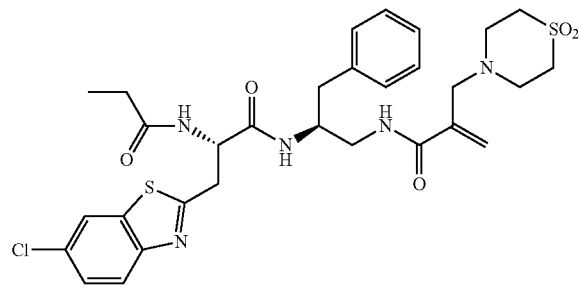
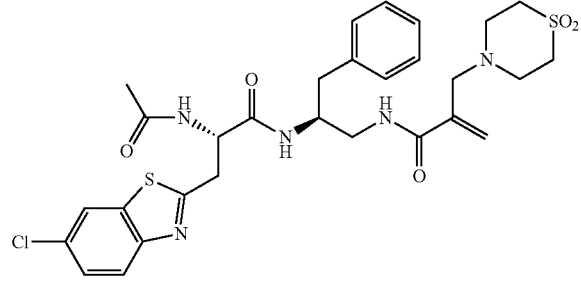
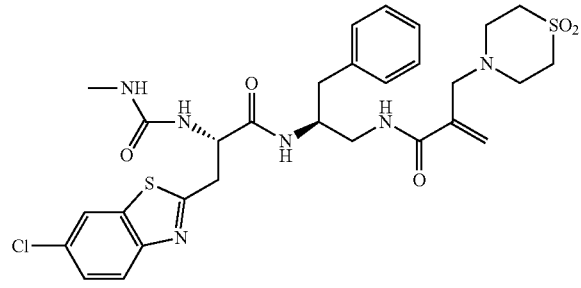
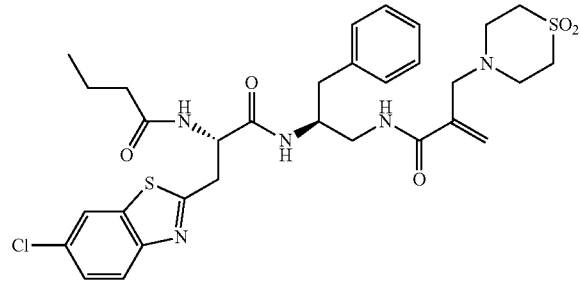
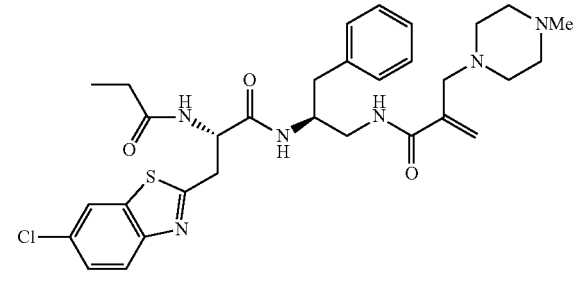
270
-continued
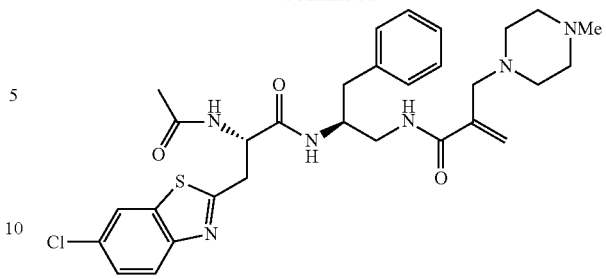
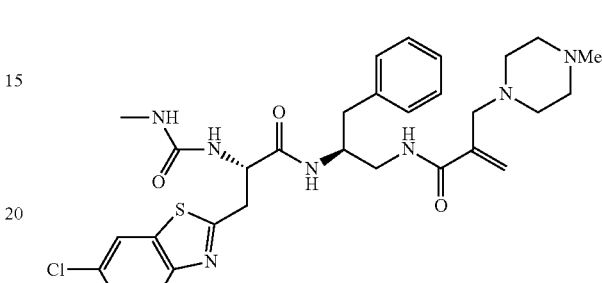
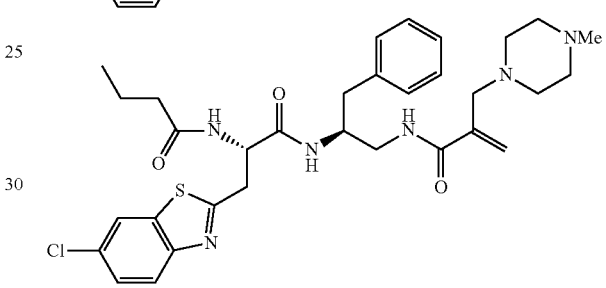
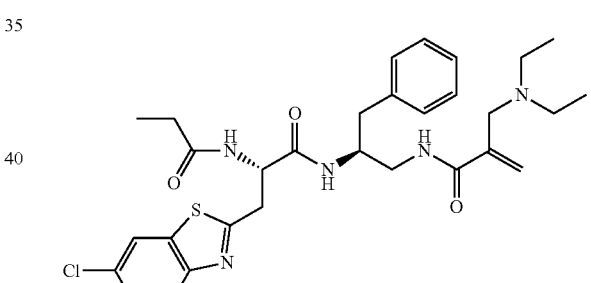
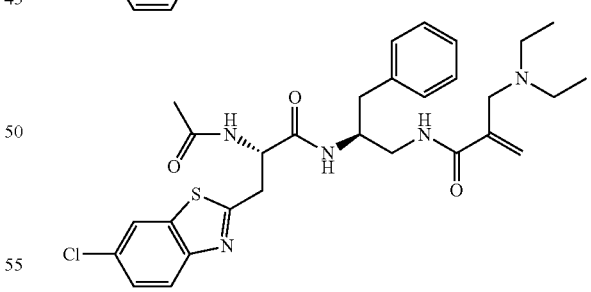
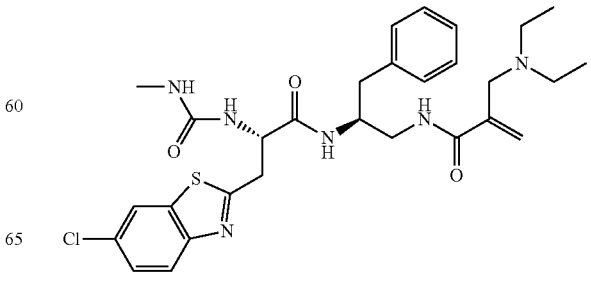

271
-continued
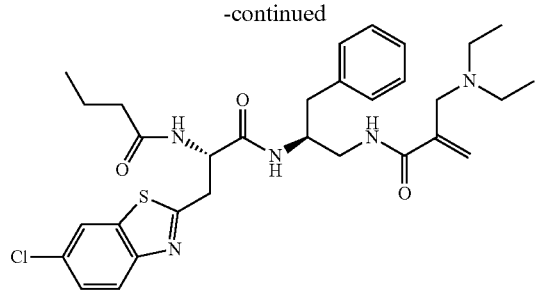
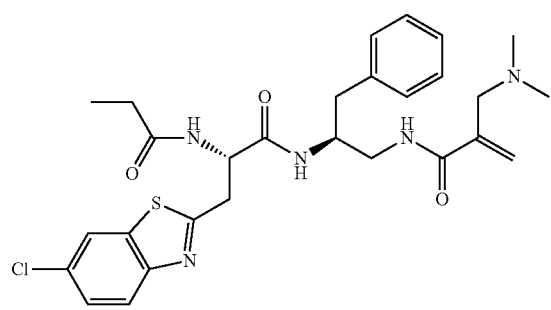
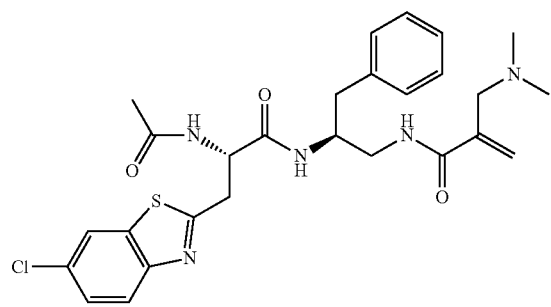
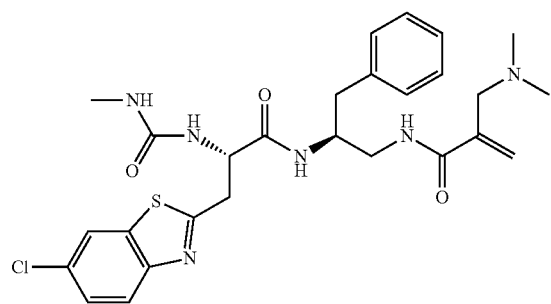
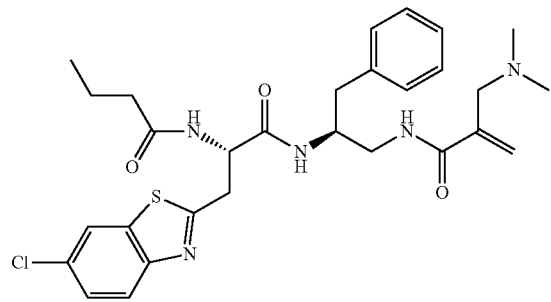
272
-continued
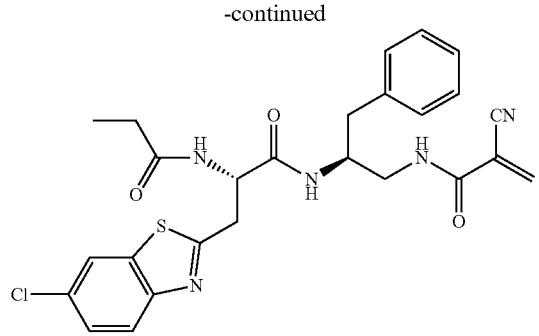
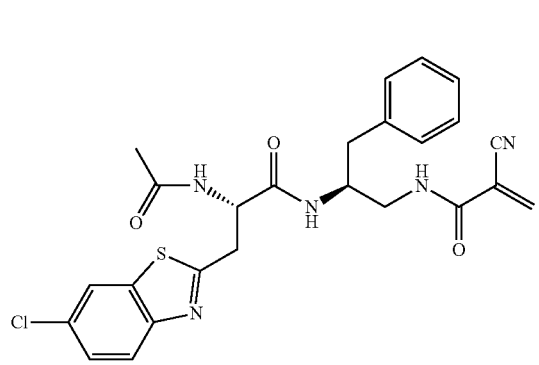
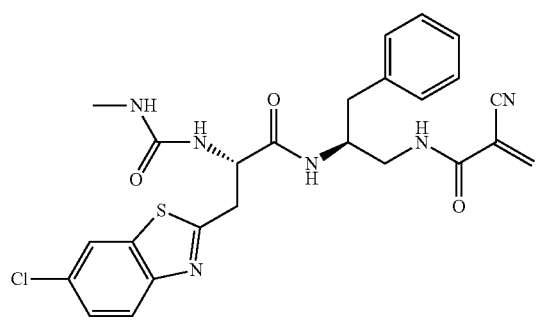
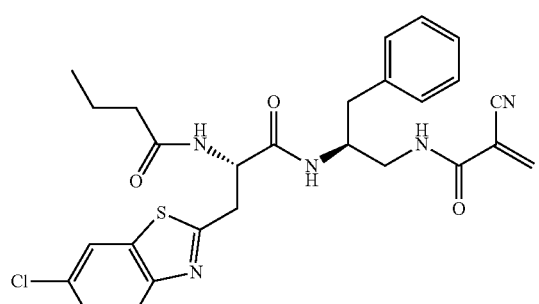
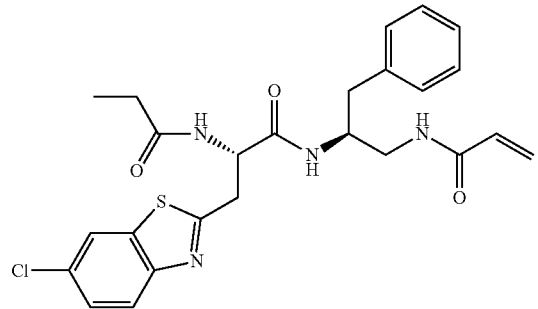

273
-continued
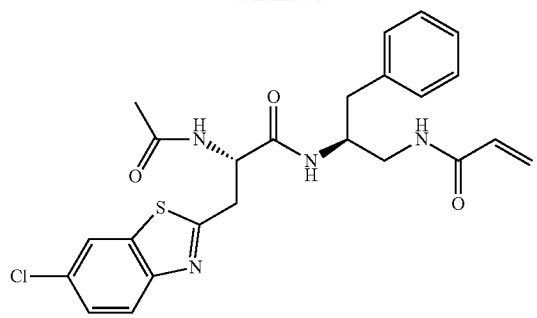
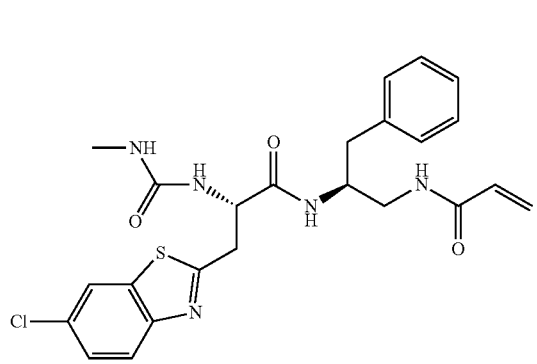
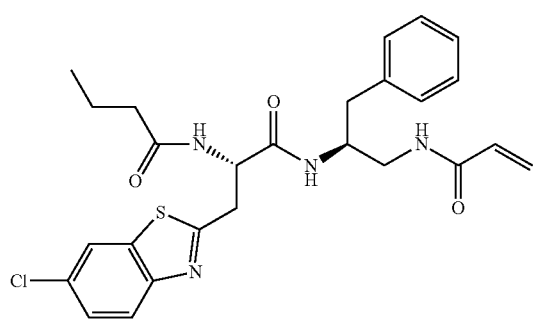
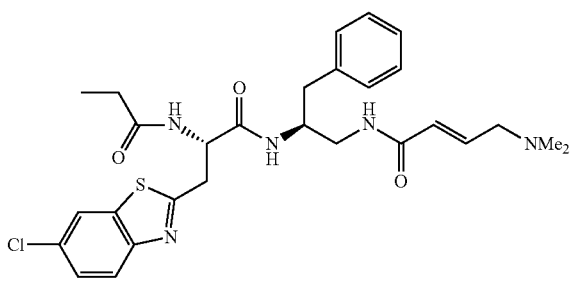
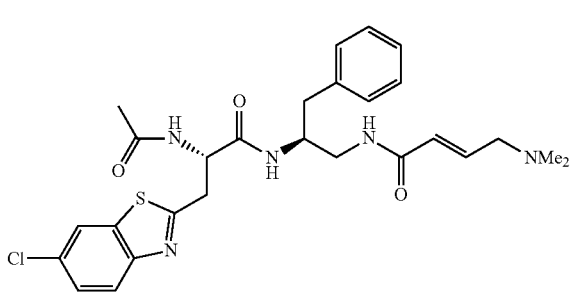
274
-continued
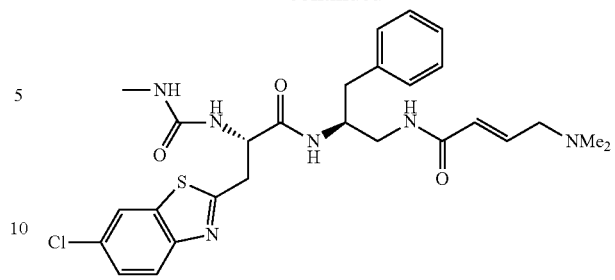
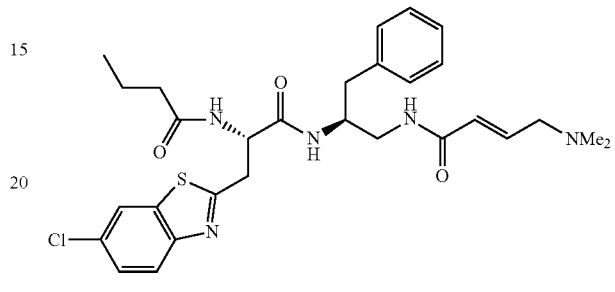
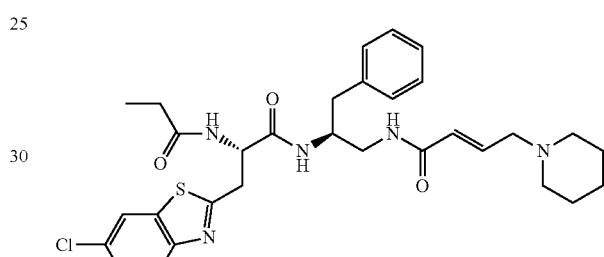
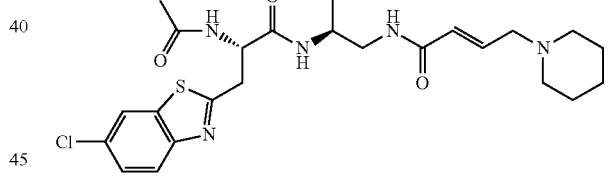
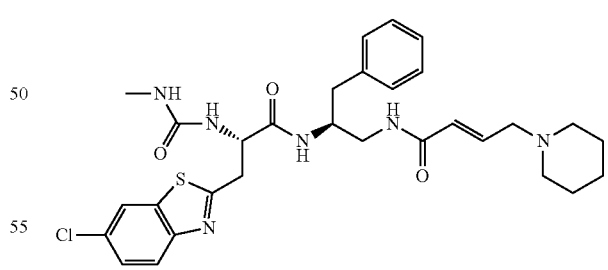

275
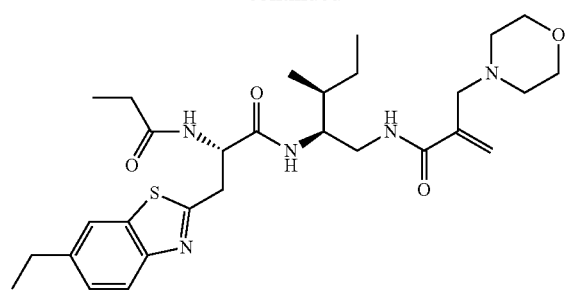
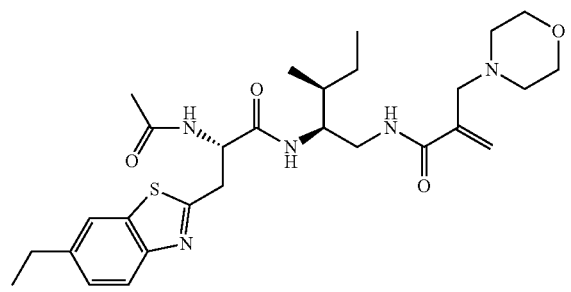
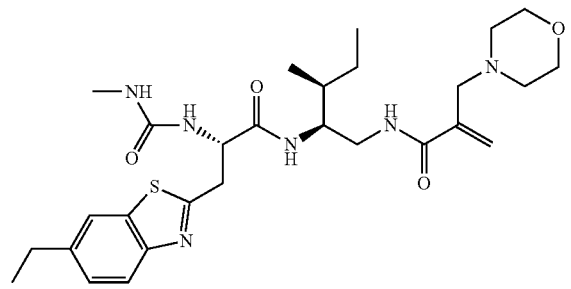
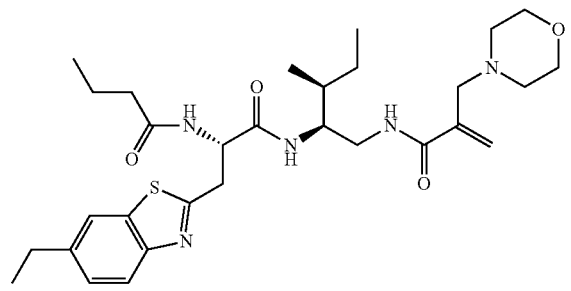
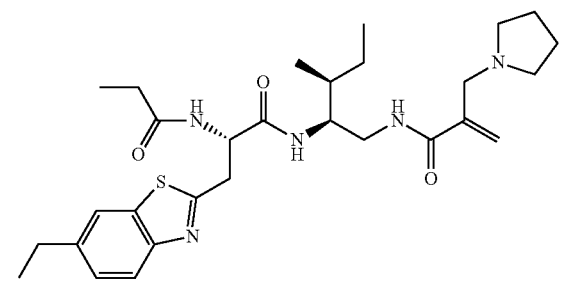
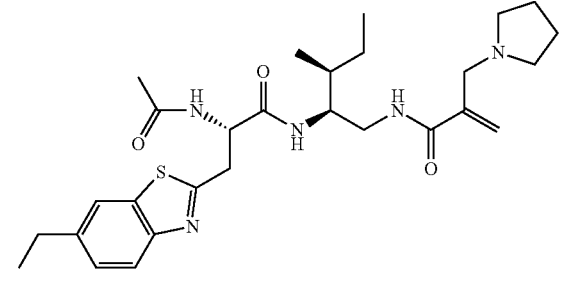
276
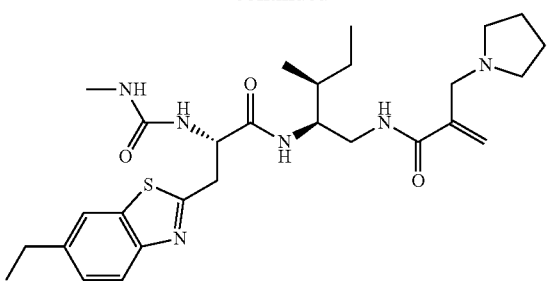
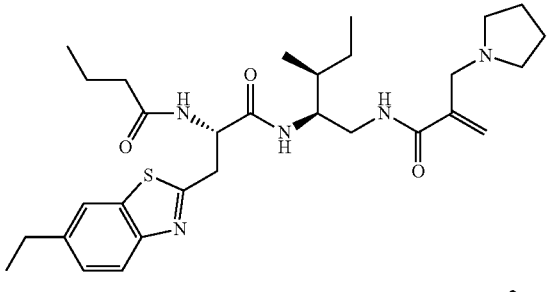
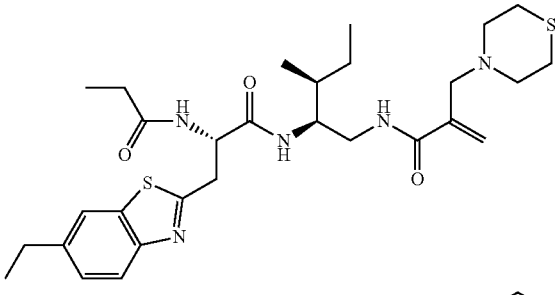
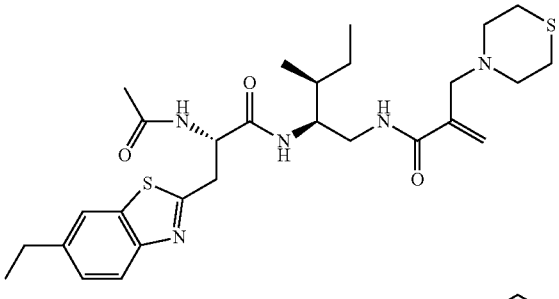
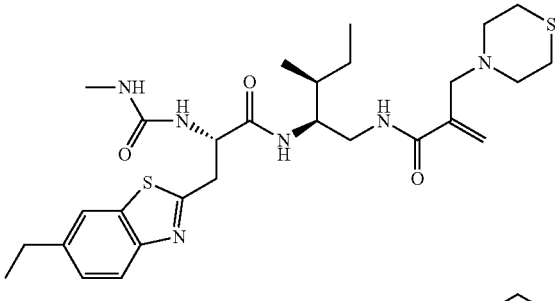
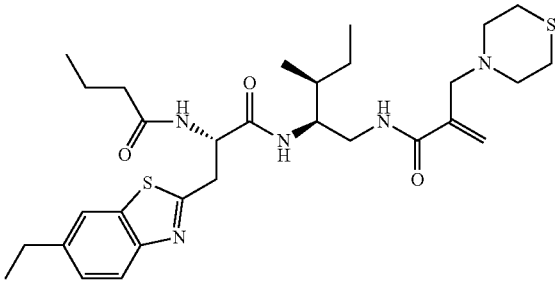

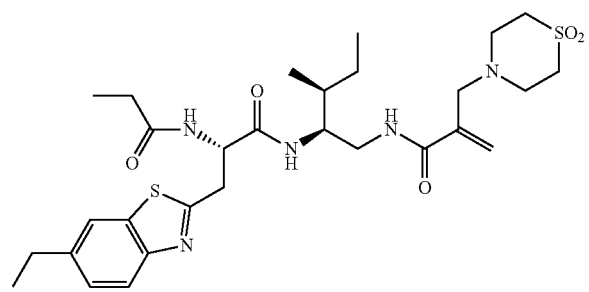
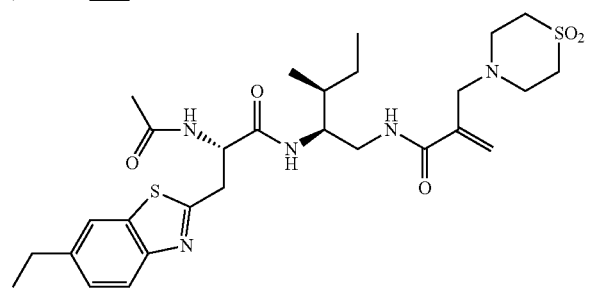
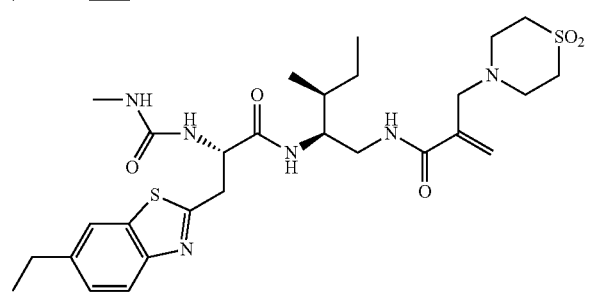
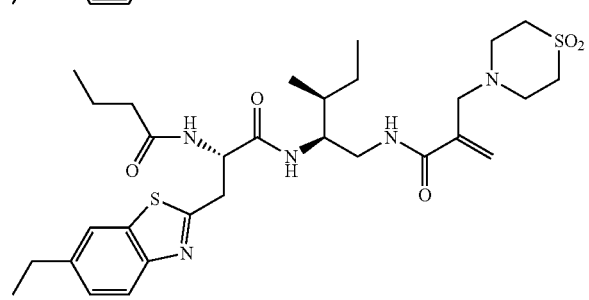
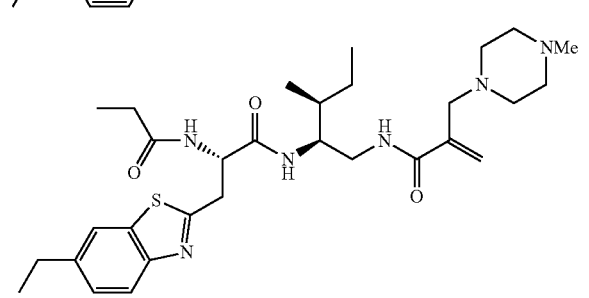
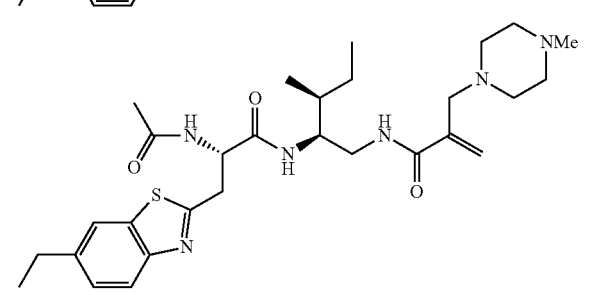
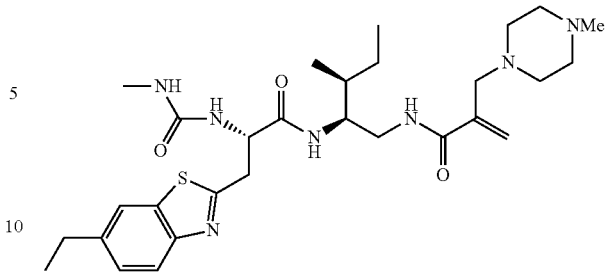
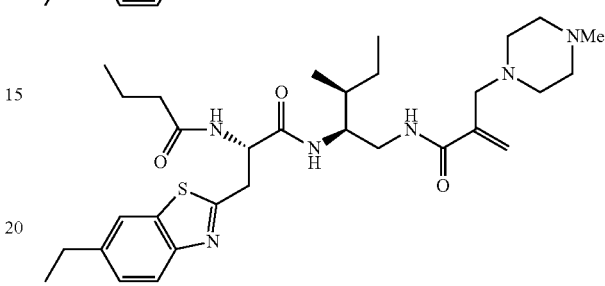
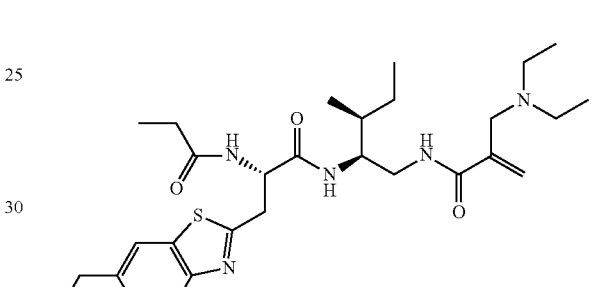
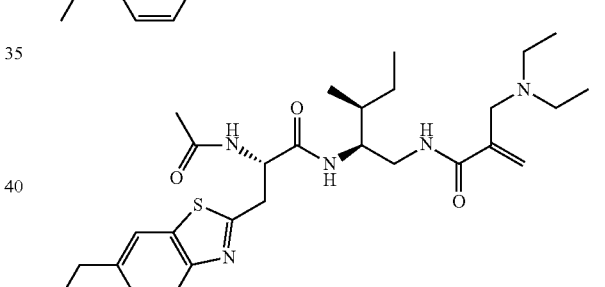
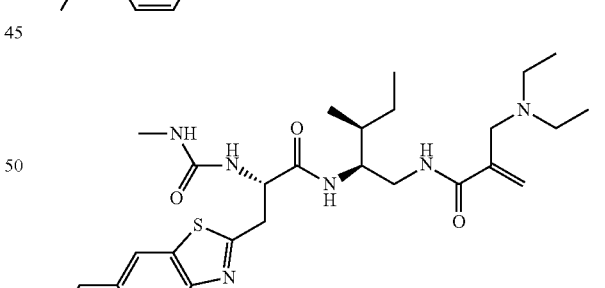
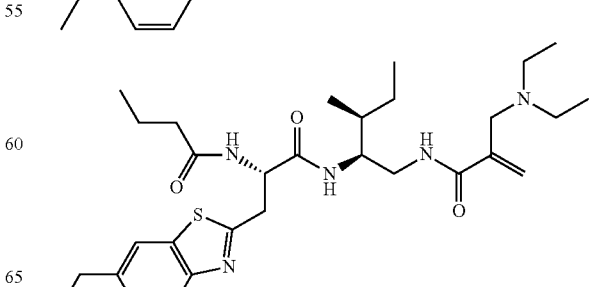

279
-continued
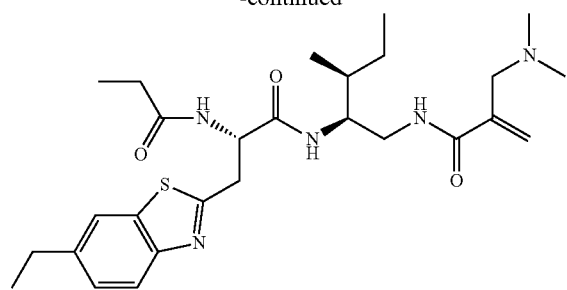
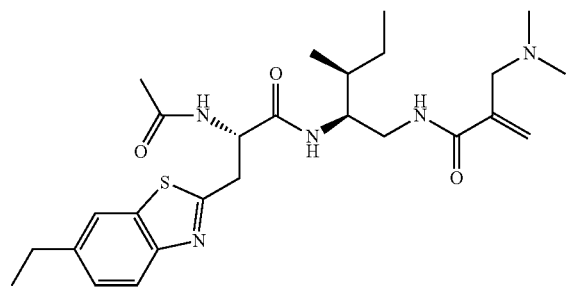
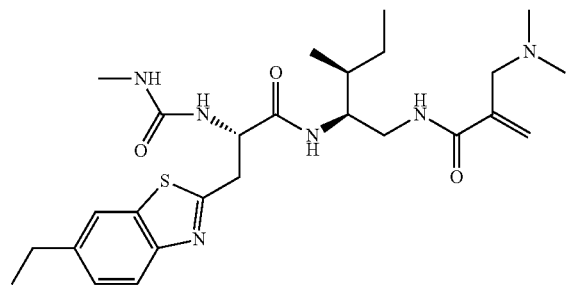
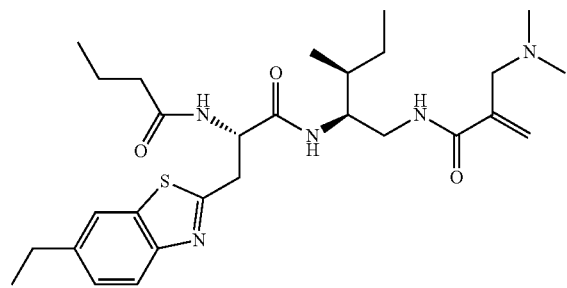
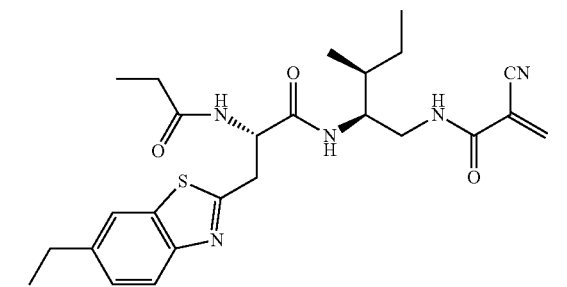
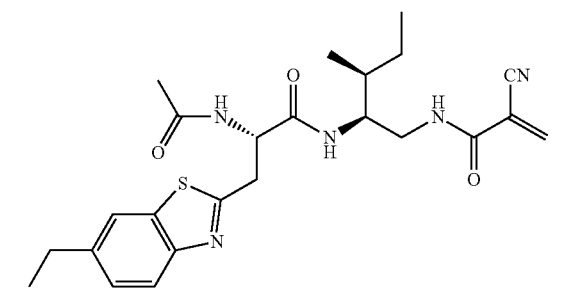
280
-continued
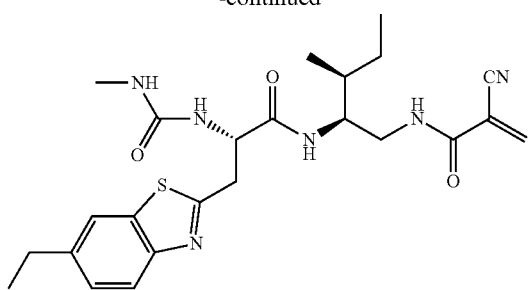
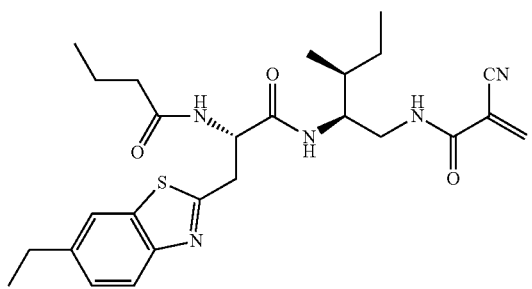
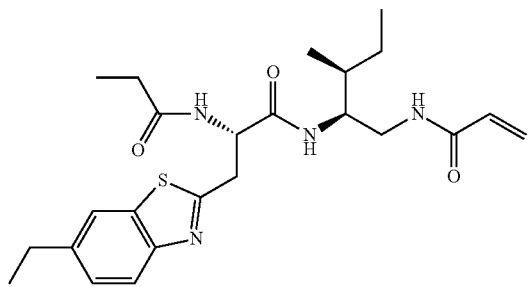
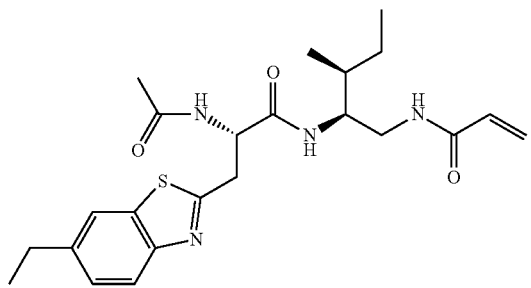
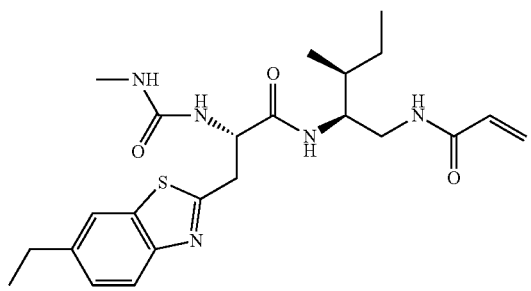
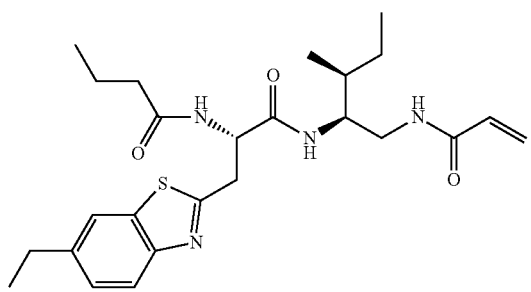

281
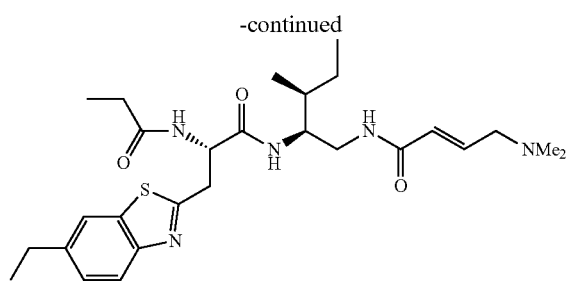
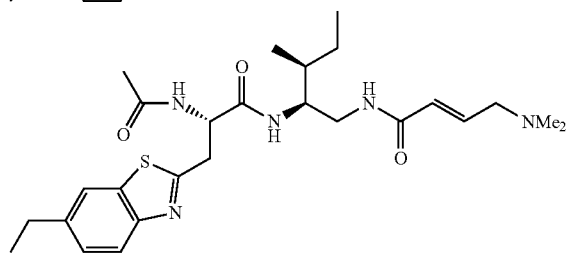
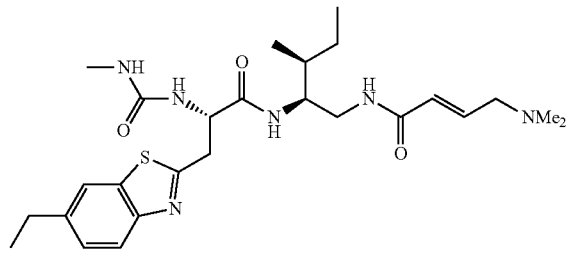
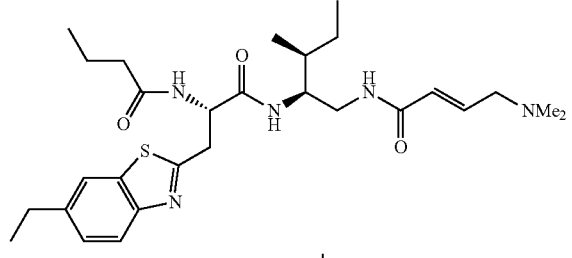
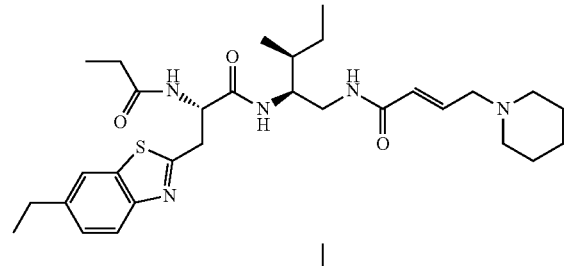
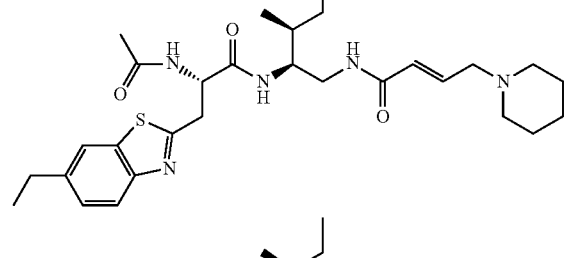
282
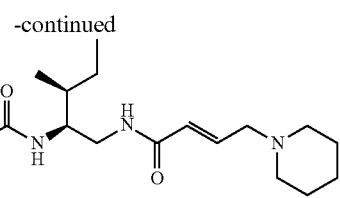
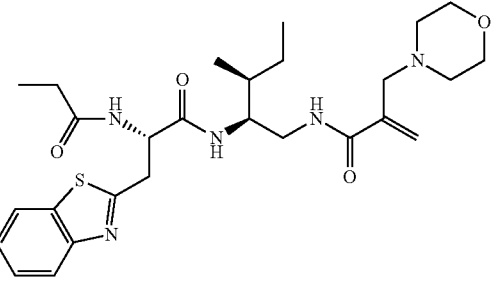
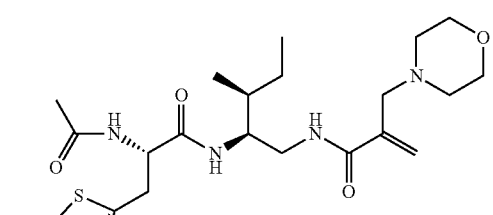
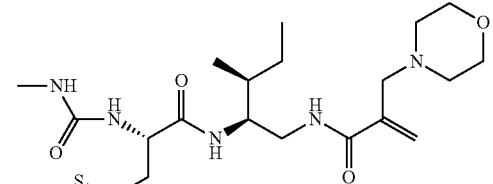
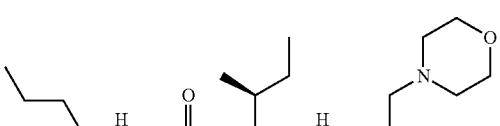
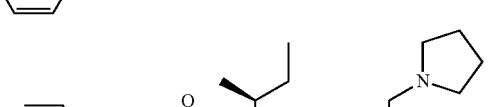

283
-continued
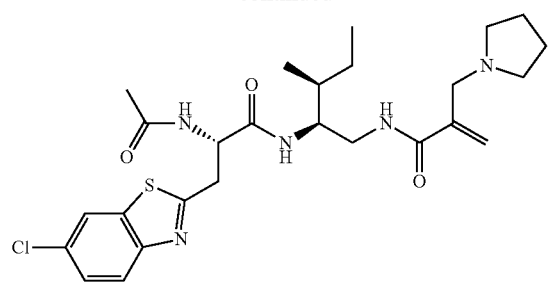
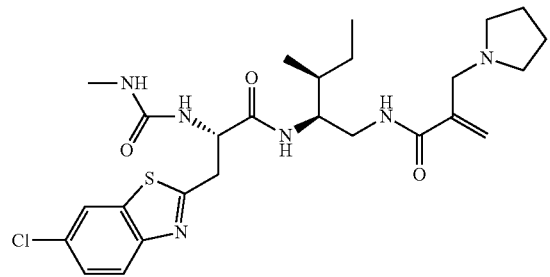
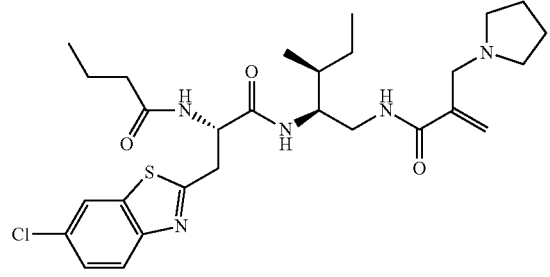
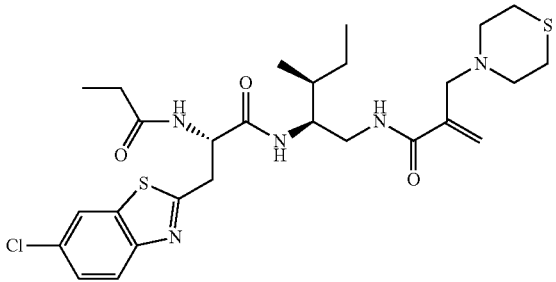
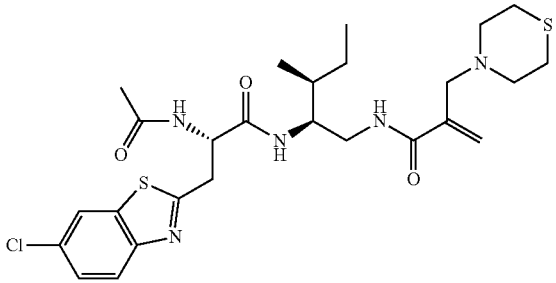
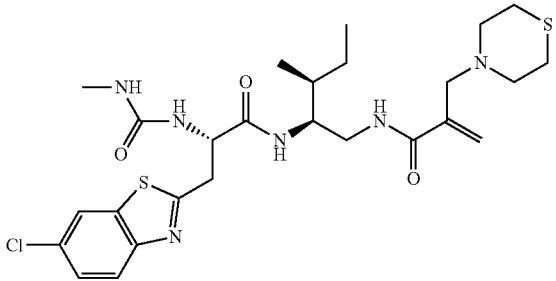
284
-continued
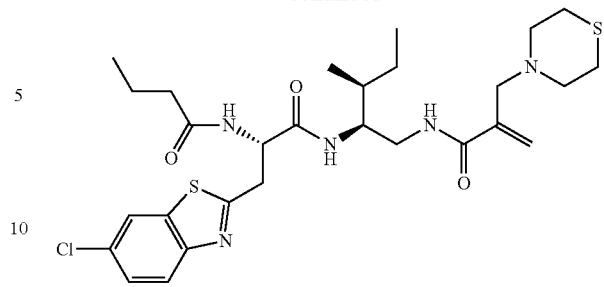
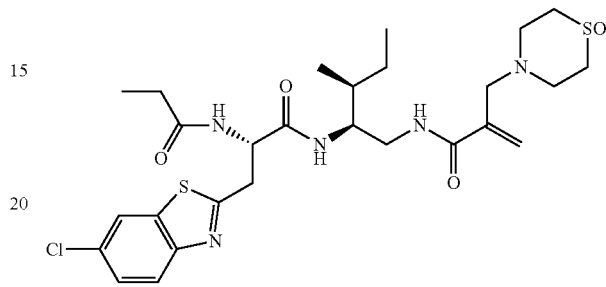
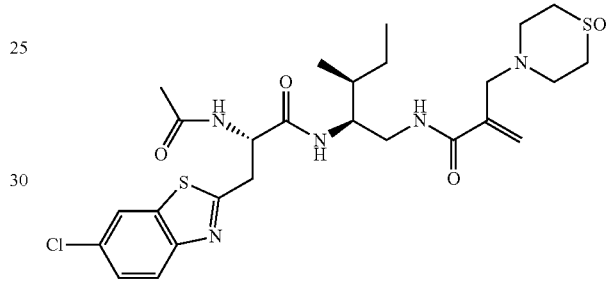
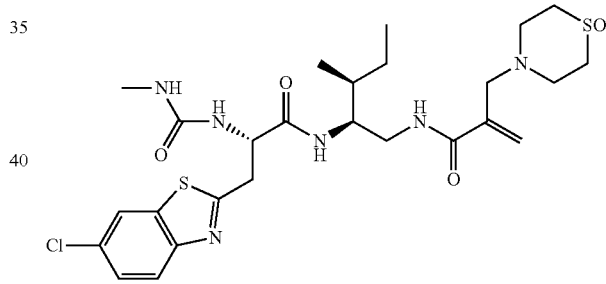
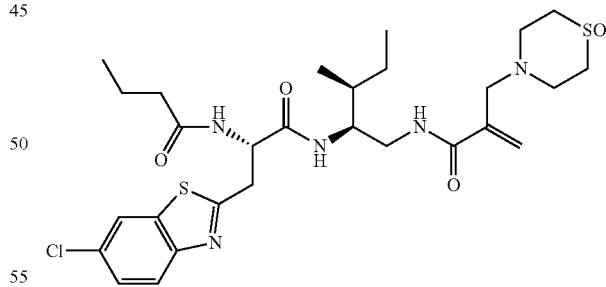
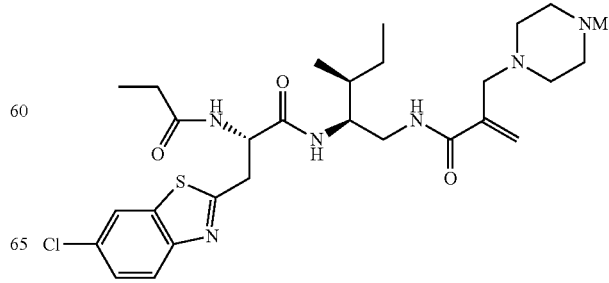

285
-continued
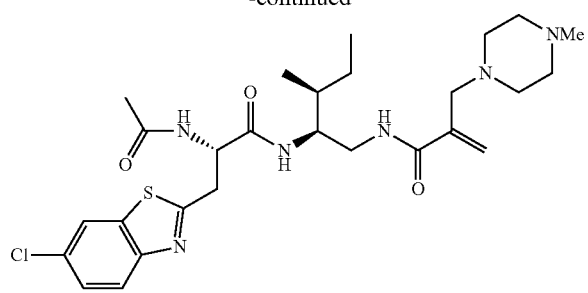
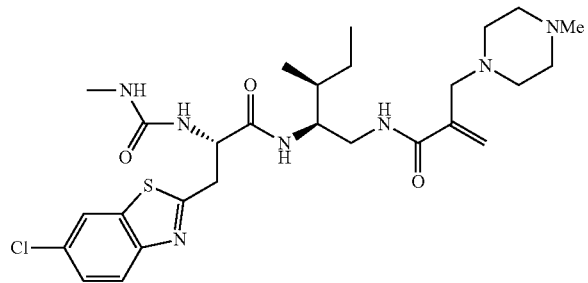
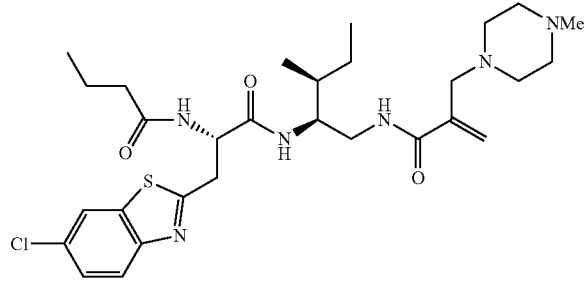
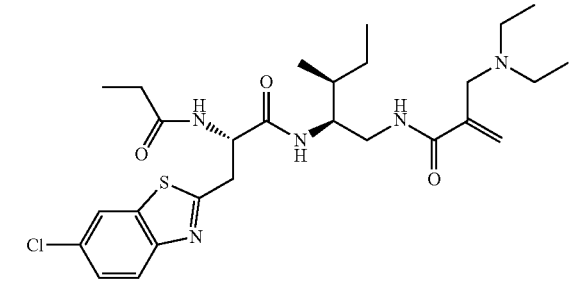
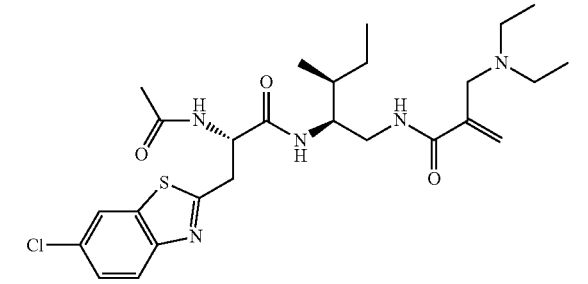
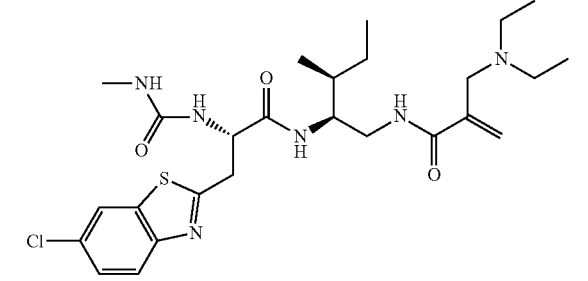
286
-continued
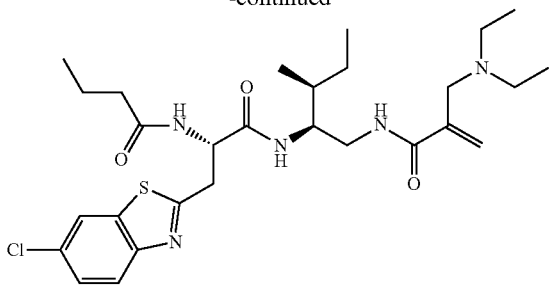
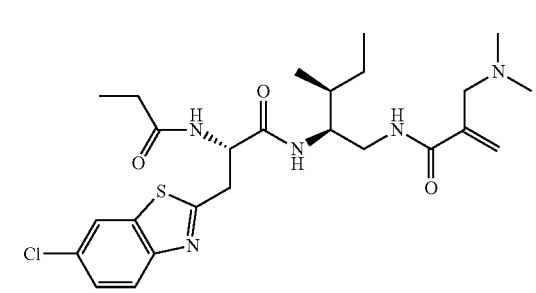
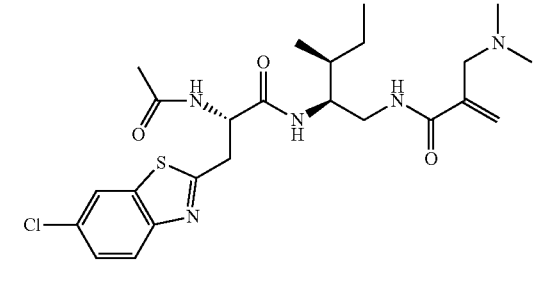
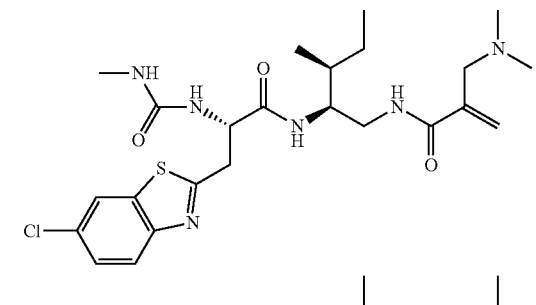
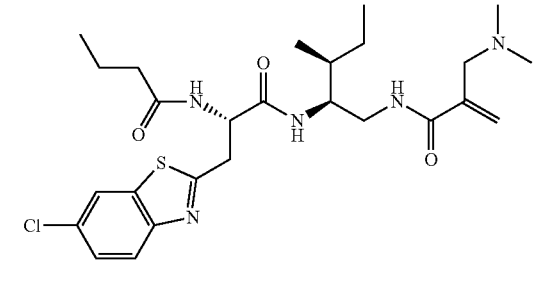
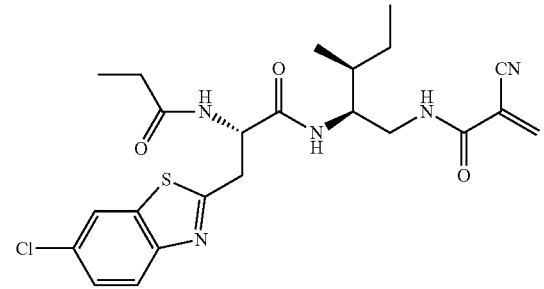

287
-continued
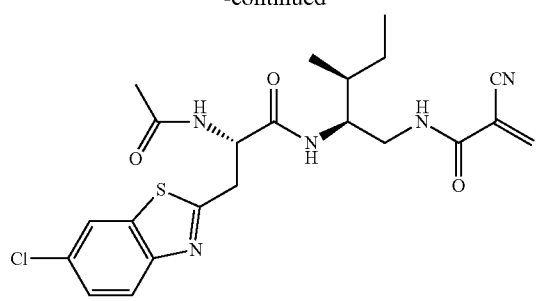
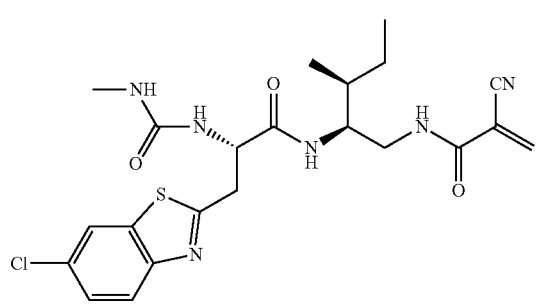
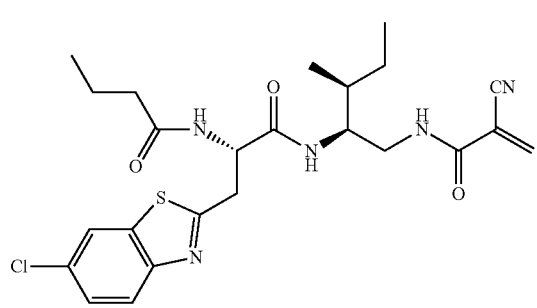
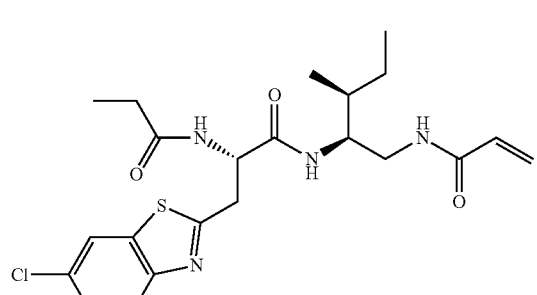
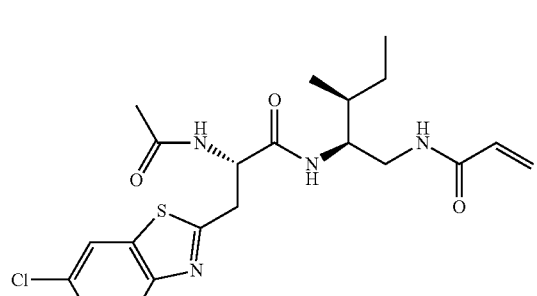
288
-continued
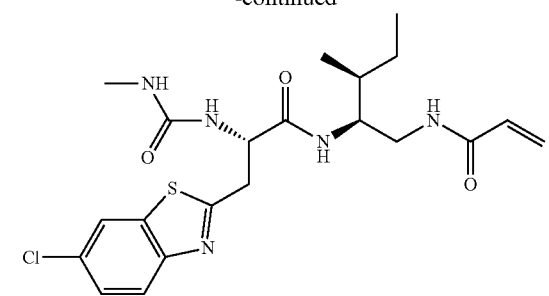
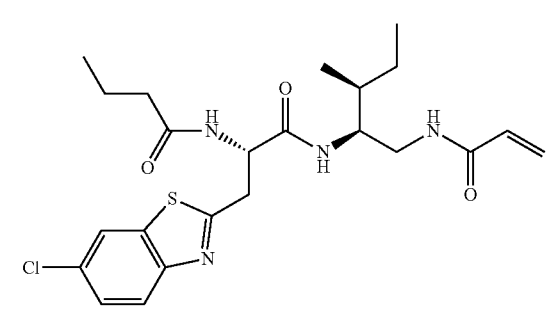
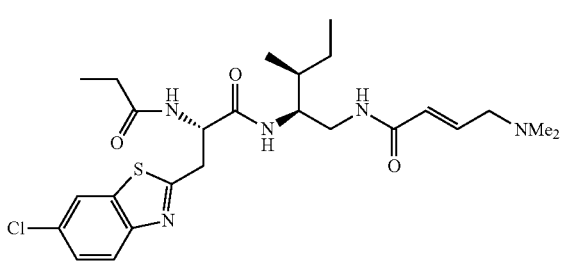
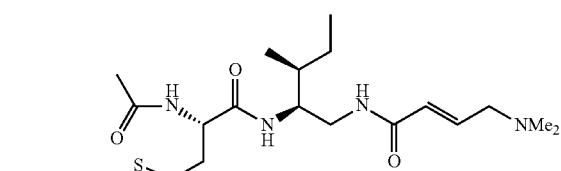
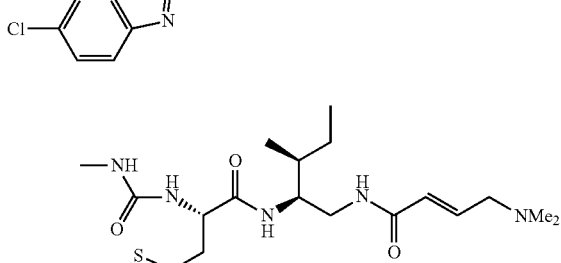
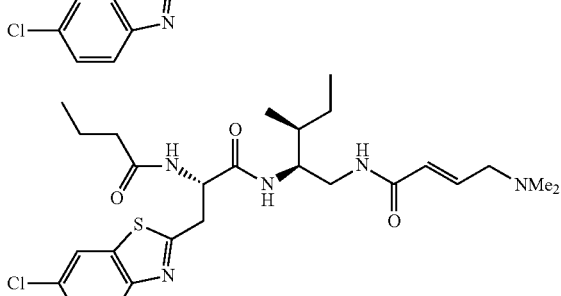

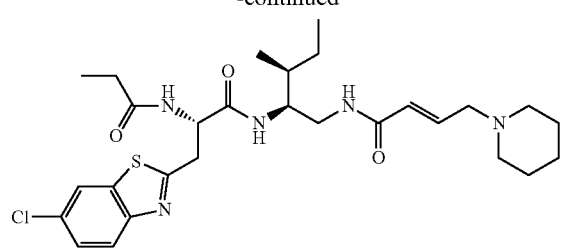
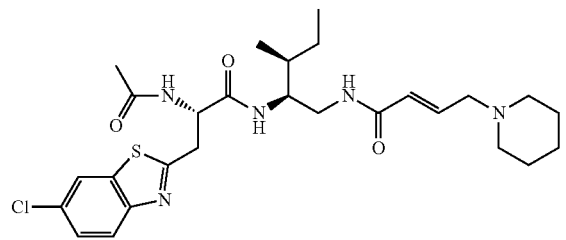
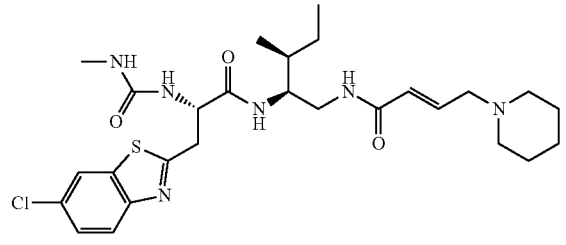
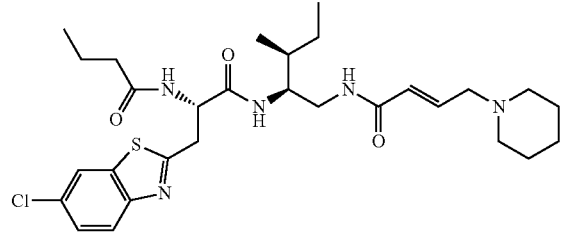
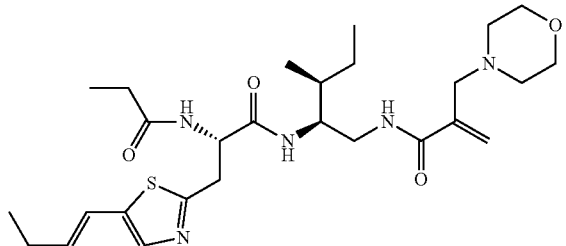
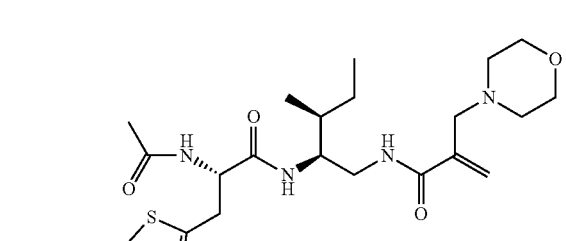
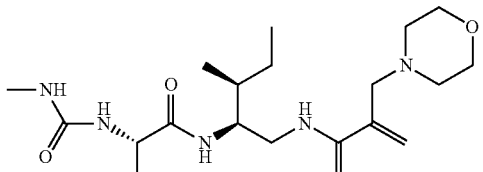
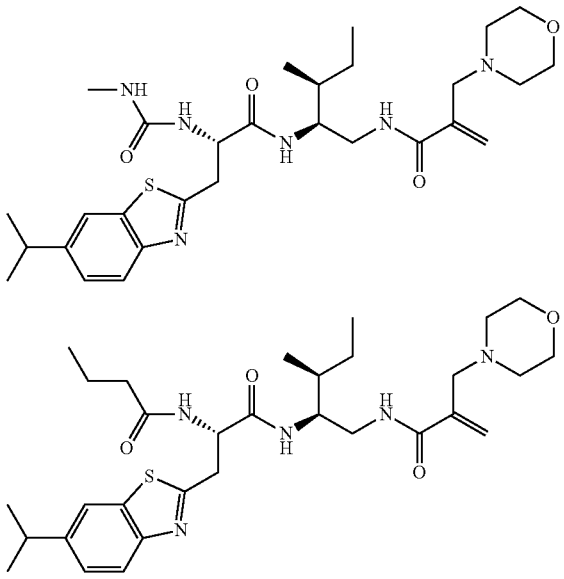
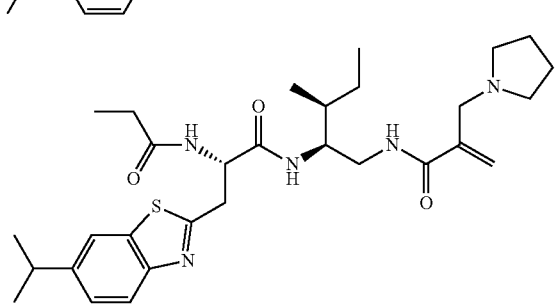
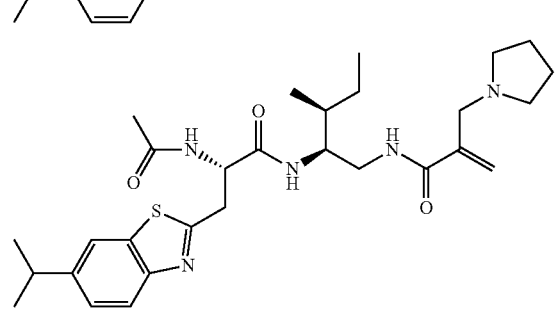

291
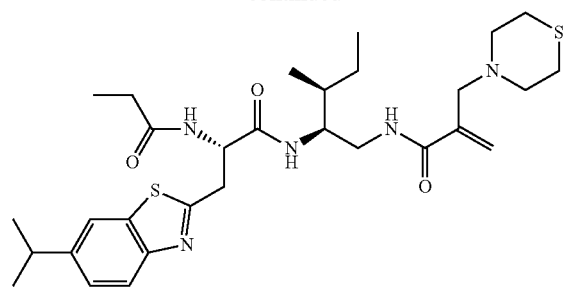
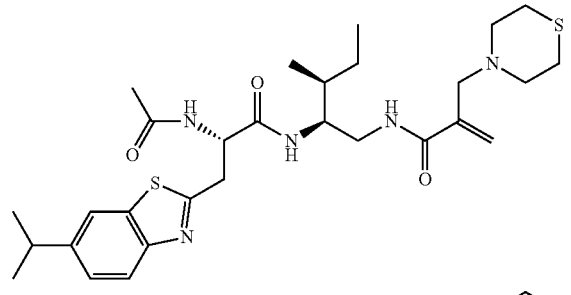
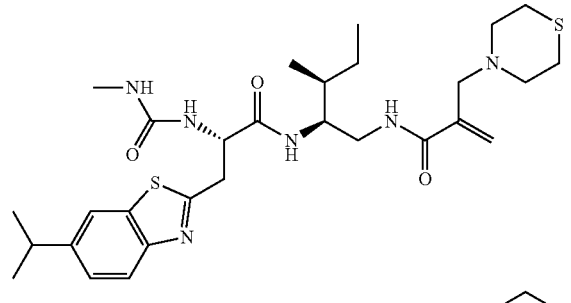
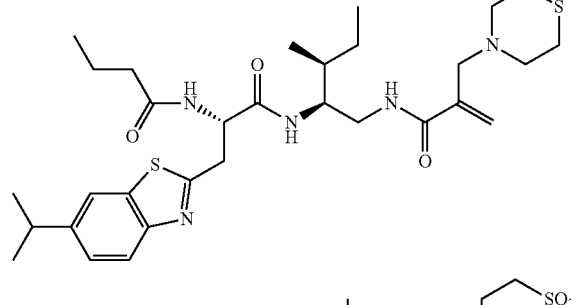
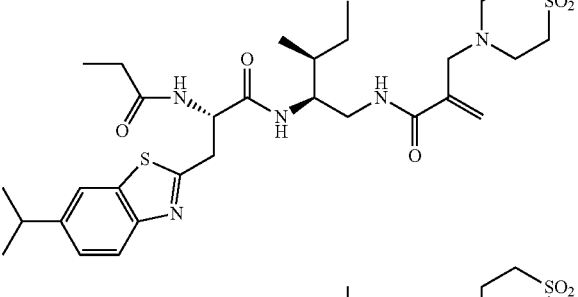
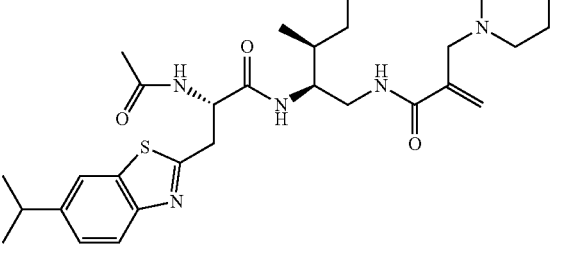
292
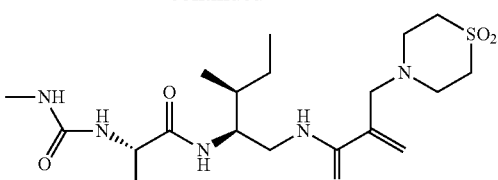
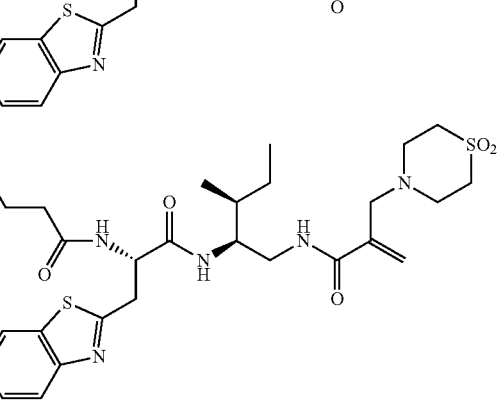
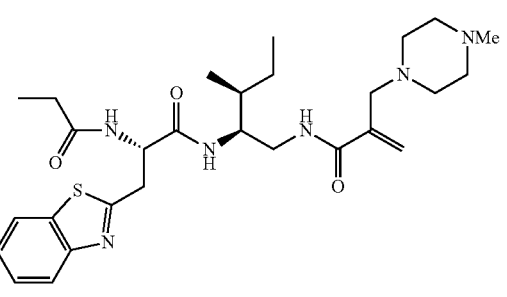
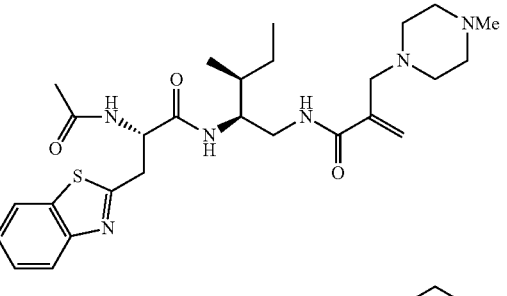
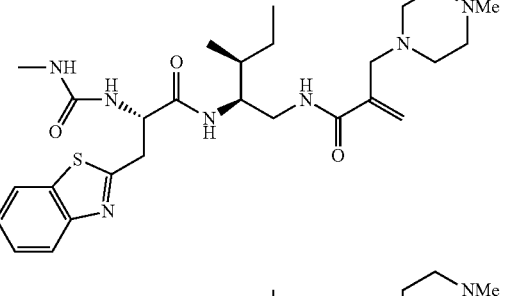
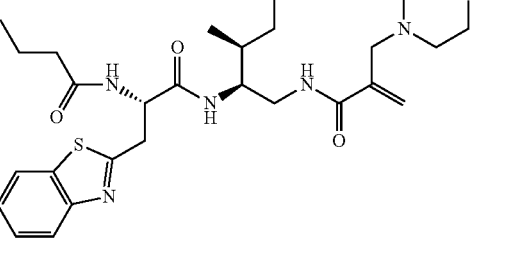

293
-continued
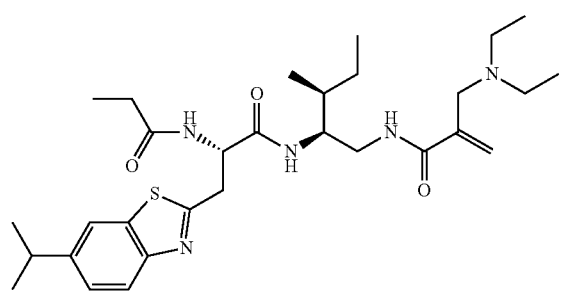
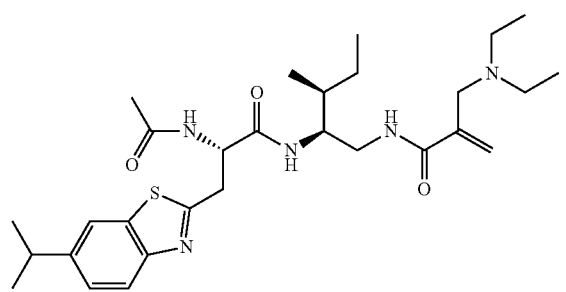
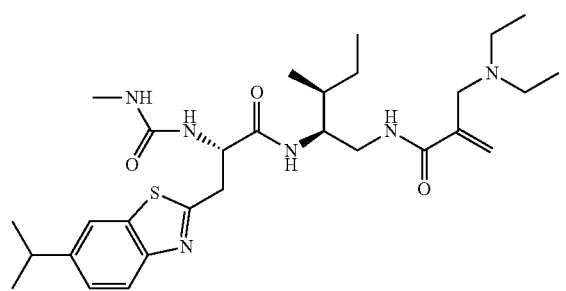
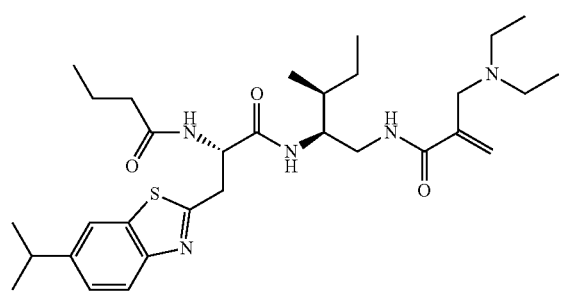
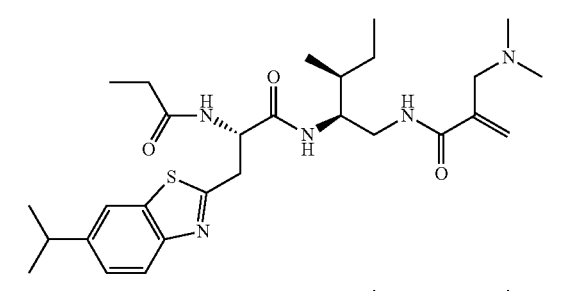
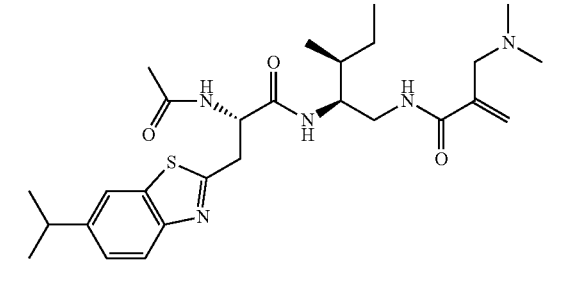
294
-continued
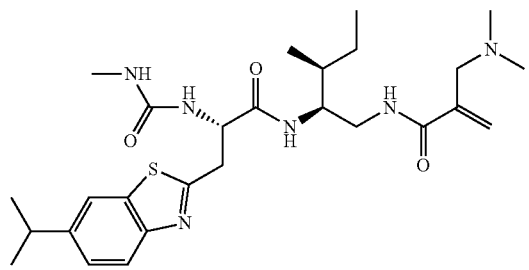
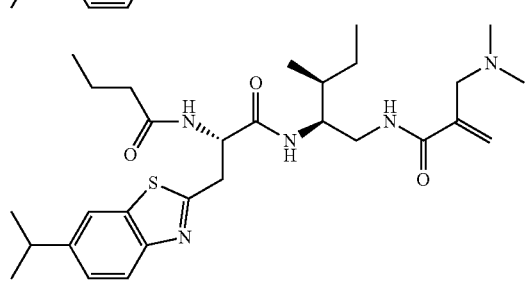
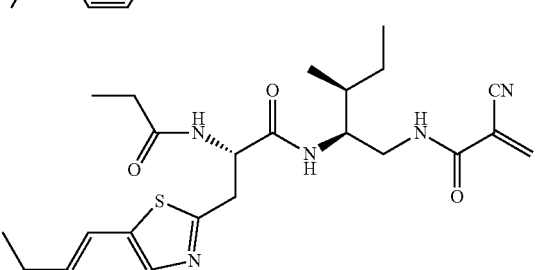
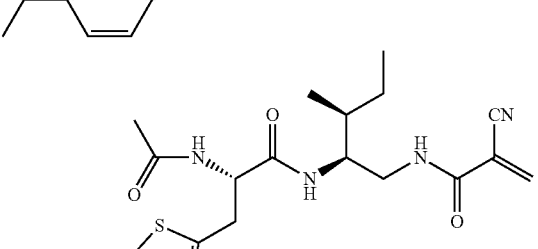
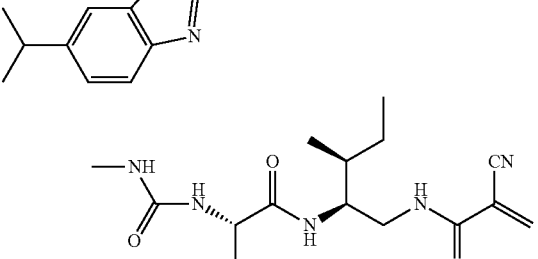
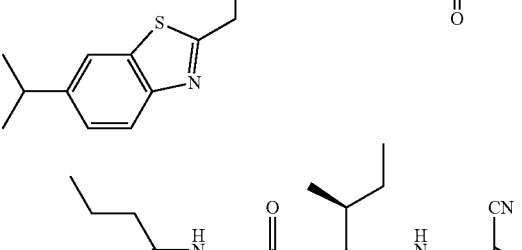
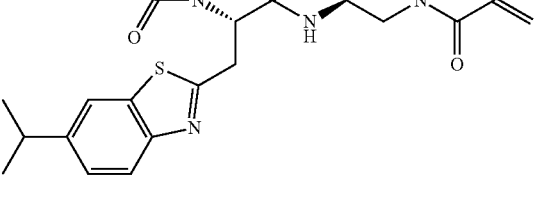

295
-continued
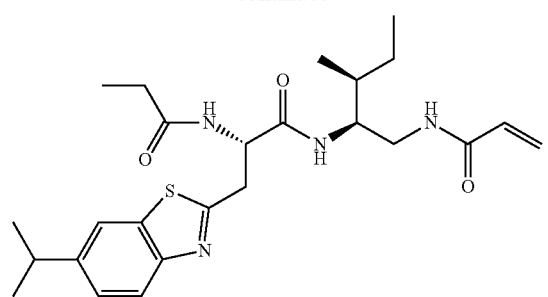
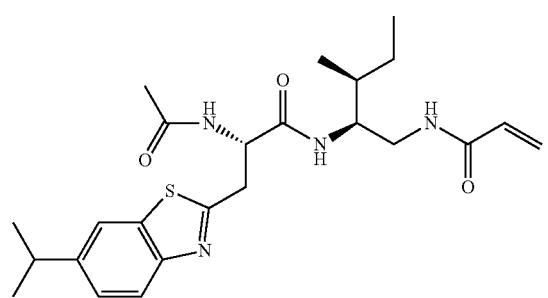
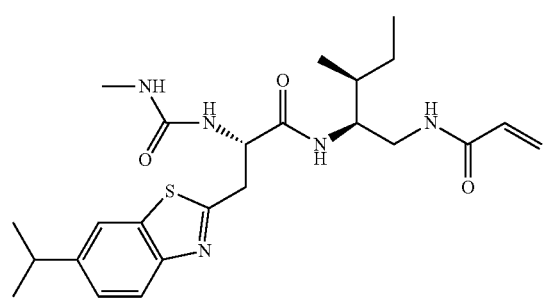
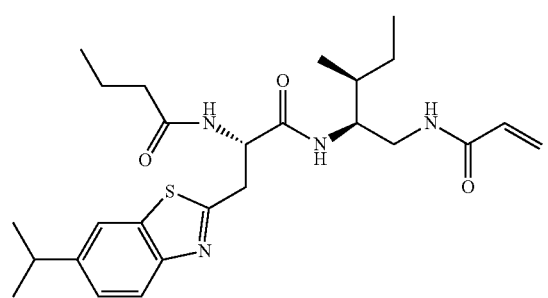
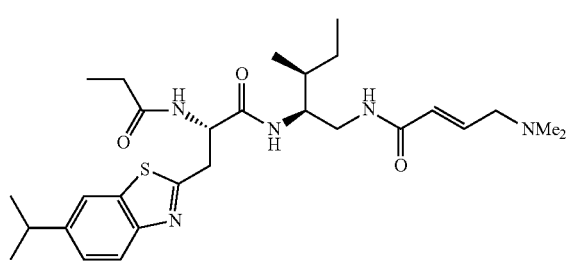
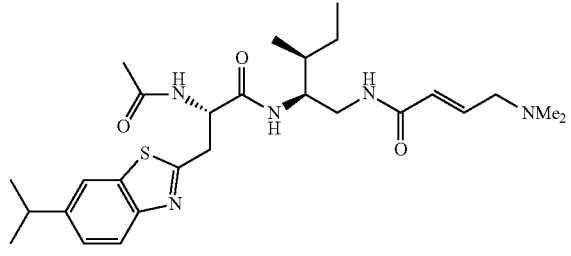
296
-continued
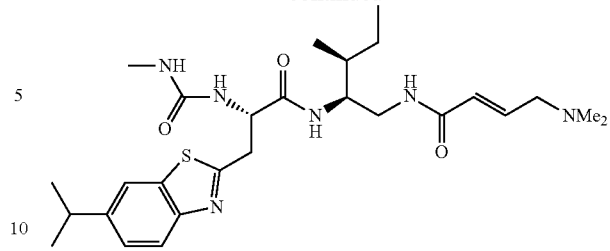
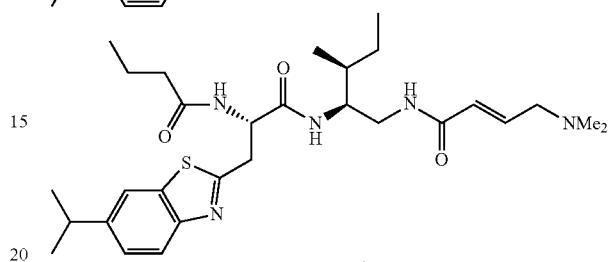
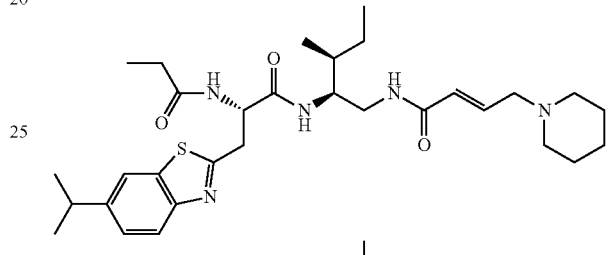
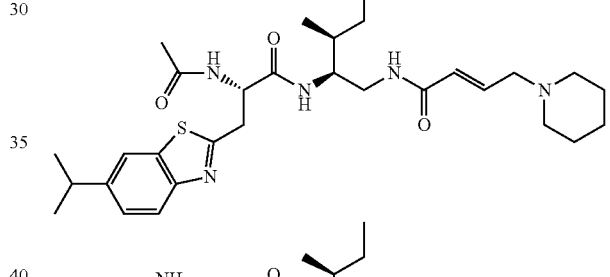
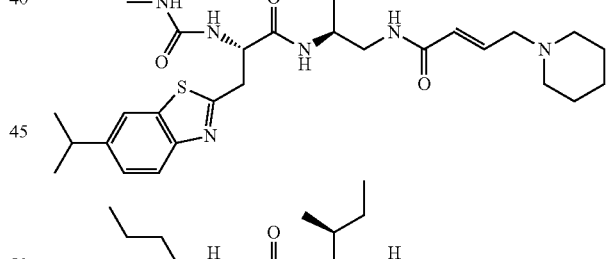
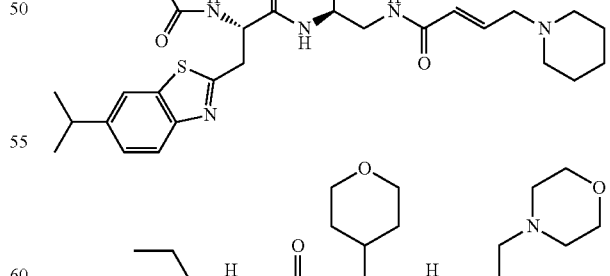
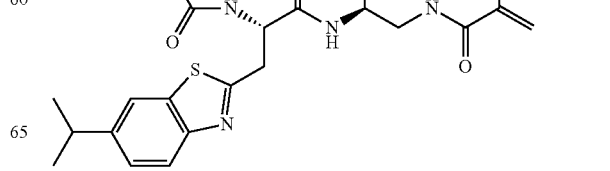

297
-continued
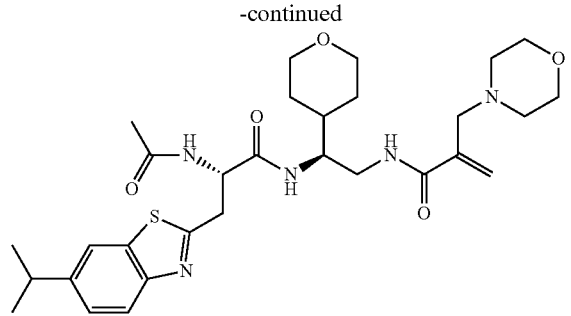
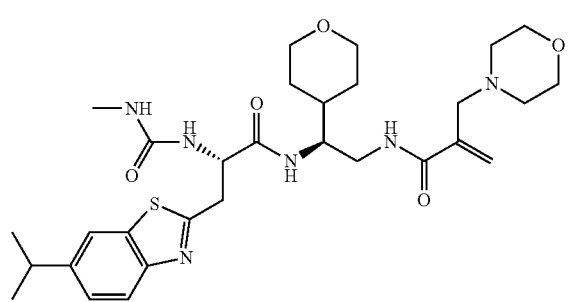
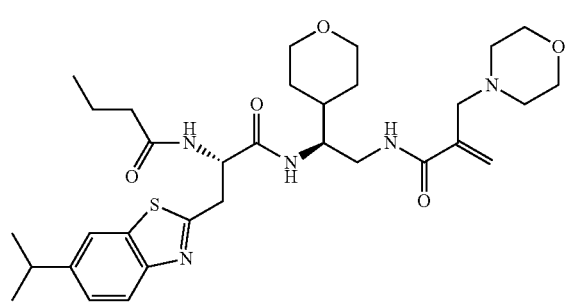
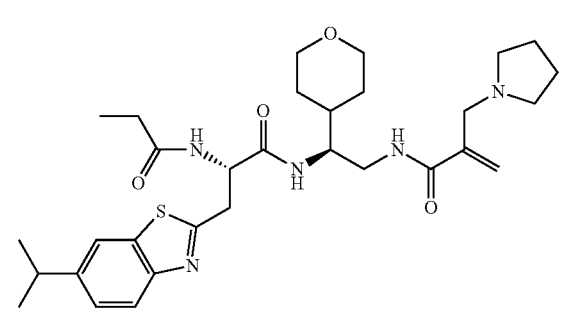
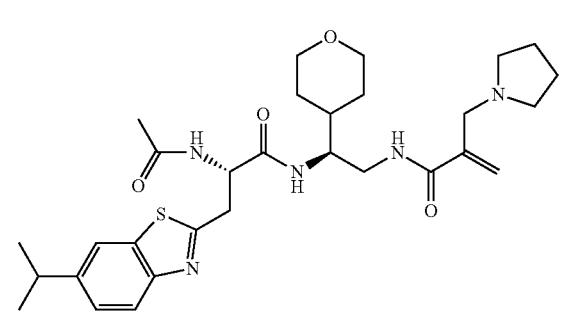
298
-continued
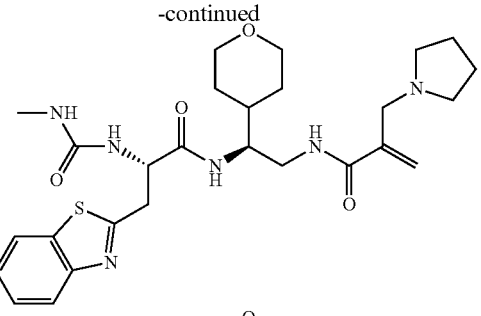
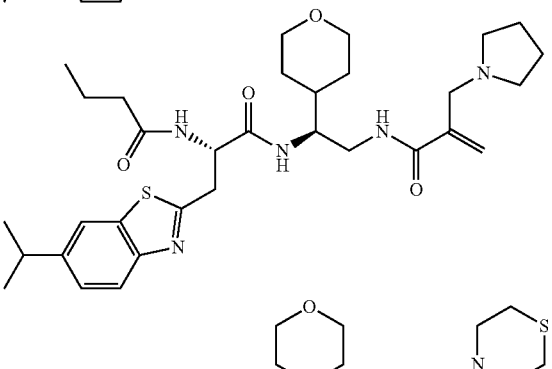
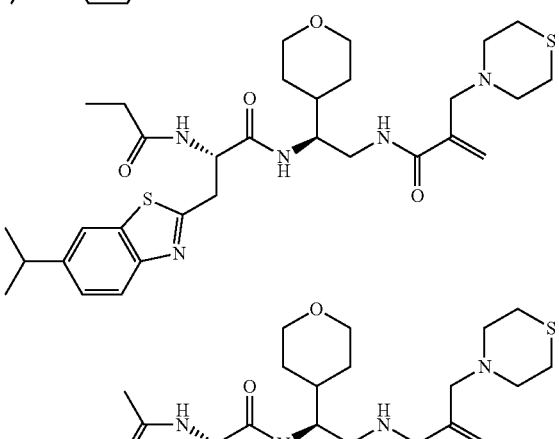
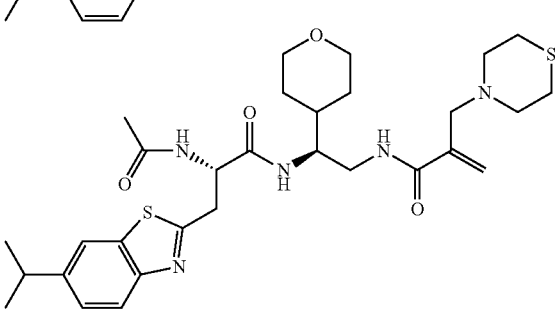
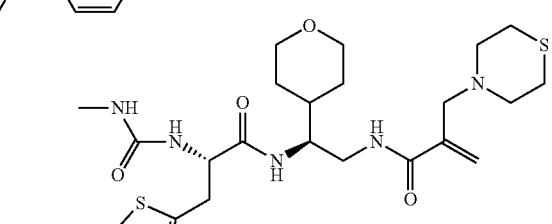
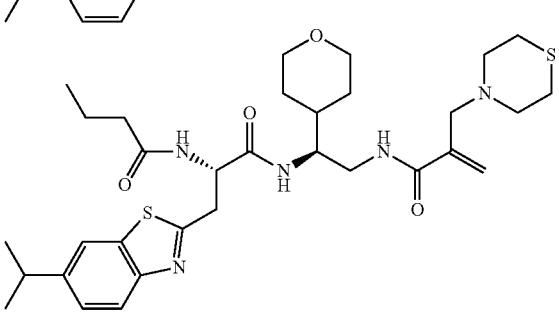

299
-continued
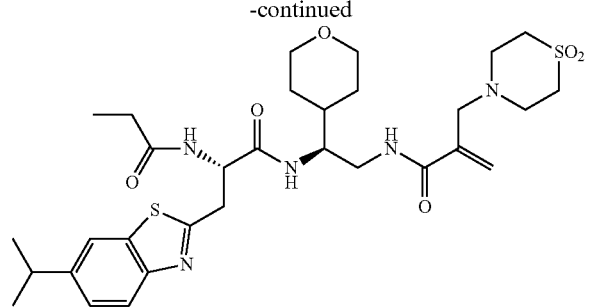
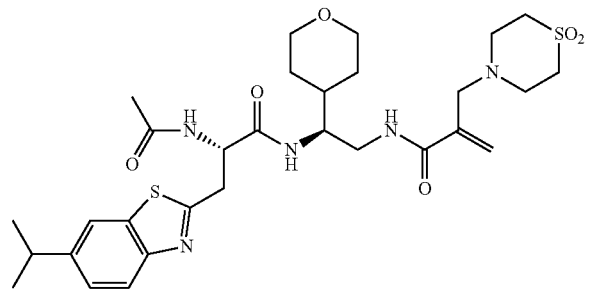
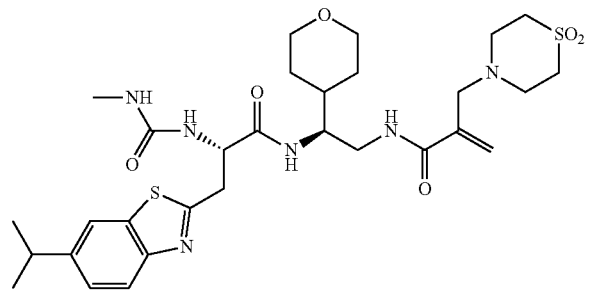
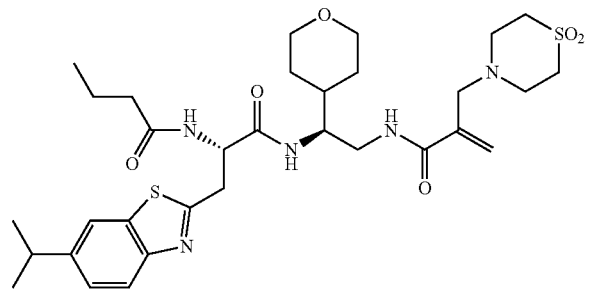
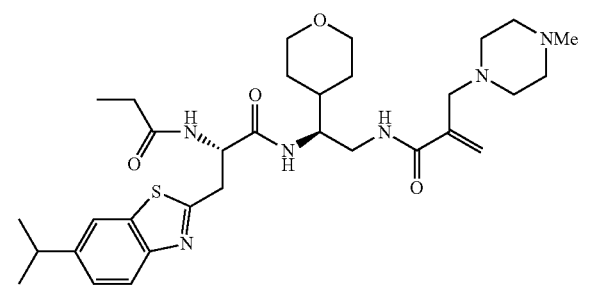
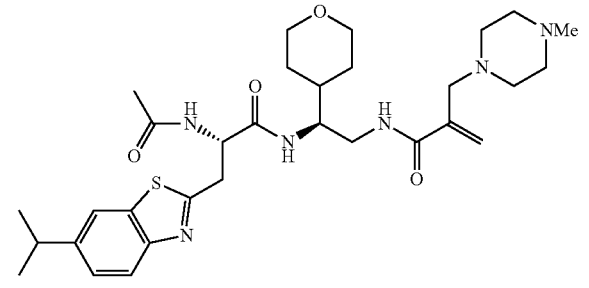
300
-continued
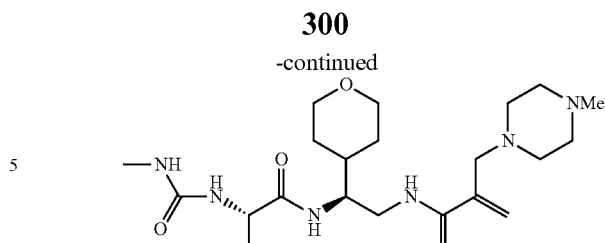
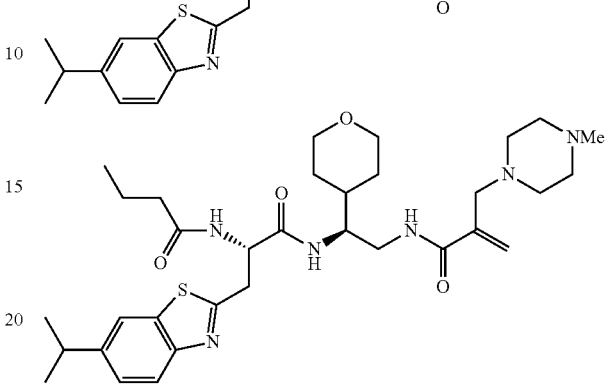
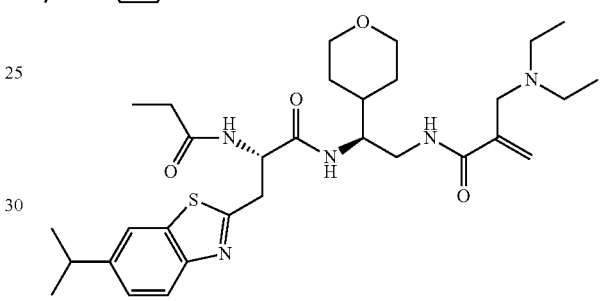
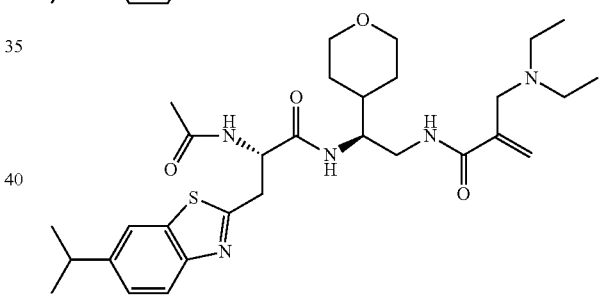
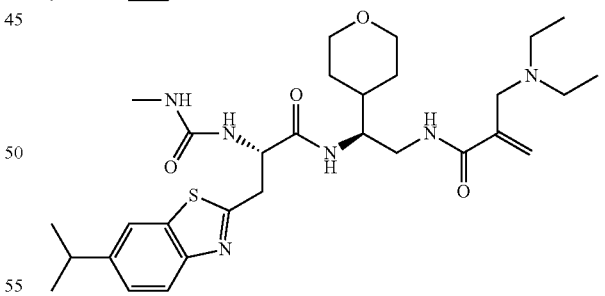
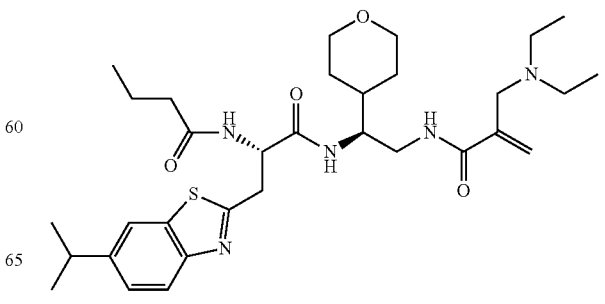

301
-continued
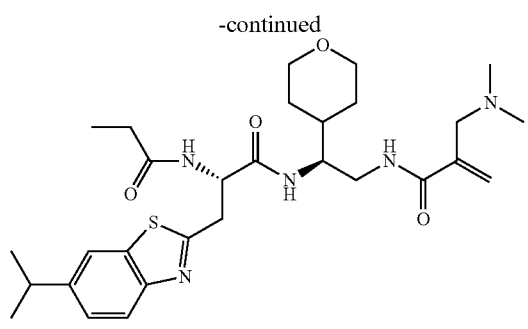
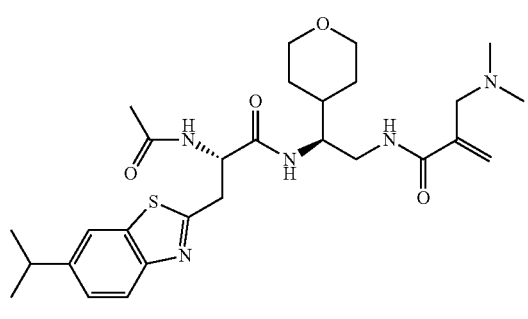
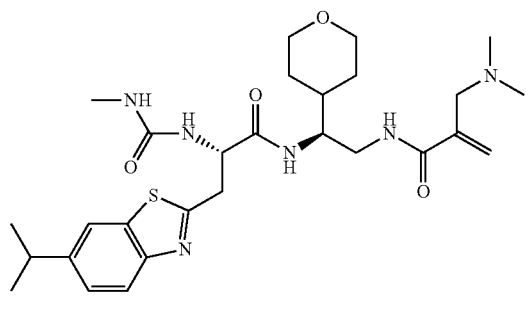
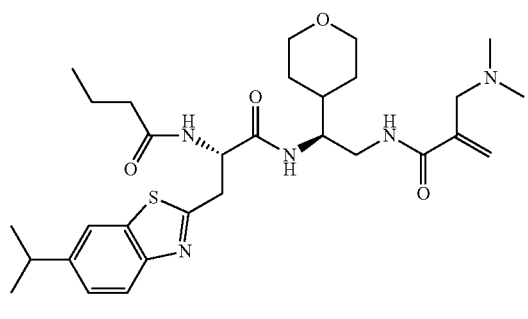
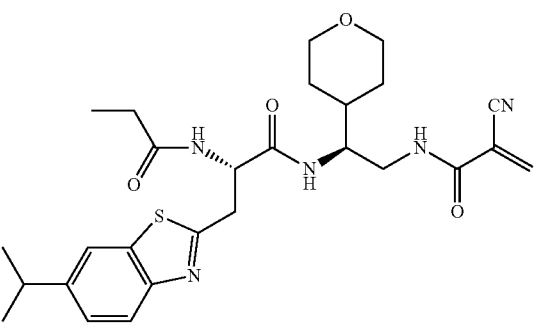
302
-continued
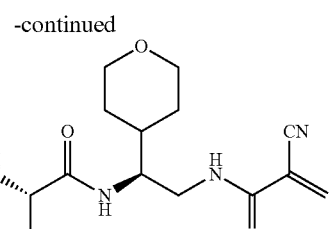
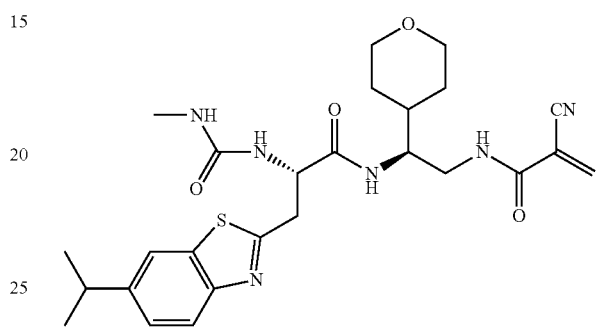
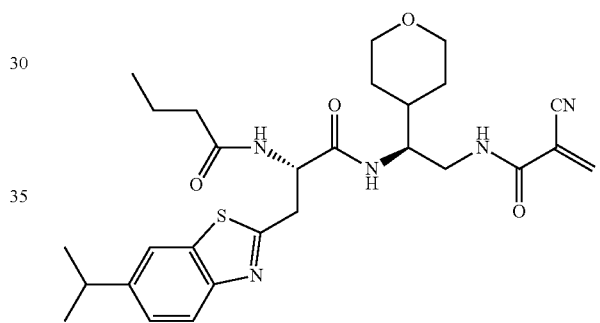
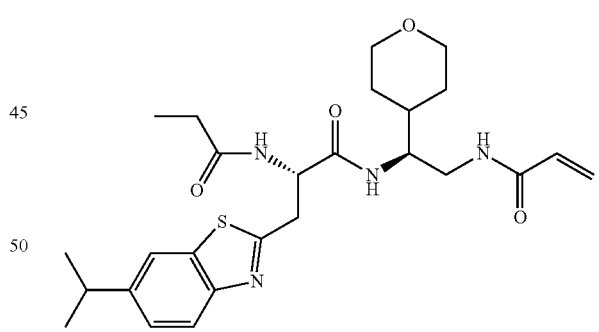
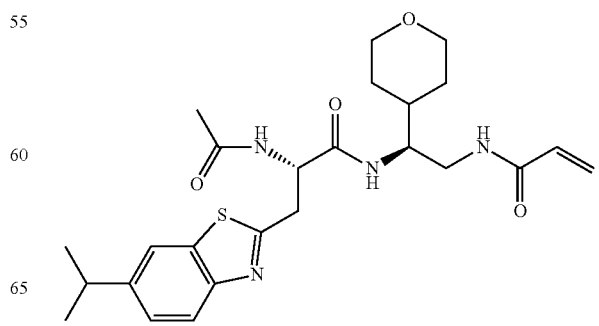

303
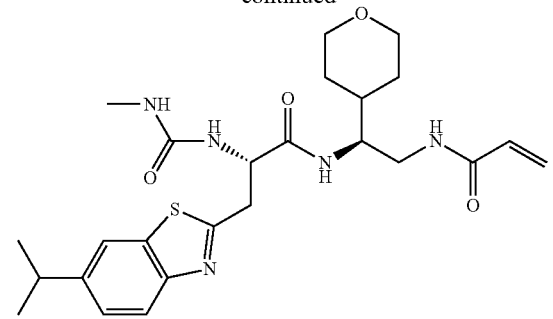
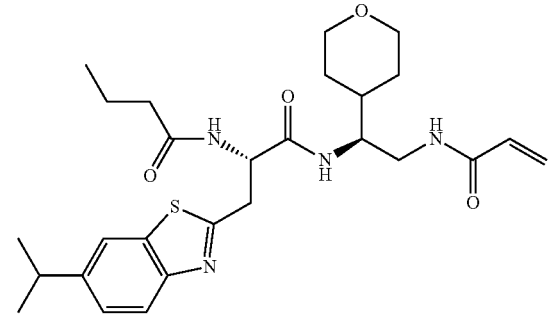
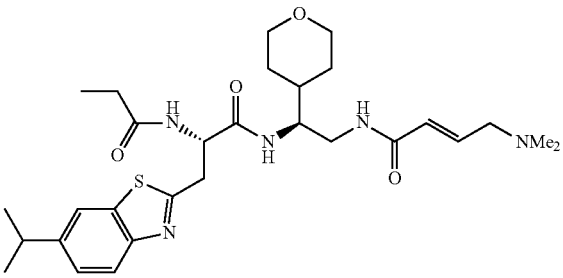
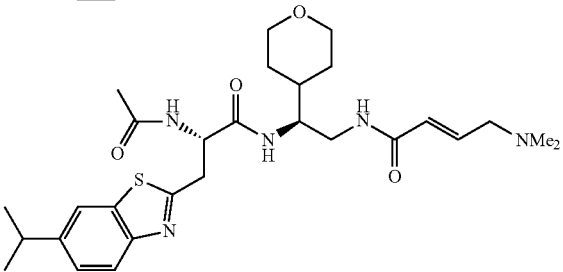
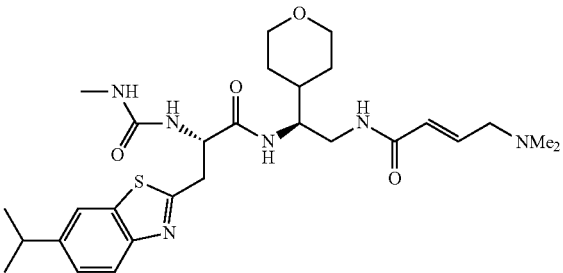
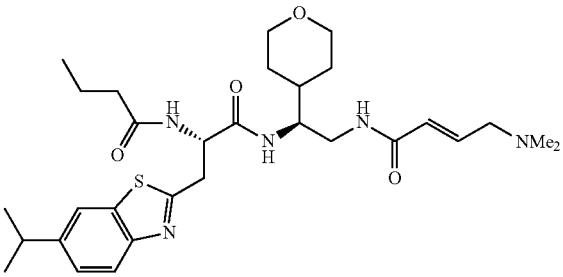
304
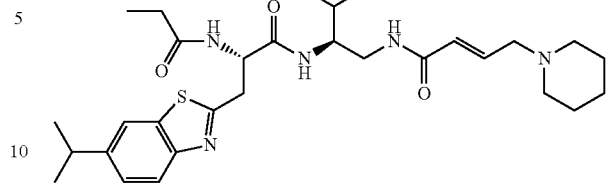
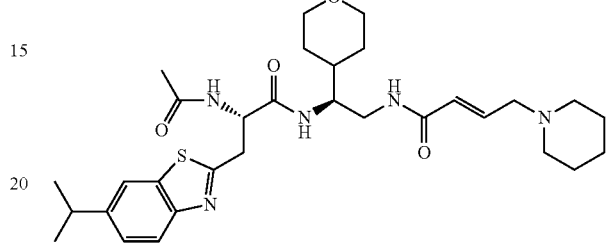
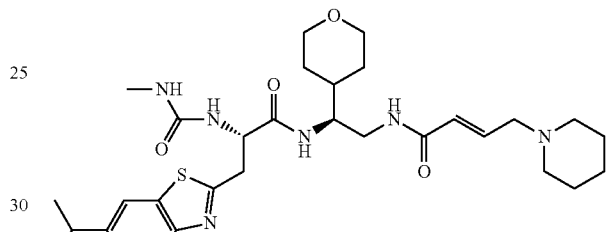
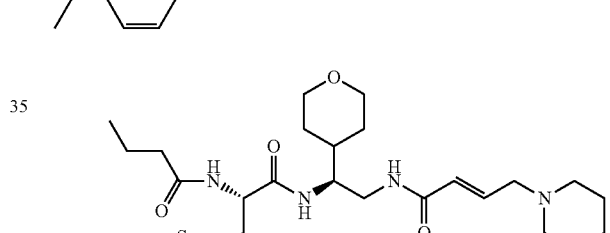
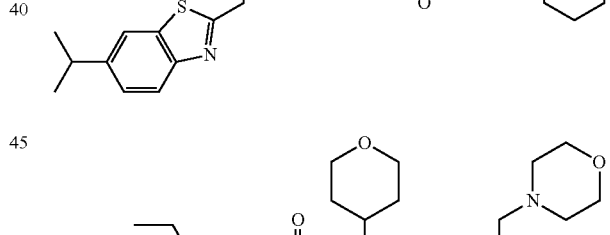
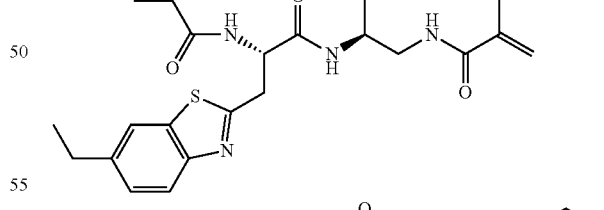
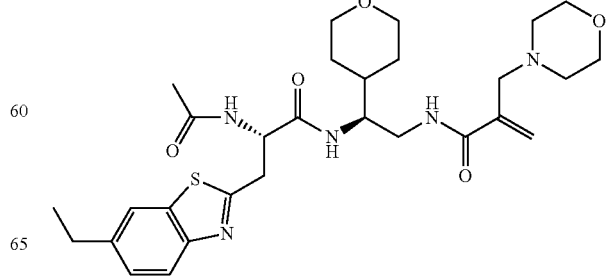

305
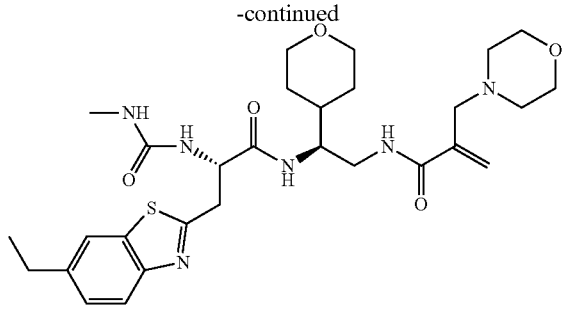
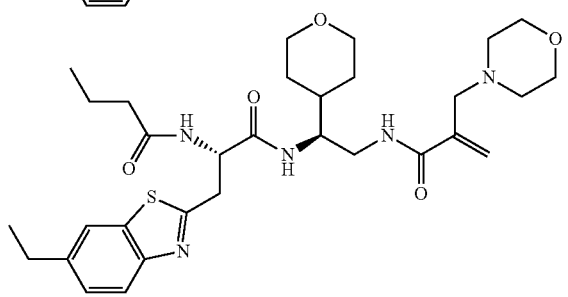
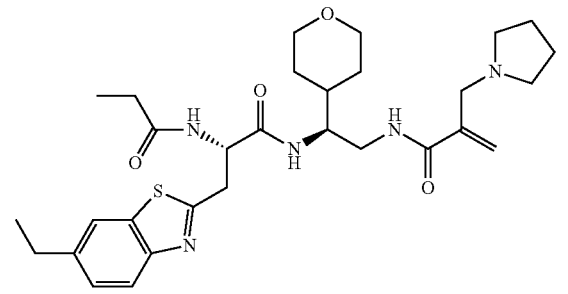
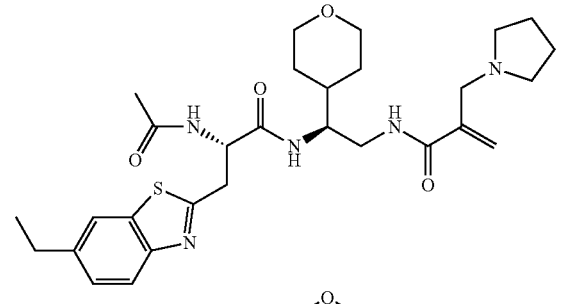
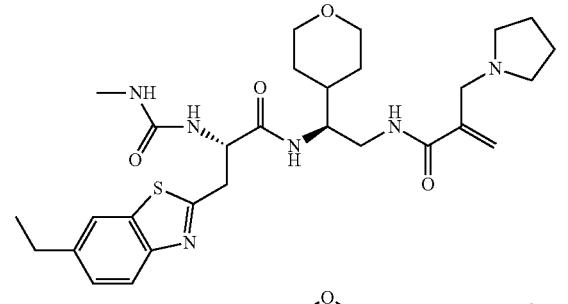
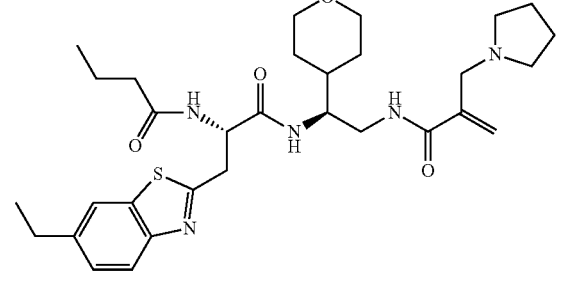
306
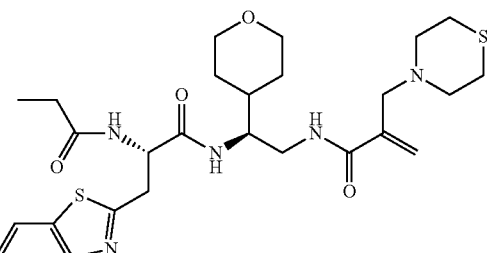
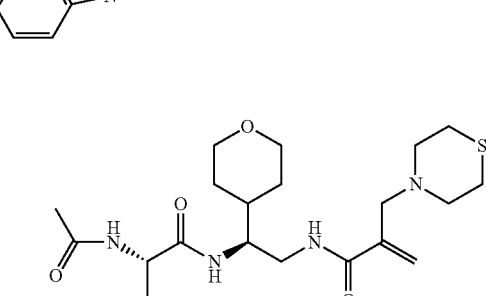
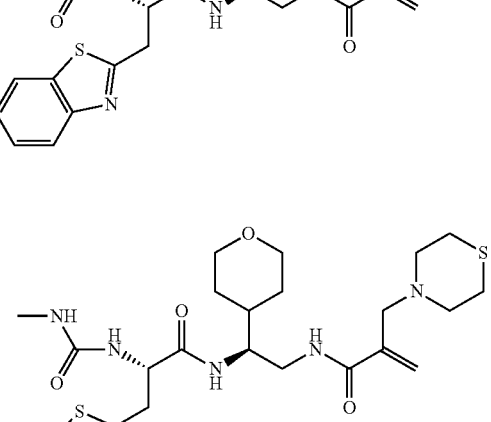
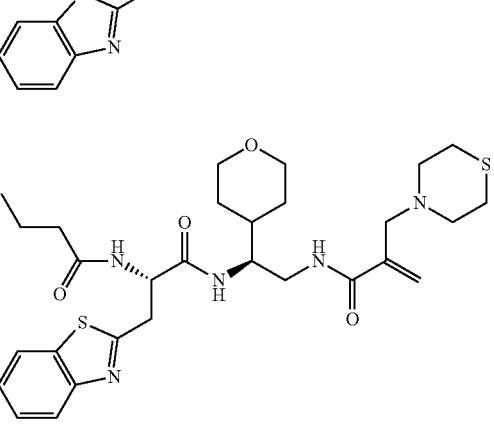
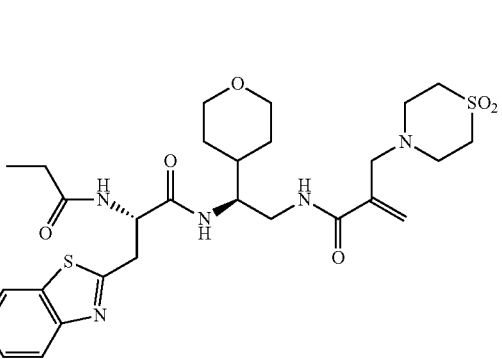

307
-continued
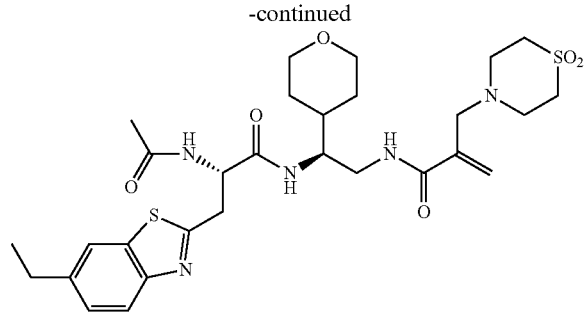
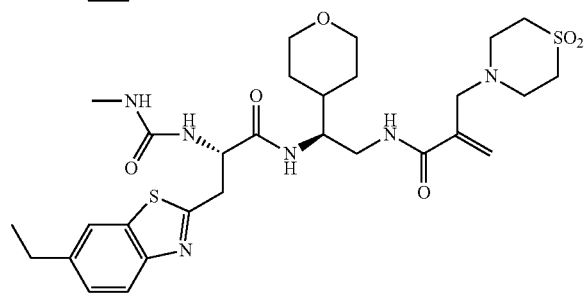
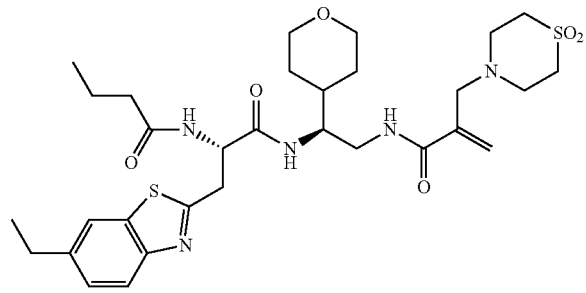
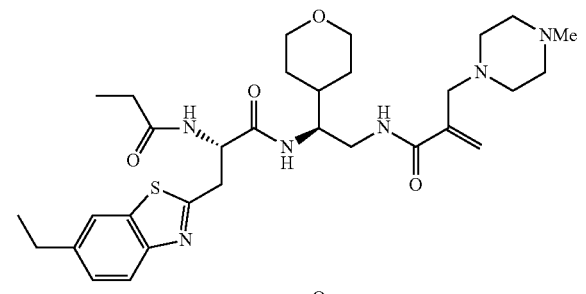
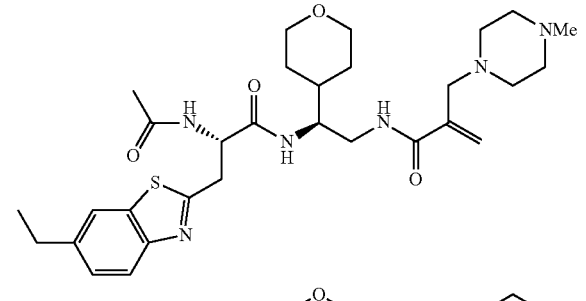
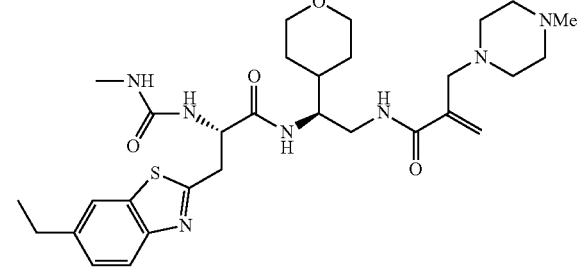
308
-continued
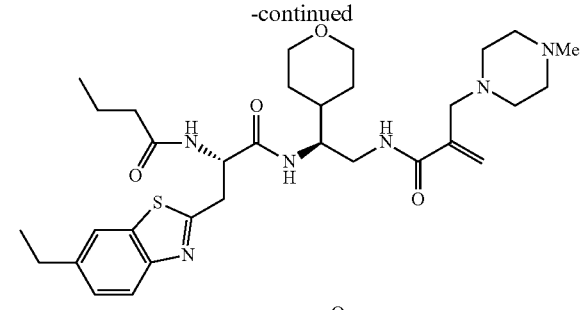
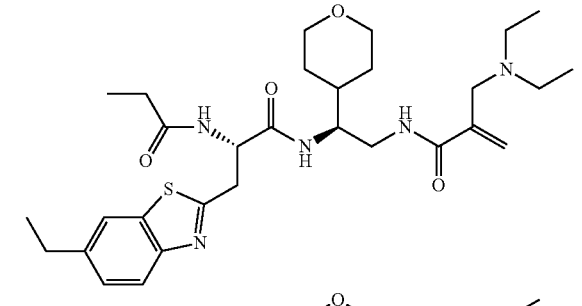
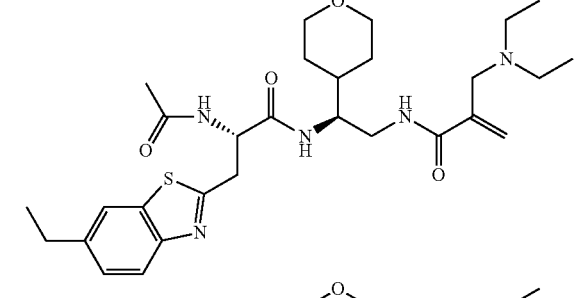
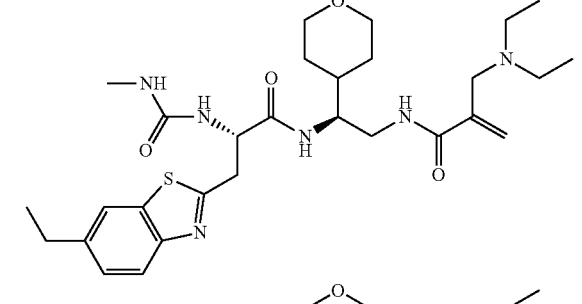
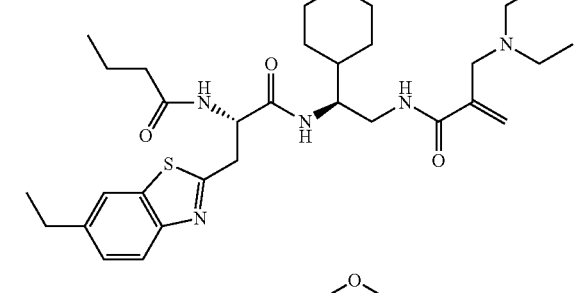
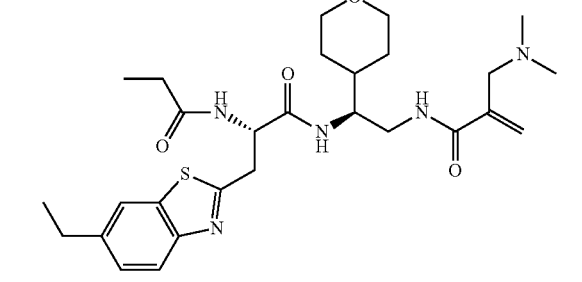

309
-continued
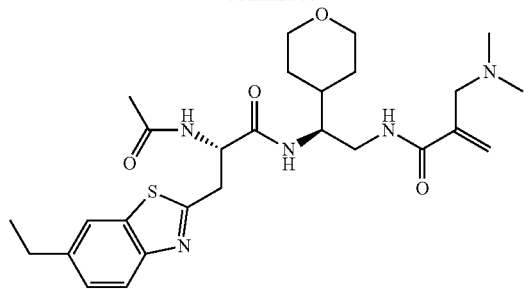
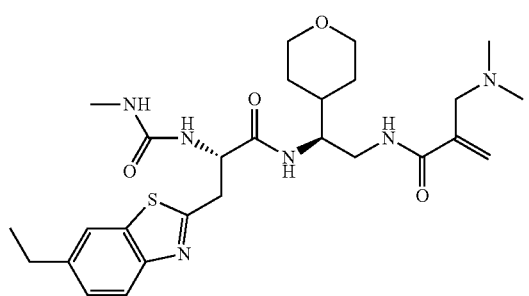
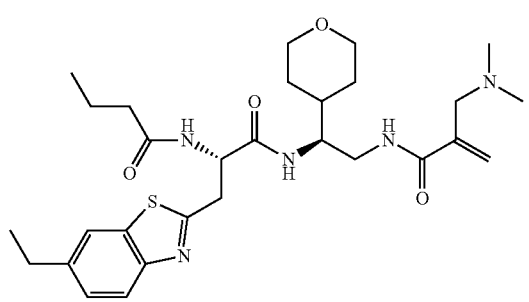
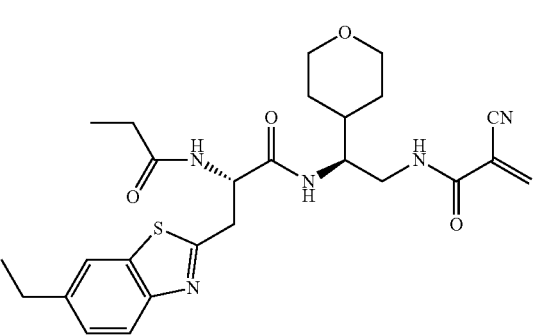
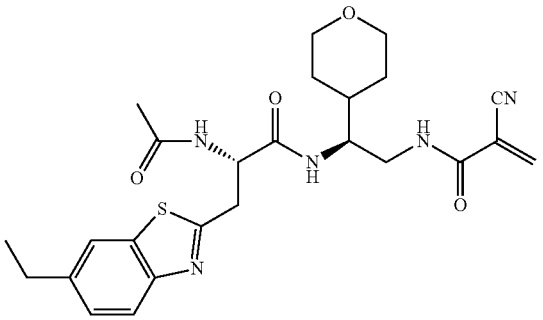
310
-continued
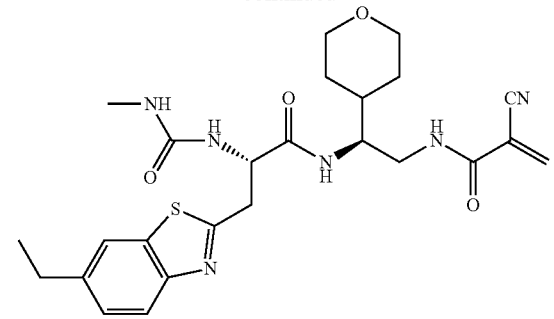
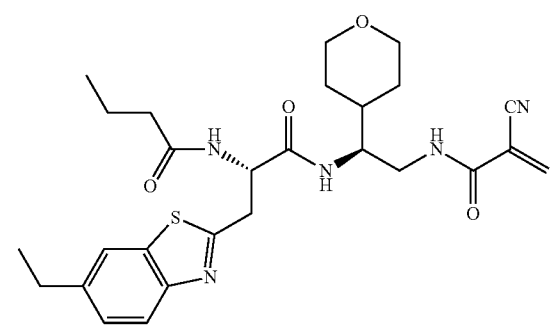
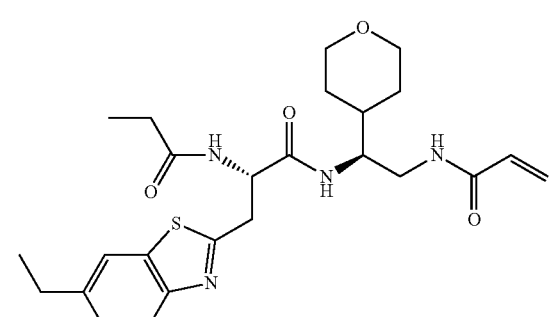
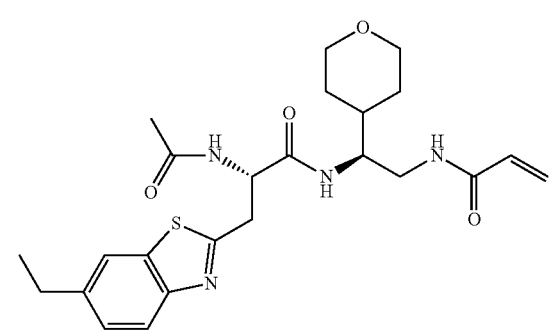
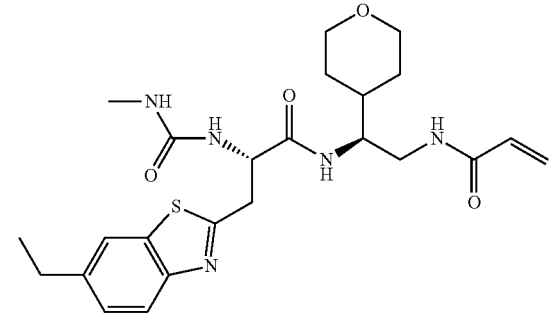

311
-continued
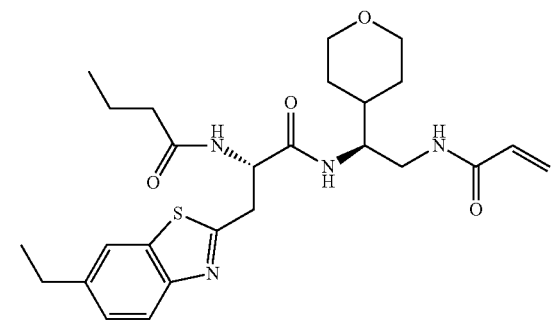
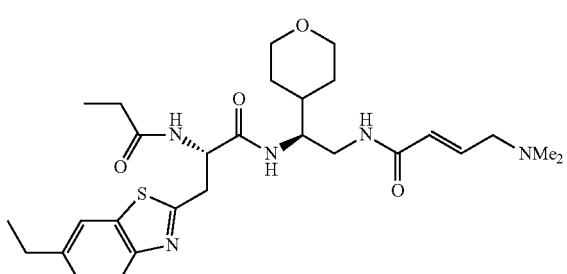
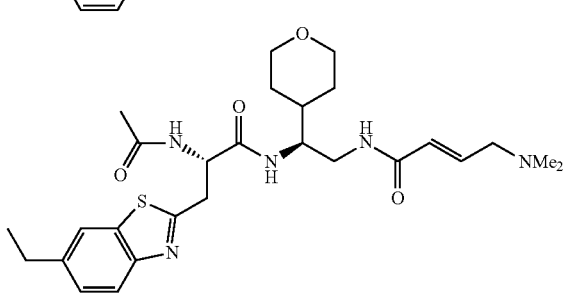
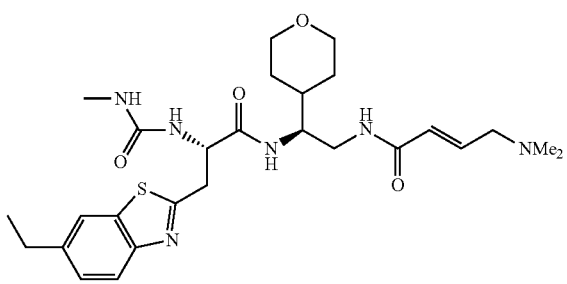
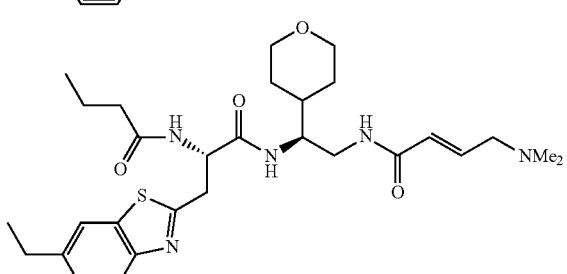
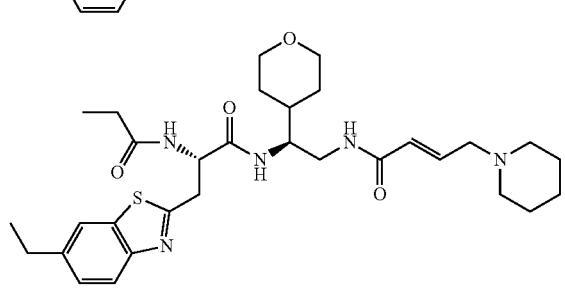
312
-continued
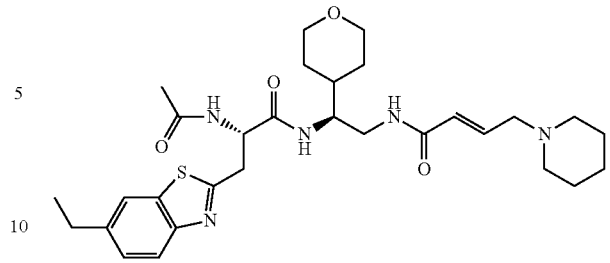
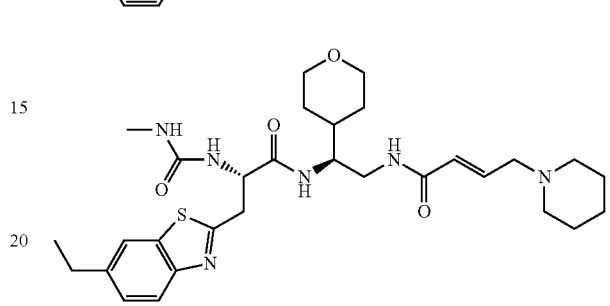
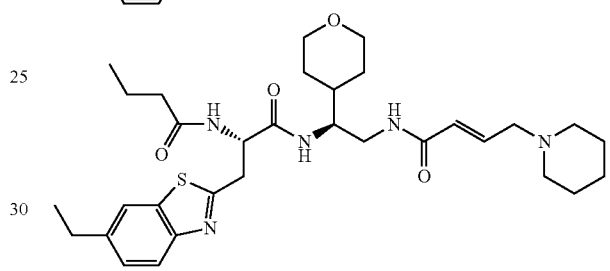
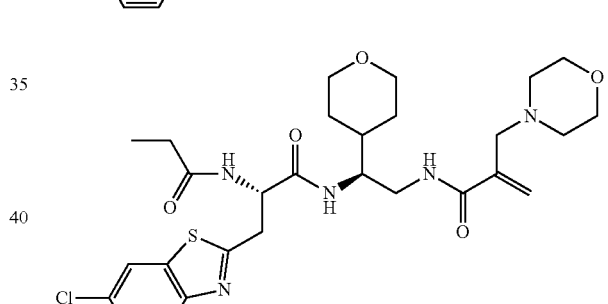
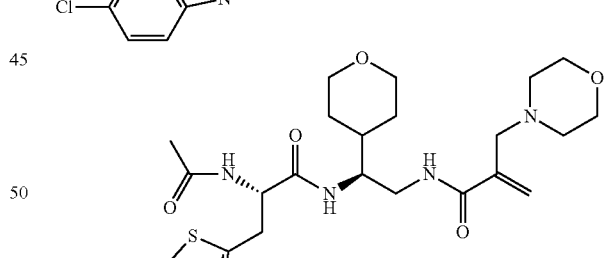
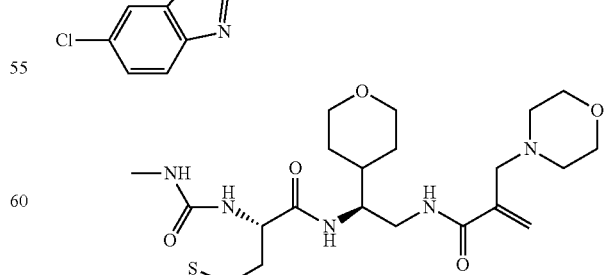

313
-continued
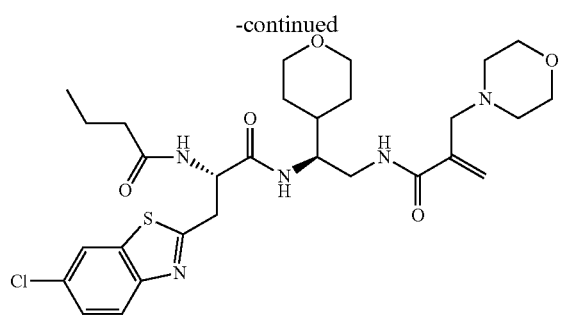
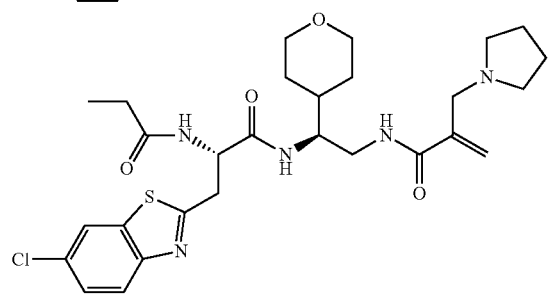
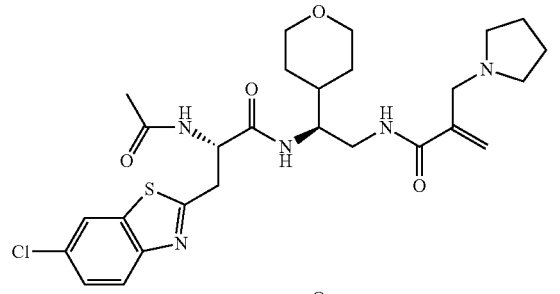
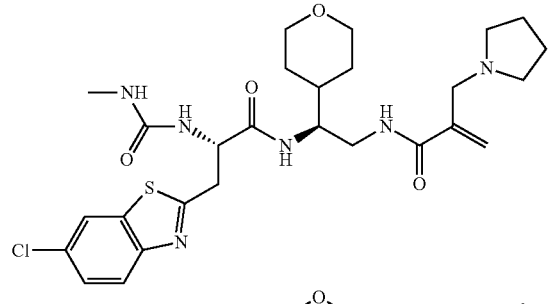
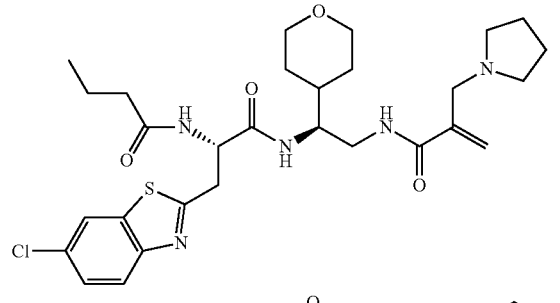
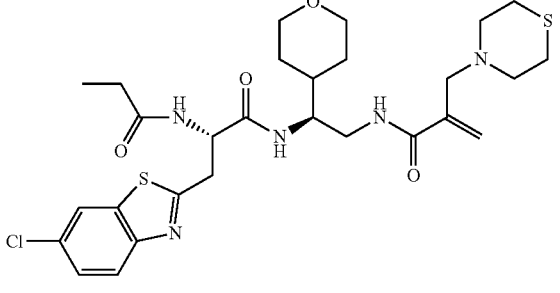
314
-continued
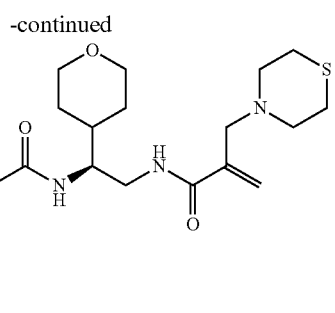
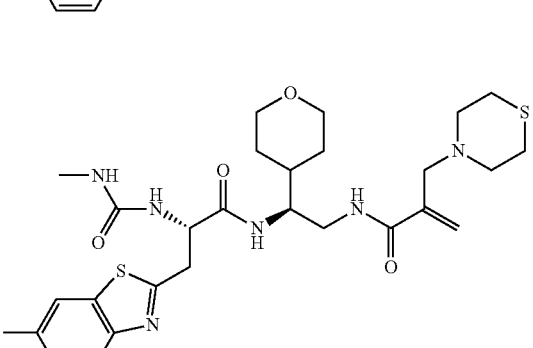
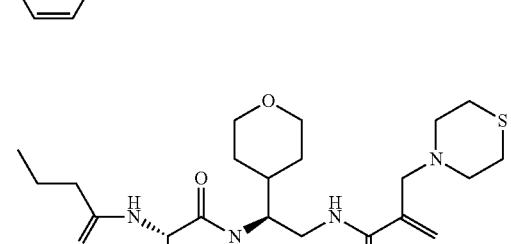
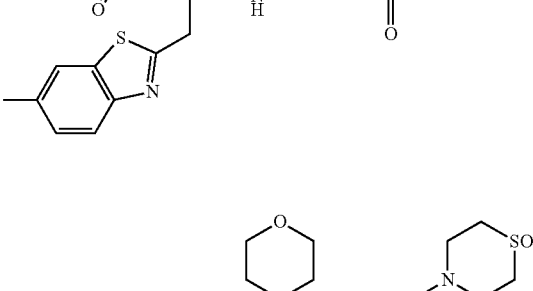
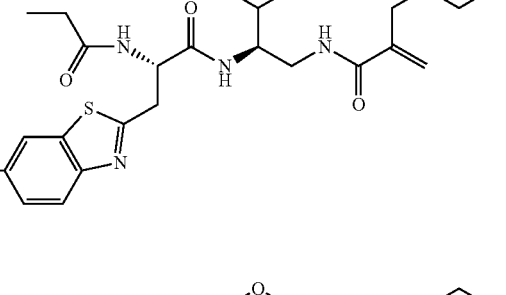
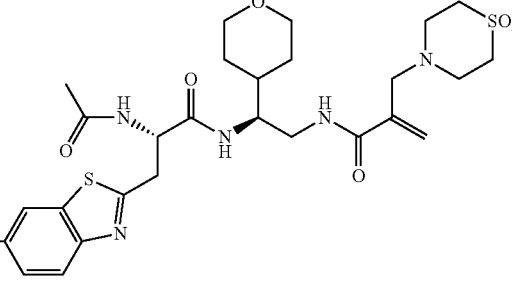

315
-continued
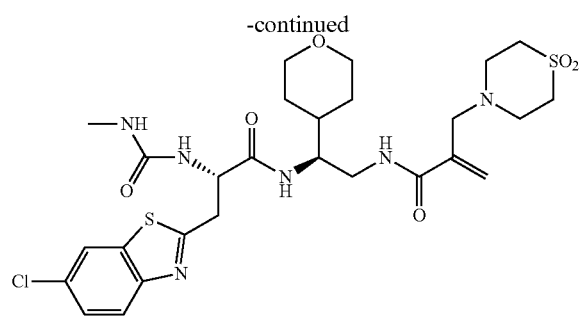
316
-continued
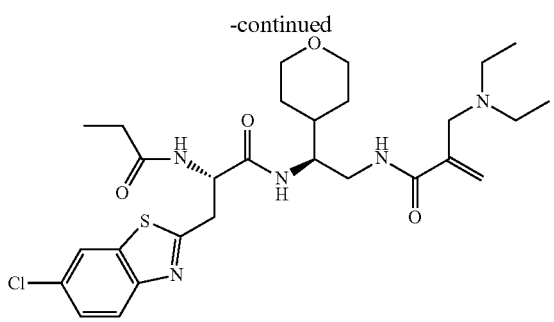
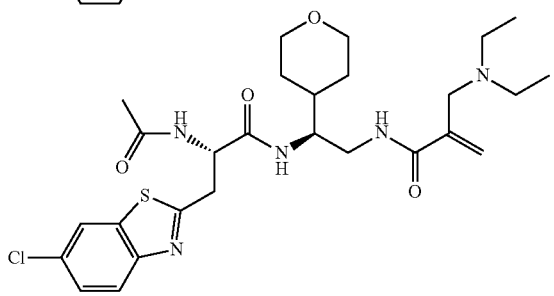
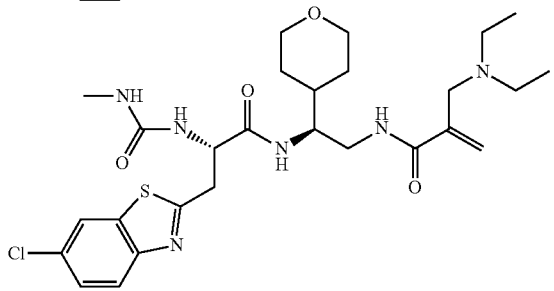
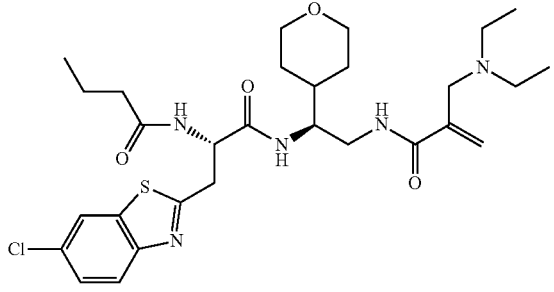
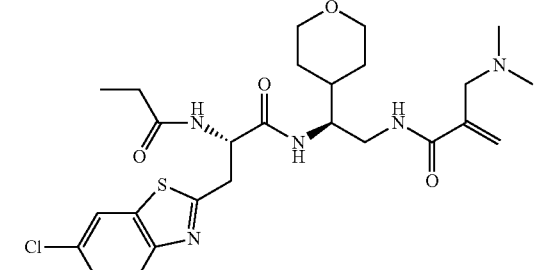
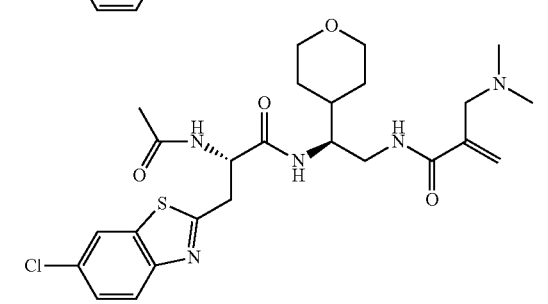

317
-continued
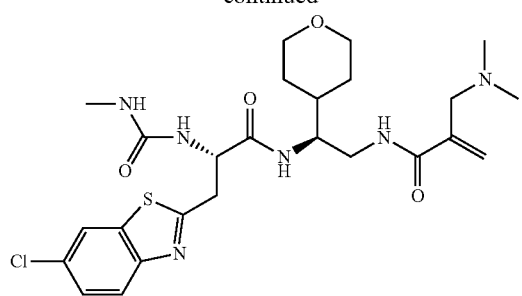
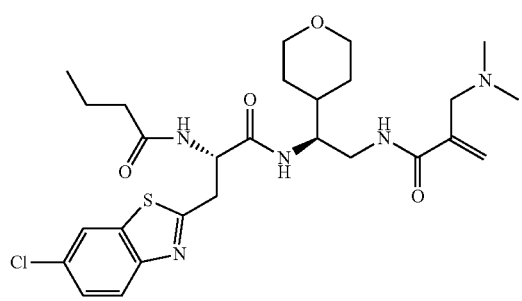
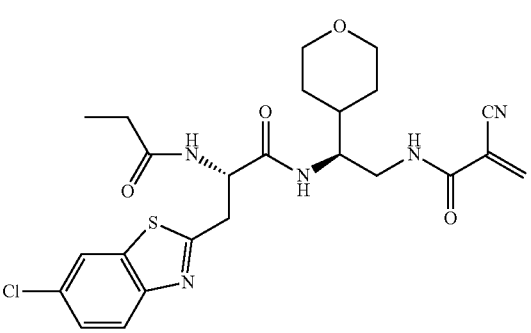
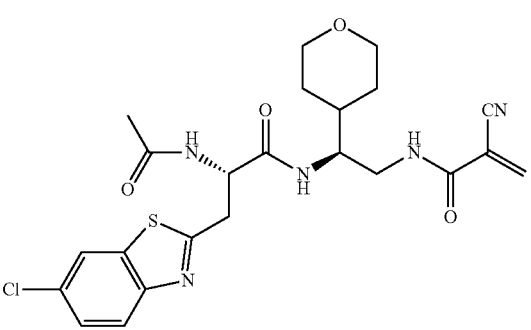
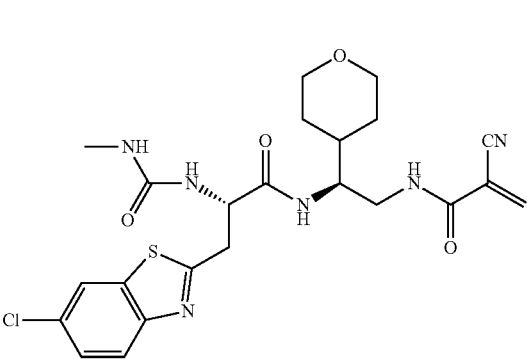
318
-continued
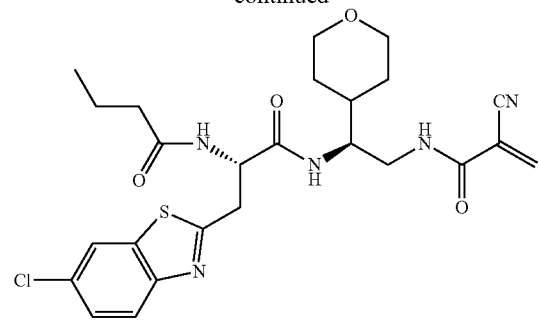
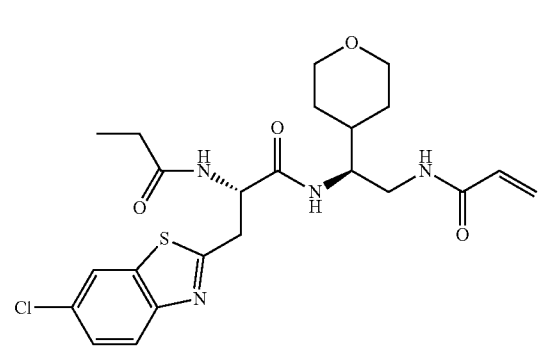
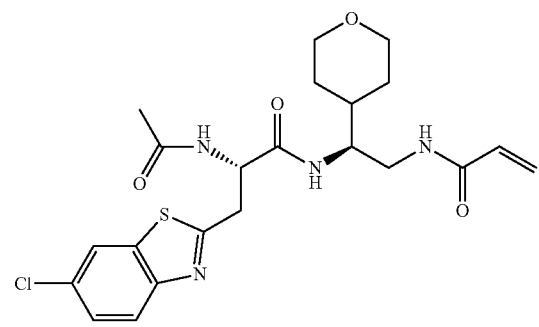
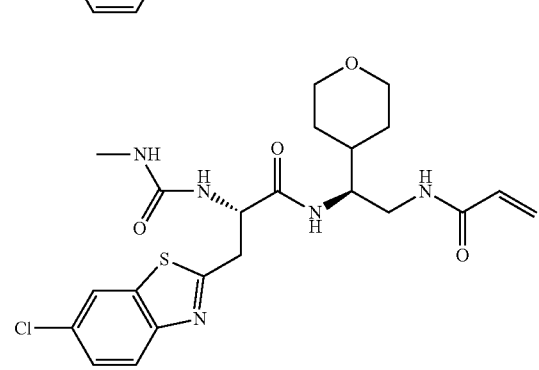
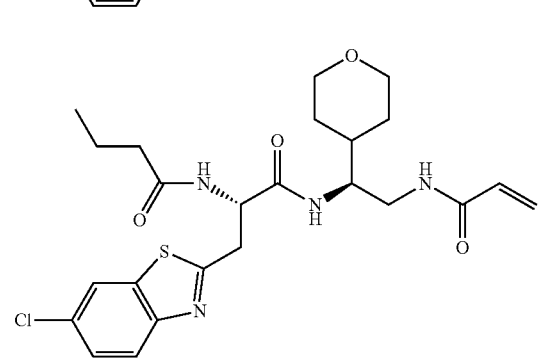

319
-continued
320
-continued
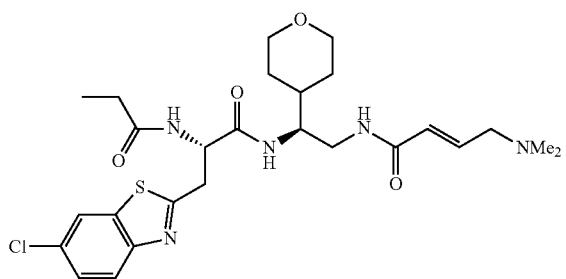
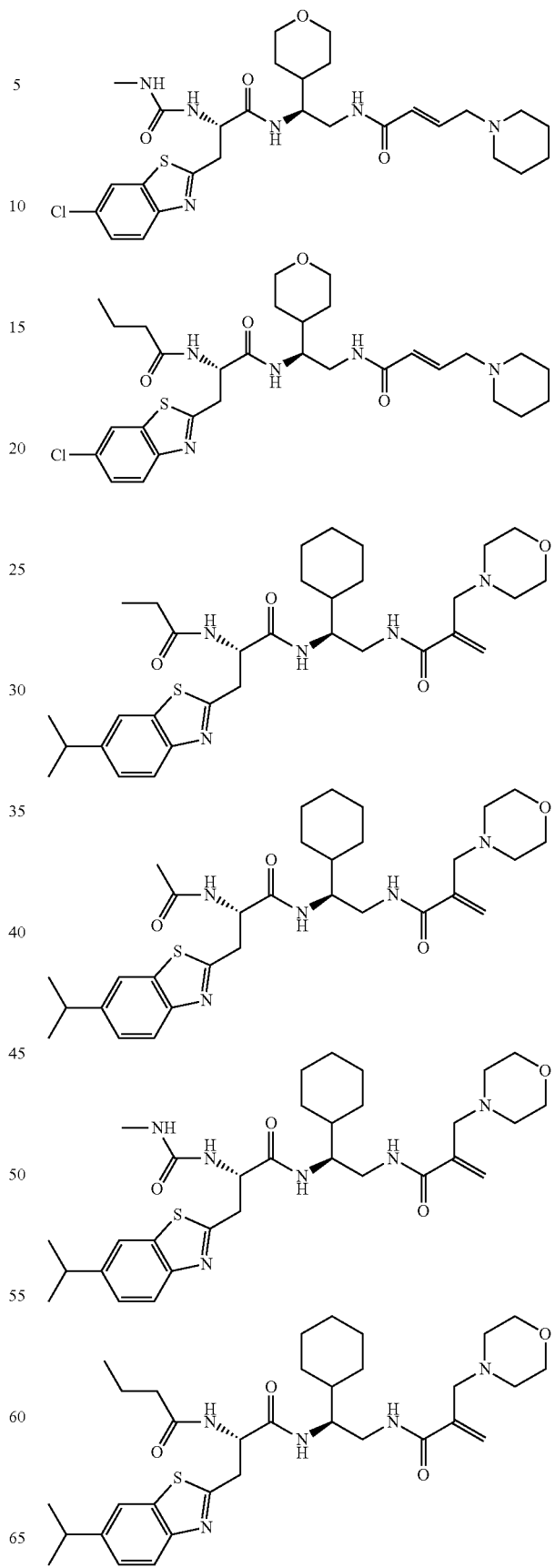

321
-continued
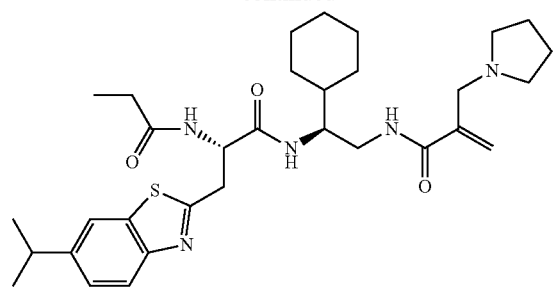
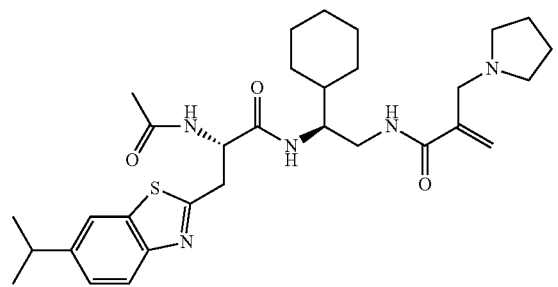
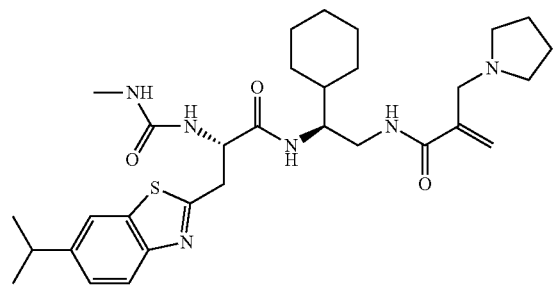
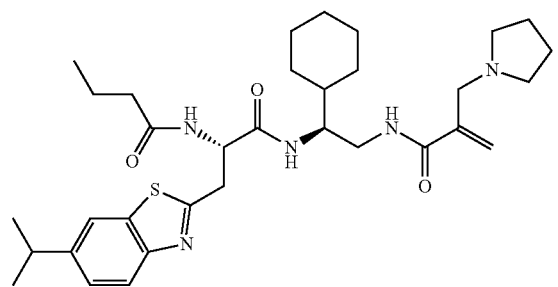
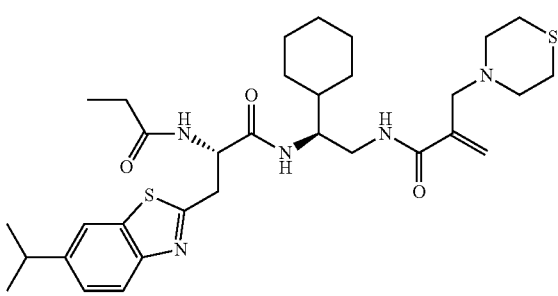
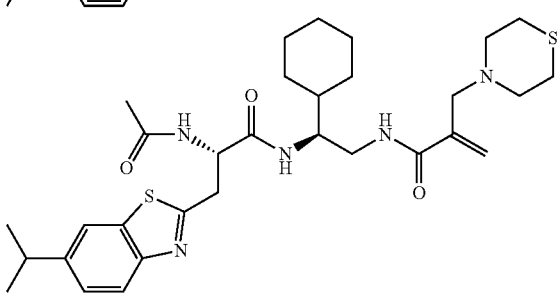
322
-continued
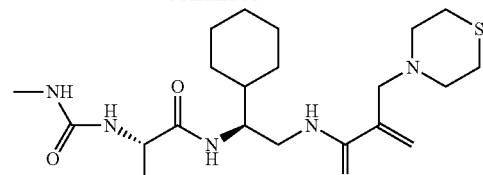
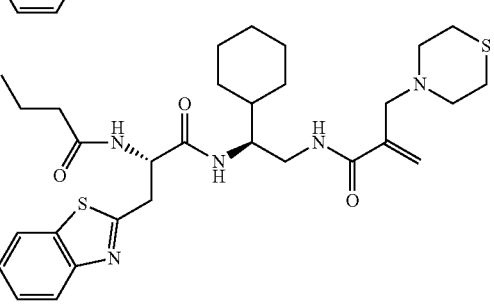
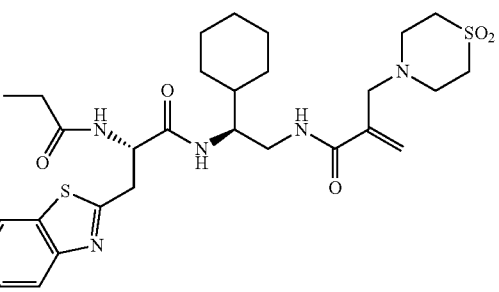
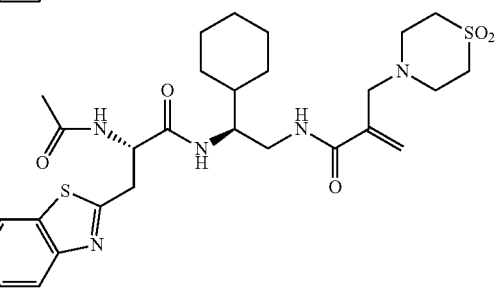
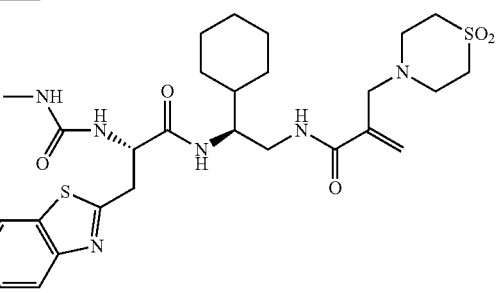
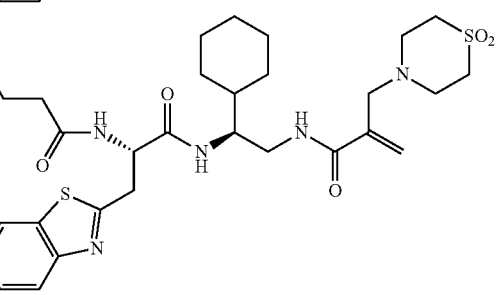

323
-continued
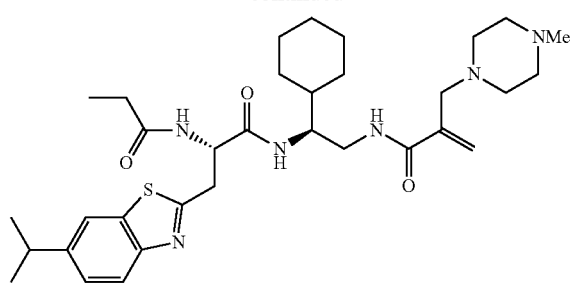
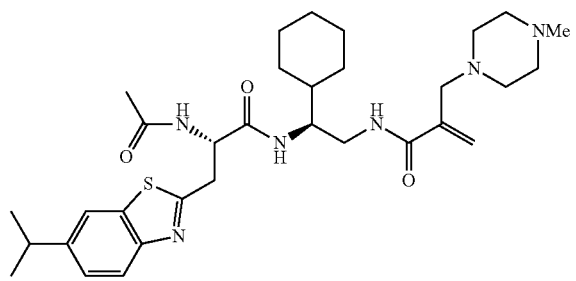
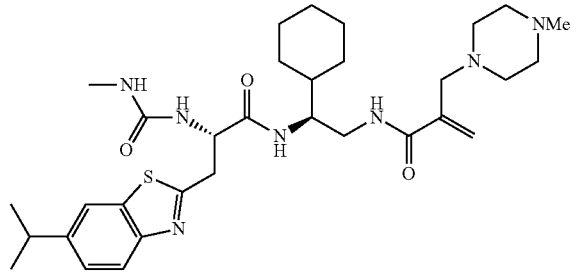
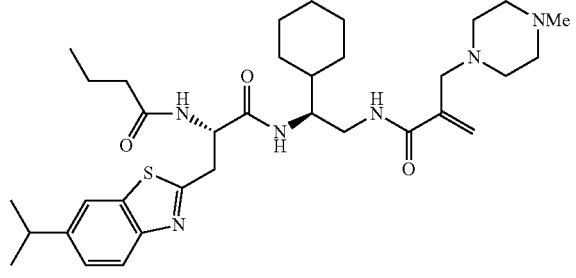
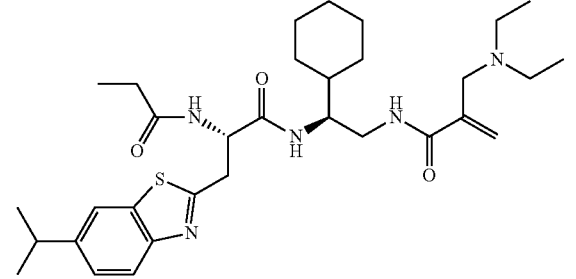
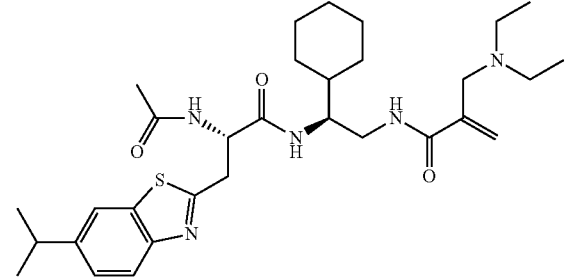
324
-continued
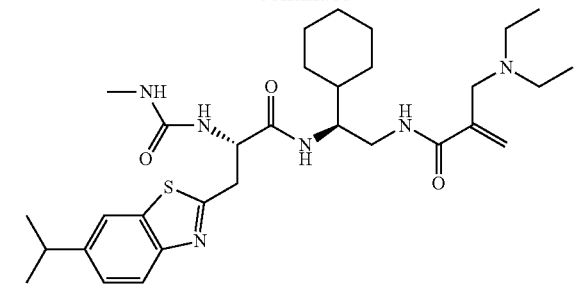
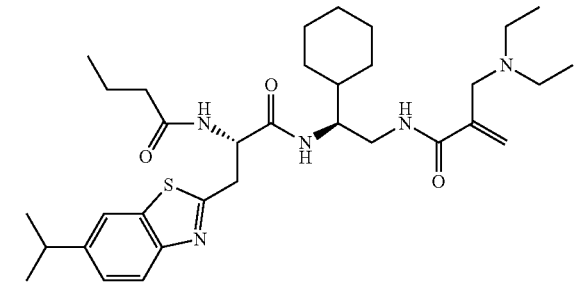
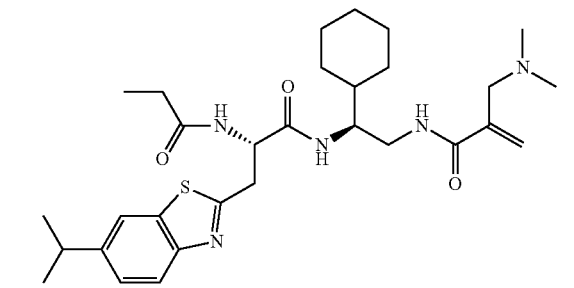
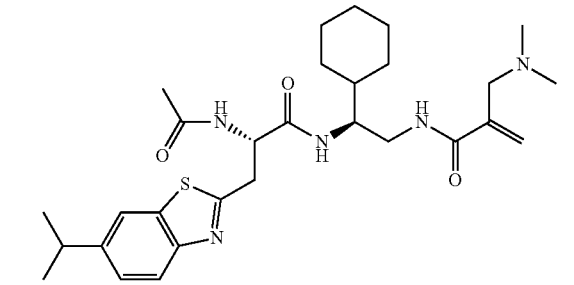
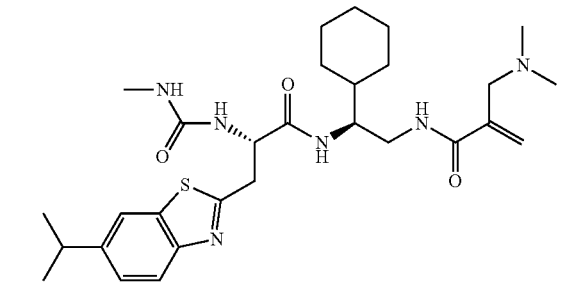
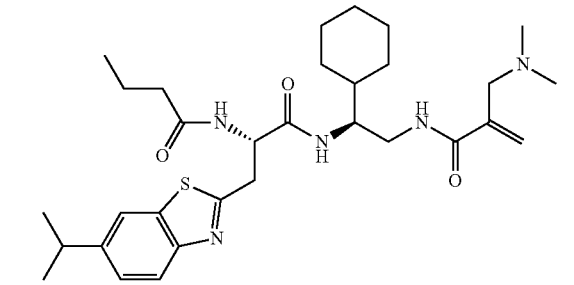

325
-continued
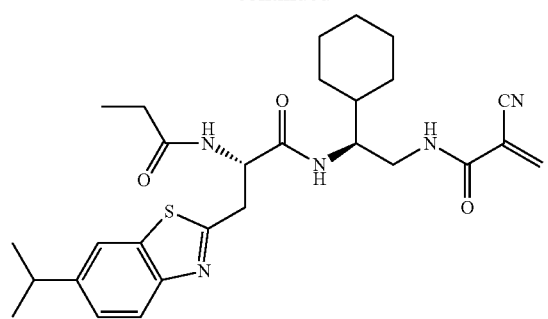
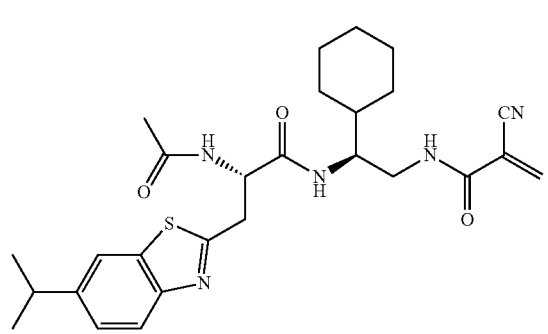
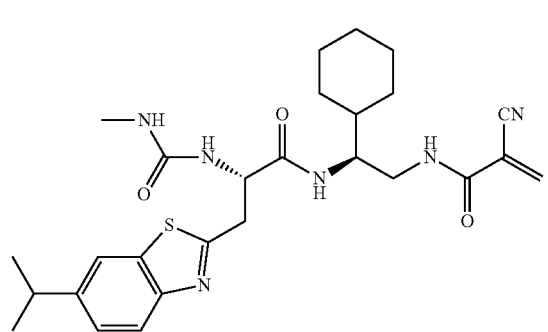
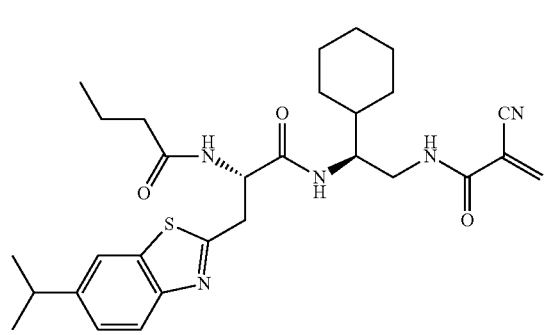
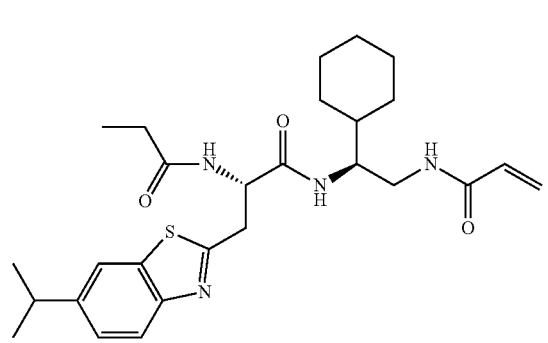
326
-continued
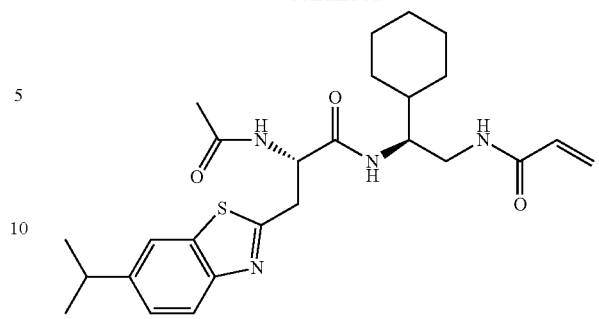
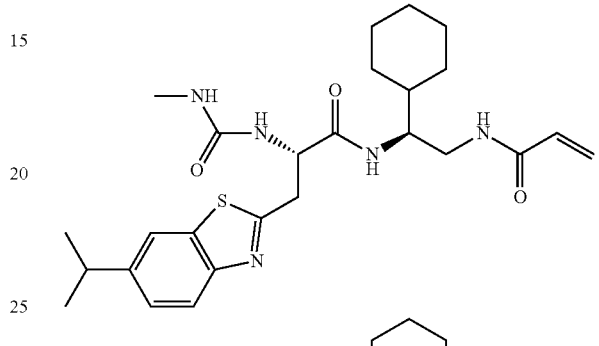
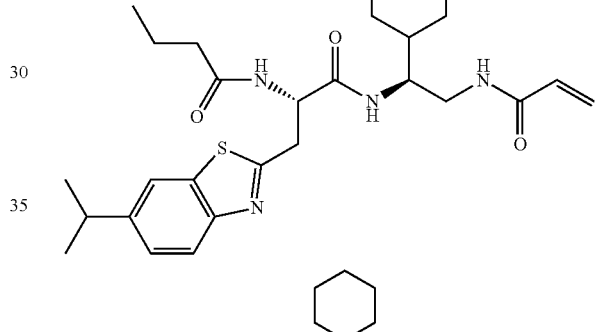
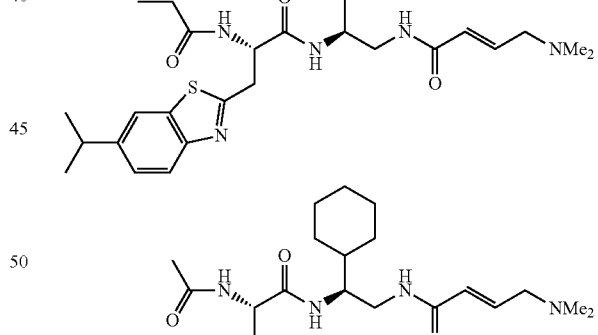
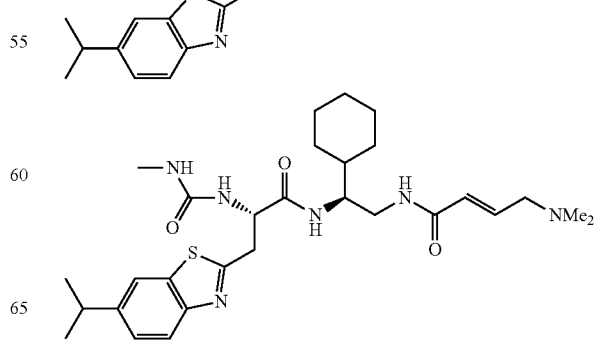

327
-continued
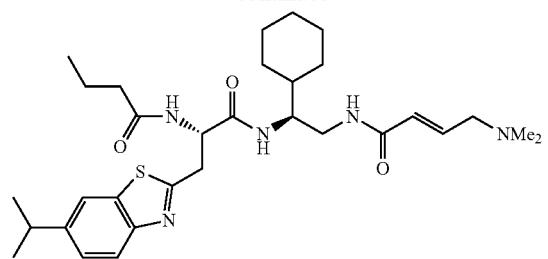
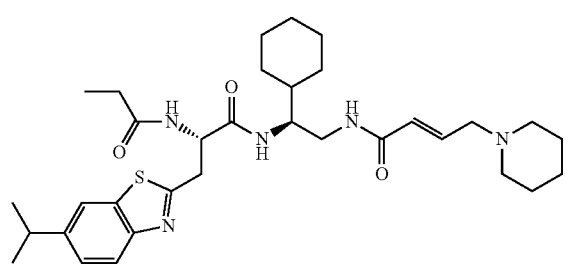
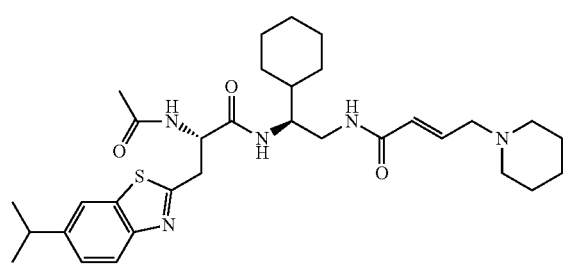
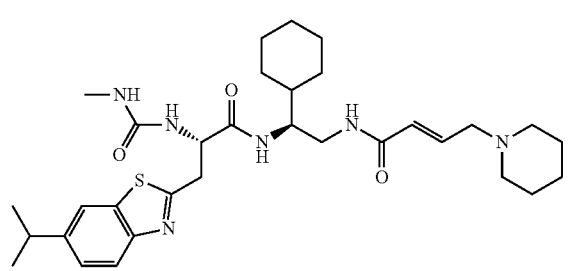
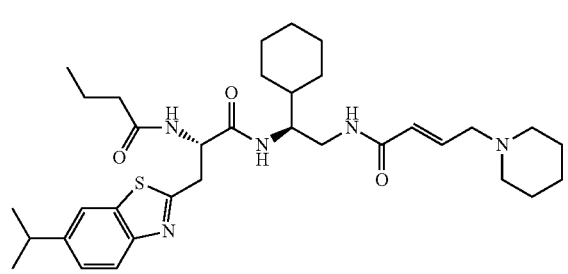
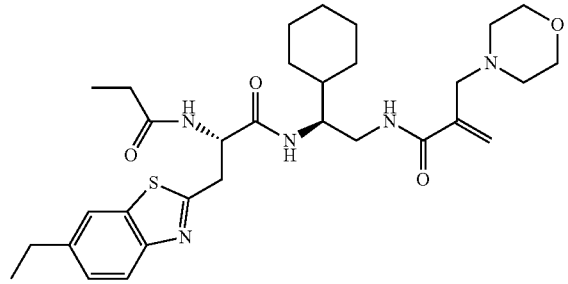
328
-continued
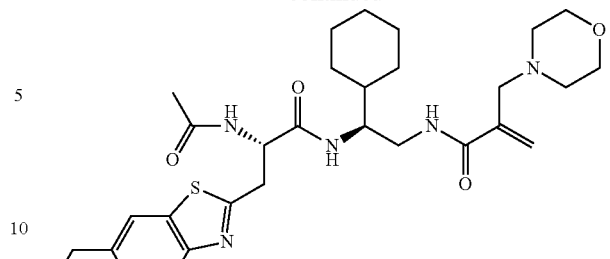
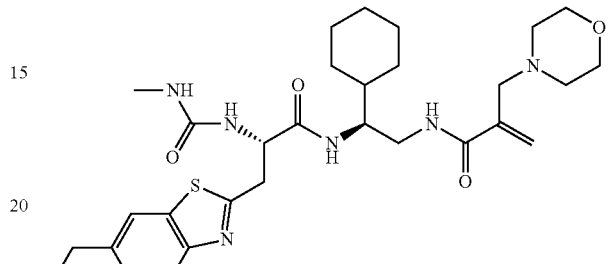
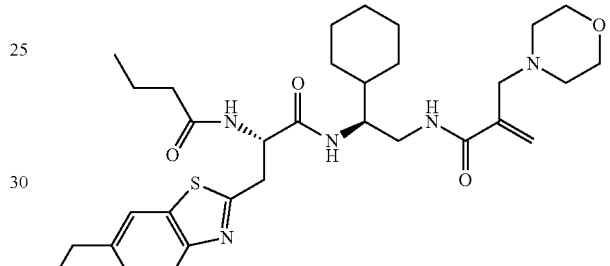
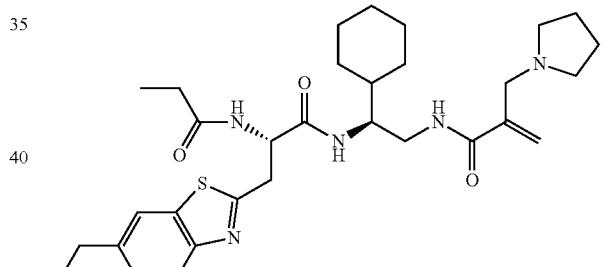
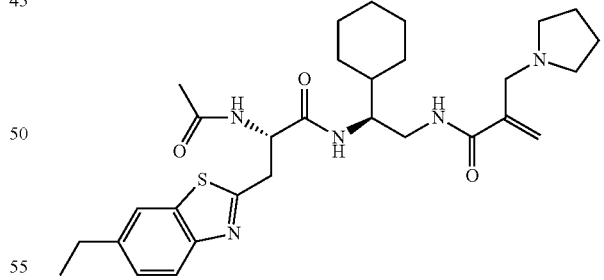
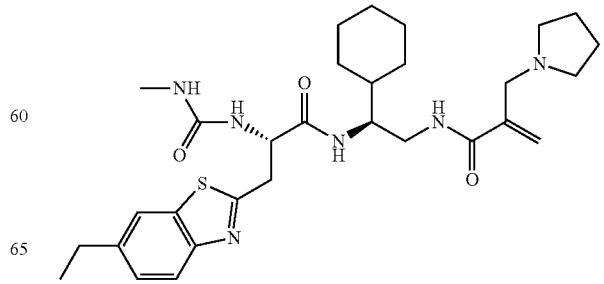

329
-continued
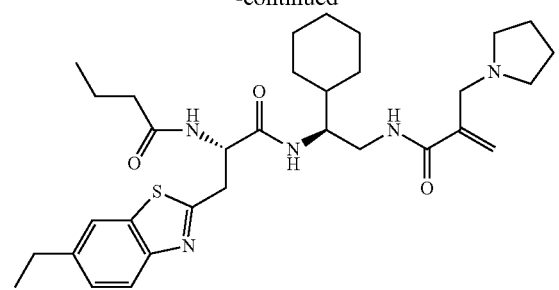
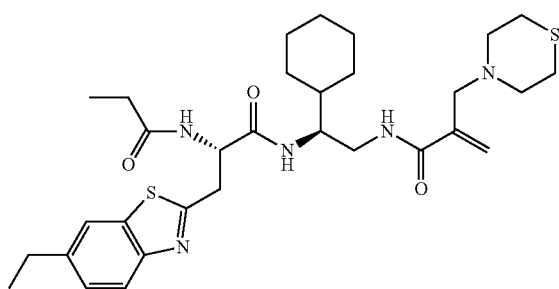
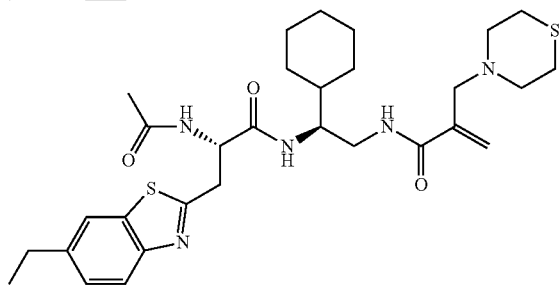
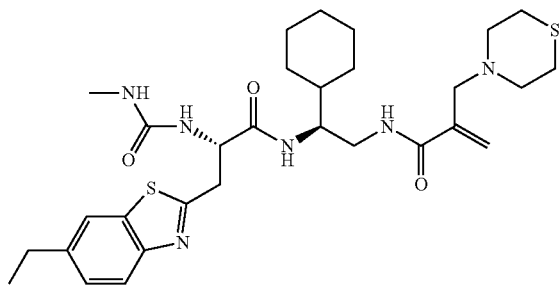
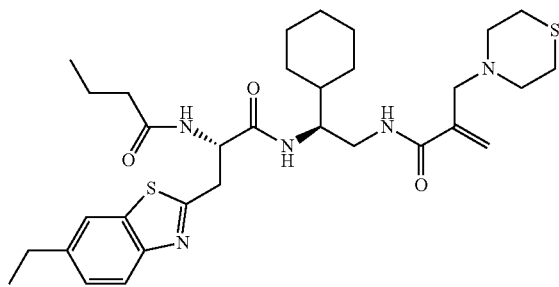
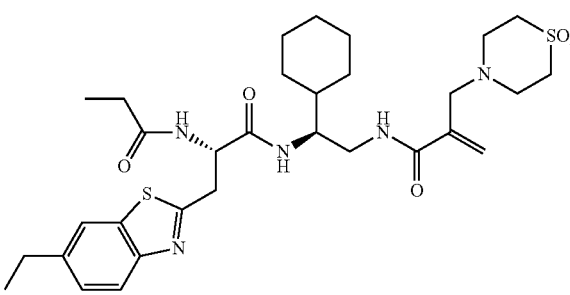
330
-continued
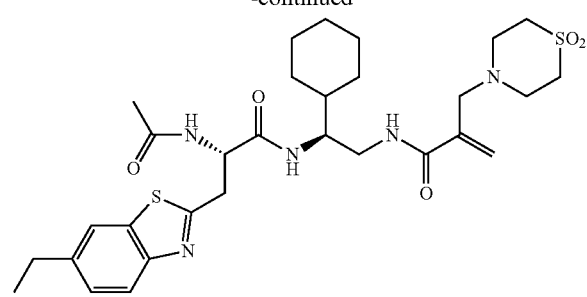
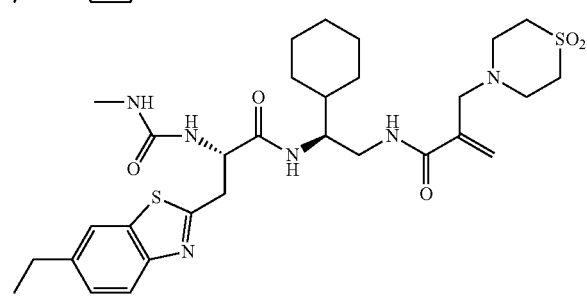
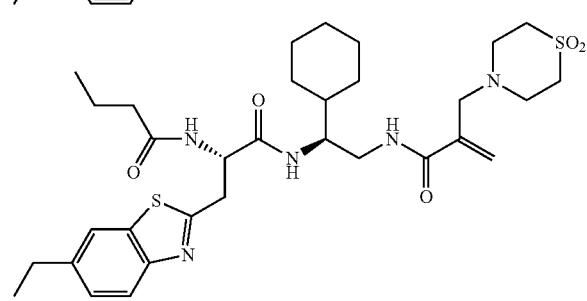
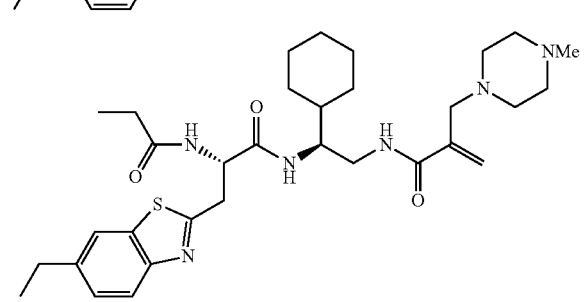
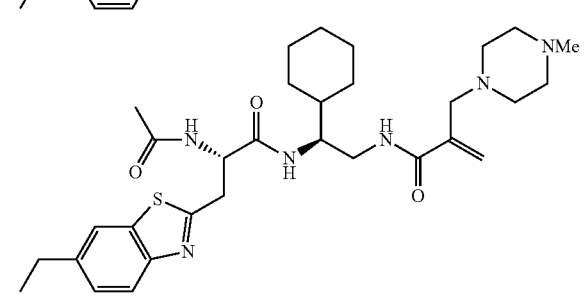
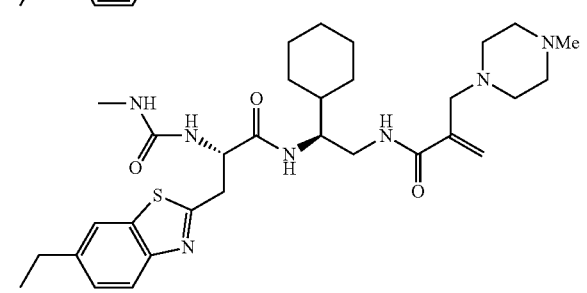

331
-continued
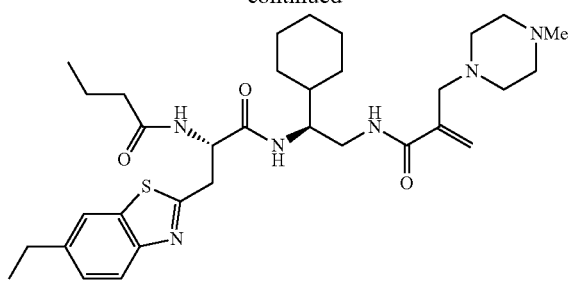
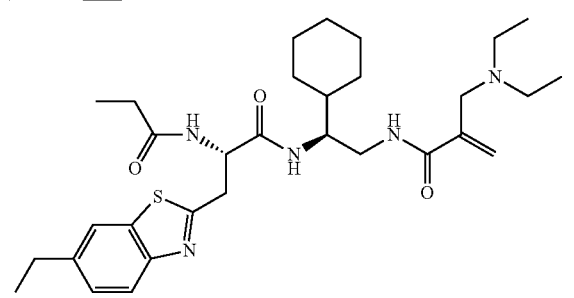
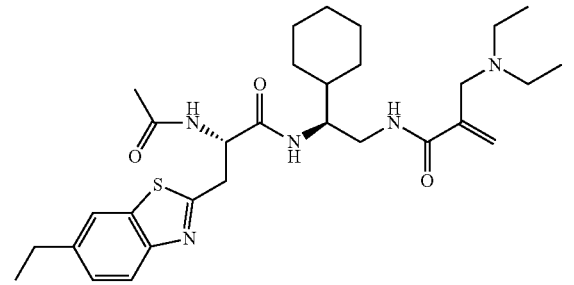
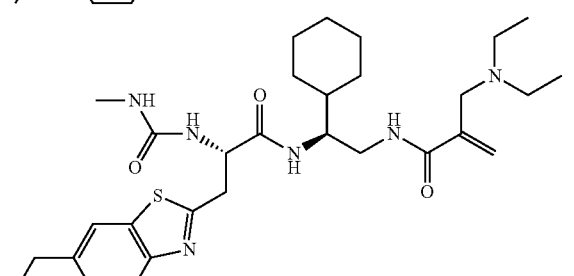
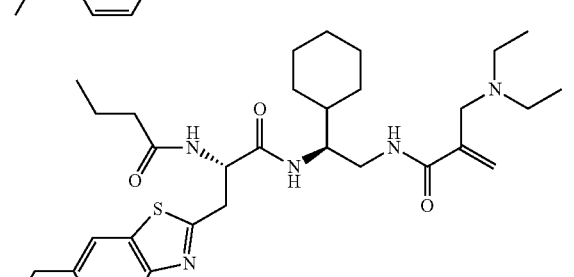
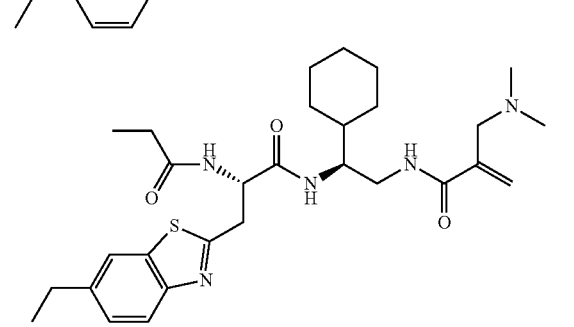
332
-continued
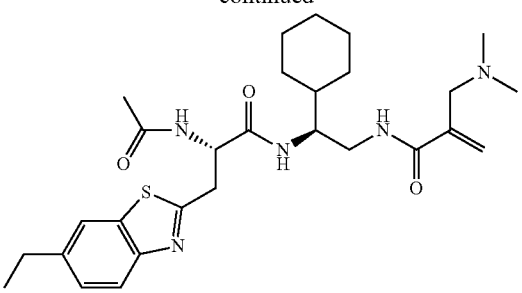
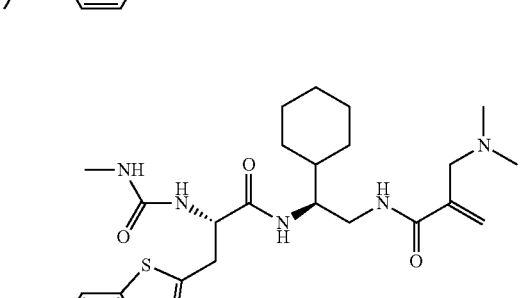
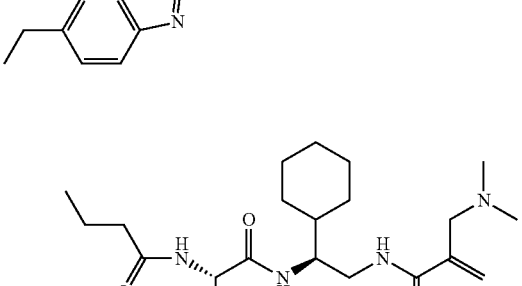
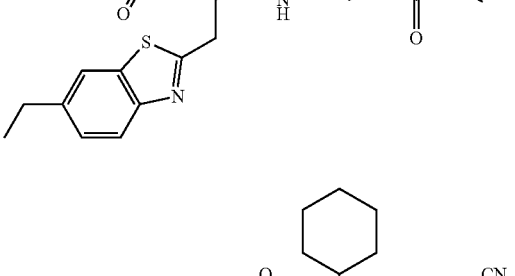
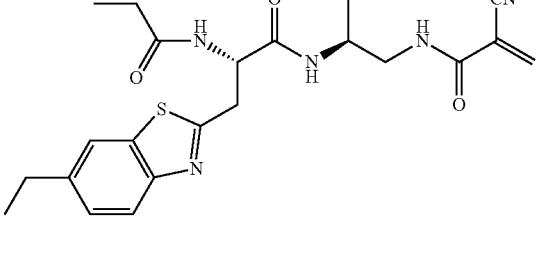
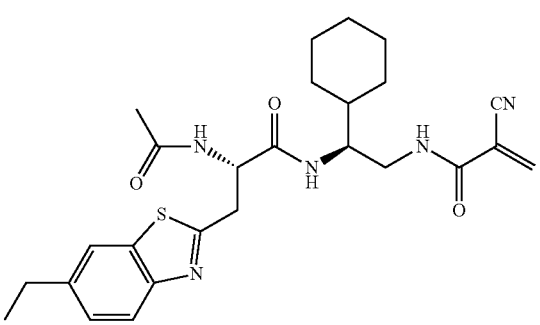

333
-continued
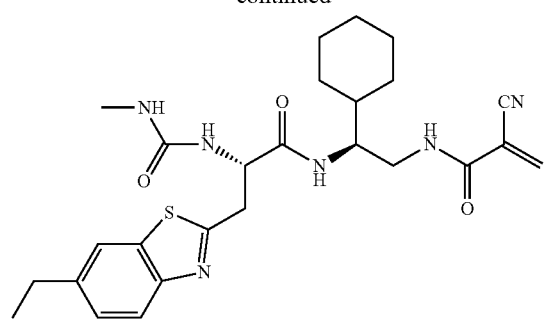
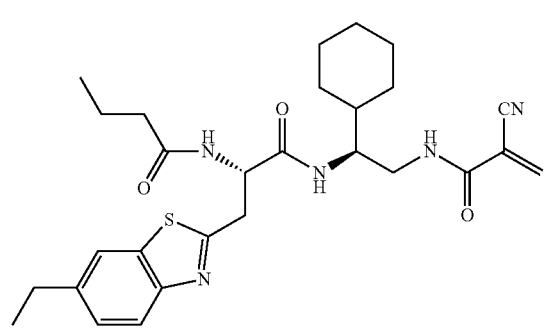
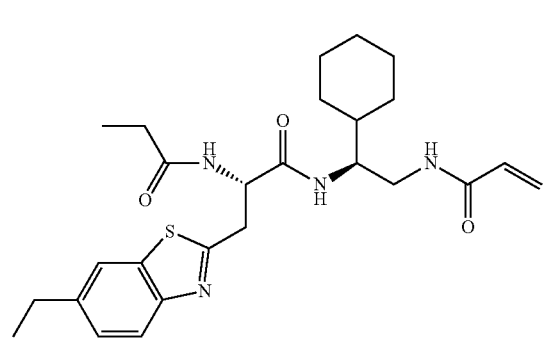
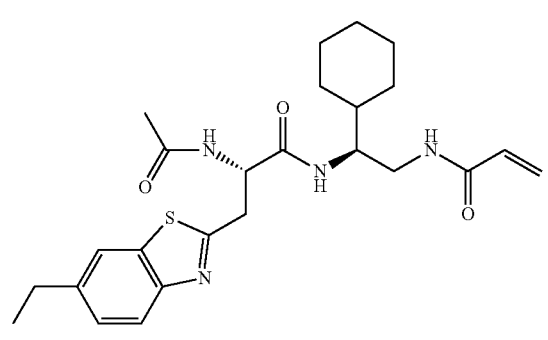
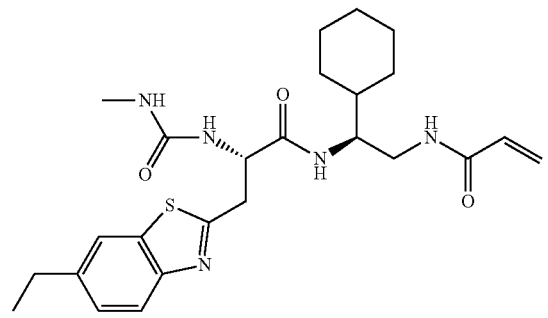
334
-continued
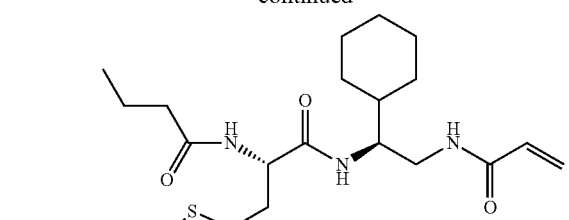
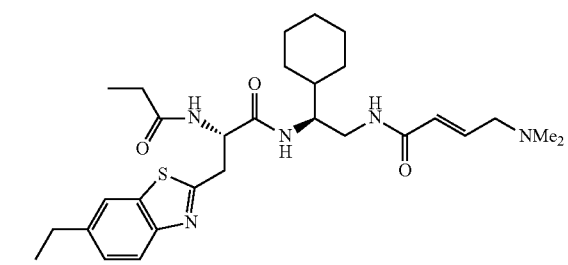
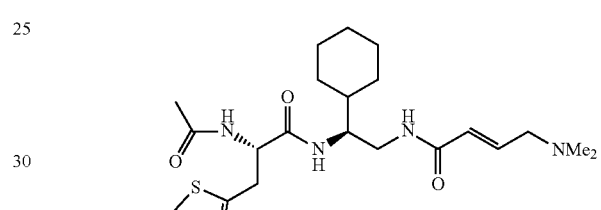
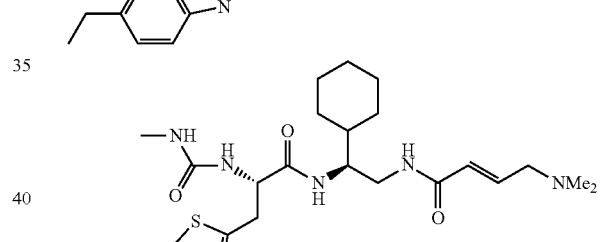
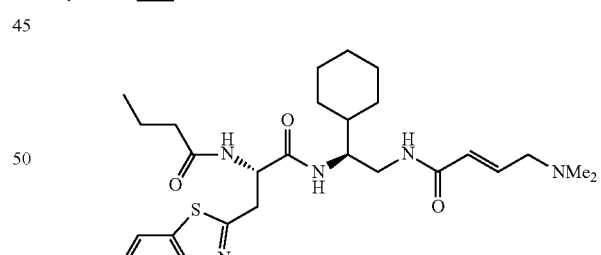
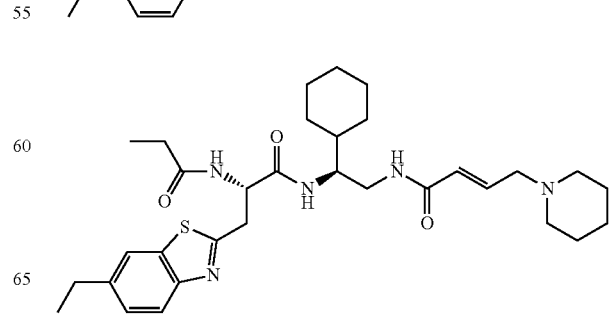

335
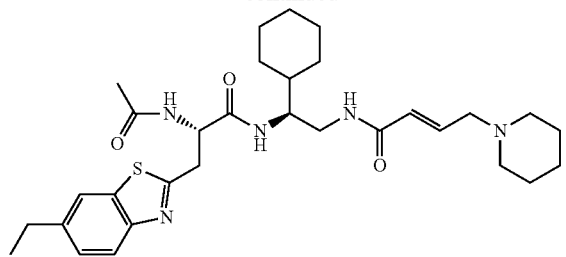
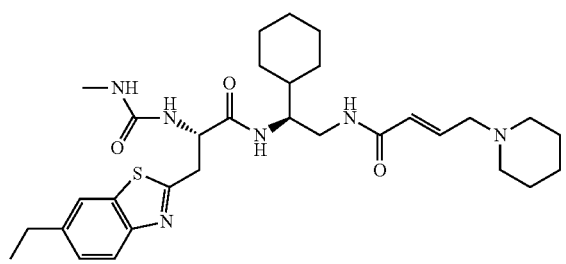
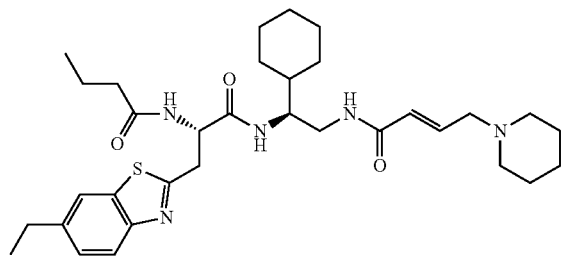
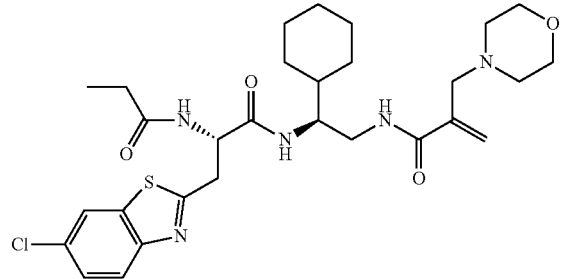
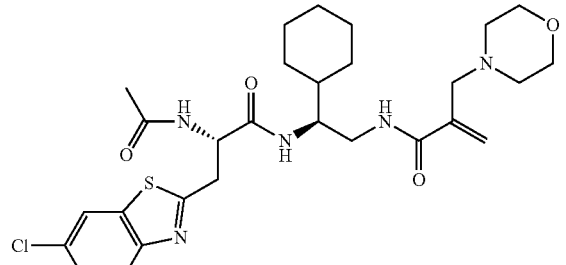
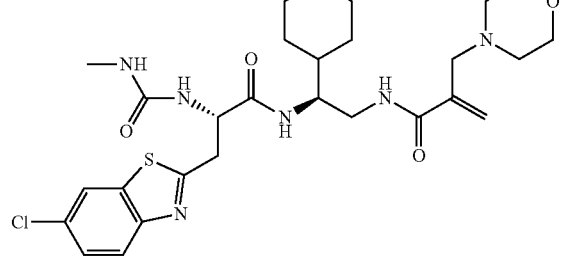
336
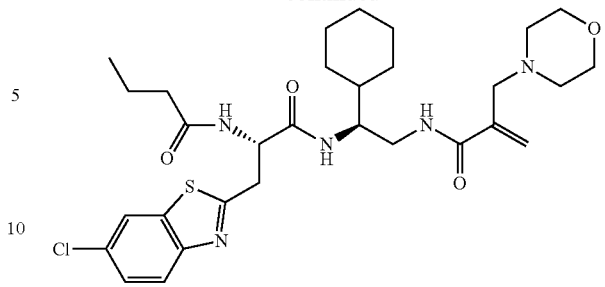
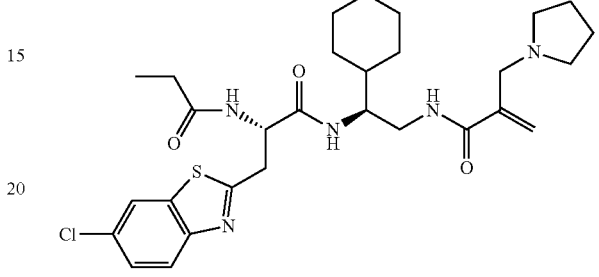
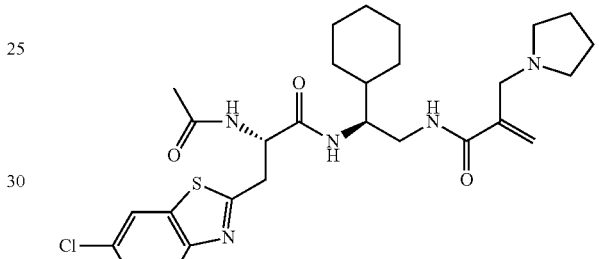
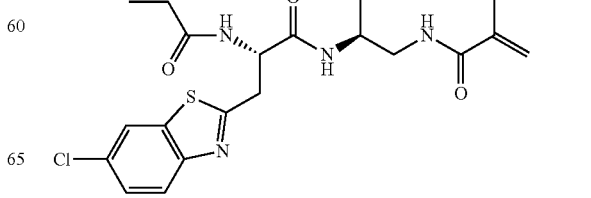

337
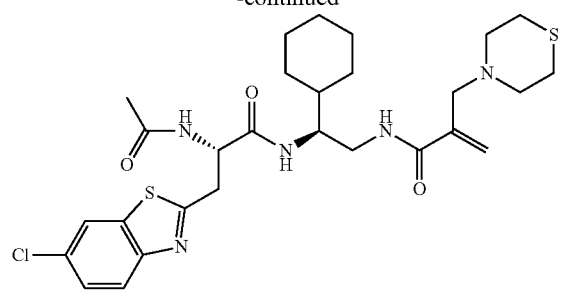
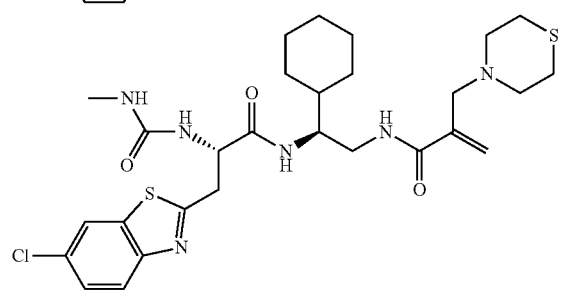
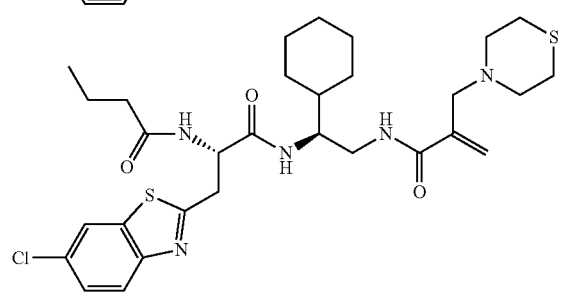
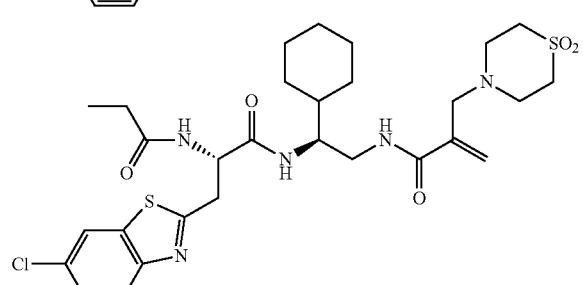
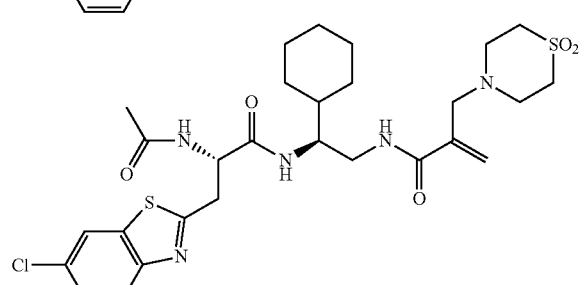
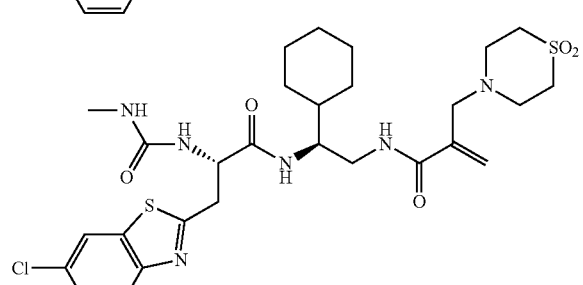
338
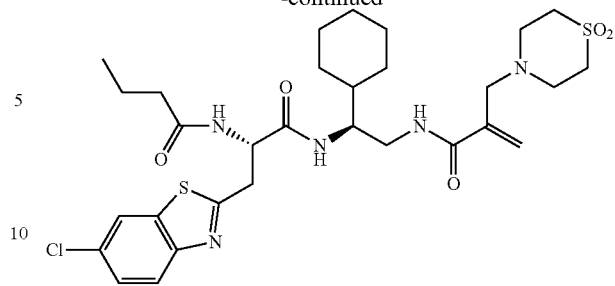
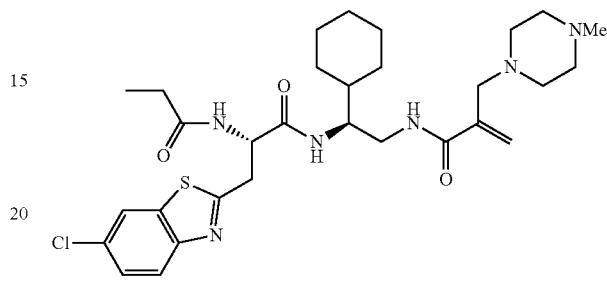
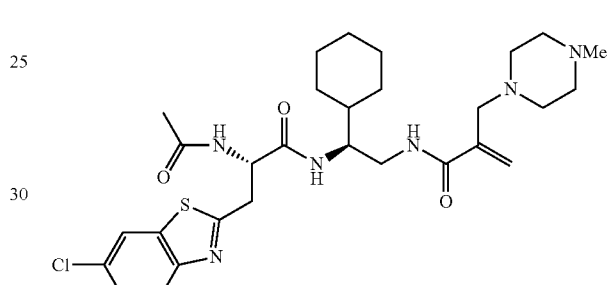
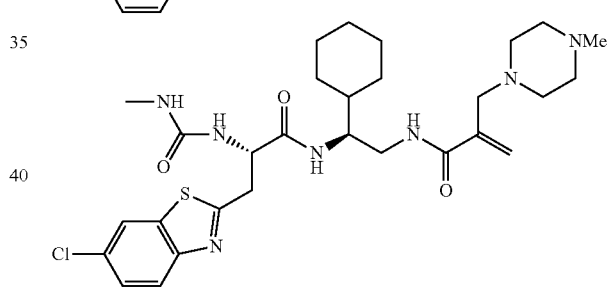
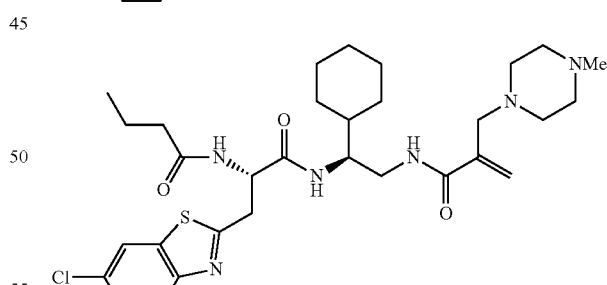
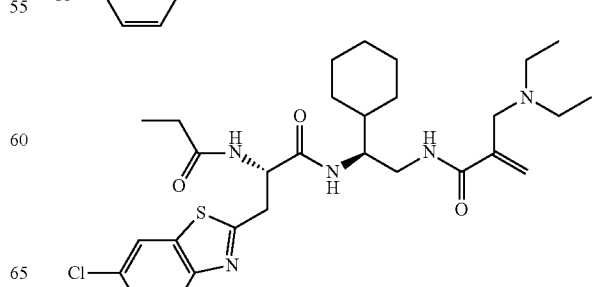

339
-continued
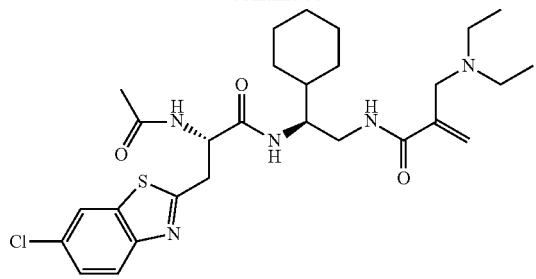
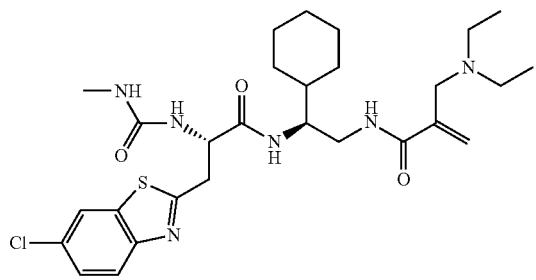
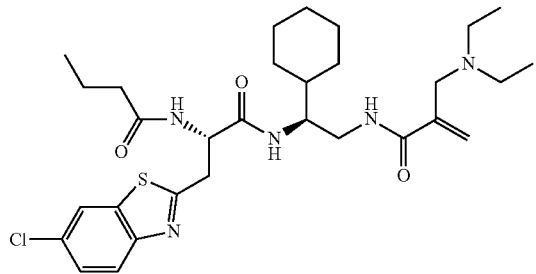
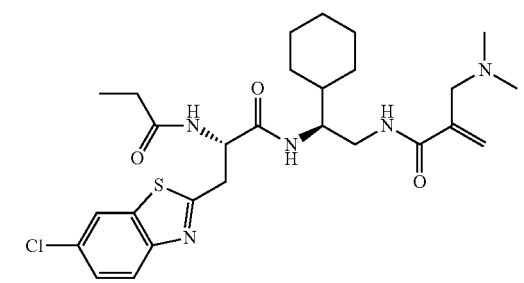
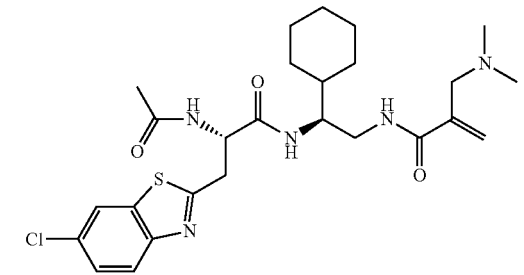
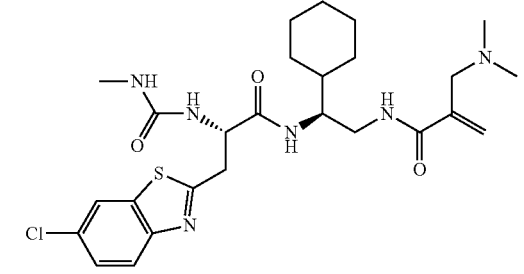
340
-continued
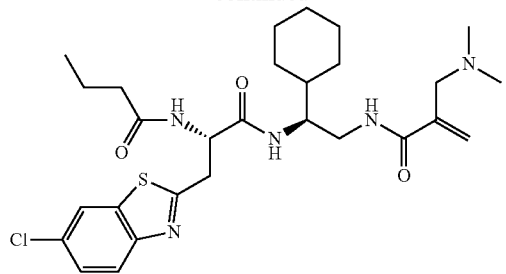
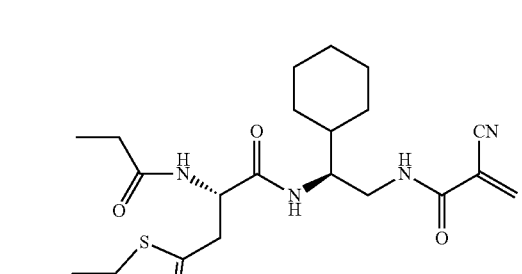
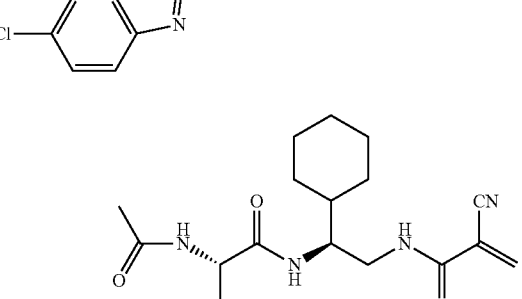
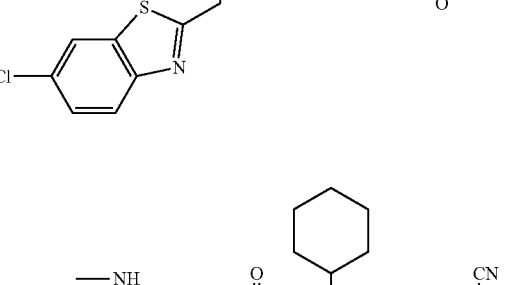
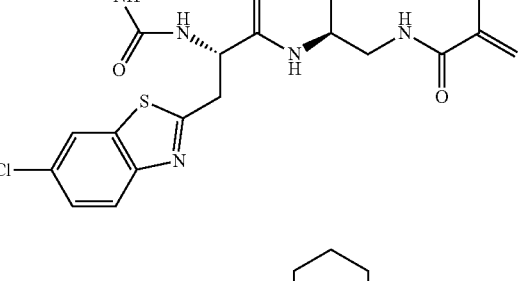
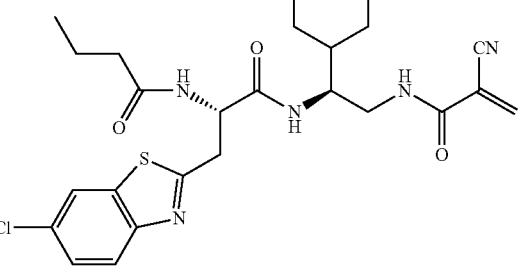

341
-continued
342
-continued
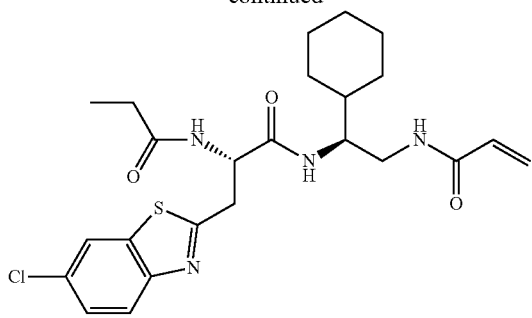
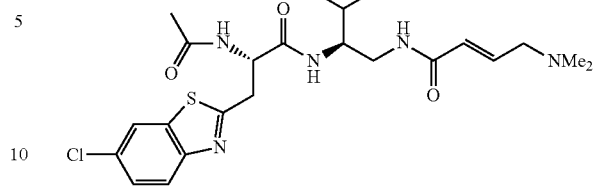
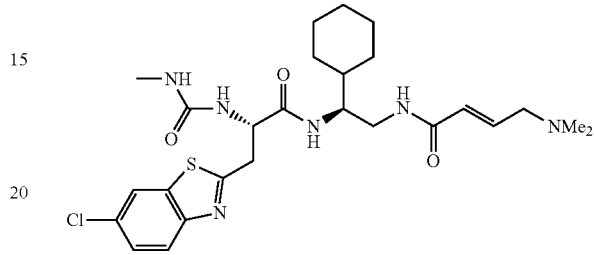
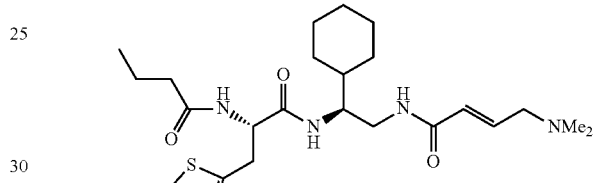
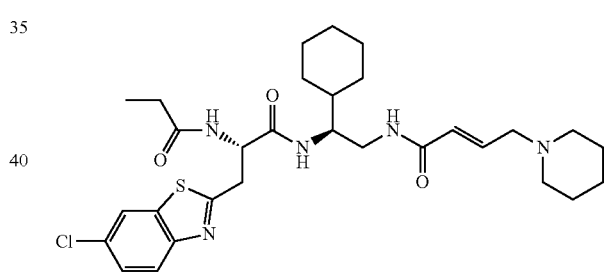
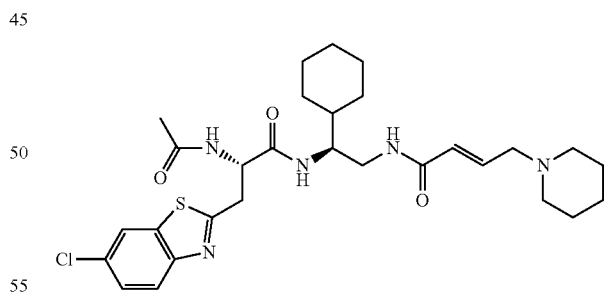
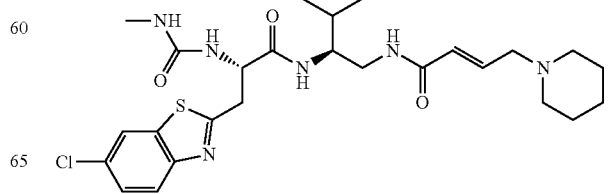

343
-continued
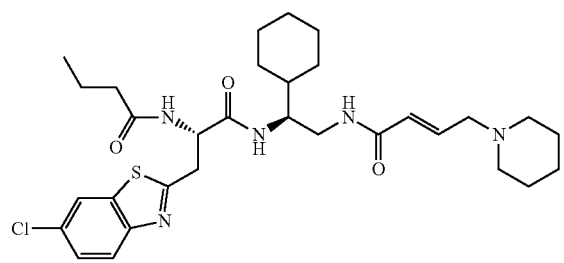
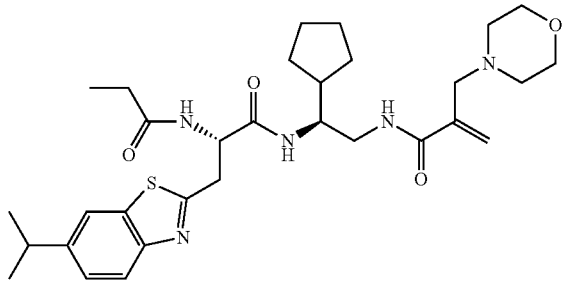
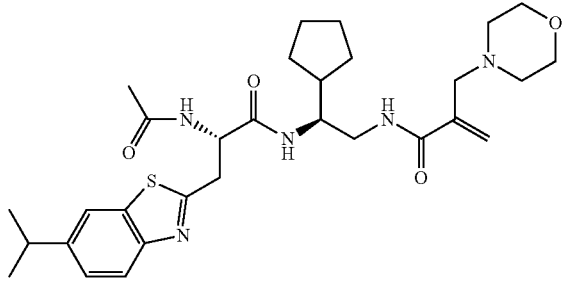
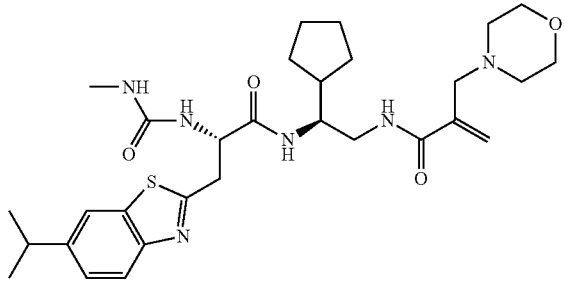
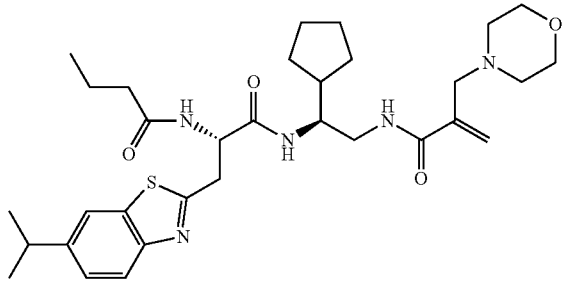
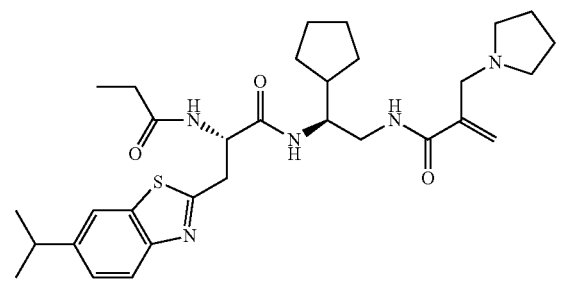
344
-continued
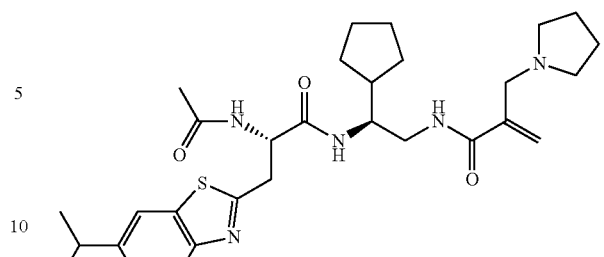
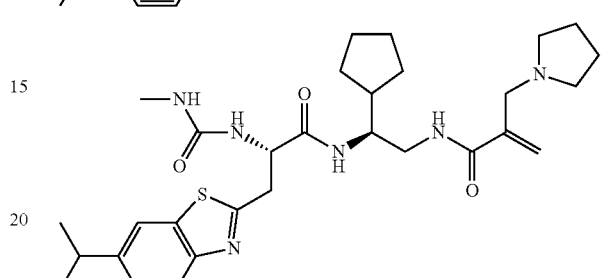
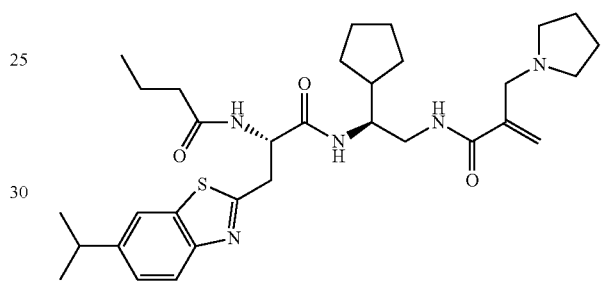
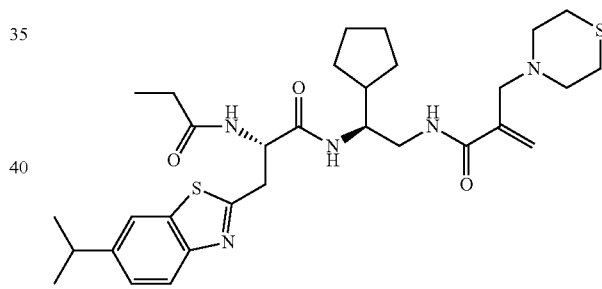
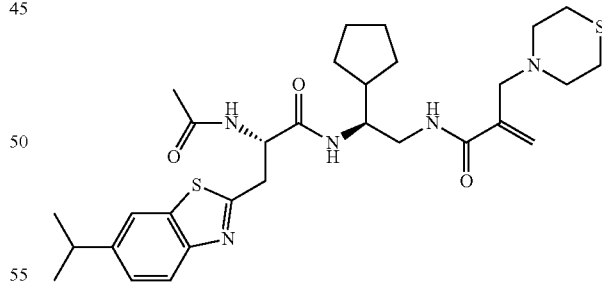
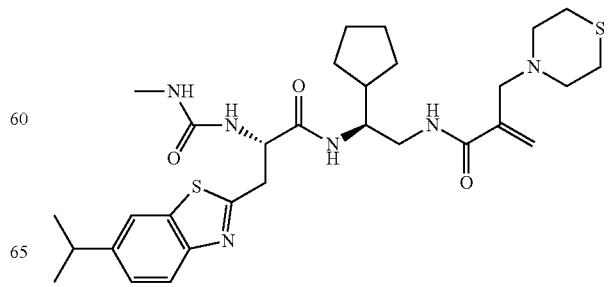

345
-continued
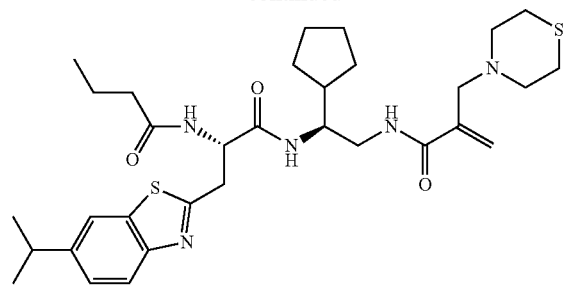
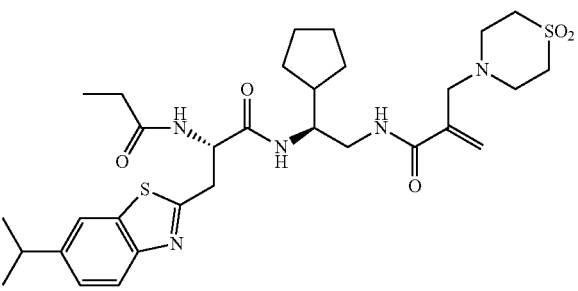
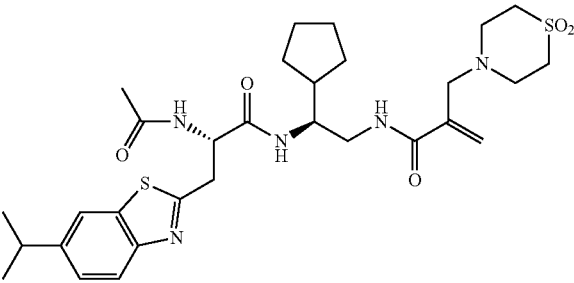
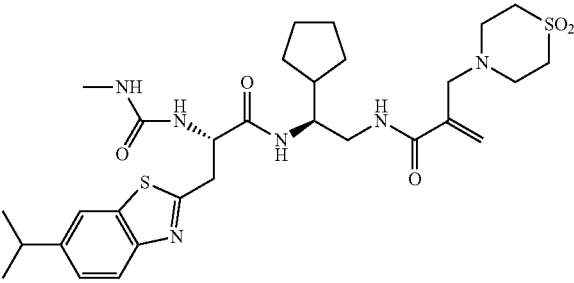
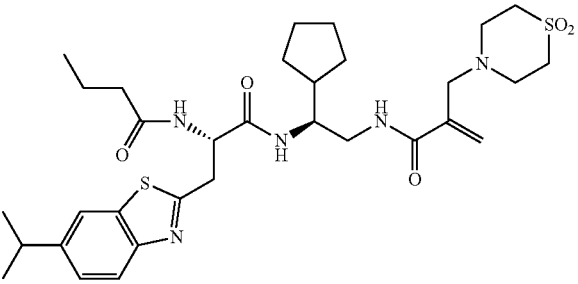
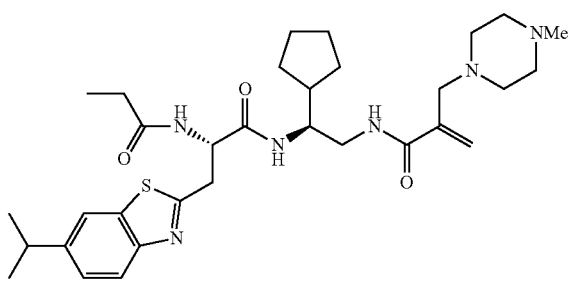
346
-continued
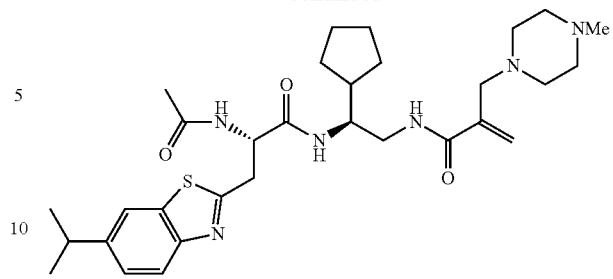
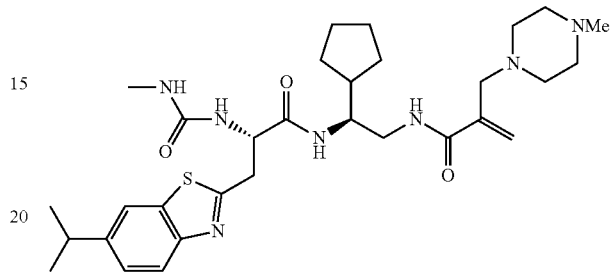
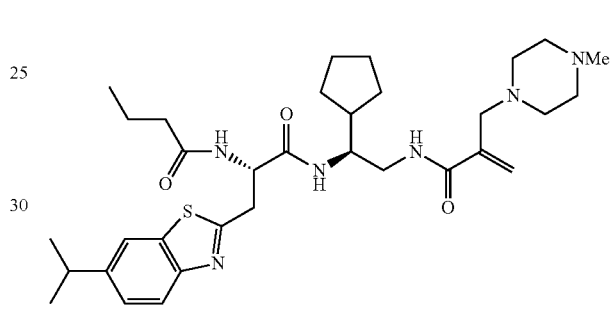
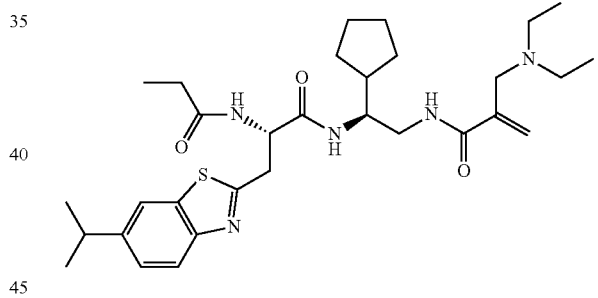
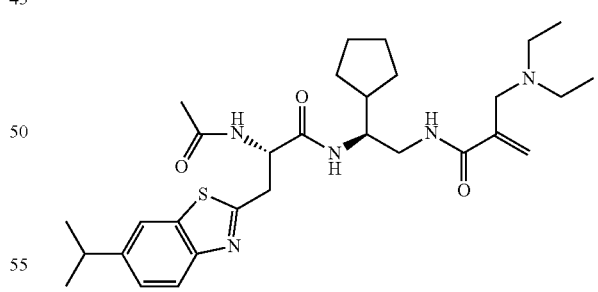
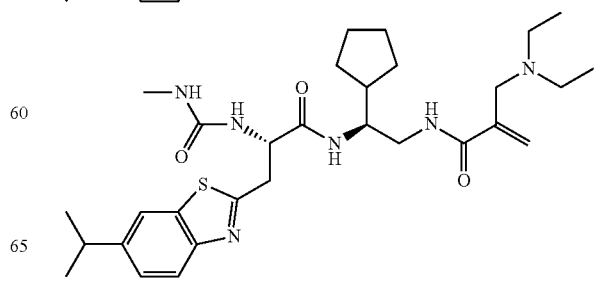

347
-continued
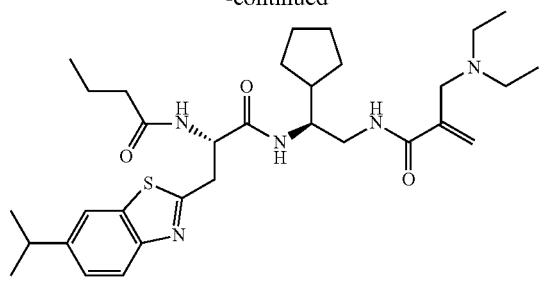
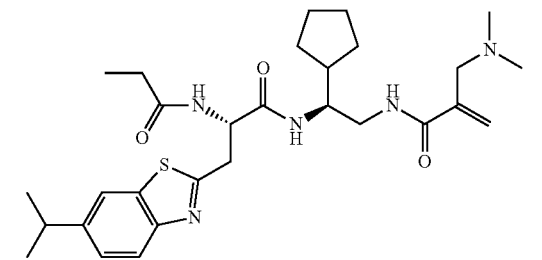
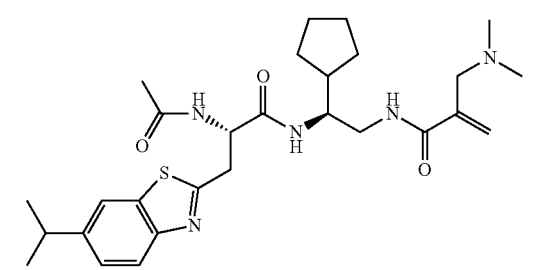
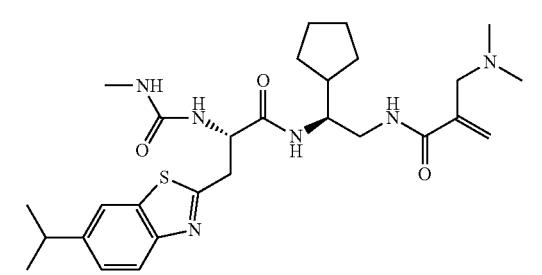
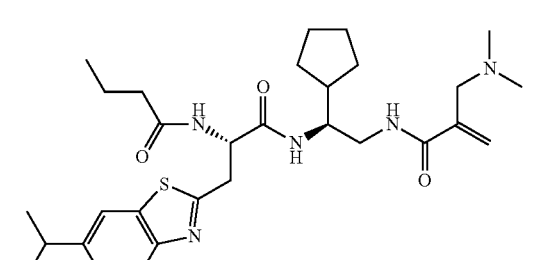
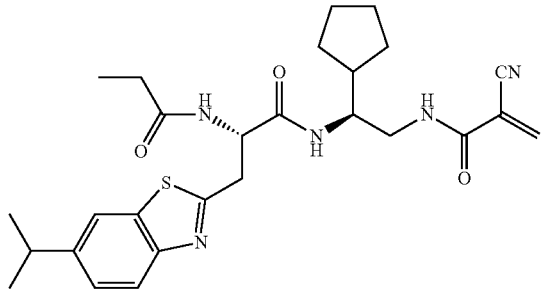
348
-continued
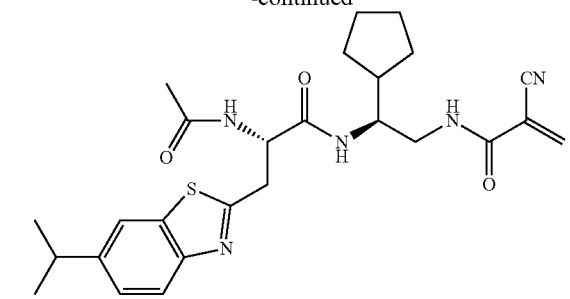
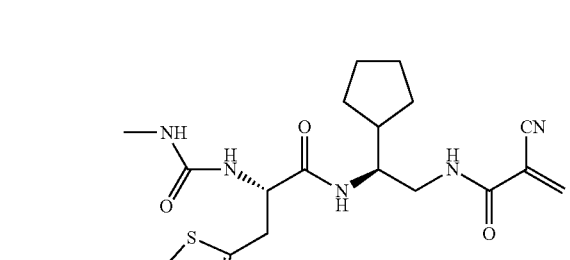
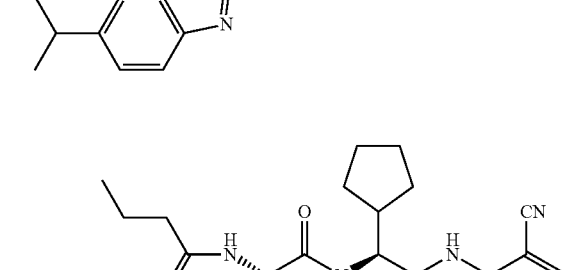
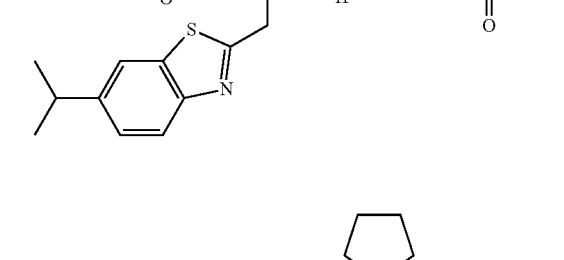
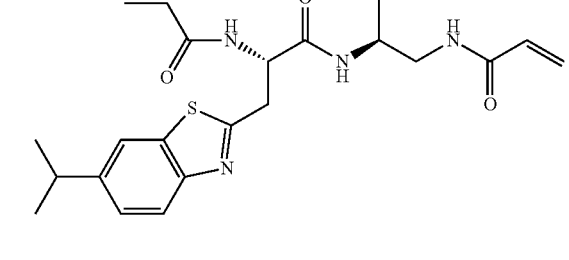
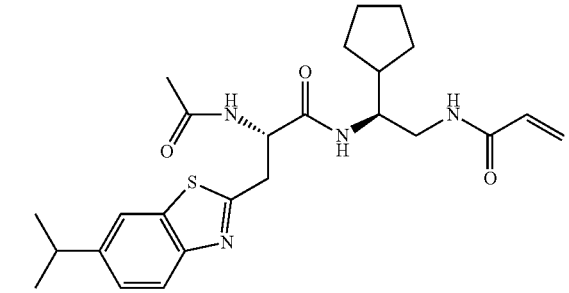

349
-continued
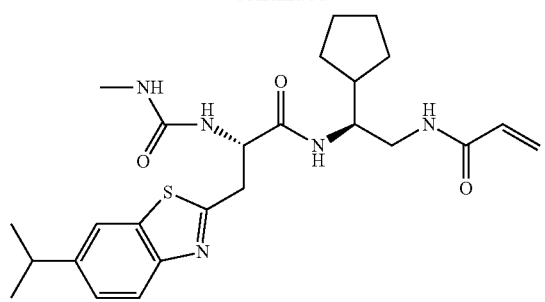
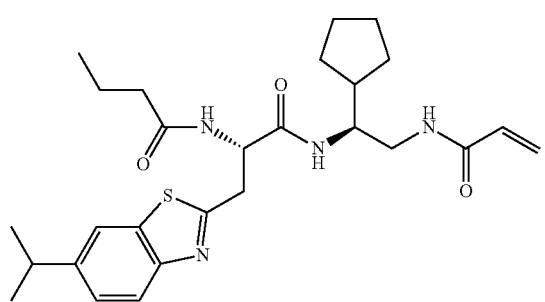
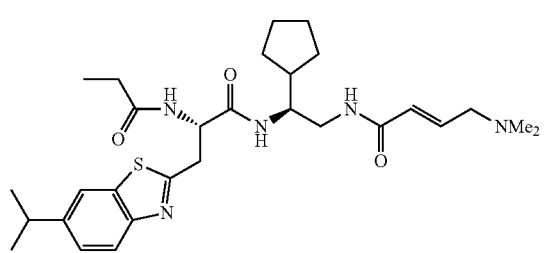
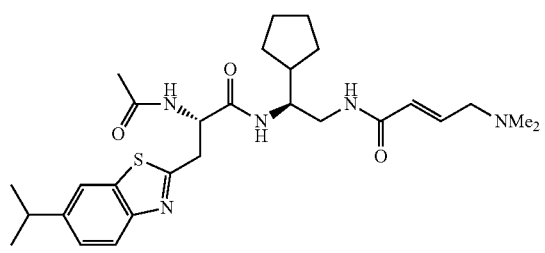
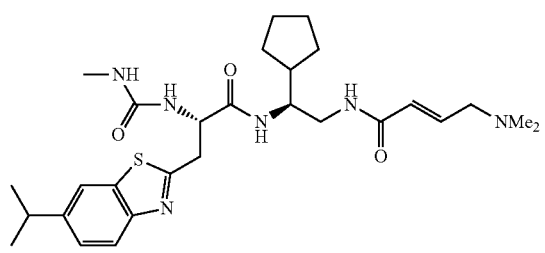
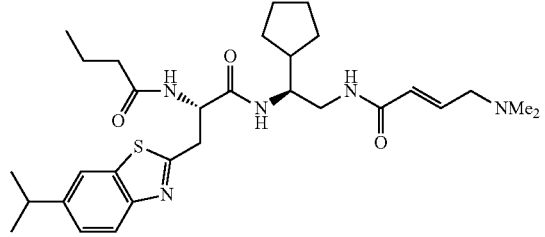
350
-continued
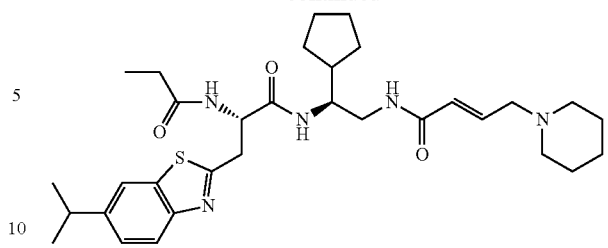
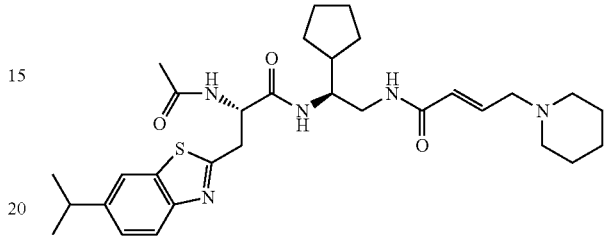
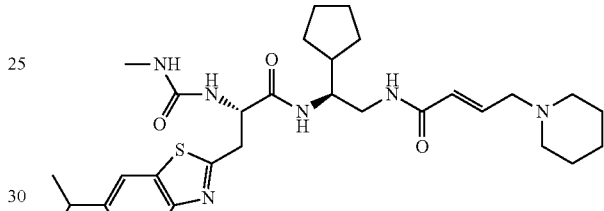
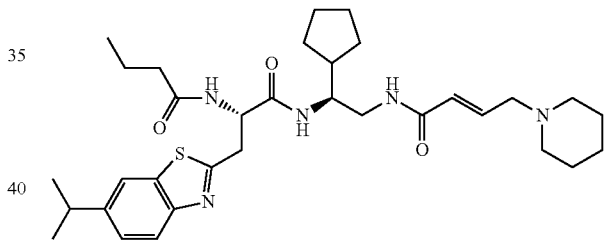
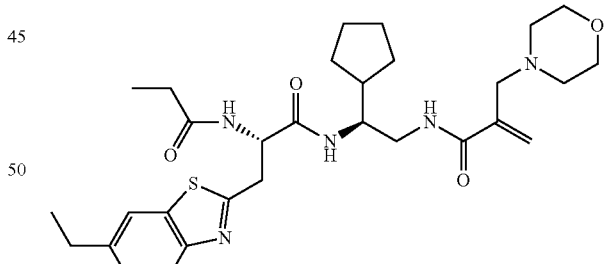
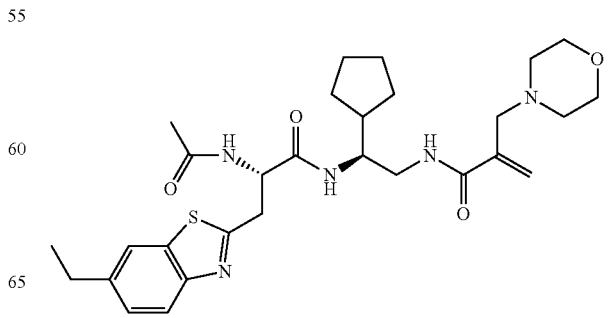

351
-continued
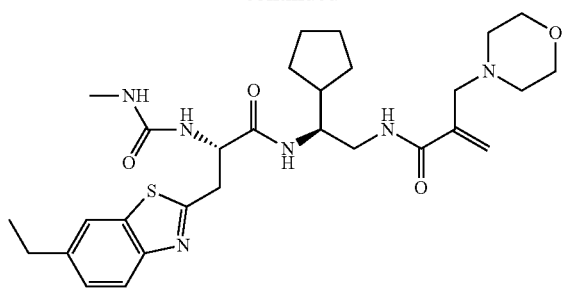
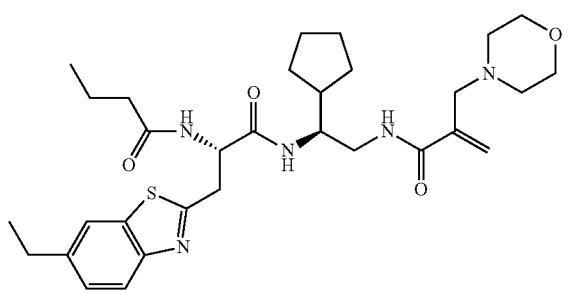
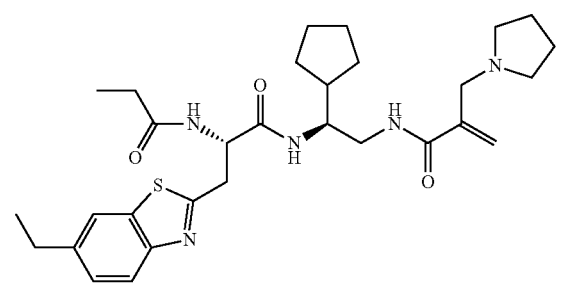
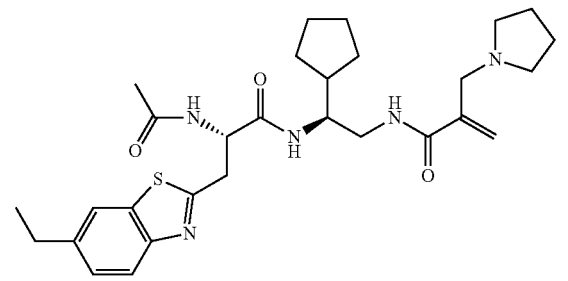
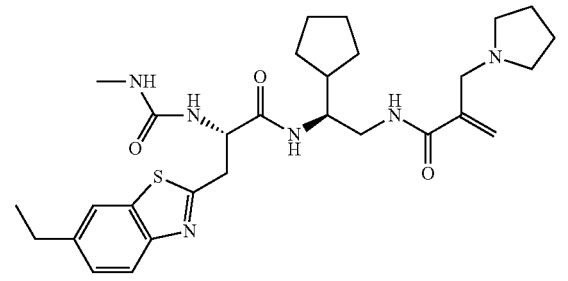
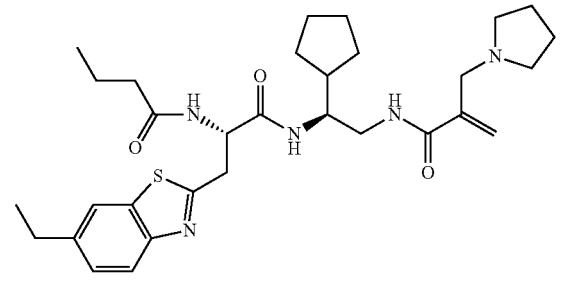
352
-continued
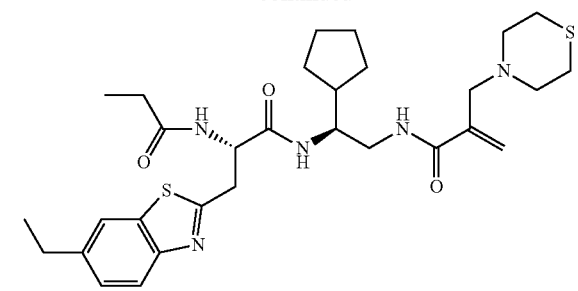
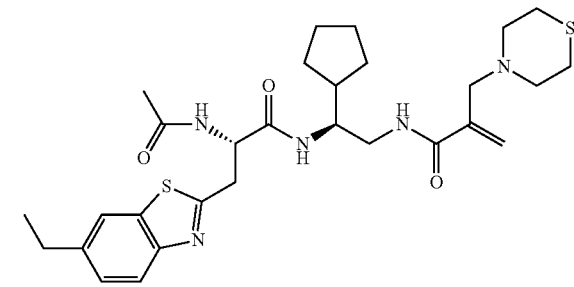
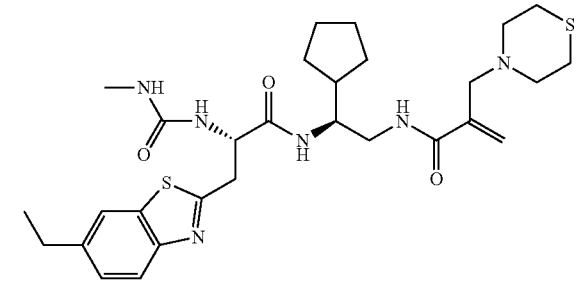
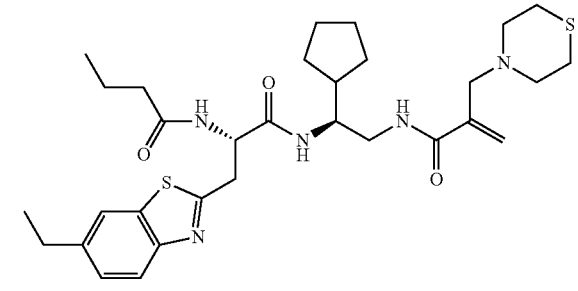
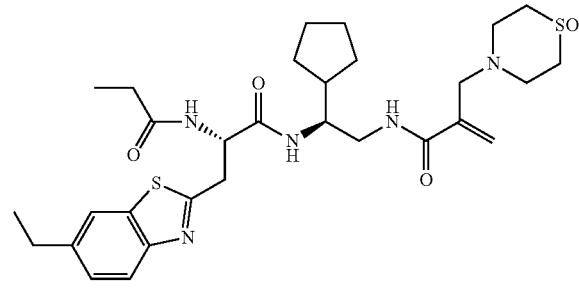
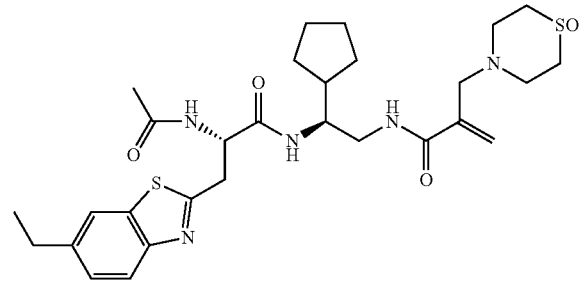

353
-continued
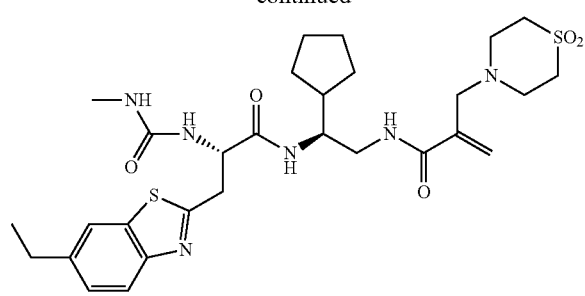
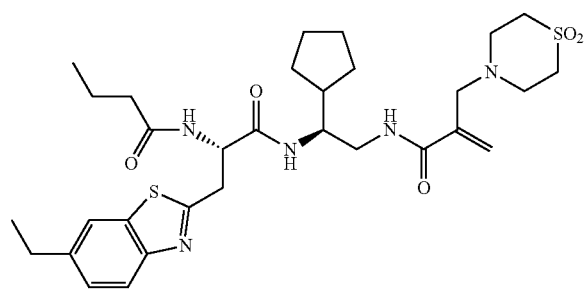
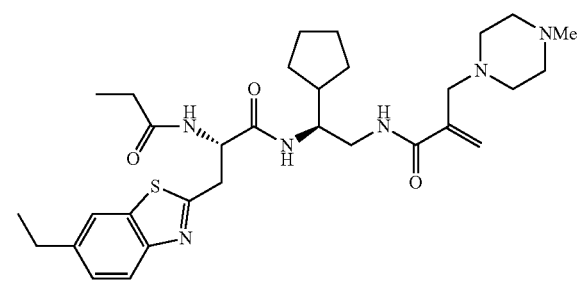
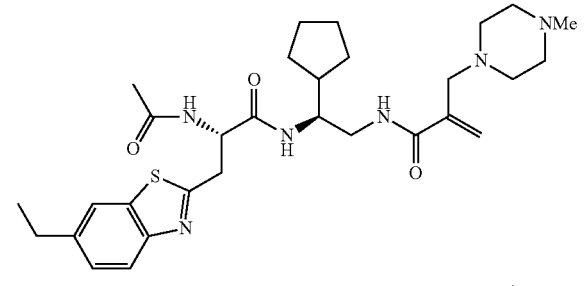
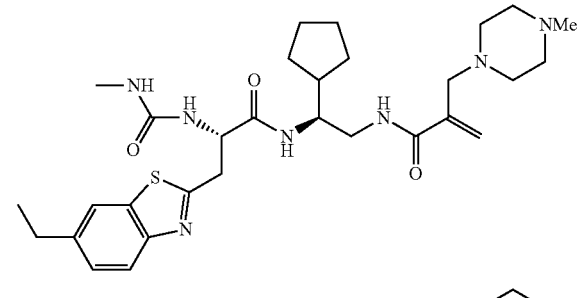
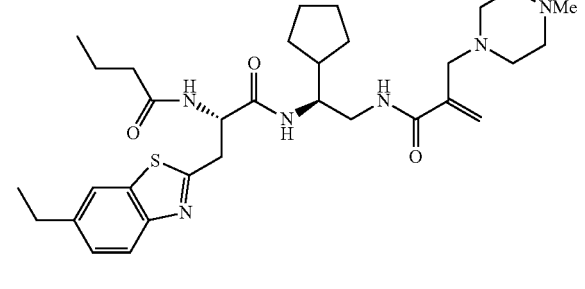
354
-continued
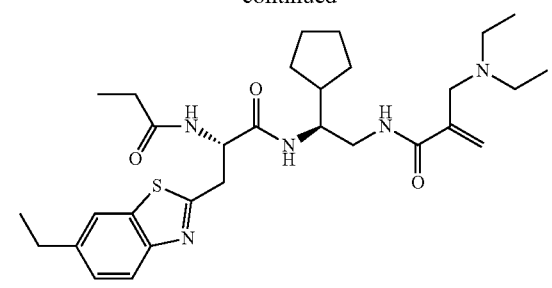
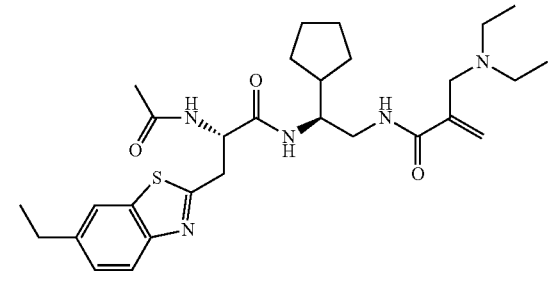
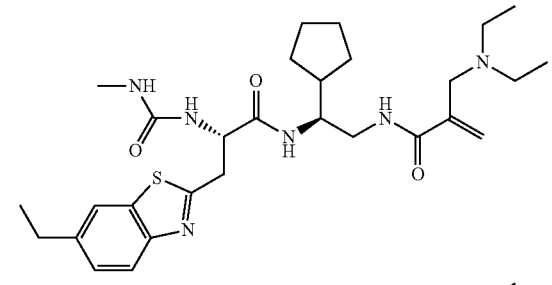
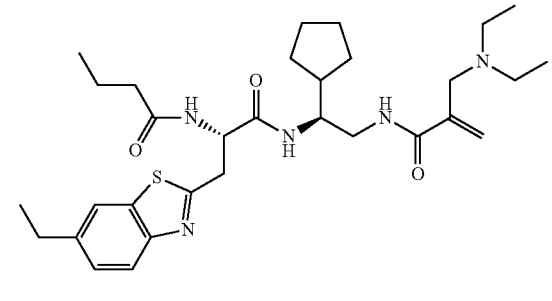
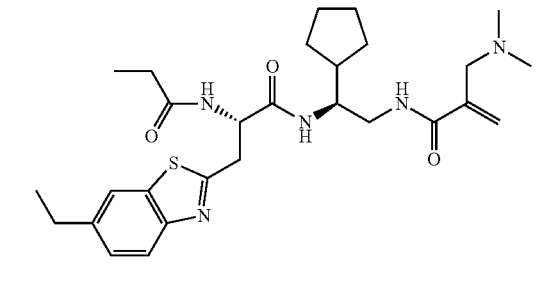
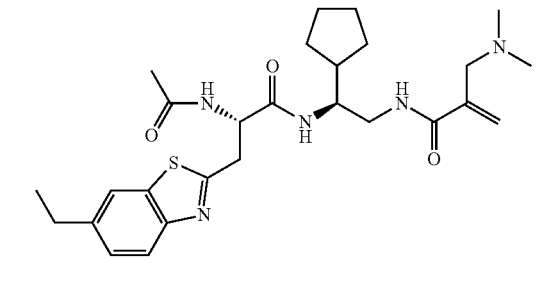

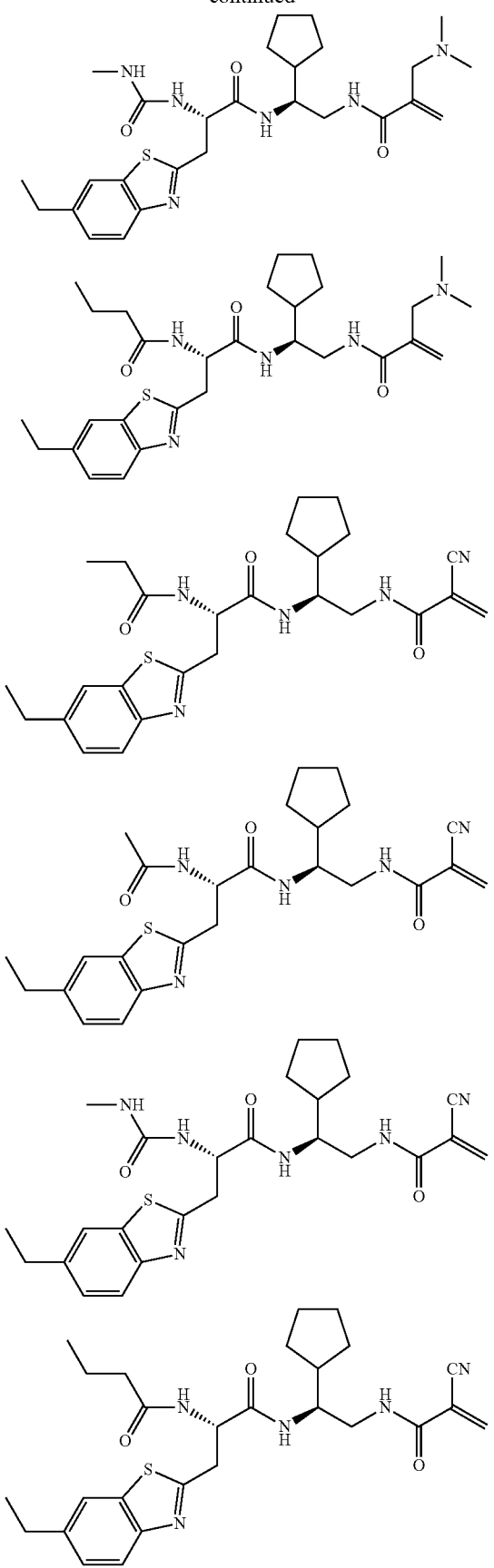
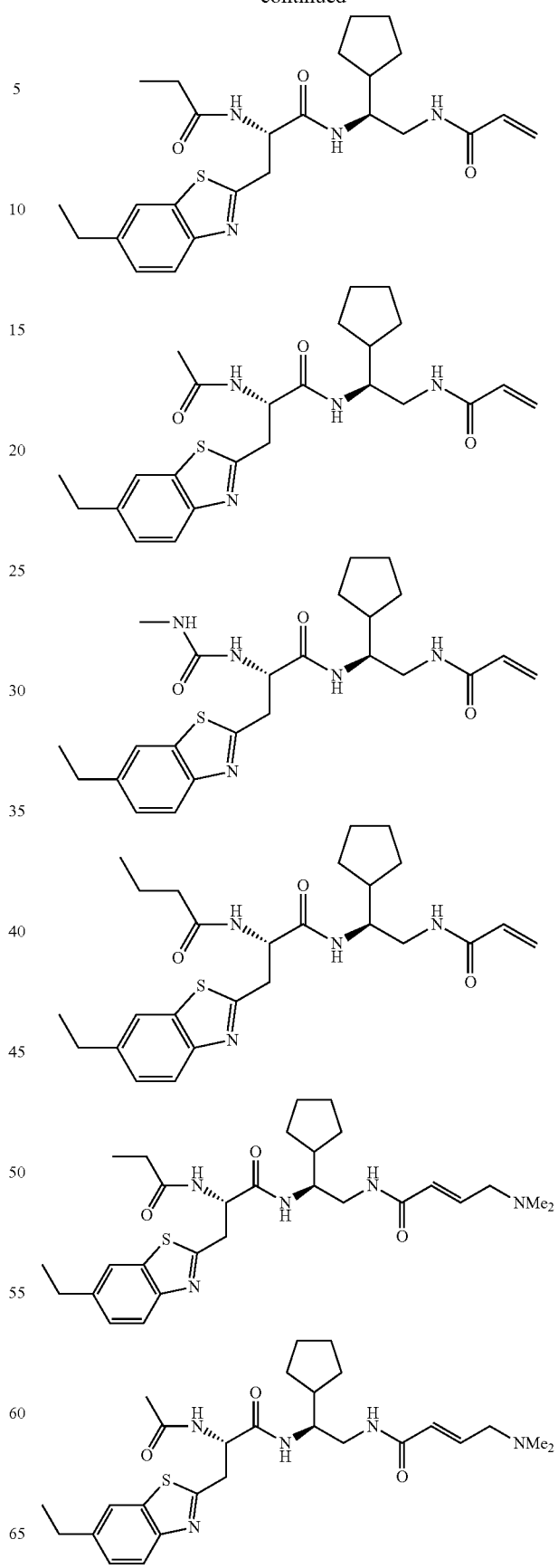

357
-continued
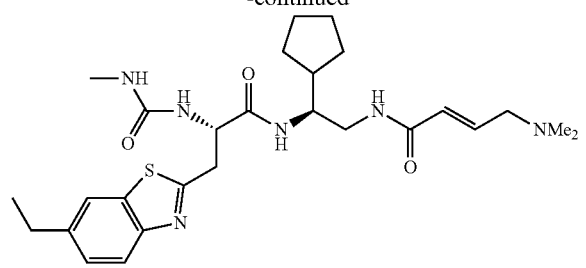
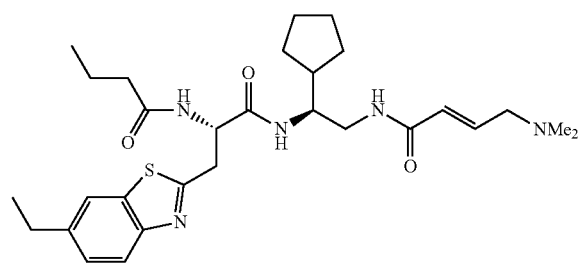
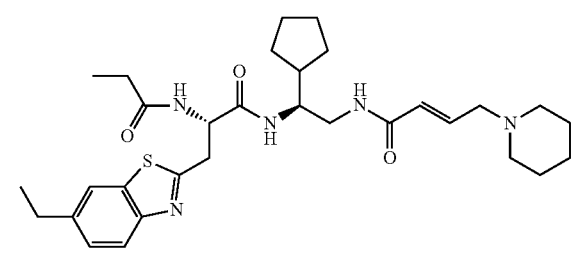
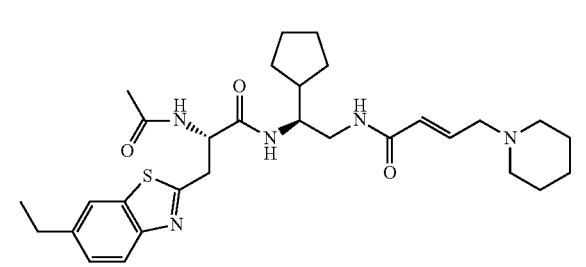
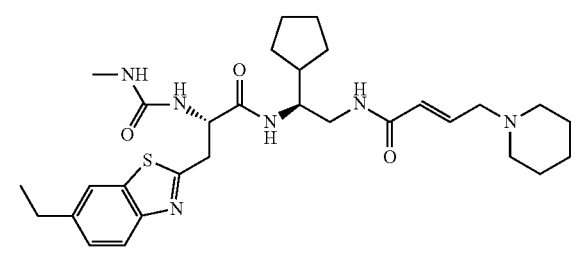
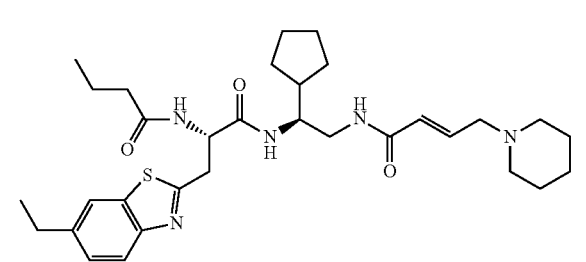
358
-continued
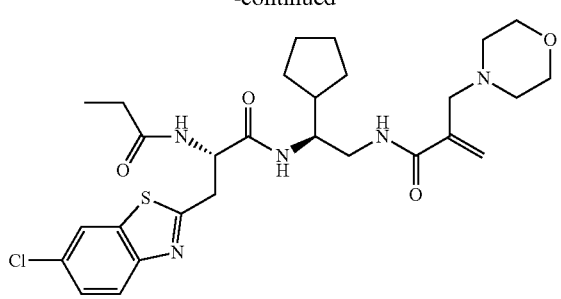
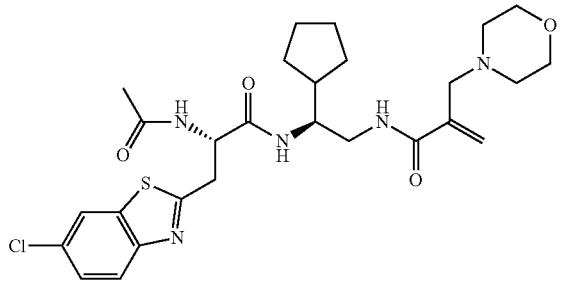
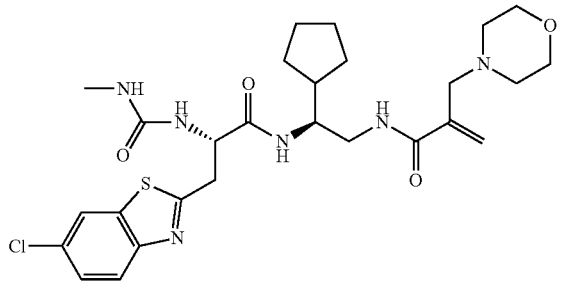
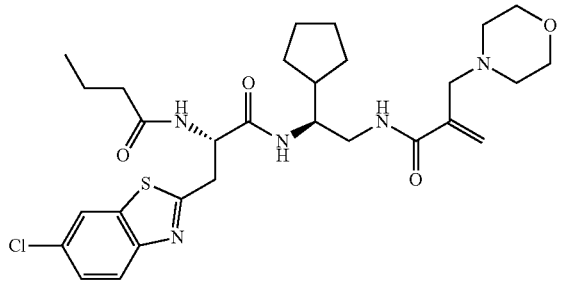
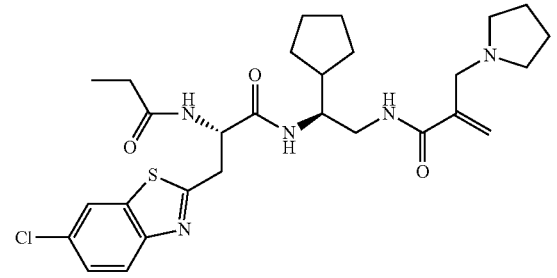
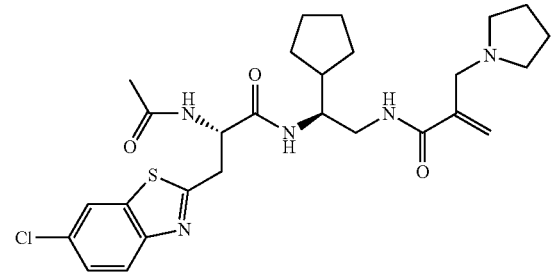

359
-continued
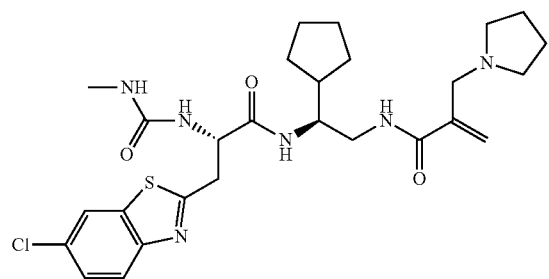
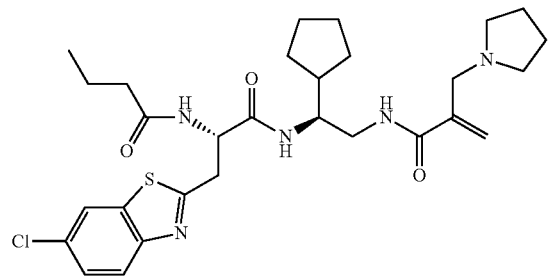
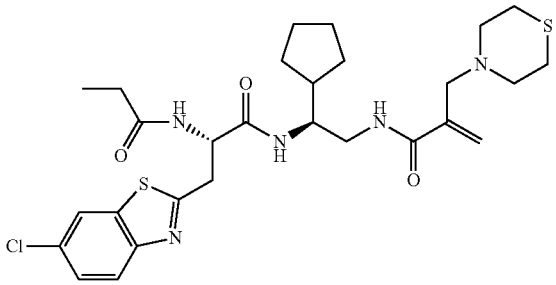
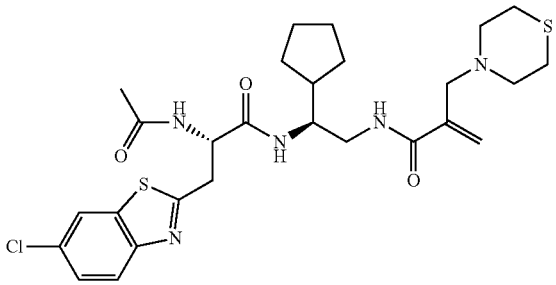
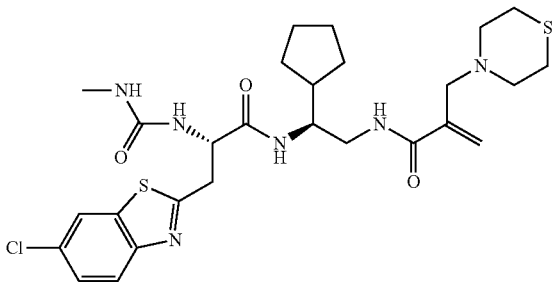
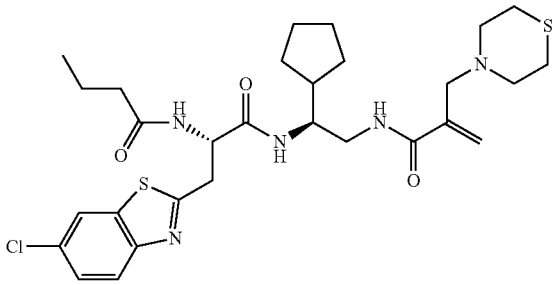
360
-continued
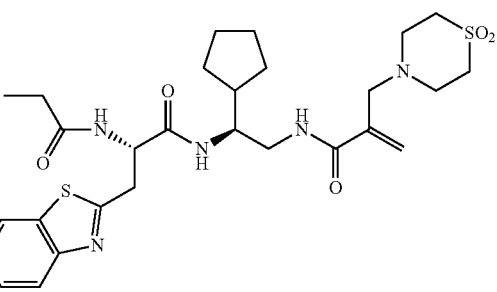
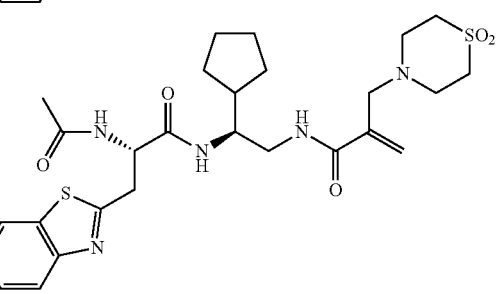
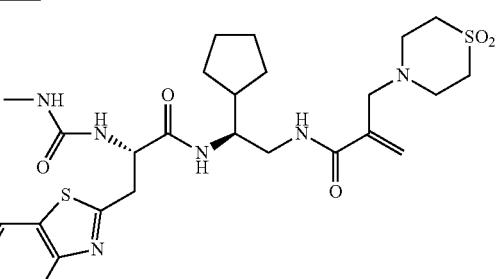
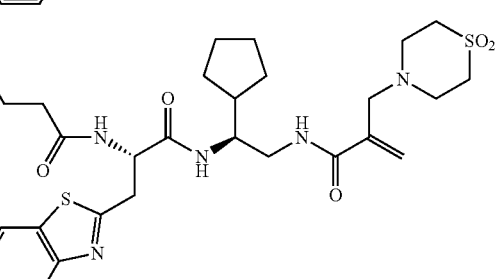
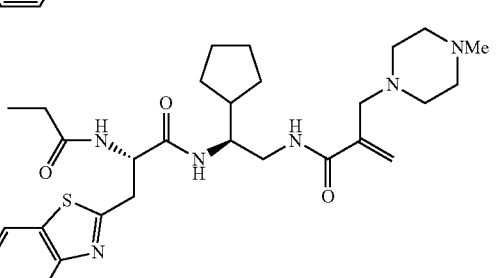
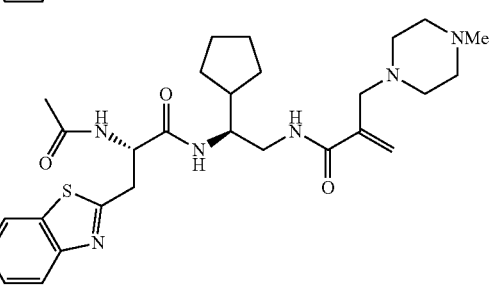

361
-continued
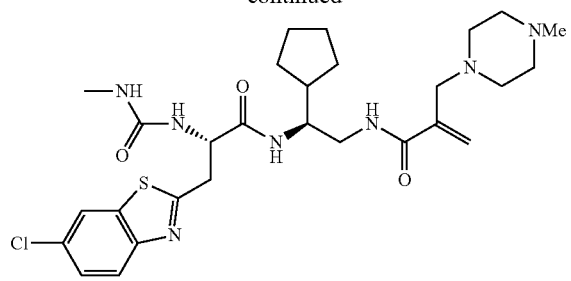
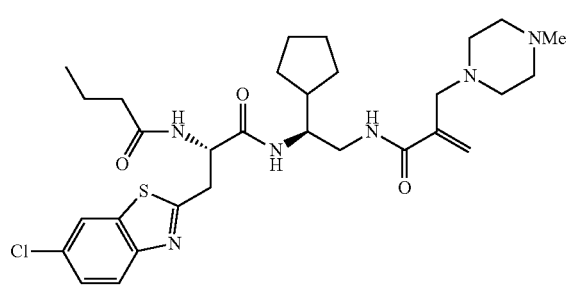
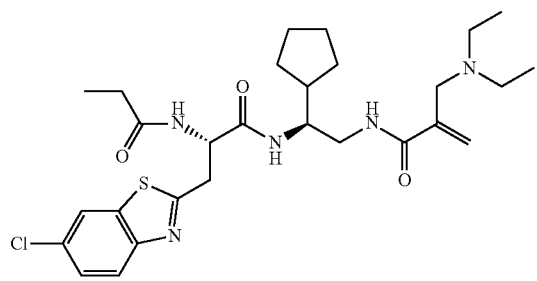
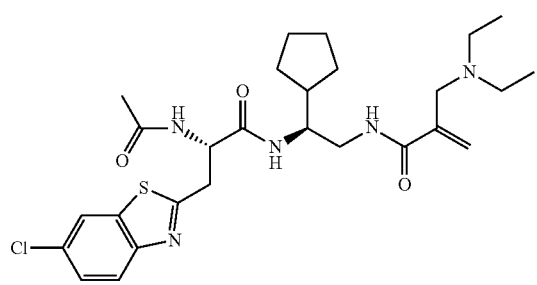
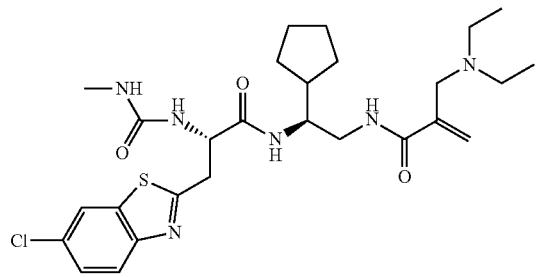
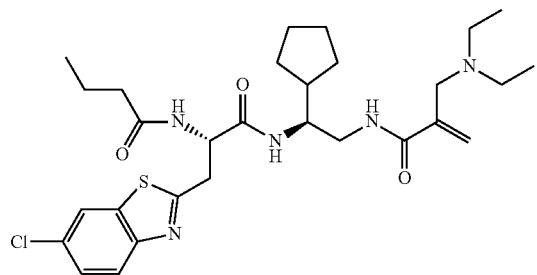
362
-continued
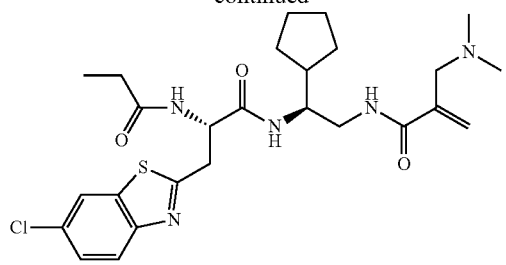
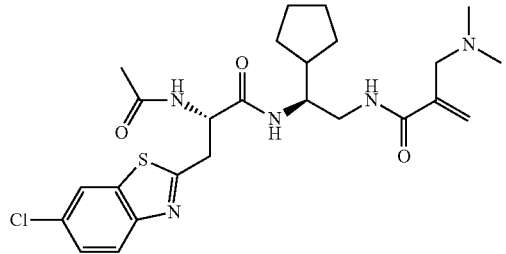
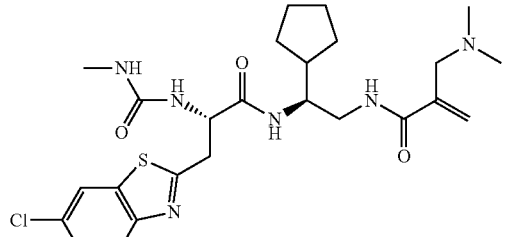
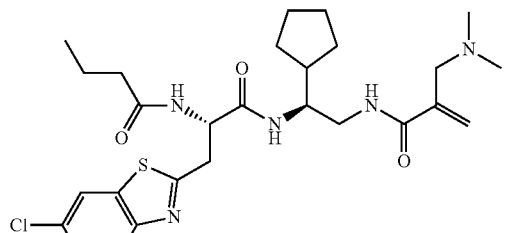
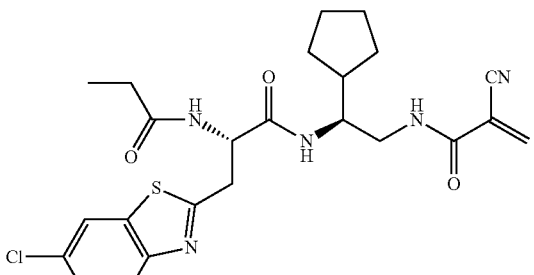
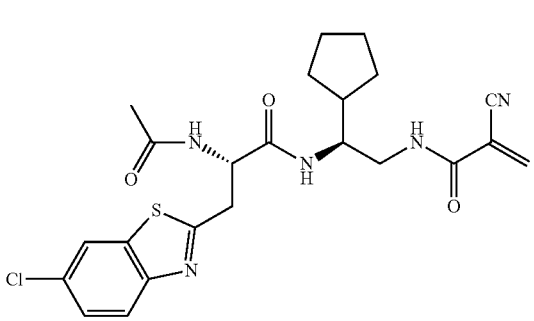

363
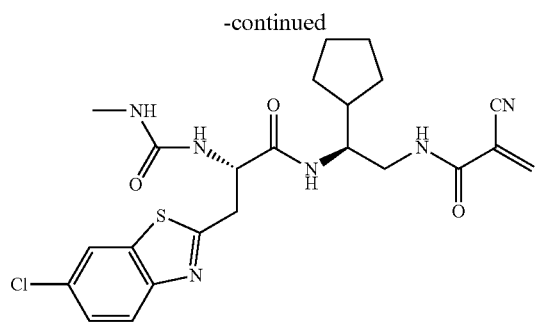
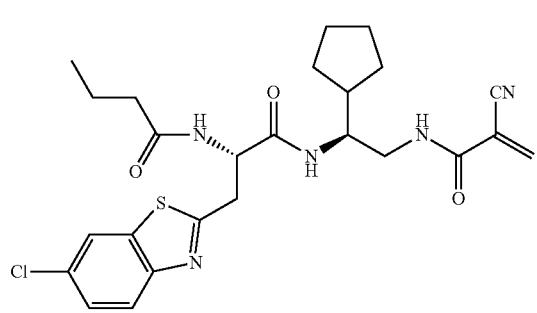
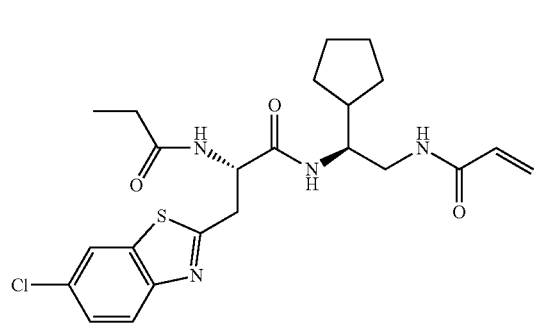
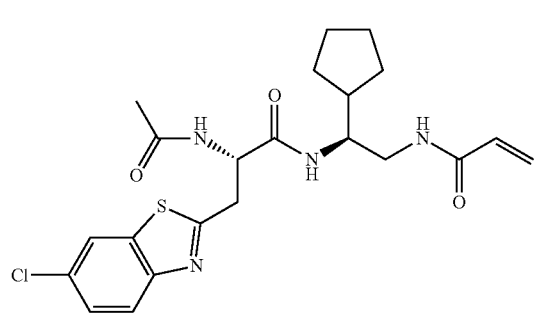
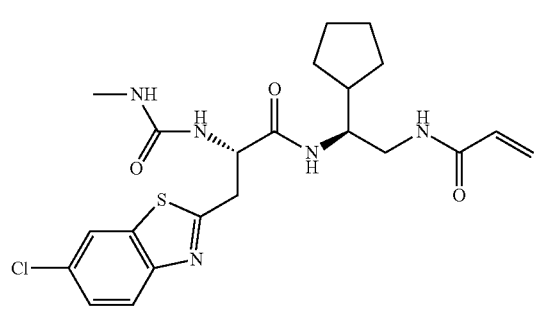
364
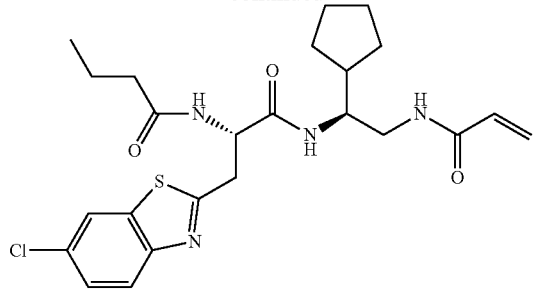
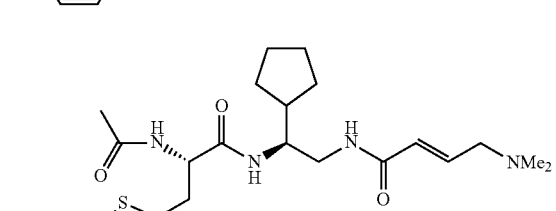
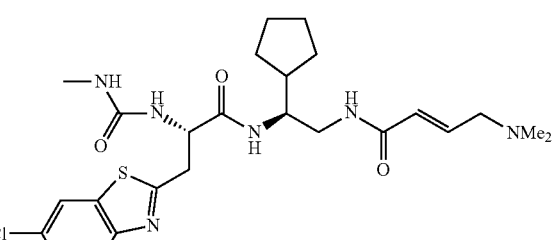
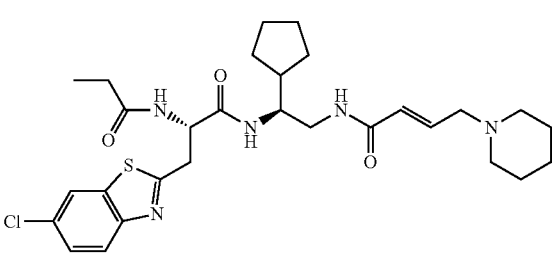

365
-continued
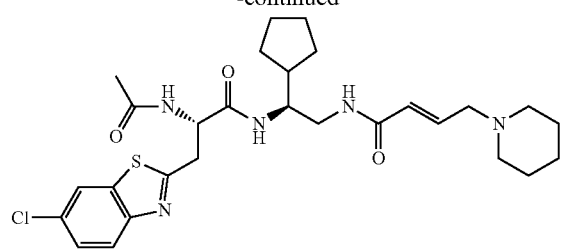
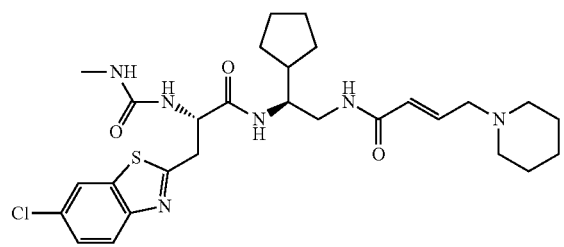
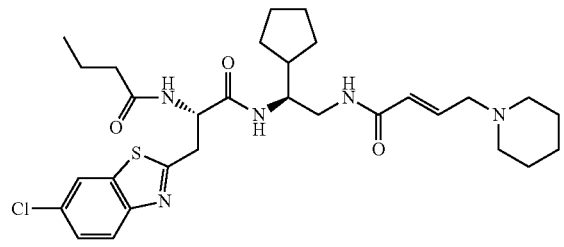
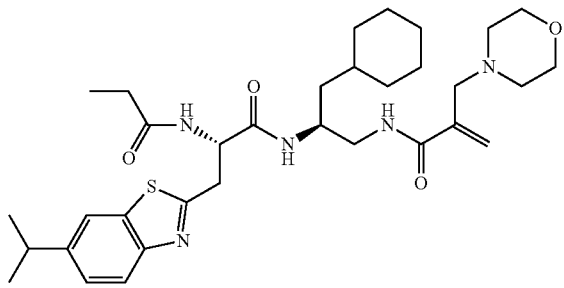
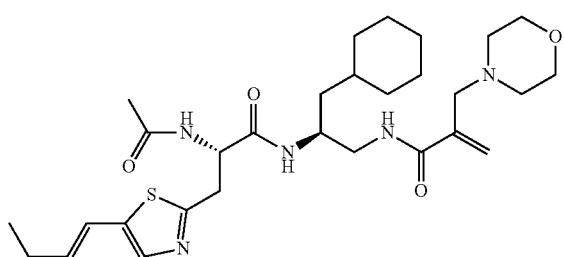
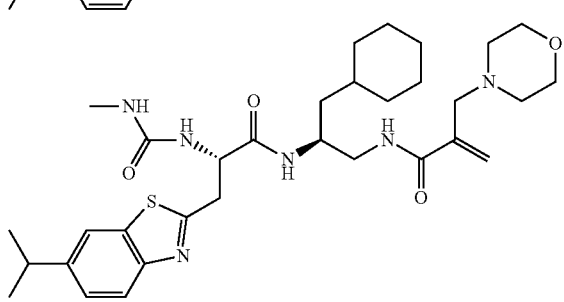
366
-continued
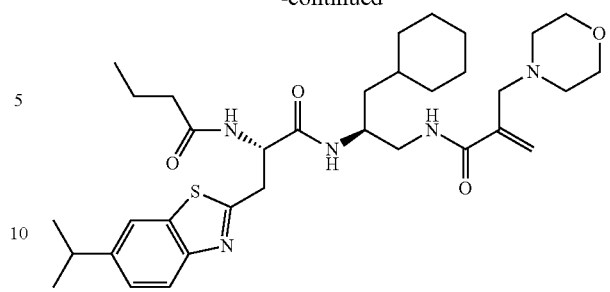
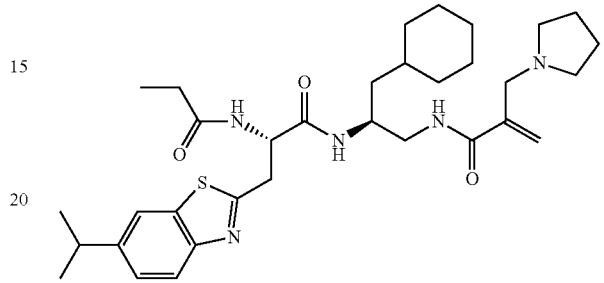
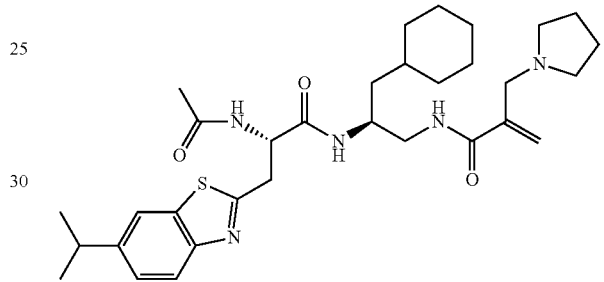
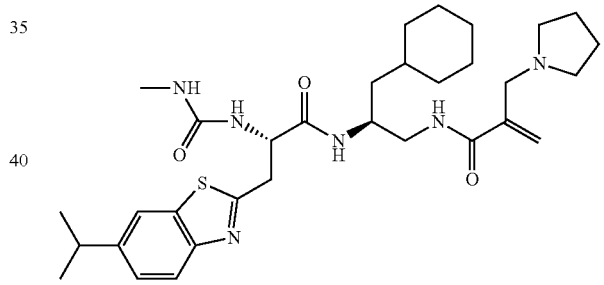
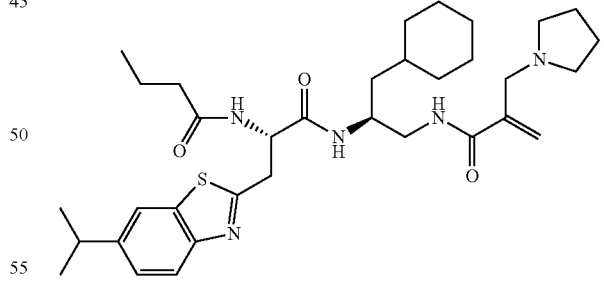
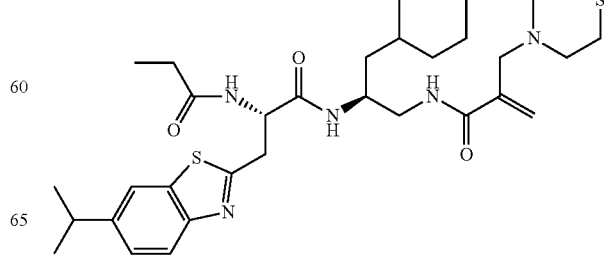

367
-continued
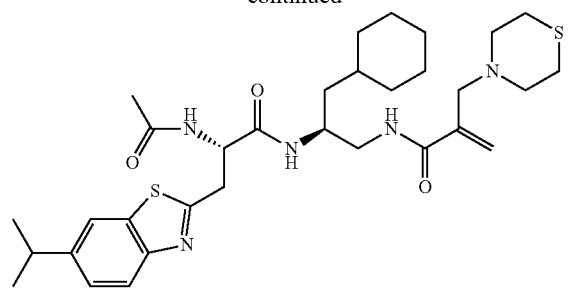
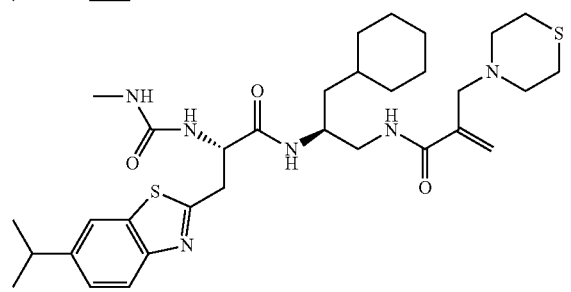
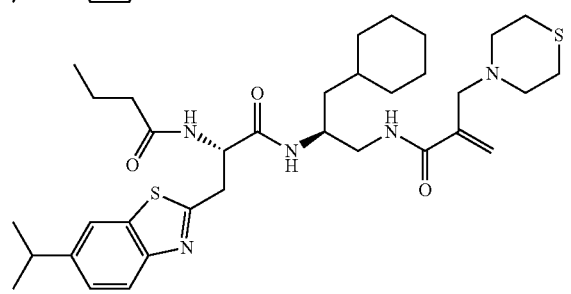
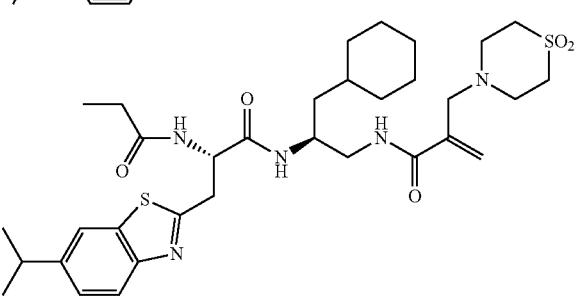
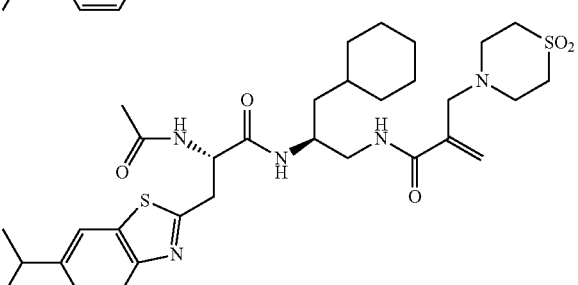
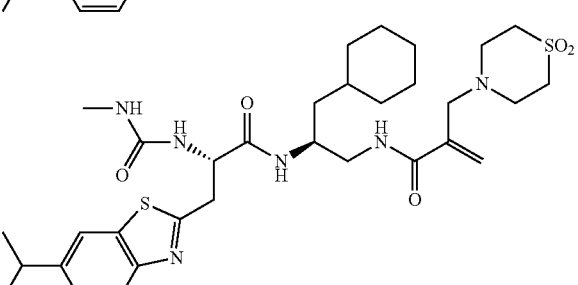
368
-continued
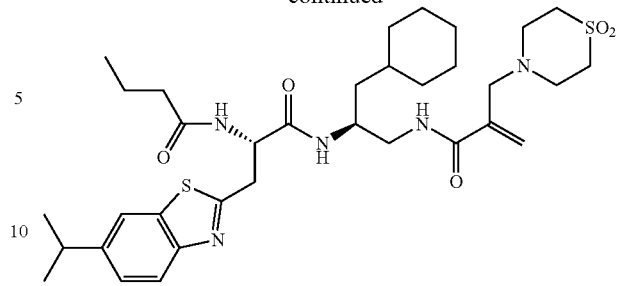
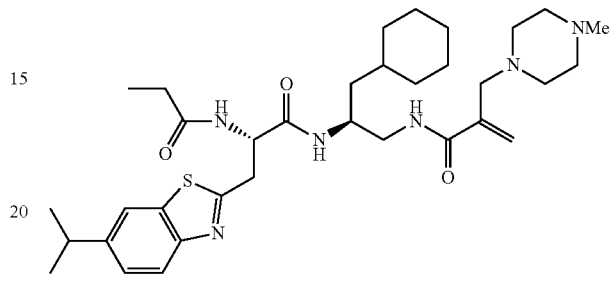
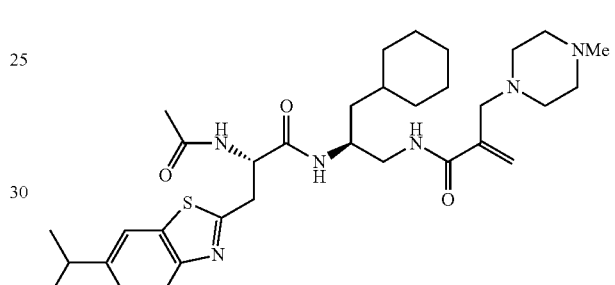
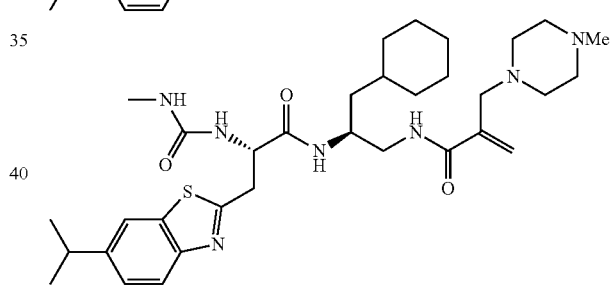
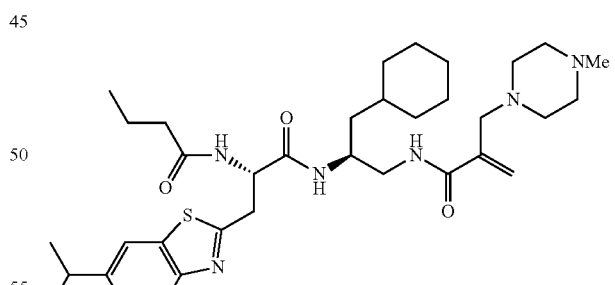
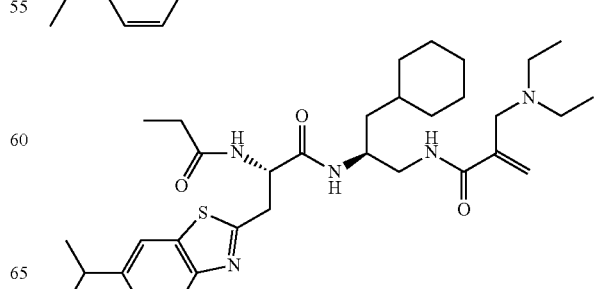

369
-continued
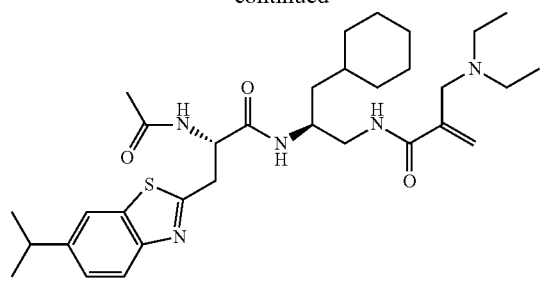
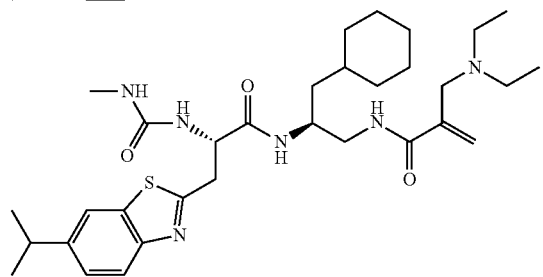
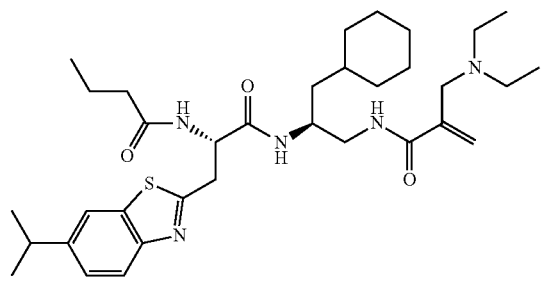
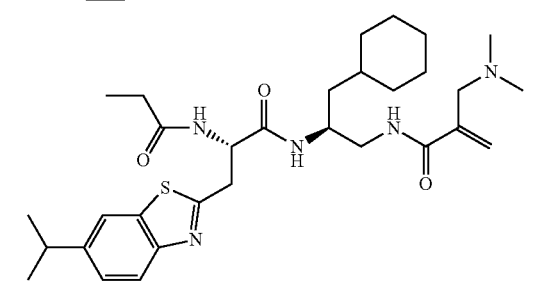
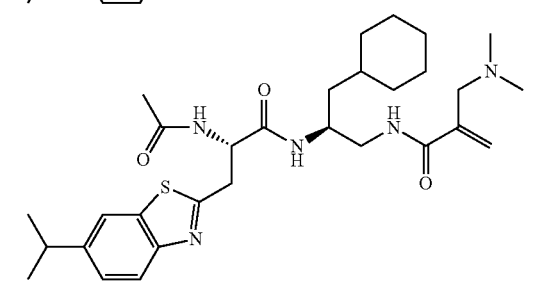
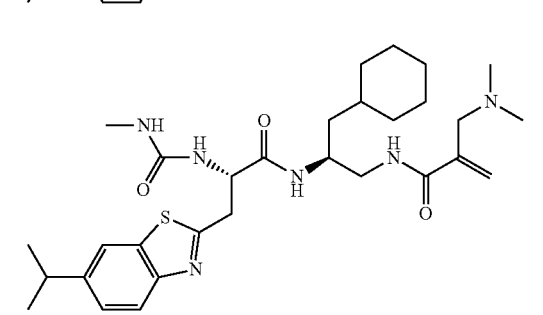
370
-continued
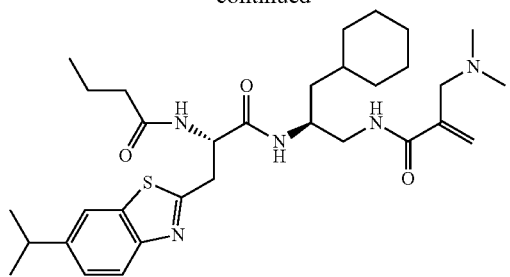
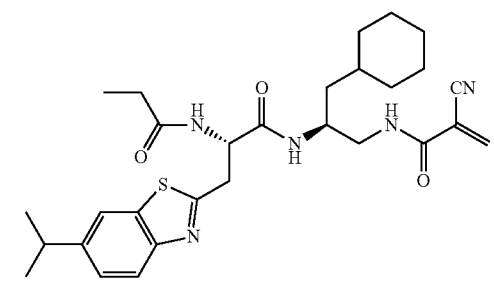
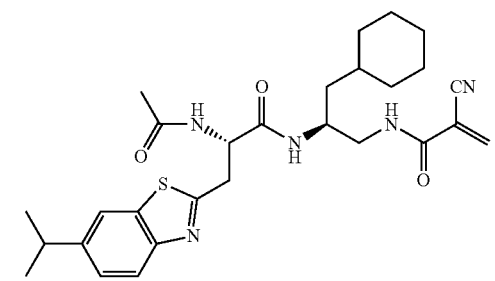
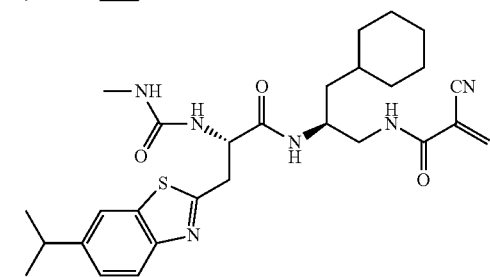
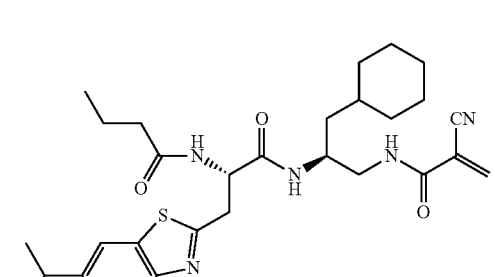
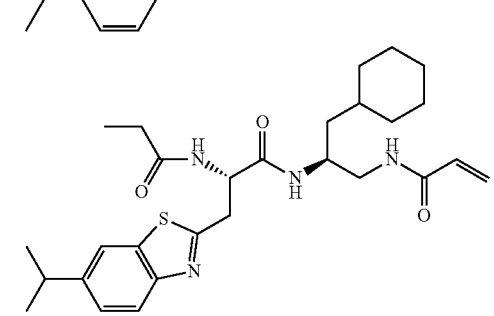

371
-continued
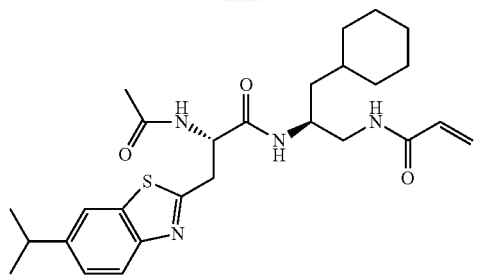
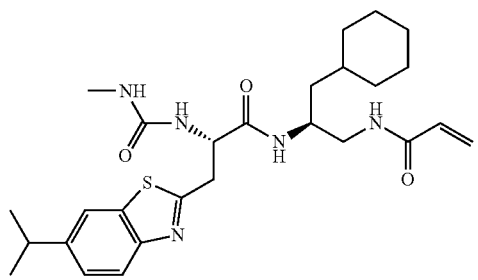
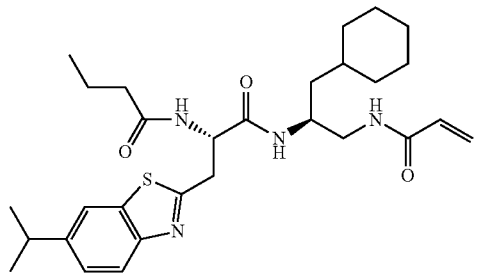
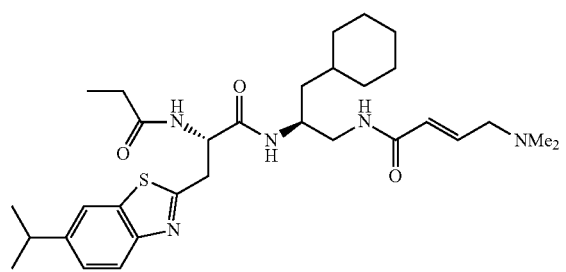
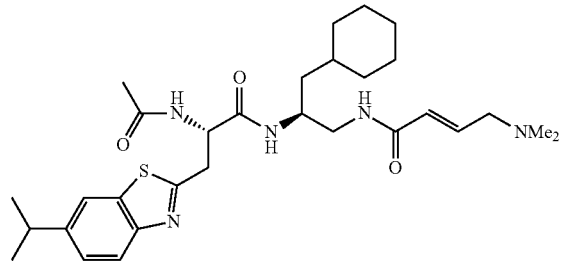
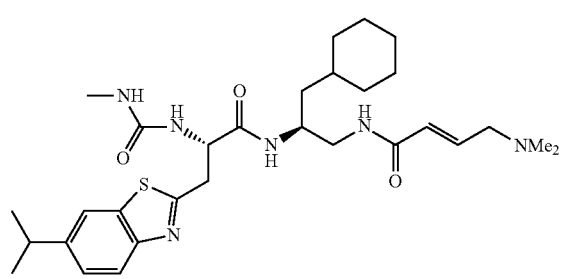
372
-continued
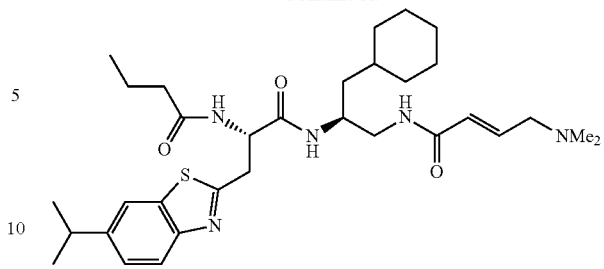
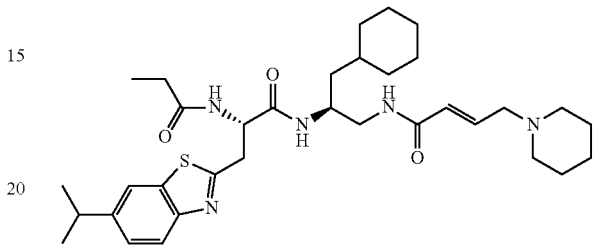
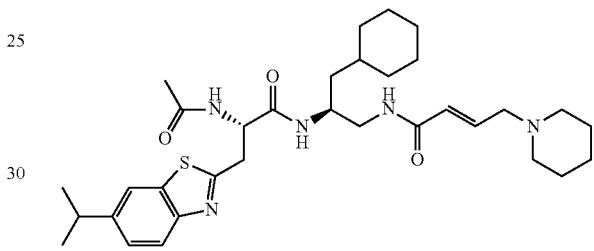
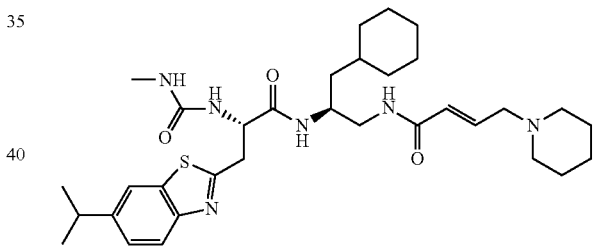
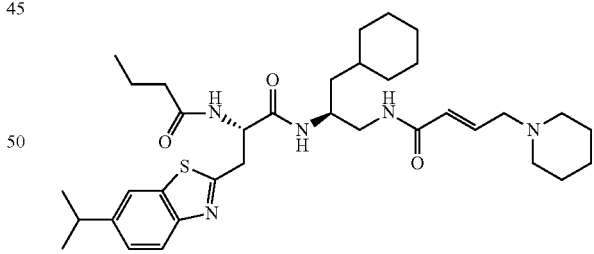
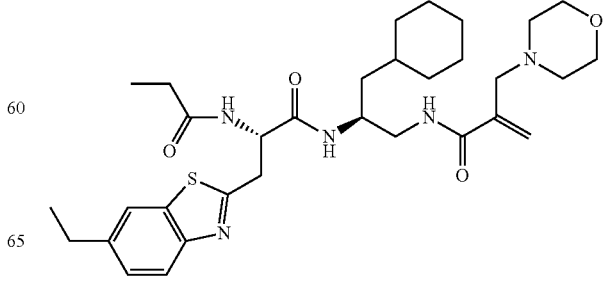

373
-continued
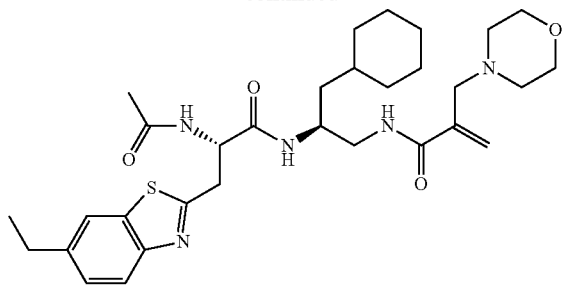
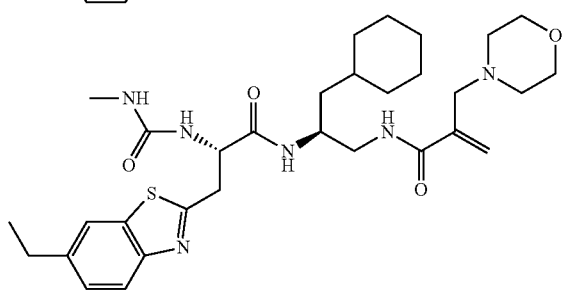
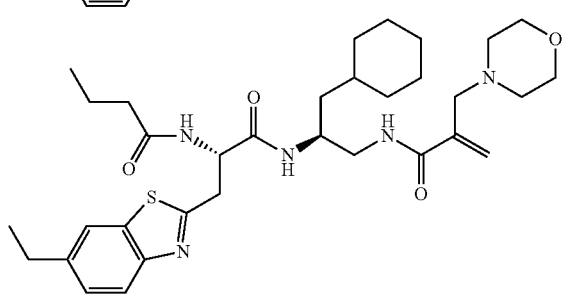
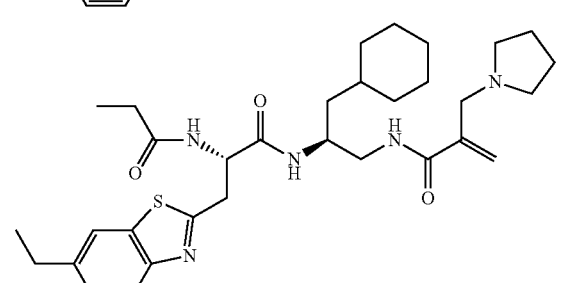
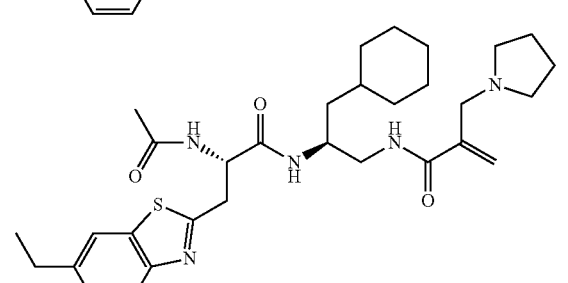
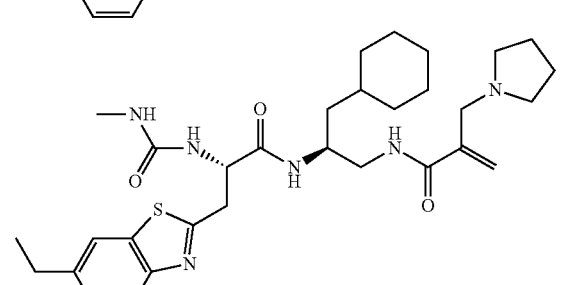
374
-continued
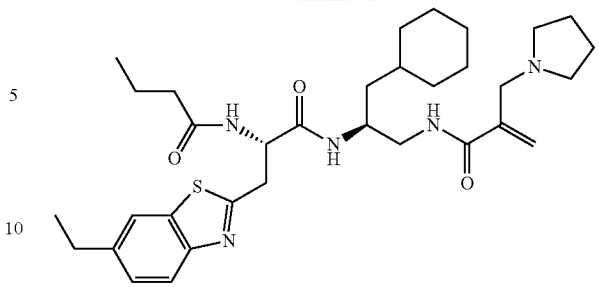
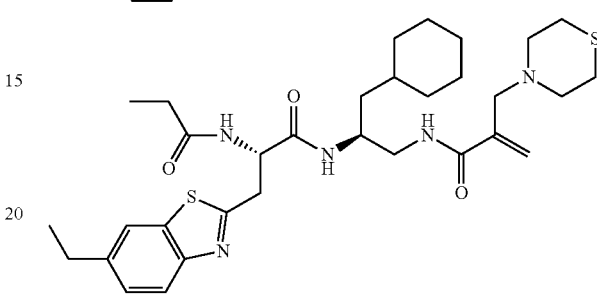
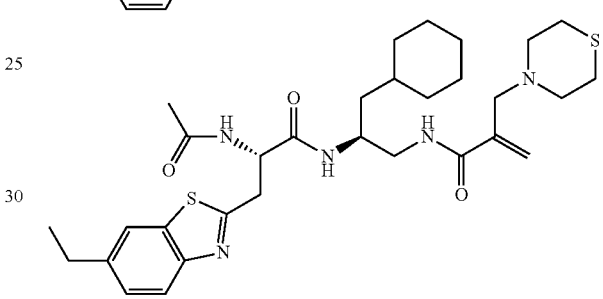
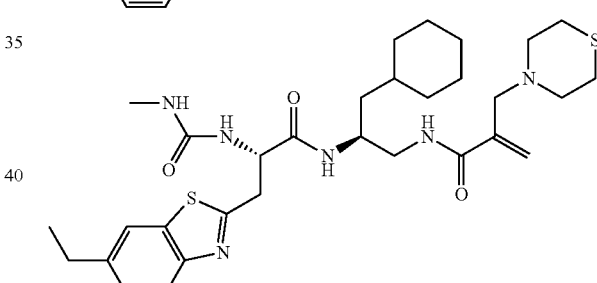
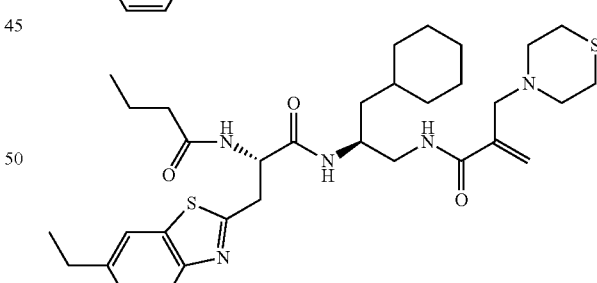
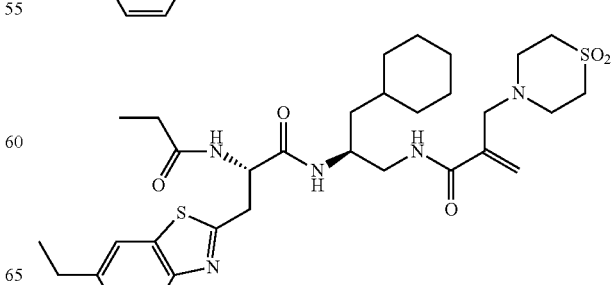

375
-continued
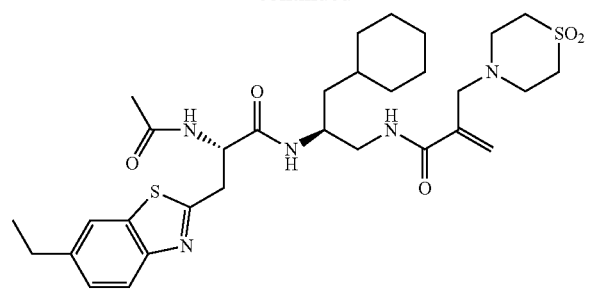
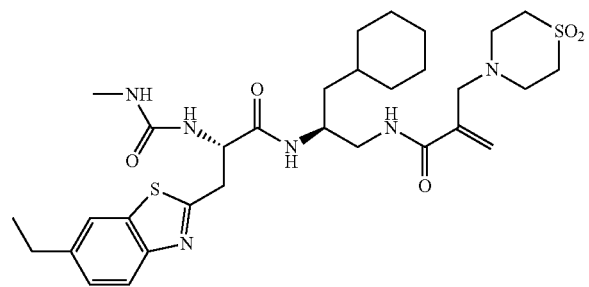
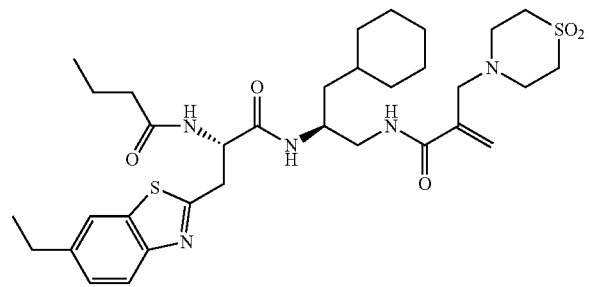
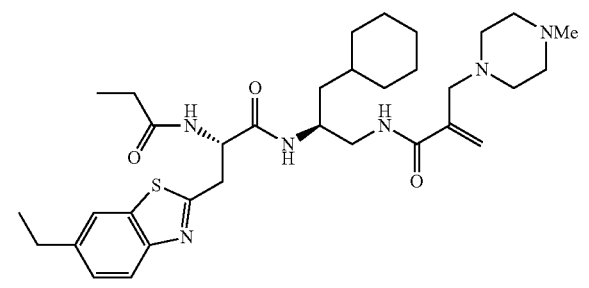
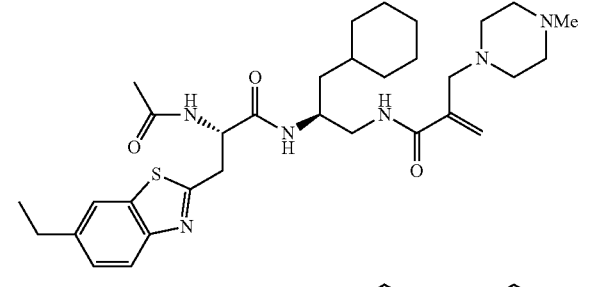
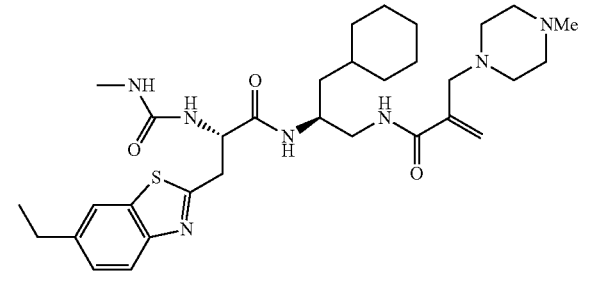
376
-continued
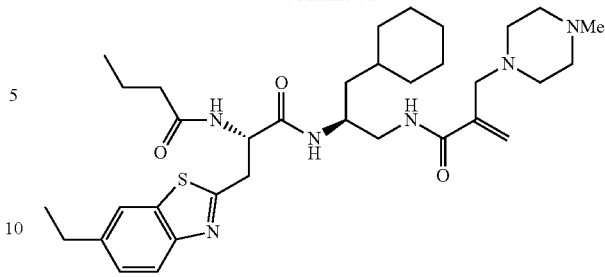
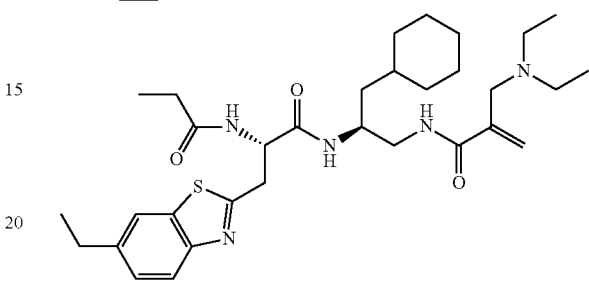
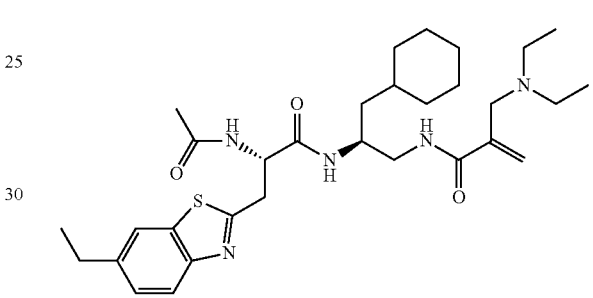
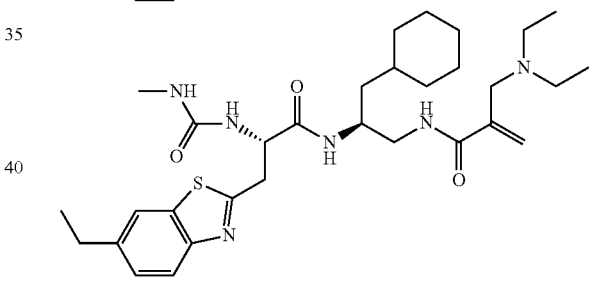
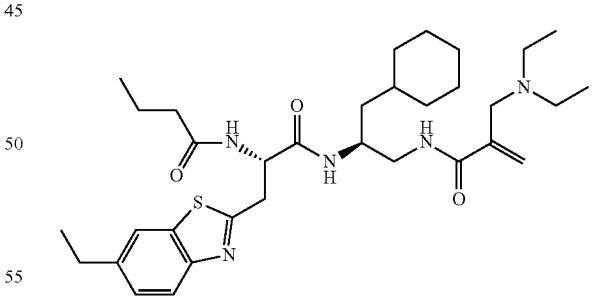
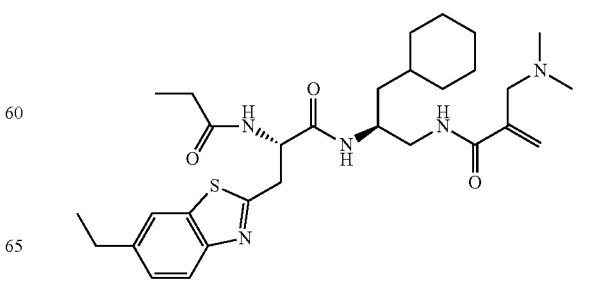

377
-continued
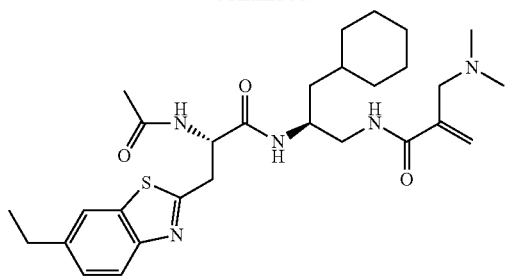
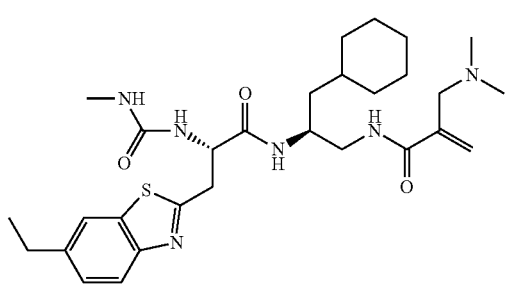
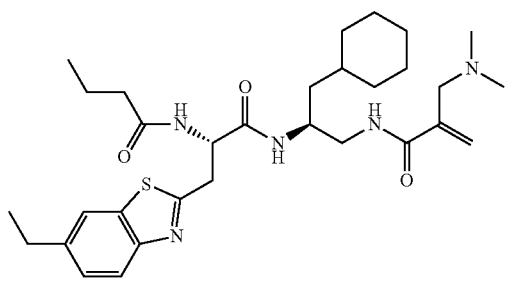
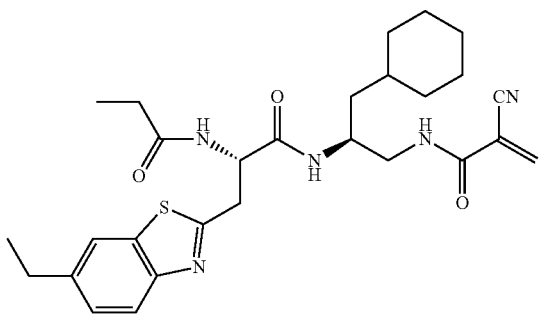
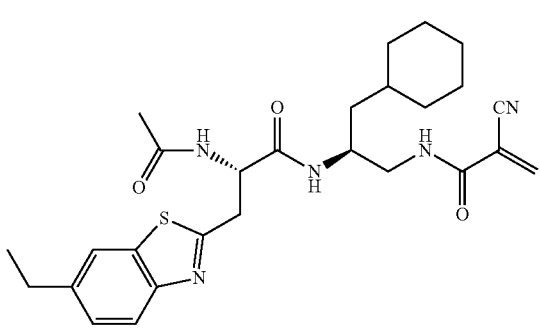
378
-continued
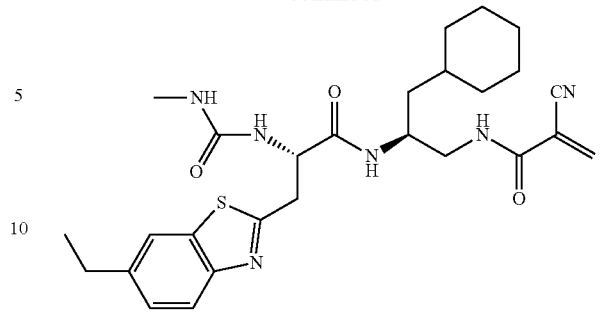
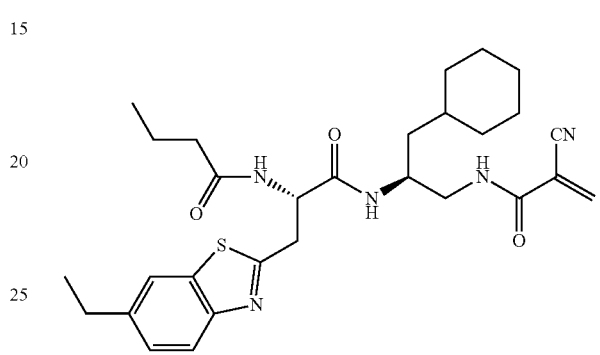
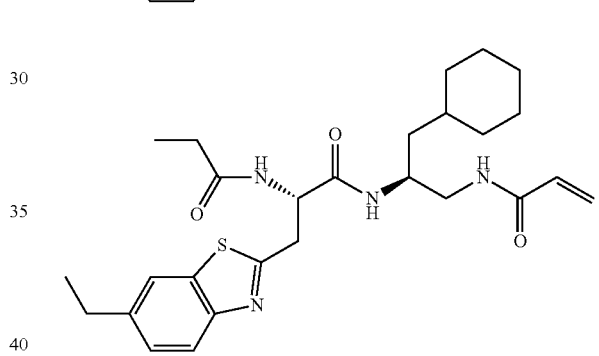
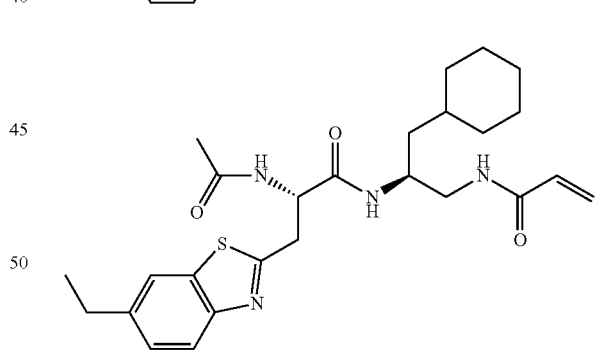
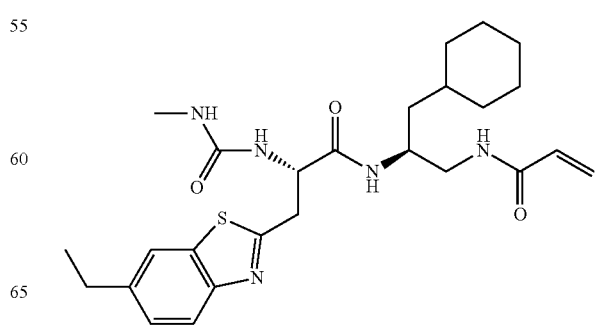

379
-continued
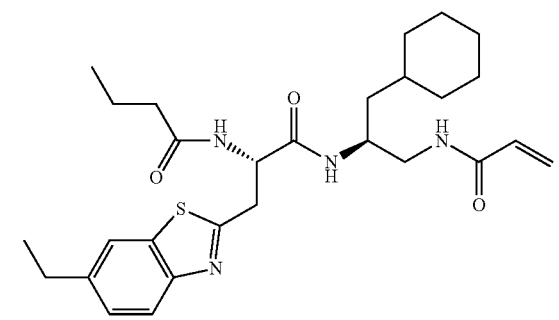
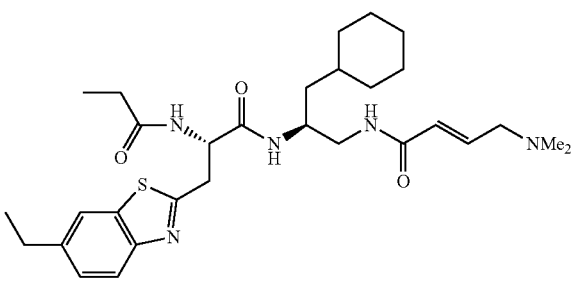
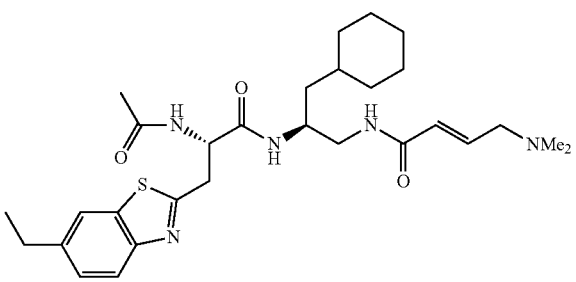
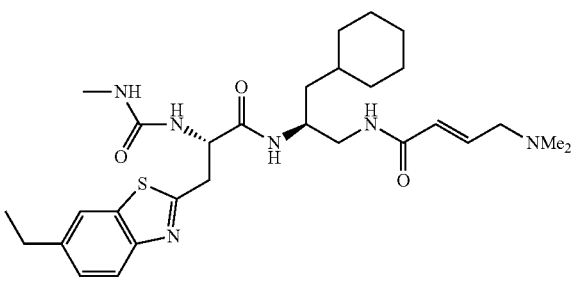
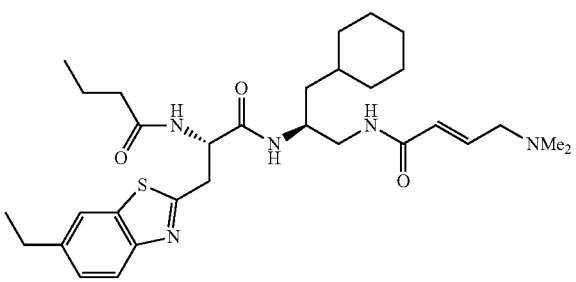
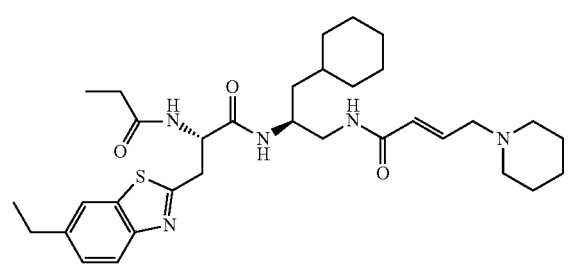
380
-continued
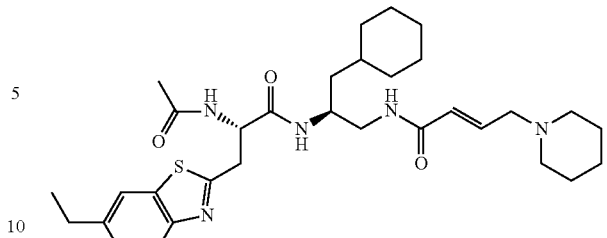
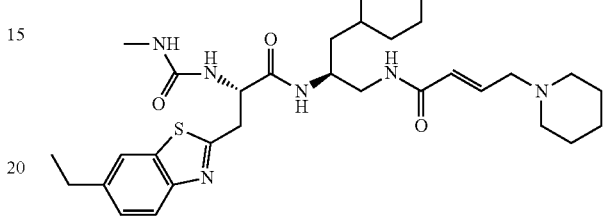
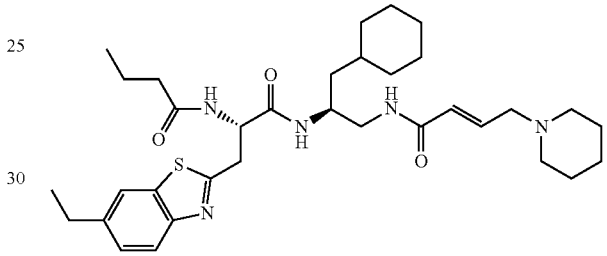
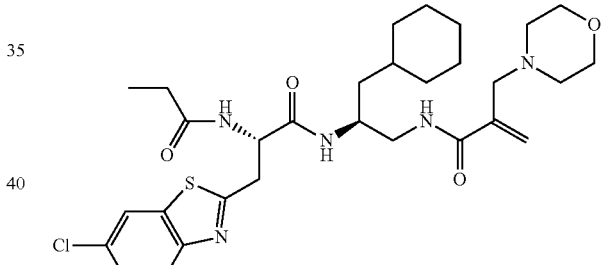
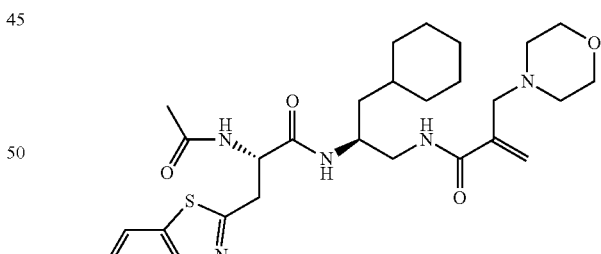
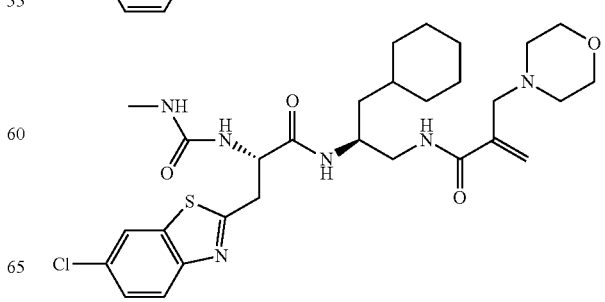

381
-continued
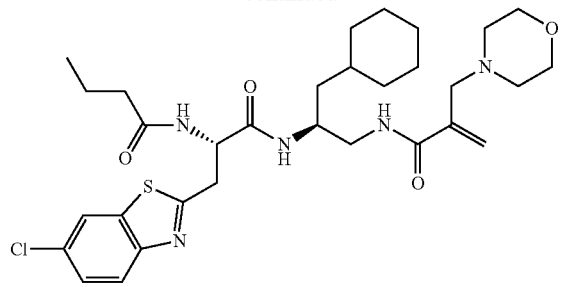
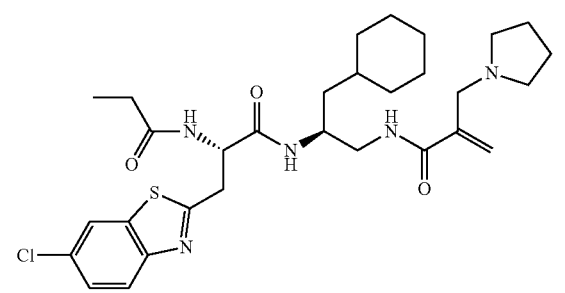
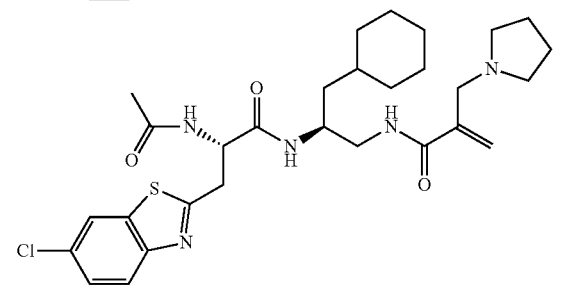
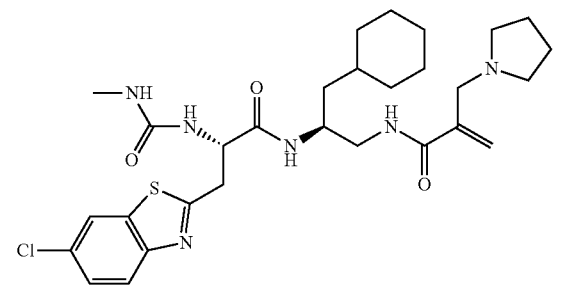
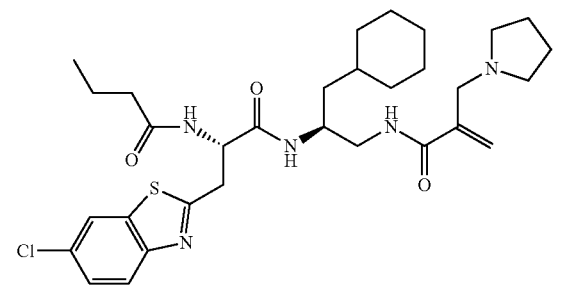
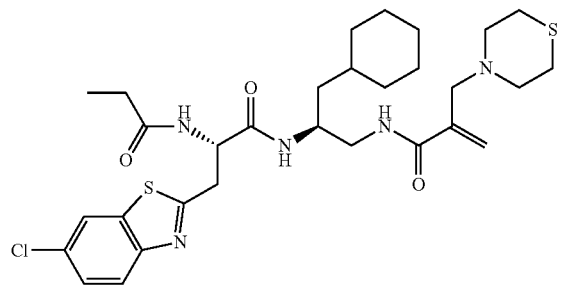
382
-continued
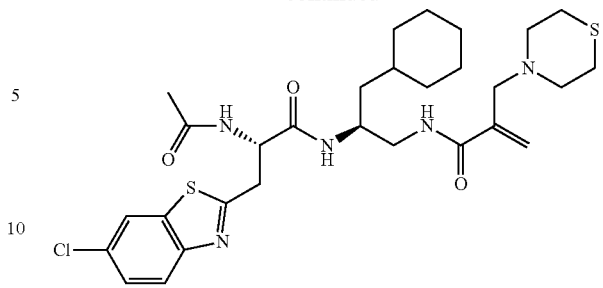
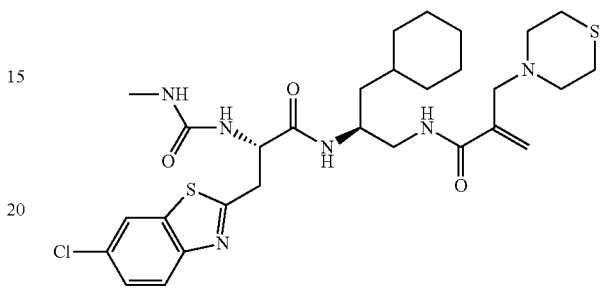
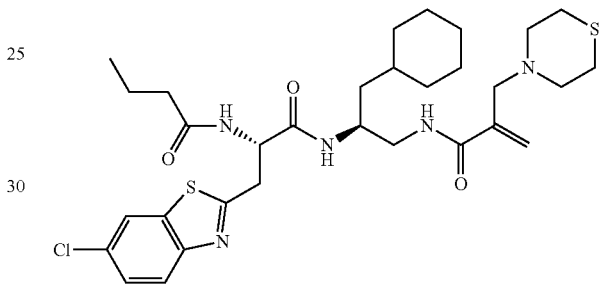
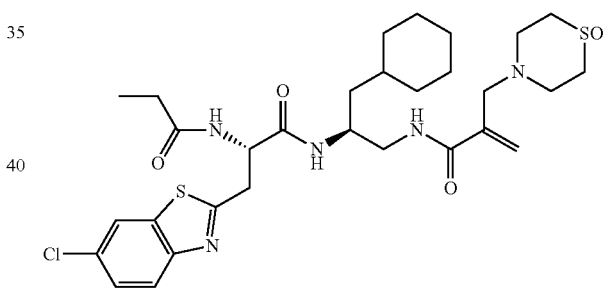
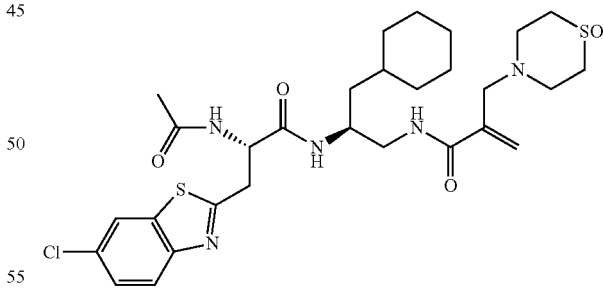
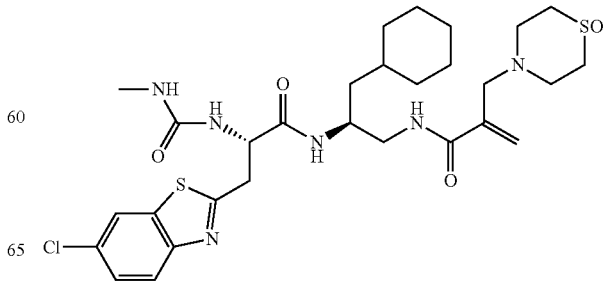

383
-continued
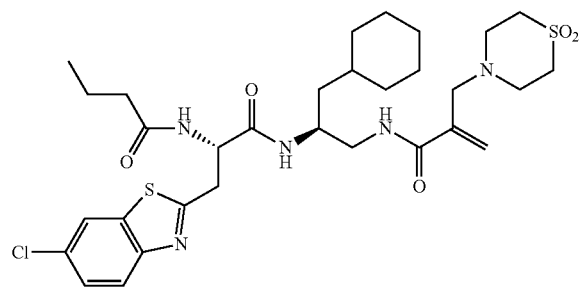
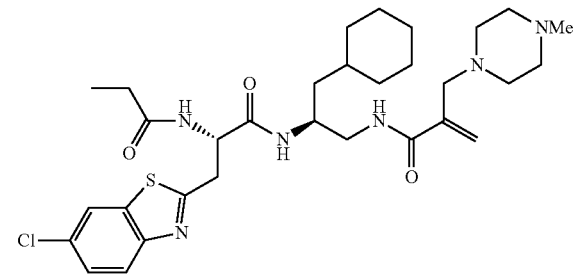
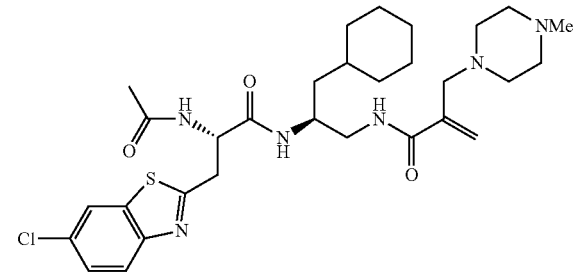
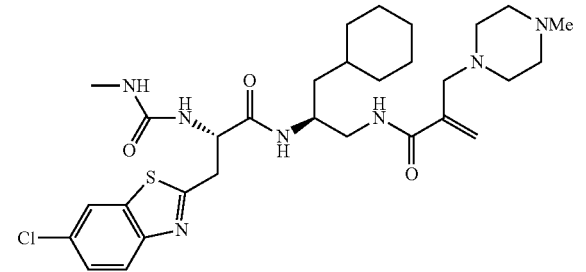
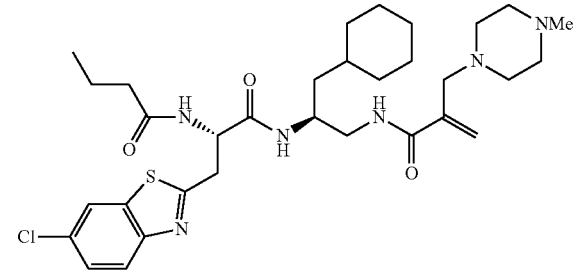
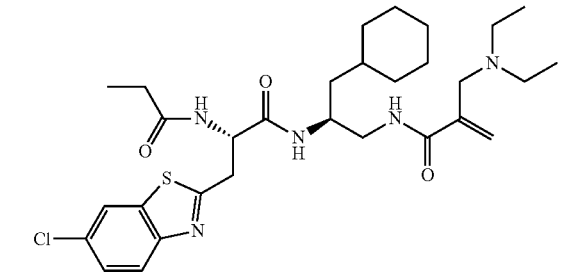
384
-continued
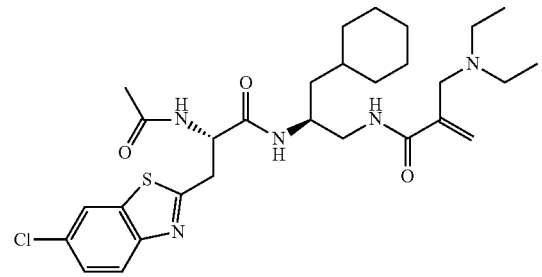
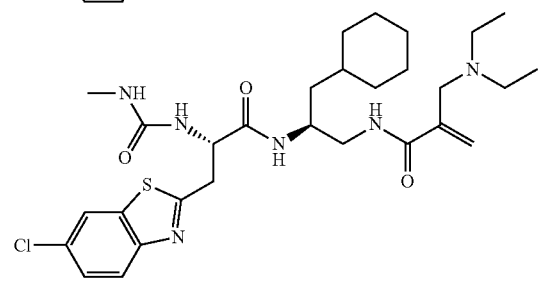
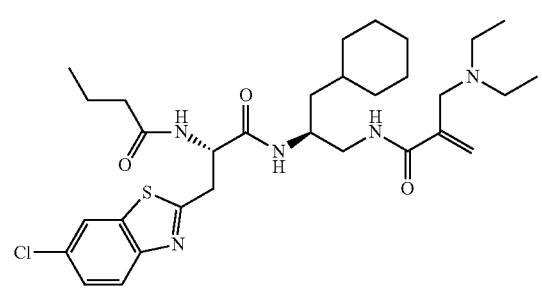
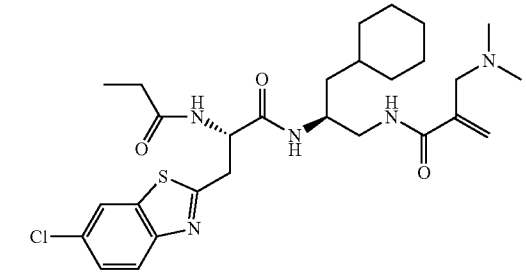
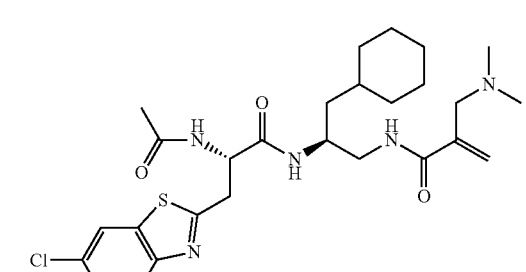
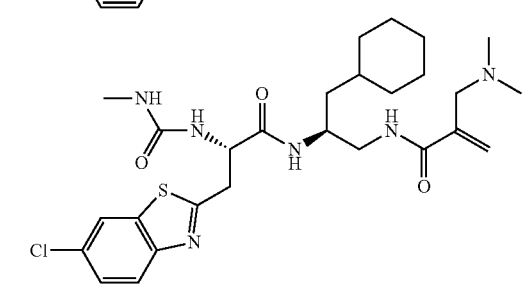

385
-continued
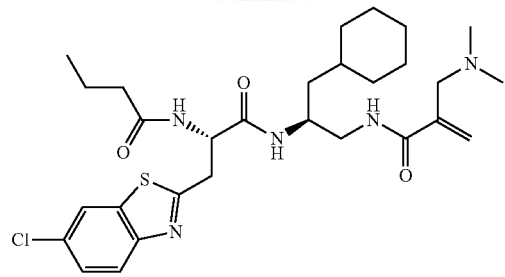
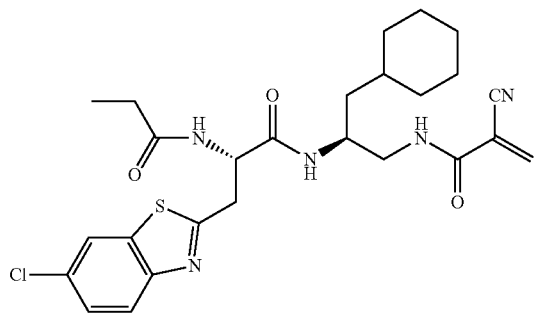
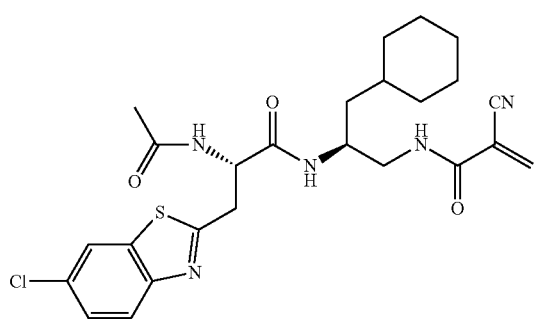
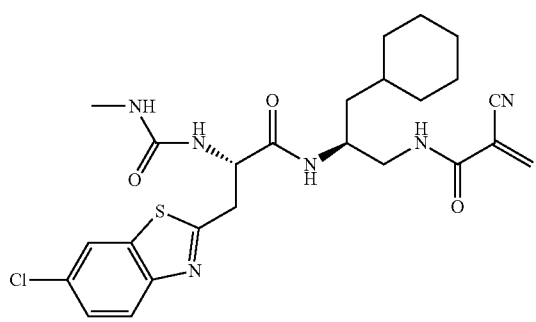
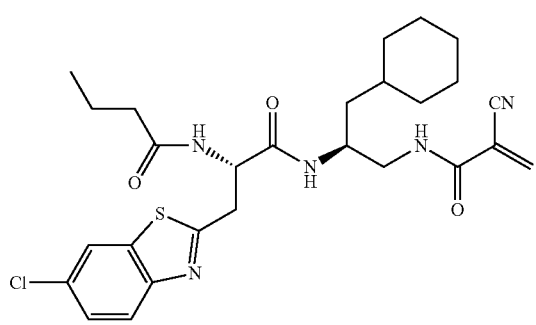
386
-continued
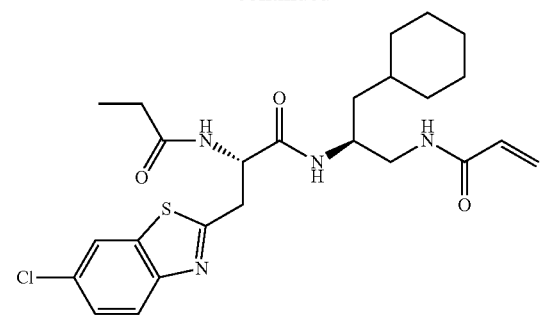
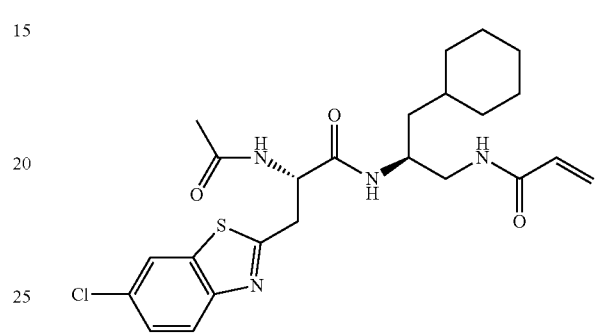
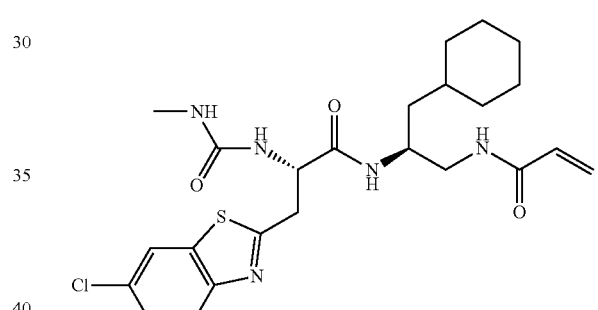
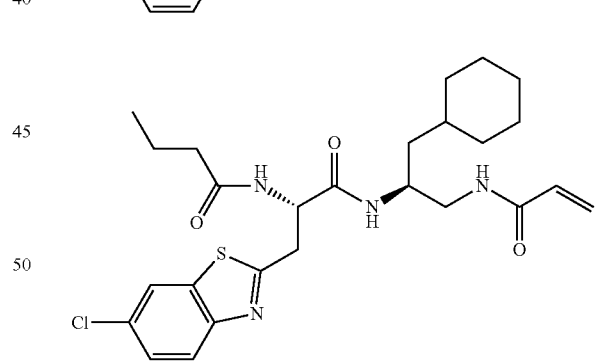
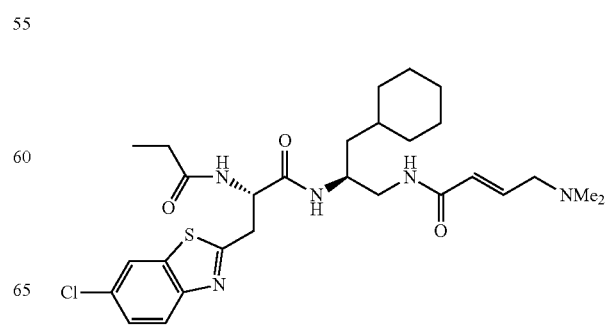

387
-continued
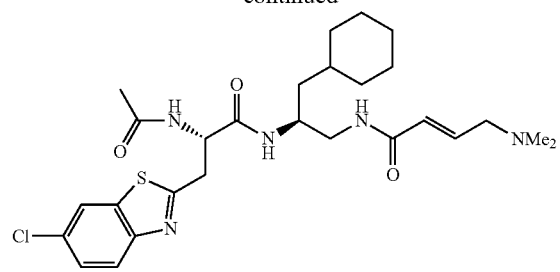
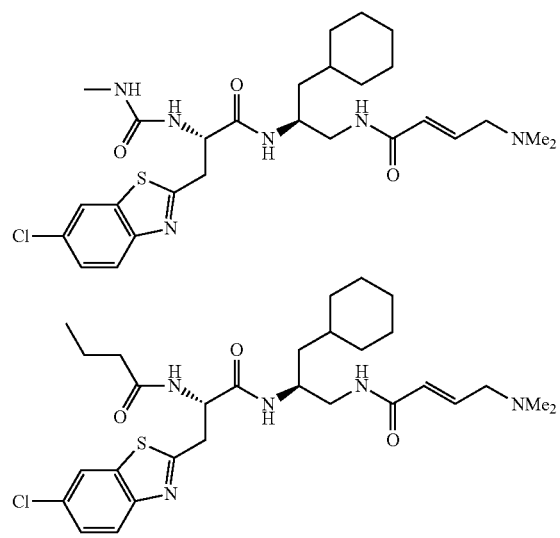
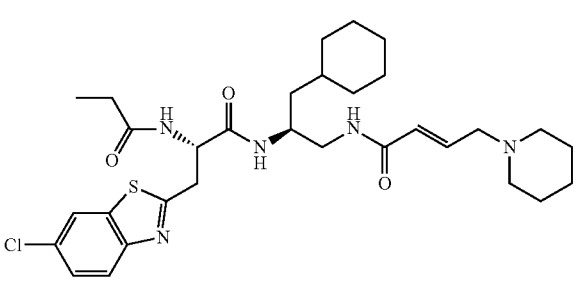
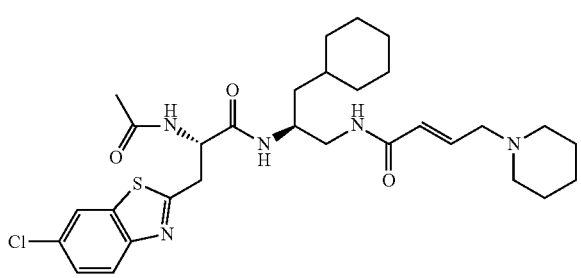
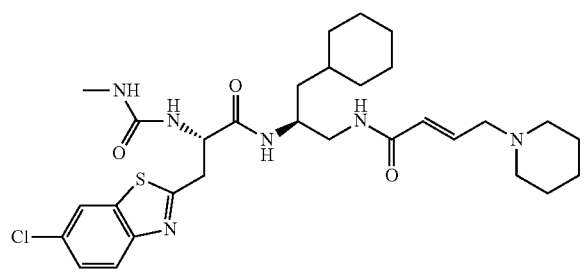
388
-continued
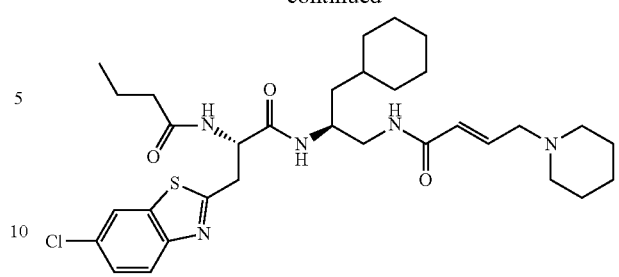
or pharmaceutically acceptable salts, hydrates or solvates thereof.
17. A compound of the following structure,
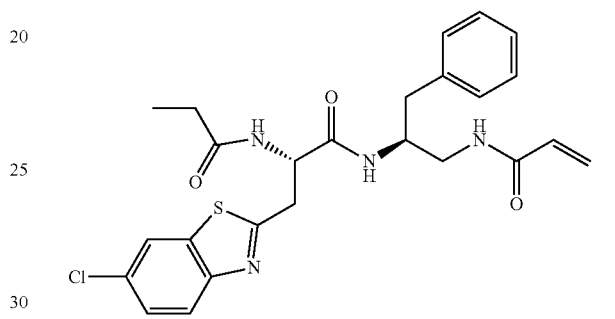
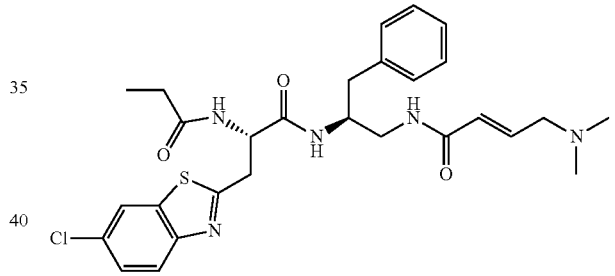
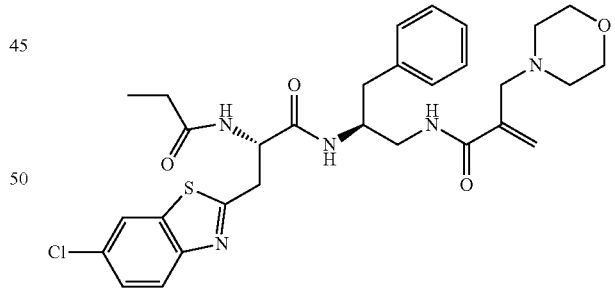
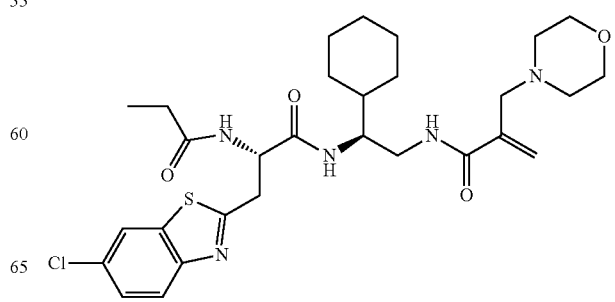

389
-continued
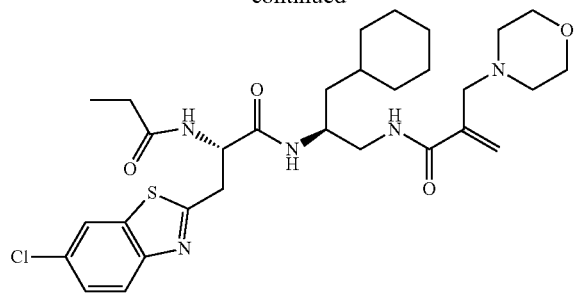
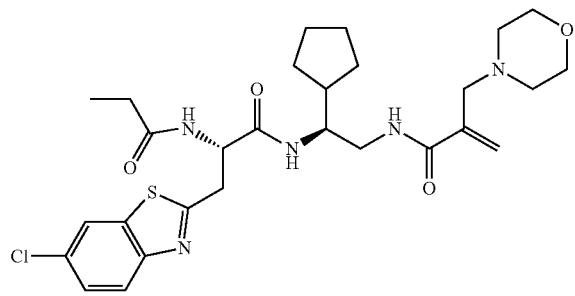
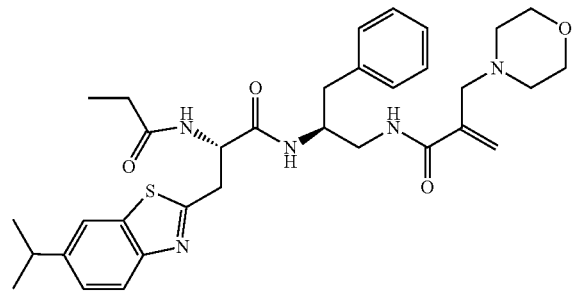
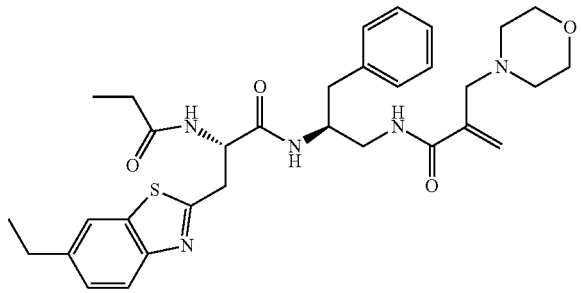
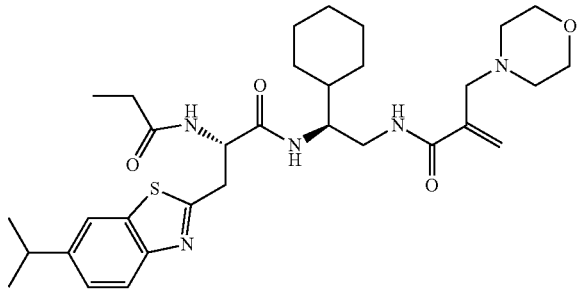
390
-continued
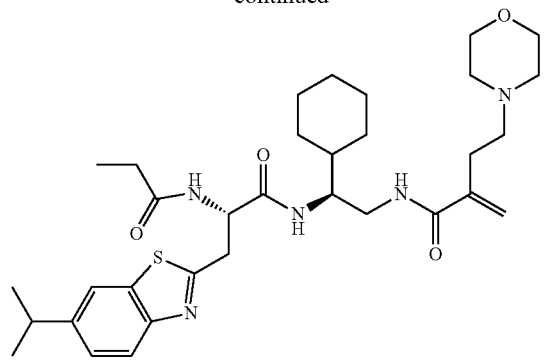
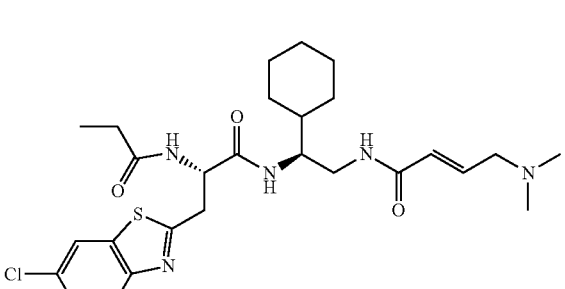
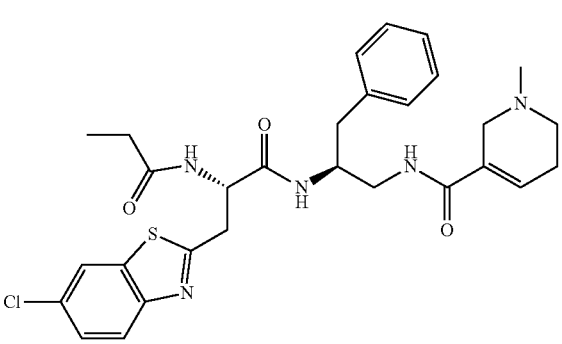
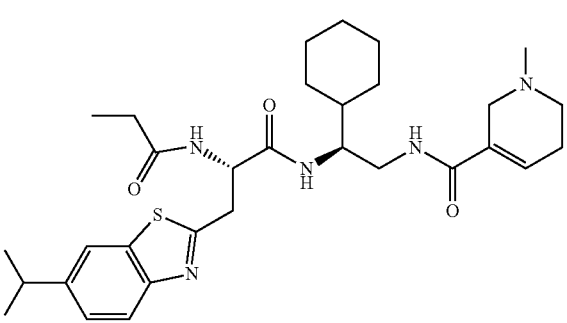
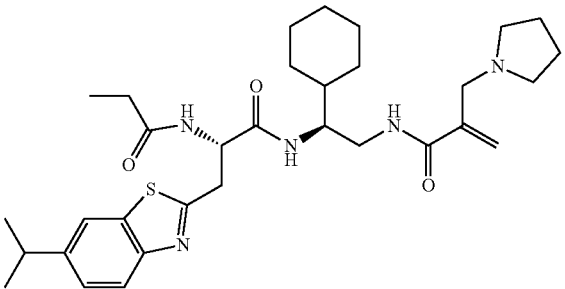

391
-continued
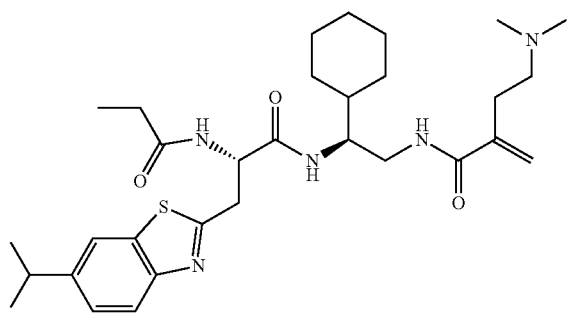
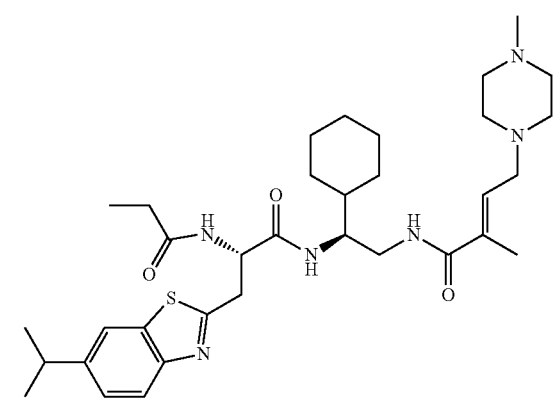
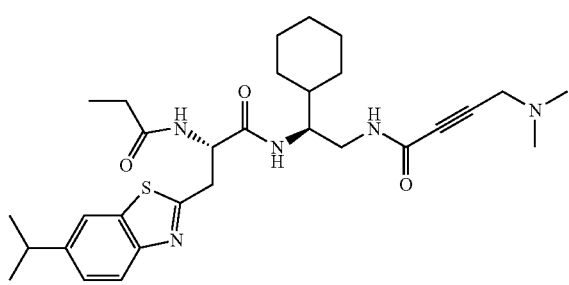
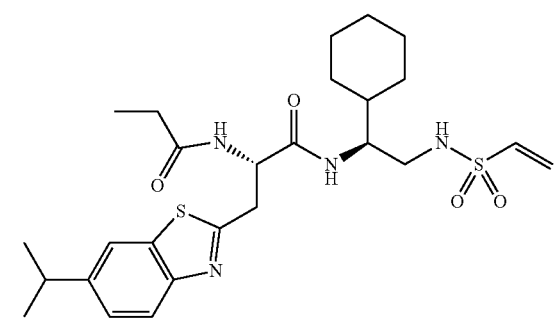
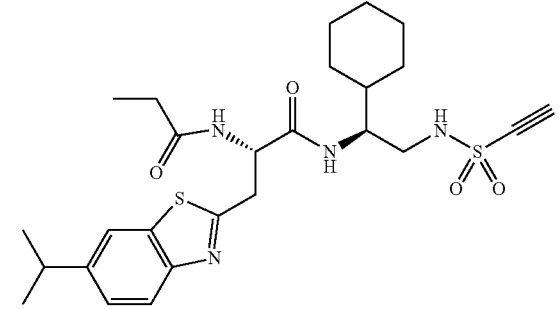
392
-continued
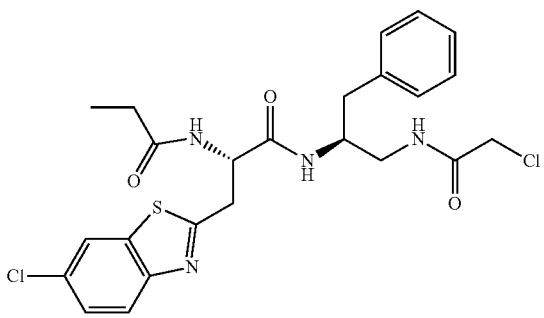
or pharmaceutically acceptable salts, hydrates or solvates thereof.
18. A compound of the following structure
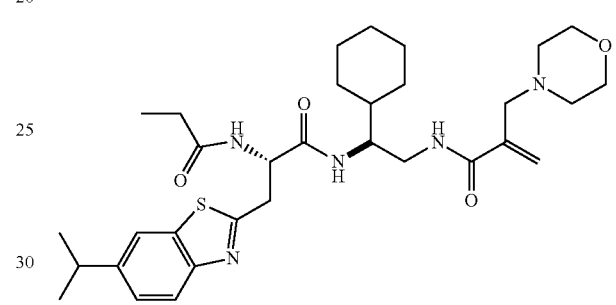
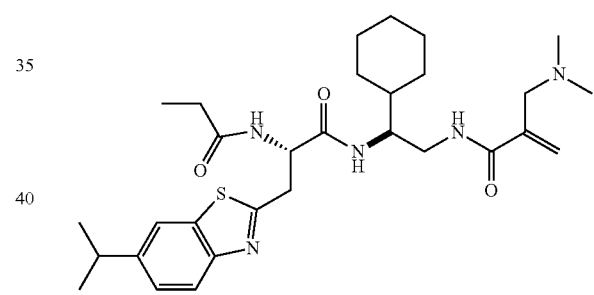
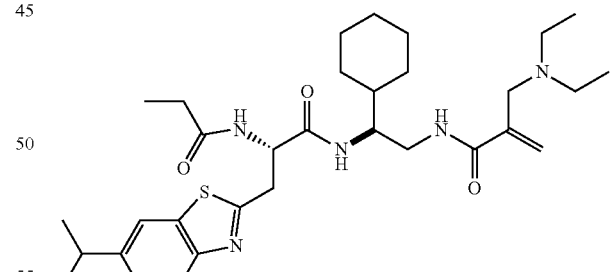
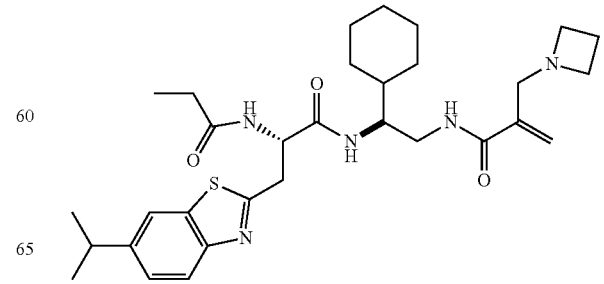

393
-continued

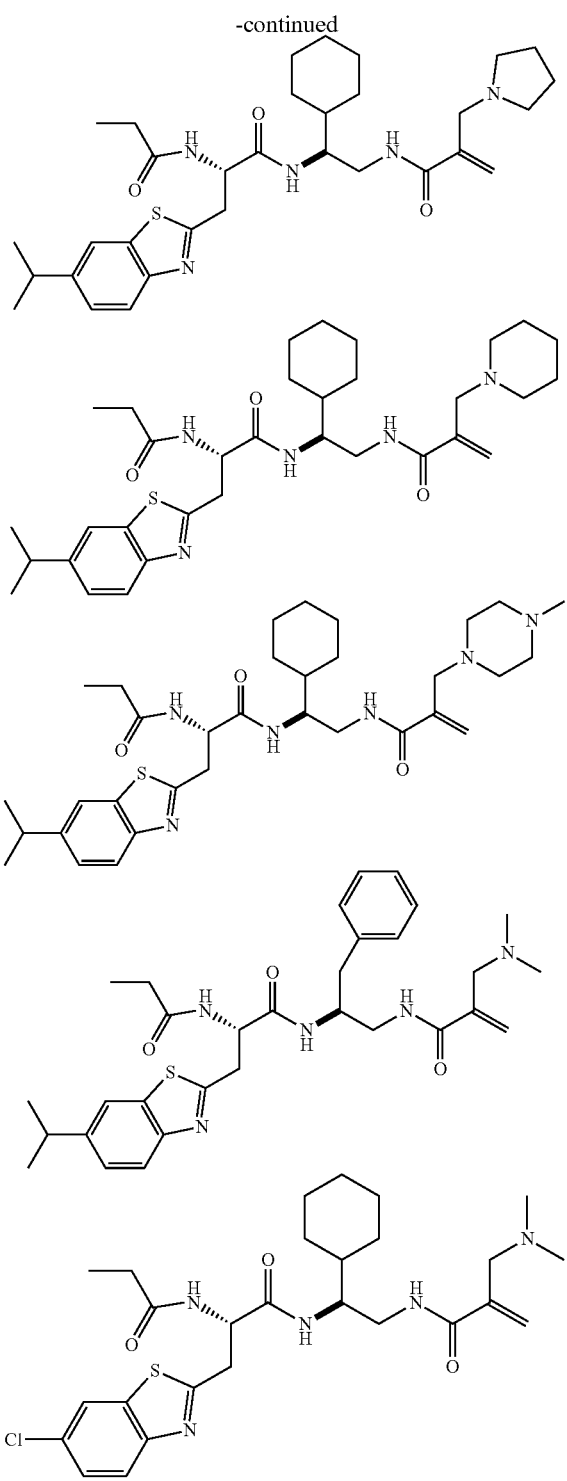

394
-continued

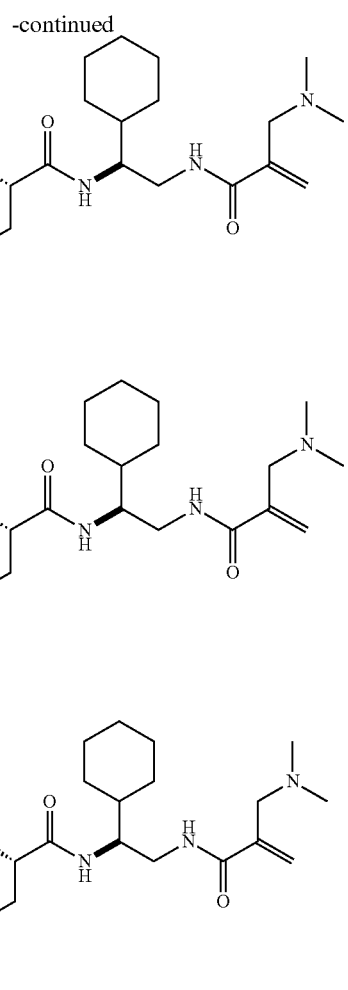

or pharmaceutically acceptable salts, hydrates or solvates thereof.

19. The compound of claim 1 which can form a covalent bond with $Cys^{115}$ of DCN1.

20. The compound of claim 1 which can form a covalent bond with $Cys^{115}$ of DCN1 in vivo, when dosed systemically to a mammal.

21. A pharmaceutical composition comprising a compound of claim 1 and a pharmaceutically acceptable carrier vehicle.

22. A method of treating acetaminophen-induced liver injury comprising administering a therapeutically effective amount of a compound of claim 1 to an individual in need thereof.

* * * * *